(12) United States Patent
Ikeda et al.

(10) Patent No.: US 10,270,040 B2
(45) Date of Patent: Apr. 23, 2019

(54) OXYGEN-CONTAINING FUSED RING AMINE COMPOUND, SULFUR-CONTAINING FUSED RING AMINE COMPOUND AND ORGANIC ELECTROLUMINESCENCE DEVICE

(71) Applicant: IDEMITSU KOSAN CO., LTD., Chiyoda-ku (JP)

(72) Inventors: Yoichi Ikeda, Chiba (JP); Hirokatsu Ito, Chiba (JP); Masahiro Kawamura, Chiba (JP); Hiroyuki Saito, Chiba (JP); Takeshi Ikeda, Chiba (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 0 days.

(21) Appl. No.: 15/658,596

(22) Filed: Jul. 25, 2017

(65) Prior Publication Data

US 2017/0324043 A1  Nov. 9, 2017

Related U.S. Application Data

(63) Continuation of application No. 14/140,806, filed on Dec. 26, 2013, now Pat. No. 9,755,156.

(30) Foreign Application Priority Data

Dec. 26, 2012 (JP) .................................. 2012-282908

(51) Int. Cl.
  *H01L 51/50* (2006.01)
  *H01L 51/00* (2006.01)
  (Continued)

(52) U.S. Cl.
  CPC ........ *H01L 51/0061* (2013.01); *C07D 209/80* (2013.01); *C07D 235/08* (2013.01);
  (Continued)

(58) Field of Classification Search
  None
  See application file for complete search history.

(56) References Cited

U.S. PATENT DOCUMENTS

| | | |
|---|---|---|
| 2011/0086454 A1 | 4/2011 | Chebotareva et al. |
| 2012/0146014 A1 | 8/2012 | Kato |

(Continued)

FOREIGN PATENT DOCUMENTS

| | | |
|---|---|---|
| JP | 2011-29220 | 2/2011 |
| JP | 2012-503027 | 2/2012 |

(Continued)

OTHER PUBLICATIONS

International Search Report dated Apr. 8, 2014 in PCT/JP2013/084765.

*Primary Examiner* — Gregory D Clark
(74) *Attorney, Agent, or Firm* — Oblon, McClelland, Maier & Neustadt, L.L.P.

(57) ABSTRACT

A fused amine compound including a furan ring or a thiophene ring and an organic electroluminescence device employing the amine compound. The organic electroluminescence device includes a cathode, an anode, and one or more organic thin film layers which are disposed between the cathode and the anode. The organic thin film layers include a light emitting layer and at least one layer of the organic thin film layers includes at least one amine compound.

18 Claims, 1 Drawing Sheet

(51) Int. Cl.
    *C07D 235/08*     (2006.01)
    *C07D 403/14*     (2006.01)
    *C07D 405/04*     (2006.01)
    *C07D 409/14*     (2006.01)
    *C07D 497/04*     (2006.01)
    *C07D 209/80*     (2006.01)
    *C07D 307/91*     (2006.01)

(52) U.S. Cl.
    CPC ......... *C07D 307/91* (2013.01); *C07D 403/14* (2013.01); *C07D 405/04* (2013.01); *C07D 409/14* (2013.01); *C07D 497/04* (2013.01); *H01L 51/0073* (2013.01); *H01L 51/5012* (2013.01)

(56) References Cited

U.S. PATENT DOCUMENTS

| | | |
|---|---|---|
| 2012/0319091 A1 | 12/2012 | Kato |
| 2013/0009137 A1 | 1/2013 | Brown et al. |
| 2014/0034915 A1 | 2/2014 | Lee et al. |

FOREIGN PATENT DOCUMENTS

| | | |
|---|---|---|
| WO | 2011/021520 A1 | 2/2011 |
| WO | 2011/090149 A1 | 7/2011 |
| WO | 2012/045710 A1 | 4/2012 |
| WO | 2013/006478 A1 | 1/2013 |

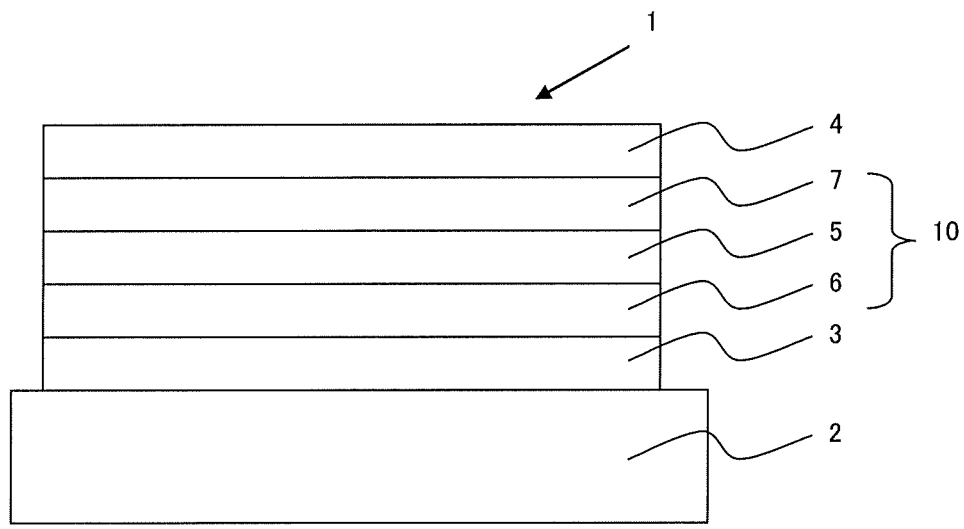

OXYGEN-CONTAINING FUSED RING AMINE COMPOUND, SULFUR-CONTAINING FUSED RING AMINE COMPOUND AND ORGANIC ELECTROLUMINESCENCE DEVICE

CROSS-REFERENCE TO RELATED APPLICATION

This application is a continuation of U.S. patent application Ser. No. 14/140,806, which is based upon and claims the benefit of priority from the prior Japanese Patent Application No. 2012-282908, filed on Dec. 26, 2012; the entire contents of which are incorporated herein by reference.

TECHNICAL FIELD

In an embodiment, the present invention relates to an oxygen-containing fused ring amine compound and a sulfur-containing fused ring amine compound, more in detail, an amine compound having a fused ring comprising a furan ring or a thiophene ring. In another embodiment, the present invention relates to an organic electroluminescence device employing the oxygen-containing fused ring amine compound and/or the sulfur-containing fused ring amine compound.

BACKGROUND ART

Generally, an organic electroluminescence device (organic EL device) is composed of an anode, a cathode, and one or more organic thin film layers sandwiched between the anode and the cathode. When a voltage is applied between the electrodes, electrons are injected from a cathode and holes are injected from an anode into a light emitting region. The injected electrons recombine with the injected holes in the light emitting region to form excited states. When the excited states return to the ground state, the energy is released as light.

Many researches have been made on the applications of organic EL device to display, etc. because of its possibility of a wide selection of emission colors by using various emitting materials in a light emitting layer. Particularly, the research on the materials which emit three primary red, green, blue colors has been made most actively, and the intensive research has been made to improve their properties.

One of the most important problems in the organic EL device is to achieve both high emission efficiency and low driving voltage. It has been known that a highly efficient light-emitting device is obtained by a light emitting layer wherein a several percent of a dopant material is doped into a host material. The host material is required to have a high carrier mobility and a uniform film-forming property, and the dopant material is required to have a high fluorescent quantum yield and a uniform dispersibility.

Patent Documents 1 to 3 describe fused ring amine compounds having a furan ring or a thiophene ring.

PRIOR ART

Patent Documents

Patent Document 1: JP 2011-29220A
Patent Document 2: JP 2012-503027A
Patent Document 3: WO 2012/045710

SUMMARY OF THE INVENTION

However, the devices employing the fused ring amine compounds having a furan ring or a thiophene ring disclosed in Patent Documents 1 to 3 are not sufficient in lifetime and emission efficiency, and a further improvement has been required.

As a result of extensive research, the inventors have found a fused ring amine compound having a furan ring or a thiophene ring which are described below in detail.

Namely, in an embodiment of the invention, the amine compound is represented by formula (1):

wherein
n is an integer of 1 to 4;
B represents a structure represented by formula (2) shown below;
A represents a group represented by formula (4) shown below; and
when n is two or more, two or more groups A may be the same or different:

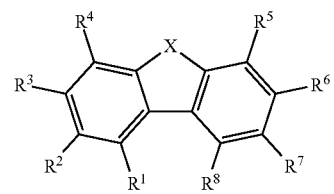

wherein two adjacent groups in at least one pair of $R^1$ and $R^2$, $R^2$ and $R^3$, $R^3$ and $R^4$, $R^5$ and $R^6$, $R^6$ and $R^7$, and $R^7$ and $R^8$ are bonded to each other to form a divalent group represented by formula (3):

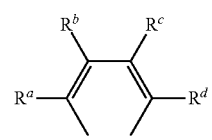

n group of $R^1$ to $R^8$ and $R^a$ to $R^d$ represents a single bond which is bonded to the group A represented by formula (4); each of $R^1$ to $R^8$ which does not form the divalent group and does not represent the single bond bonded to the group A represented by formula (4), and each of $R^a$ to $R^d$ which does not represent the single bond bonded to the group A represented by formula (4) are independently selected from a hydrogen atom, a fluorine atom, a cyano group, a substituted or unsubstituted alkyl group having 1 to 20 carbon atoms, a substituted or unsubstituted cycloalkyl group having 3 to 20 ring carbon atoms, a substituted or unsubstituted aryl group having 6 to 30 ring carbon atoms, a substituted or unsubstituted alkoxy group having 1 to 20 carbon atoms, a substituted or unsubstituted aryloxy group having 6 to 30 ring carbon atoms, a substituted or unsubstituted alkylthio group having 1 to 20 carbon atoms, a substituted or unsubstituted arylthio group having 6 to 30 ring carbon atoms, a substituted or unsubstituted alkylsilyl group having 3 to 50 carbon atoms, a substituted or unsubstituted arylsilyl group having 6 to 50 ring carbon atoms, and a substituted or unsubstituted heterocyclic group having 5 to 30 ring atoms; and X represents an oxygen atom or a sulfur atom, provided that when X represent a sulfur atom, n represents an integer of 2 to 4; and

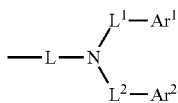

(4)

wherein:

each of $Ar^1$ and $Ar^2$ independently represents a substituted or unsubstituted aryl group having 6 to 30 ring carbon atoms or a substituted or unsubstituted heterocyclic group having 5 to 30 ring atoms;

each of L, $L^1$ and $L^2$ independently represents a single bond, an arylene group having 6 to 30 ring carbon atoms, a heteroarylene group having 5 to 30 ring atoms, or a divalent linking group formed by bonding 2 to 4 groups selected from the arylene groups and the heteroarylene groups;

provided that when $Ar^1$ and $Ar^2$ both represent the substituted or unsubstituted aryl groups each having 6 to 30 ring carbon atoms, L represents a single bond.

In another embodiment of the invention, the organic electroluminescence device comprises a cathode, an anode and one or more organic thin film layers which are disposed between the cathode and the anode, wherein the organic thin film layers comprise a light emitting layer and at least one layer of the organic thin film layers comprises at least one amine compound mentioned above.

BRIEF DESCRIPTION OF THE DRAWINGS

FIG. 1 is a schematic cross-sectional view of an example of the organic electroluminescence device in an aspect of the invention.

MODE FOR CARRYING OUT THE INVENTION

The carbon number of a to b in the expression of "a substituted or unsubstituted X group having a to b carbon atoms" referred to herein is the carbon number of the unsubstituted X group and does not include the carbon atom or atoms of the optional substituent of the X group.

The definition of hydrogen atom includes isotopes different in the neutron numbers, i.e., light hydrogen (protium), heavy hydrogen (deuterium), and tritium.

Examples of the optional substituent when saying "substituted or unsubstituted" herein include an alkyl group having 1 to 50, preferably 1 to 10, more preferably 1 to 5 carbon atoms; a cycloalkyl group having 3 to 50, preferably 3 to 6, more preferably 5 or 6 ring carbon atoms; an aryl group having 6 to 50, preferably 6 to 24, more preferably 6 to 12 ring carbon atoms; an aralkyl group composed of an aryl group having 6 to 50, preferably 6 to 24, more preferably 6 to 12 ring carbon atoms and an alkyl portion having 1 to 50, preferably 1 to 10, more preferably 1 to 5 carbon atoms; an amino group; a mono- or dialkylamino group having an alkyl group having 1 to 50, preferably 1 to 10, more preferably 1 to 5 carbon atoms; a mono- or diarylamino group having an aryl group having 6 to 50, preferably 6 to 24, more preferably 6 to 12 ring carbon atoms; an alkoxy group having an alkyl group having 1 to 50, preferably 1 to 10, more preferably 1 to 5 carbon atoms; an aryloxy group having an aryl group having 6 to 50, preferably 6 to 24, more preferably 6 to 12 ring carbon atoms; a mono-, di- or tri-substituted silyl group having a group selected from an alkyl group having 1 to 50, preferably 1 to 10, more preferably 1 to 5 carbon atoms and an aryl group having 6 to 50, preferably 6 to 24, more preferably 6 to 12 ring carbon atoms; a heterocyclic group having 5 to 50, preferably 5 to 24, more preferably 5 to 12 ring atoms and 1 to 5, preferably 1 to 3, more preferably 1 to 2 hetero atoms, such as a nitrogen atom, an oxygen atom and a sulfur atom; a haloalkyl group having 1 to 50, preferably 1 to 10, more preferably 1 to 5 carbon atoms and 1 to 8, preferably 1 to 5, more preferably 1 to 3 halogen atoms, such as a fluorine atom, a chlorine atom, a bromine atom and an iodine atom; a halogen atom, such as a fluorine atom, a chlorine atom, a bromine atom and an iodine atom; a cyano group; and a nitro group.

The optional group is preferably selected from a halogen atom, a cyano group, a trialkylsilyl group having an alkyl group having 1 to 5 carbon atoms, an alkyl group having 1 to 5 carbon atoms, a cycloalkyl group having 5 or 6 ring carbon atoms, and an aryl group having 6 to 12 ring carbon atoms.

The amine compound is represented by formula (1):

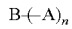 (1)

In formula (1), n is an integer of 1 to 4, preferably 1 or 2, and more preferably 2.

In formula (1), B represents a structure represented by formula (2):

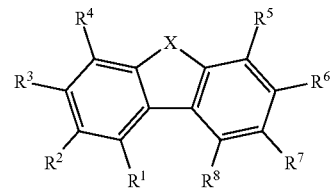

(2)

In formula (2), two adjacent groups in at least one pair, preferably one or two pairs, and more preferably two pairs of $R^1$ and $R^2$, $R^2$ and $R^3$, $R^3$ and $R^4$, $R^5$ and $R^6$, $R^6$ and $R^7$, and $R^7$ and $R^8$ are bonded to each other to form a divalent group represented by formula (3):

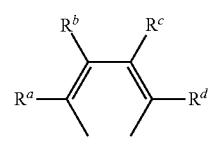

(3)

In formula (2), n group of $R^1$ to $R^8$ and $R^a$ to $R^d$ represents a single bond which is bonded to the group A.

Each of $R^1$ to $R^8$ which does not form the divalent group and does not represent the single bond bonded to the group A, and each of $R^a$ to $R^d$ which does not represent the single bond bonded to the group A are independently selected from a hydrogen atom, a fluorine atom, a cyano group, a substituted or unsubstituted alkyl group having 1 to 20 carbon atoms, a substituted or unsubstituted cycloalkyl group having 3 to 20 ring carbon atoms, a substituted or unsubstituted aryl group having 6 to 30 ring carbon atoms, a substituted or unsubstituted alkoxy group having 1 to 20 carbon atoms, a substituted or unsubstituted aryloxy group having 6 to 30 ring carbon atoms, a substituted or unsubstituted alkylthio group having 1 to 20 carbon atoms, a substituted or unsubstituted arylthio group having 6 to 30 ring carbon atoms, a substituted or unsubstituted alkylsilyl group having 3 to 50 carbon atoms, a substituted or unsubstituted arylsilyl group having 6 to 50 ring carbon atoms, and a substituted or unsubstituted heterocyclic group having 5 to 30 ring atoms; preferably selected from a hydrogen atom, a substituted or unsubstituted alkyl group having 1 to 20 carbon atoms, a substituted or unsubstituted cycloalkyl group having 3 to 20 ring carbon atoms, a substituted or unsubstituted aryl group having 6 to 30 ring carbon atoms, and a substituted or unsubstituted heterocyclic group having 5 to 30 ring atoms; and more preferably selected from a hydrogen atom and a substituted or unsubstituted aryl group having 6 to 30 ring carbon atoms; with a hydrogen atom being particularly preferred.

X represents an oxygen atom or a sulfur atom, preferably an oxygen atom.

Examples of the alkyl group having 1 to 20, preferably 1 to 10, and more preferably 1 to 5 carbon atoms included a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), an octyl group (inclusive of isomeric groups), a nonyl group (inclusive of isomeric groups), a decyl group (inclusive of isomeric groups), an undecyl group (inclusive of isomeric groups), and a dodecyl group (inclusive of isomeric groups), with a methyl group, an ethyl group, a n-propyl group, an isopropyl group, a n-butyl group, an isobutyl group, a s-butyl group, a t-butyl group, and a pentyl group (inclusive of isomeric groups) being preferred; a methyl group, an ethyl group, a n-propyl group, an isopropyl group, a n-butyl group, an isobutyl group, a s-butyl group, and a t-butyl group being more preferred; and a methyl group, an ethyl group, an isopropyl group, and a t-butyl group being particularly preferred.

Examples of the cycloalkyl group having 3 to 20, preferably 3 to 6, and more preferably 5 or 6 ring carbon atoms include a cyclopropyl group, a cyclobutyl group, a cyclopentyl group, a cyclohexyl group, a cycloheptyl group, an cyclooctyl group, and an adamantyl group, with a cyclopentyl group and a cyclohexyl group being preferred.

Examples of the aryl group having 6 to 30, preferably 6 to 24, and more preferably 6 to 18 ring carbon atoms include a phenyl group, a naphthylphenyl group, a biphenylyl group, a terphenylyl group, a naphthyl group, an acenaphthylenyl group, an anthryl group, a benzanthryl group, an aceanthryl group, a phenanthryl group, a benzo[c]phenanthryl group, a phenalenyl group, a fluorenyl group, a picenyl group, a pentaphenyl group, a pyrenyl group, a chrysenyl group, a benzo[g]chrysenyl group, a s-indacenyl group, an as-indacenyl group, a fluoranthenyl group, a benzo[k]fluoranthenyl group, a triphenylenyl group, a benzo[b]triphenylenyl group, and a perylenyl group, with a phenyl group, a biphenylyl group, a terphenylyl group, and a naphthyl group being preferred, a phenyl group, a biphenylyl group, and a terphenylyl group being more preferred, and a phenyl group being particularly preferred.

Examples of the substituted aryl group include a phenylnaphthyl group, a naphthylphenyl group, a tolyl group, a xylyl group, a 9,9-dimethylfluorenyl group, and a 9,9-diphenylfluorenyl group.

Examples of the alkyl portion of the alkoxy group having 1 to 20, preferably 1 to 10, and more preferably 1 to 5 carbon atoms, the preferred alkyl portion, the more preferred alkyl portion, and the particularly preferred alkyl portion are as described above with respect to the alkyl group.

Examples of the aryl portion of the aryloxy group having 6 to 30, preferably 6 to 24, and more preferably 6 to 18 ring carbon atoms, the preferred aryl portion, more preferred aryl portion, and the particularly preferred aryl portion are as described above with respect to the aryl group.

Examples of the alkyl portion of the alkylthio group having 1 to 20, preferably 1 to 10, and more preferably 1 to 10 carbon atoms, the preferred alkyl portion, the more preferred alkyl portion, and the particularly preferred alkyl portion are as described above with respect to the alkyl group.

Examples of the aryl portion of the arylthio group having 6 to 30, preferably 6 to 24, and more preferably 6 to 18 ring carbon atoms, the preferred aryl portion, more preferred aryl portion, and the particularly preferred aryl portion are as described above with respect to the aryl group.

Examples of the alkylsilyl group having 3 to 50, preferably 3 to 12, and more preferably 3 to 6 carbon atoms include a monoalkylsilyl group, a dialkylsilyl group, and a trialkylsilyl group. The alkyl portion of the alkylsilyl group, the preferred alkyl portion, the more preferred alkyl portion, and the particularly preferred alkyl portion are as described above with respect to the alkyl group.

Examples of the arylsilyl group having 6 to 50, preferably 6 to 18, and more preferably 6 to 10 ring carbon atoms include a monoarylsilyl group, a diarylsilyl group, and a triarylsilyl group. The aryl portion of the arylsilyl group, the preferred aryl portion, more preferred aryl portion, and the particularly preferred aryl portion are as described above with respect to the aryl group.

The heterocyclic group having 5 to 30, preferably 6 to 24, and more preferably 6 to 18 ring atoms comprises at least one, preferably 1 to 5 hetero atoms, such as a nitrogen atom, a sulfur atom and an oxygen atom. Examples of the heterocyclic group include a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, a tetrazolyl group, an indolyl group, an isoindolyl group, a benzofuranyl group, an isobenzofuranyl group, a benzothiophenyl group, an isobenzothiophenyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a dibenzothiophenyl group, a carbazolyl group, a phenanthridinyl group, an acridinyl group, a phenanthrolinyl group, a phenazinyl group, a phenothiazinyl group, a phenoxazinyl group, and a xanthenyl group, with a furyl group, a thienyl group, a pyridyl group, a pyridazinyl group, a pyrimidinyl group, a pyrazinyl group, a triazinyl group, a benzofuranyl group, a benzothiophenyl group, a dibenzofuranyl group, and a dibenzothiophenyl group being preferred, and a benzofuranyl group, a benzothiophenyl group, a dibenzofuranyl group, and a dibenzothiophenyl group being more preferred.

The structure B of formula (1), wherein one pair selected from $R^1$ and $R^2$, $R^2$ and $R^3$, $R^3$ and $R^4$, $R^5$ and $R^6$, $R^6$ and $R^7$, and $R^7$ and $R^8$ forms the divalent group represented by formula (3) is preferably represented by any of the following formulae (11) to (13), more preferably by formula (11) or (13):

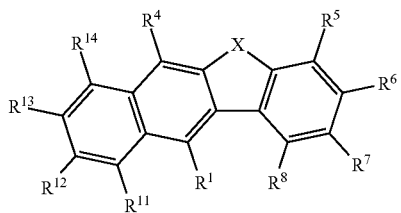

(11)

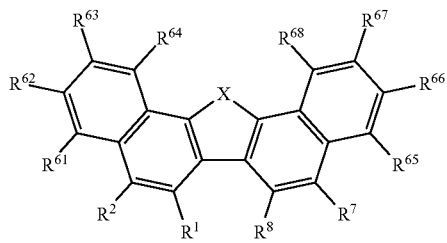

(16)

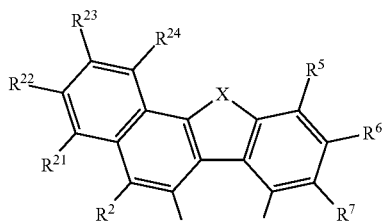

(12)

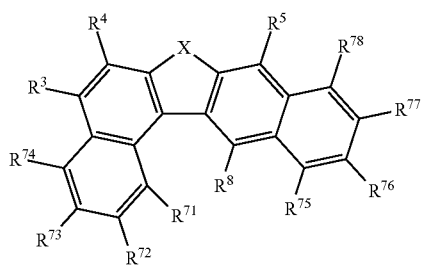

(17)

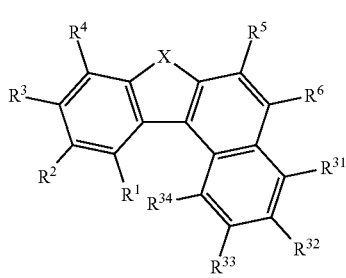

(13)

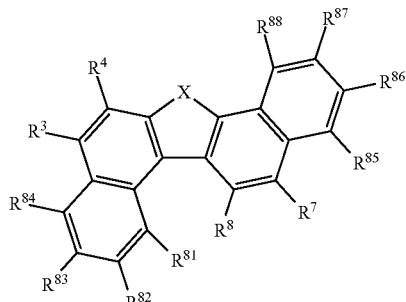

(18)

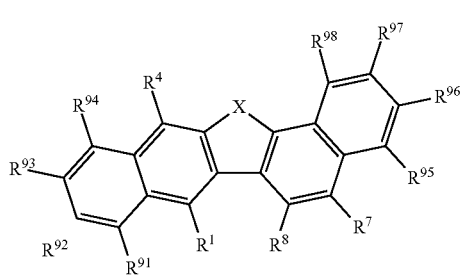

(19)

wherein X and $R^1$ to $R^8$ are as defined above, $R^{11}$ to $R^{14}$, $R^{21}$ to $R^{24}$, and $R^{31}$ to $R^{34}$ are defined as in $R^a$ to $R^d$, and each of 1 to 4 groups, preferably 1 or 2 groups, and more preferably 2 groups selected from ten $R^x$ groups in each of formulae (11) to (13) represents a single bond bonded to the group A.

The structure B of formula (1), wherein two pairs selected from $R^1$ and $R^2$, $R^2$ and $R^3$, $R^3$ and $R^4$, $R^5$ and $R^6$, $R^6$ and $R^7$, and $R^7$ and $R^8$ form the divalent groups represented by formula (3) is preferably represented by any of the following formulae (14) to (19), more preferably by any of the following formulae (14) to (16):

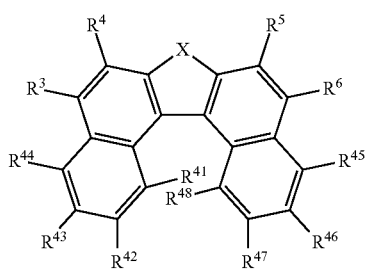

(14)

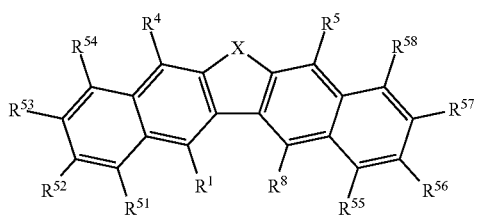

(15)

wherein X and $R^8$ are as defined above, $R^{41}$ to $R^{48}$, $R^{51}$ to $R^{58}$, $R^{61}$ to $R^{68}$, $R^{71}$ to $R^{78}$, $R^{81}$ to $R^{88}$, and $R^{91}$ to $R^{98}$ are defined as in $R^a$ to $R^d$, and each of 1 to 4 groups, preferably 1 or 2 groups, and more preferably 2 groups selected from twelve $R^x$ groups in each of formulae (14) to (19) represents a single bond bonded to the group A.

The structure B represented by formulae (11) to (19) is preferably represented by any of the following formulae (20) to (54), more preferably by any of formulae (22) to (23), (25), (31), (33) to (36), (40) to (42), (45), (46), (48), and (51).

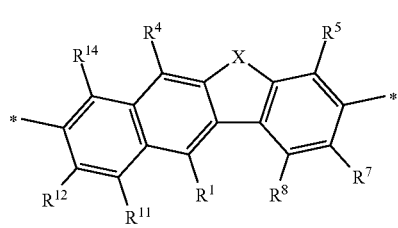

(20)

-continued
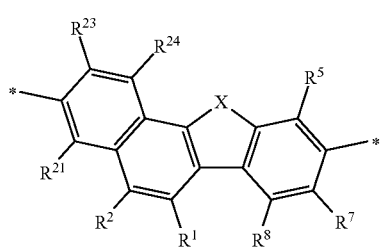
(21)
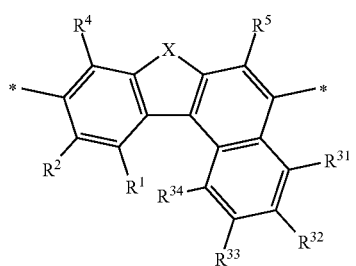
(22)
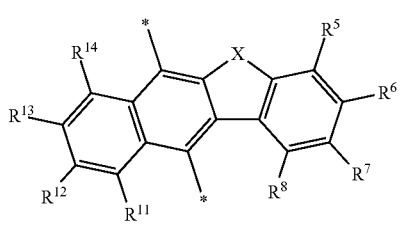
(23)
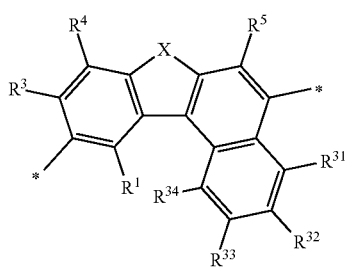
(24)
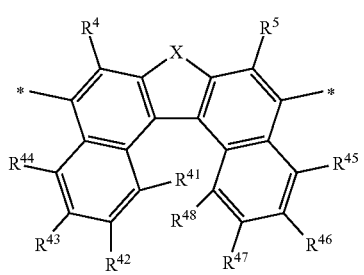
(25)
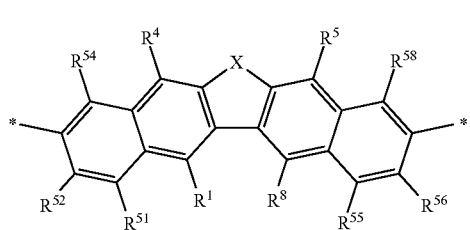
(26)
-continued
(27)
(28)
(29)
(30)
(31)

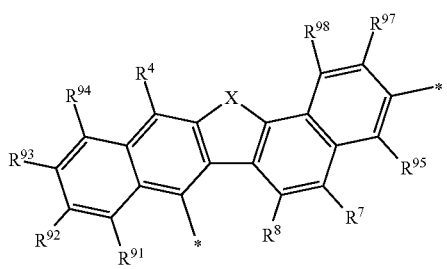
(32)
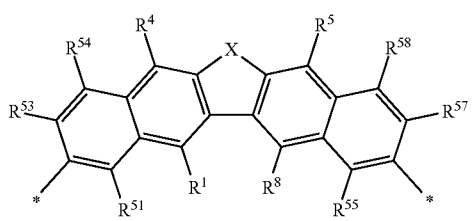
(33)
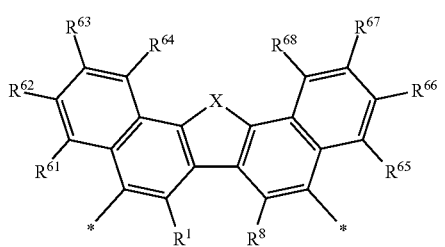
(34)
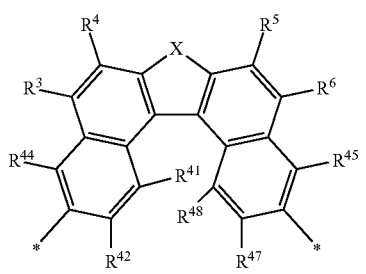
(35)
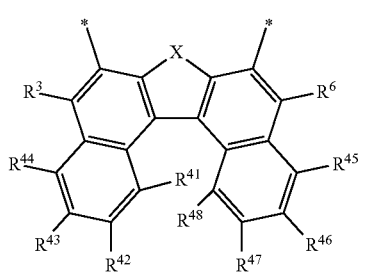
(36)
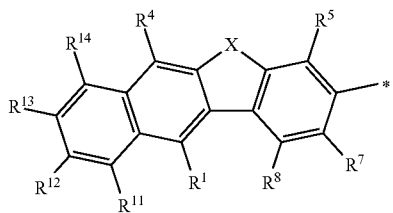
(37)
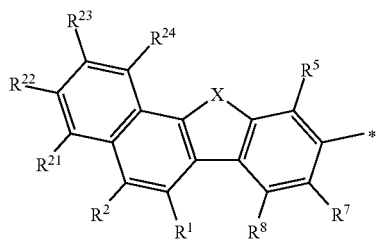
(38)
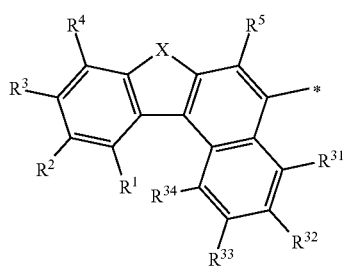
(39)
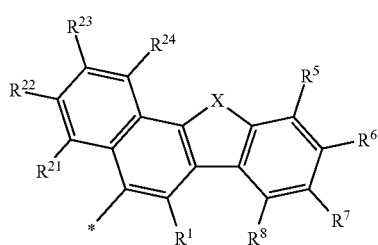
(40)
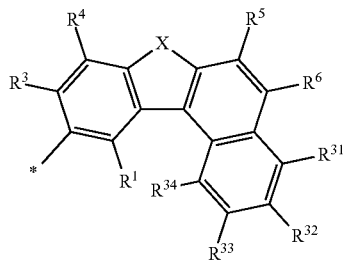
(41)
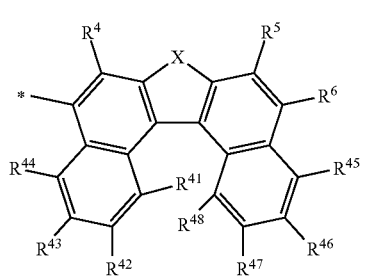
(42)
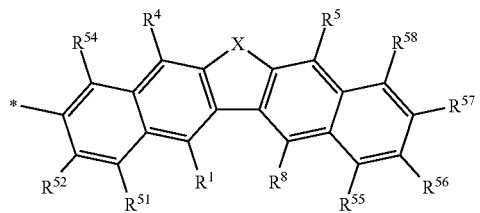
(43)

-continued
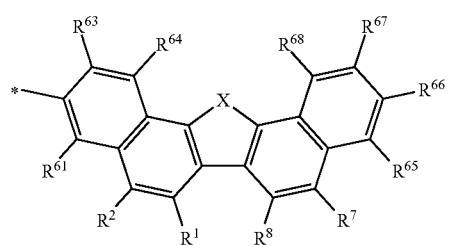
(44)
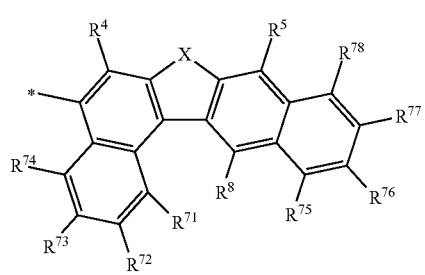
(45)
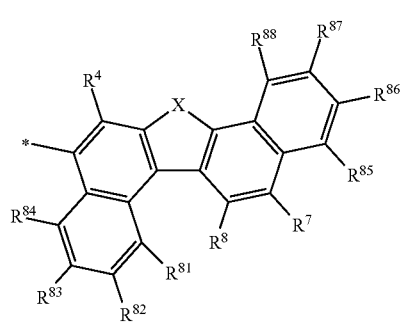
(46)
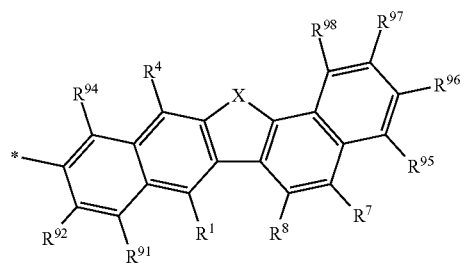
(47)
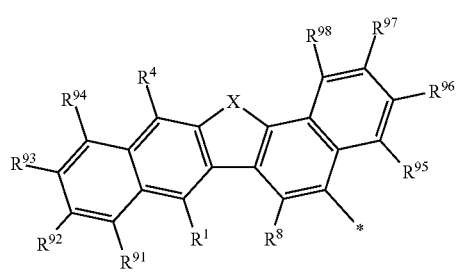
(48)
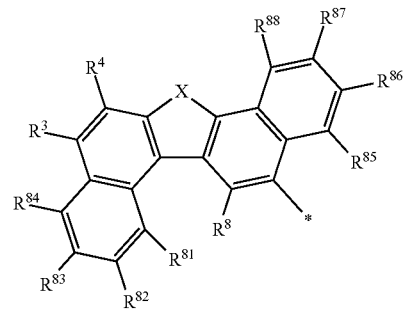
(49)
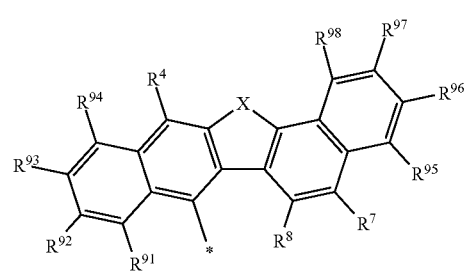
(50)
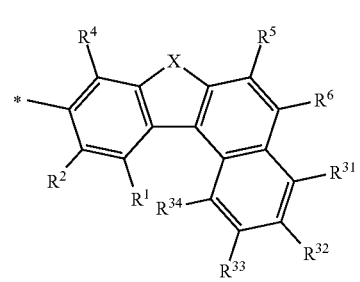
(51)
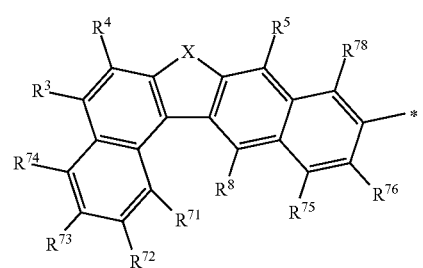
(52)
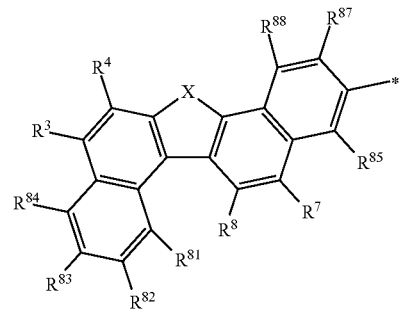
(53)

-continued

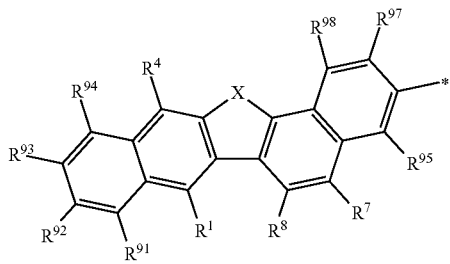

(54)

In formulae (20) to (54), X, $R^1$ to $R^8$, $R^{11}$ to $R^{14}$, $R^{21}$ to $R^{24}$, $R^{31}$ to $R^{34}$, $R^{41}$ to $R^{48}$, $R^{51}$ to $R^{58}$, $R^{61}$ to $R^{68}$, $R^{71}$ to $R^{78}$, $R^{81}$ to $R^{88}$, and $R^{91}$ to $R^{98}$ are as defined above, and the character * represents a single bond bonded to the group A.

A is a group represented by formula (4). When n is two or more, two or more groups A may be the same or different.

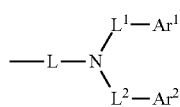

(4)

In formula (4), each of $Ar^1$ and $Ar^2$ independently represents a substituted or unsubstituted aryl group having 6 to 30 ring carbon atoms or a substituted or unsubstituted heterocyclic group having 5 to 30 ring atoms.

Each of L, $L^1$ and $L^2$ independently represents a single bond, an arylene group having 6 to 30 ring carbon atoms, a heteroarylene group having 5 to 30 ring atoms, or a divalent linking group formed by bonding 2 to 4 groups selected from the arylene groups and the heteroarylene groups, preferably a single bond or the arylene group having 6 to 30 ring carbon atoms, and particularly preferably a single bond. When both of $Ar^1$ and $Ar^2$ represent the substituted or unsubstituted aryl groups having 6 to 30 ring carbon atoms, L represents a single bond.

Examples of the aryl group having 6 to 30, preferably 6 to 24, more preferably 6 to 18 ring carbon atoms include a phenyl group, a naphthylphenyl group, a biphenylyl group, a terphenylyl group, a naphthyl group, an acenaphthylenyl group, an anthryl group, a benzanthryl group, an aceanthryl group, a phenanthryl group, a benzo[c]phenanthryl group, a phenalenyl group, a fluorenyl group, a 9,9-dimethylfluorenyl group, a picenyl group, a pentaphenyl group, a pyrenyl group, a chrysenyl group, a benzo[g]chrysenyl group, a s-indacenyl group, an as-indacenyl group, a fluoranthenyl group, a benzo[k]fluoranthenyl group, a triphenylenyl group, a benzo[b]triphenylenyl group, and a perylenyl group, with a phenyl group, a biphenylyl group, a terphenylyl group, a naphthyl group, a phenanthryl group, and a fluorenyl group being preferred.

The optional substituent of the aryl group is selected from a fluorine atom, a cyano group, a substituted or unsubstituted alkyl group having 1 to 20 carbon atoms, a substituted or unsubstituted cycloalkyl group having 3 to 20 ring carbon atoms, a substituted or unsubstituted aryl group having 6 to 30 ring carbon atoms, a substituted or unsubstituted alkoxy group having 1 to 20 carbon atoms, a substituted or unsubstituted aryloxy group having 6 to 30 ring carbon atoms, a substituted or unsubstituted alkylthio group having 1 to 20 carbon atoms, a substituted or unsubstituted arylthio group having 6 to 30 ring carbon atoms, a substituted or unsubstituted alkylsilyl group having 3 to 50 carbon atoms, a substituted or unsubstituted arylsilyl group having 6 to 50 ring carbon atoms, and a substituted or unsubstituted heterocyclic group having 5 to 30 ring atoms, and preferably selected from an alkyl group having 1 to 20, preferably 1 to 10, more preferably 1 to 5 carbon atoms, a cycloalkyl group having 3 to 20, preferably 3 to 6, more preferably 5 or 6 ring carbon atoms, a mono-, di- or trialkylsilyl group having an alkyl group having 1 to 20, preferably 1 to 10, more preferably 1 to 5 carbon atoms, a fluorine atom, and a cyano group. An alkyl group having 1 to 20 is particularly preferred.

Examples of a preferred substituted aryl group include a phenyl group, a biphenylyl group, a terphenylyl group, a naphthyl group, a phenanthryl group, and a fluorenyl group, each substituted by the substituent mentioned above.

The heterocyclic group having 5 to 30, preferably 6 to 24, more preferably 6 to 18 ring atoms comprises at least one, preferably 1 to 5 hetero atoms, such as a nitrogen atom, a sulfur atom and an oxygen atom. Examples of the heterocyclic group include a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, a tetrazolyl group, an indolyl group, an isoindolyl group, a benzofuranyl group, an isobenzofuranyl group, a benzothiophenyl group, an isobenzothiophenyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a dibenzothiophenyl group, a carbazolyl group, a phenanthridinyl group, an acridinyl group, a phenanthrolinyl group, a phenazinyl group, a phenothiazinyl group, a phenoxazinyl group, and a xanthenyl group, with a furyl group, a thienyl group, a pyridyl group, a pyridazinyl group, a pyrimidinyl group, a pyrazinyl group, a triazinyl group, a benzofuranyl group, a benzothiophenyl group, a dibenzofuranyl group, and a dibenzothiophenyl group being preferred, and a benzofuranyl group, a benzothiophenyl group, a dibenzofuranyl group, and a dibenzothiophenyl group being more preferred.

The optional substituent of the heterocyclic group is selected from a fluorine atom, a cyano group, a substituted or unsubstituted alkyl group having 1 to 20 carbon atoms, a substituted or unsubstituted cycloalkyl group having 3 to 20 ring carbon atoms, a substituted or unsubstituted aryl group having 6 to 30 ring carbon atoms, a substituted or unsubstituted alkoxy group having 1 to 20 carbon atoms, a substituted or unsubstituted aryloxy group having 6 to 30 ring carbon atoms, a substituted or unsubstituted alkylthio group having 1 to 20 carbon atoms, a substituted or unsubstituted arylthio group having 6 to 30 ring carbon atoms, a substituted or unsubstituted alkylsilyl group having 3 to 50 carbon atoms, a substituted or unsubstituted arylsilyl group having 6 to 50 ring carbon atoms, and a substituted or unsubstituted heterocyclic group having 5 to 30 ring atoms, and preferably selected from an alkyl group having 1 to 20, preferably 1 to 10, more preferably 1 to 5 carbon atoms, a cycloalkyl group having 3 to 20, preferably 3 to 6, more preferably 5 or 6 ring carbon atoms, and an aryl group having 6 to 30, preferably 6 to 24, more preferably 6 to 18 ring carbon atoms.

Examples of a preferred substituted heterocyclic group include a furyl group, a thienyl group, a pyridyl group, a pyridazinyl group, a pyrimidinyl group, a pyrazinyl group, a triazinyl group, a benzofuranyl group, a benzothiophenyl group, a dibenzofuranyl group, and a dibenzothiophenyl group, each substituted by the substituent mentioned above.

The arylene group having 6 to 30 ring carbon atoms and the heteroarylene group having 5 to 30 ring atoms for L, $L^1$ and $L^2$ are divalent groups obtained by removing one hydrogen atom from the aryl group and the heterocyclic group, respectively, which are mentioned above with respect to $Ar^1$ and $Ar^2$. L preferably represents a single bond. Each of $L^1$ and $L^2$ preferably represents a single bond or the arylene group having 6 to 30 ring carbon atoms, more preferably a single bond, 1,2-phenylene group, 1,3-phenylene group, or 1,4-phenylene group. Still more preferably, both of $L^1$ and $L^2$ are single bonds.

The amino group represented by formula (4) is represented preferably by formula (5) or (6), and more preferably by formula (6).

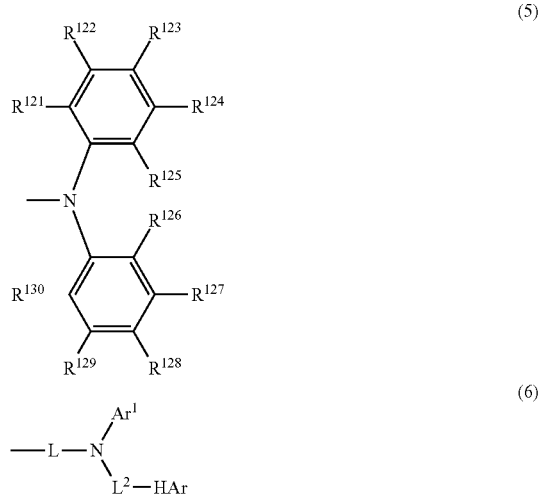

In formula (5), each of $R^{121}$ to $R^{130}$ independently represents a hydrogen atom, a fluorine atom, a cyano group, a substituted or unsubstituted alkyl group having 1 to 20 carbon atoms, a substituted or unsubstituted cycloalkyl group having 3 to 20 ring carbon atoms, a substituted or unsubstituted aryl group having 6 to 30 ring carbon atoms, a substituted or unsubstituted alkoxy group having 1 to 20 carbon atoms, a substituted or unsubstituted aryloxy group having 6 to 30 ring carbon atoms, a substituted or unsubstituted alkylthio group having 1 to 20 carbon atoms, a substituted or unsubstituted arylthio group having 6 to 30 ring carbon atoms, a substituted or unsubstituted alkylsilyl group having 3 to 50 carbon atoms, a substituted or unsubstituted arylsilyl group having 6 to 50 ring carbon atoms, or a substituted or unsubstituted heterocyclic group having 5 to 30 ring atoms, with a hydrogen atom, a fluorine atom, a cyano group, a substituted or unsubstituted alkyl group having 1 to 20 carbon atoms, a substituted or unsubstituted cycloalkyl group having 3 to 20 ring carbon atoms, and a substituted or unsubstituted aryl group having 6 to 30 ring carbon atoms being preferred. Examples and preferred examples of these groups are as described above with respect to the structure B and the optional groups of the aryl groups represented by $Ar^1$ and $Ar^2$.

In formula (6), each of L, $L^2$ and $Ar^1$ are as defined above. $Ar^1$ represents preferably a substituted or unsubstituted aryl group having 6 to 30 ring carbon atoms and more preferably a substituted or unsubstituted phenyl group, a substituted or unsubstituted biphenylyl group, a substituted or unsubstituted terphenylyl group, a substituted or unsubstituted naphthyl group, a substituted or unsubstituted phenanthryl group, or a substituted or unsubstituted fluorenyl group.

The optional substituent of the aryl group is selected from an alkyl group having 1 to 20, preferably 1 to 10, more preferably 1 to 5 carbon atoms, a cycloalkyl group having 3 to 20, preferably 3 to 6, and more preferably 5 or 6 ring carbon atoms, a mono-, di- or trialkylsilyl group having an alkyl group having 1 to 20, preferably 1 to 10, more preferably 1 to 5 carbon atoms, a fluorine atom, and a cyano group, with the alkyl group having 1 to 20 carbon atoms being preferred.

Examples of preferred substituted aryl groups include a phenyl group, a biphenylyl group, a terphenylyl group, a naphthyl group, a phenanthryl group, and a fluorenyl group, each being substituted with the above substituent.

In formula (6), HAr represents a structure represented by formula (7):

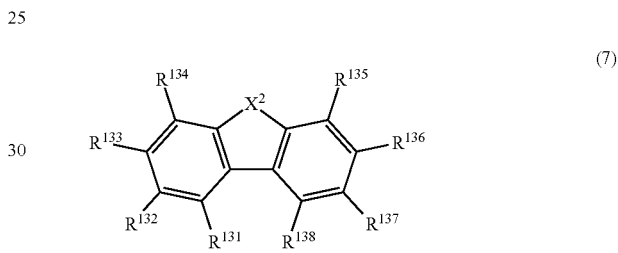

In formula (7), $X^2$ represents an oxygen atom or a sulfur atom, preferably an oxygen atom.

One of $R^{131}$ to $R^{138}$, preferably one of $R^{132}$, $R^{134}$, $R^{135}$ and $R^{137}$, and more preferably one of $R^{134}$ and $R^{135}$ represents a single bond bonded to $L^2$.

The others of $R^{131}$ to $R^{138}$ each independently represent a hydrogen atom, a fluorine atom, a cyano group, a substituted or unsubstituted alkyl group having 1 to 20 carbon atoms, a substituted or unsubstituted cycloalkyl group having 3 to 20 ring carbon atoms, a substituted or unsubstituted aryl group having 6 to 30 ring carbon atoms, a substituted or unsubstituted alkoxy group having 1 to 20 carbon atoms, a substituted or unsubstituted aryloxy group having 6 to 30 ring carbon atoms, a substituted or unsubstituted alkylthio group having 1 to 20 carbon atoms, a substituted or unsubstituted arylthio group having 6 to 30 ring carbon atoms, a substituted or unsubstituted alkylsilyl group having 3 to 50 carbon atoms, a substituted or unsubstituted arylsilyl group having 6 to 50 ring carbon atoms, or a substituted or unsubstituted heterocyclic group having 5 to 30 ring atoms. Examples and preferred examples of these groups are as described above with respect to the structure B and the optional group of the heterocyclic group represented by $Ar^1$ and $Ar^2$.

$R^{131}$ to $R^{138}$ other than a single bond bonded to $L^2$ are preferably selected from a hydrogen atom, an alkyl group having 1 to 20, preferably 1 to 10, more preferably 1 to 5 carbon atoms, a cycloalkyl group having 3 to 20, preferably 3 to 6, more preferably 5 or 6 ring carbon atoms, and an aryl group having 6 to 30, preferably 6 to 24, more preferably 6 to 18 ring carbon atoms. More preferably, one of $R^{134}$ and $R^{135}$ represents a single bond bonded to $L^2$ and the other of $R^{134}$ and $R^{135}$, and $R^{131}$ to $R^{133}$, $R^{136}$ and $R^{138}$ are selected from a hydrogen atom, the alkyl group having 1 to 20 carbon atoms, the cycloalkyl group having 3 to 20 ring carbon atoms, and the aryl group having 6 to 30 ring carbon atoms.
Examples of the amine compound represented by formula (1) are described below, although not limited to the following compounds.
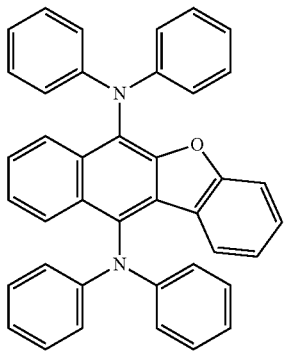
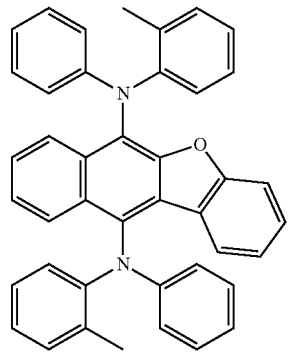
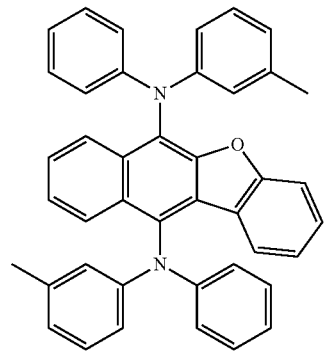
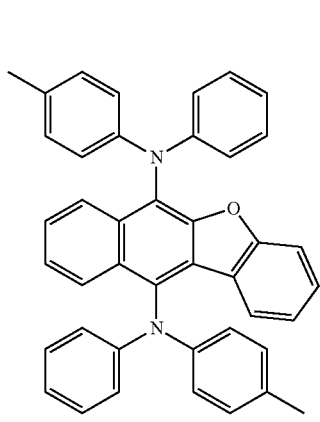
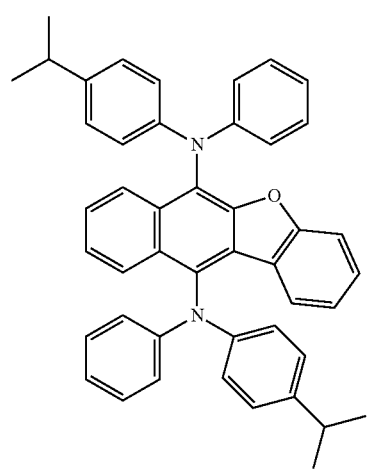
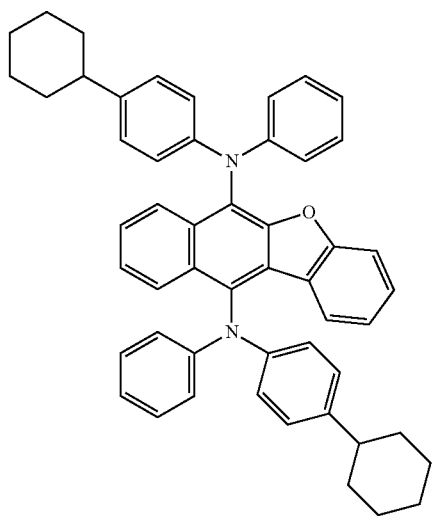
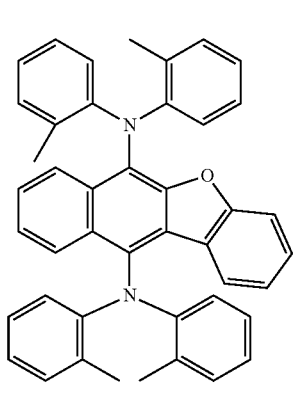
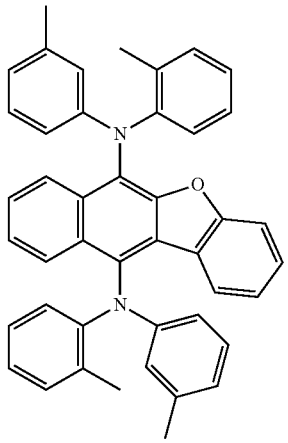
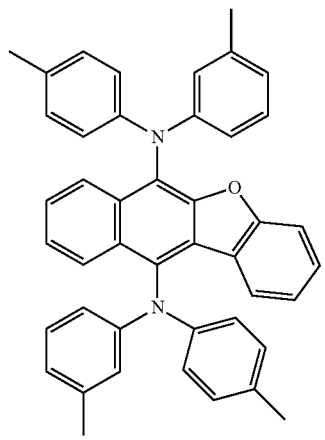

-continued
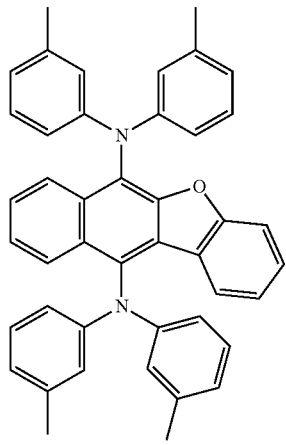 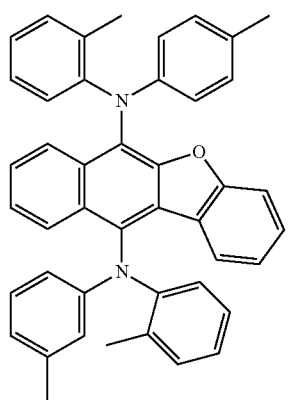 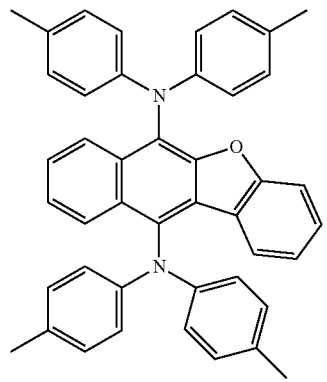
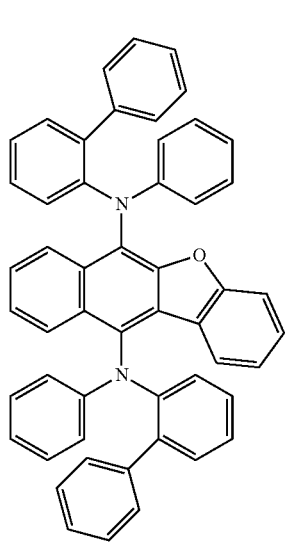 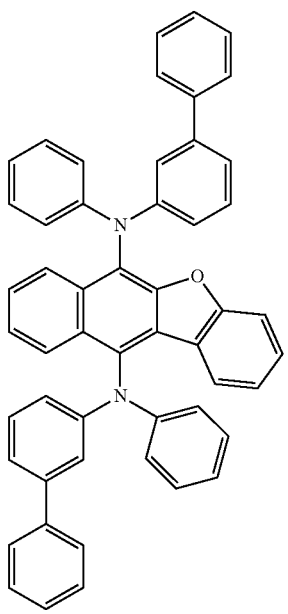 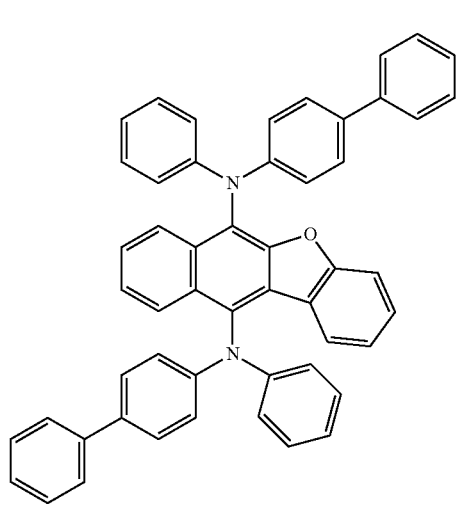
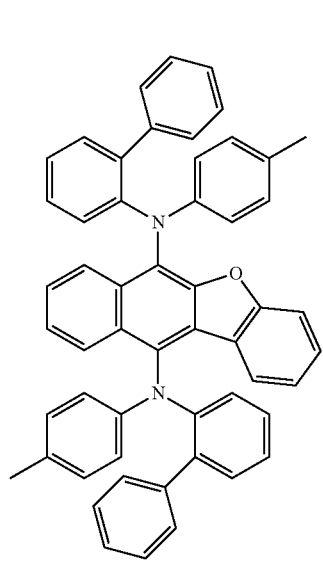 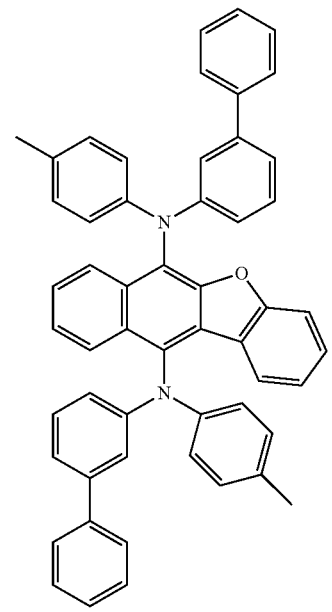 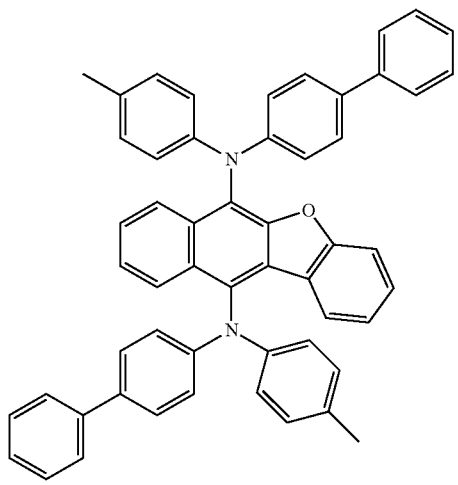

-continued
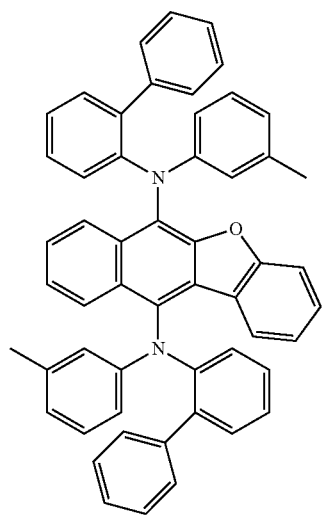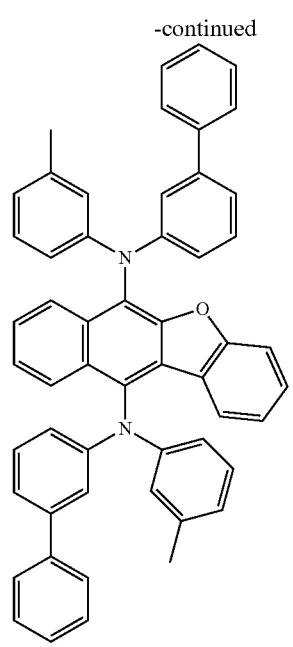
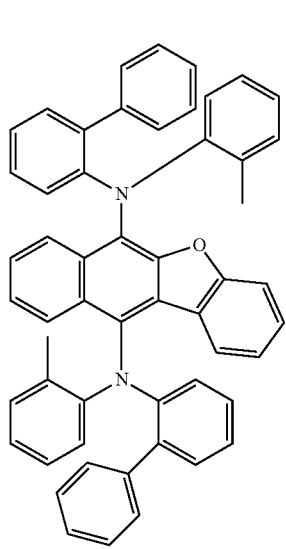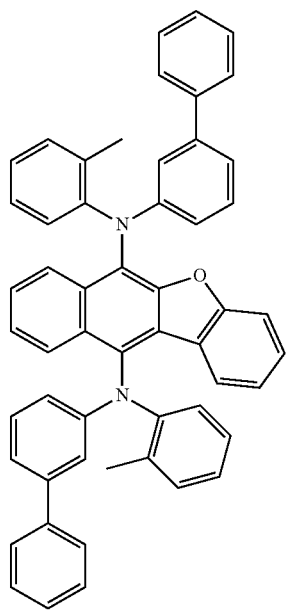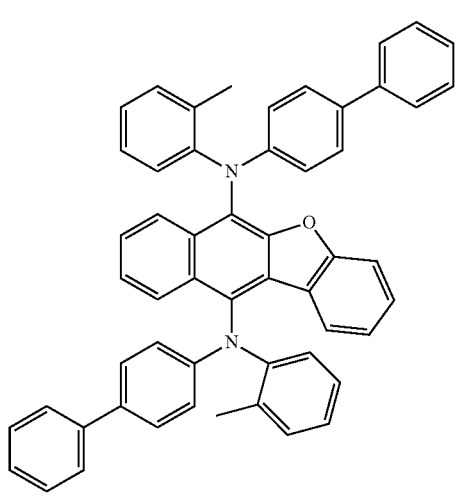

-continued
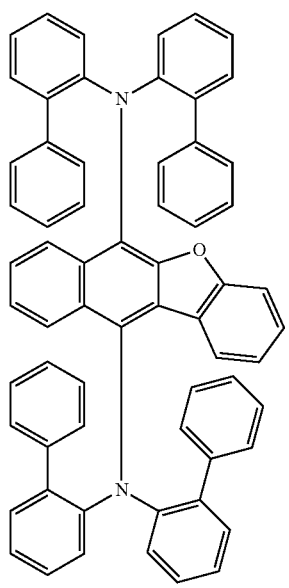
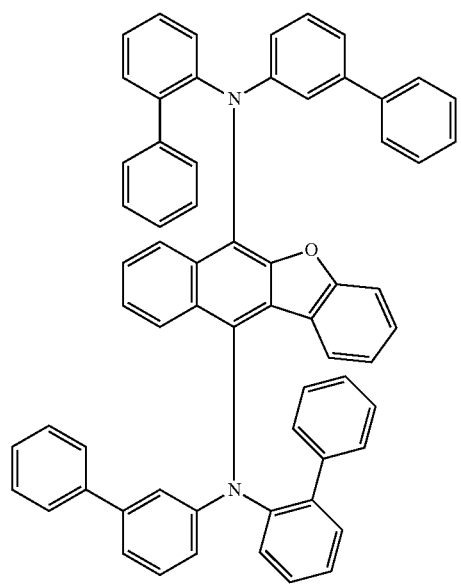
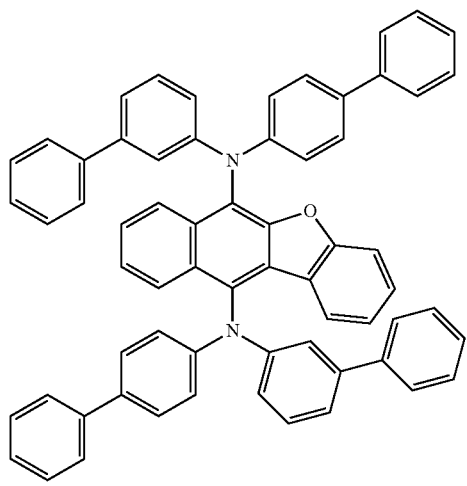
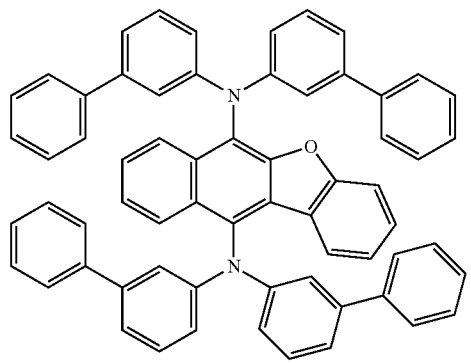
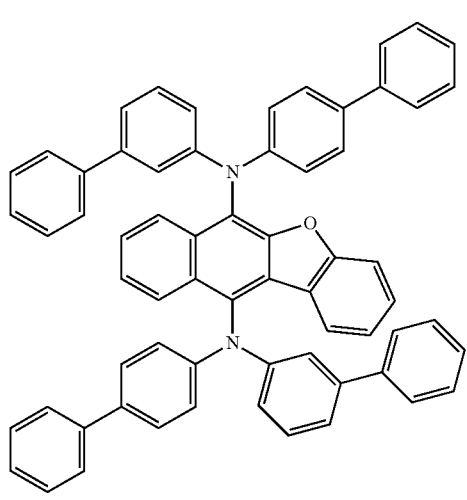
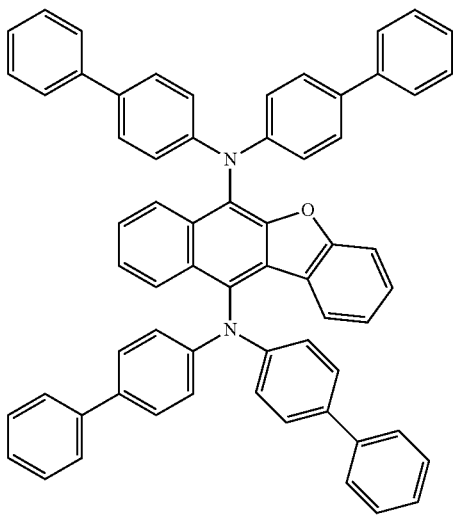

27  -continued  28
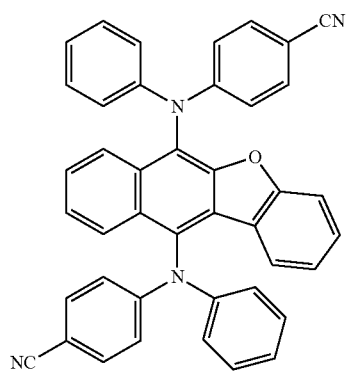
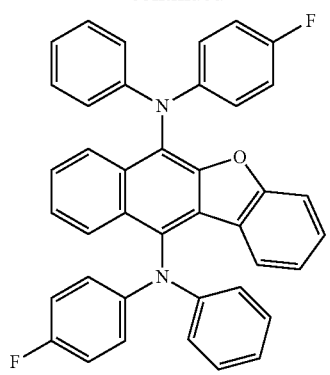
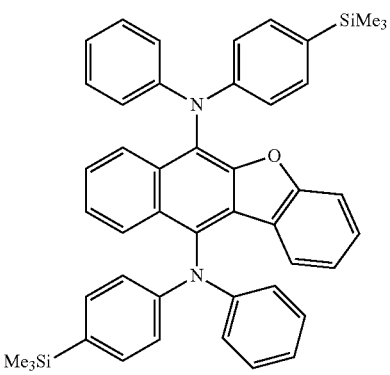
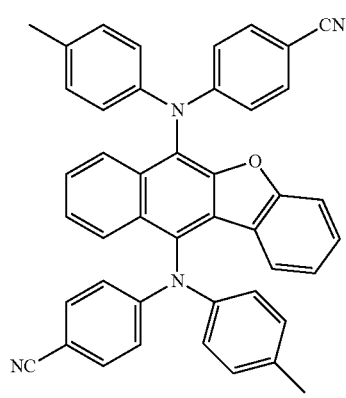
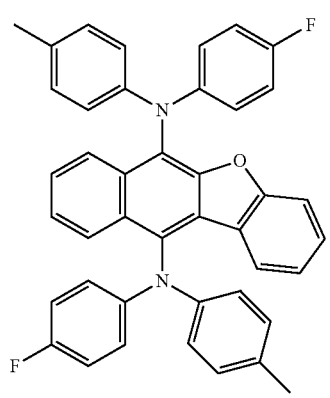
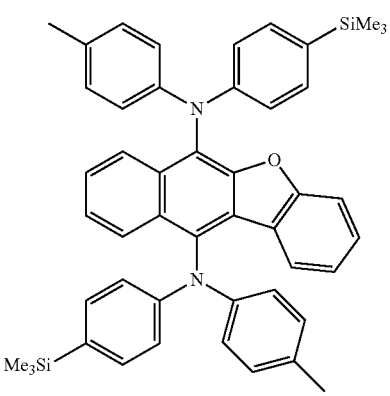
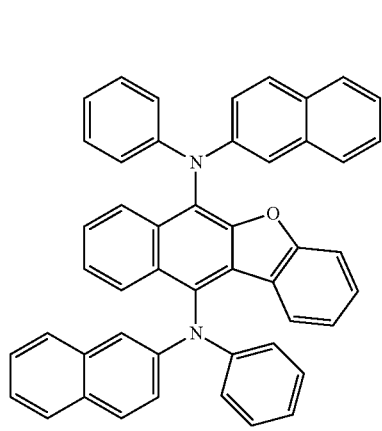
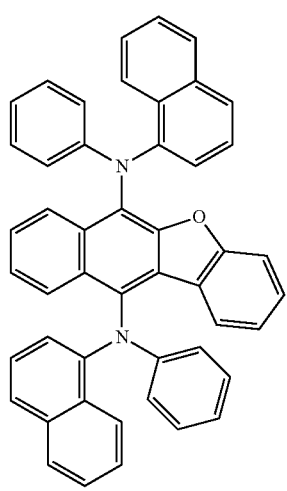
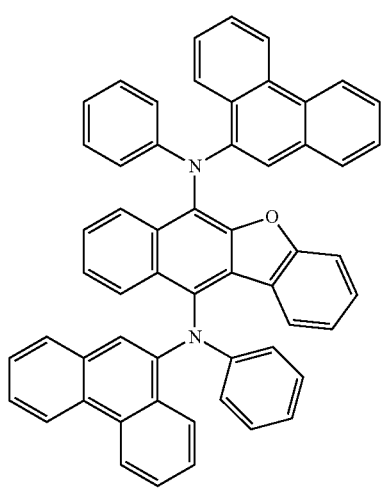

-continued
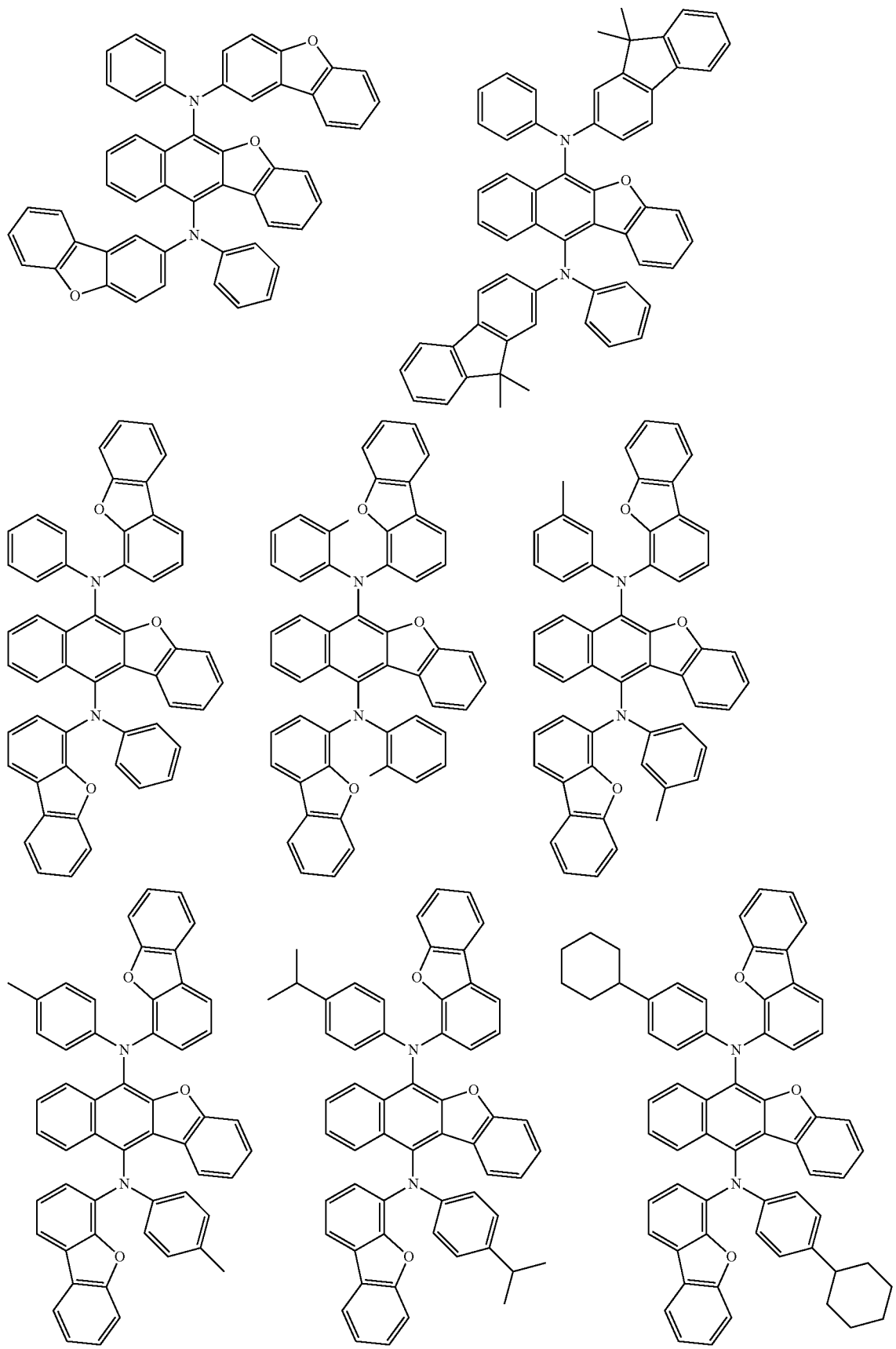

-continued
31
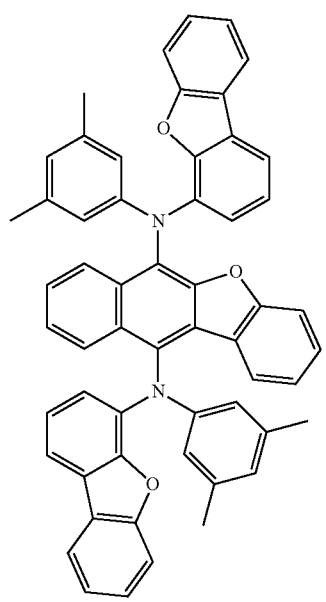
32
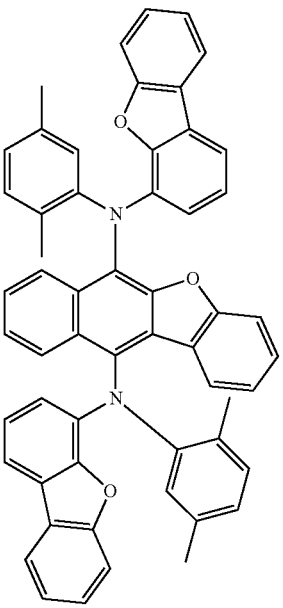
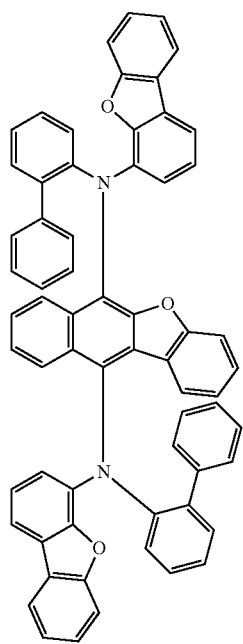
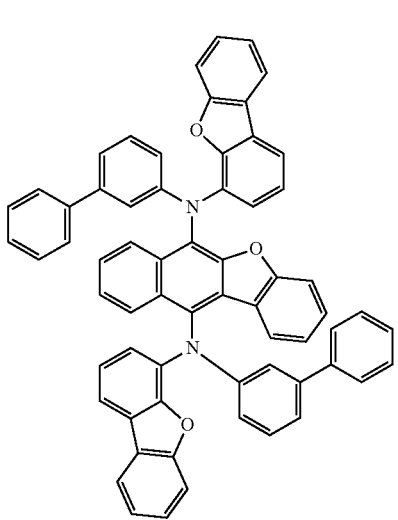

33 -continued 34
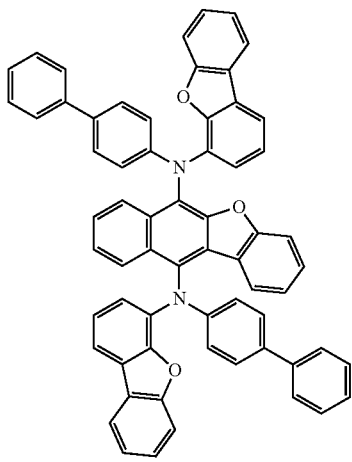
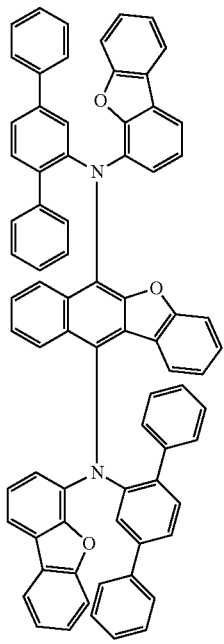
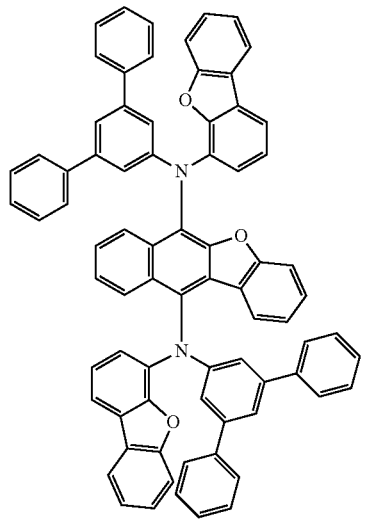
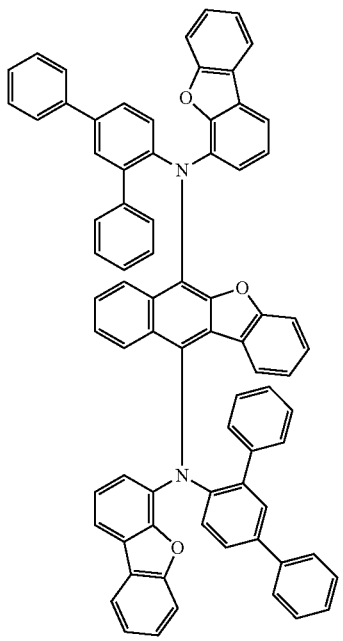
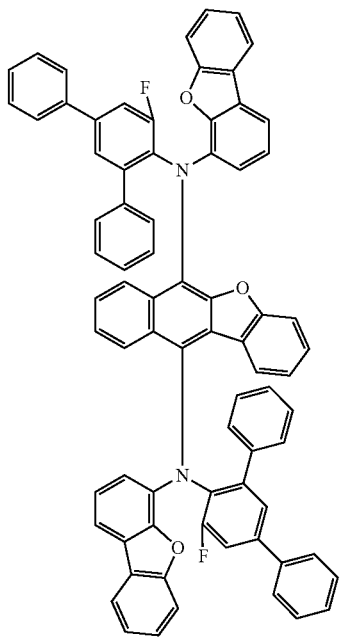
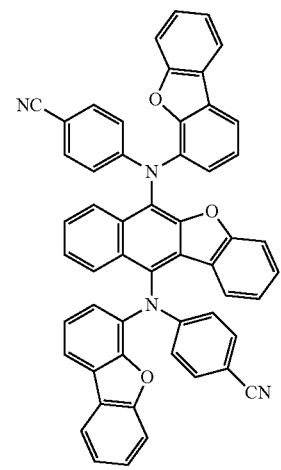

-continued
35
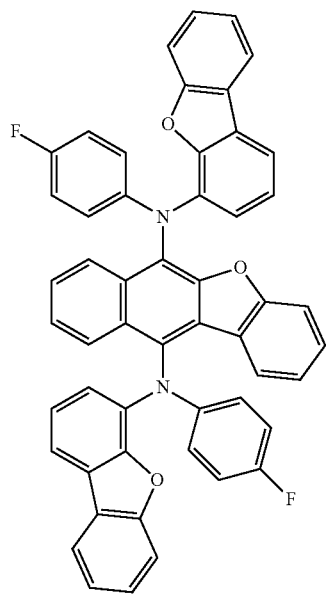 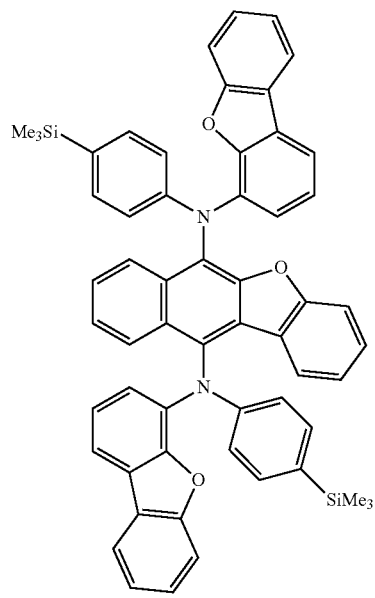
36
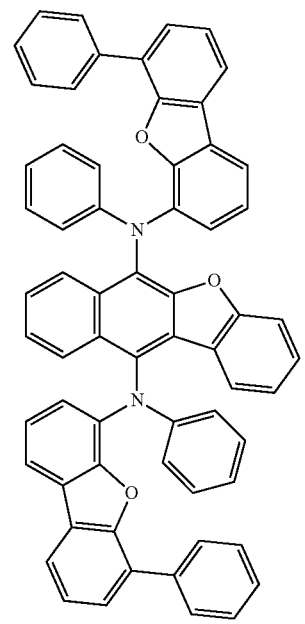
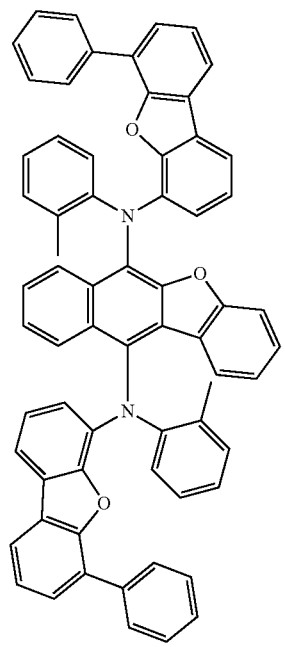 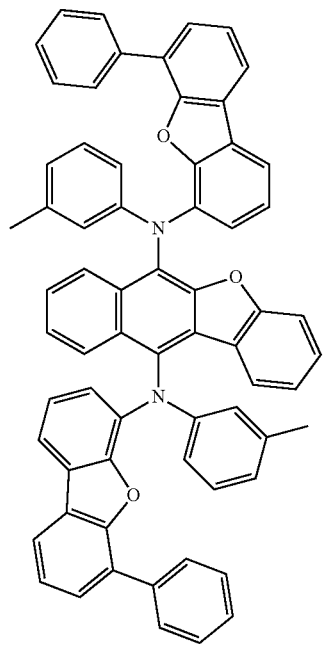 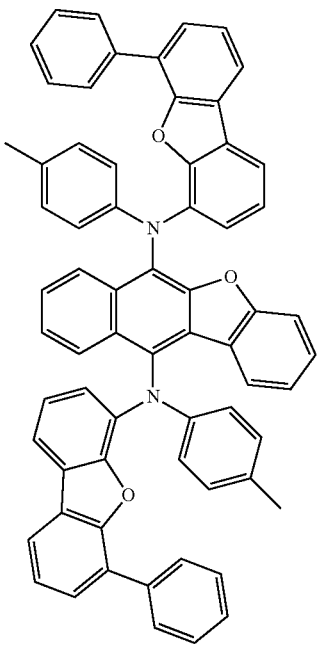

37
-continued
38
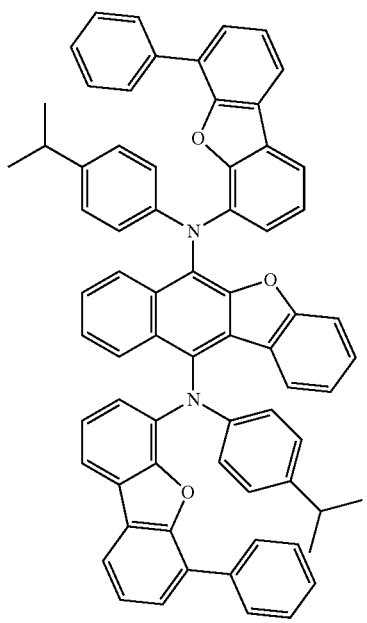 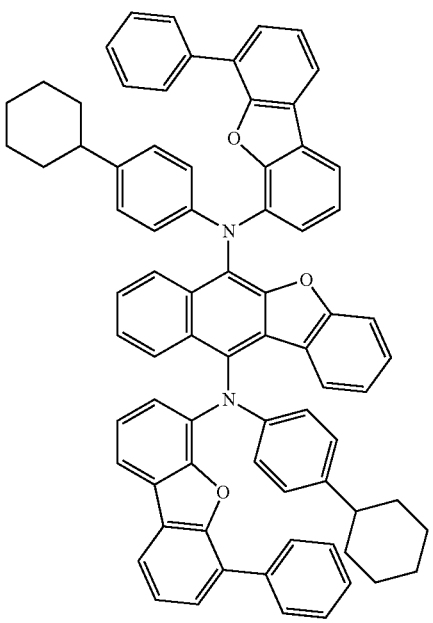 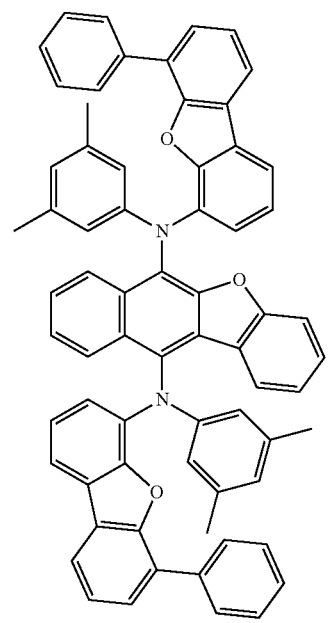
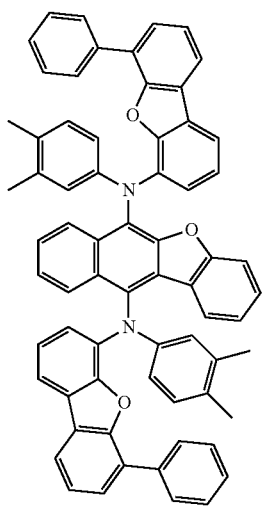 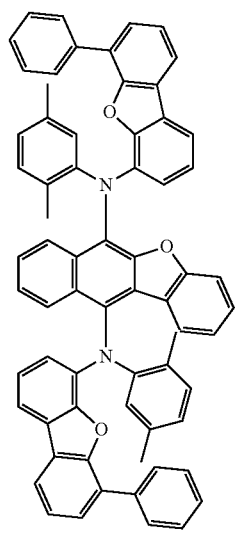 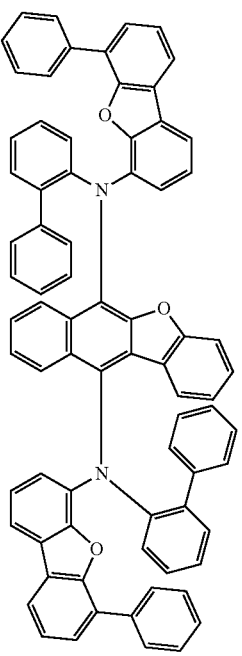

-continued
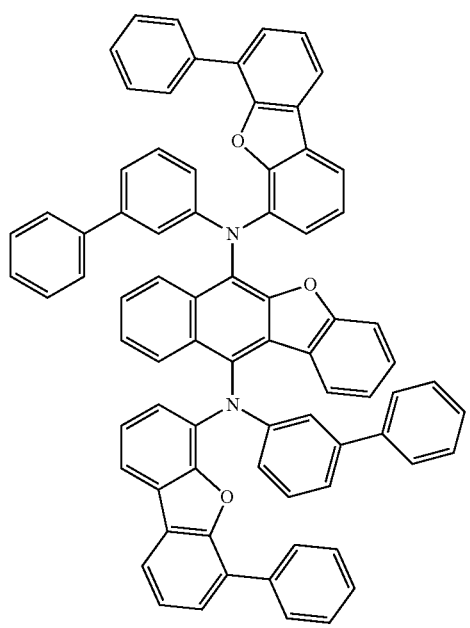
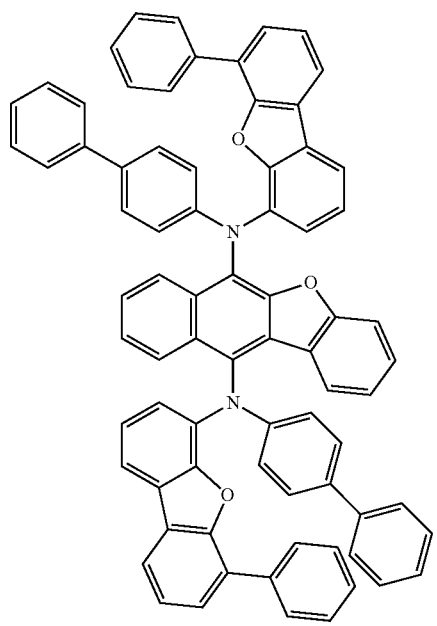
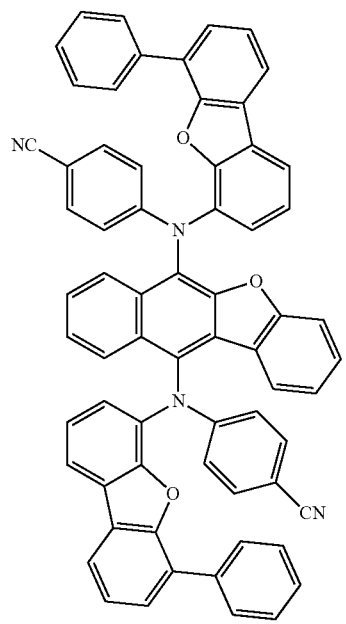
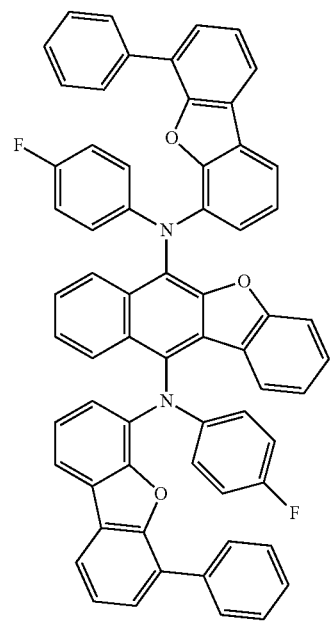
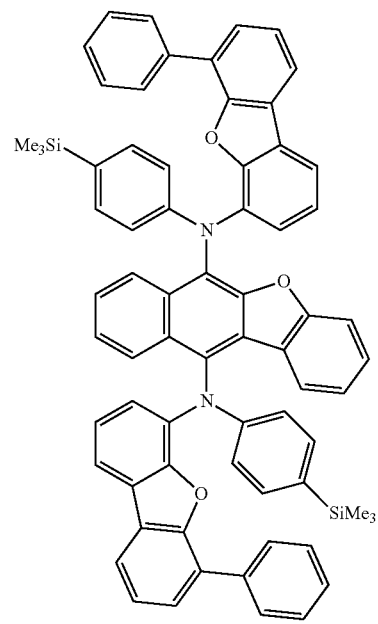

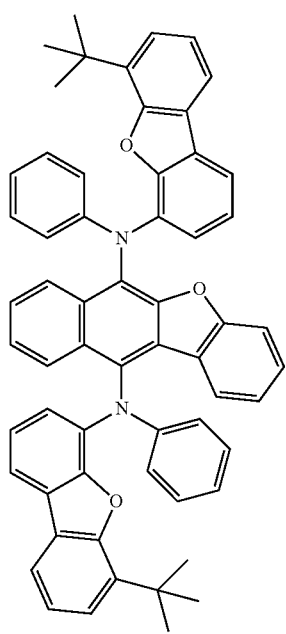 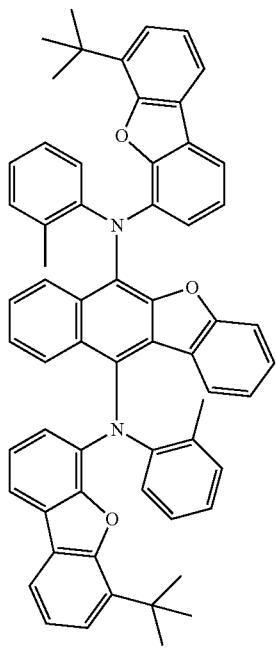 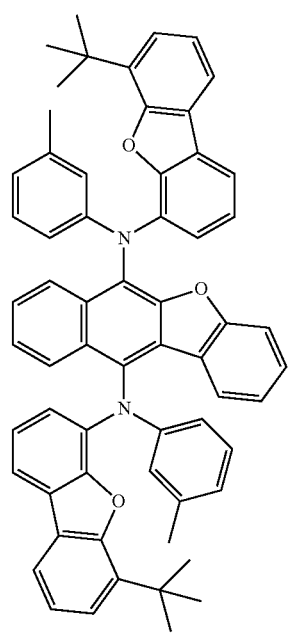
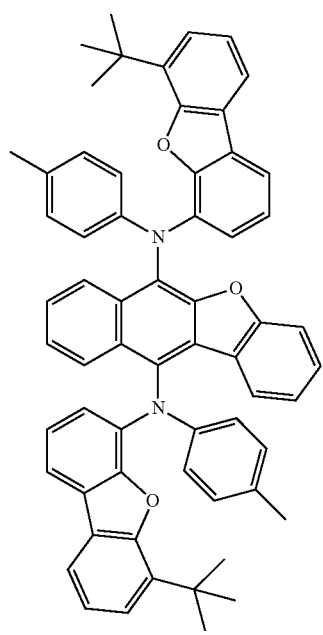 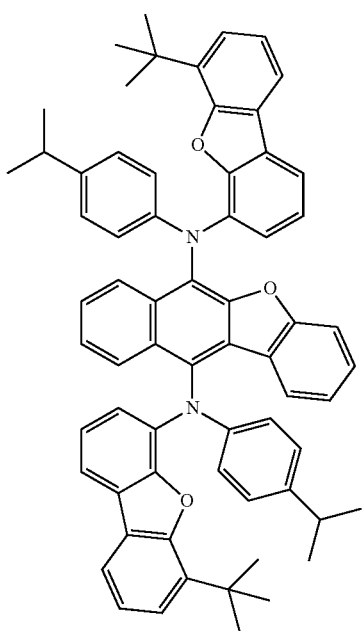 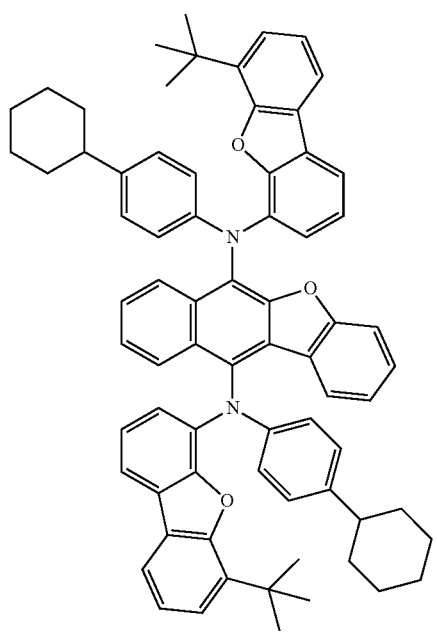

-continued
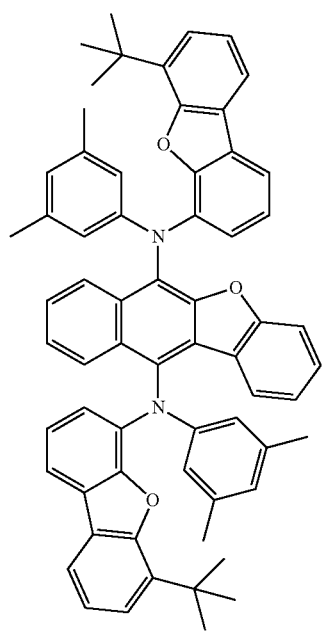
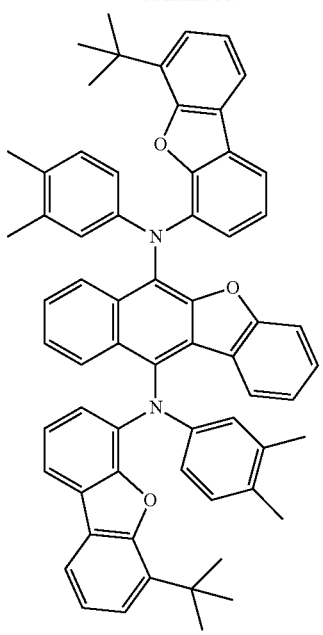
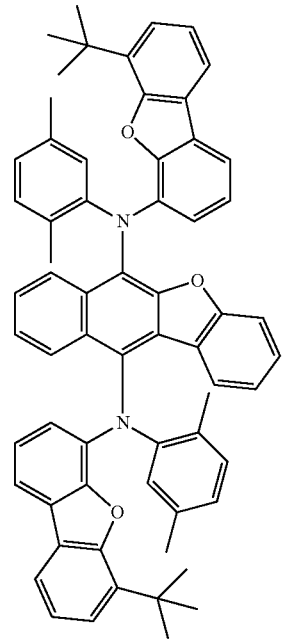
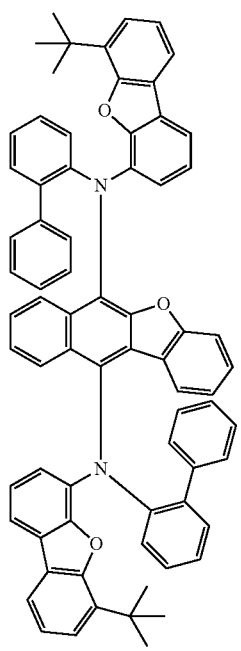
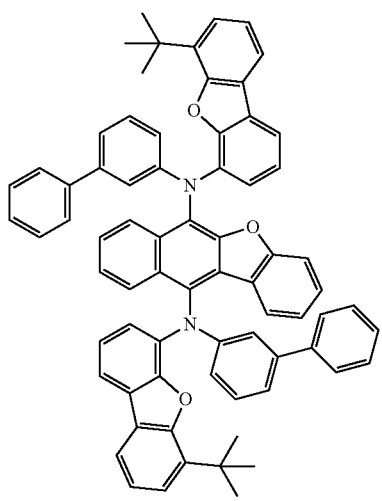

45
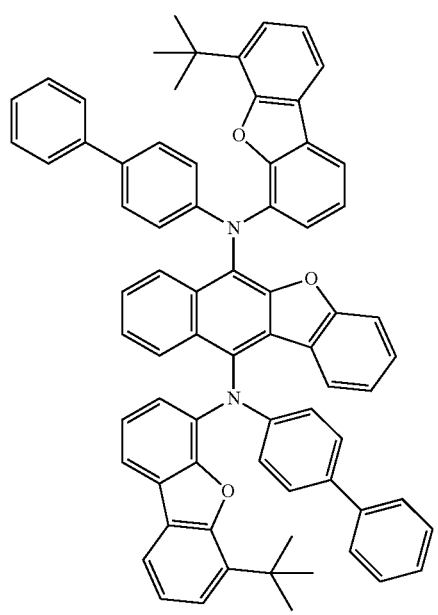
-continued
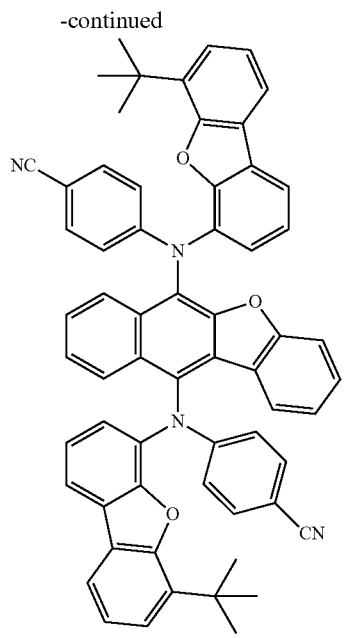
46
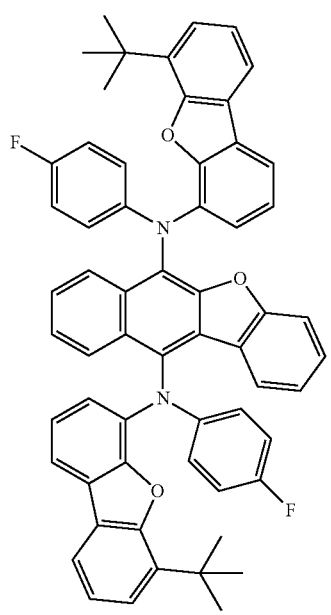
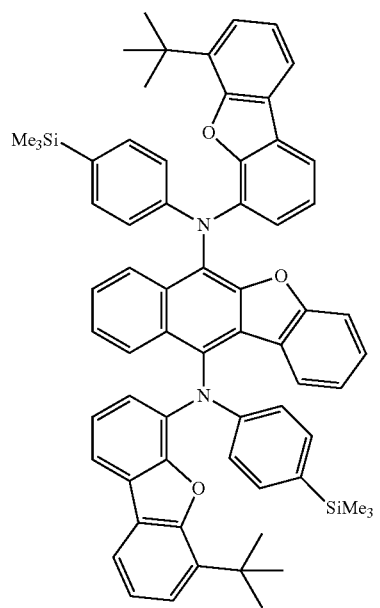
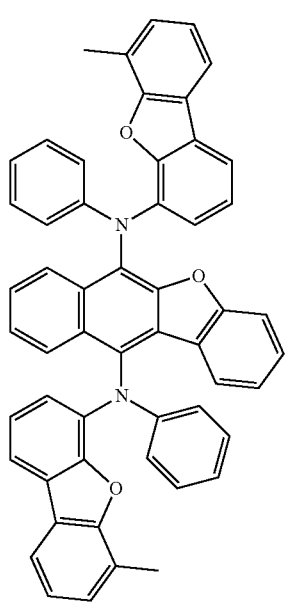
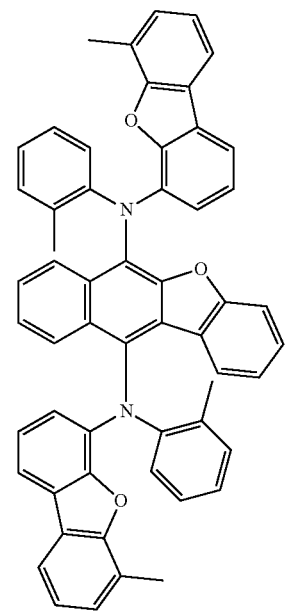

47
-continued
48
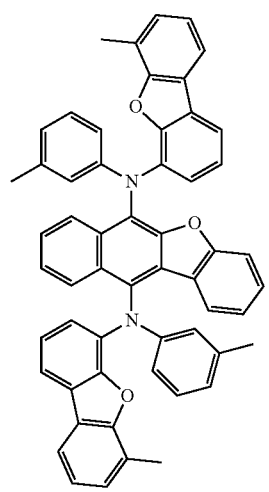
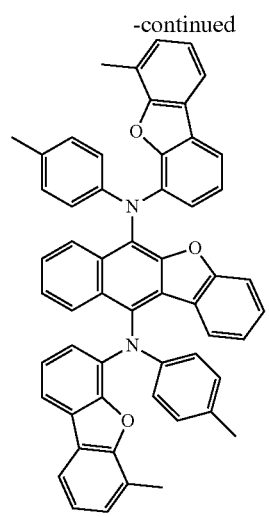
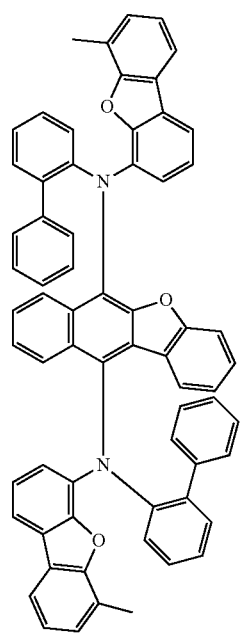
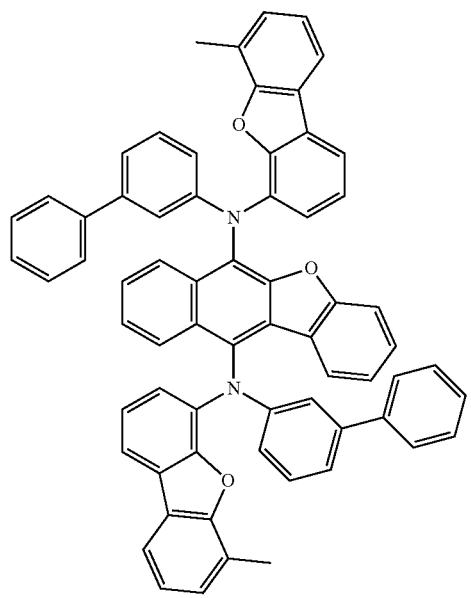
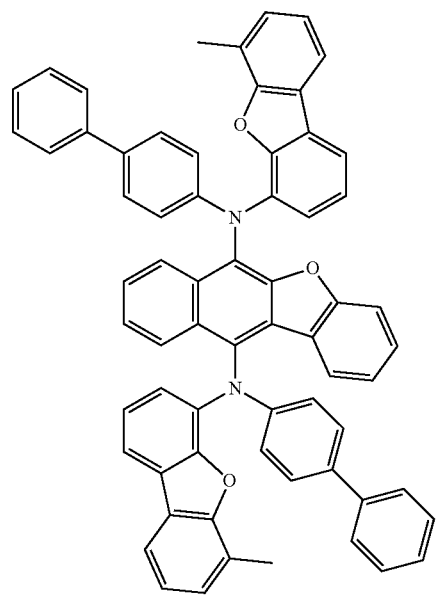

49
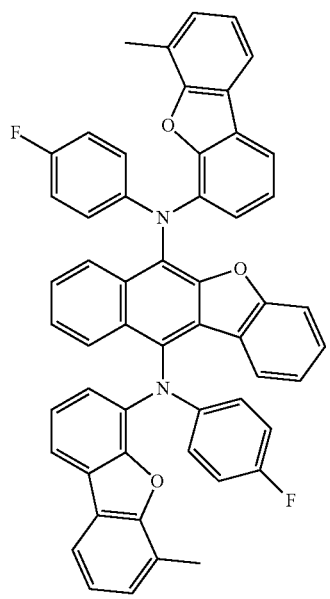
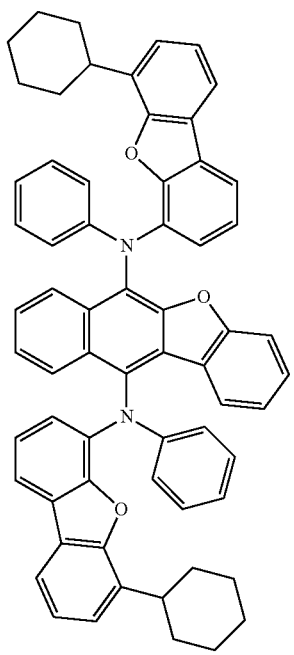
50
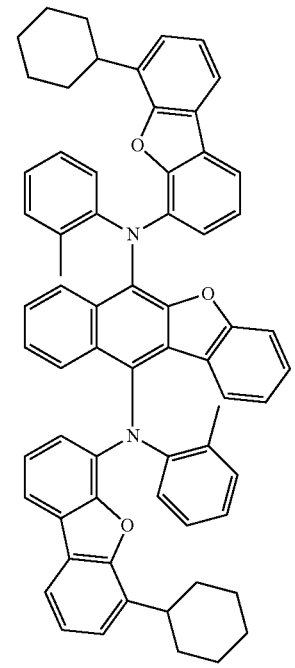
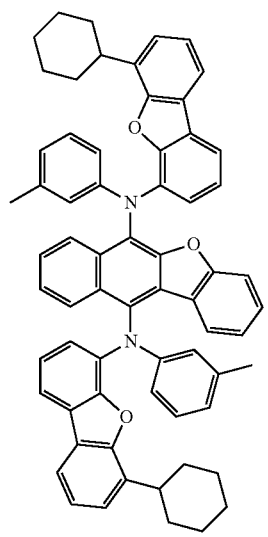
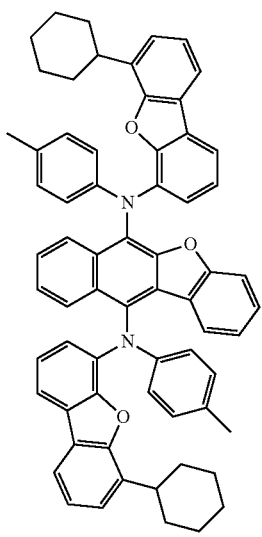
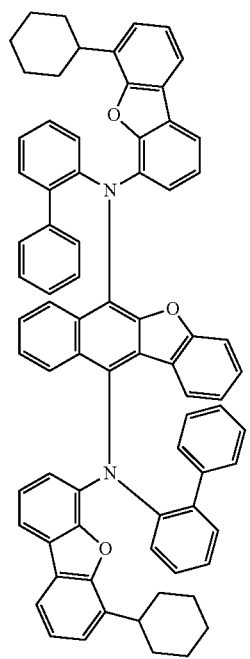

-continued
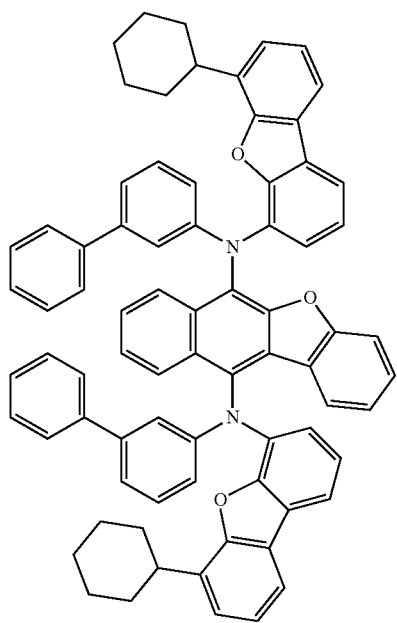
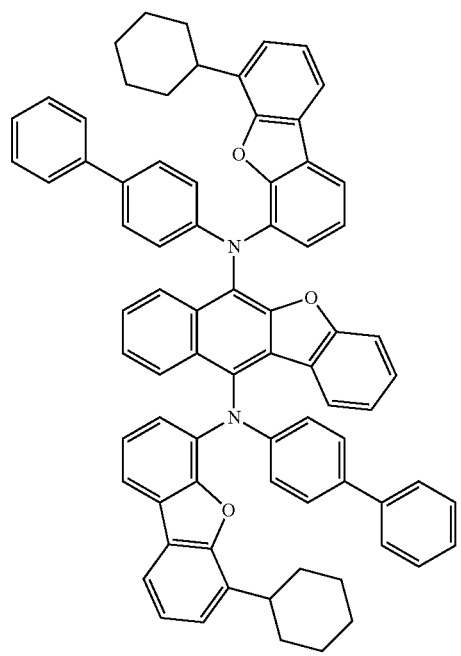
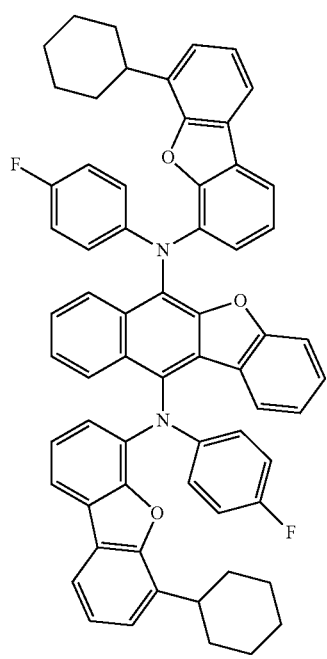
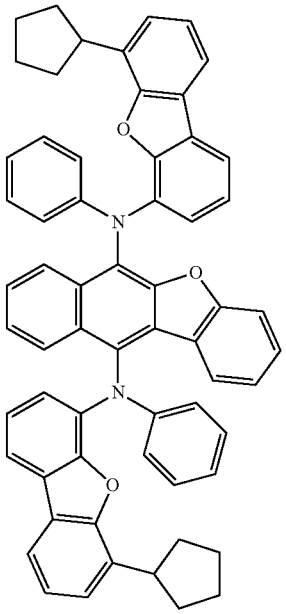
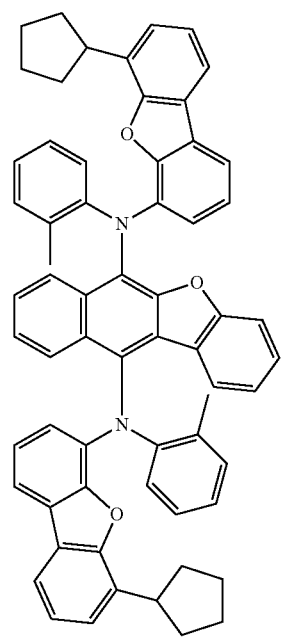

53
-continued
54
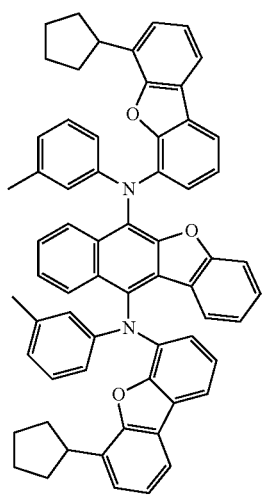
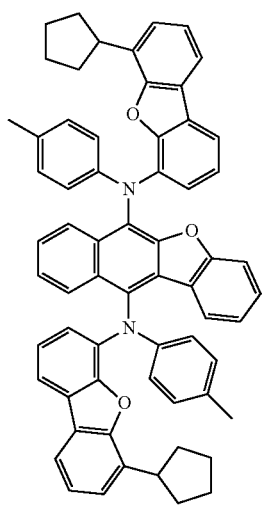
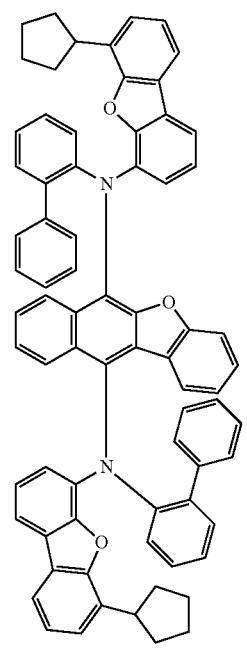
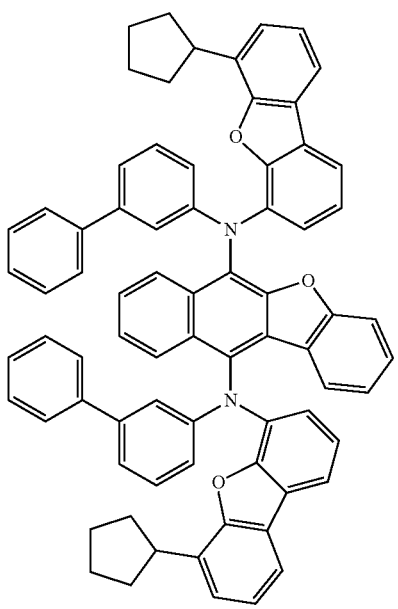
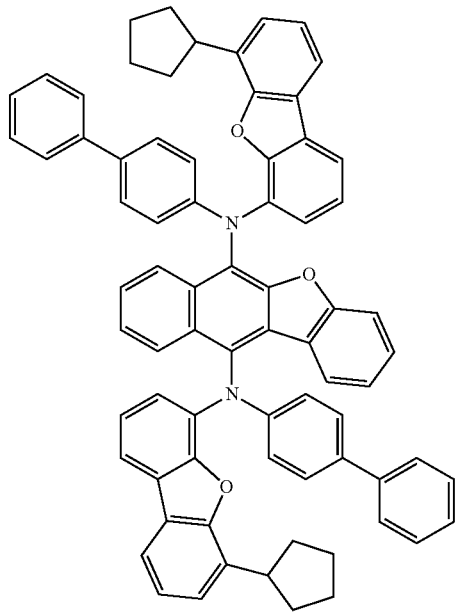

55
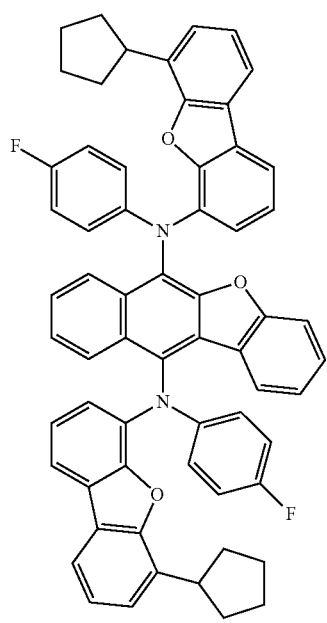
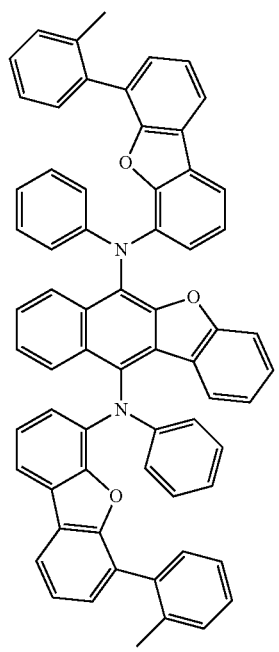
-continued
56
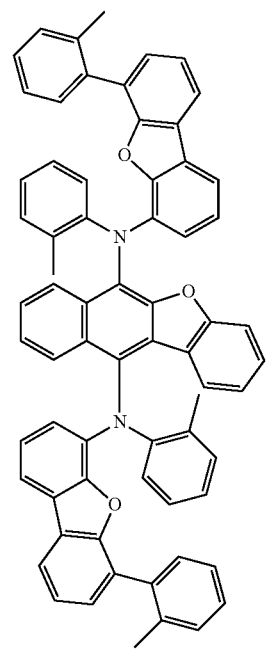
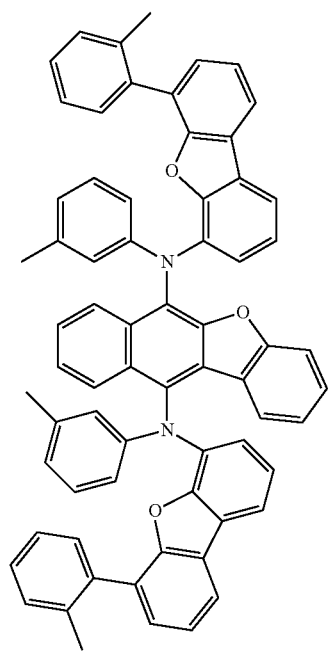
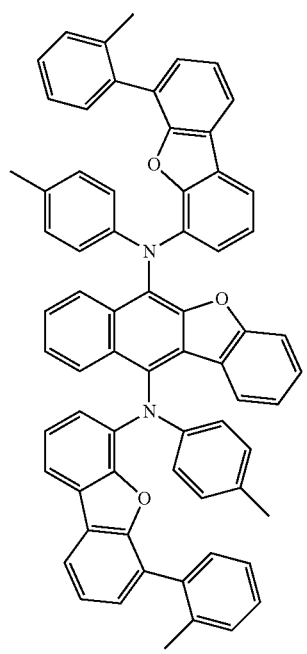
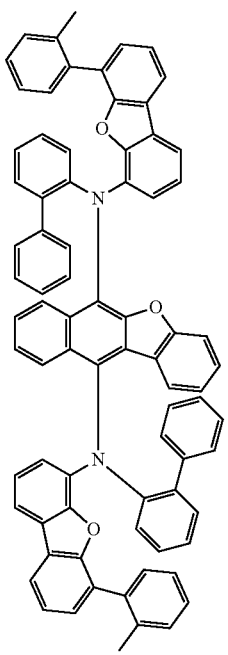

57
58
-continued
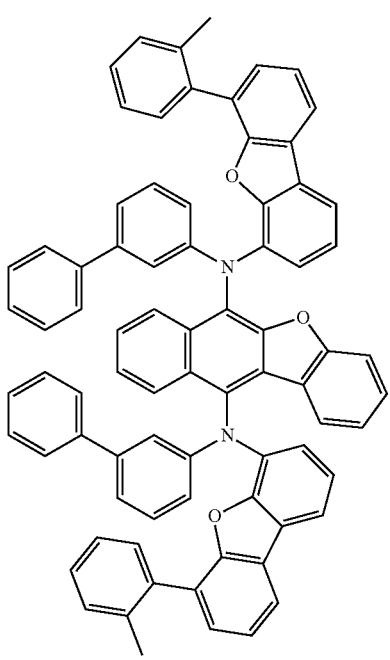
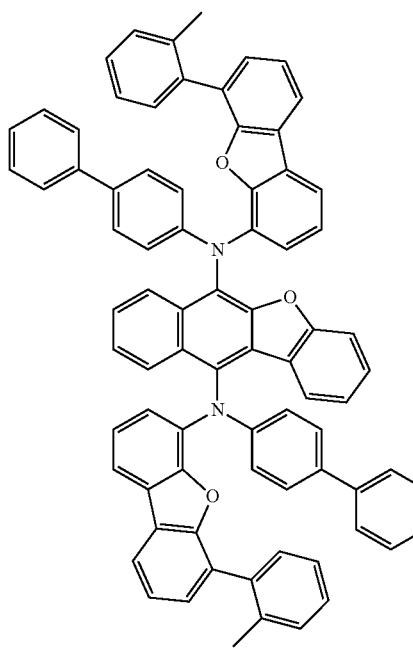
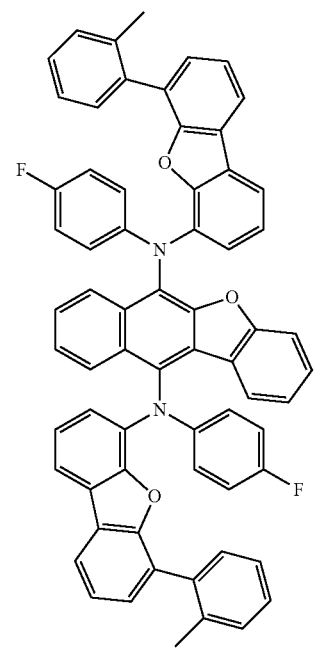
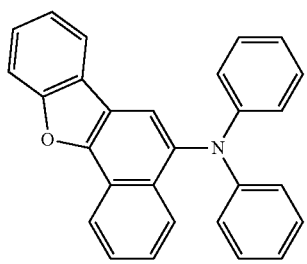
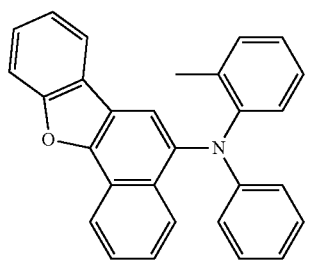
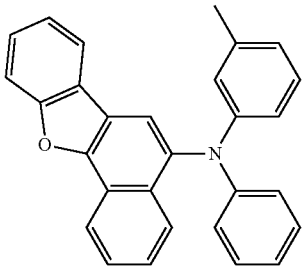
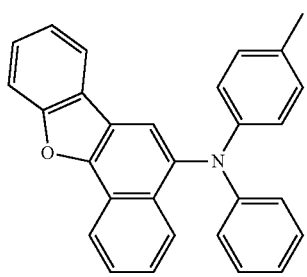
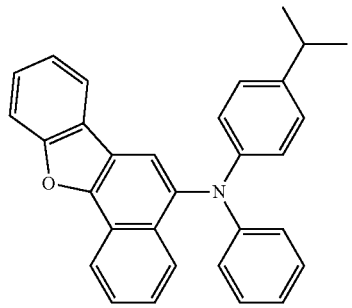
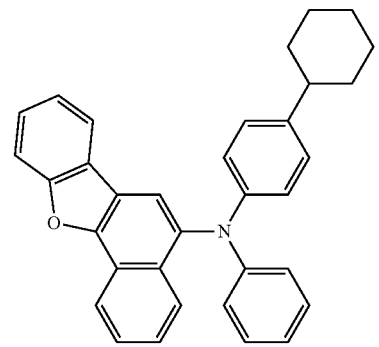
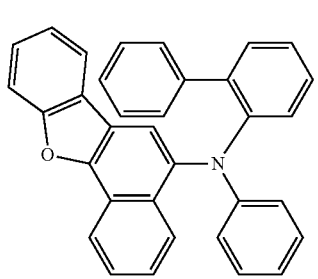
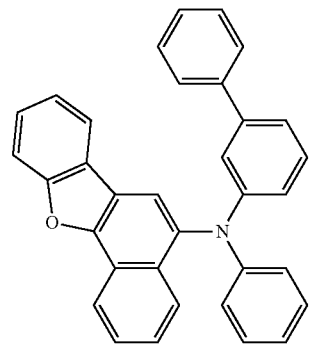
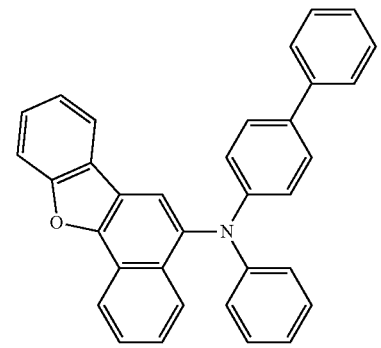

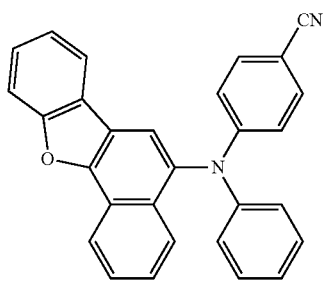
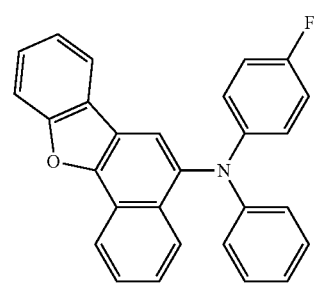
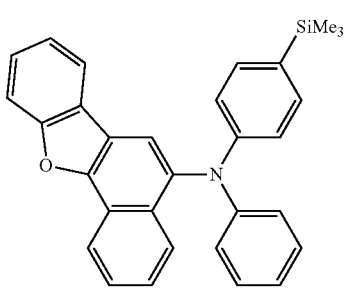
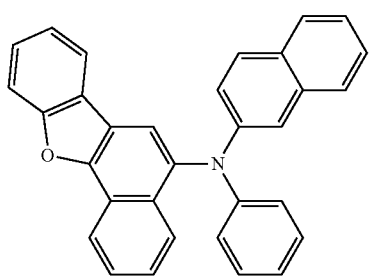
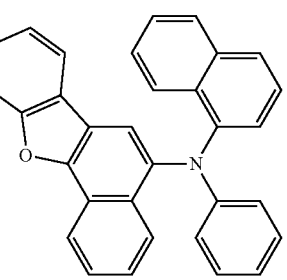
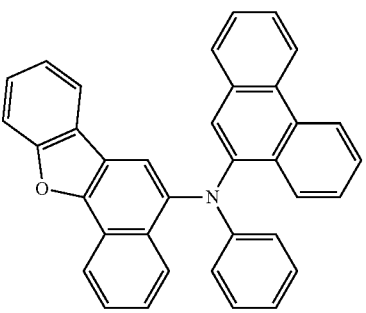
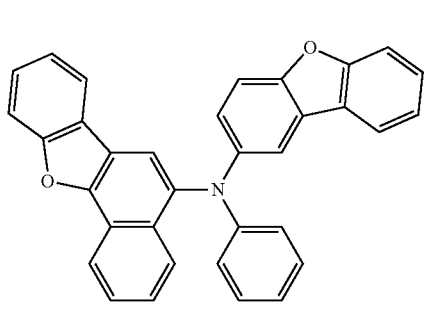
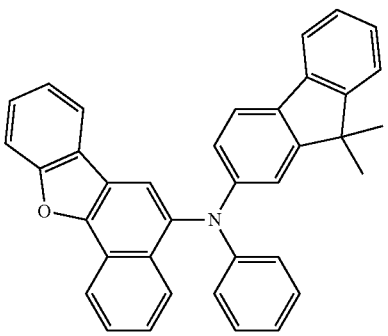
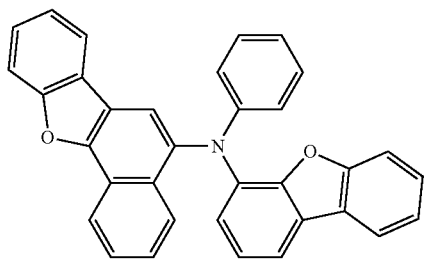
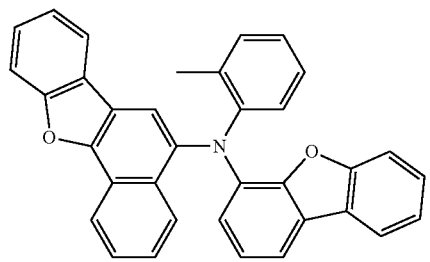
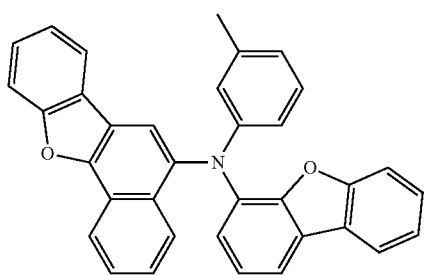
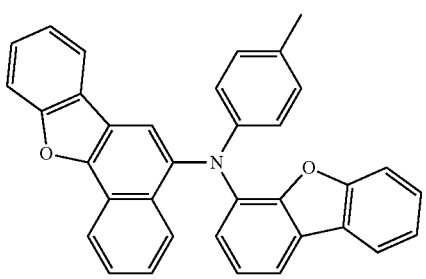

-continued
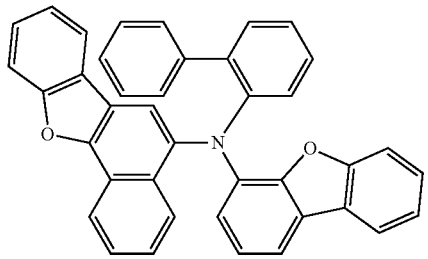
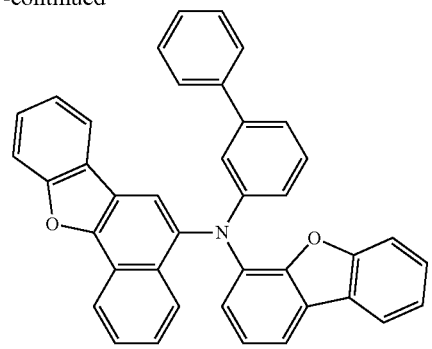
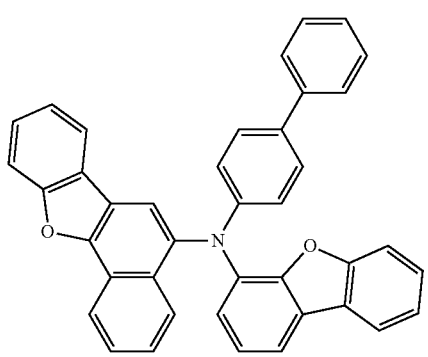
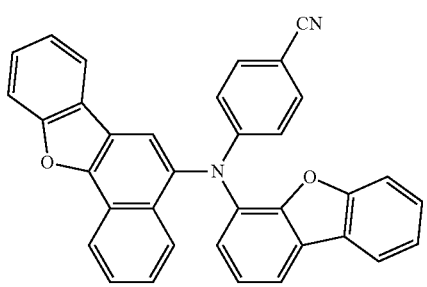
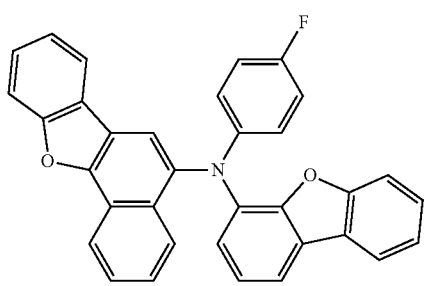
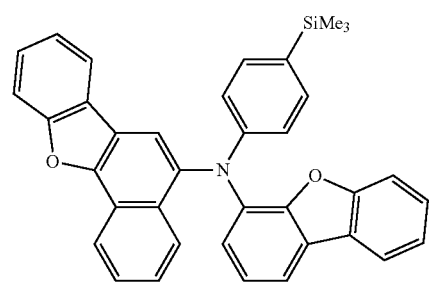
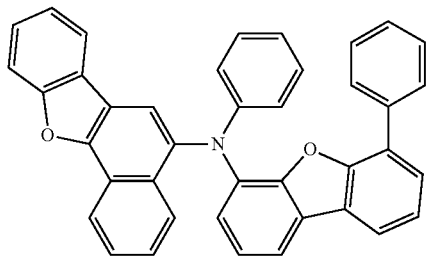
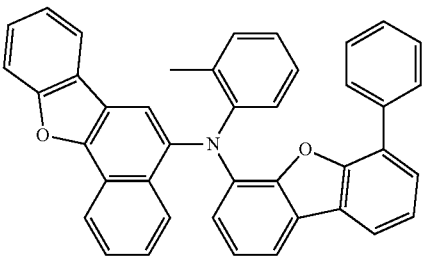
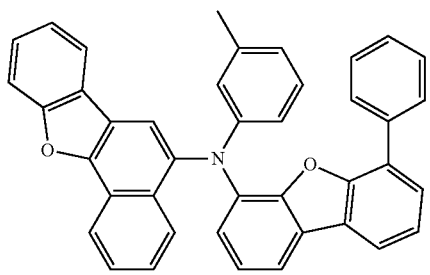
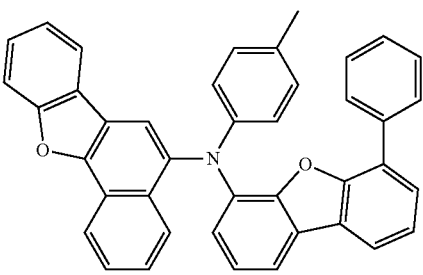

-continued
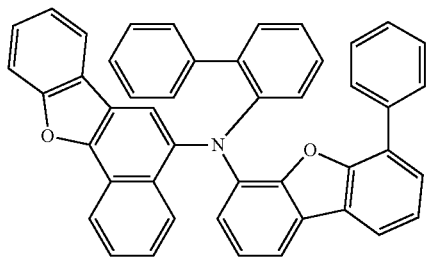
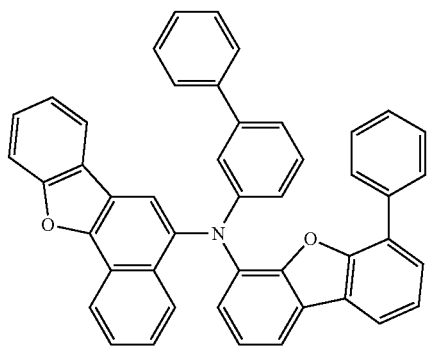
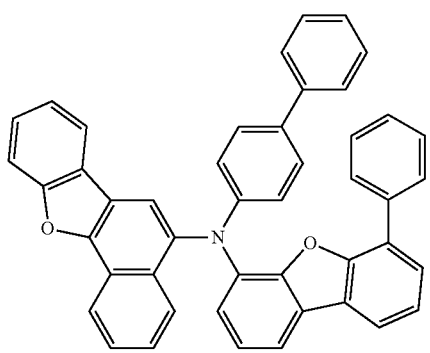
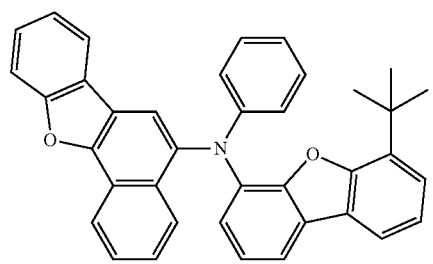
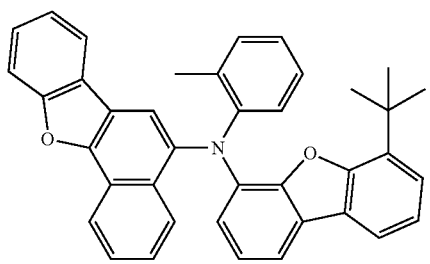
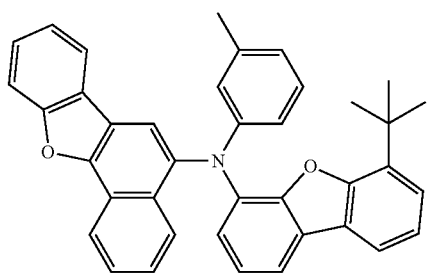
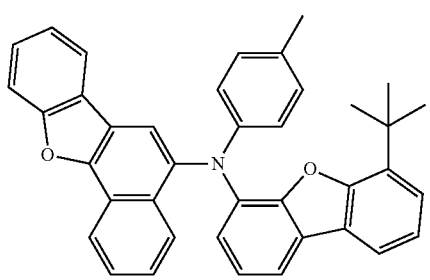
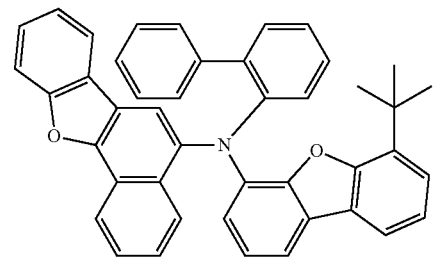
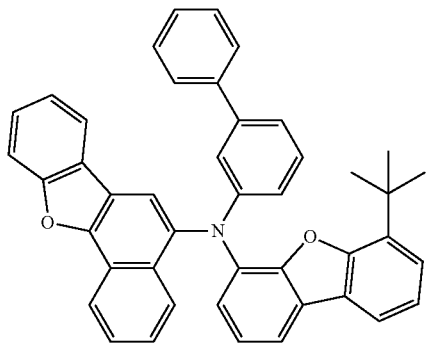
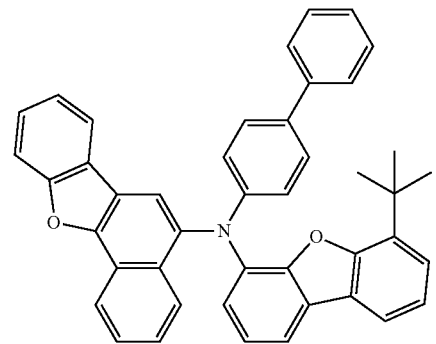

-continued
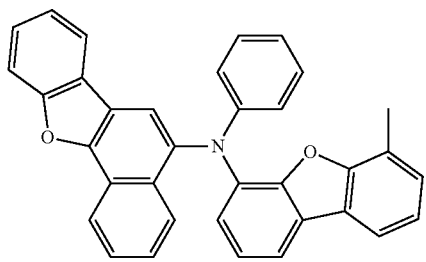
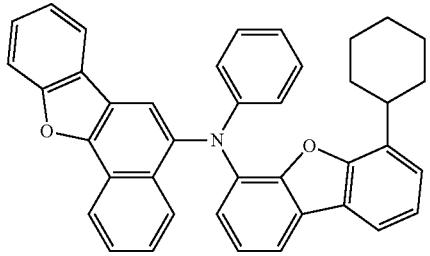
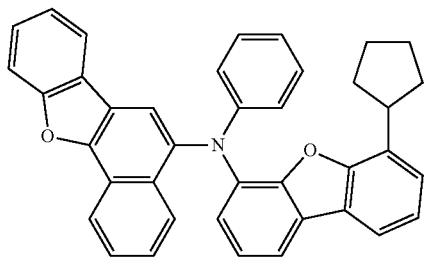
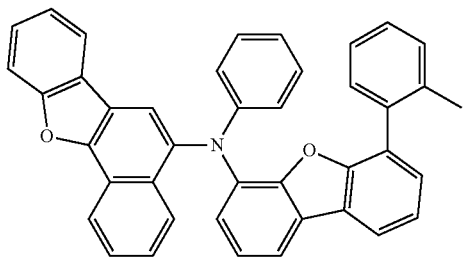
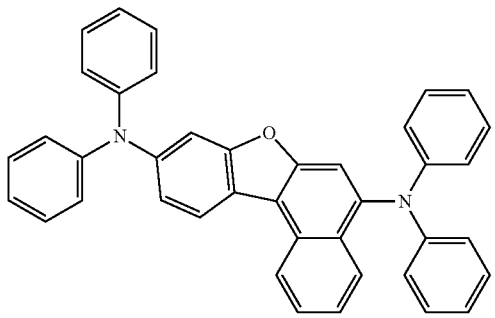
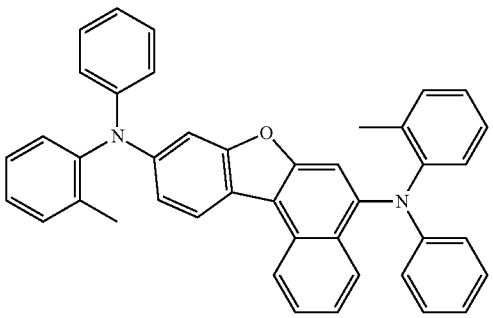
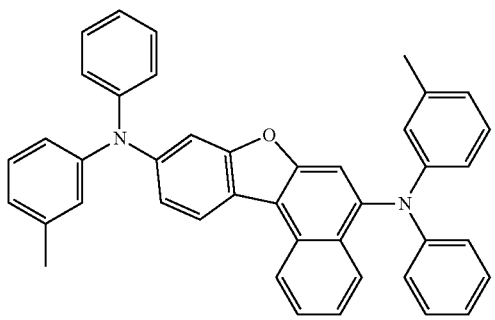
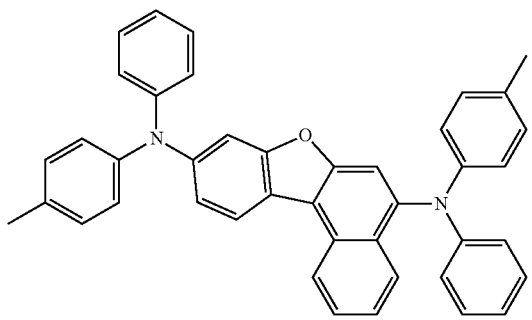
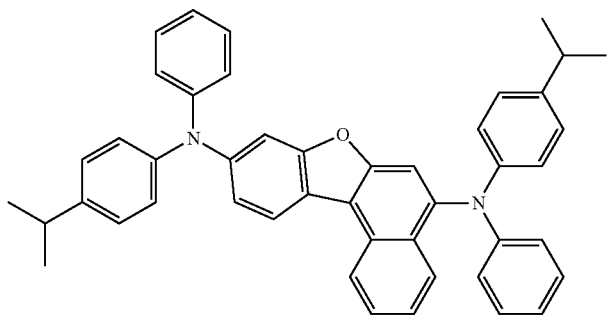

-continued
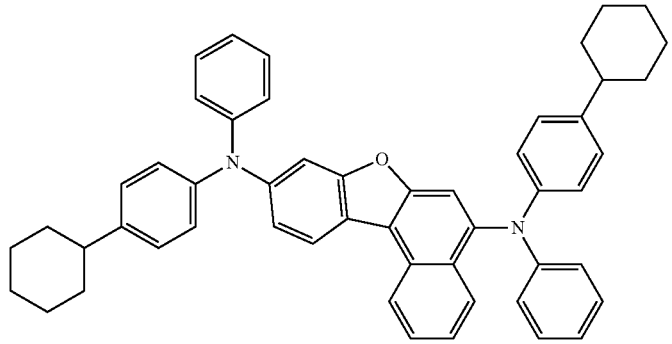
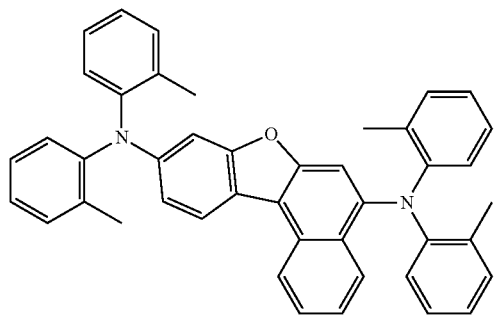
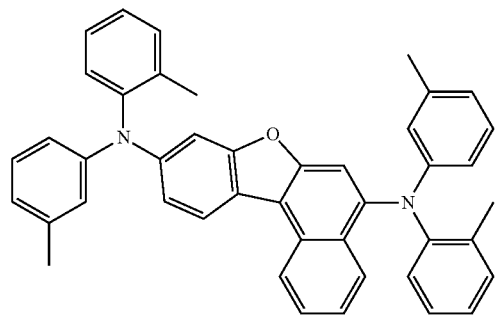
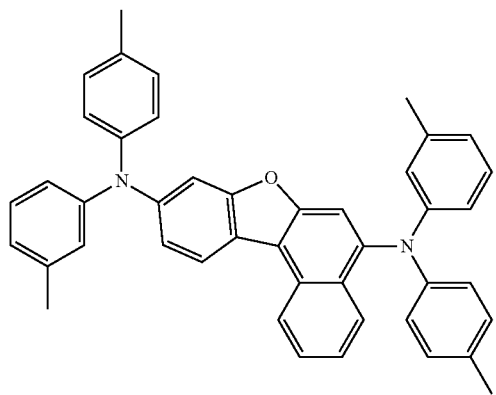
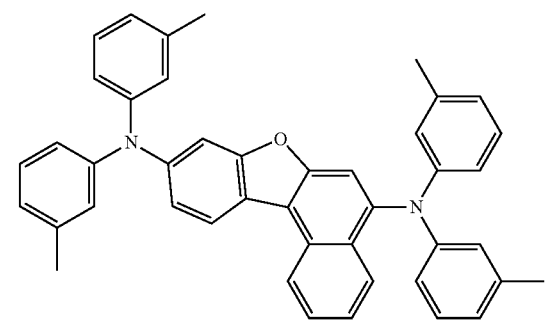
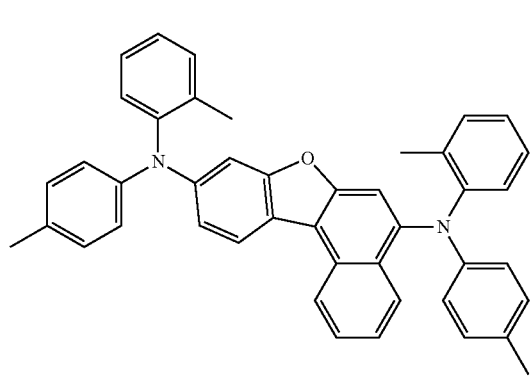
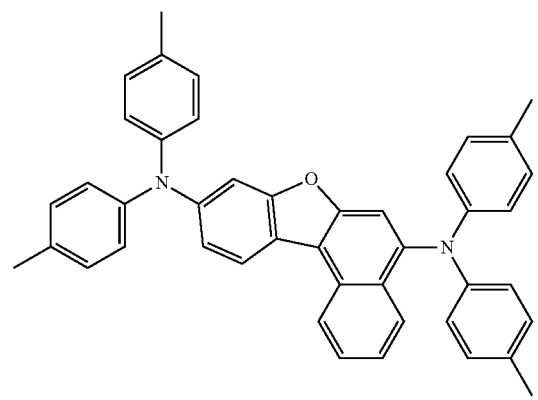

-continued
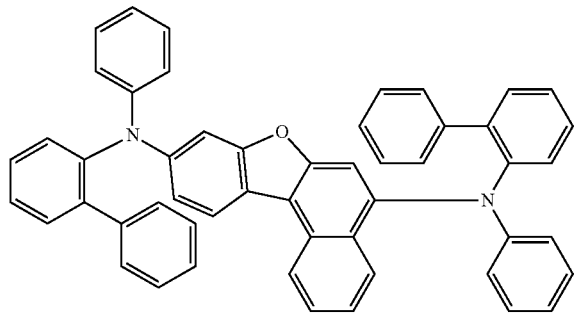
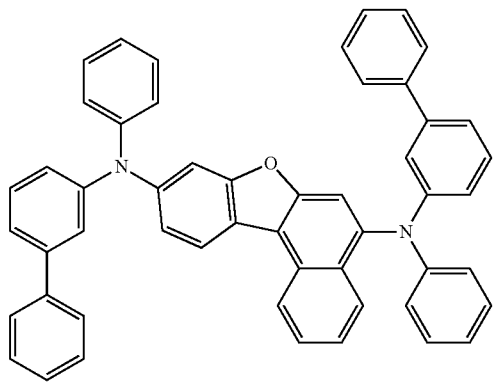
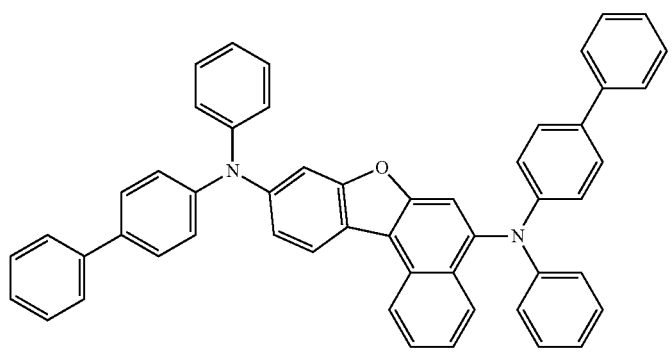
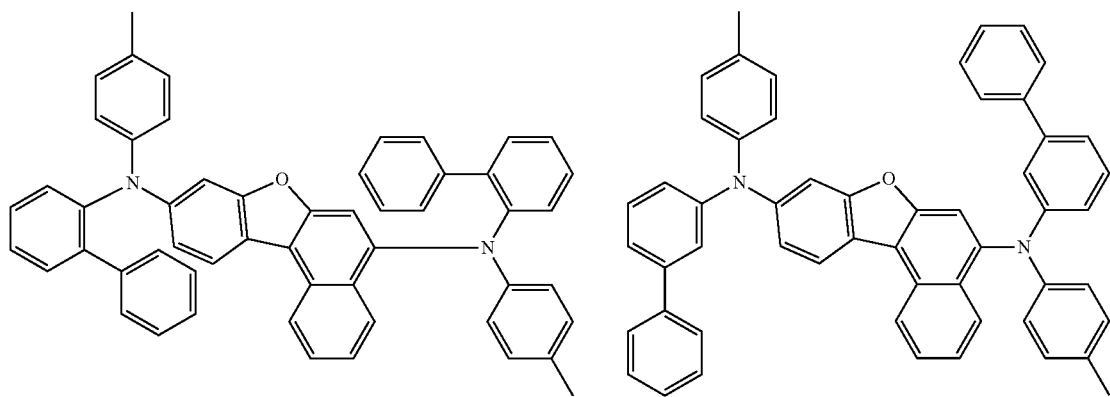
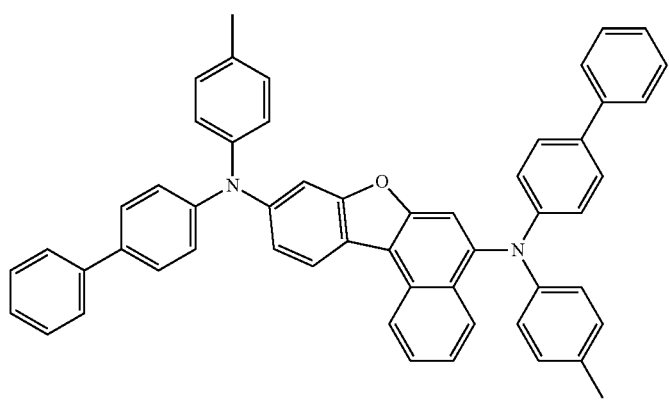

71
72
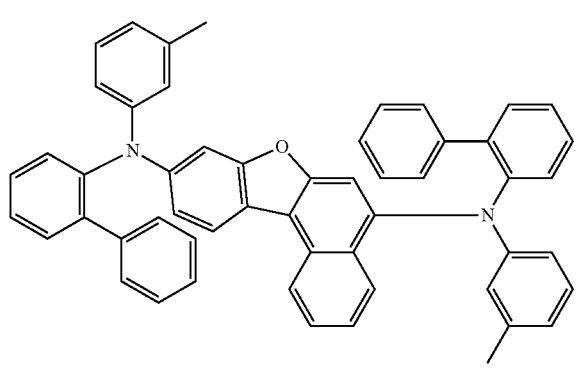
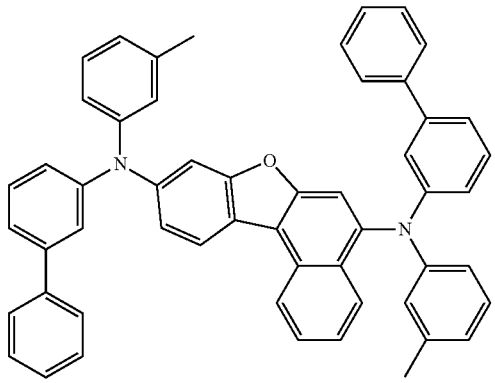
-continued
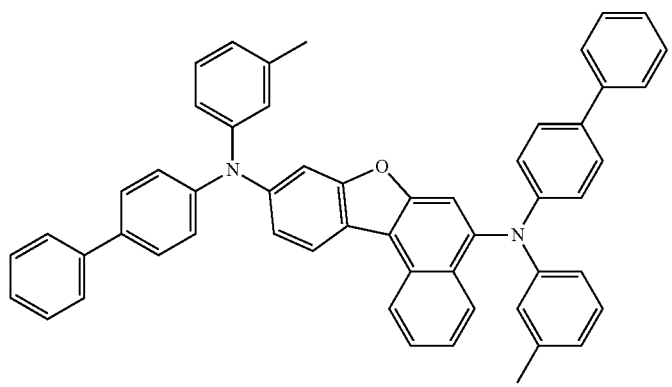
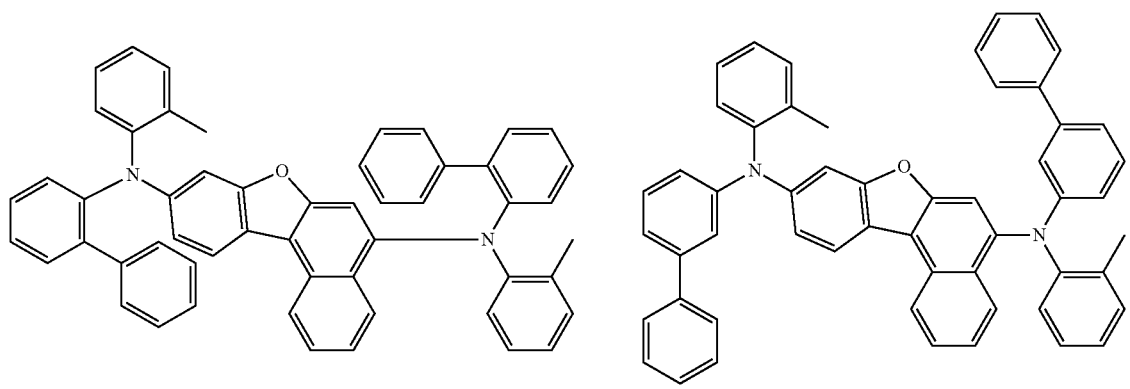
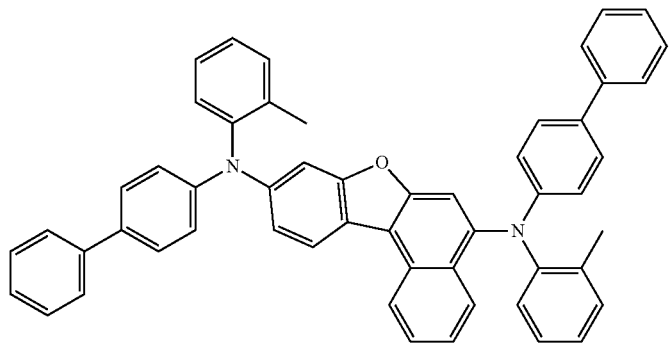

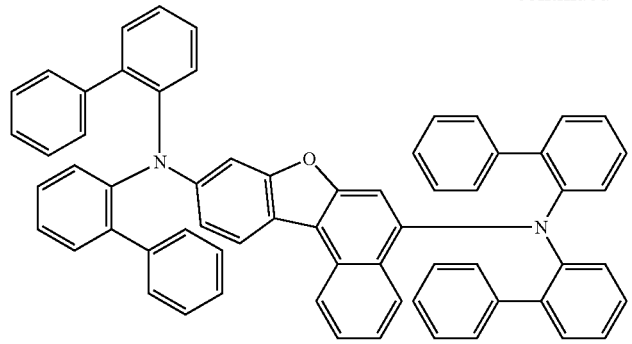
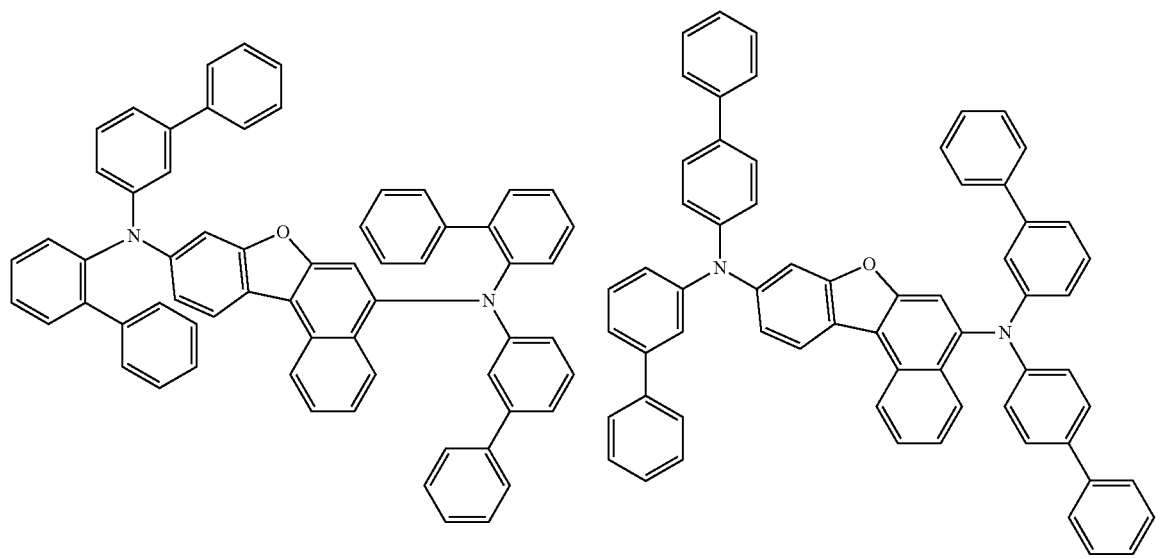
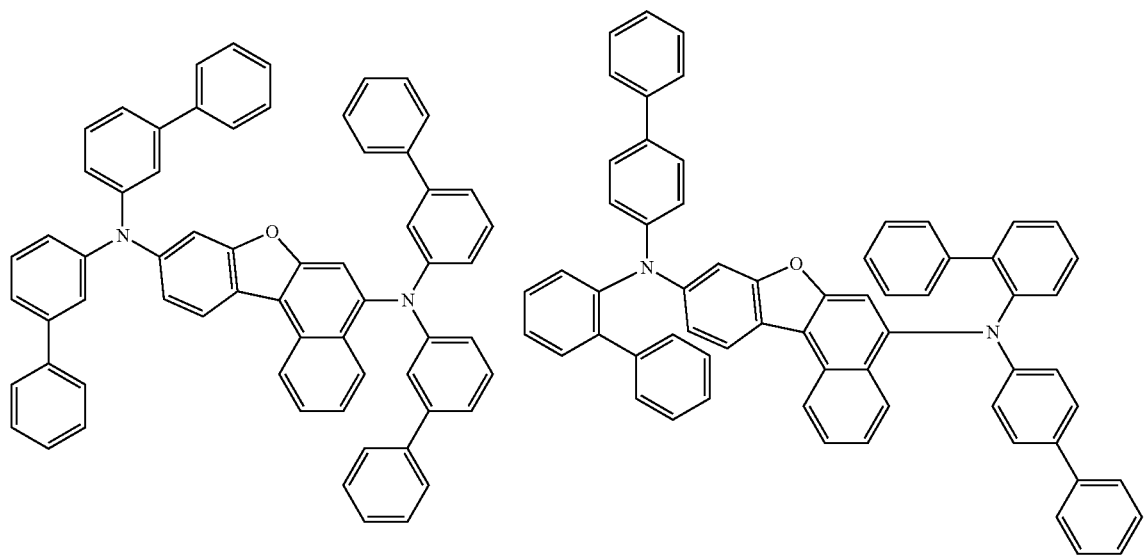

-continued
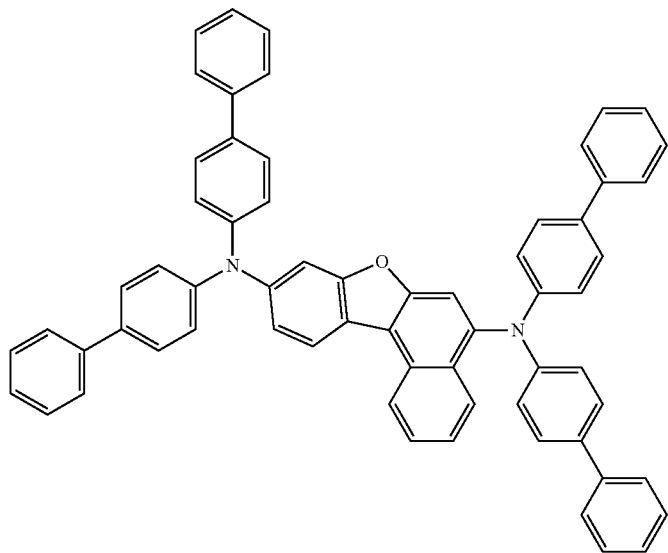
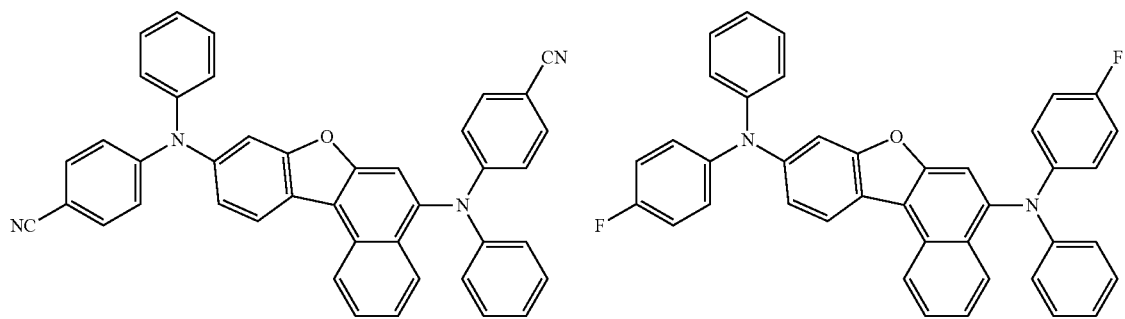
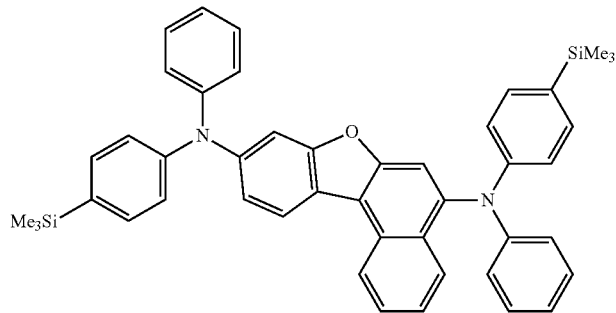
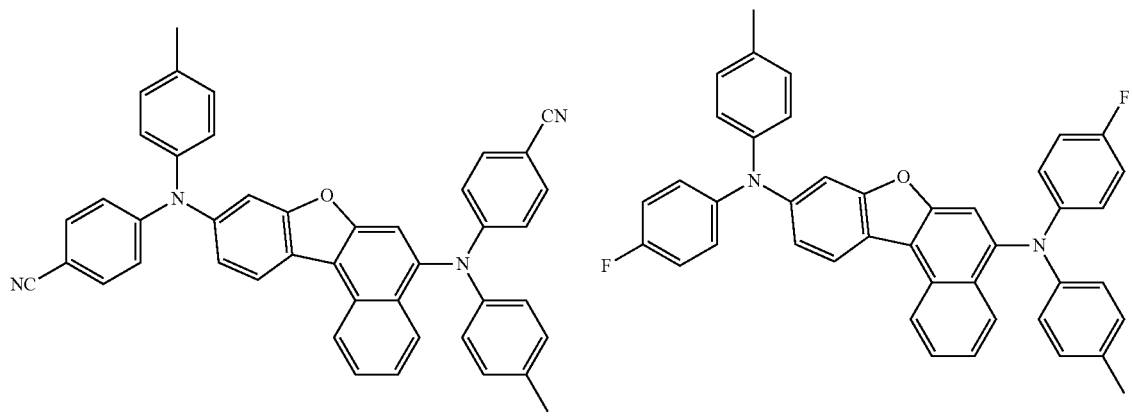

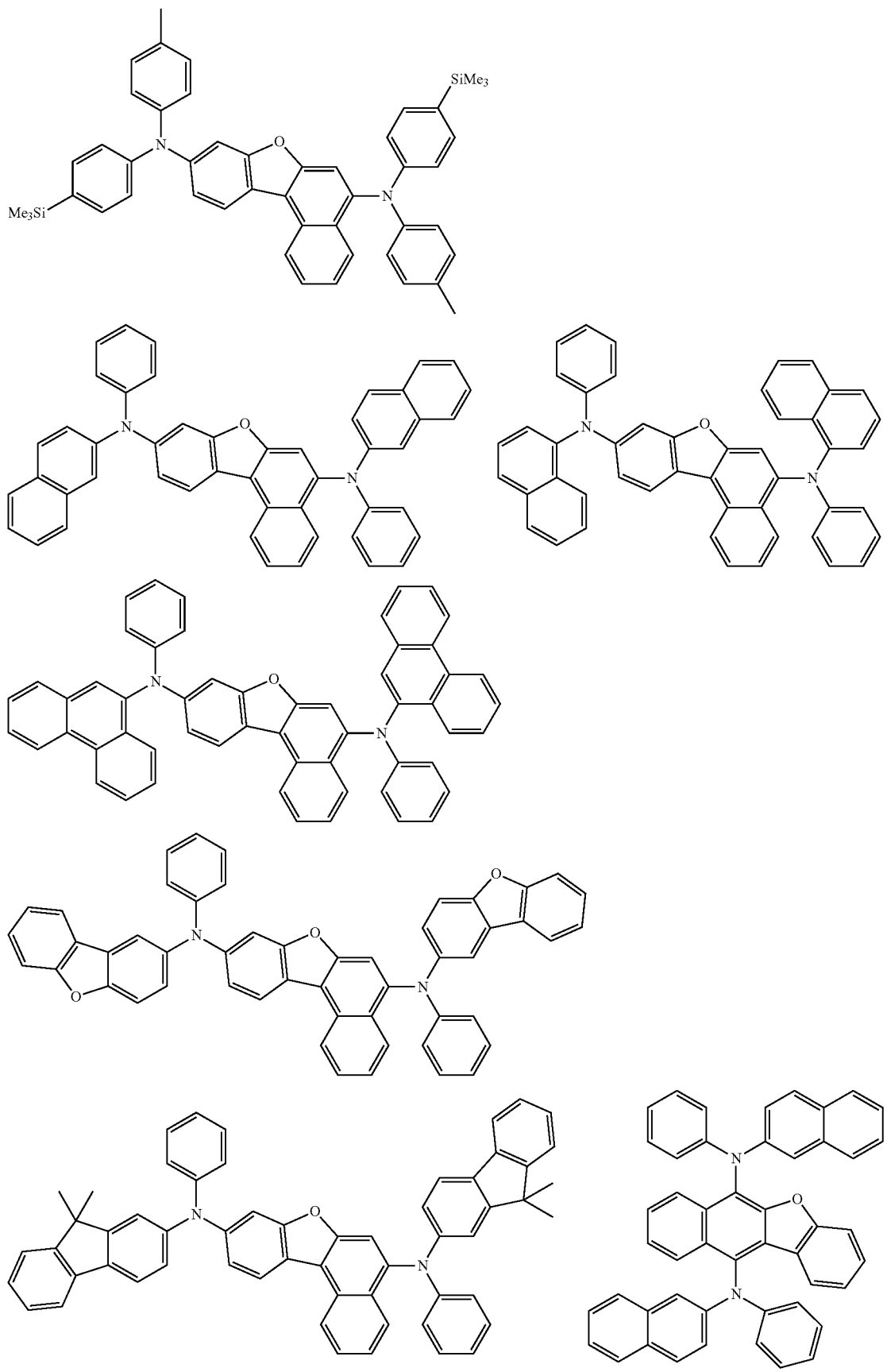

79
-continued
80
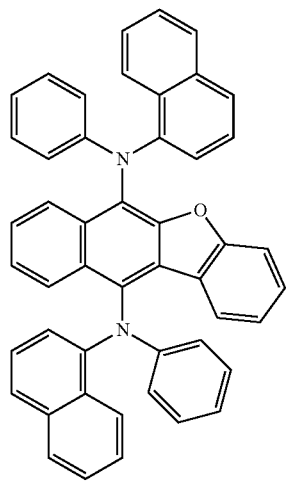
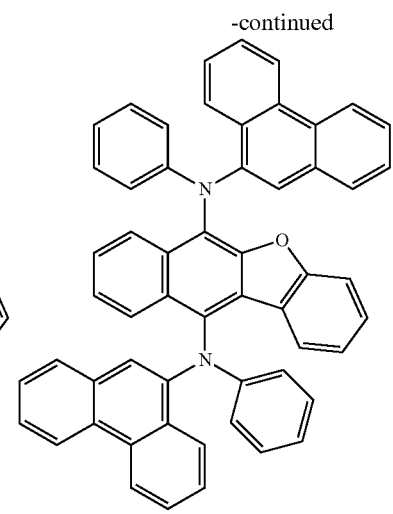
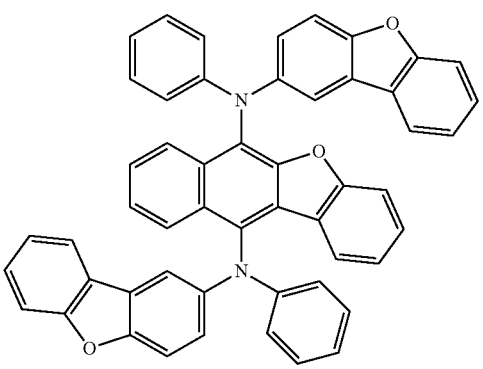
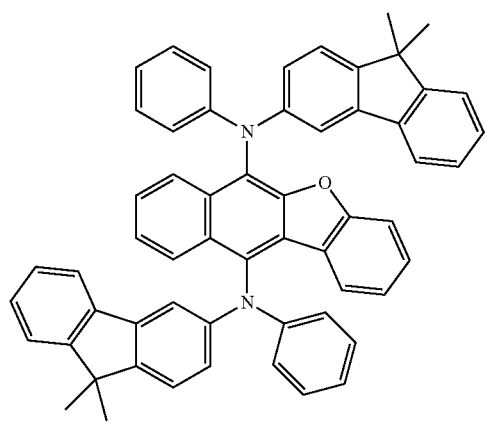
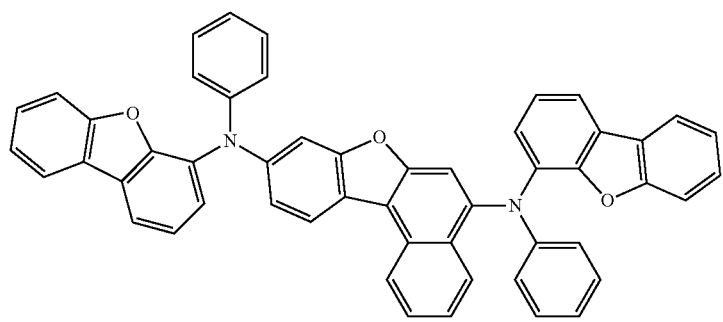
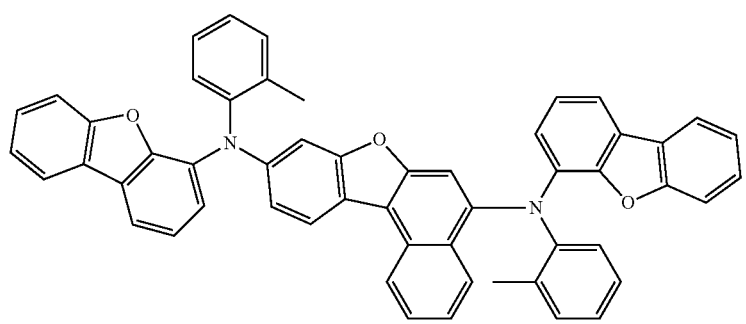

-continued
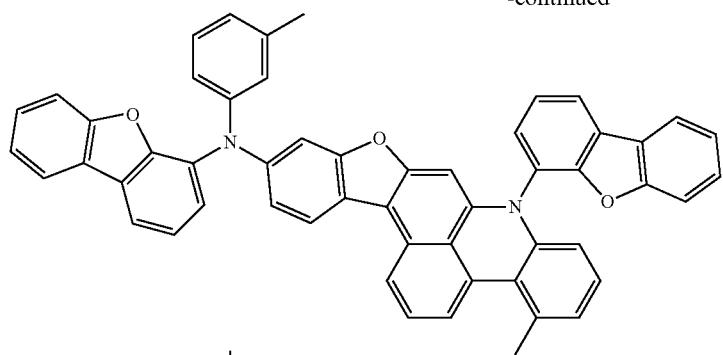
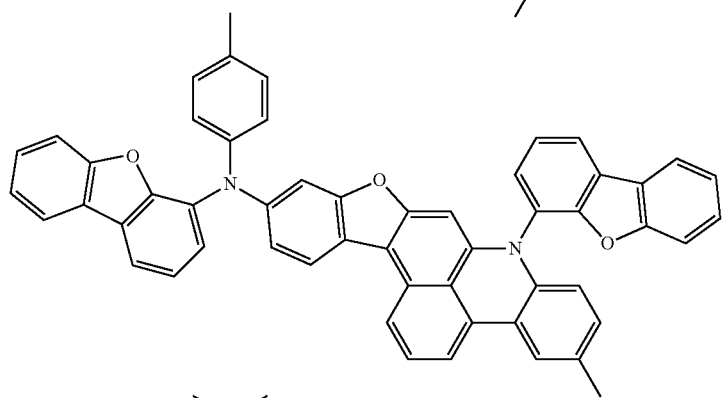
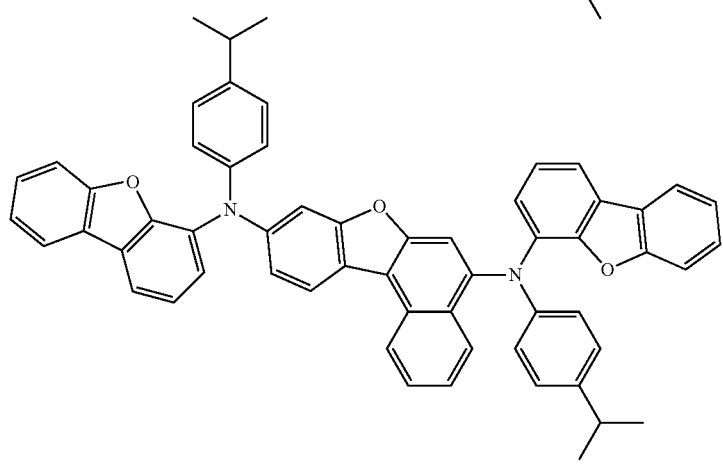
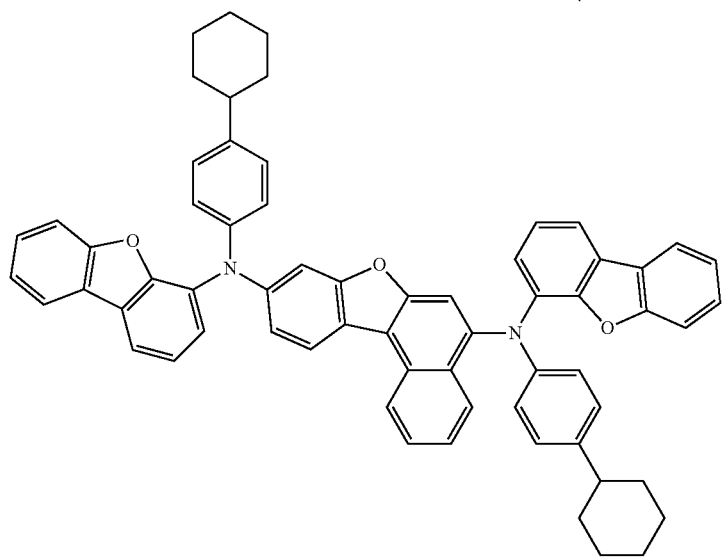

-continued
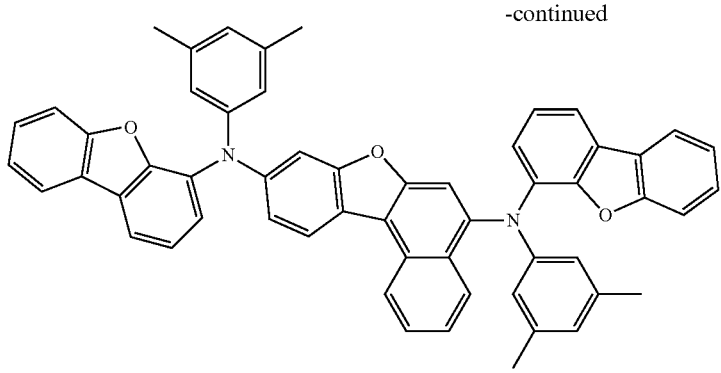
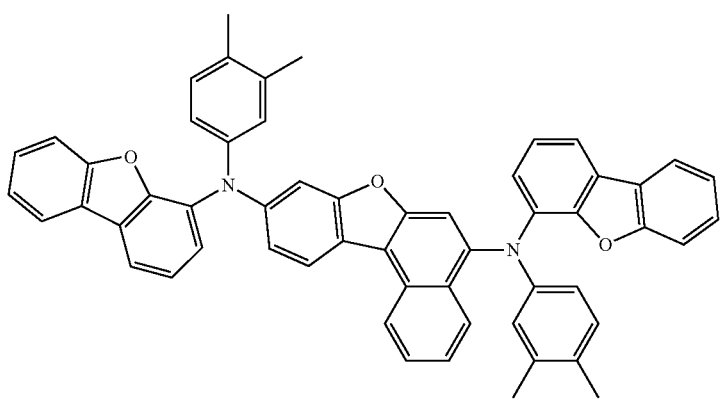
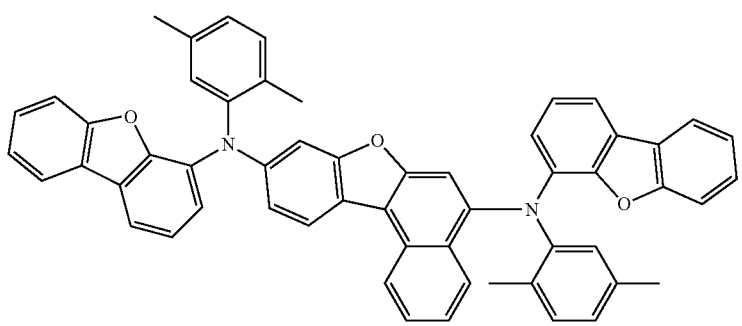
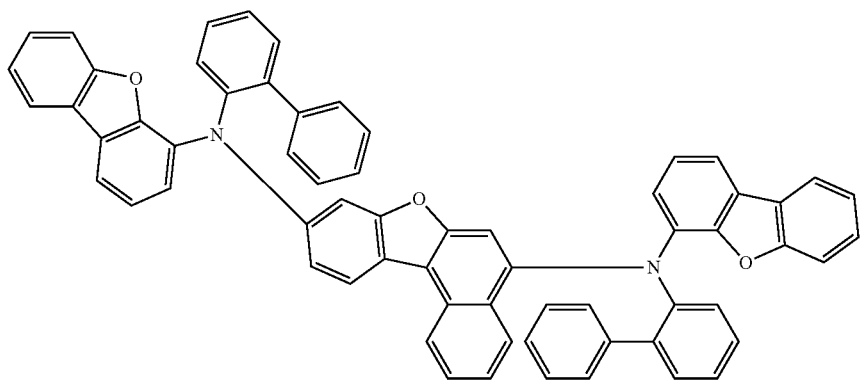

-continued
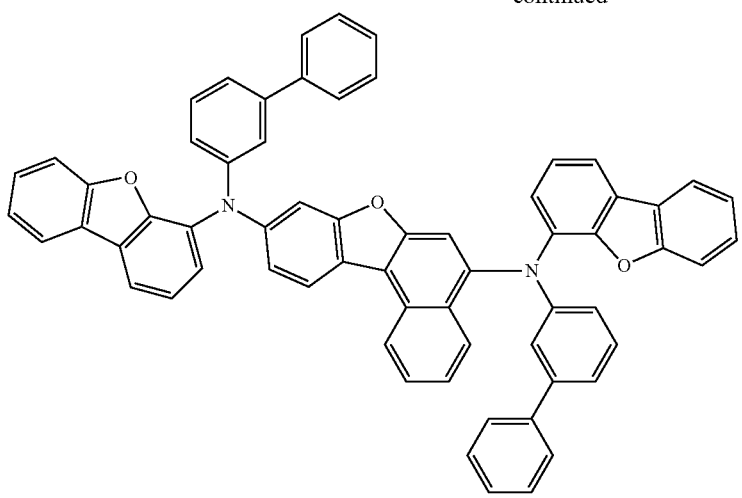
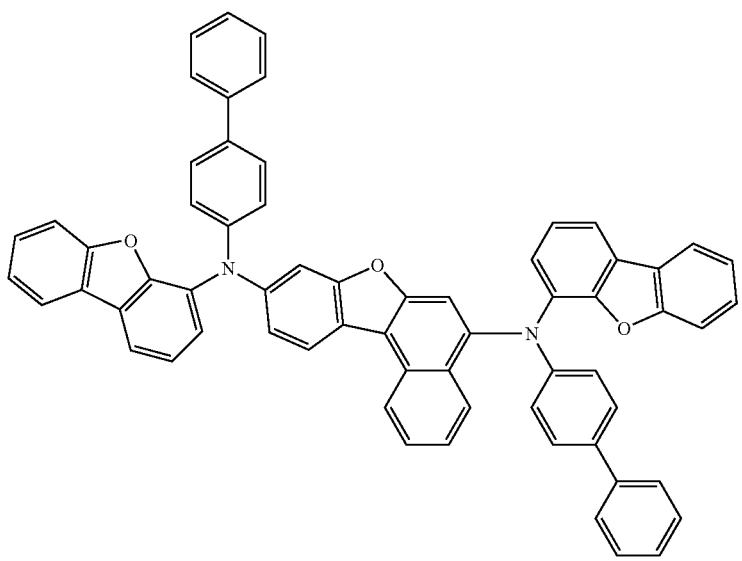
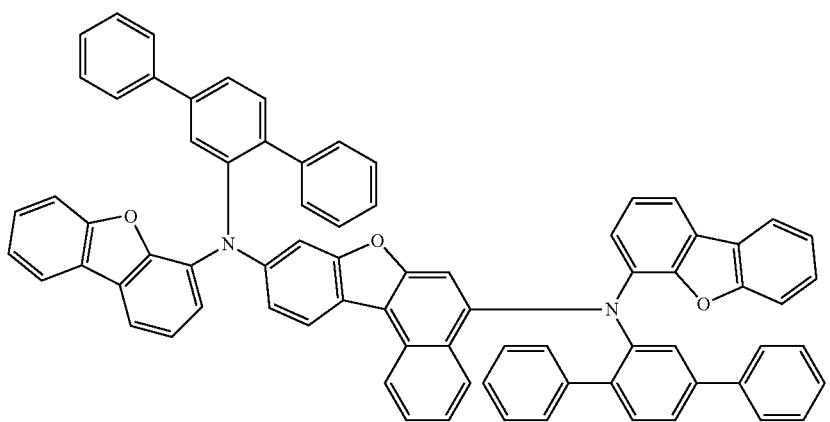

-continued
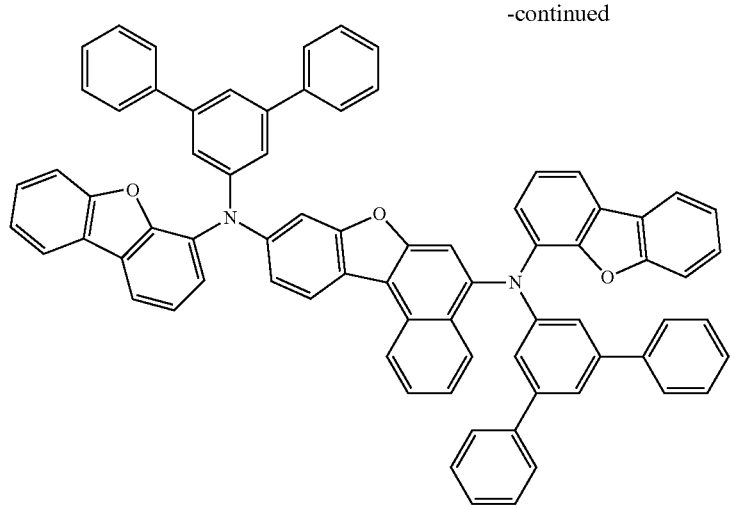
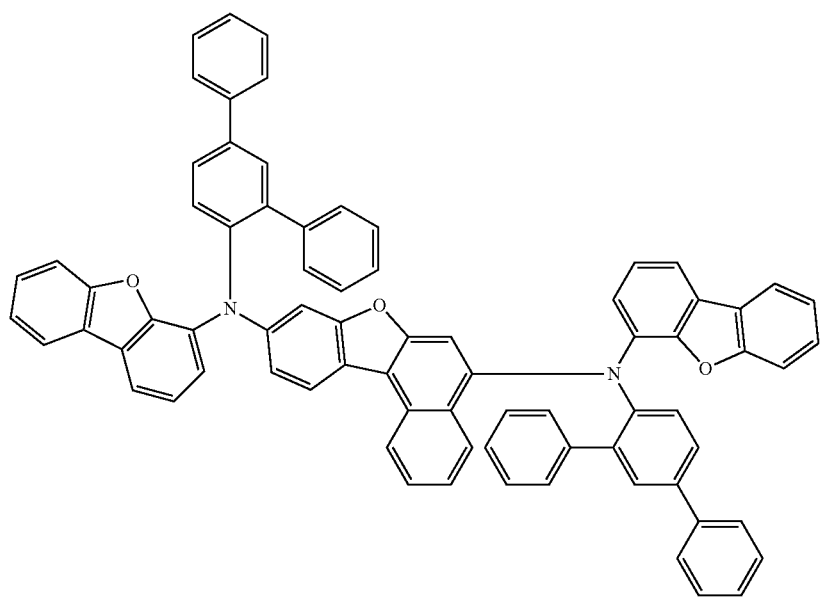
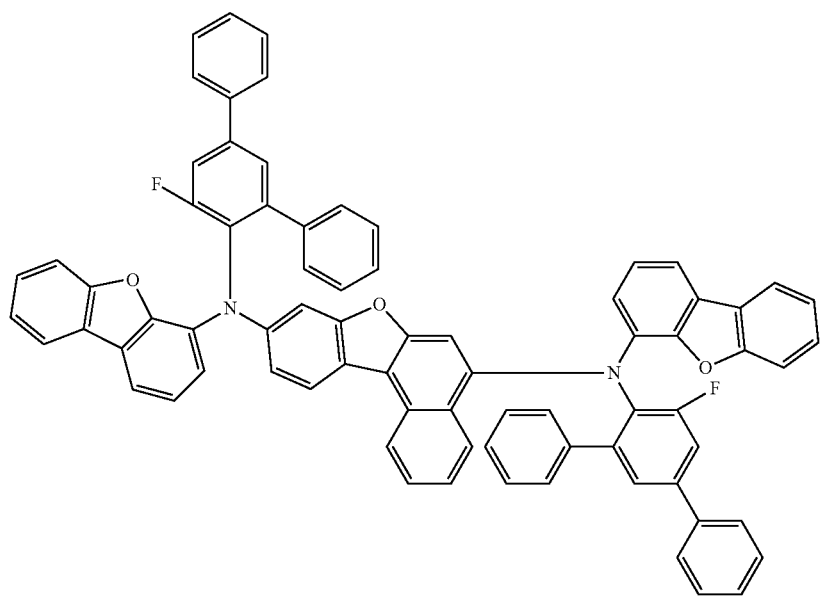

-continued
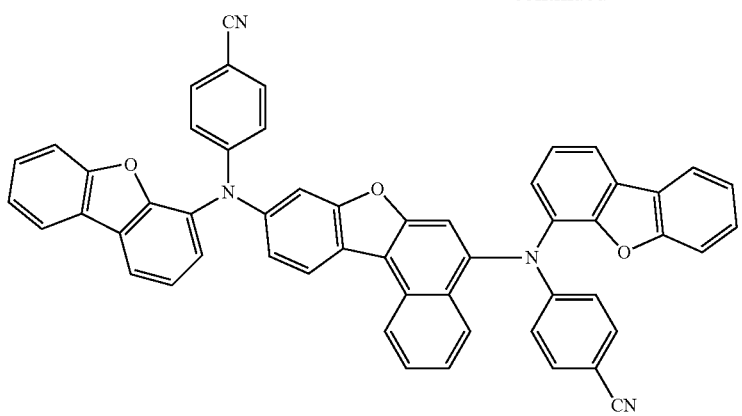
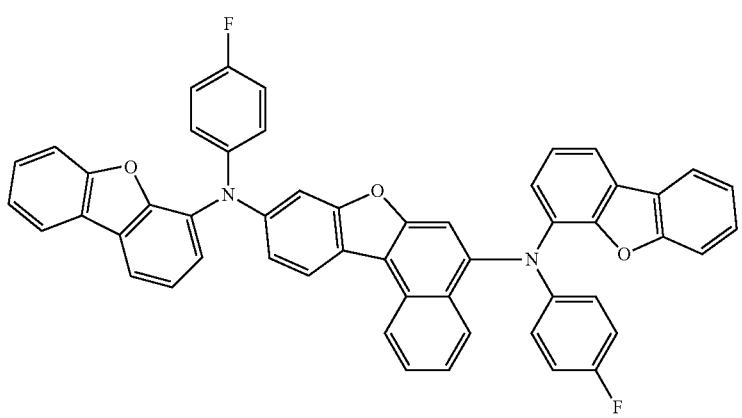
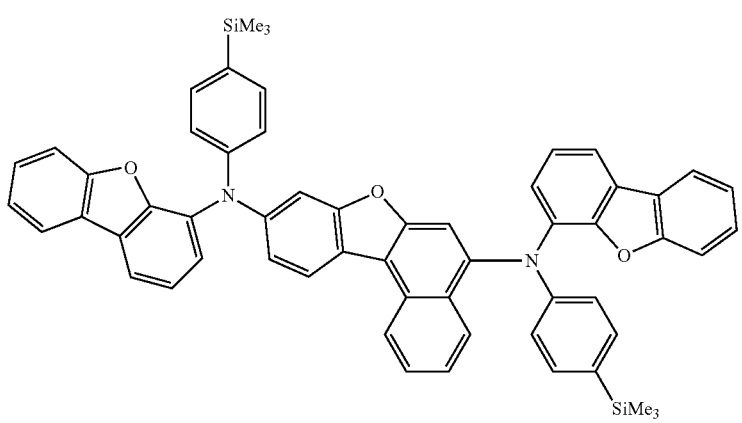
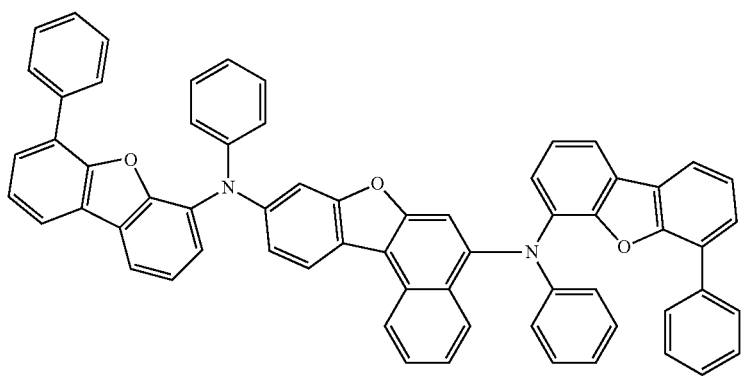

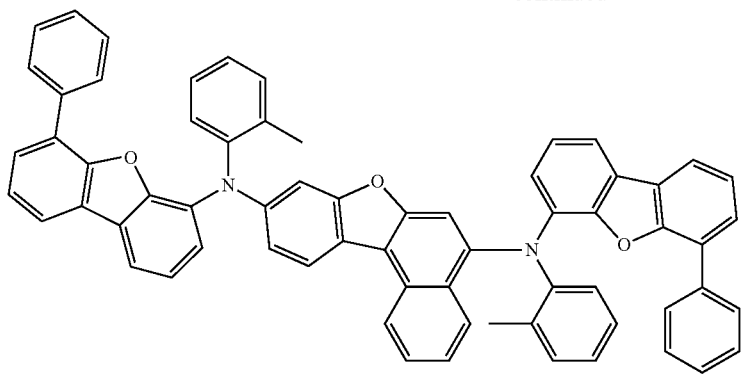
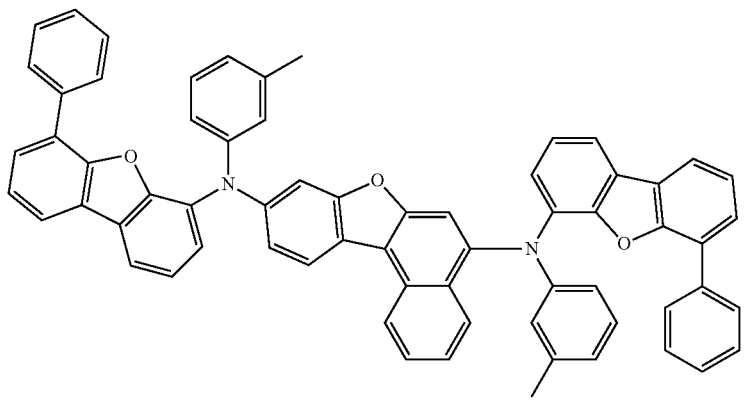
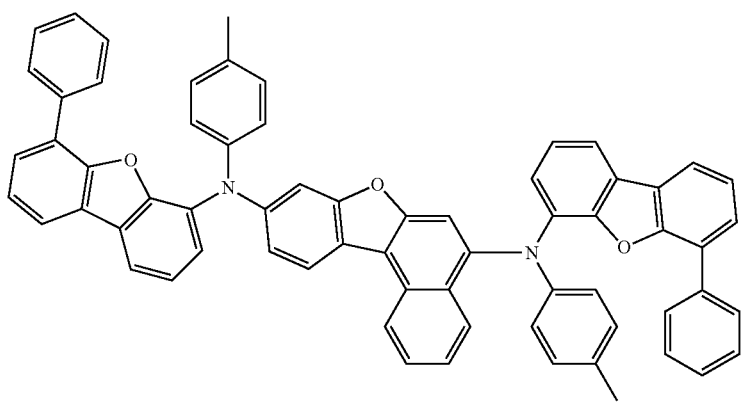
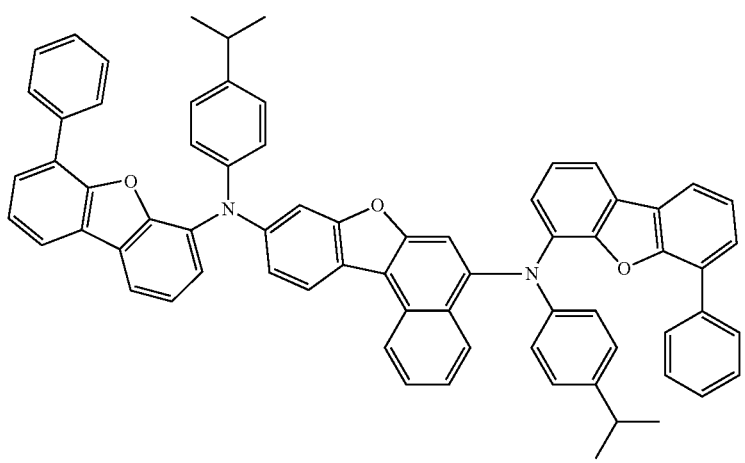

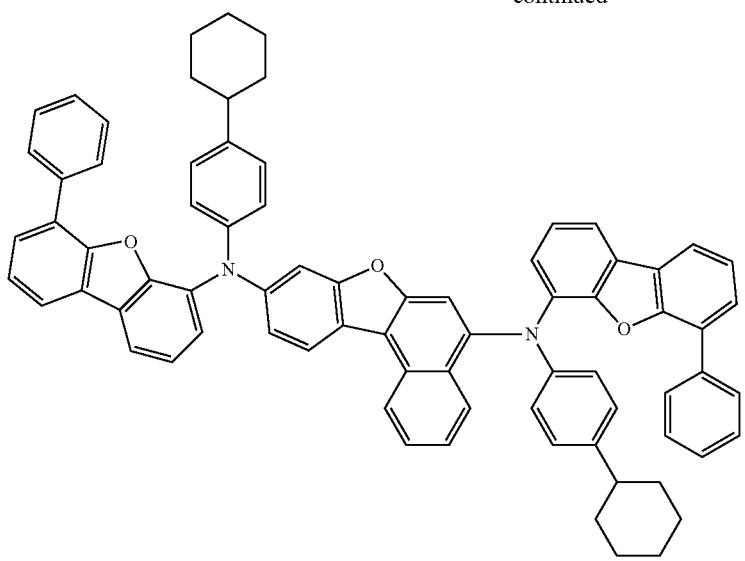
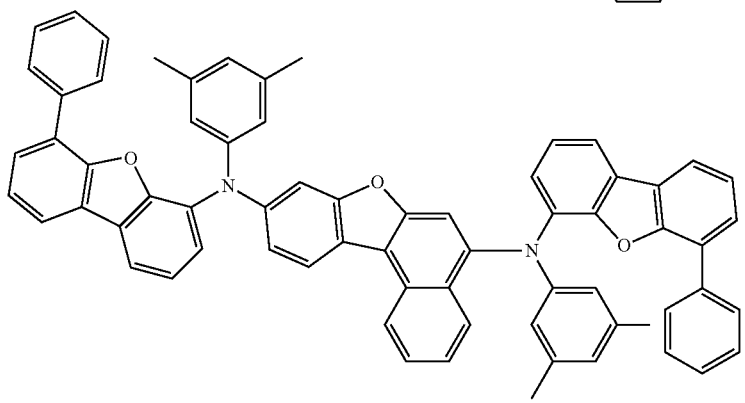
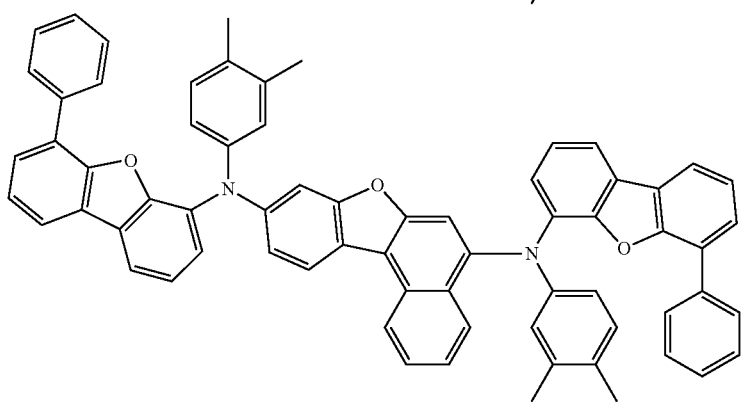
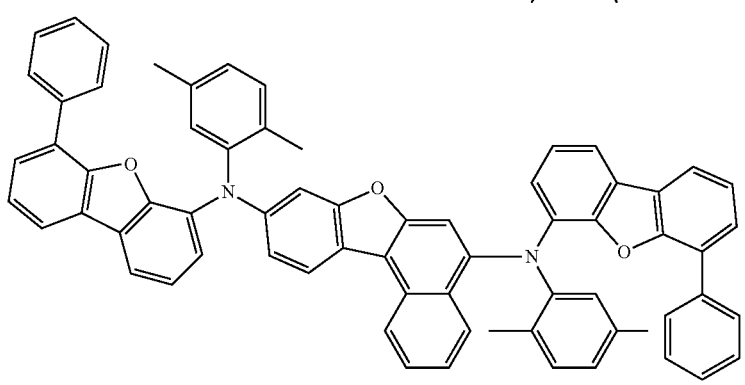

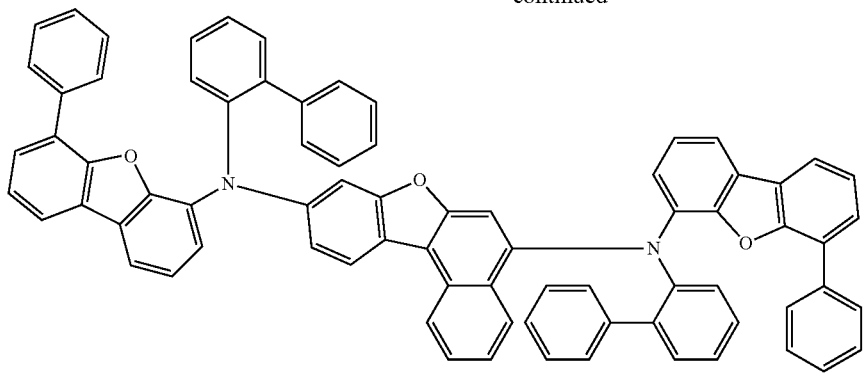
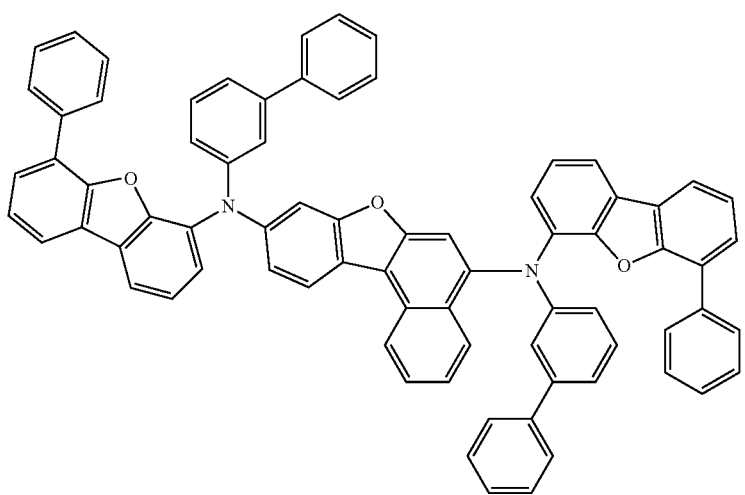
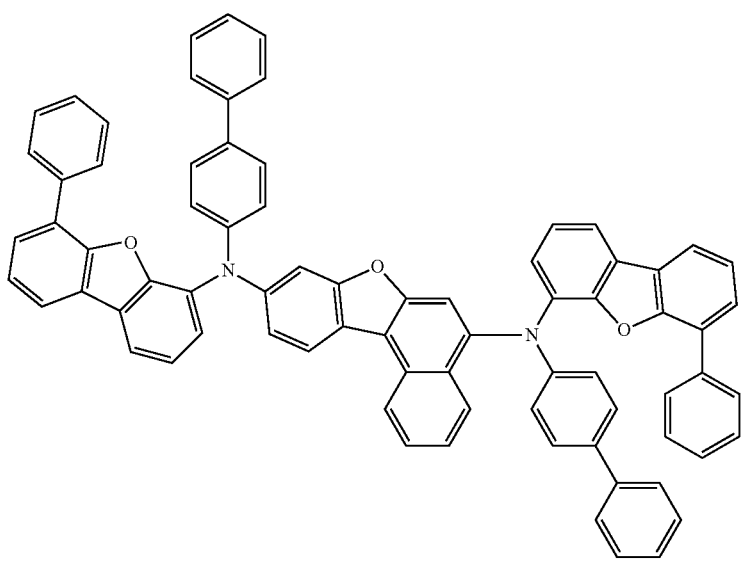

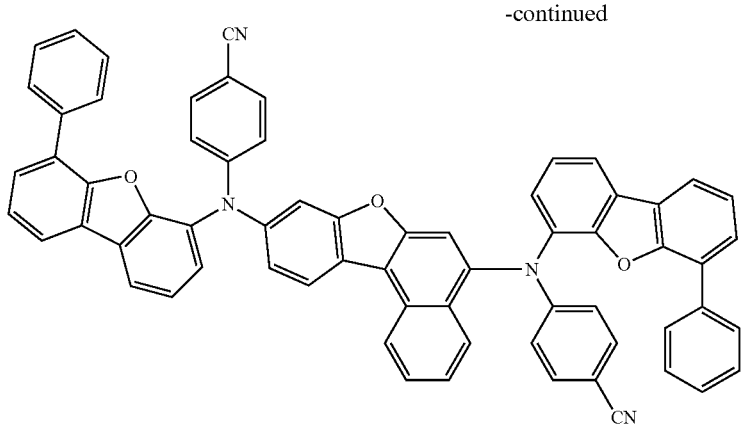
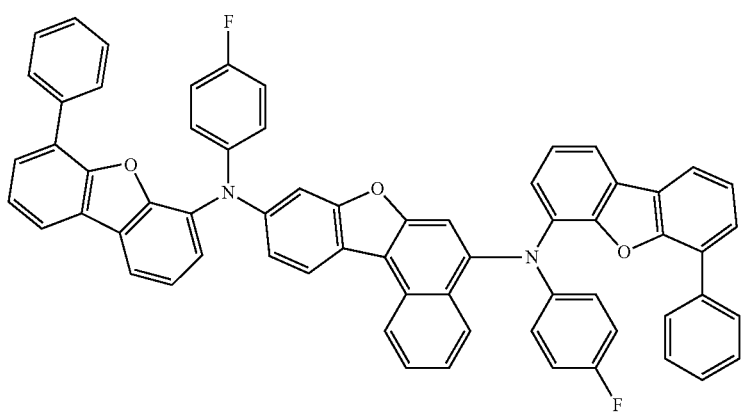
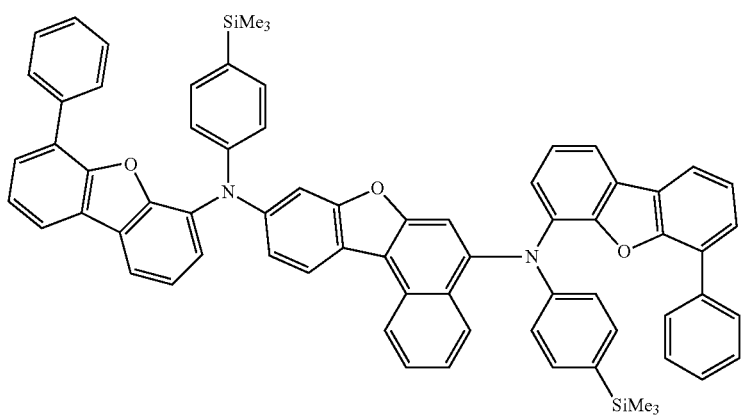
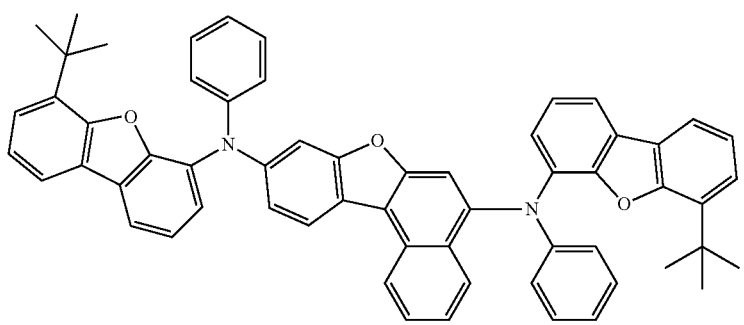

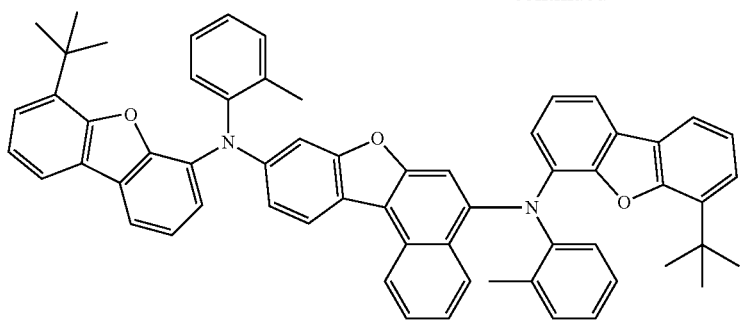
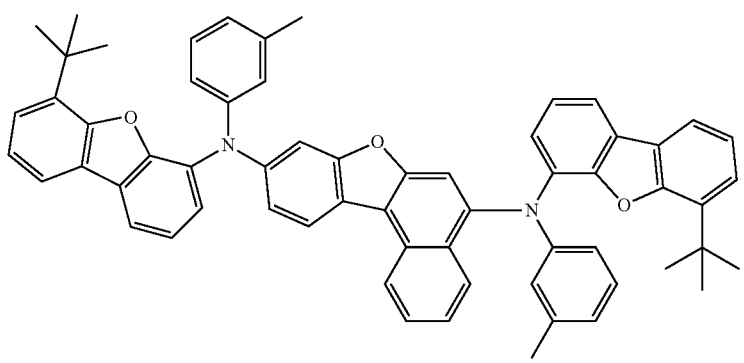
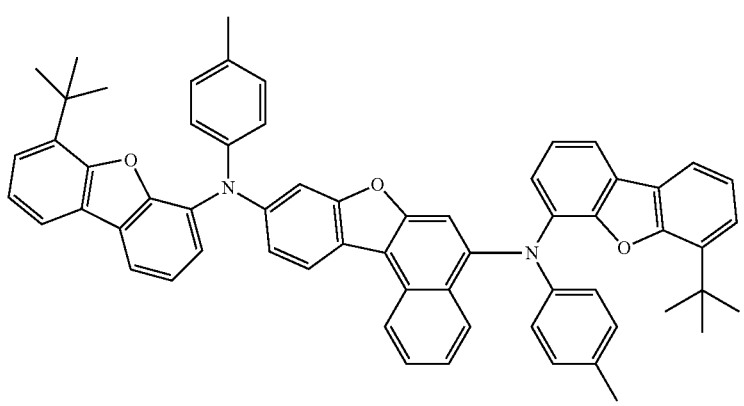
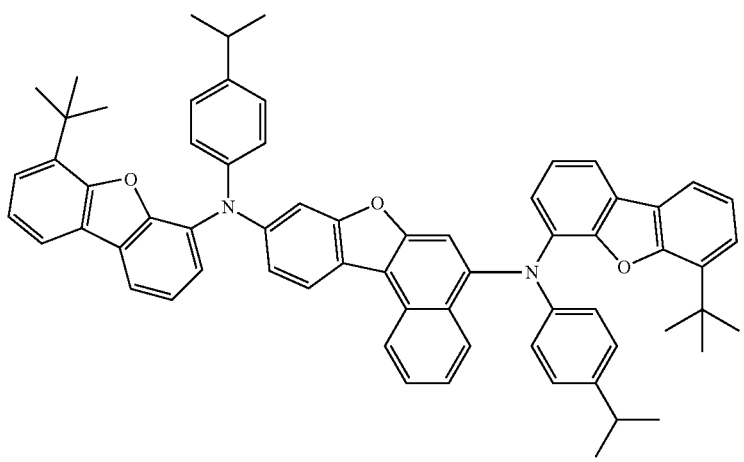

-continued
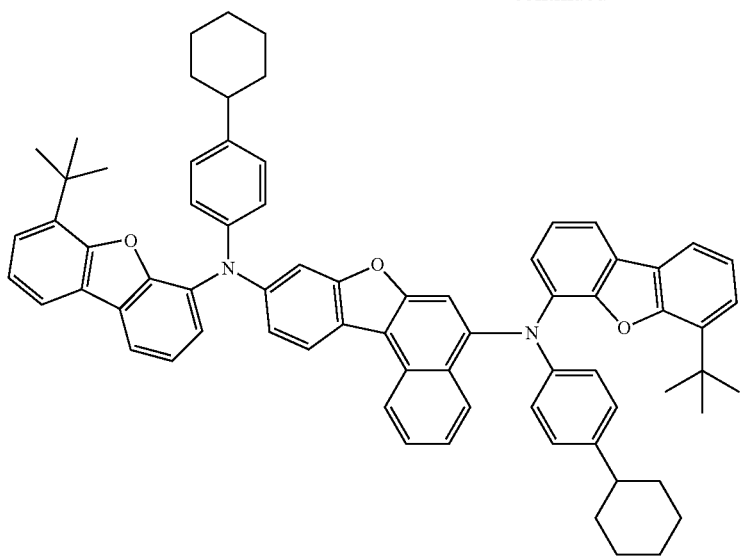
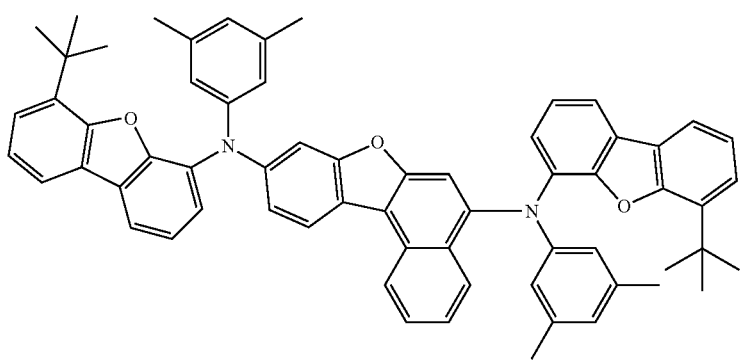
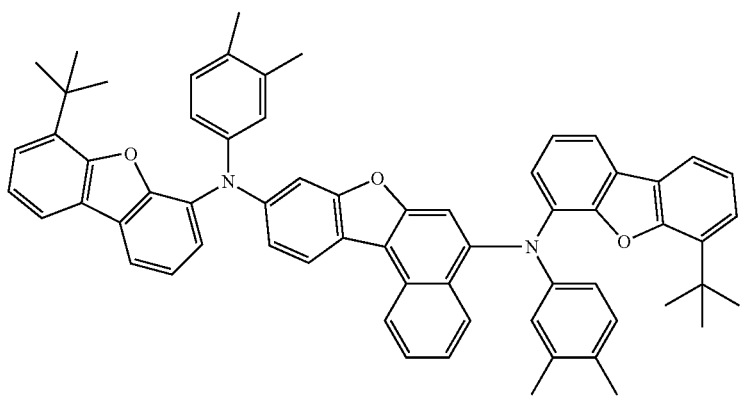
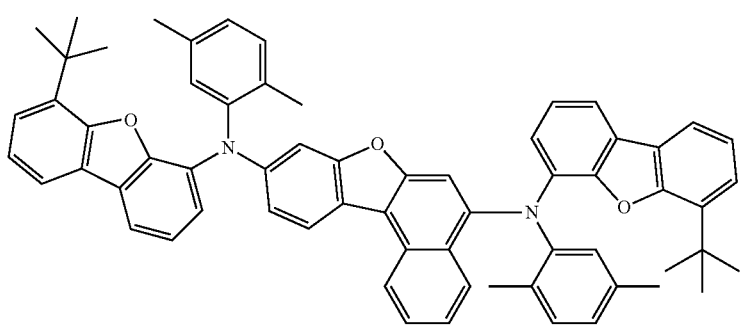

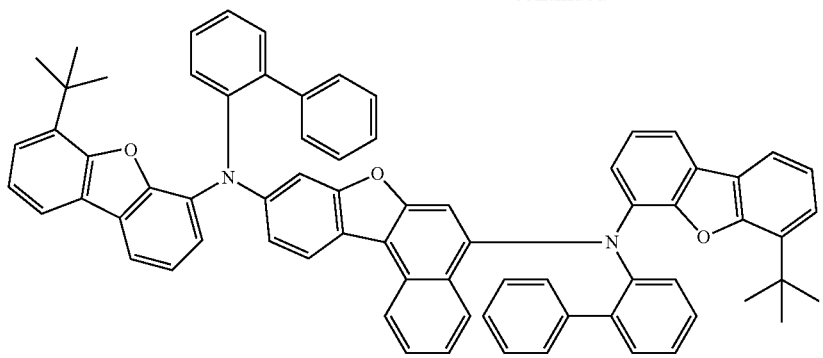
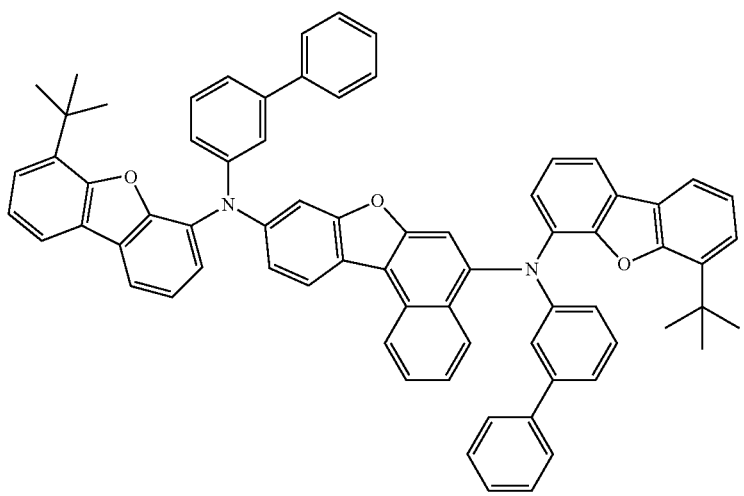
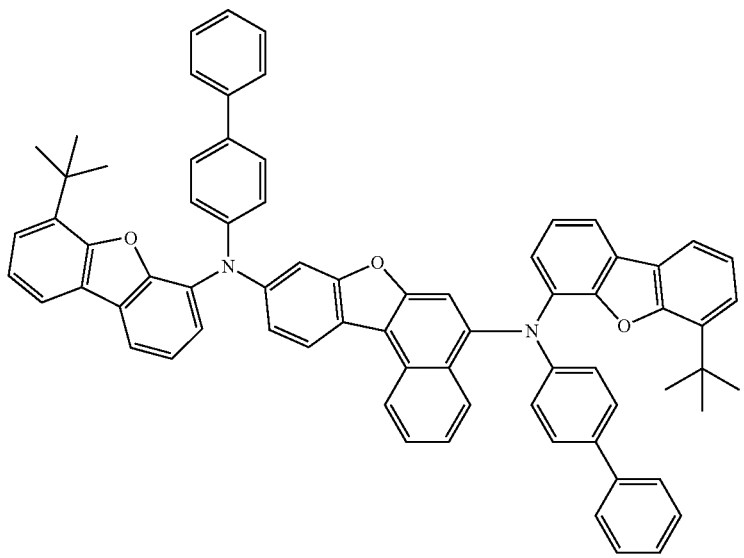

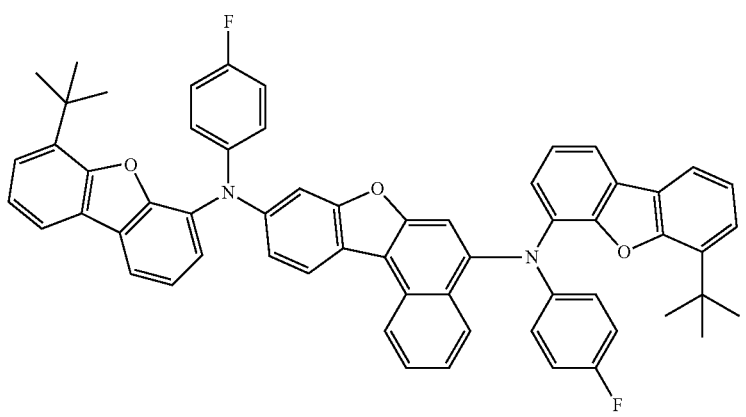
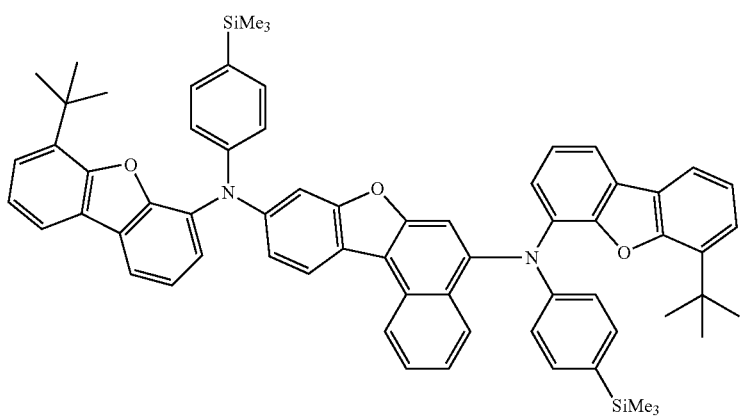
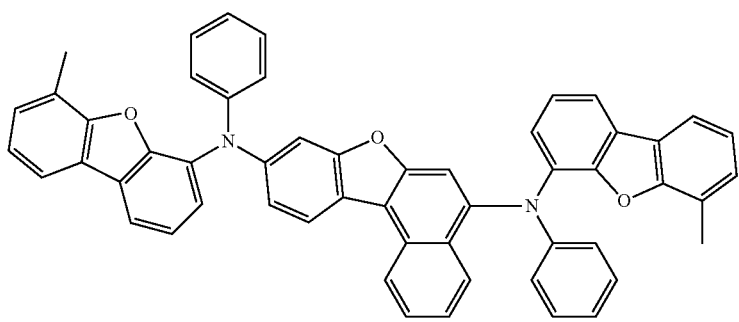

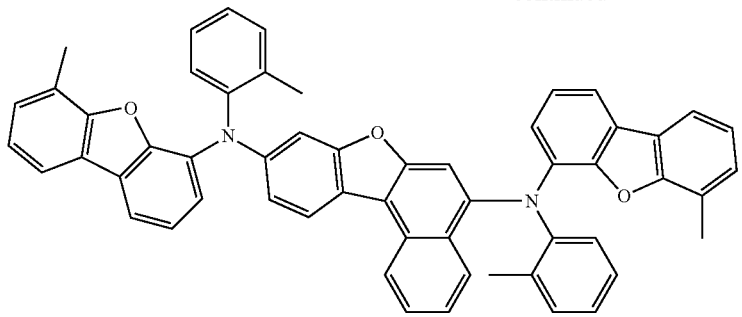
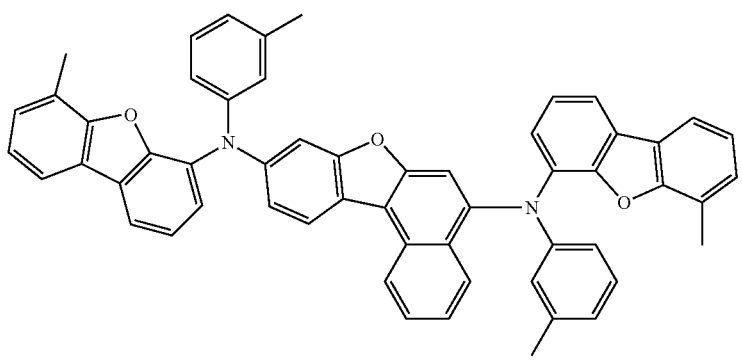
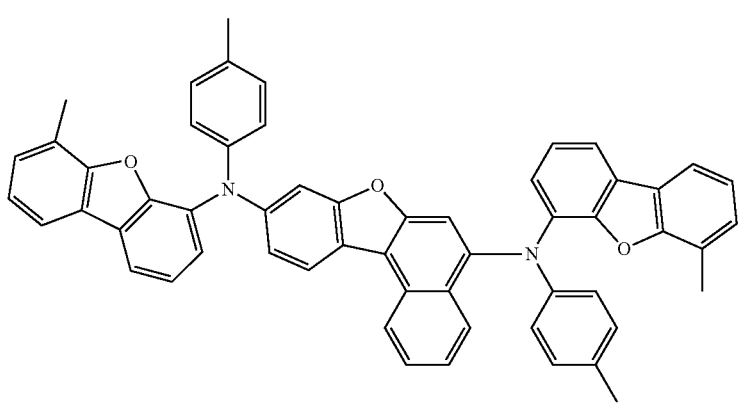
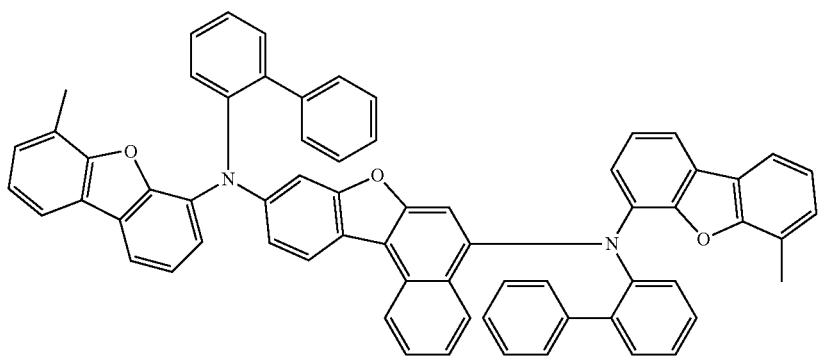

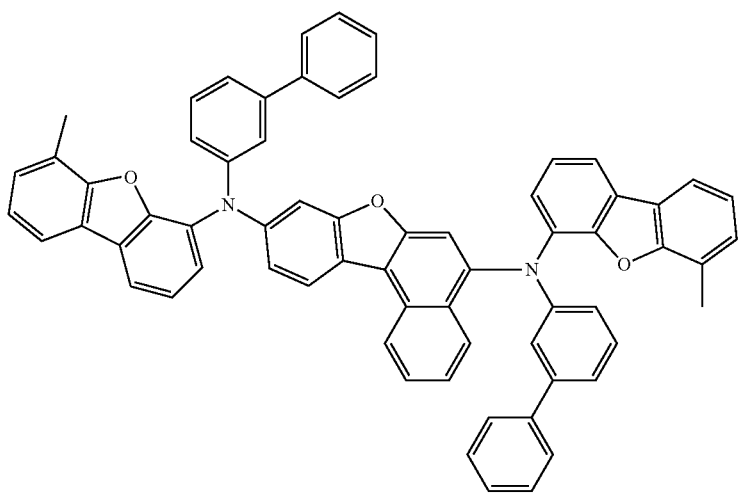
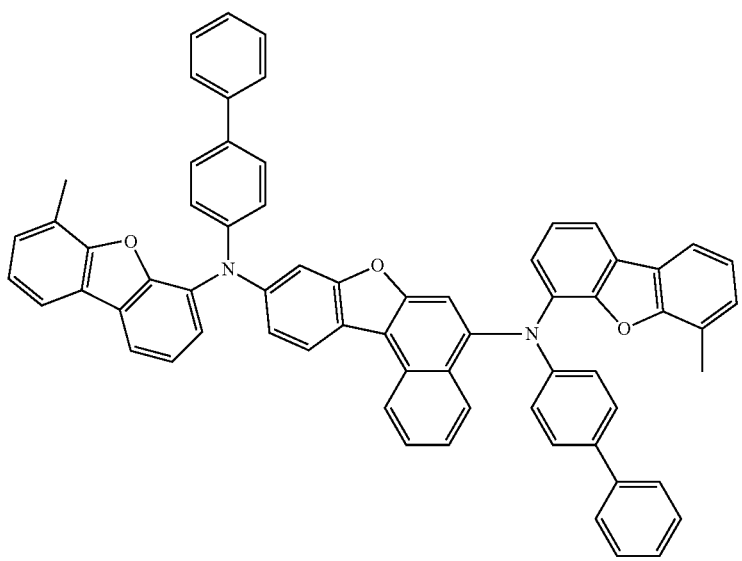
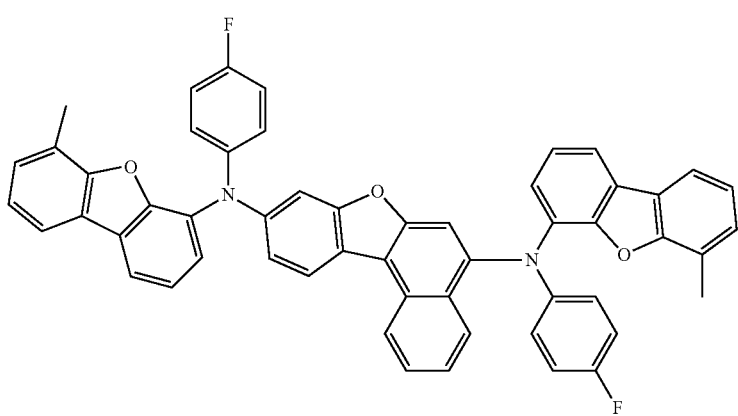

-continued
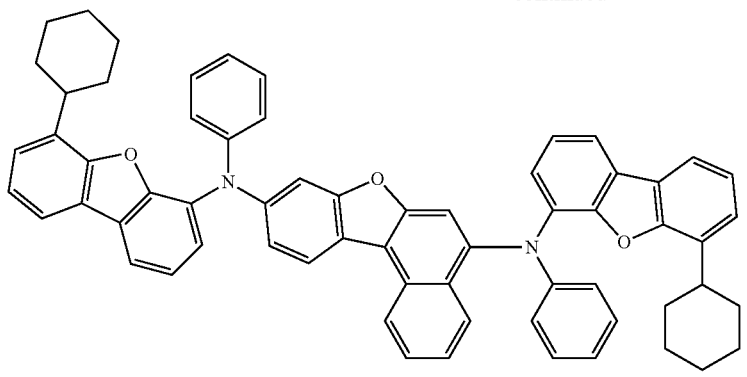
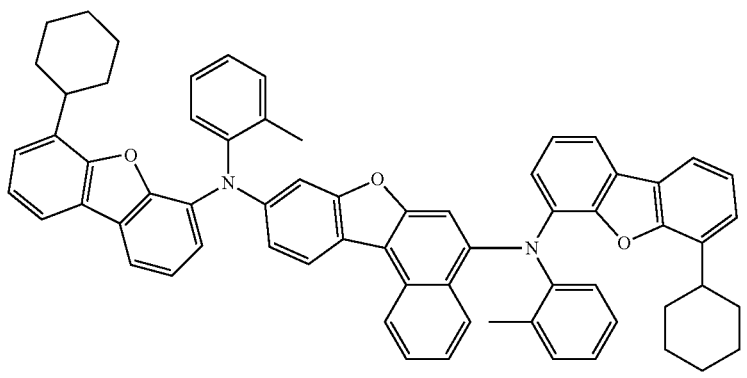
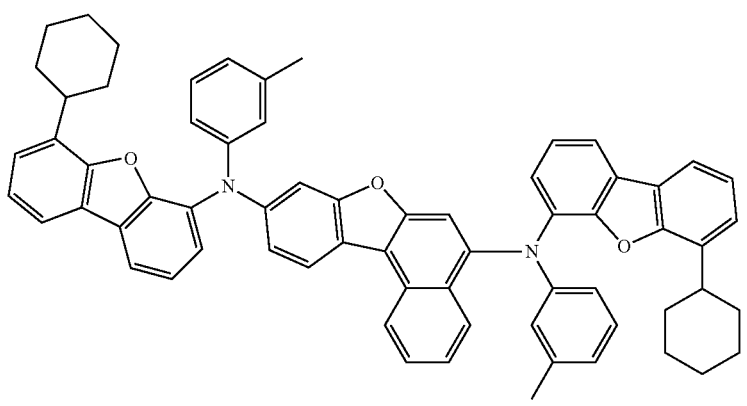
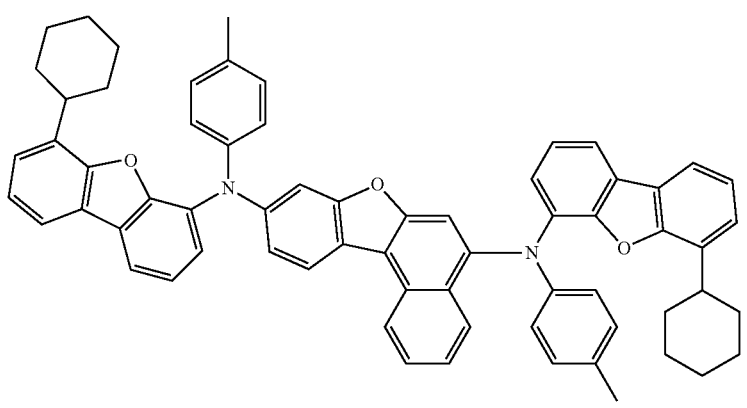

-continued
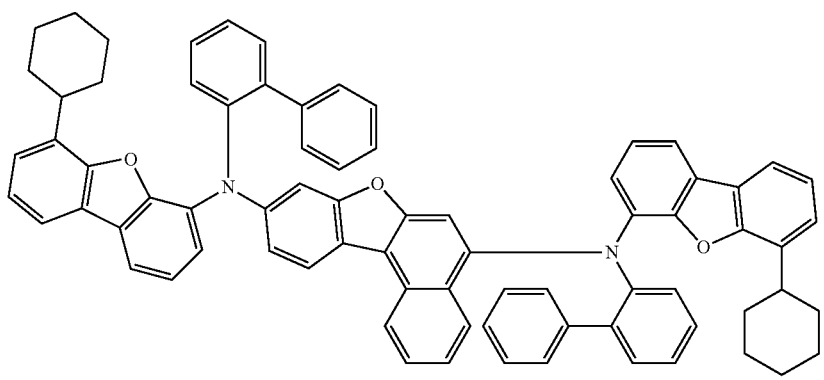
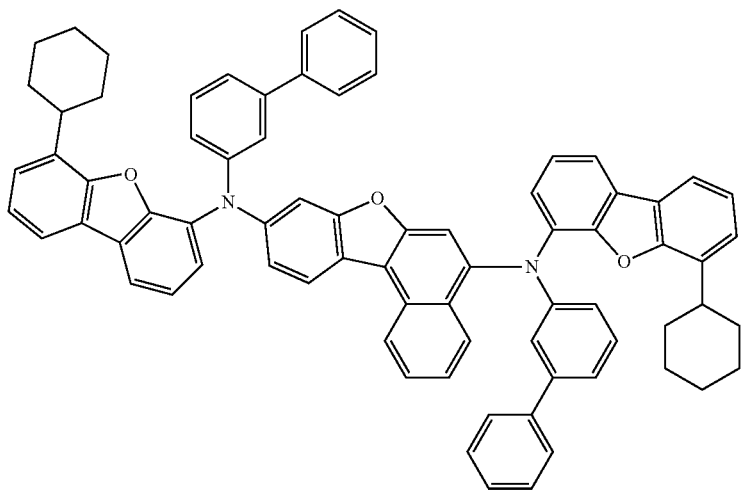
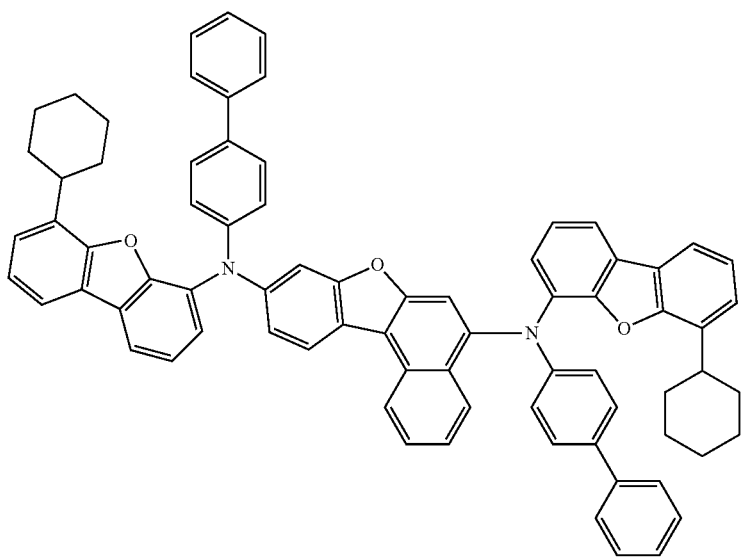

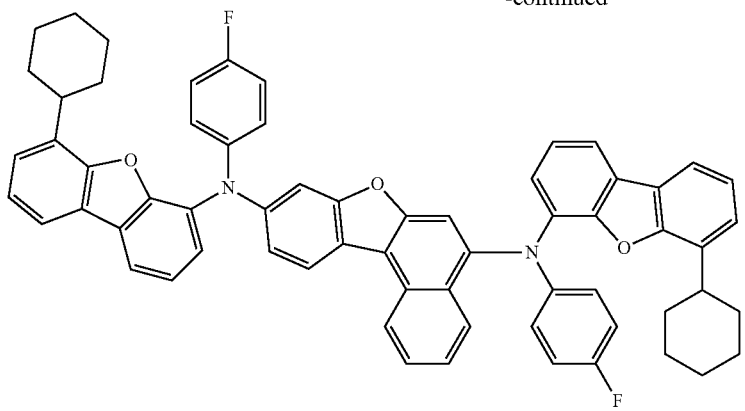
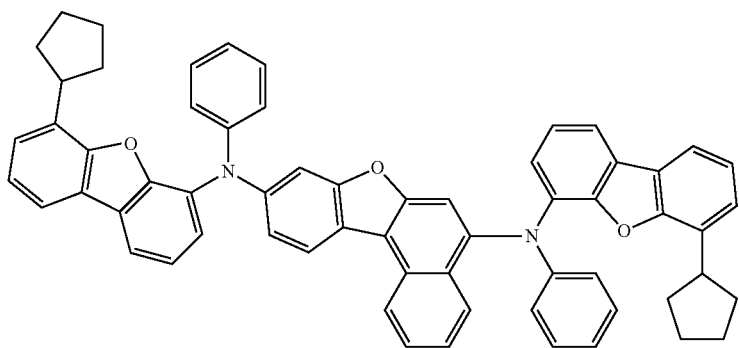
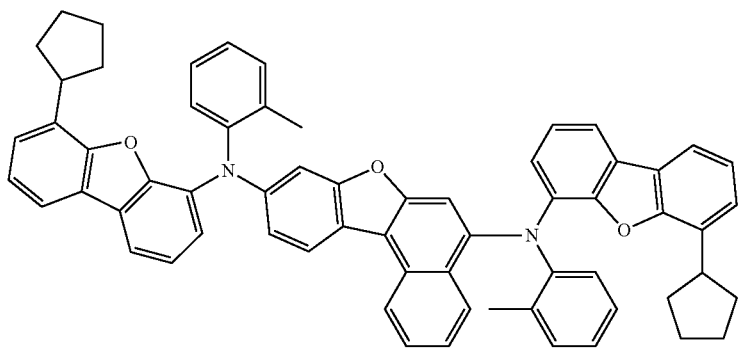
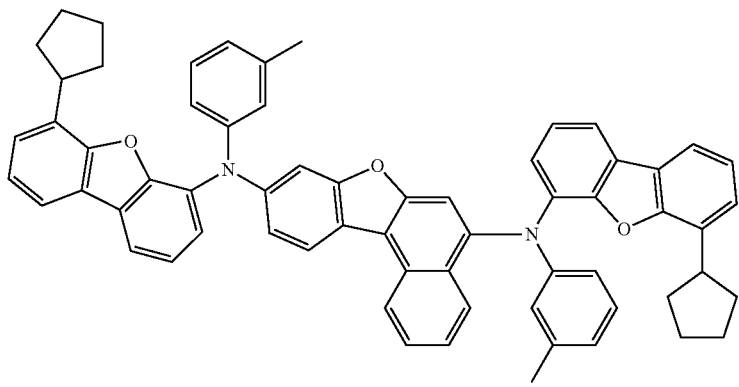

-continued
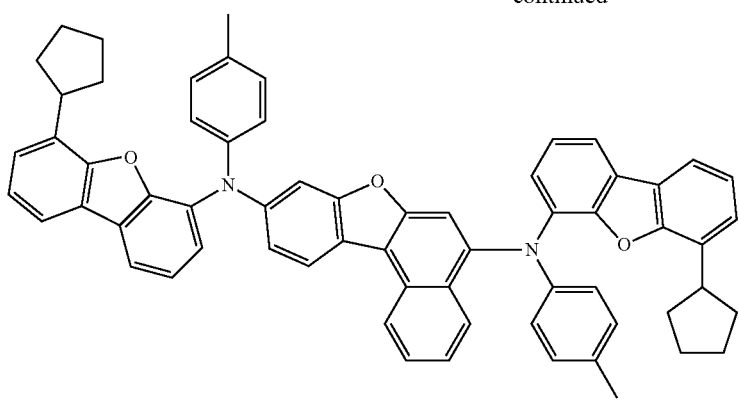
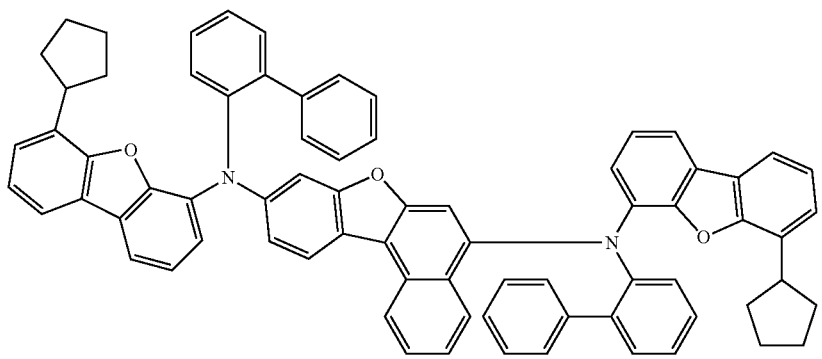
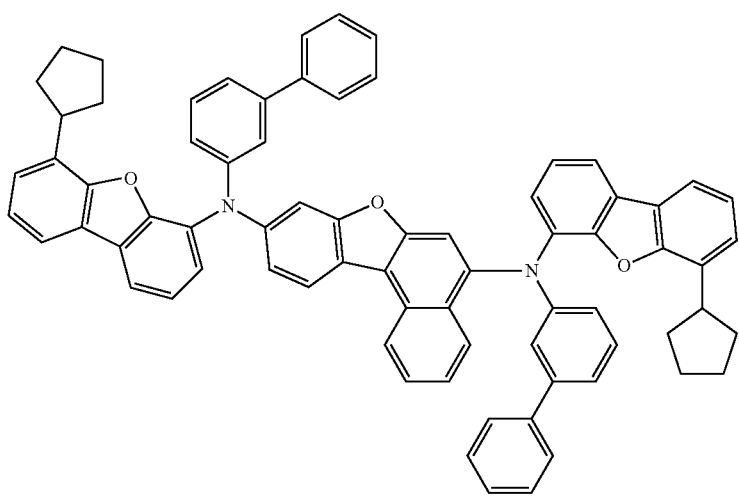

-continued
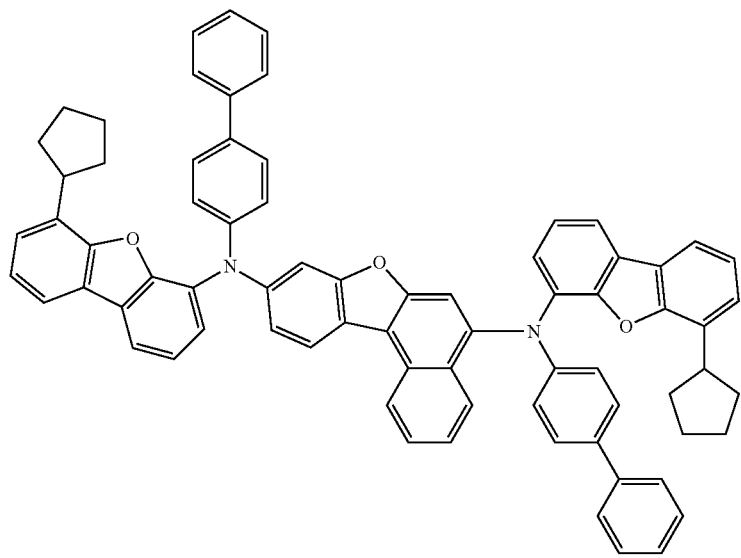
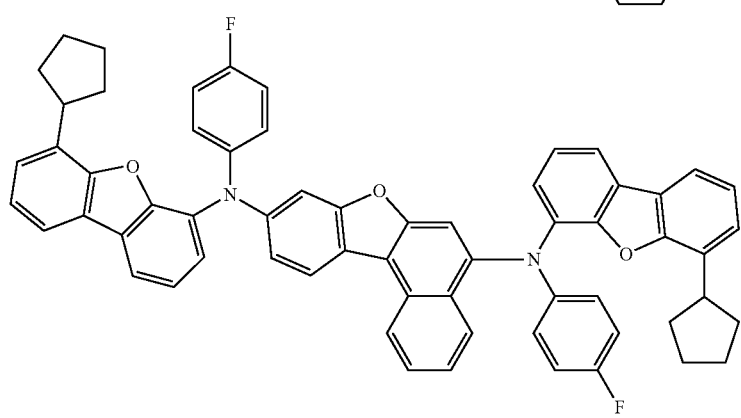
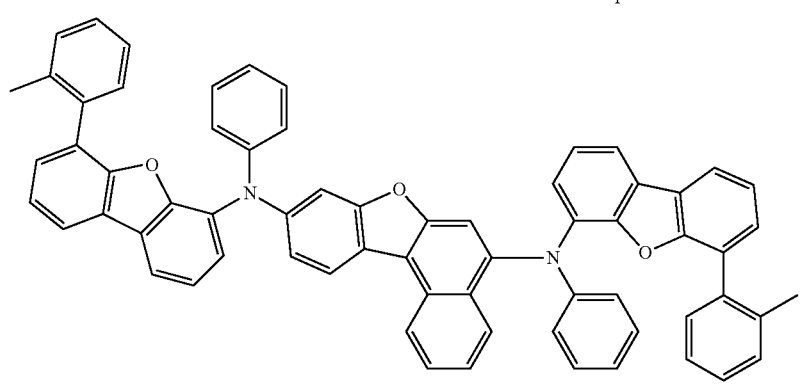
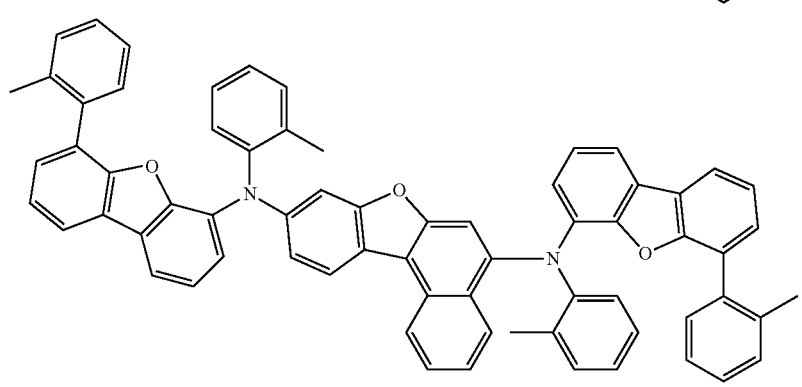

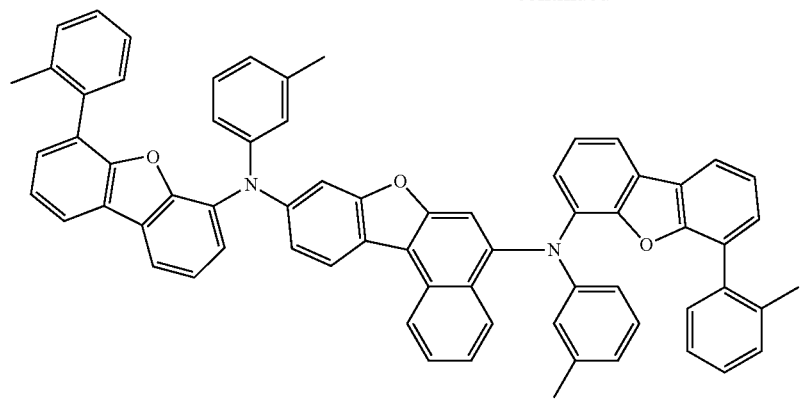
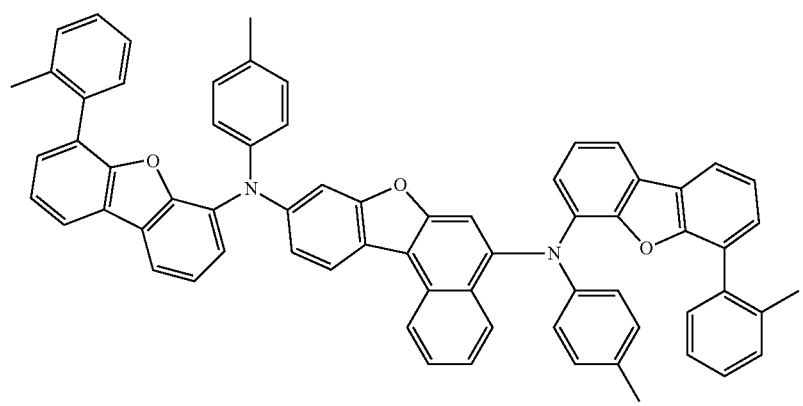
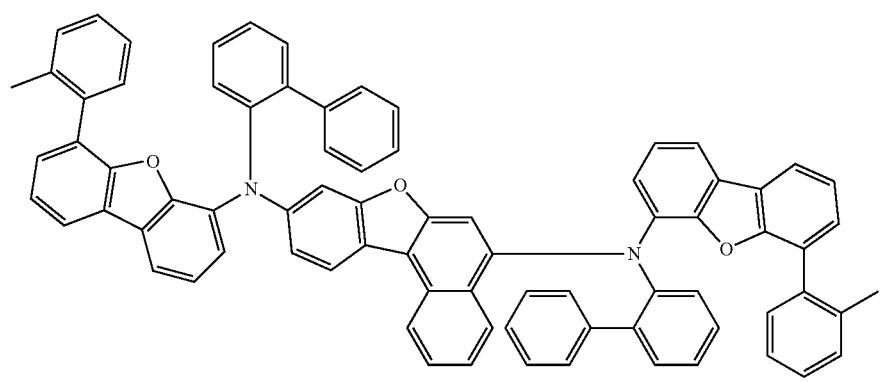
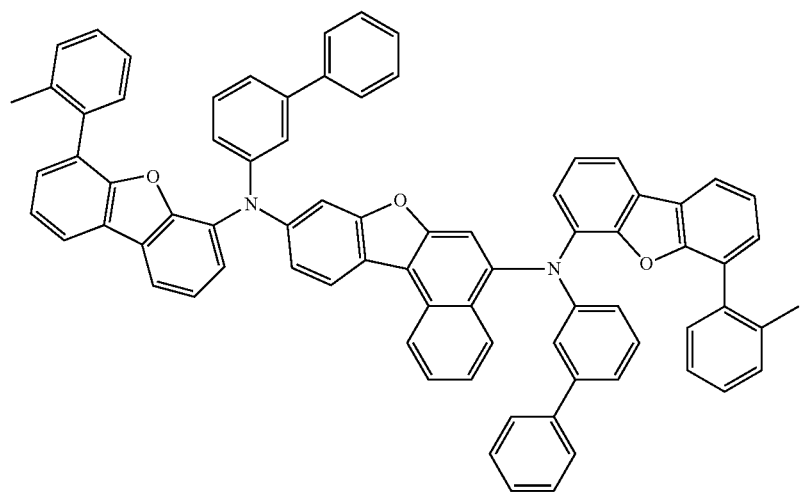

-continued
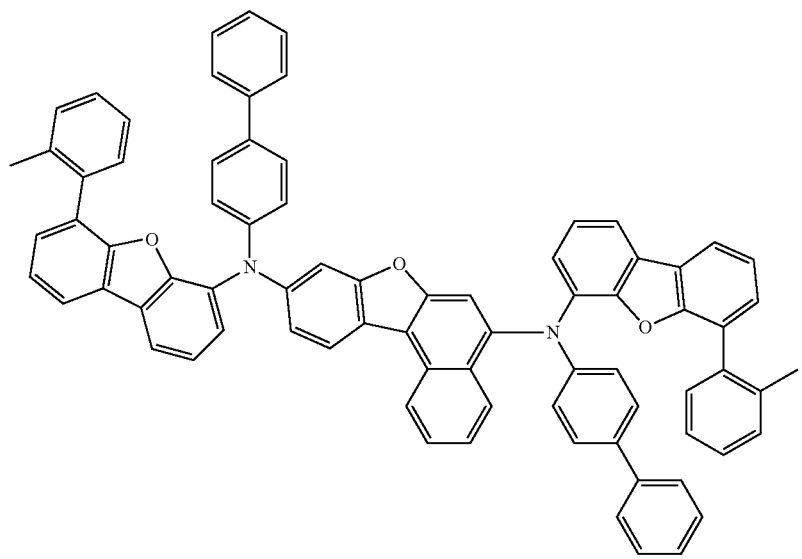
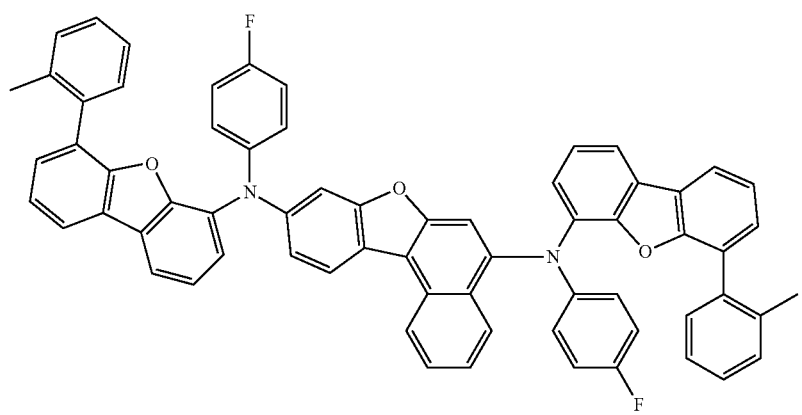
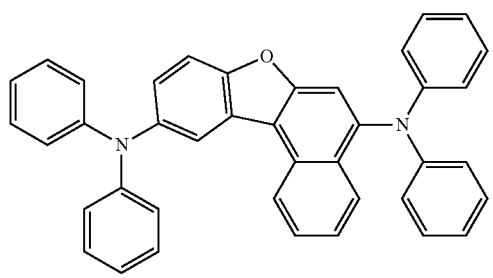 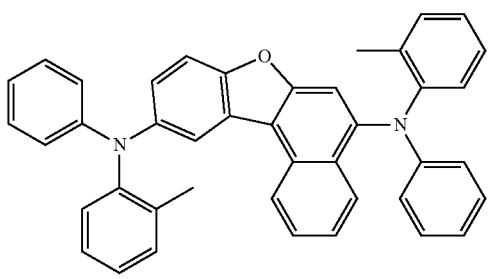
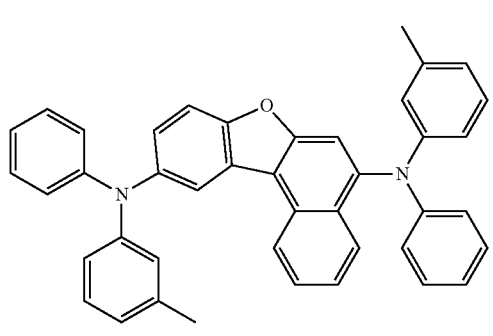 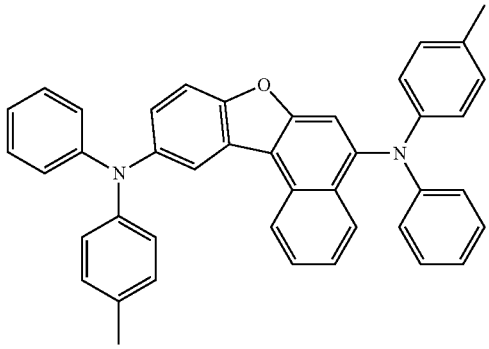

127
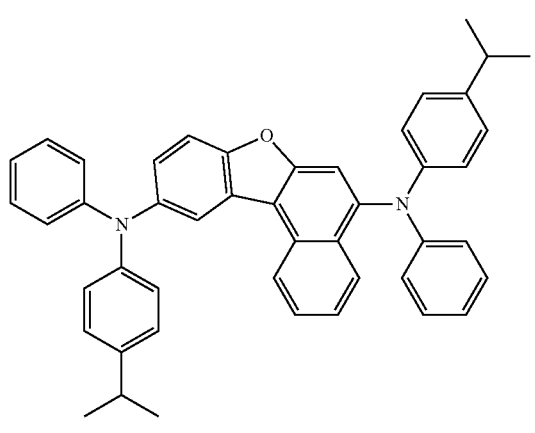
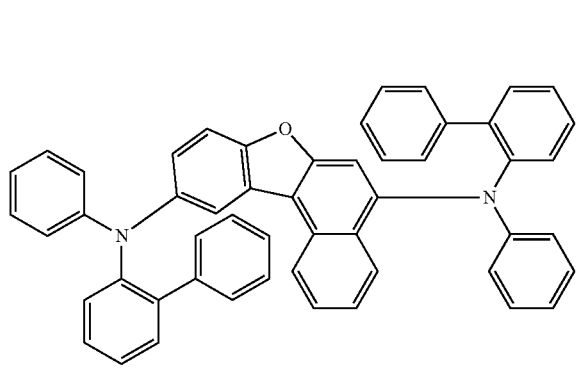
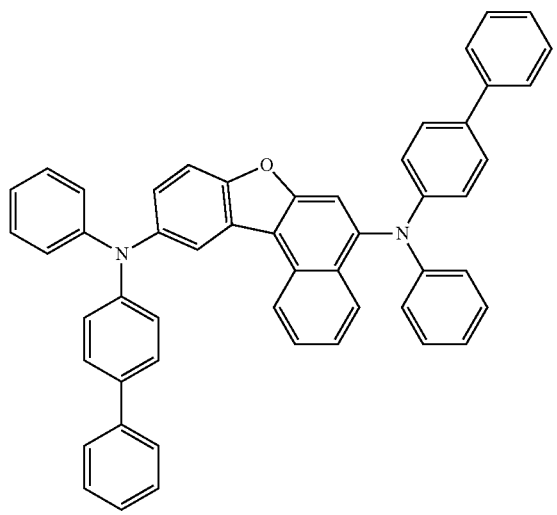
128
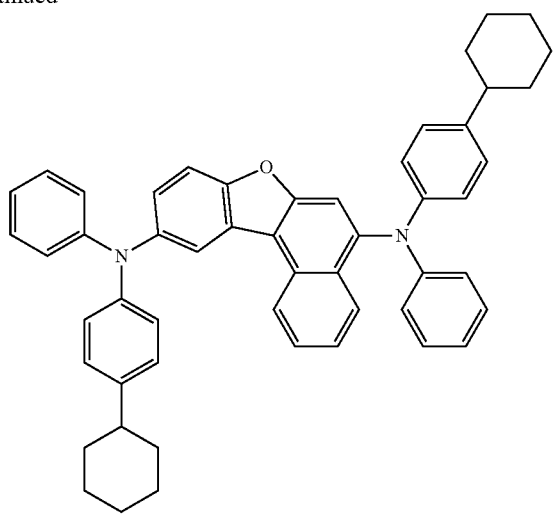
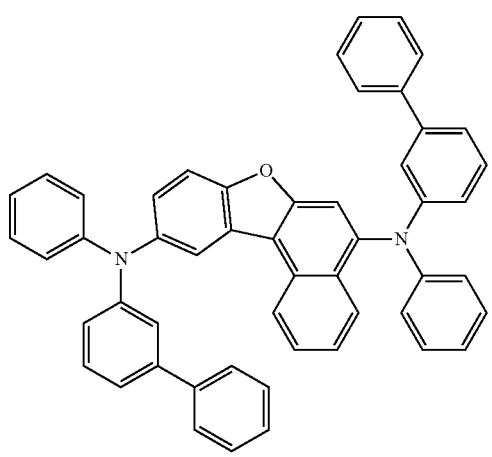
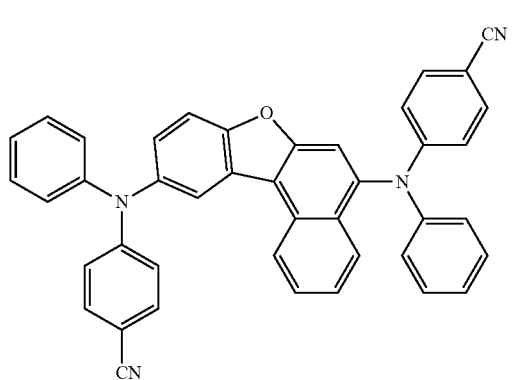

-continued
| 129 | 130 |
|---|---|
| 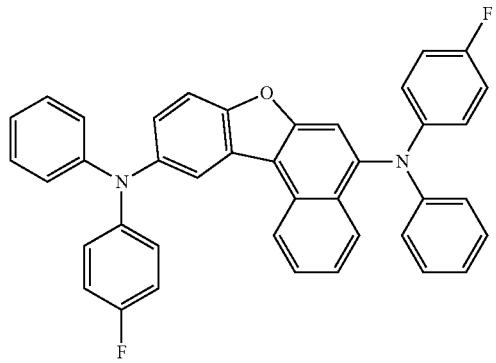 | 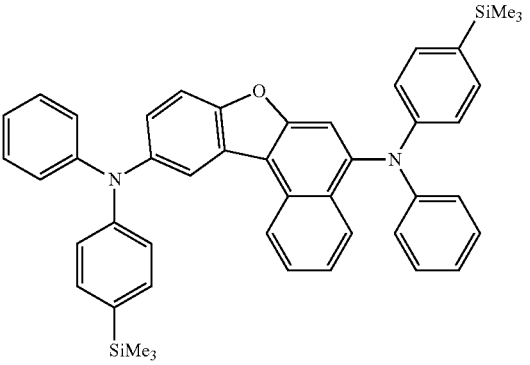 |
| 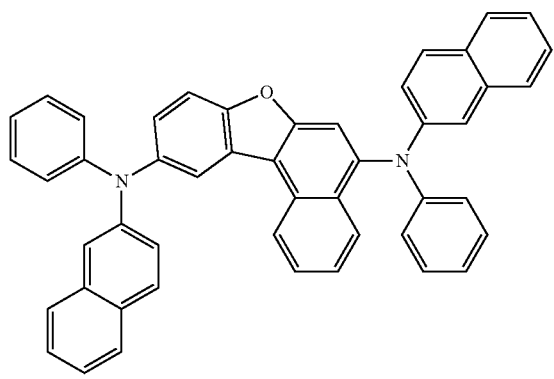 | 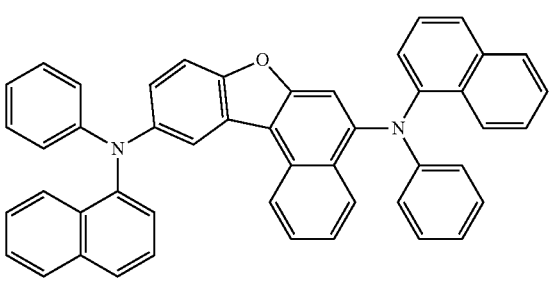 |
| 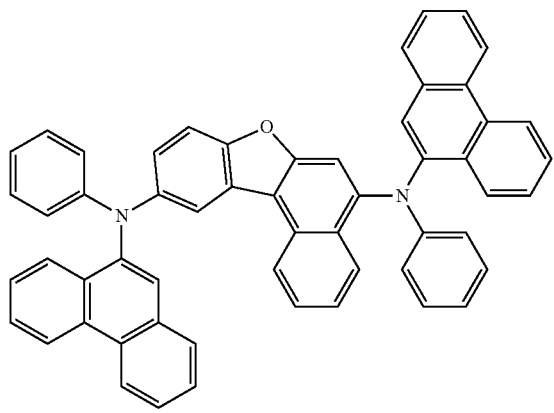 | |
| 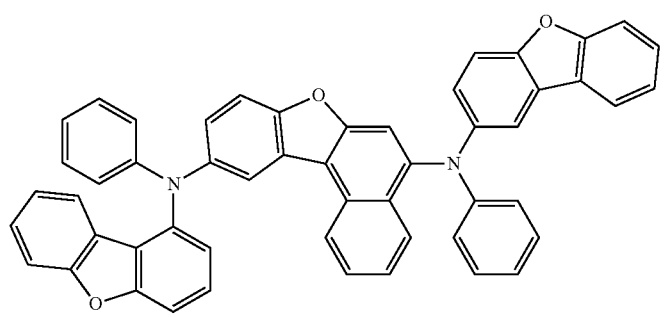 | |

-continued
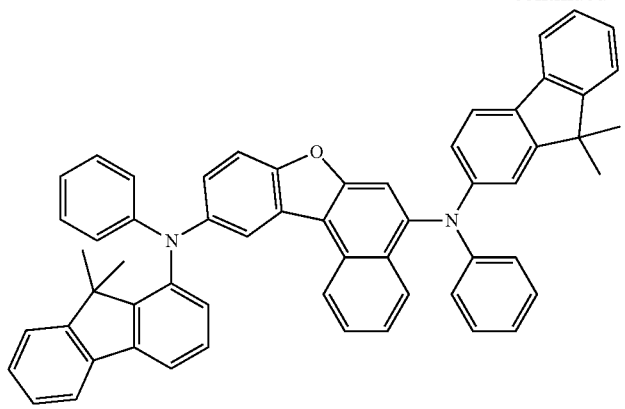
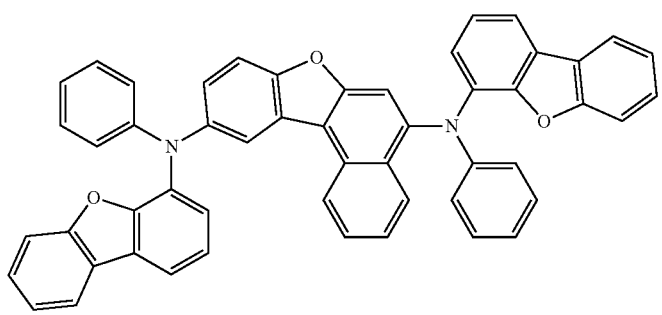
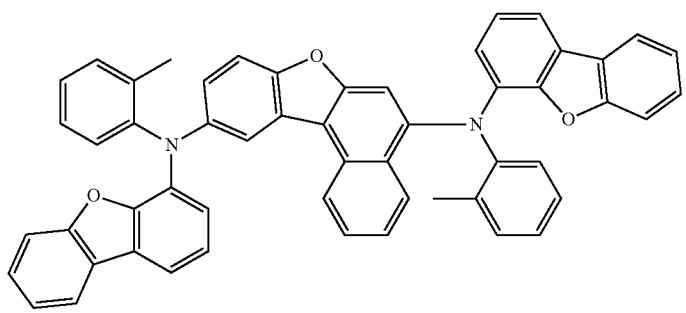
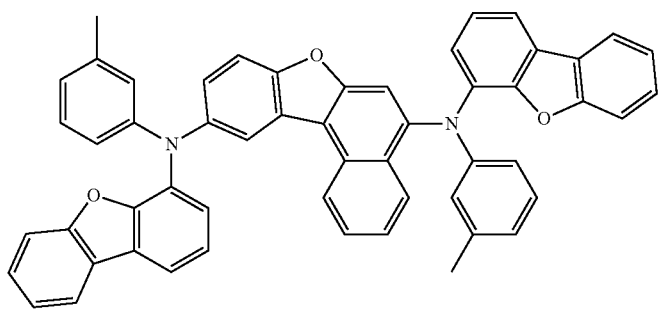
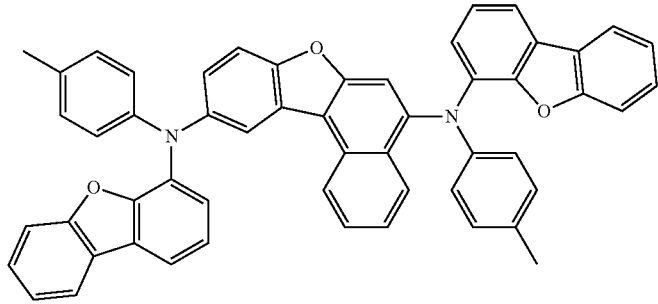

-continued
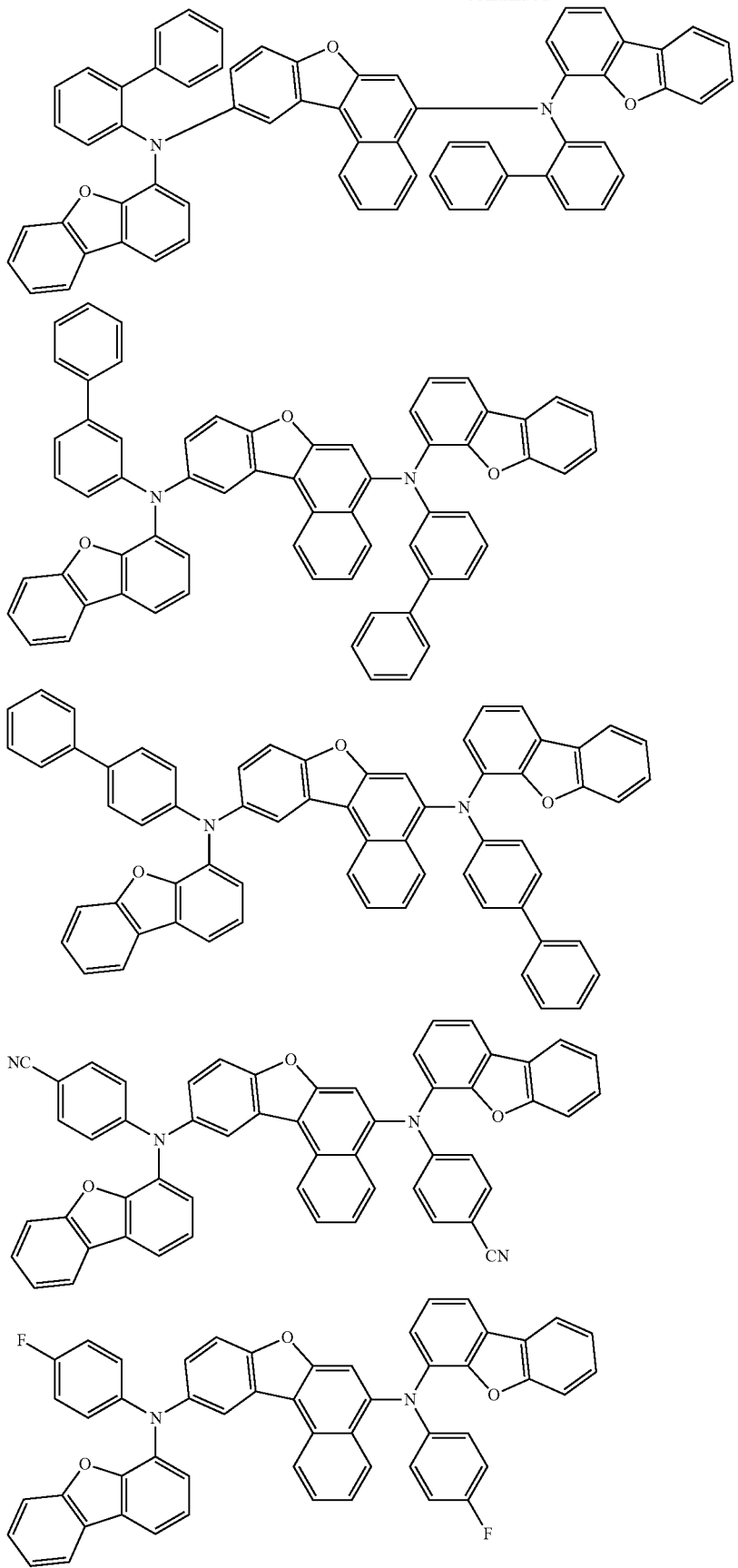

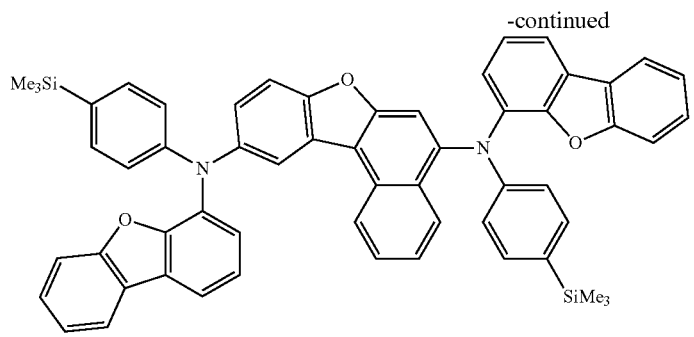
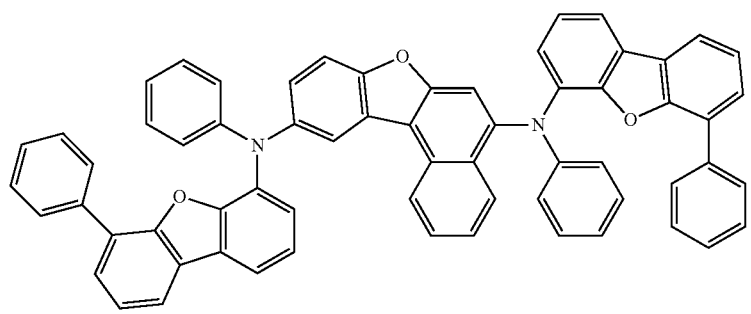
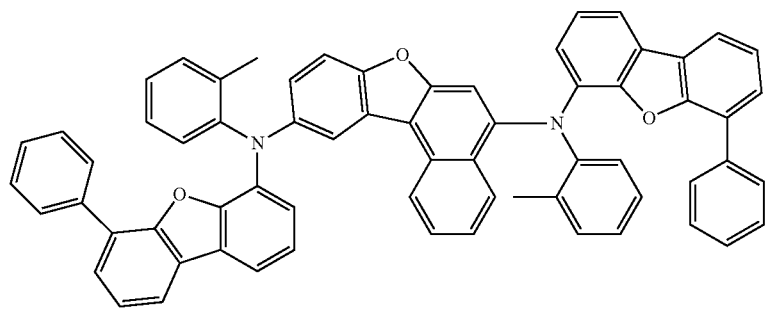
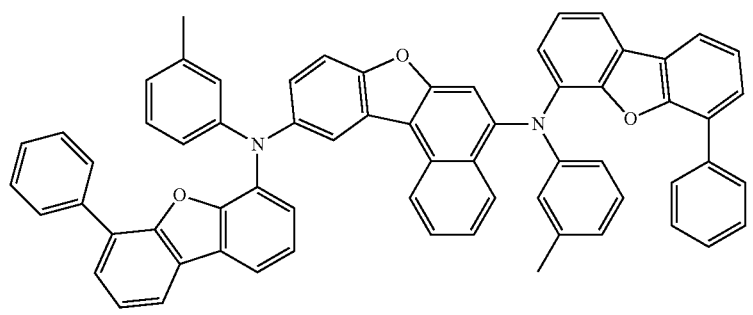
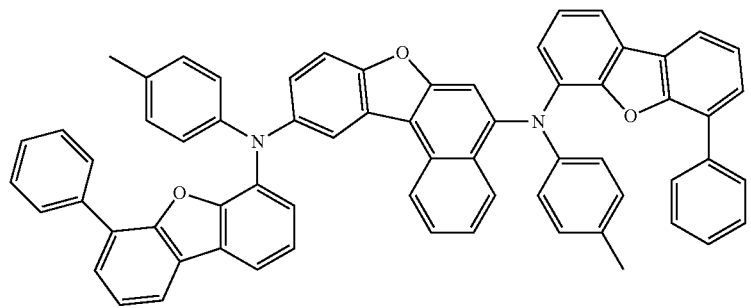

-continued
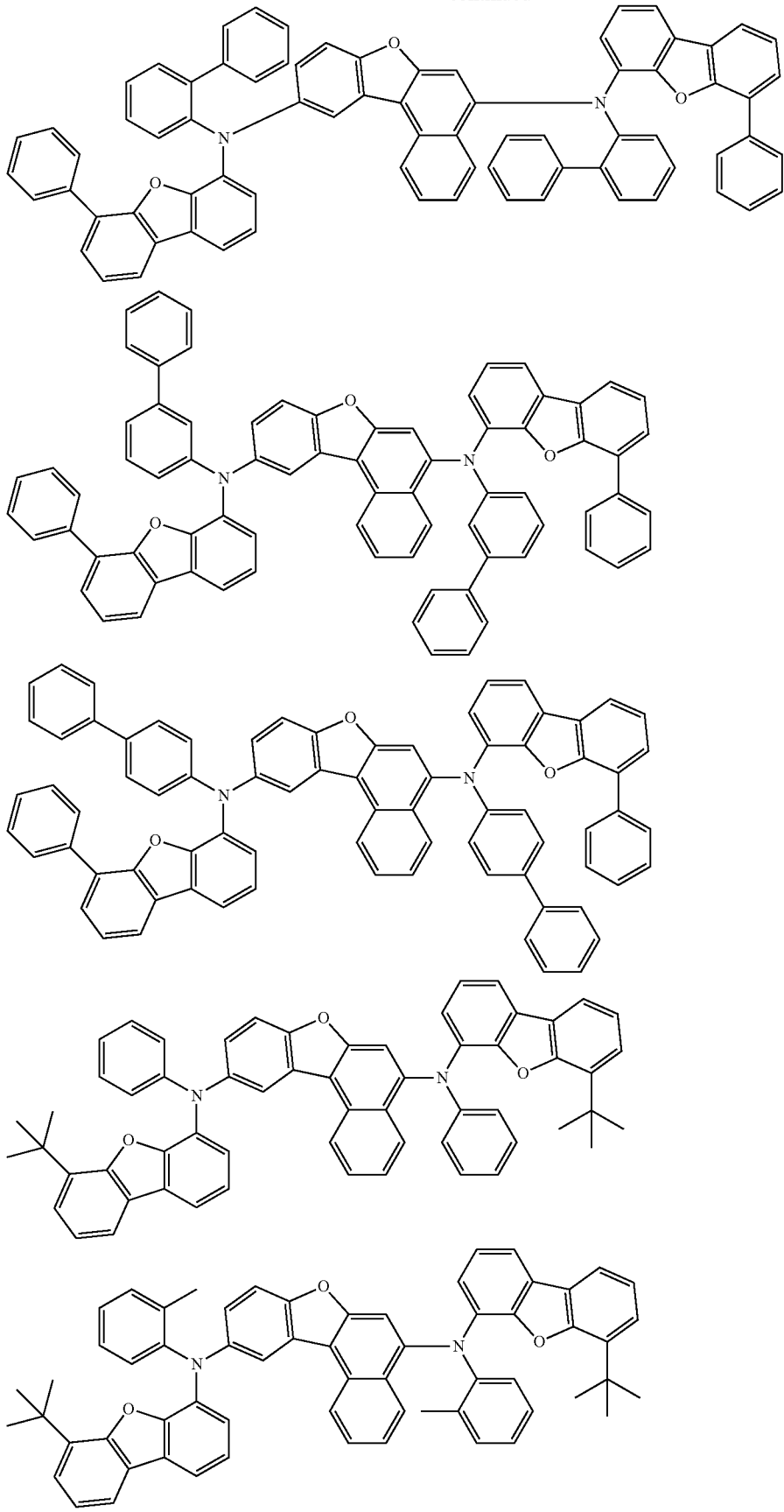

-continued
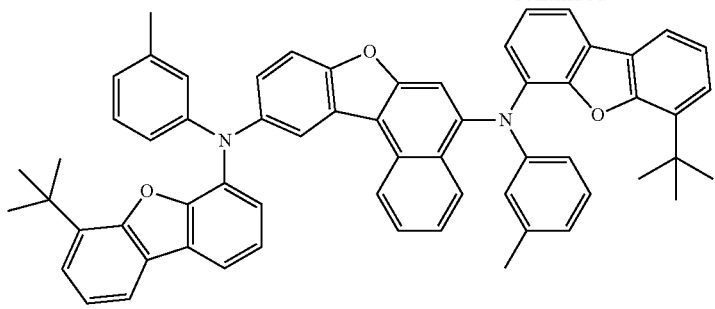
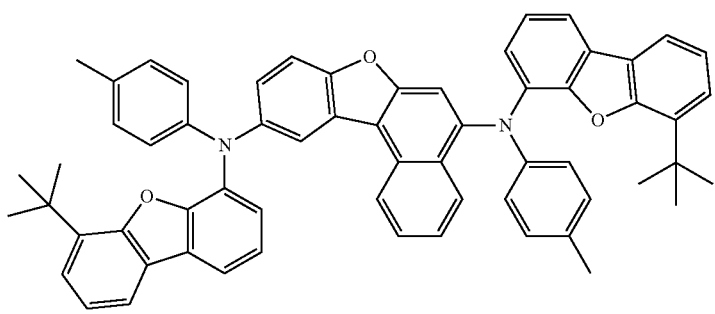
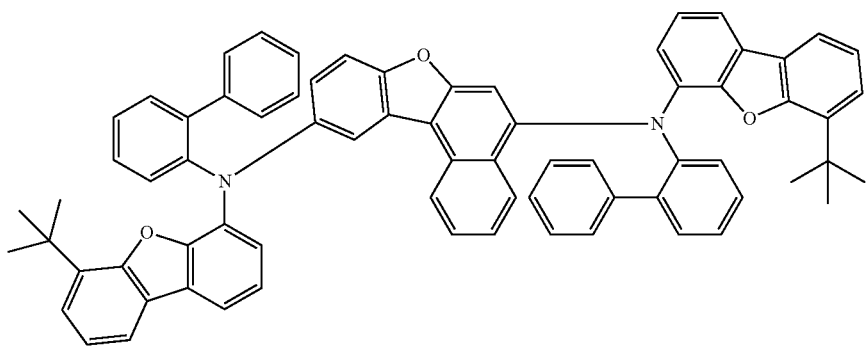
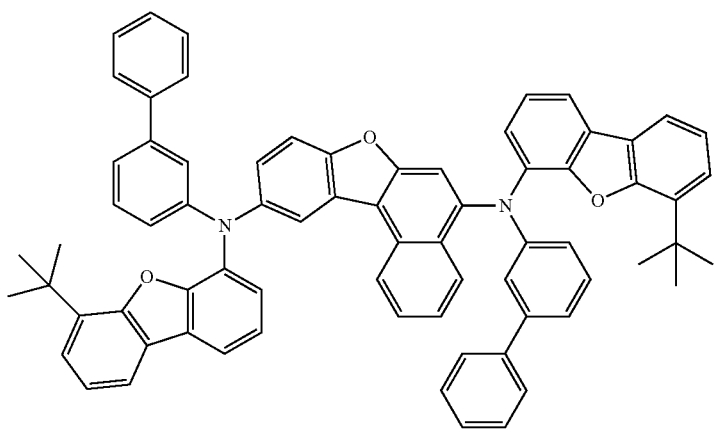

-continued
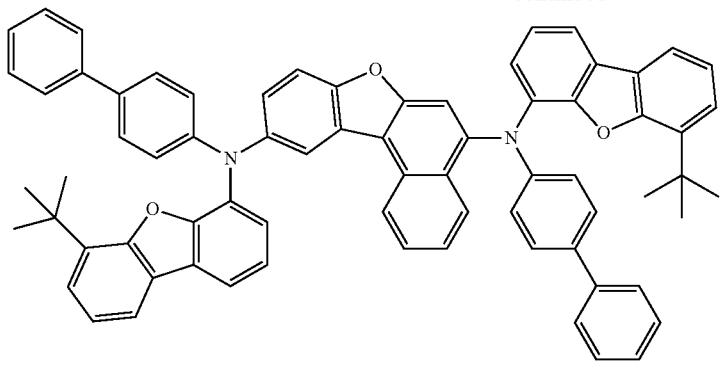
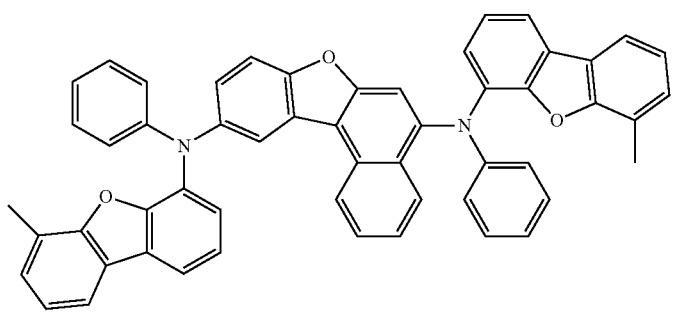
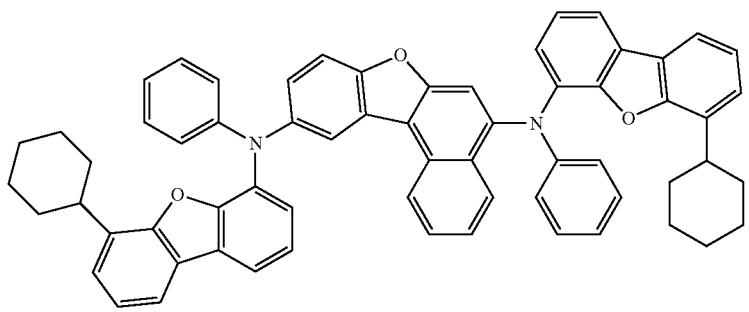
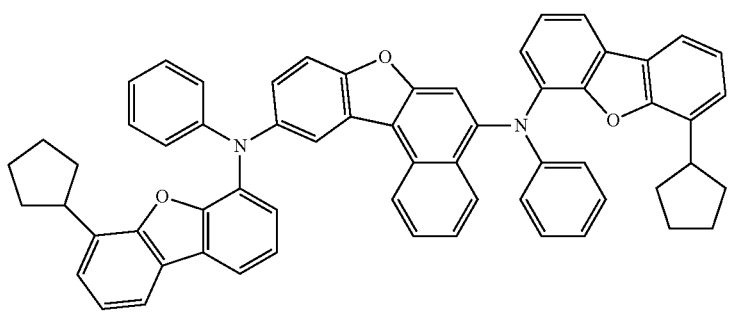
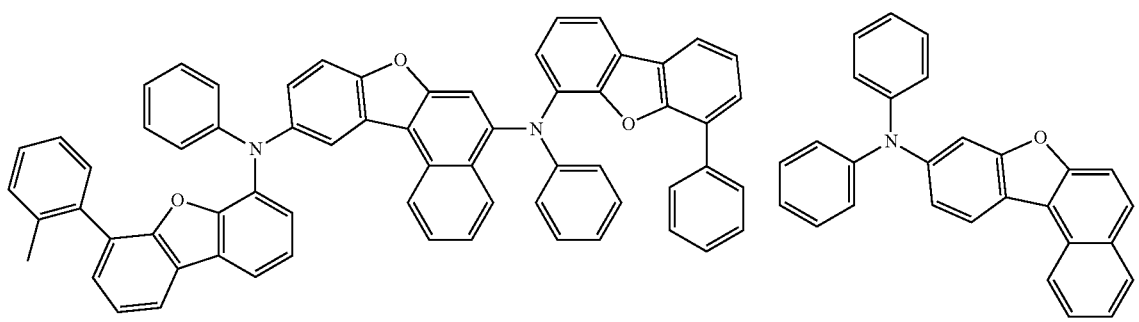

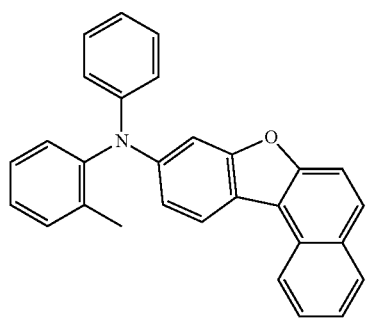
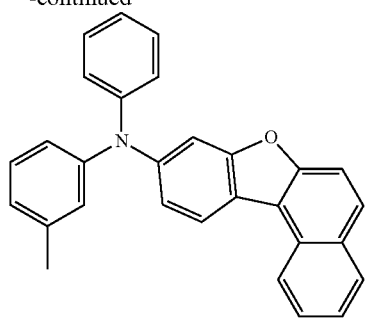
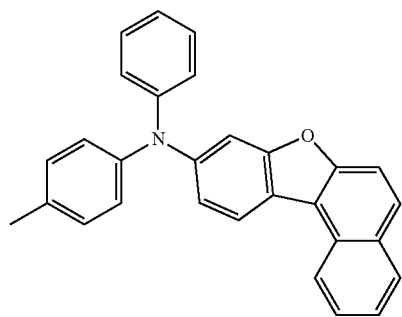
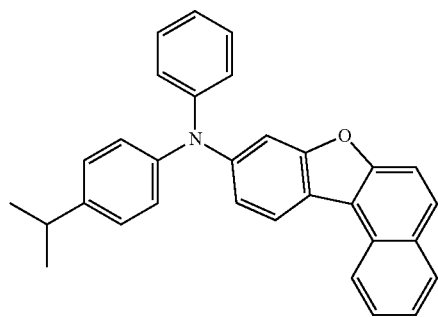
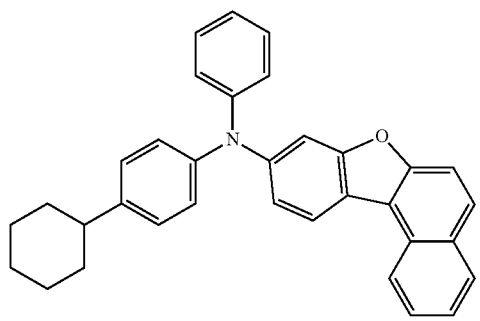
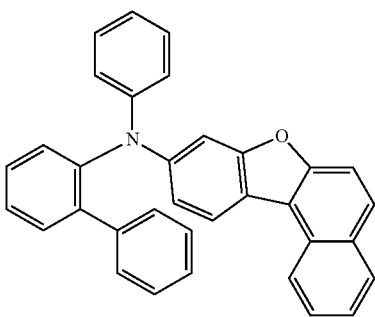
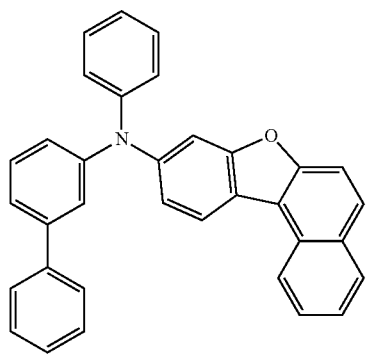
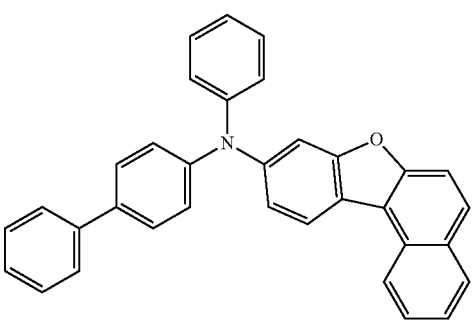
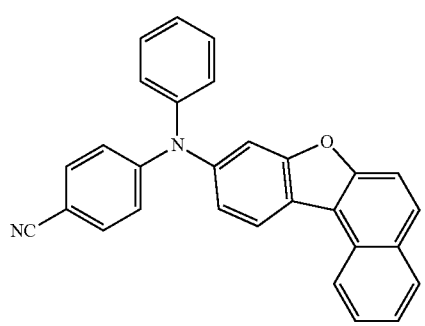
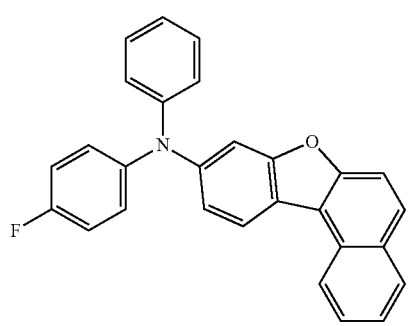

-continued
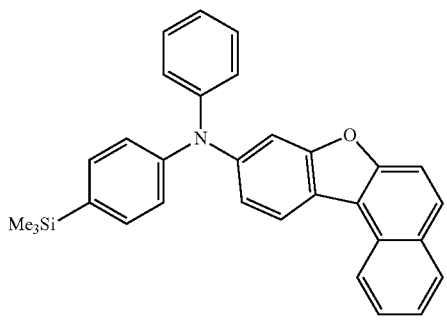 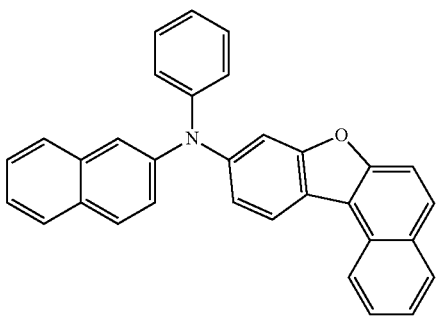
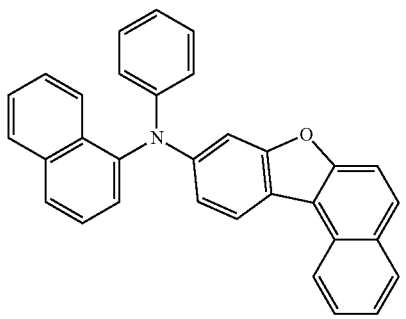 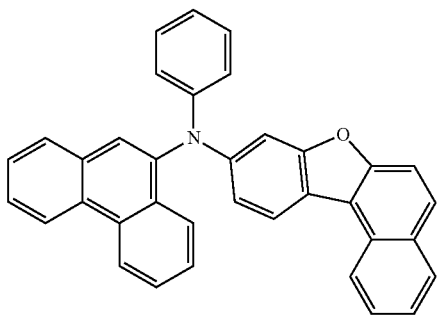
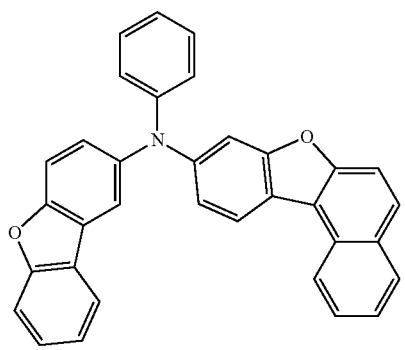 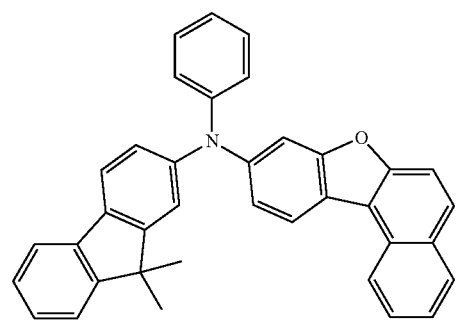
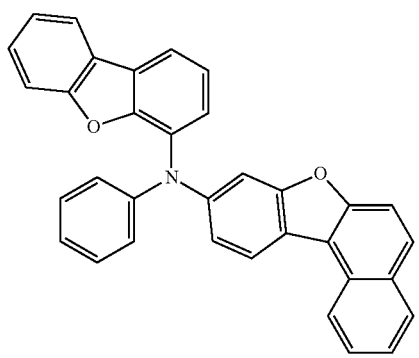 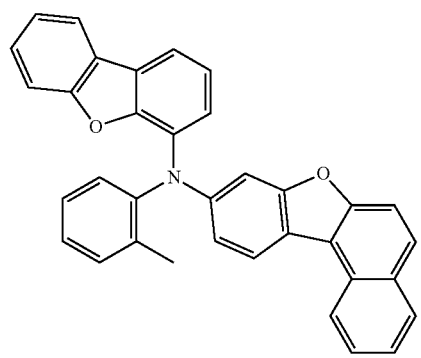
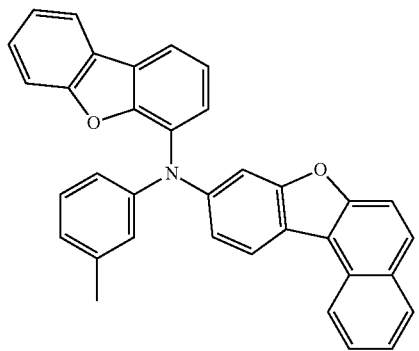 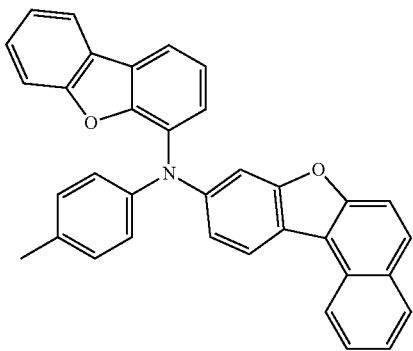

-continued
| 147 | 148 |
|---|---|
| 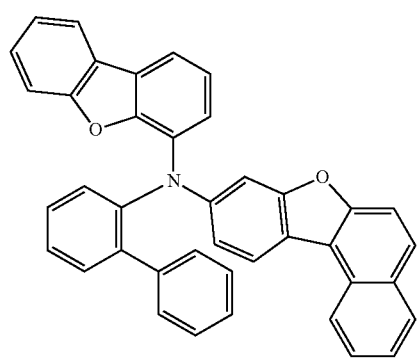 | 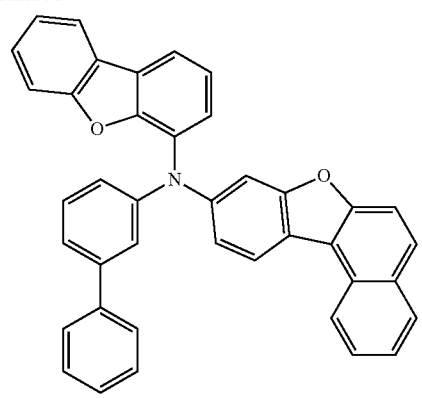 |
| 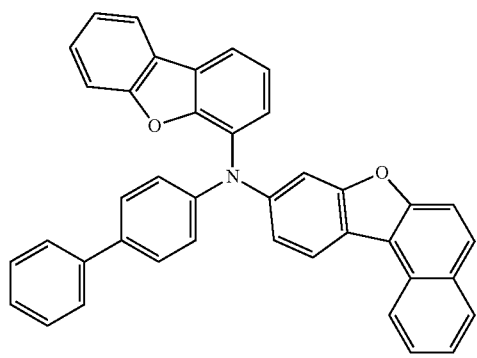 | 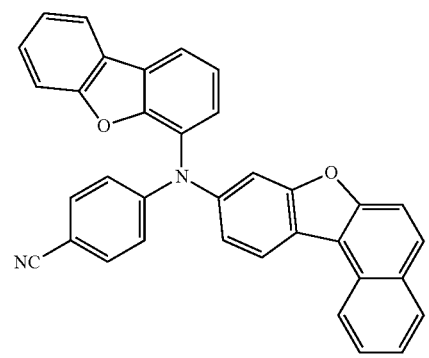 |
| 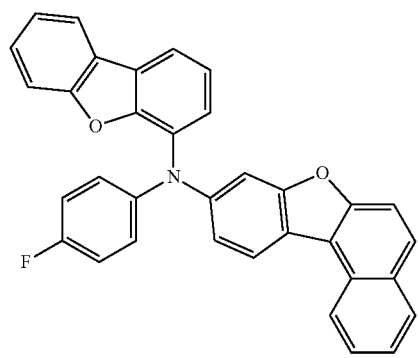 | 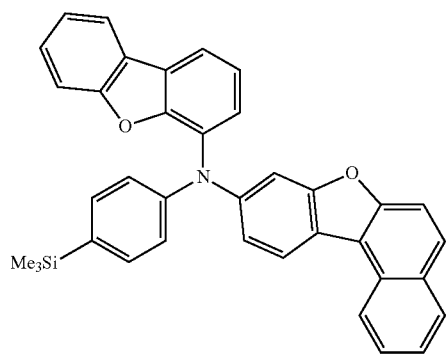 |
| 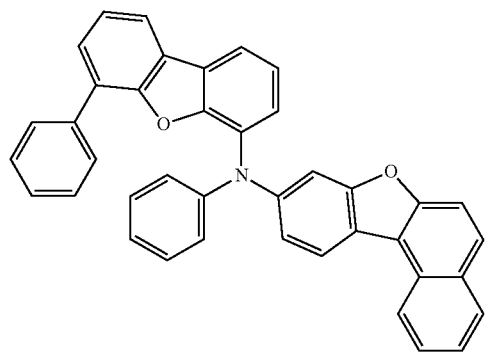 | 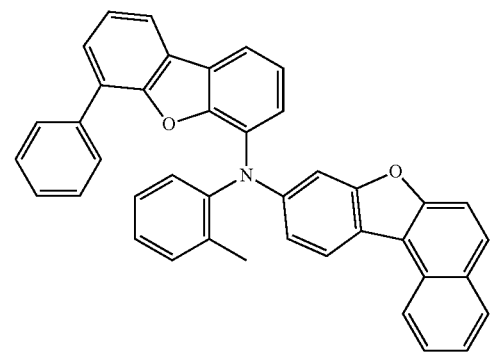 |

149
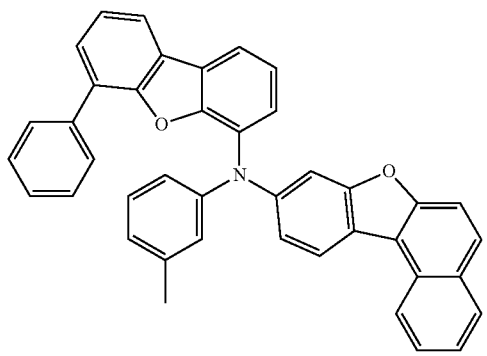
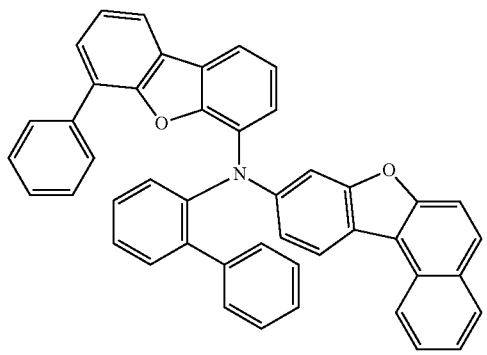
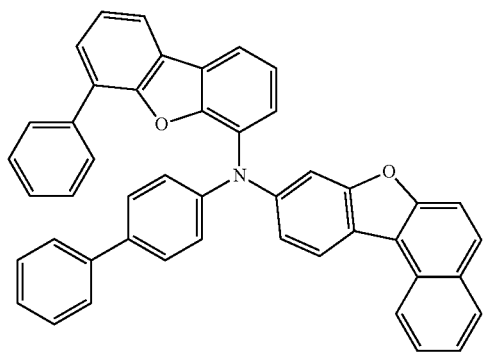
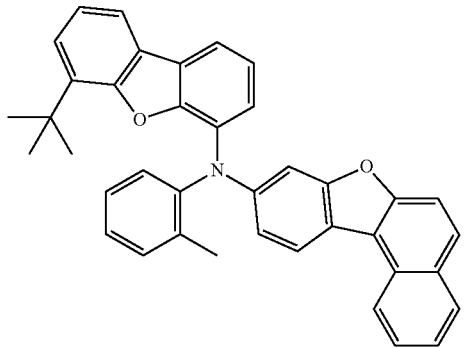
150
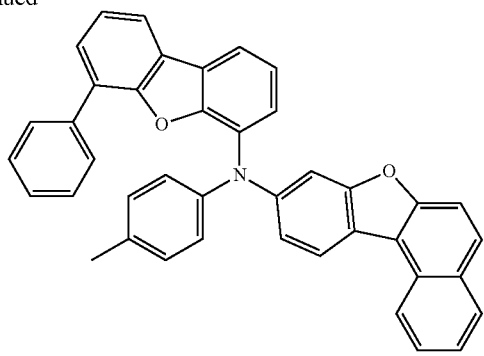
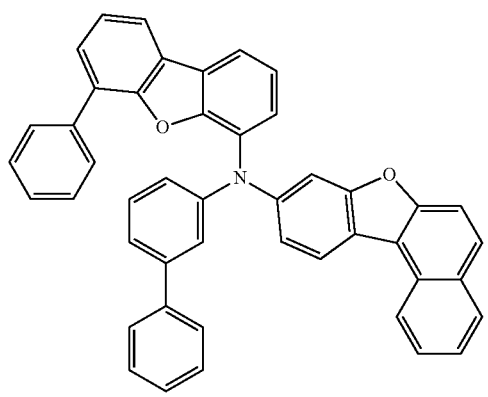
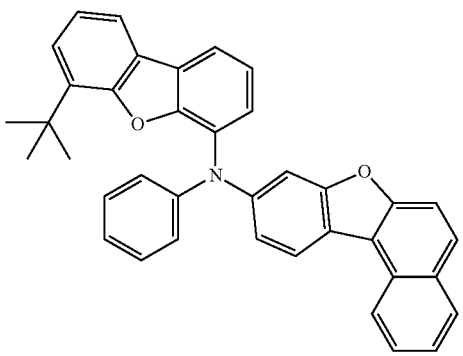
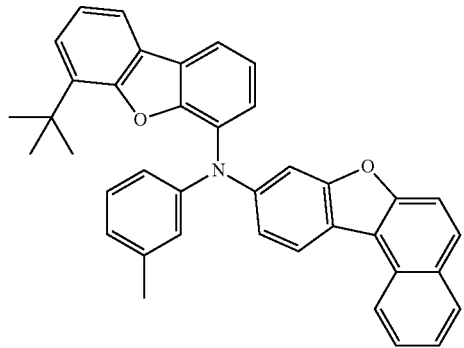

-continued
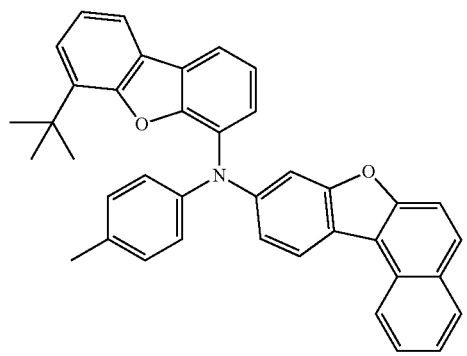
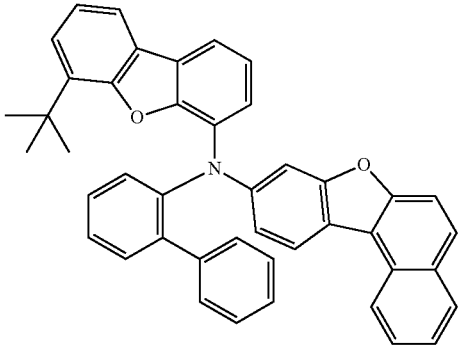
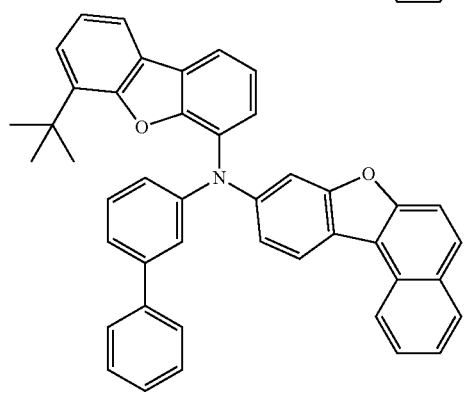
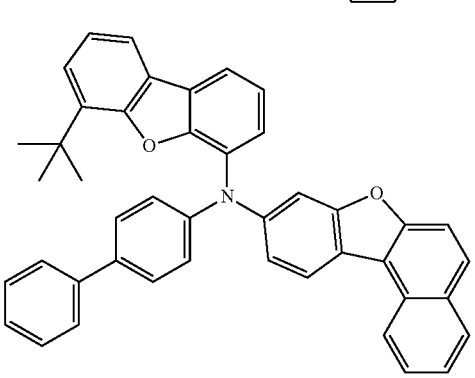
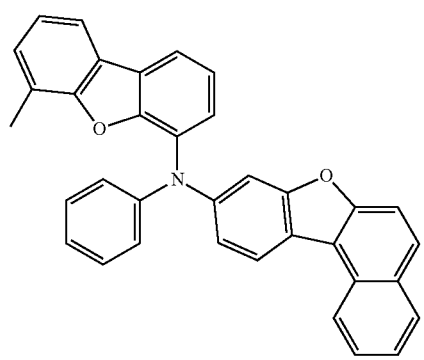
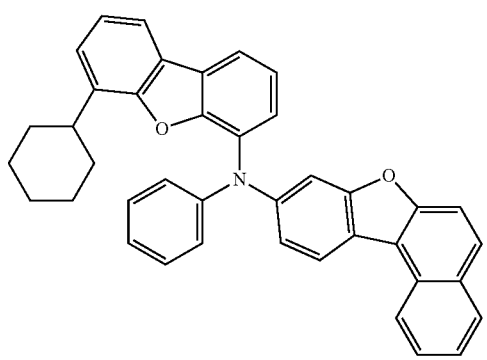
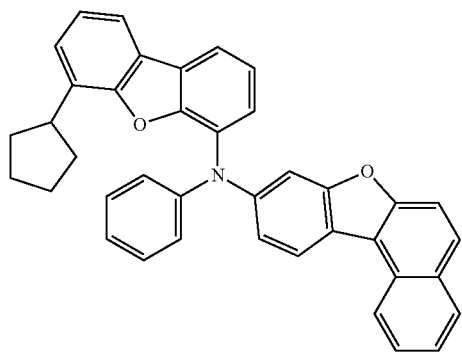
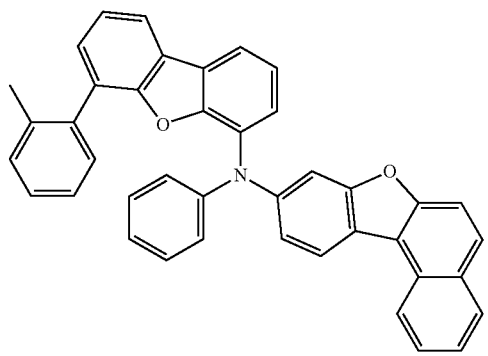
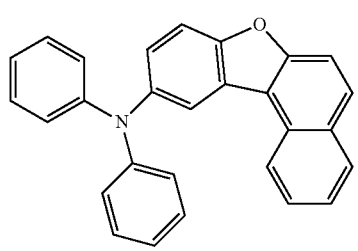
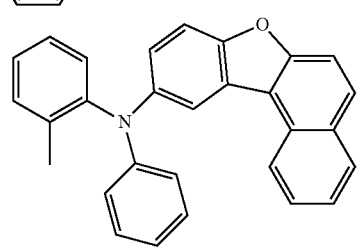
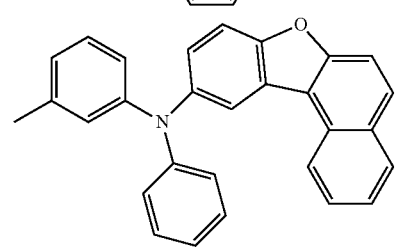

-continued
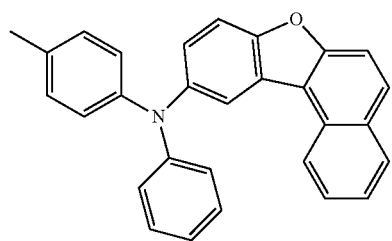
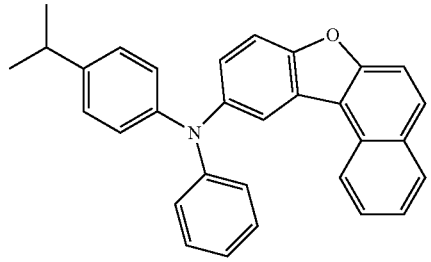
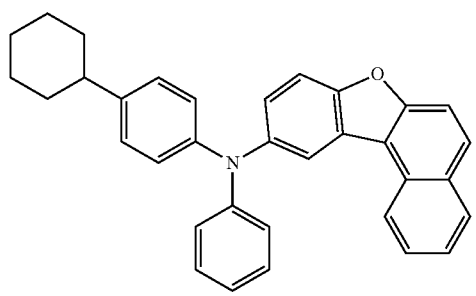
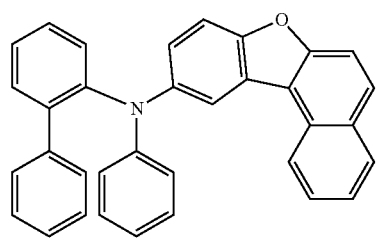
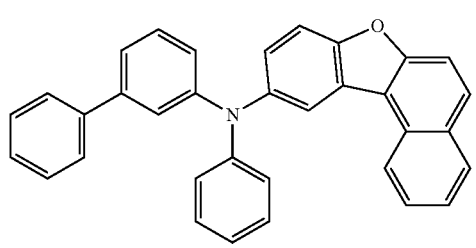
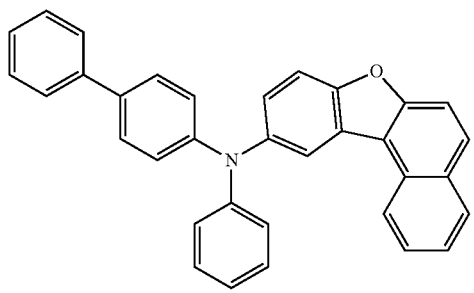
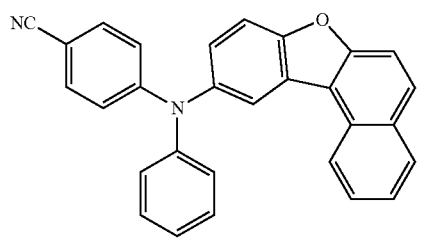
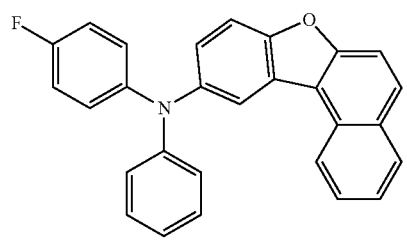
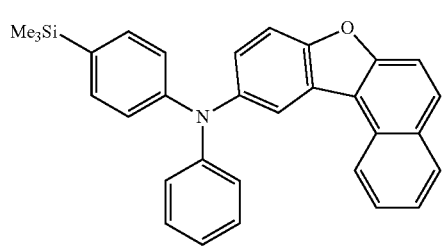
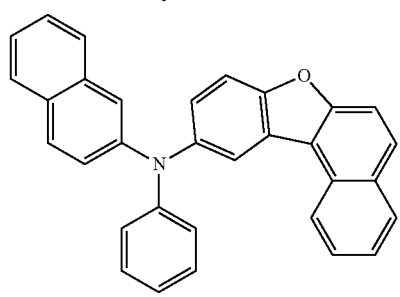
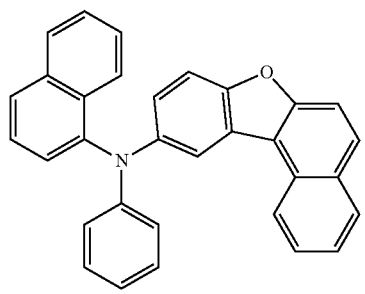
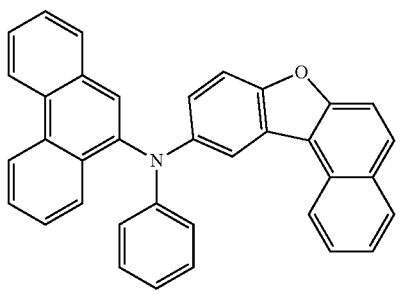

-continued
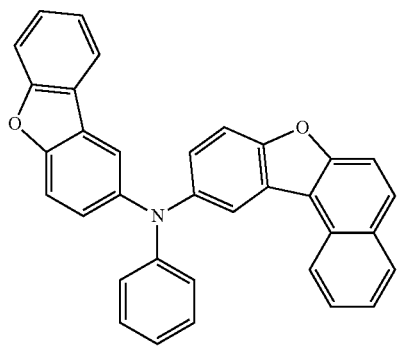 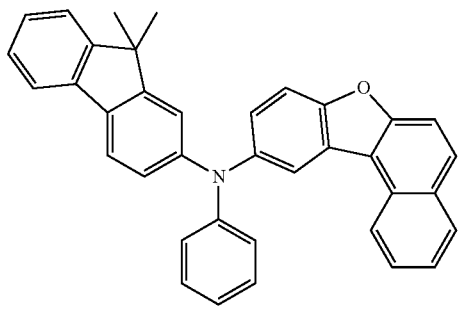
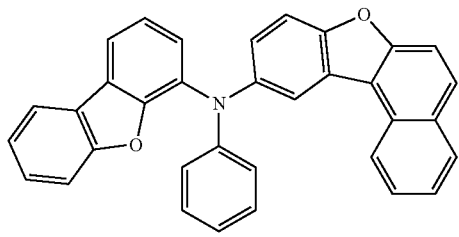 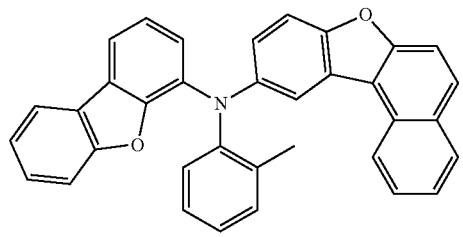
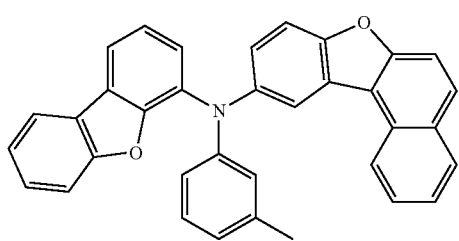 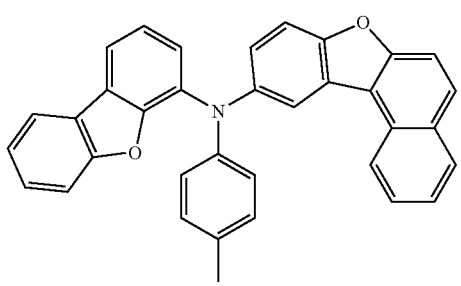
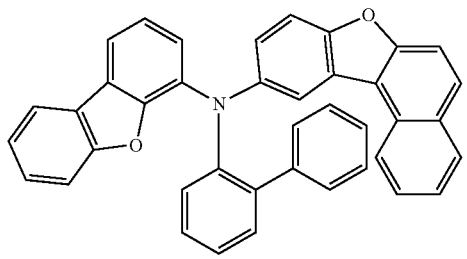 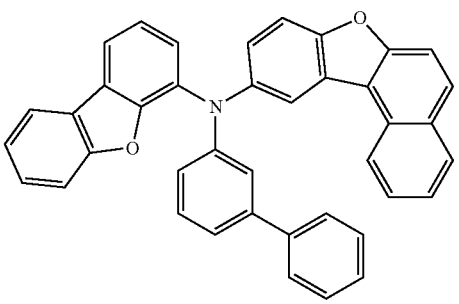
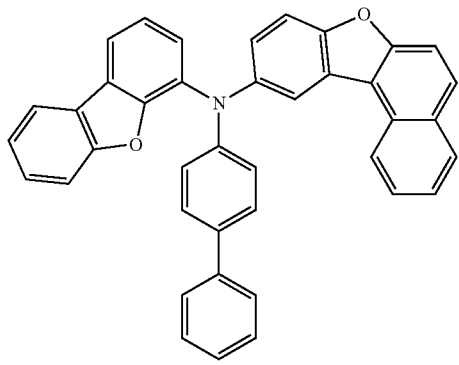 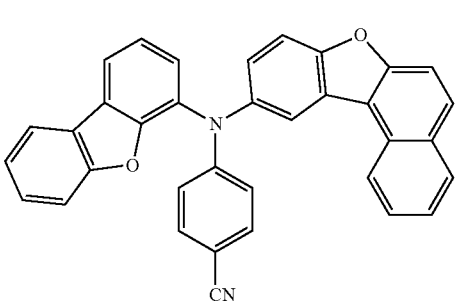

-continued
157
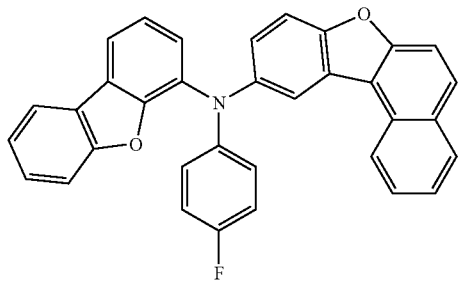
158
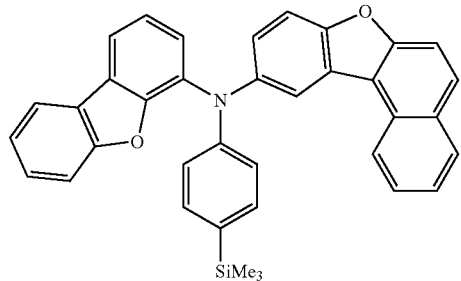
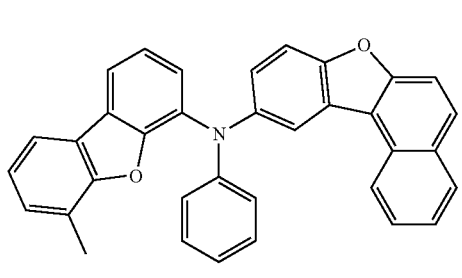
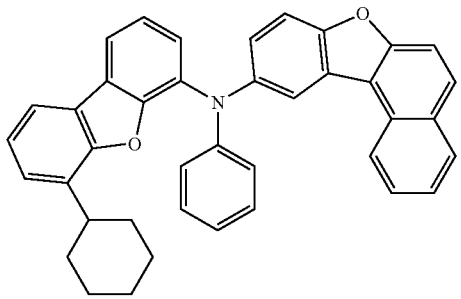
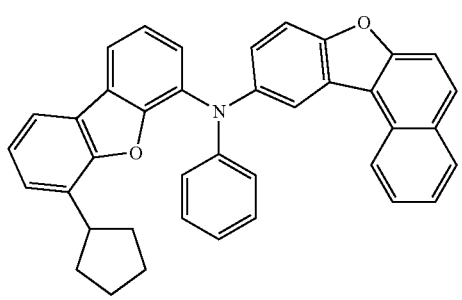
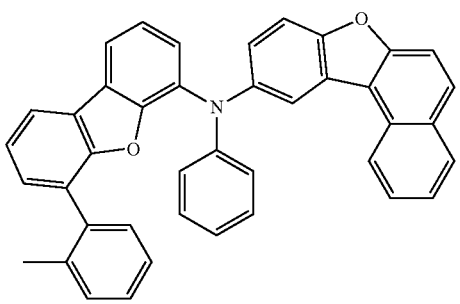
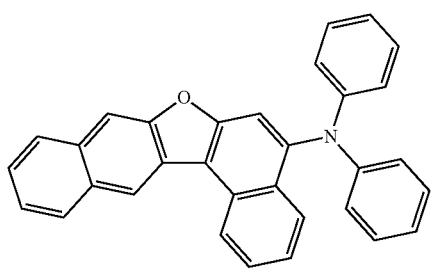
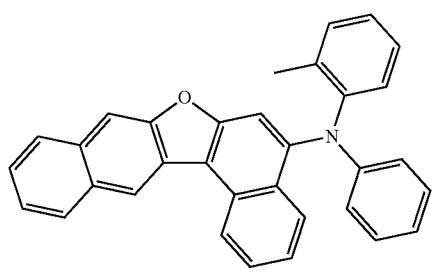
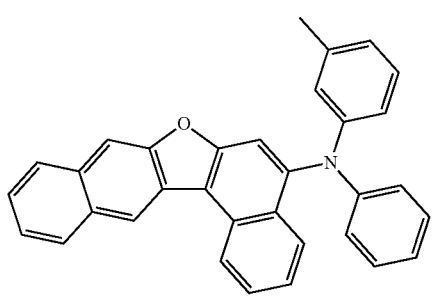
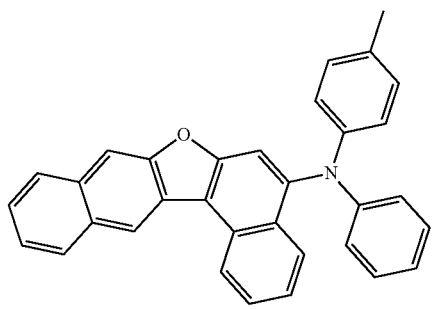

159                                                                  160
-continued
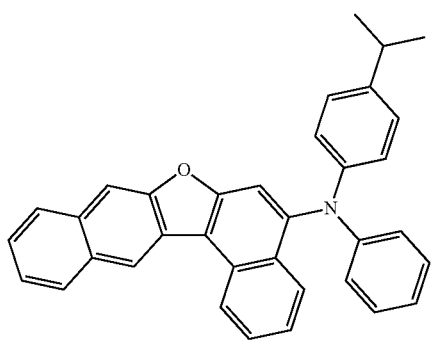 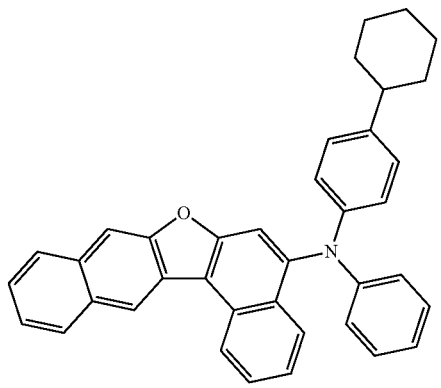
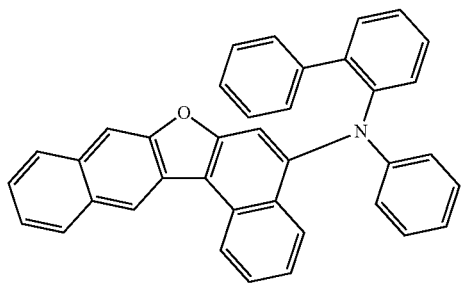 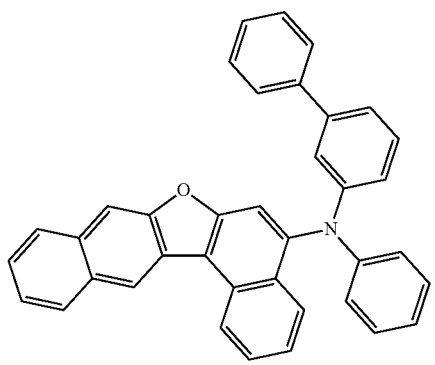
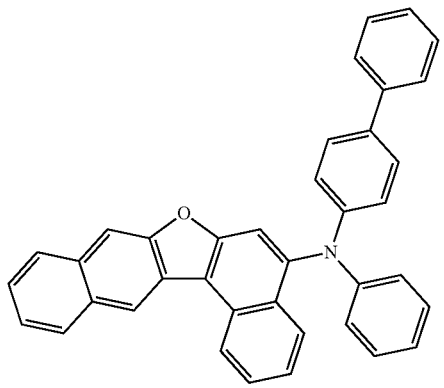 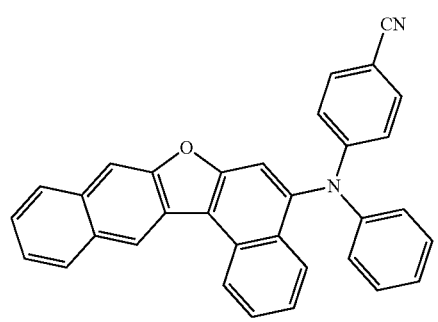
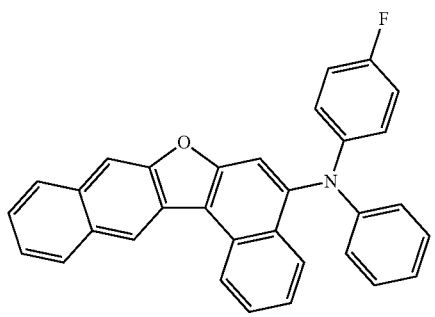 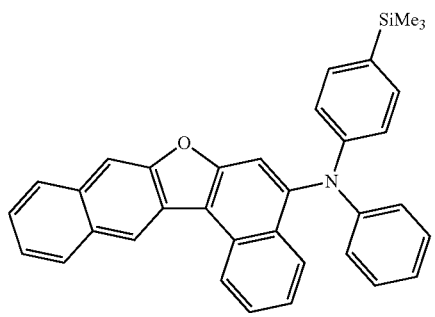

-continued
161
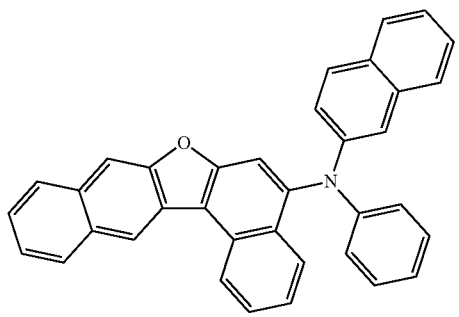
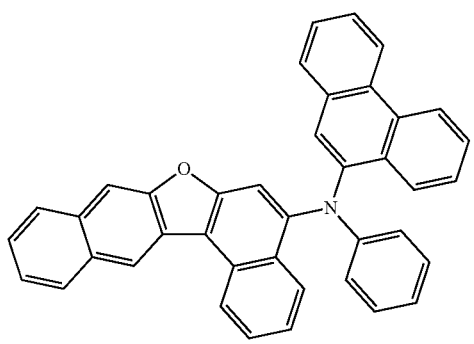
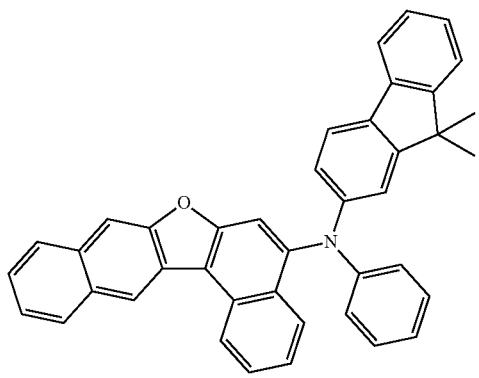
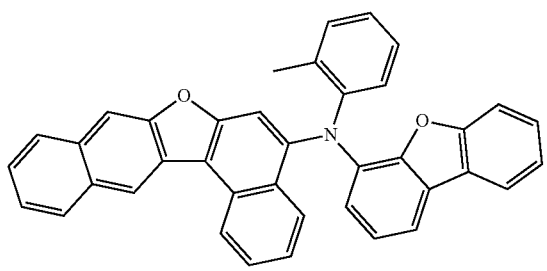
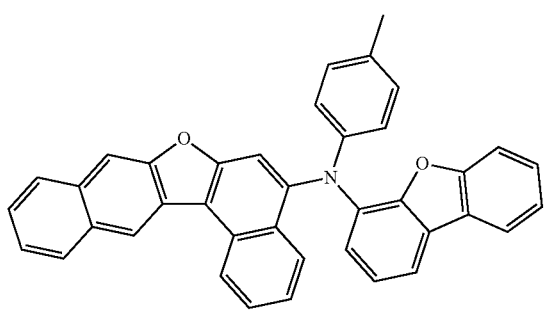
162
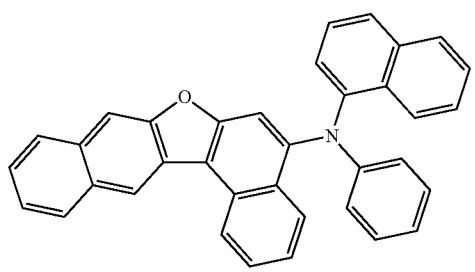
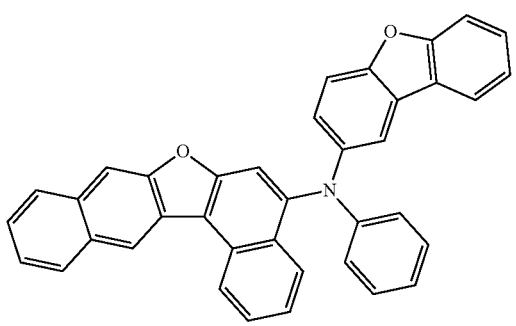
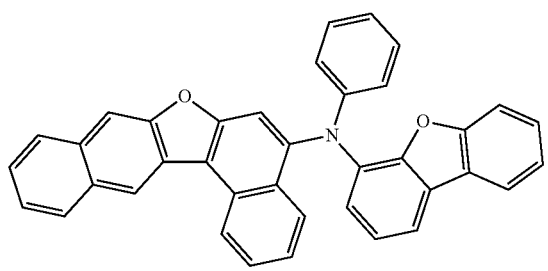
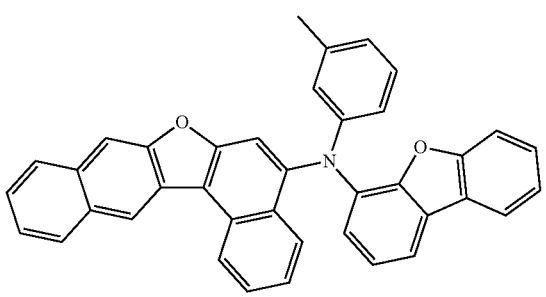
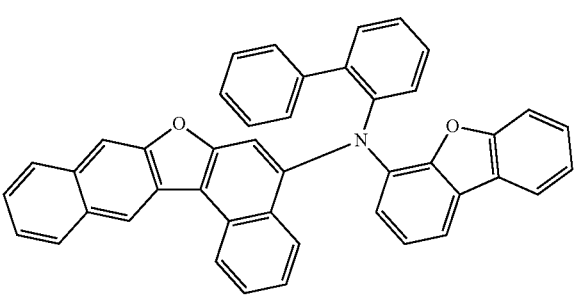

-continued
163
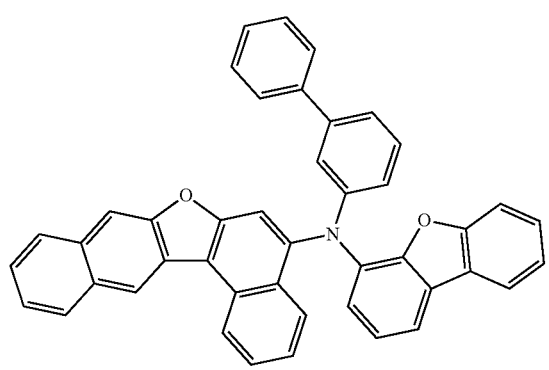
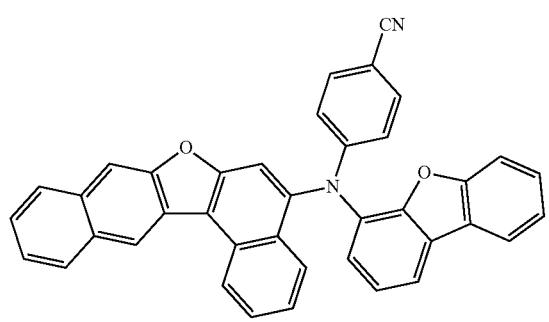
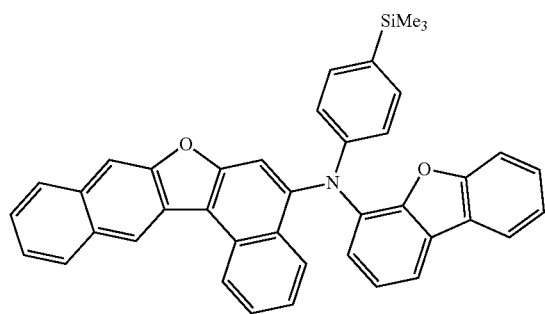
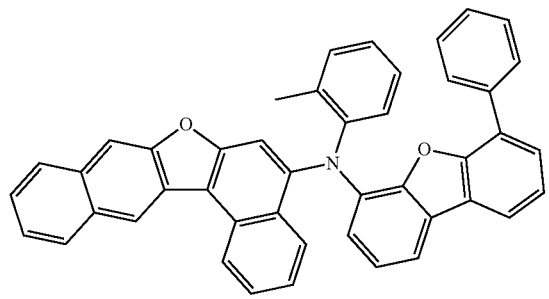
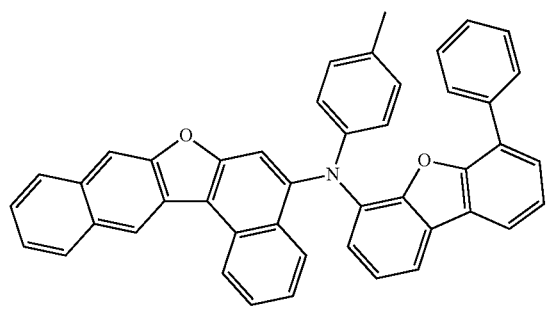
164
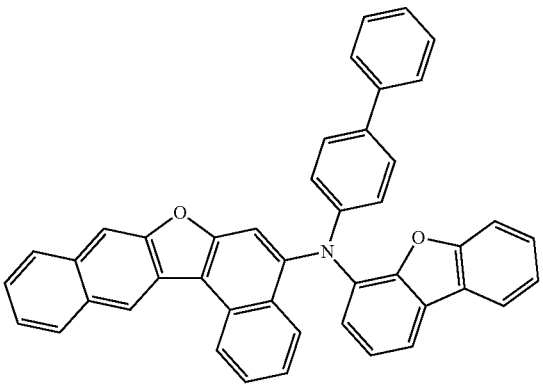
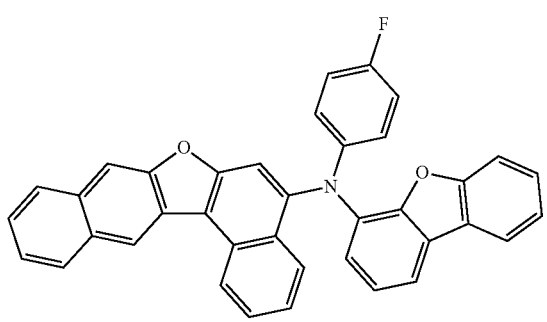
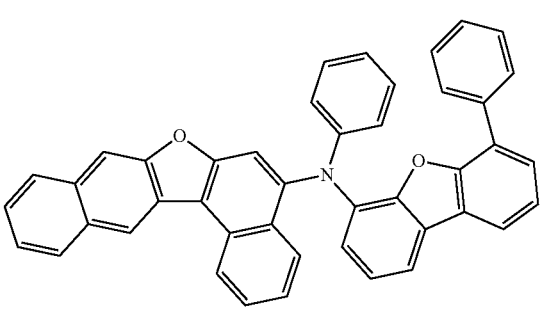
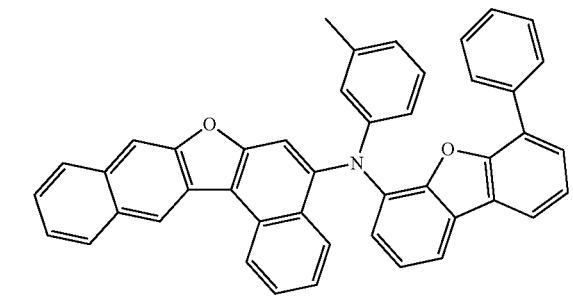
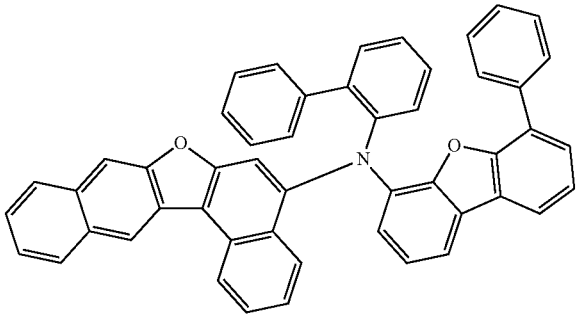

165
166
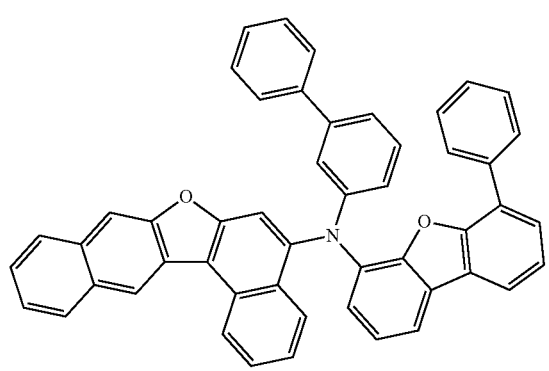
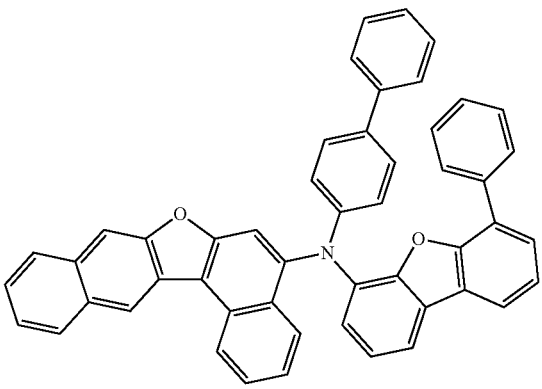
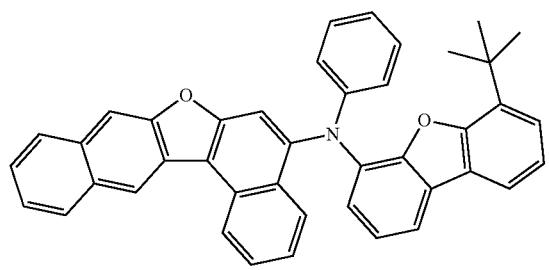
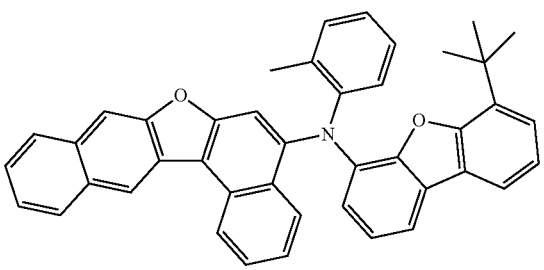
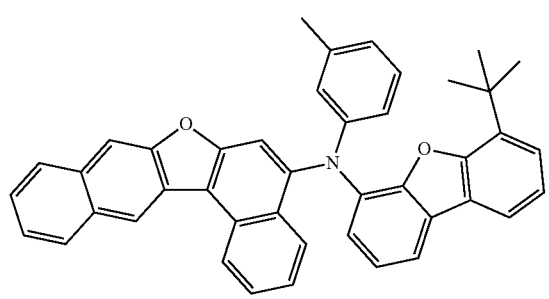
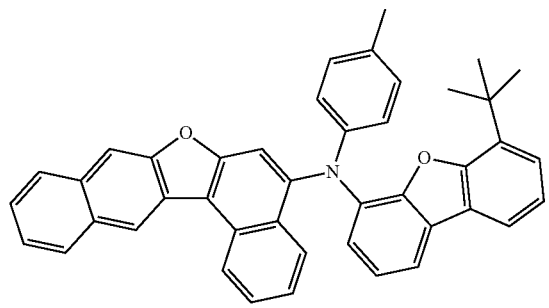
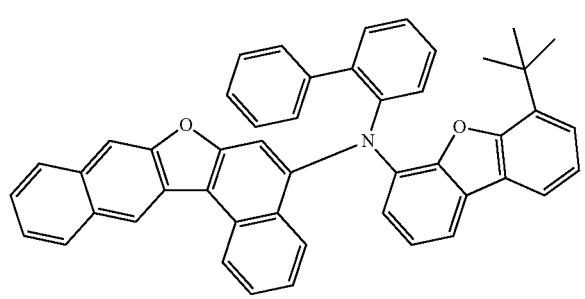
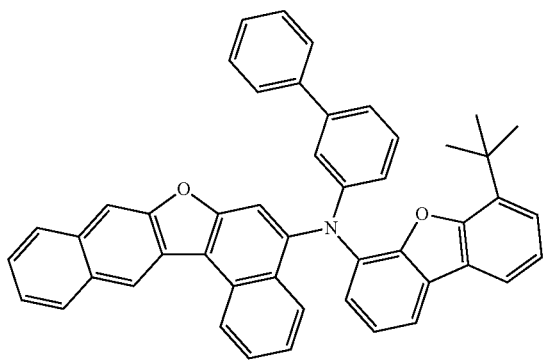
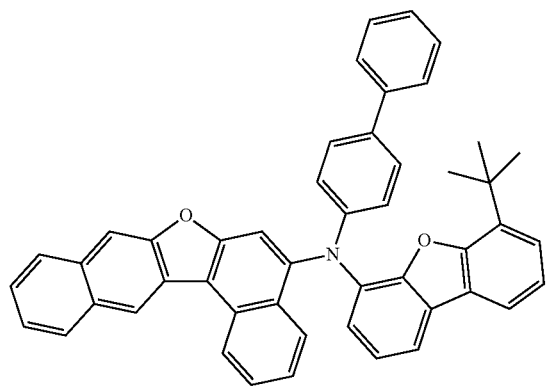
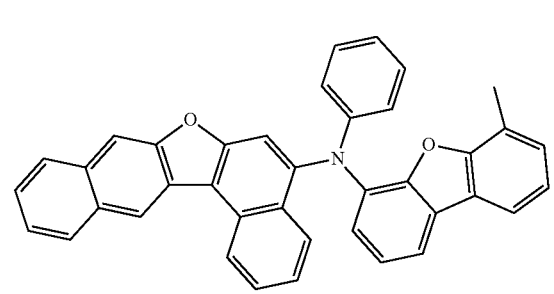

167
168
-continued
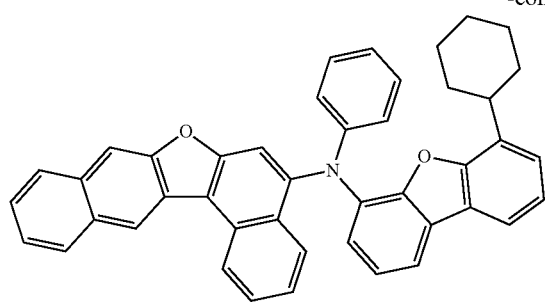
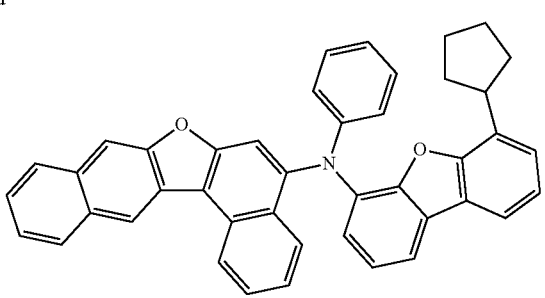
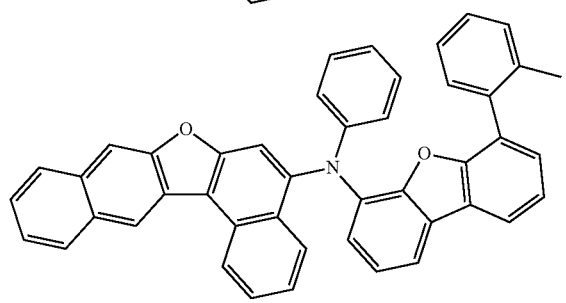
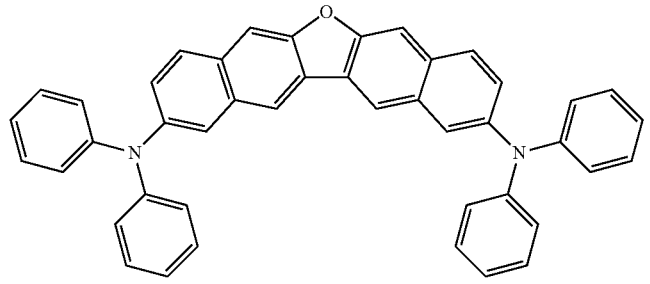
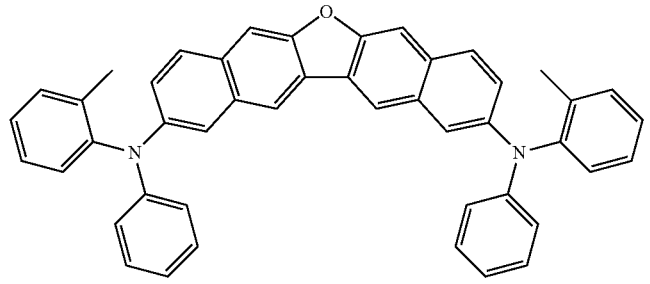
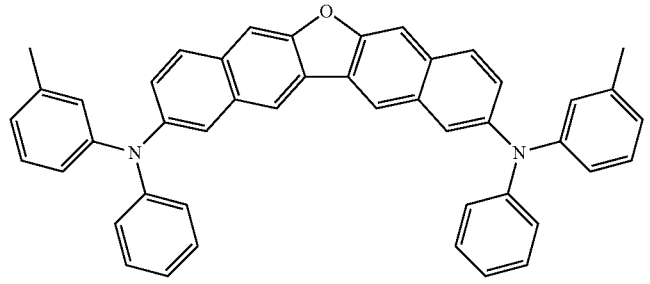
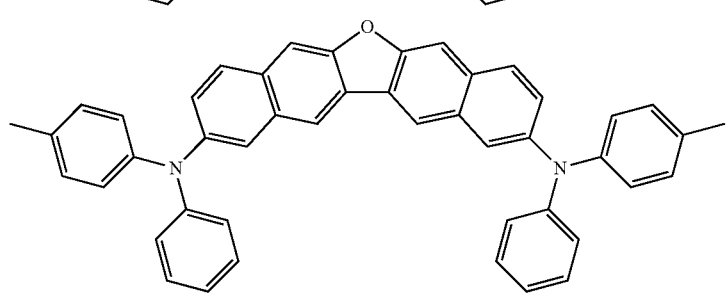

-continued
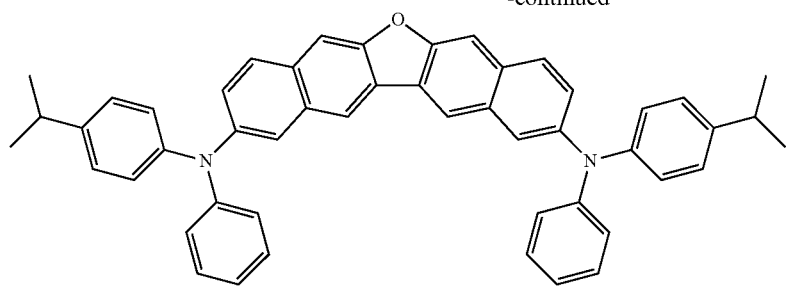
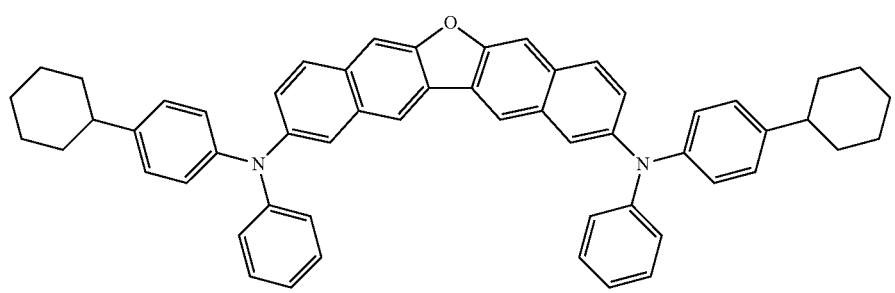
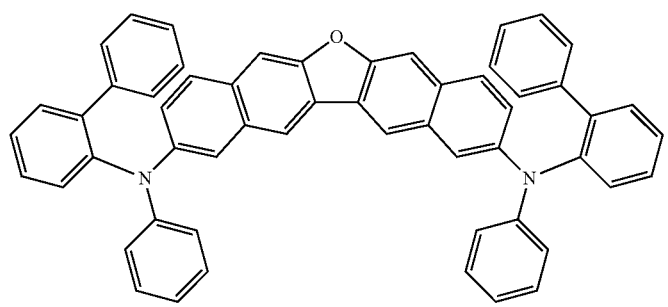
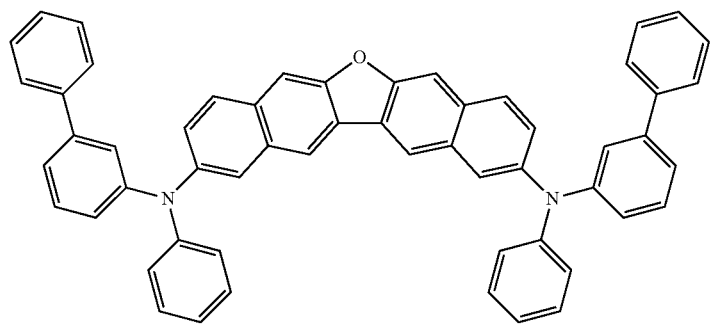
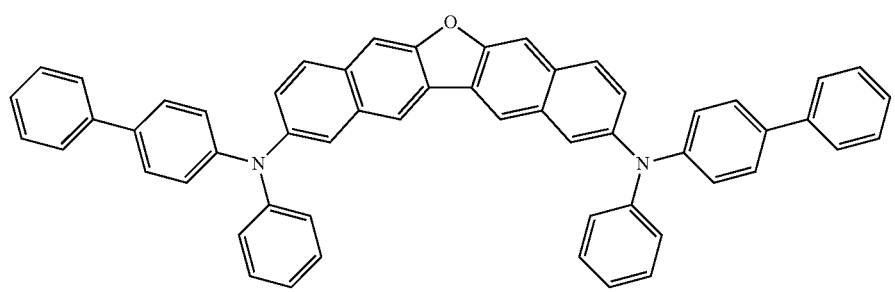

-continued
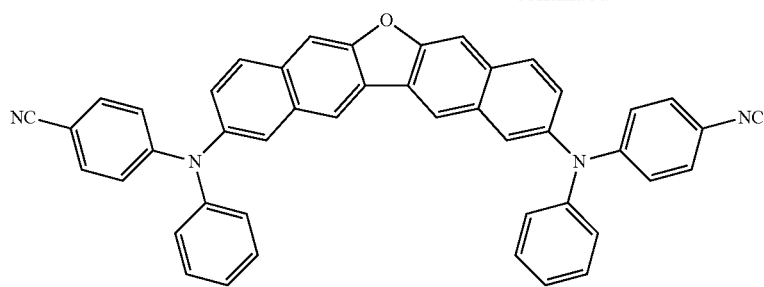
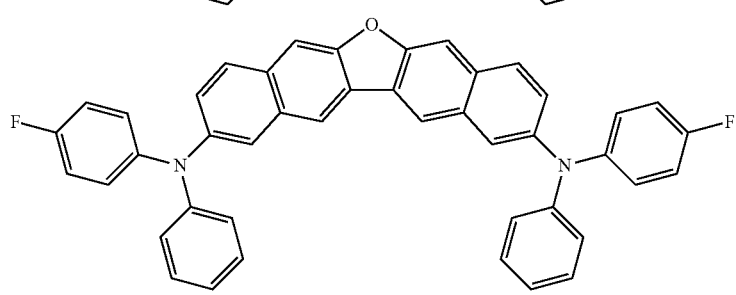
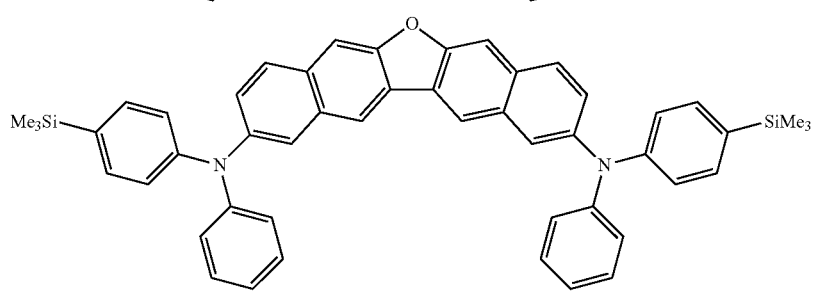
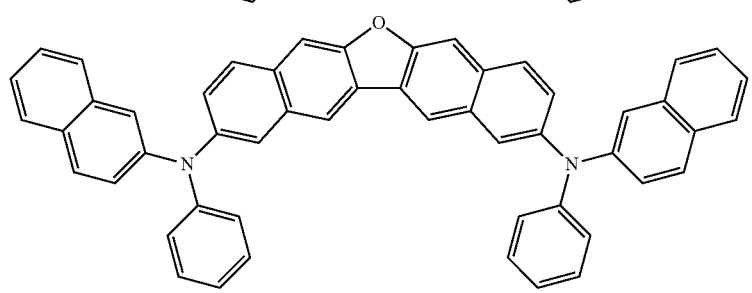
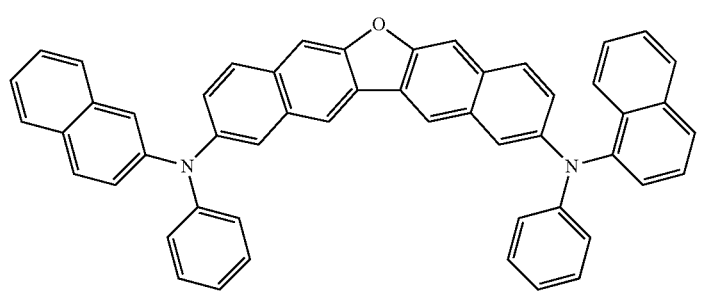
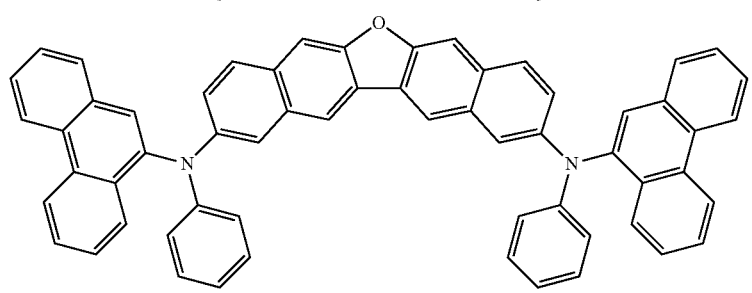

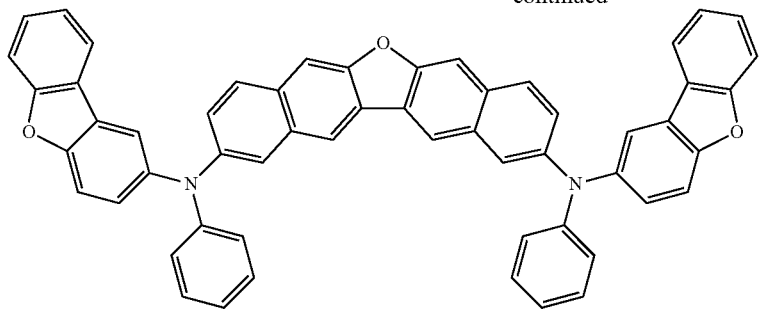
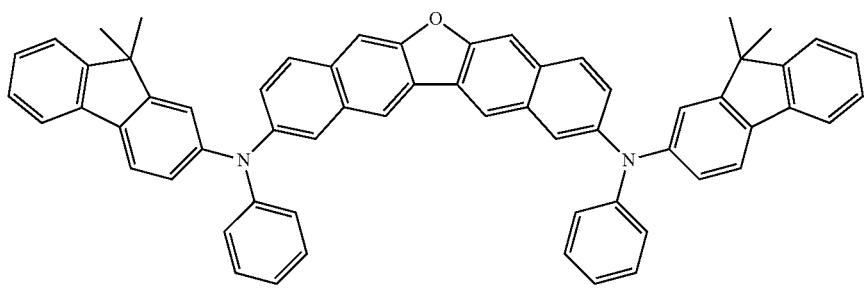
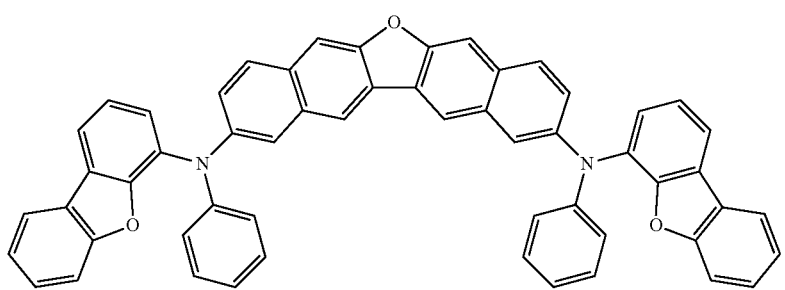
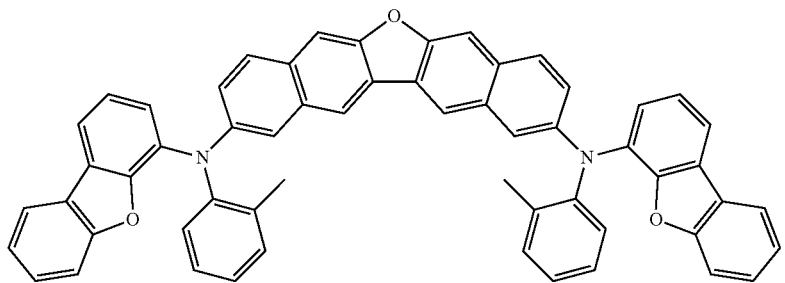
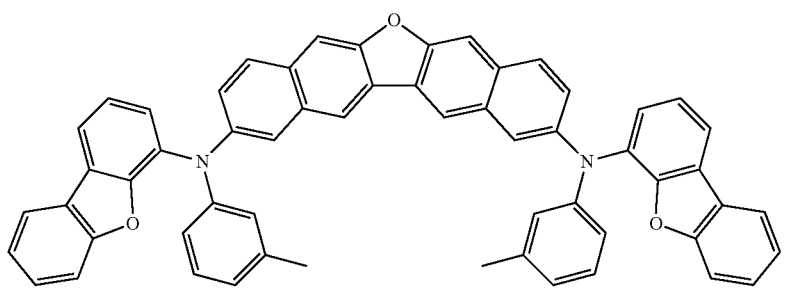

-continued
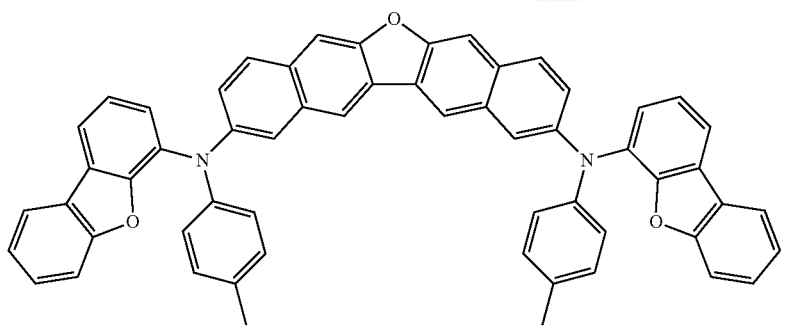
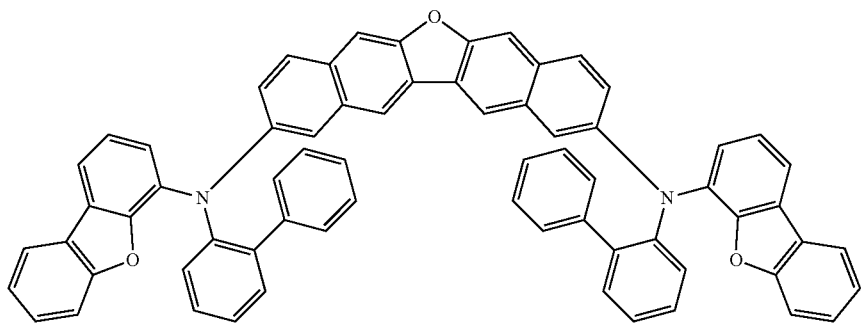
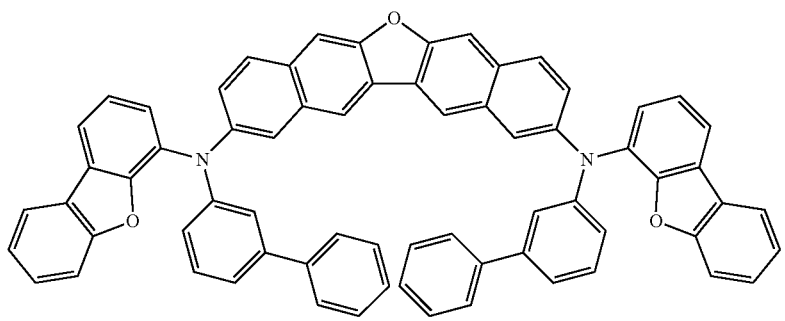
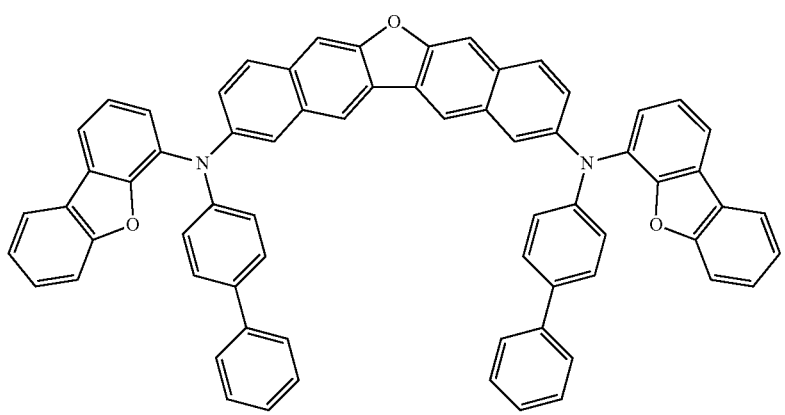
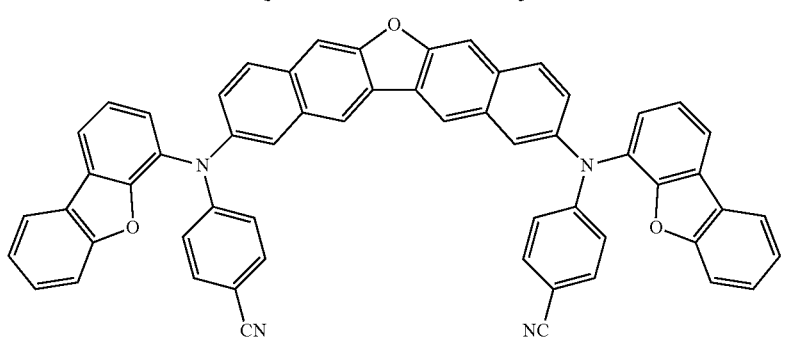

-continued
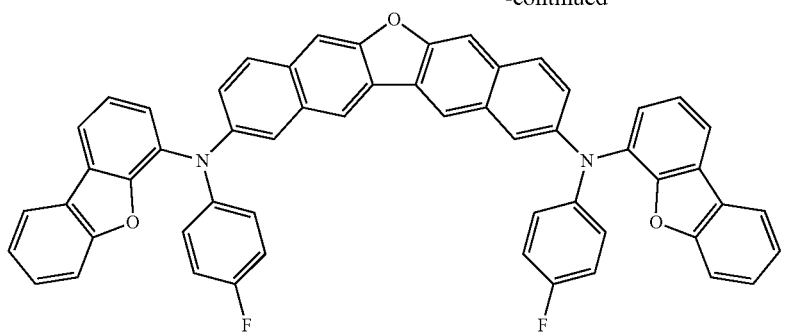
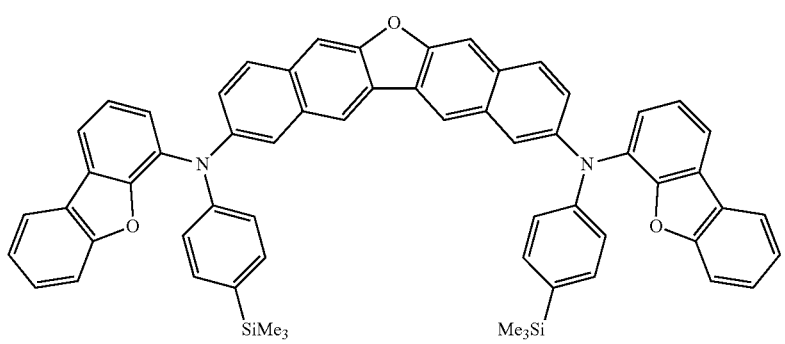
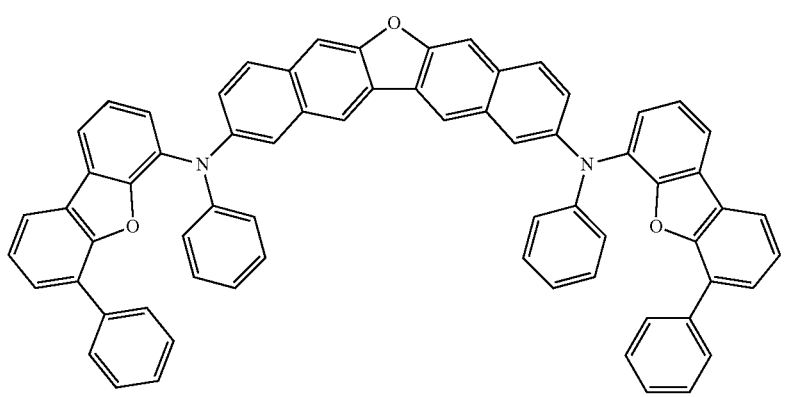
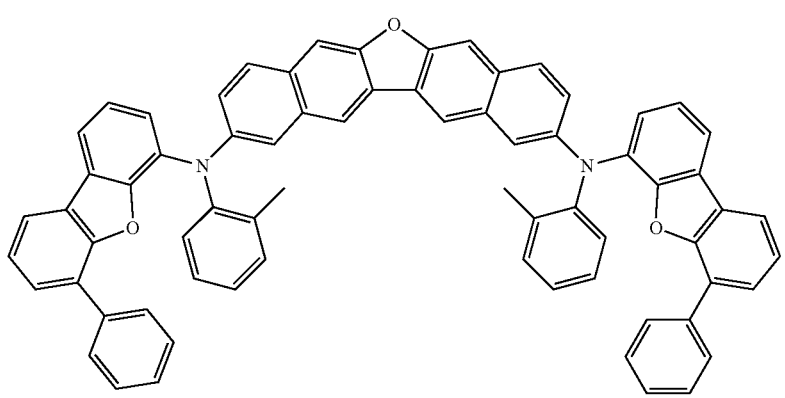

-continued
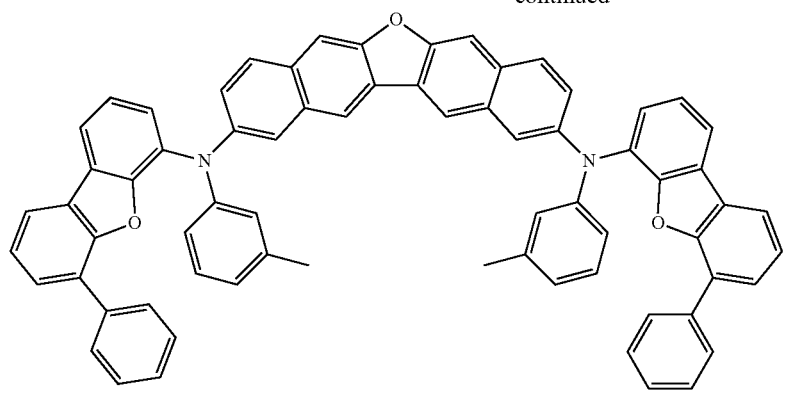
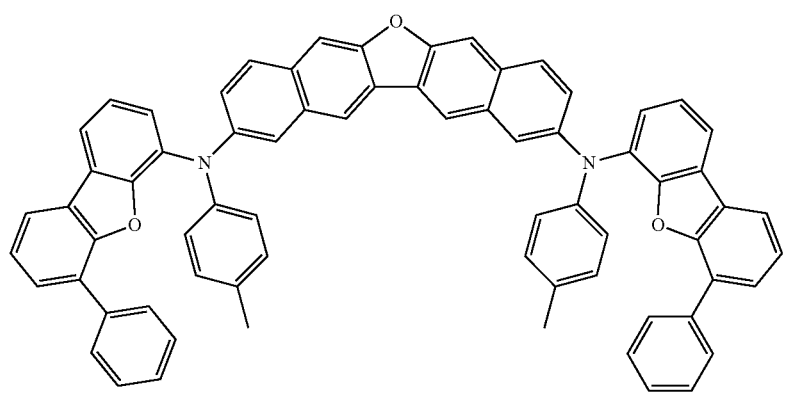
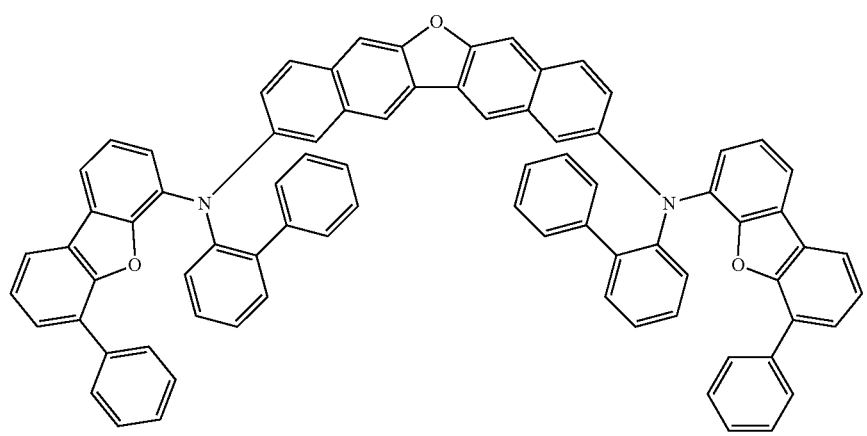
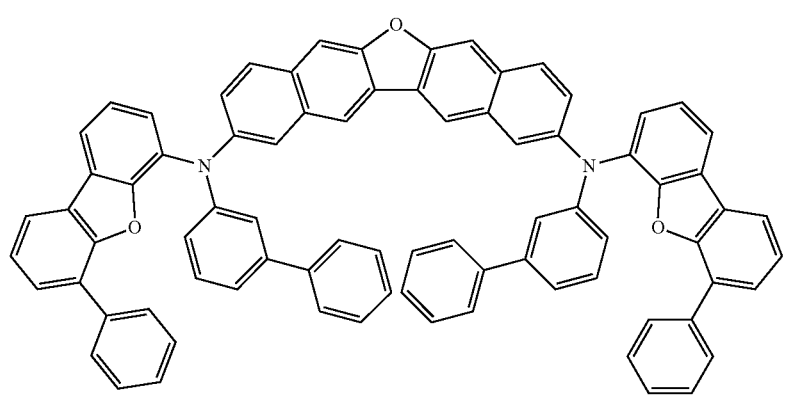

-continued
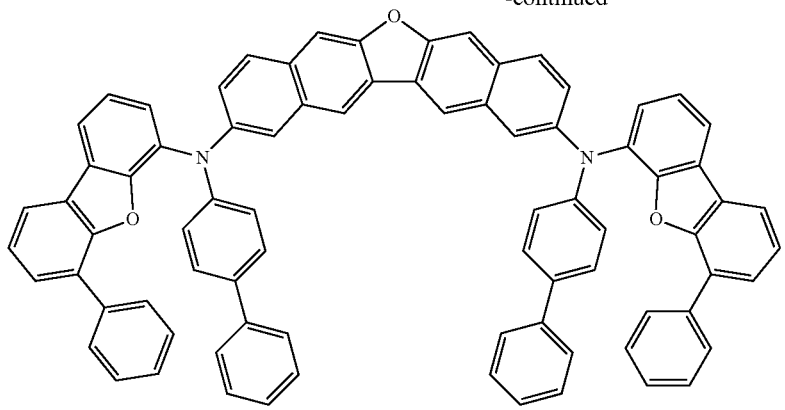
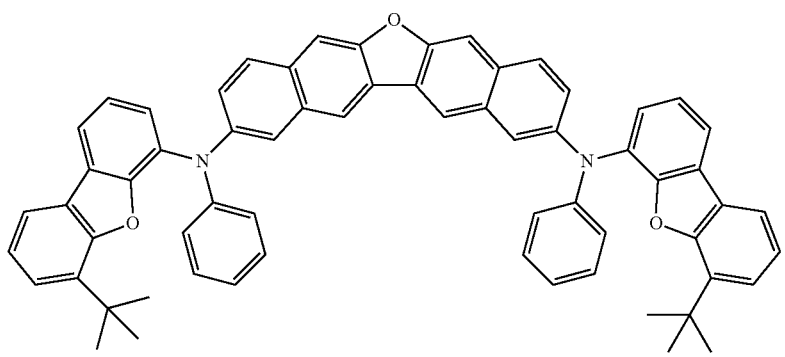
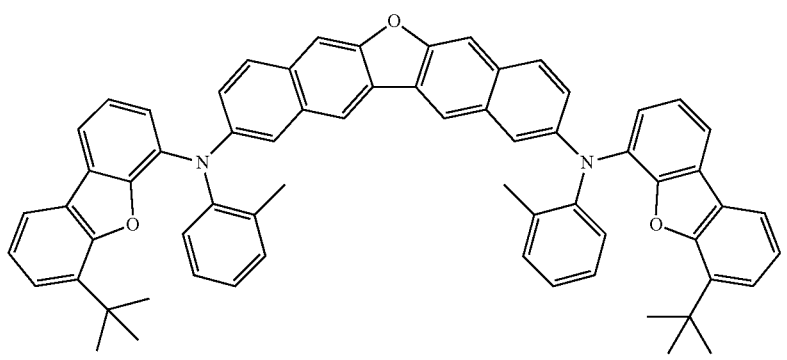
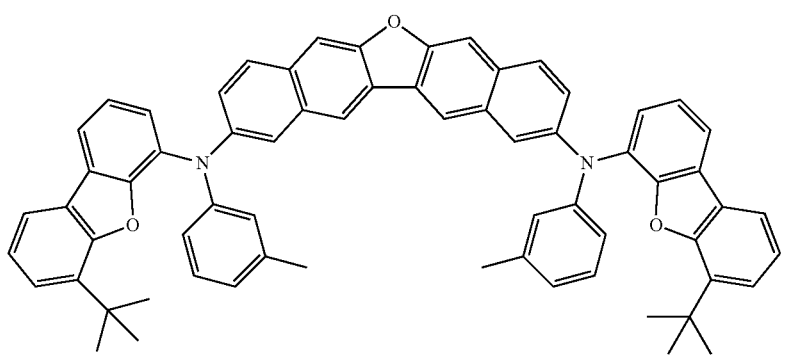

-continued
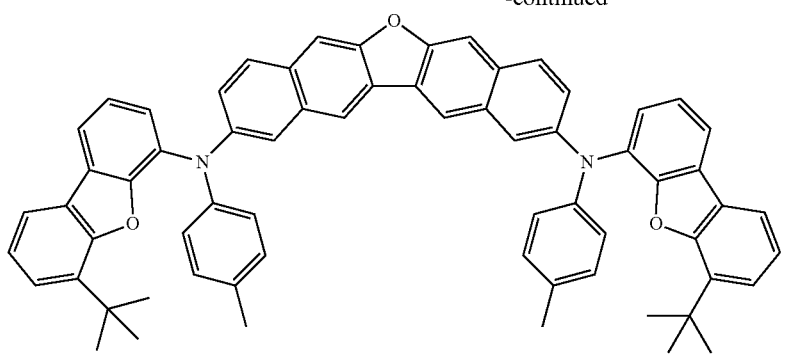

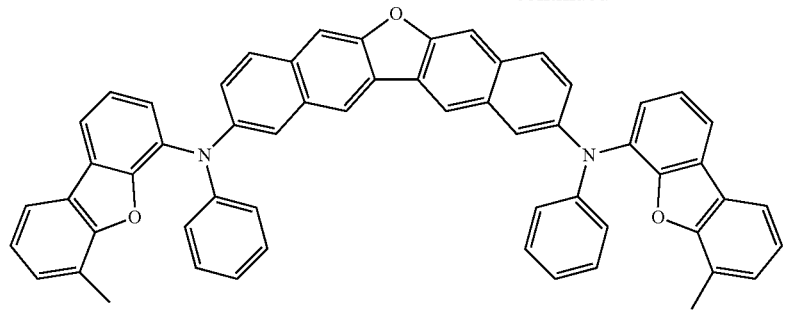
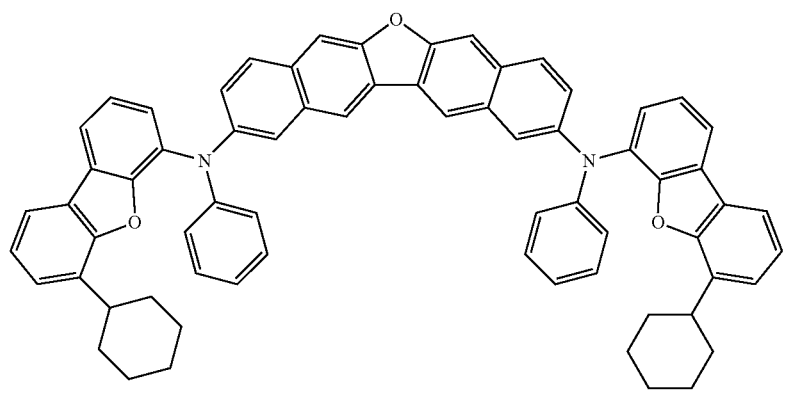
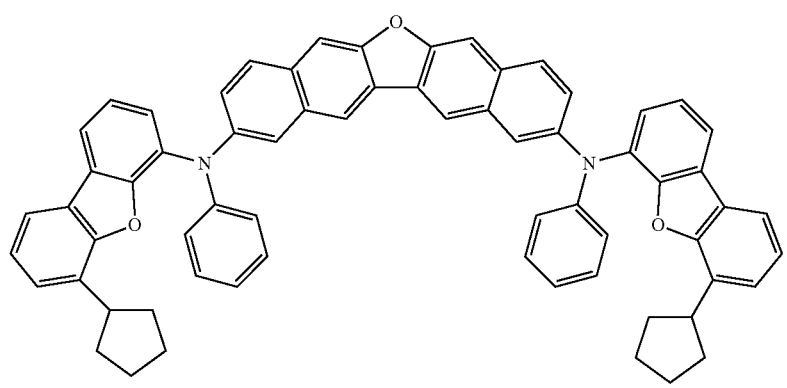
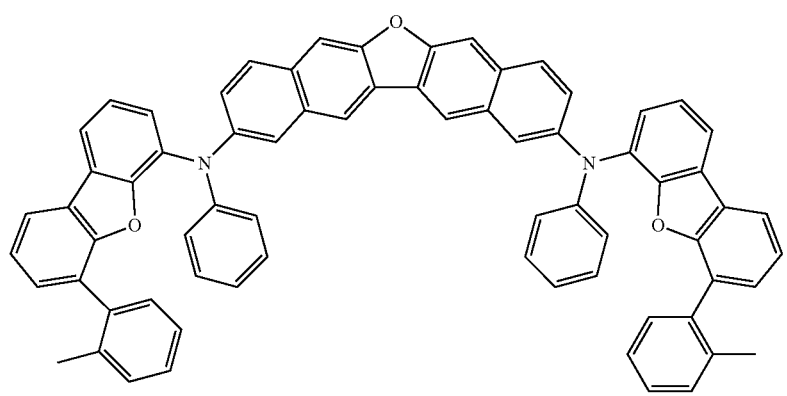

187 188
-continued
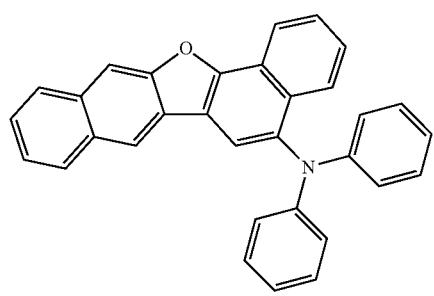
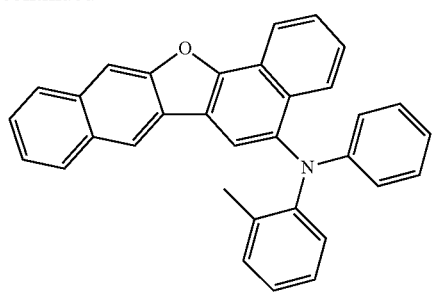
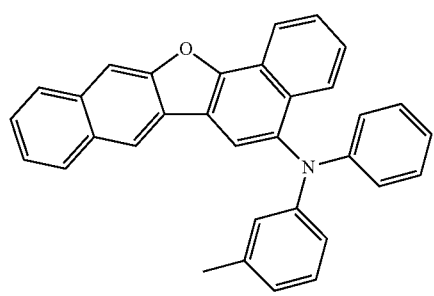
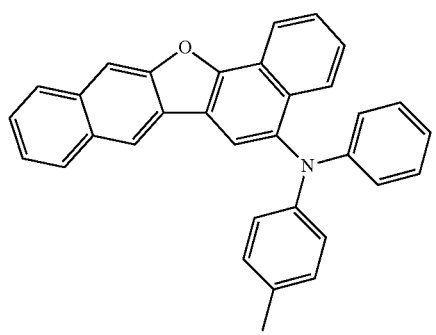
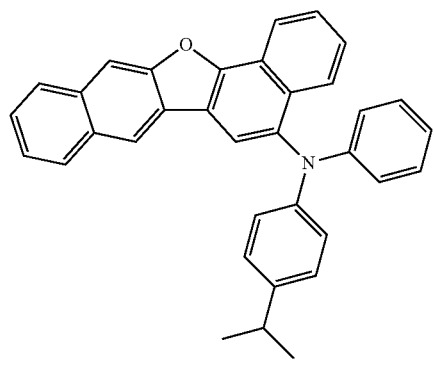
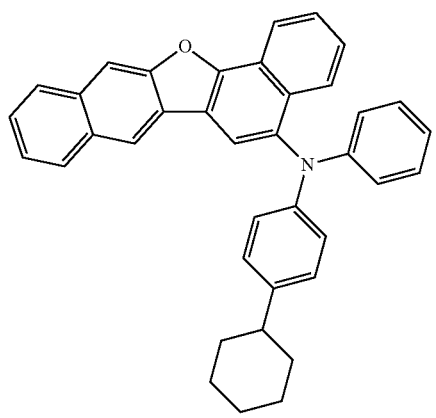
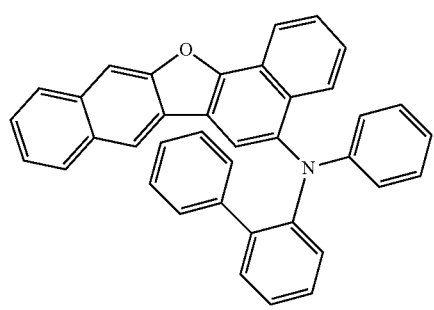
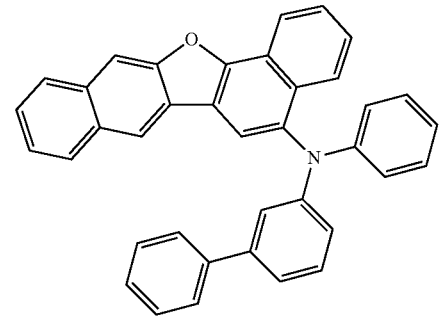

-continued
189
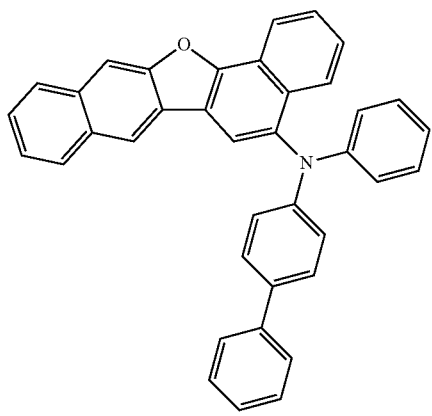
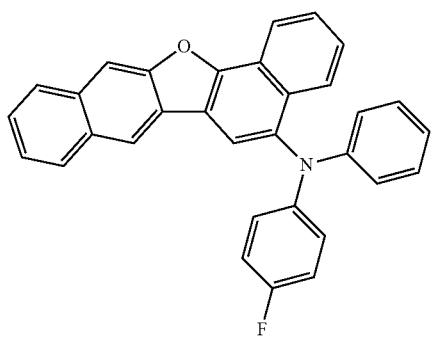
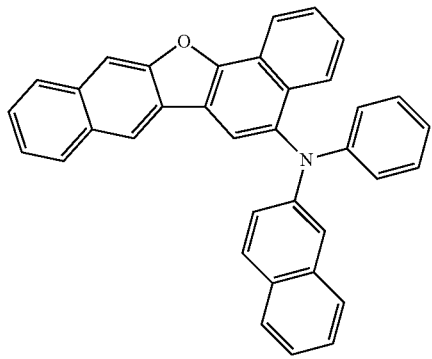
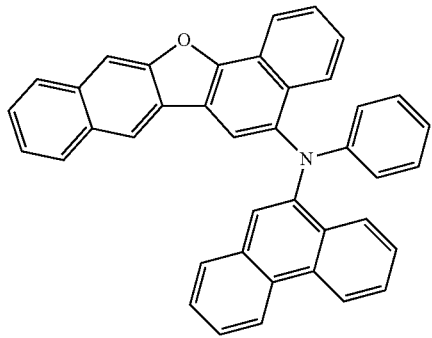
190
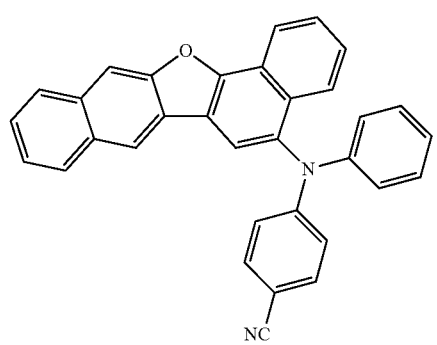
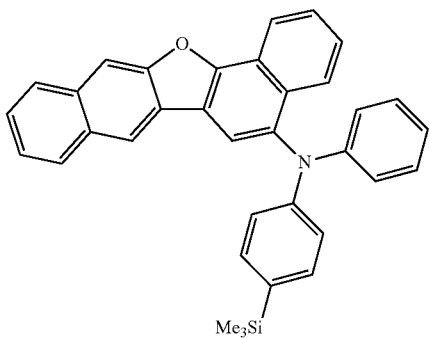
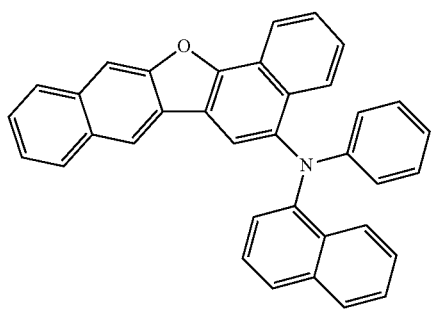
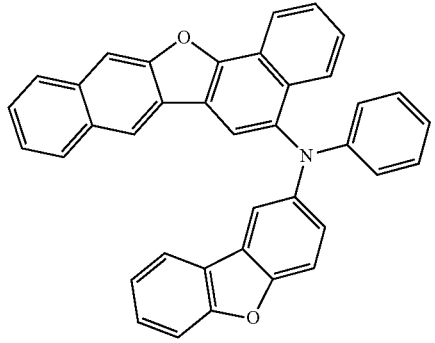

-continued
| 191 | 192 |
|---|---|
| 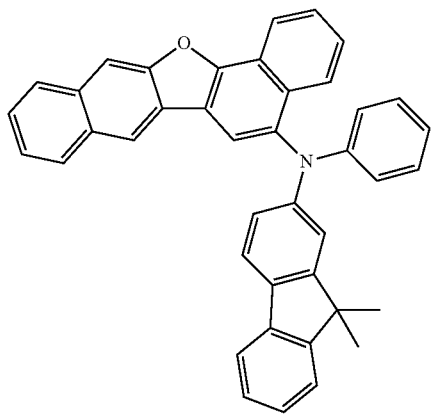 | 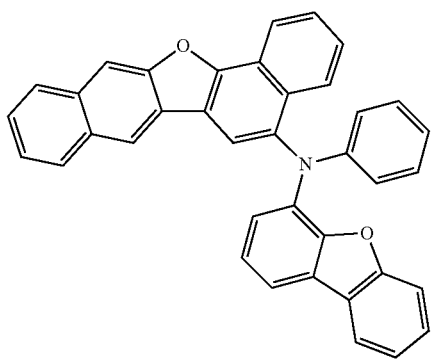 |
| 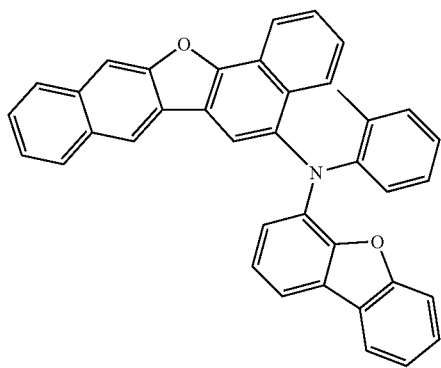 | 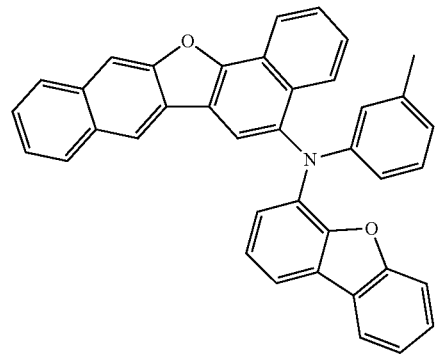 |
| 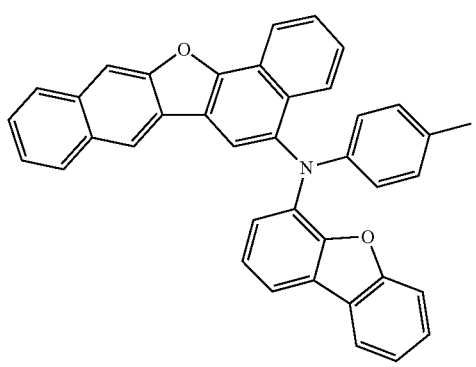 | 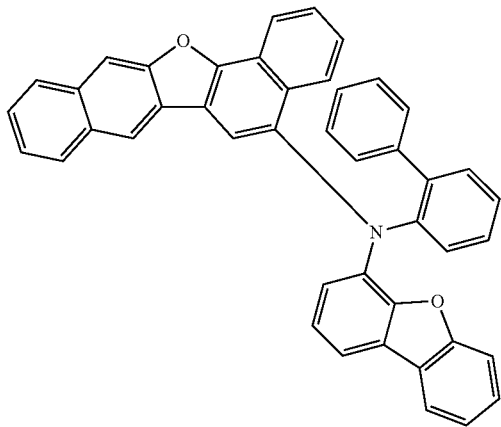 |
| 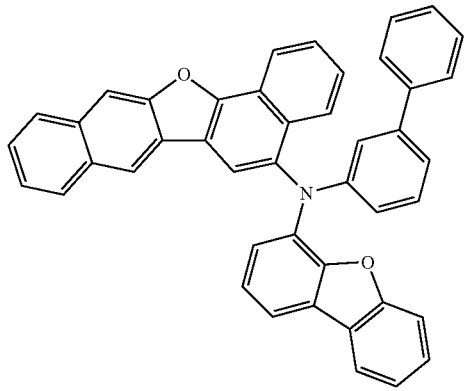 | 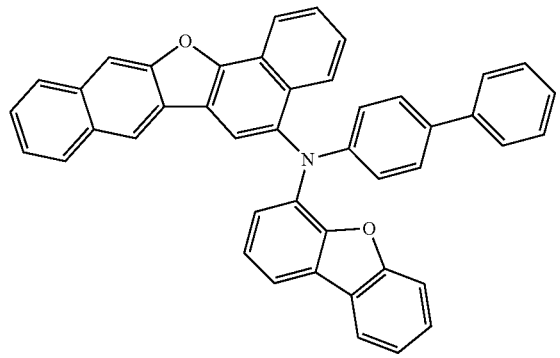 |

-continued
| 193 | 194 |
|---|---|
| 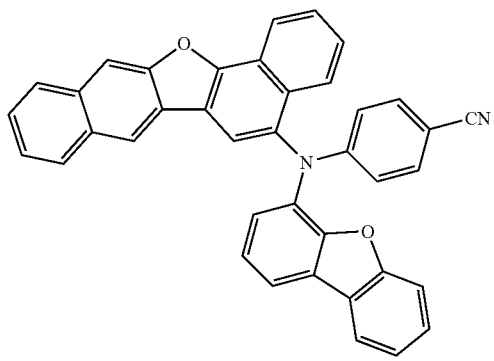 | 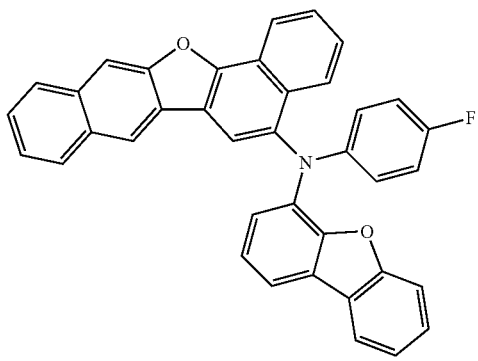 |
| 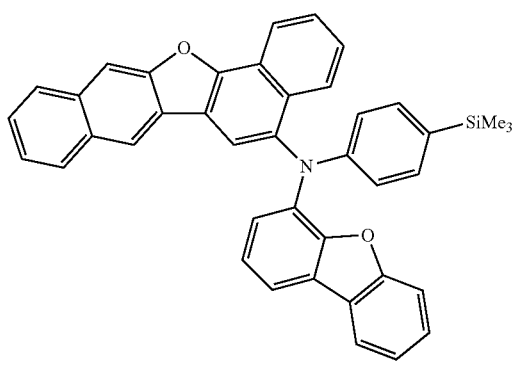 | 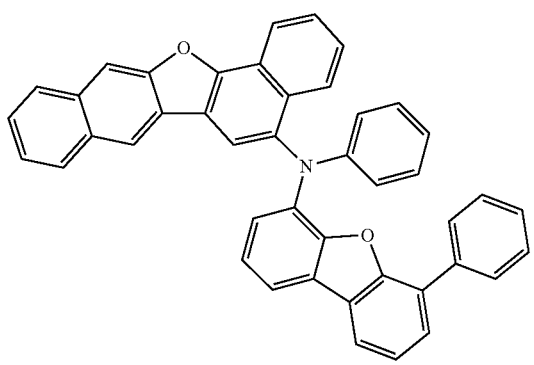 |
| 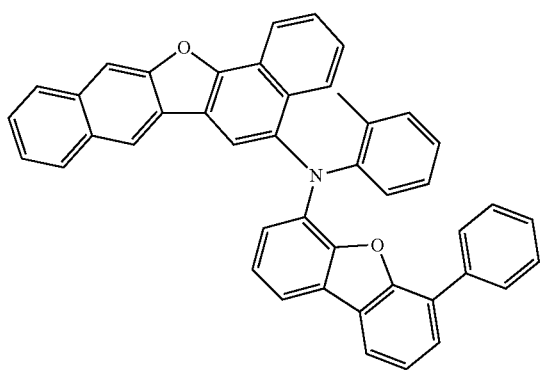 | 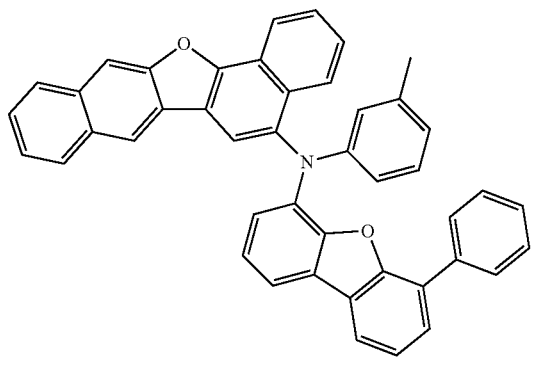 |
| 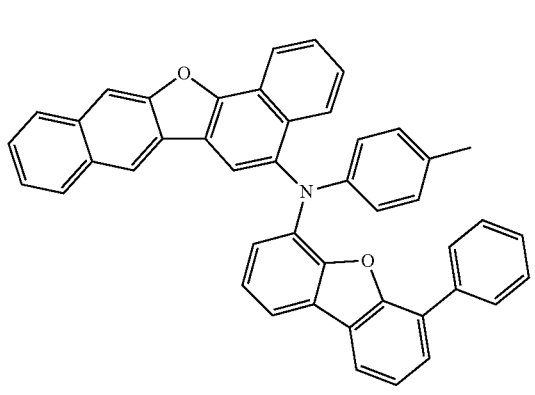 | 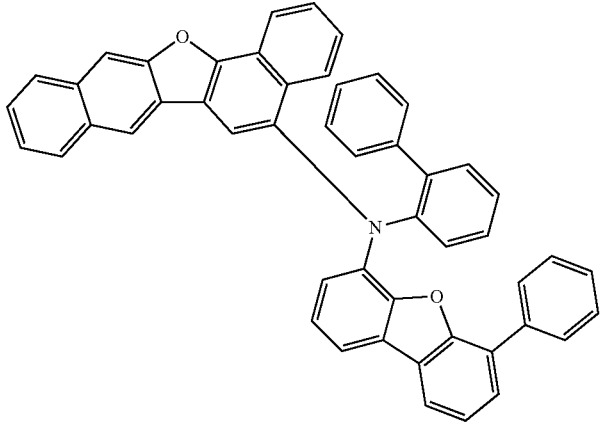 |

195 196
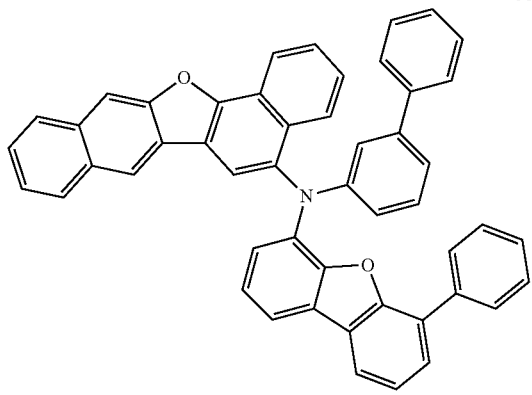
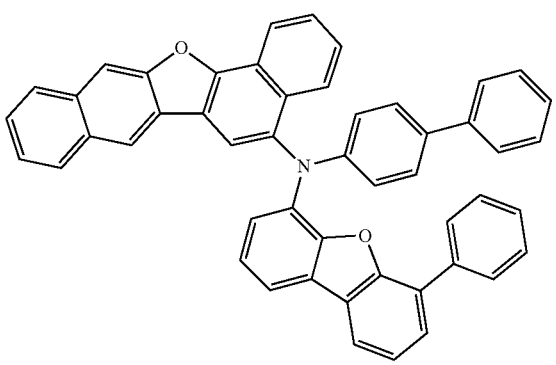
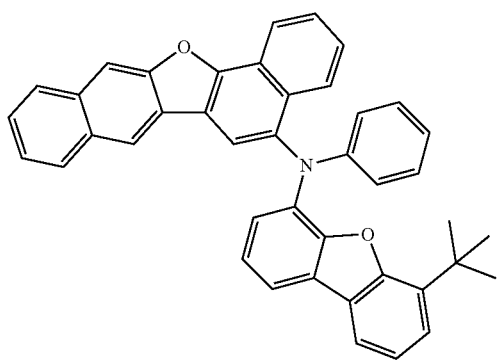
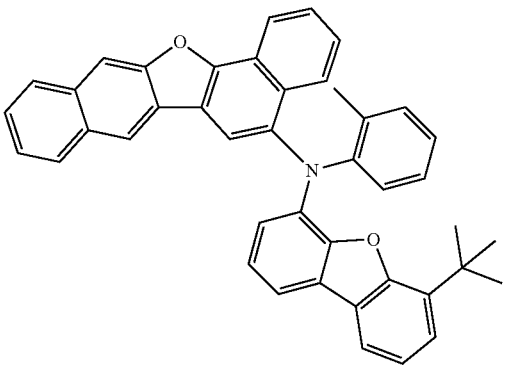
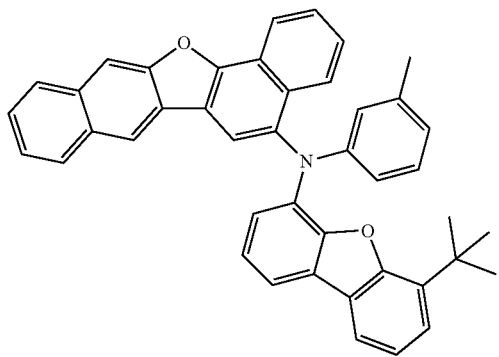
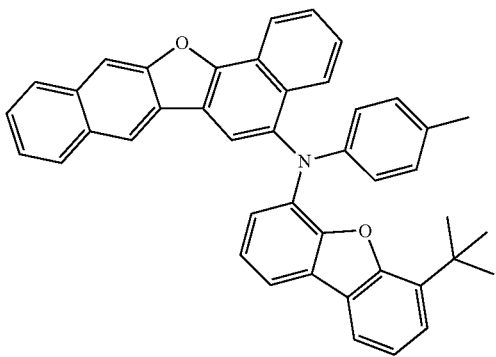
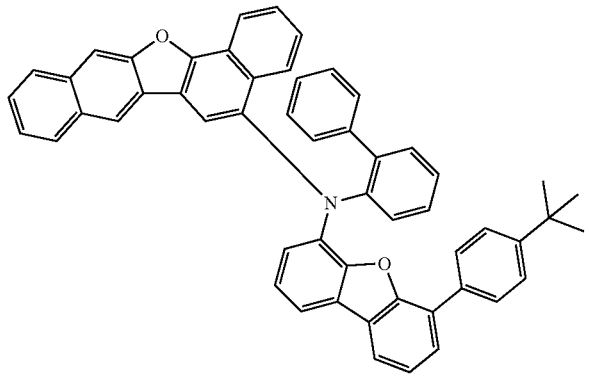
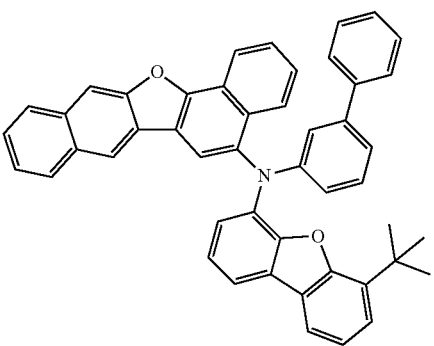

197 198
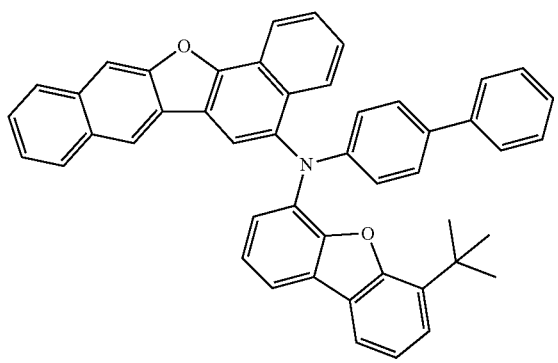 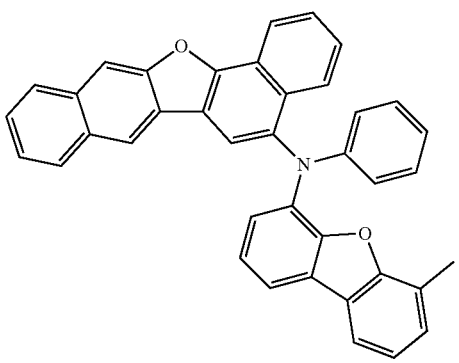
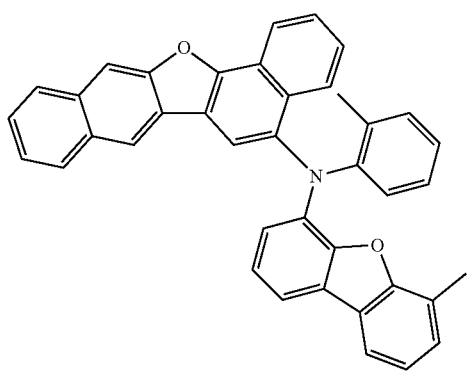 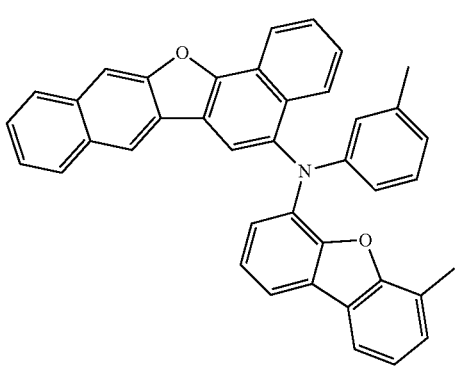
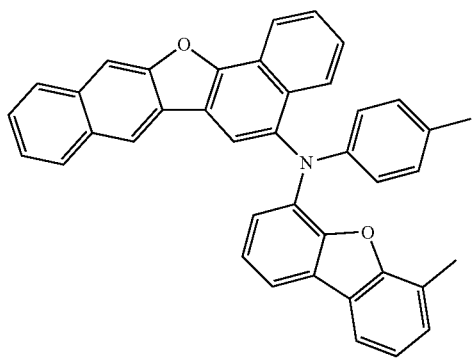 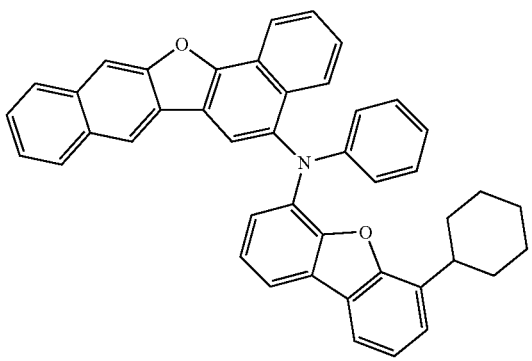
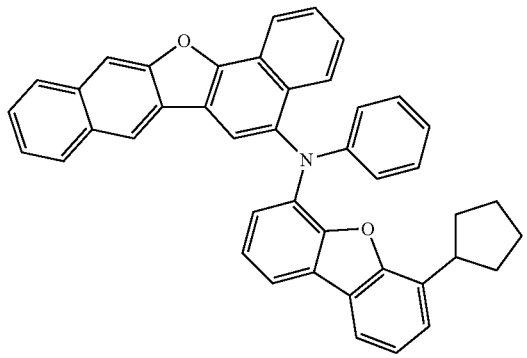 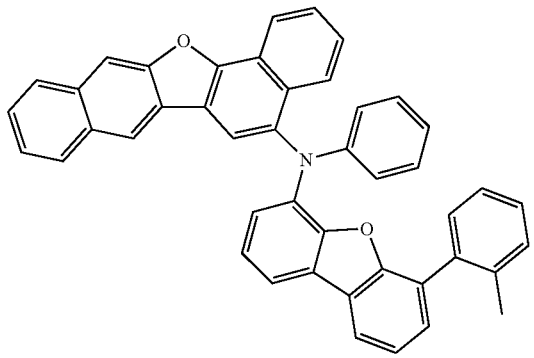

-continued
| 199 | 200 |
|---|---|
| 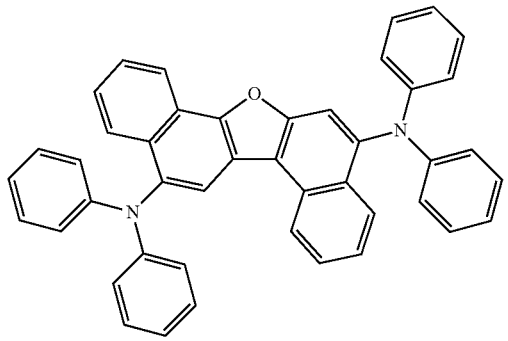 | 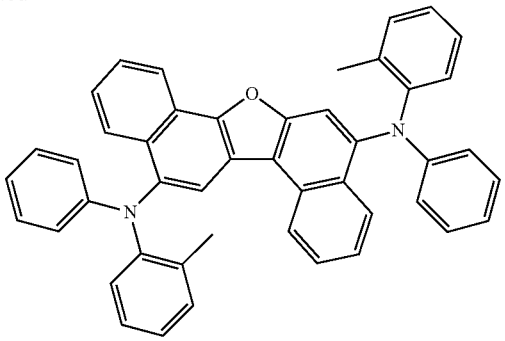 |
| 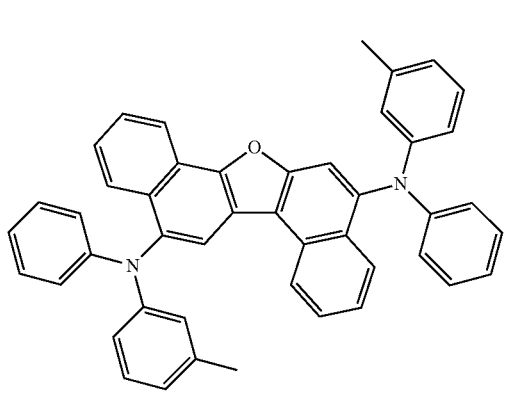 | 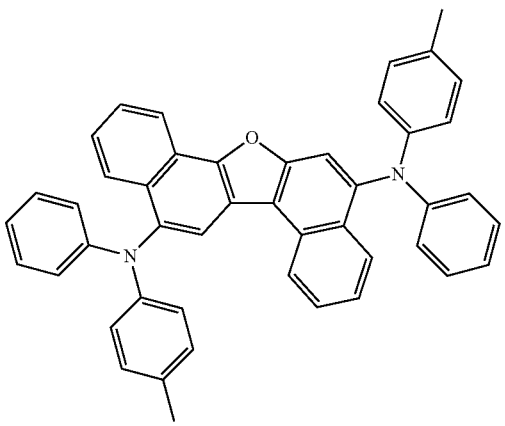 |
| 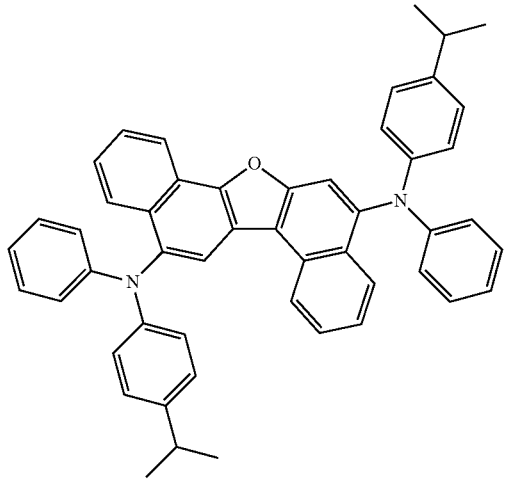 | 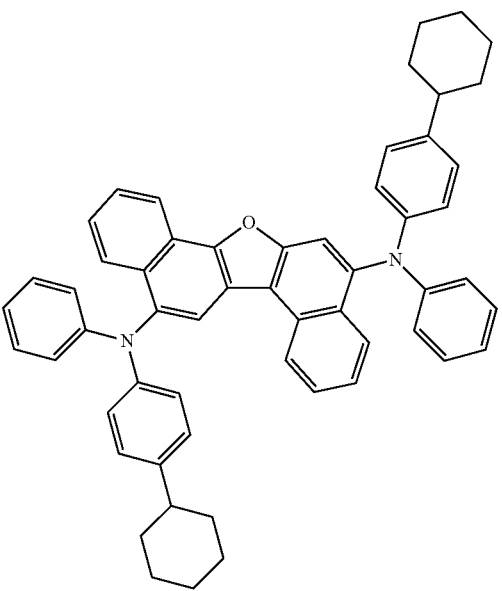 |

-continued
201
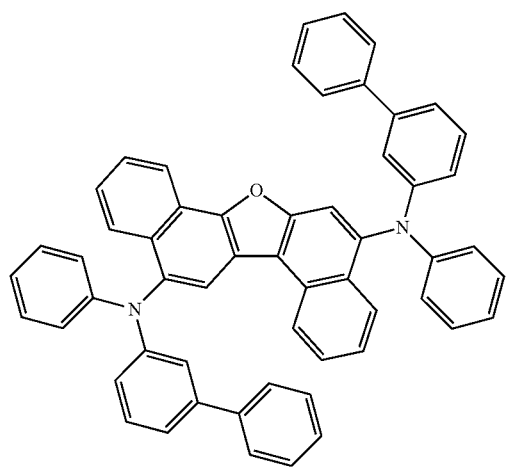
202
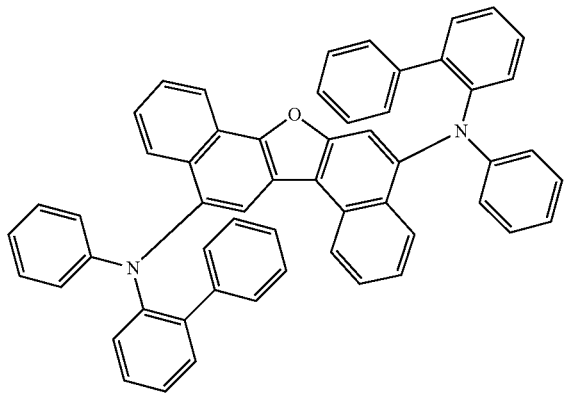
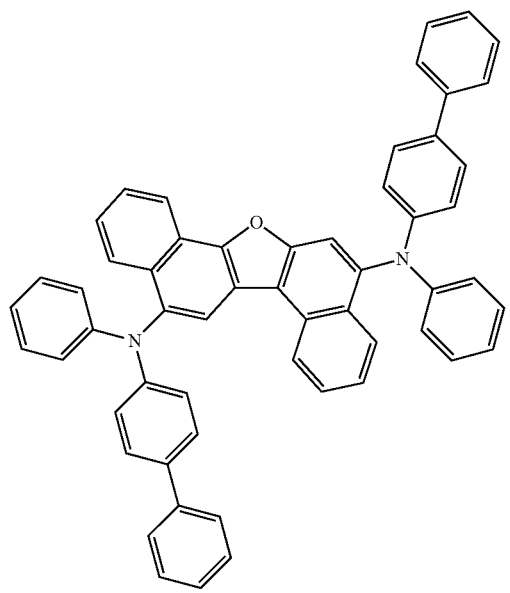
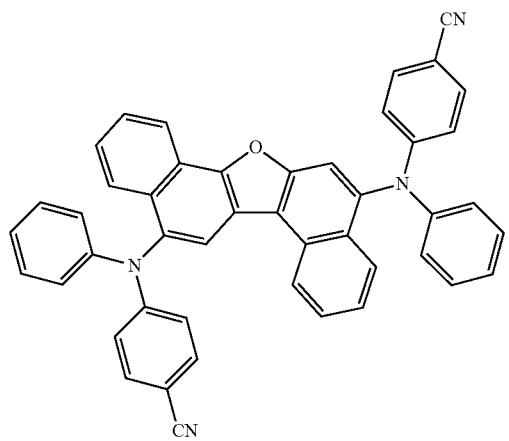
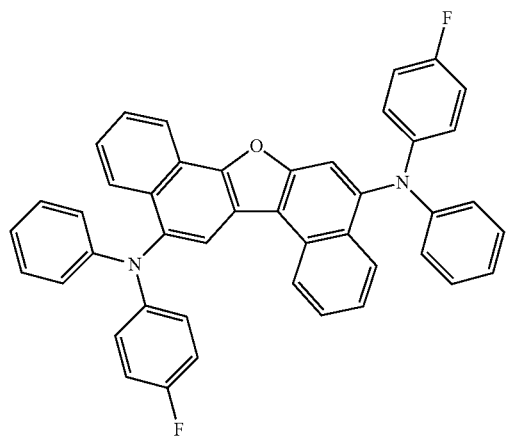
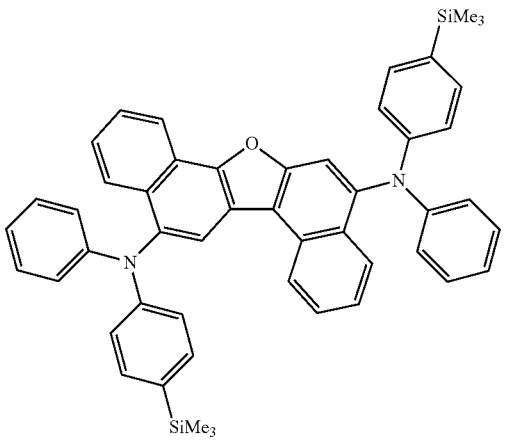

-continued
203
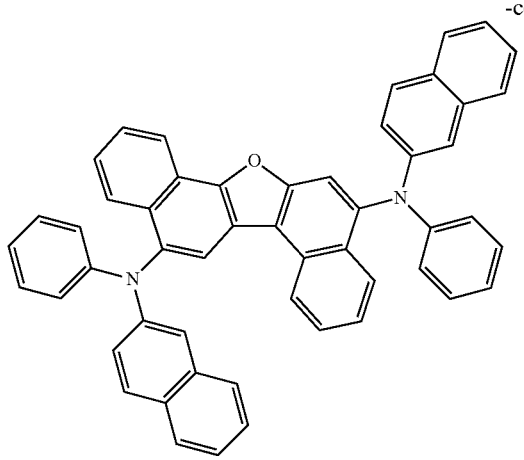
204
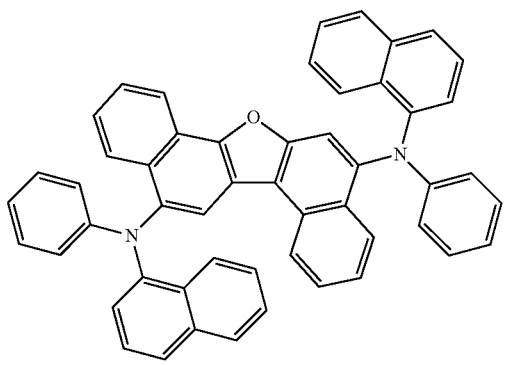
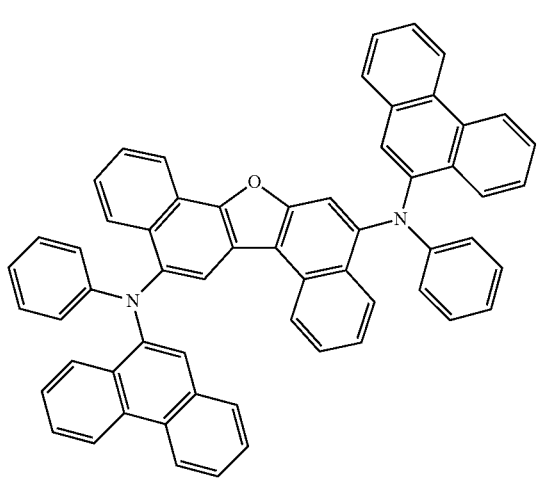
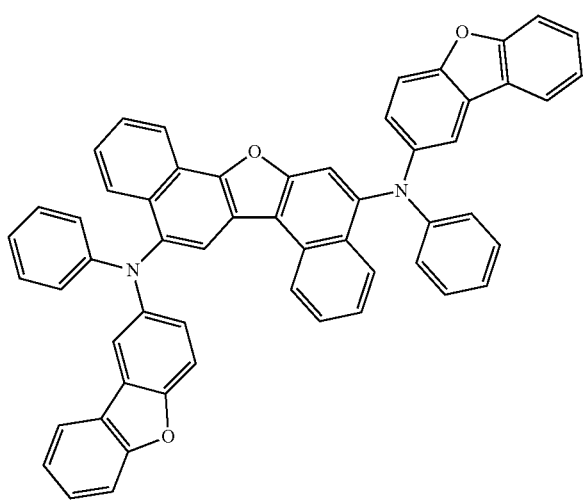
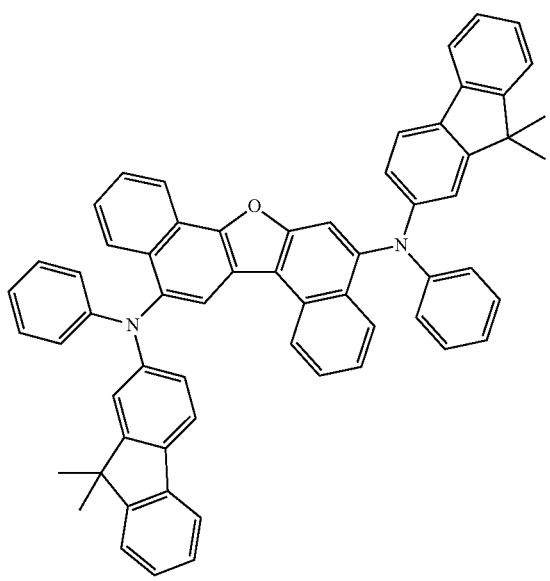
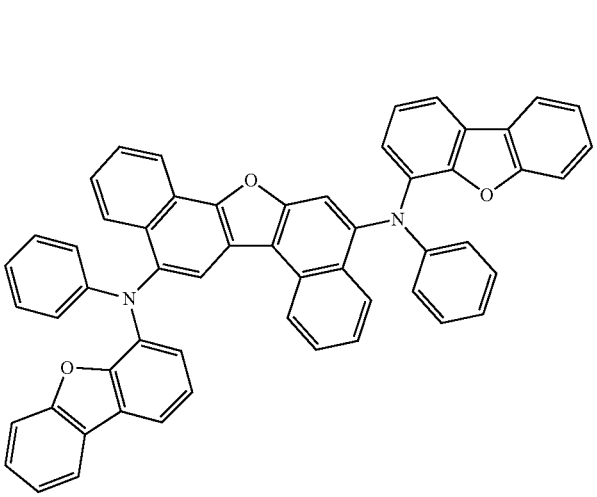

-continued
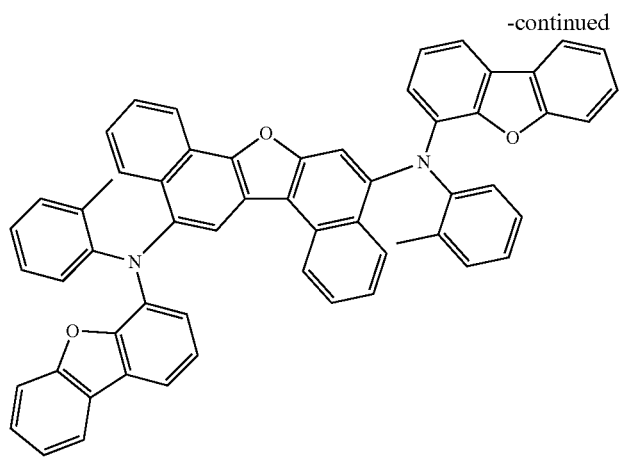
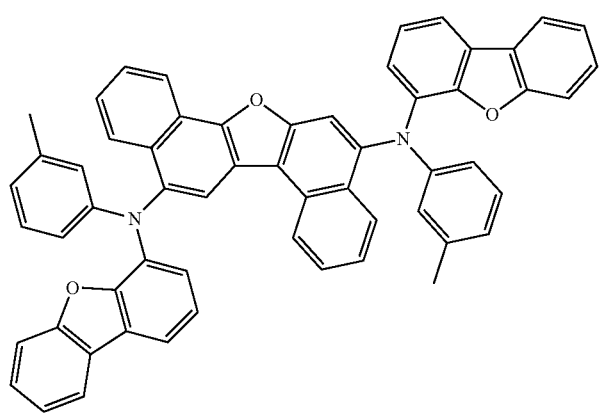
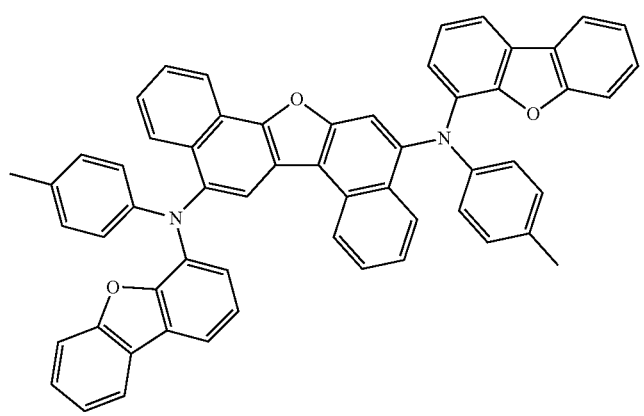

-continued
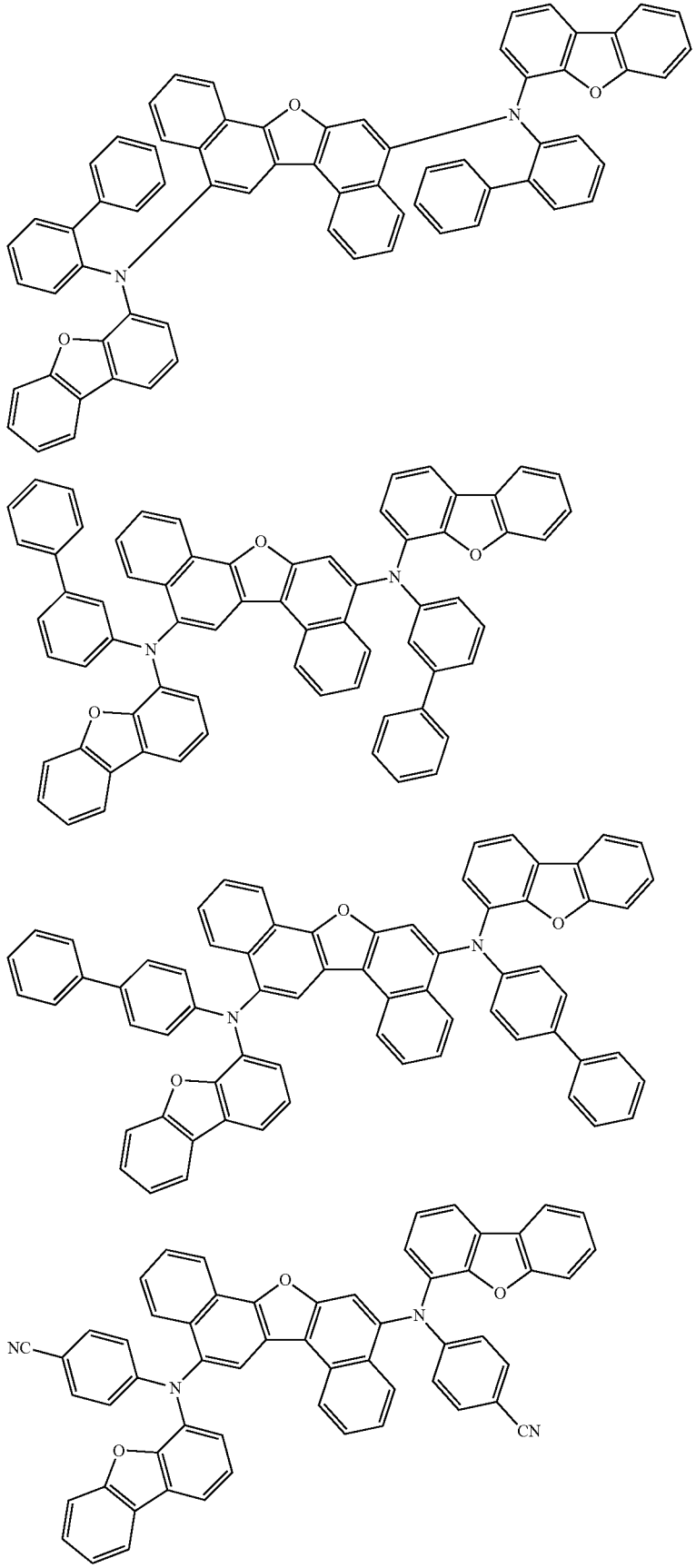

-continued
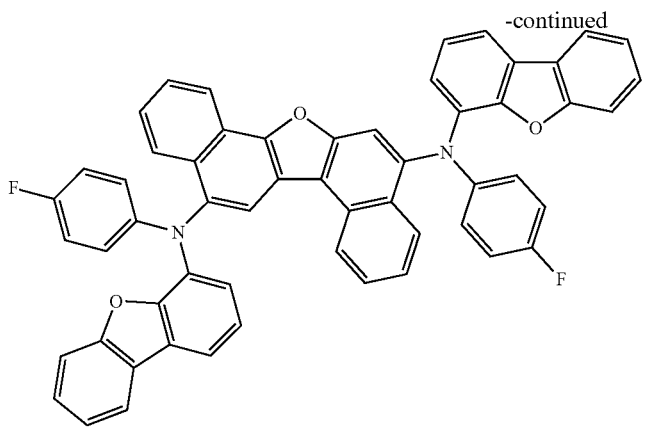
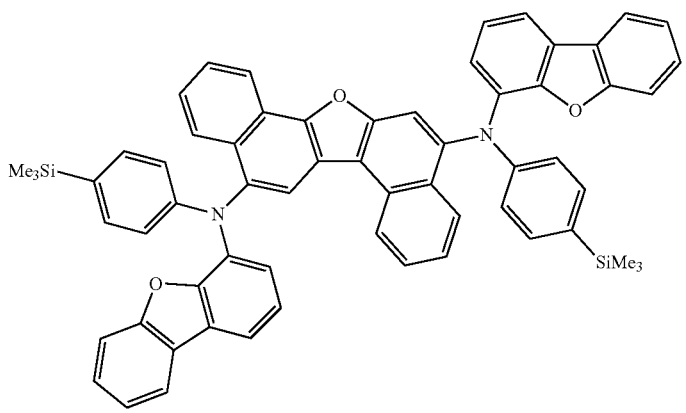
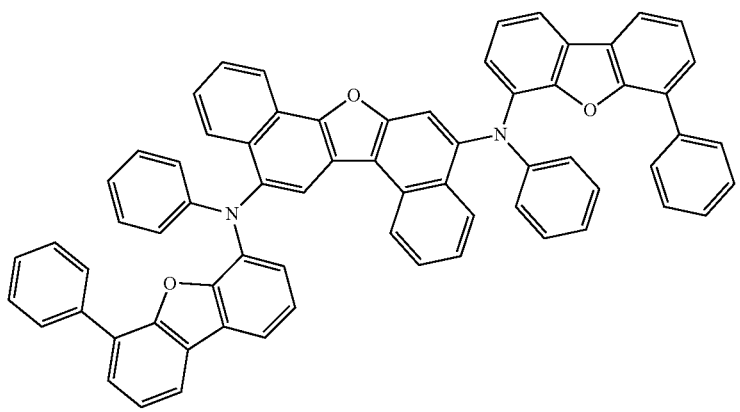
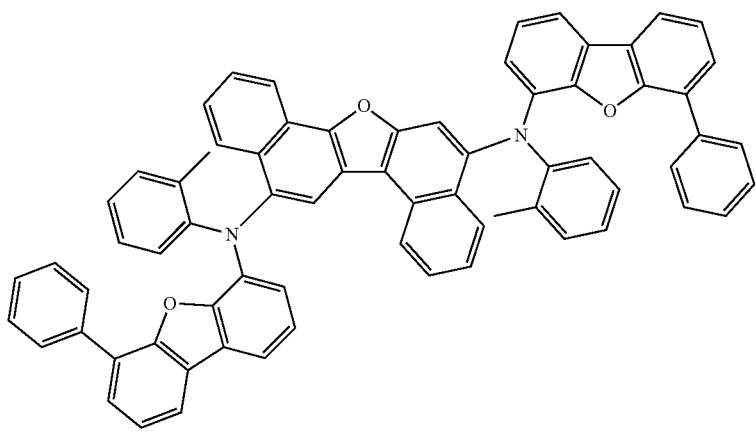

-continued
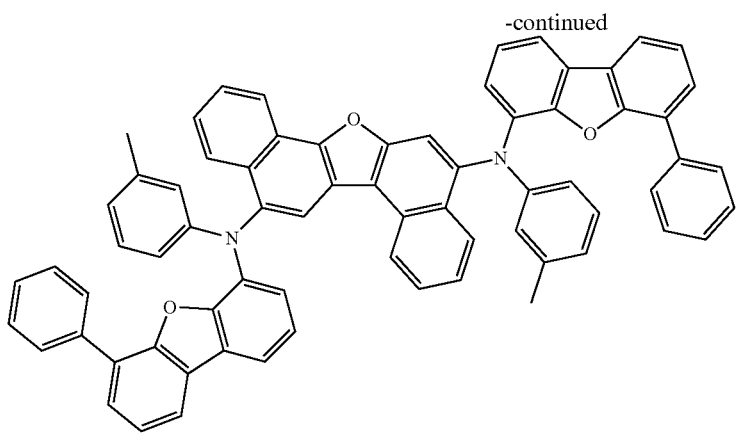
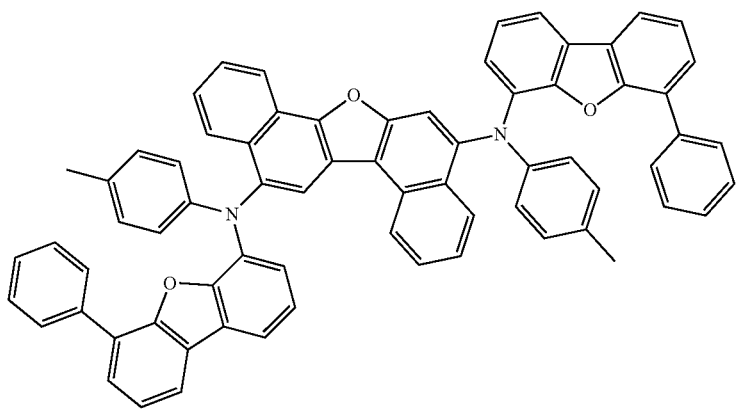
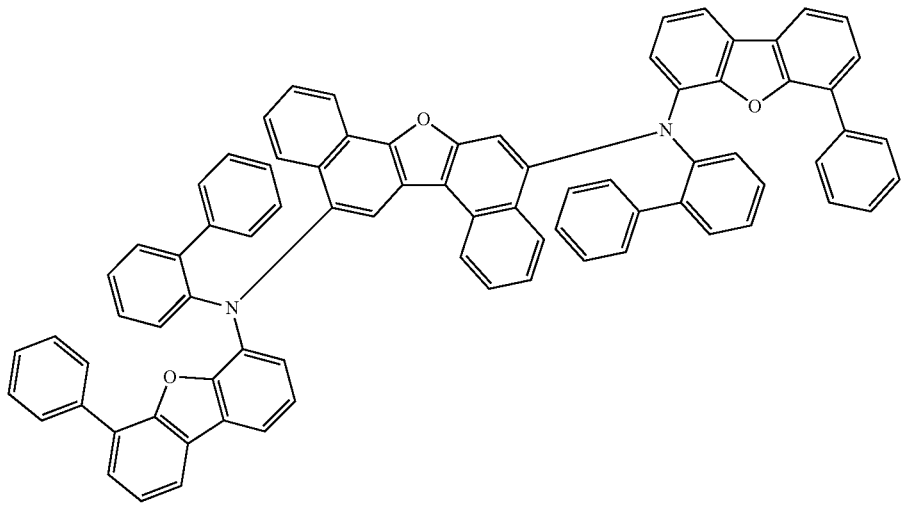
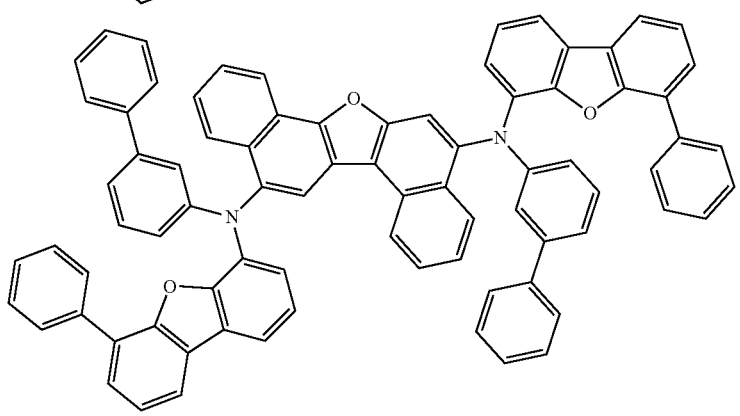

-continued
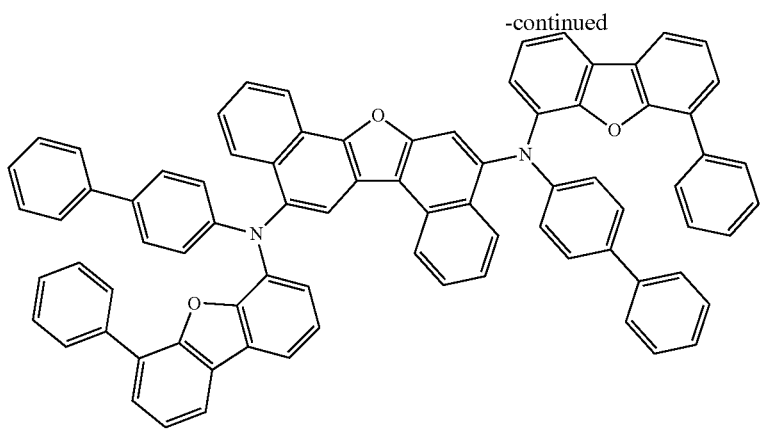
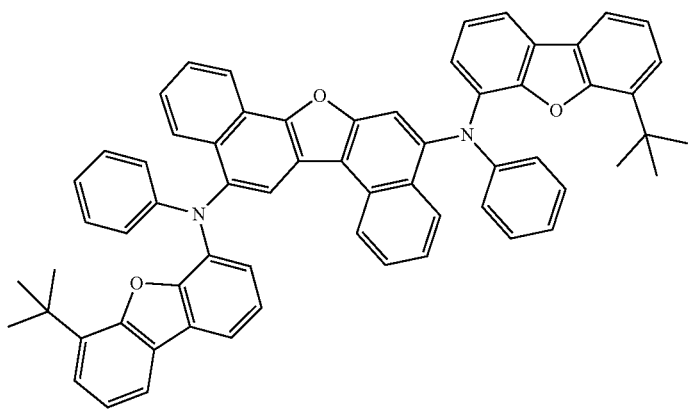
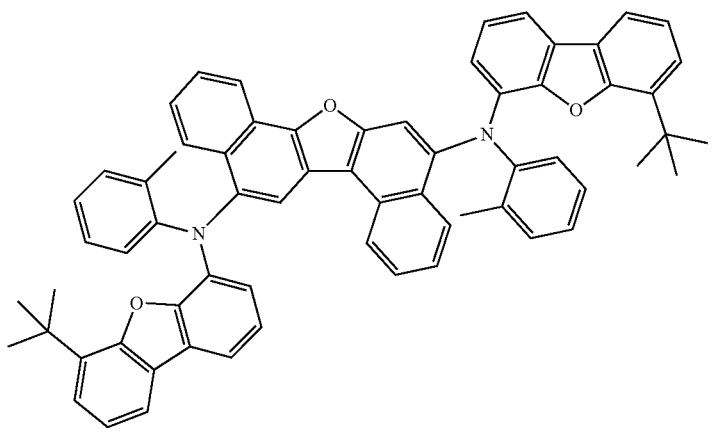
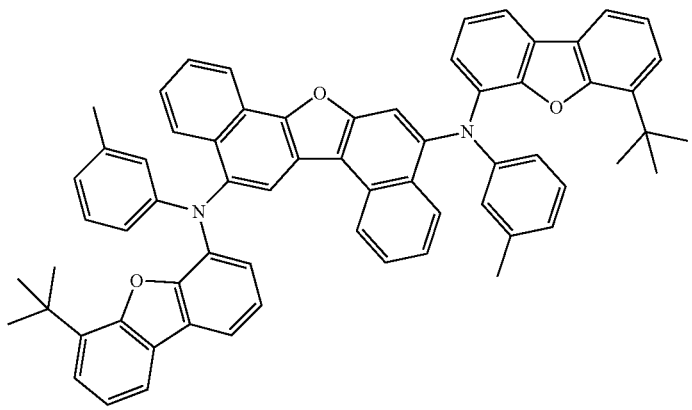

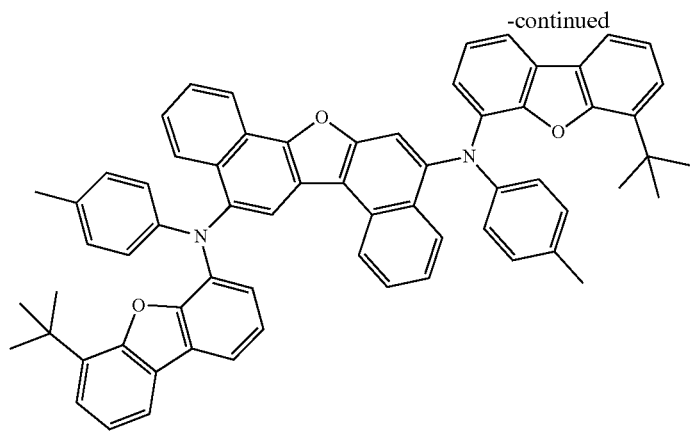
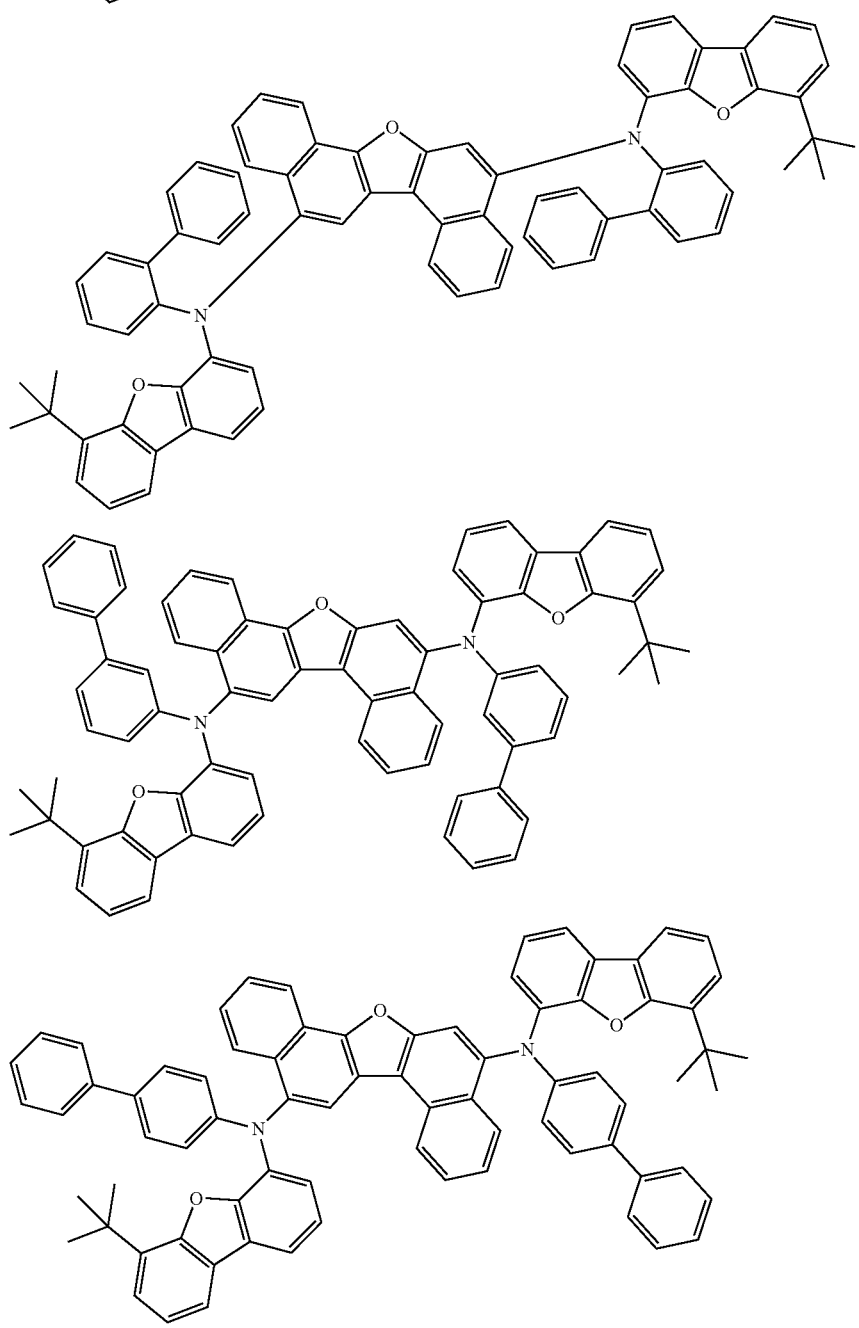

-continued
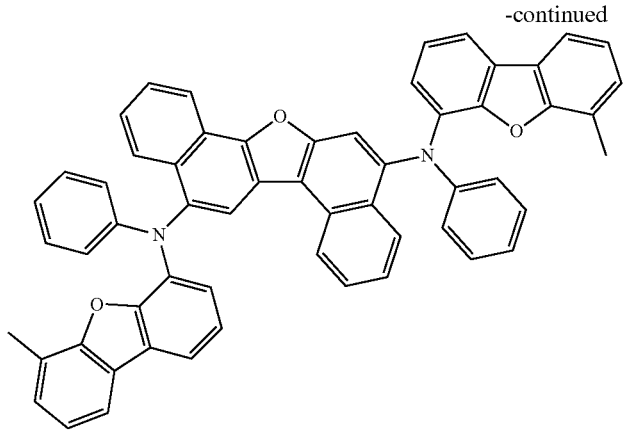
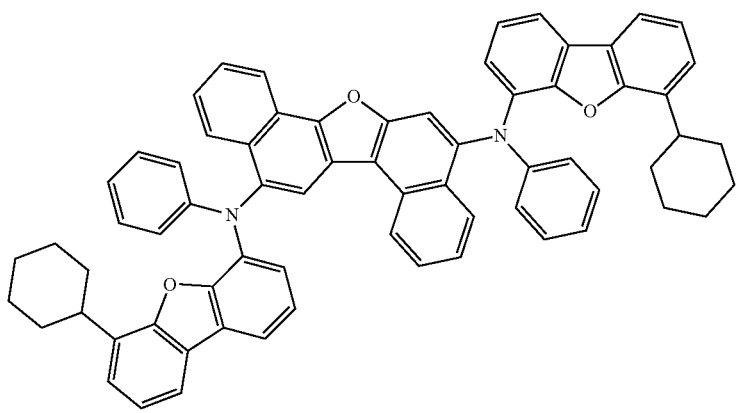
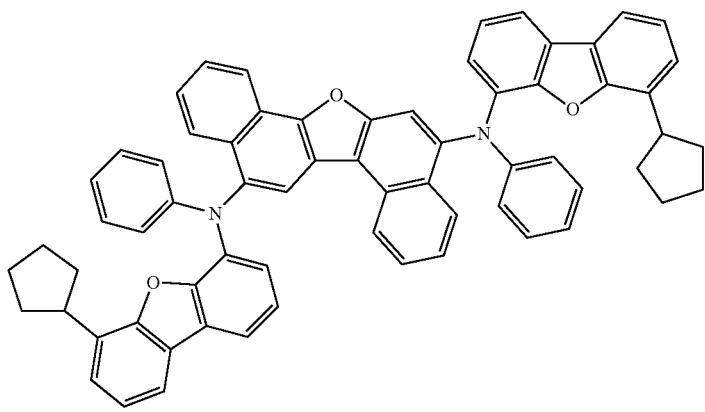
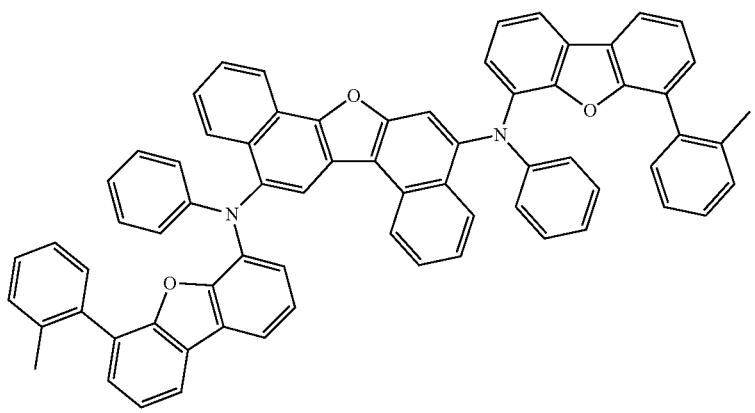

219 220
-continued
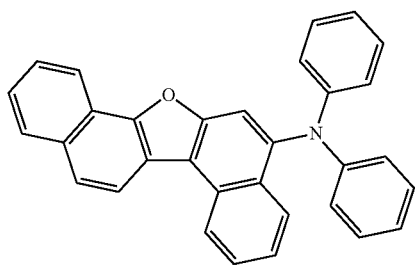 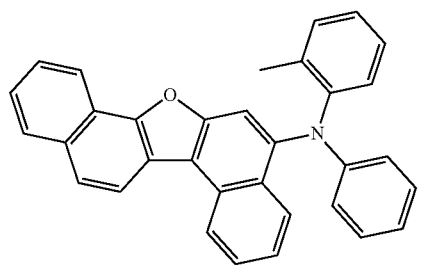
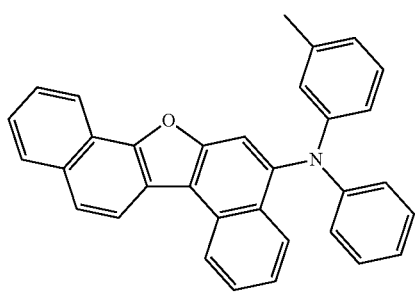 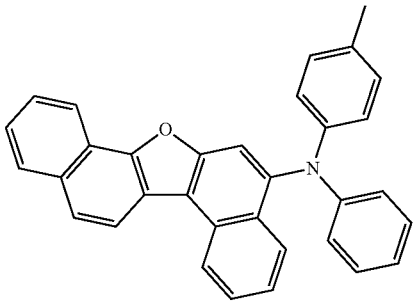
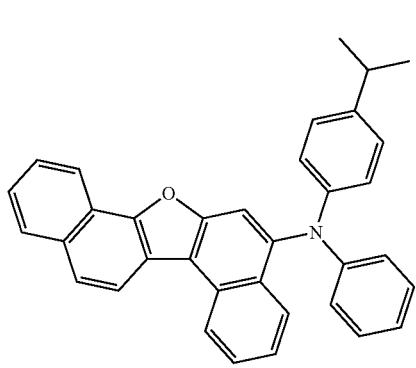 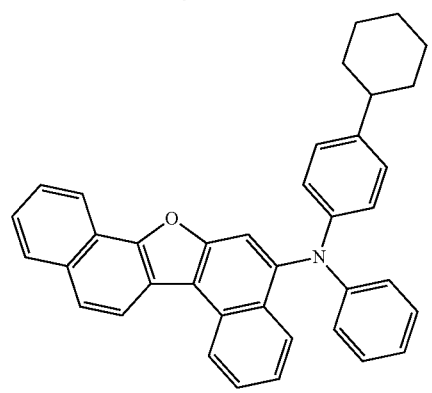
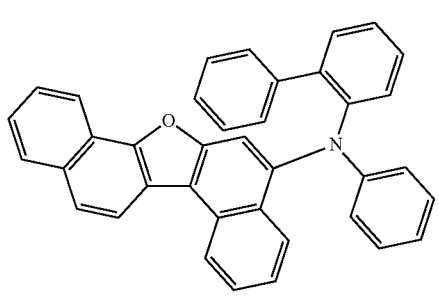 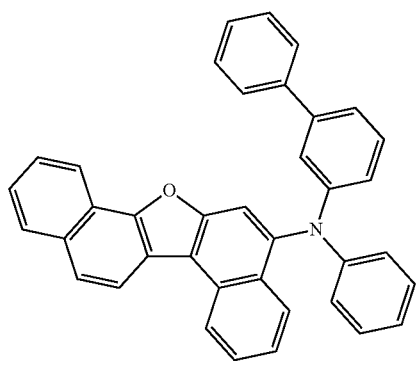
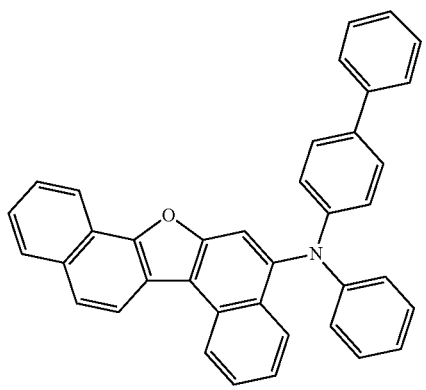 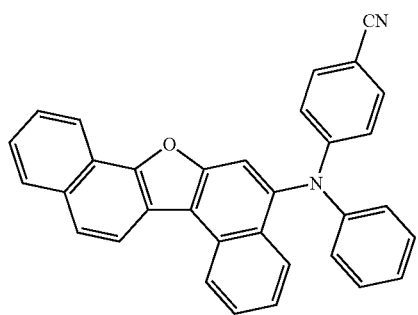

221 222
-continued
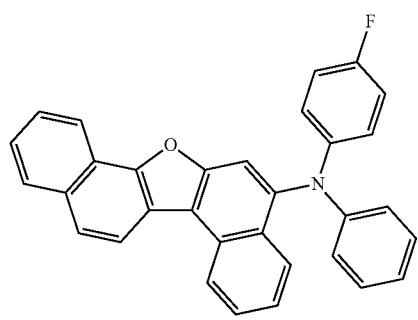 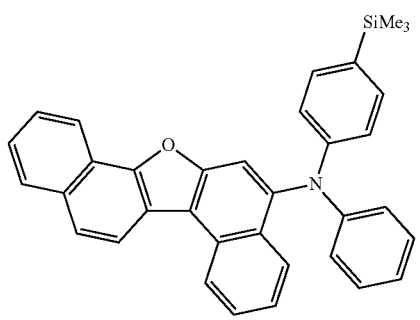
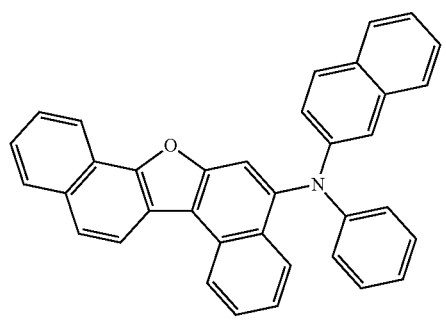 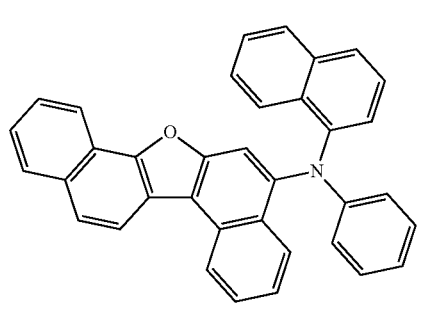
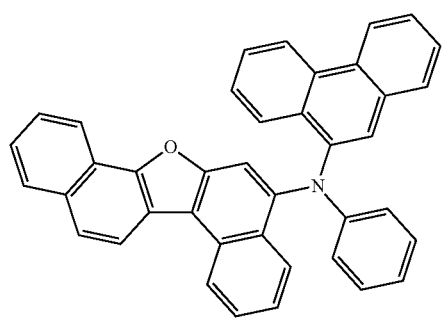 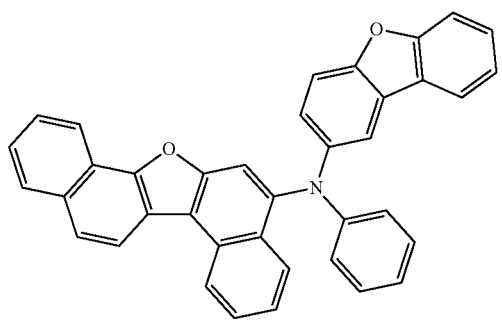
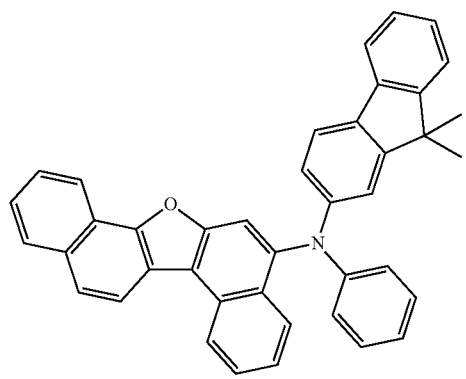 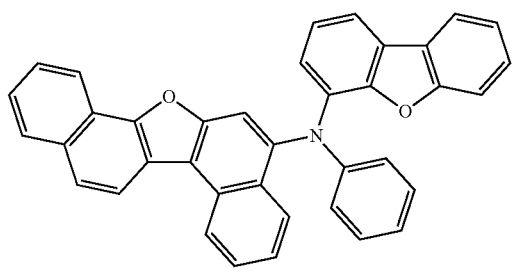
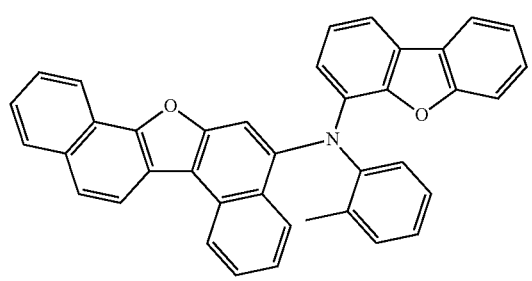 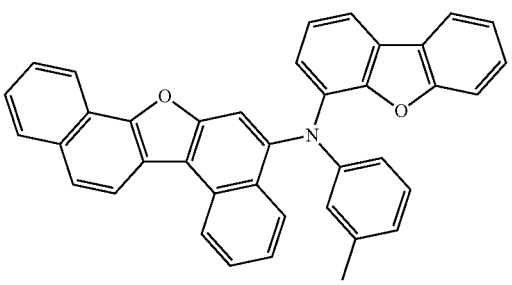

-continued
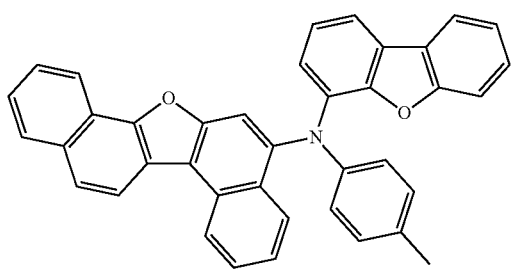
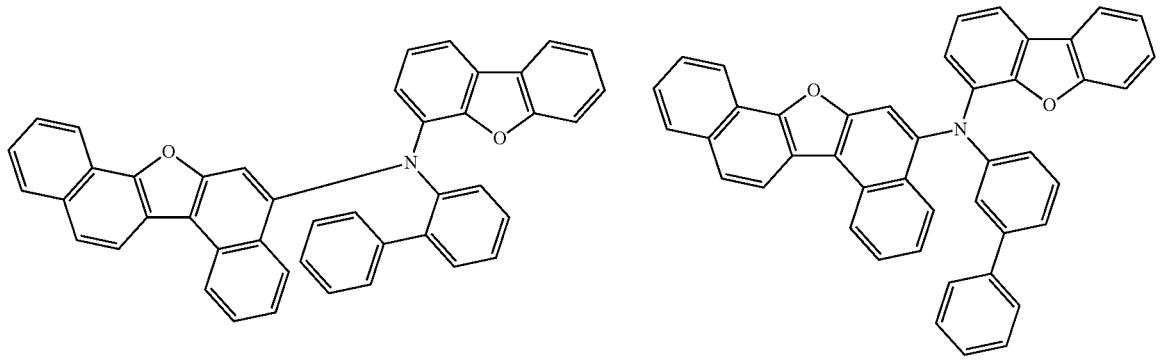
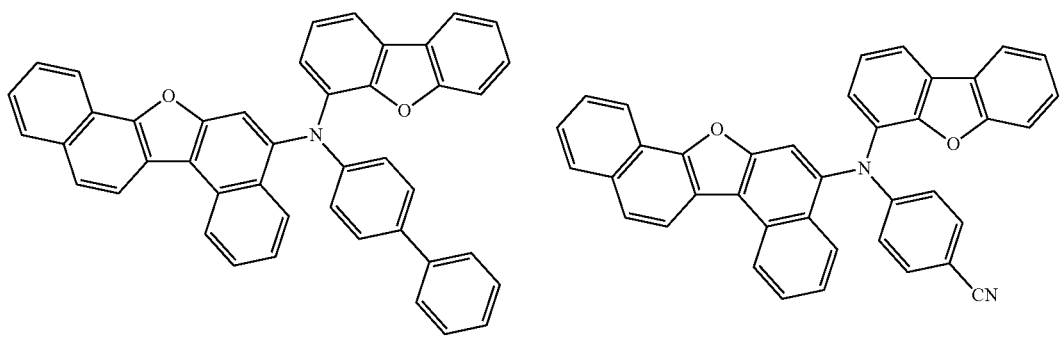
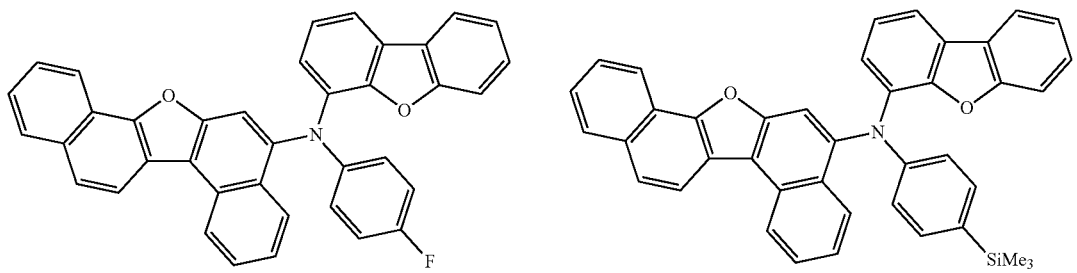
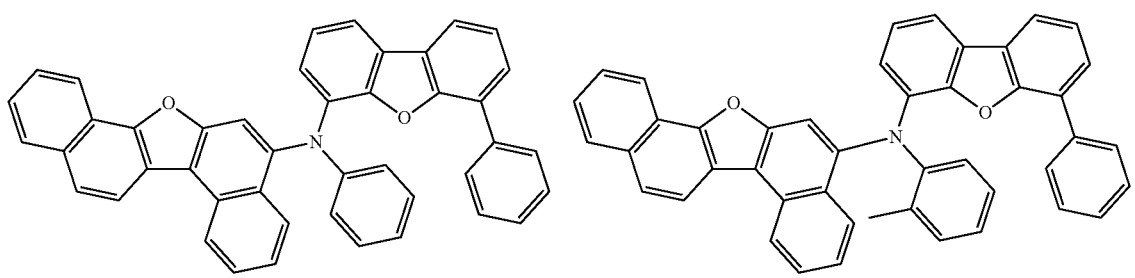

-continued
225    226
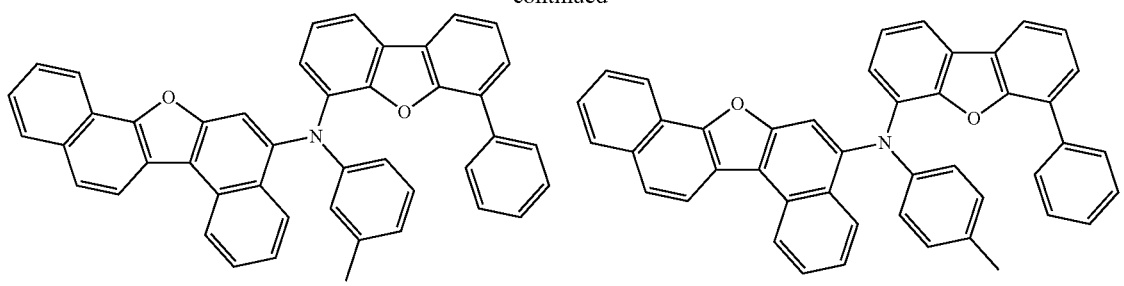
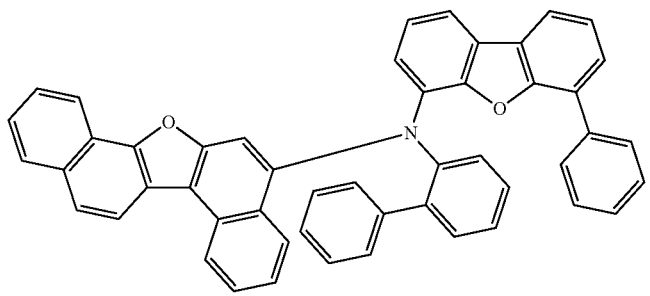
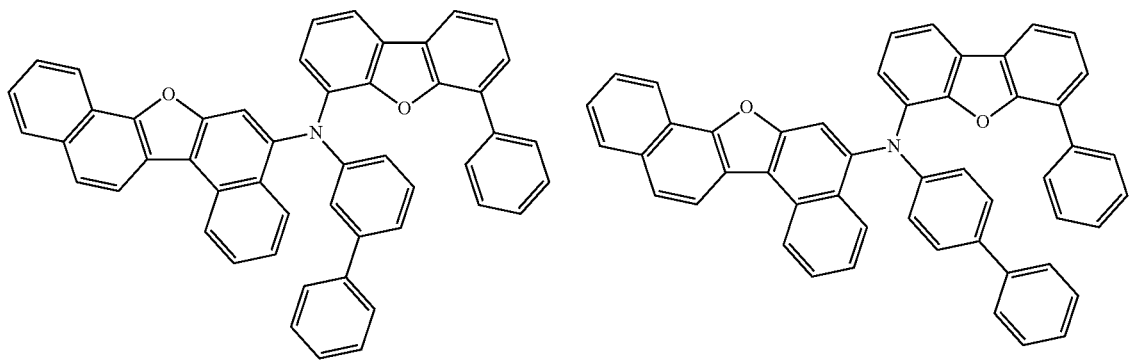
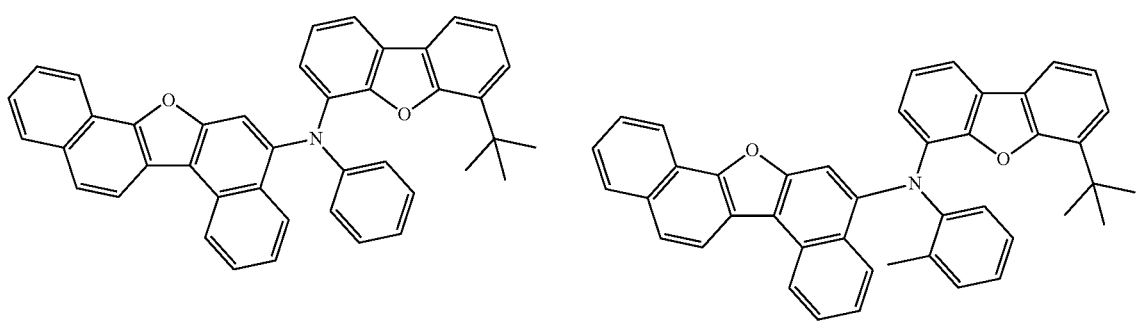
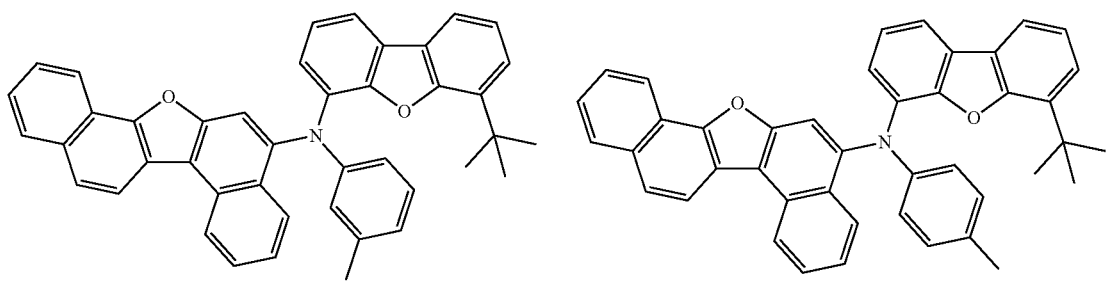

227
-continued
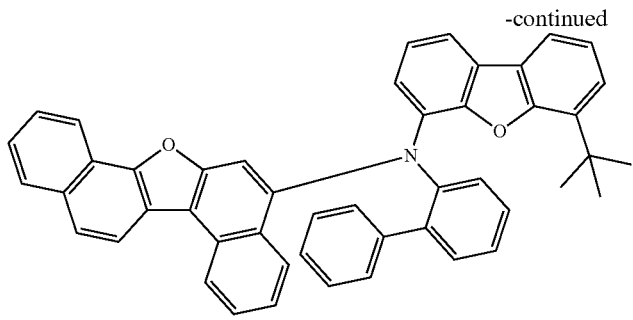
228
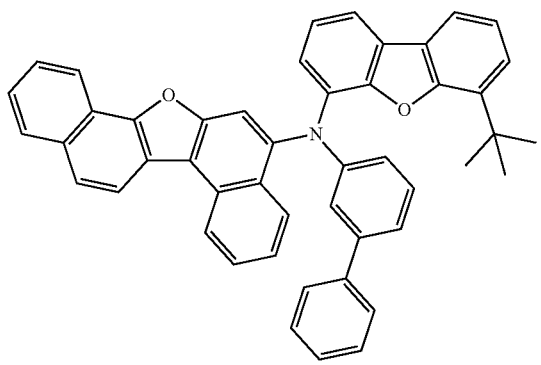
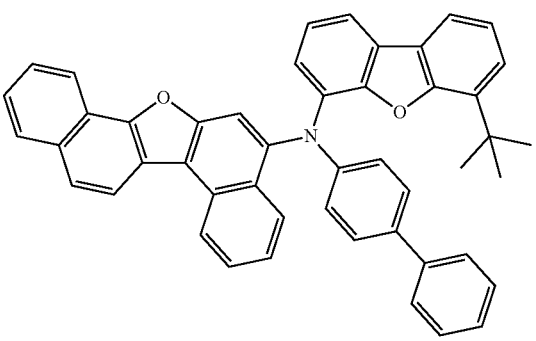
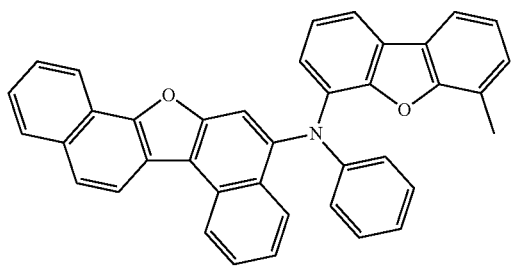
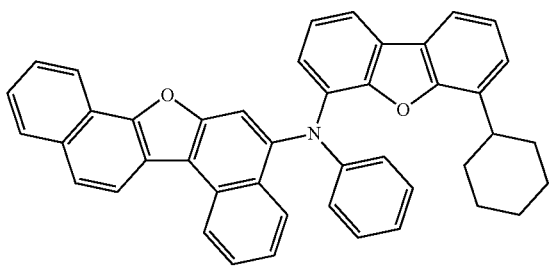
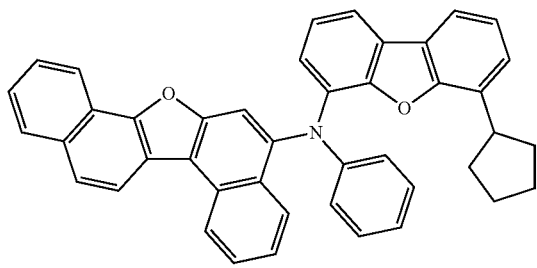
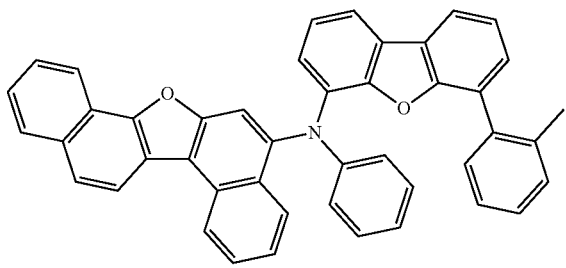
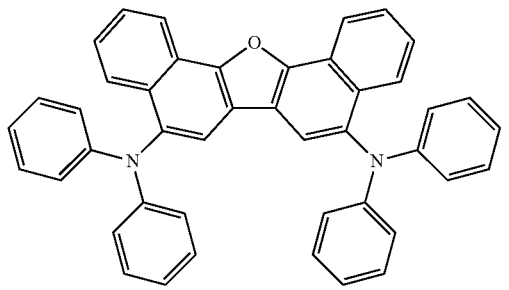
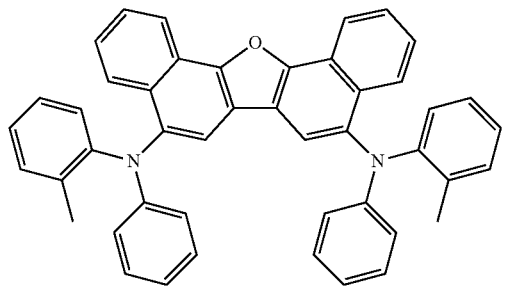

| 229 | 230 |
|---|---|
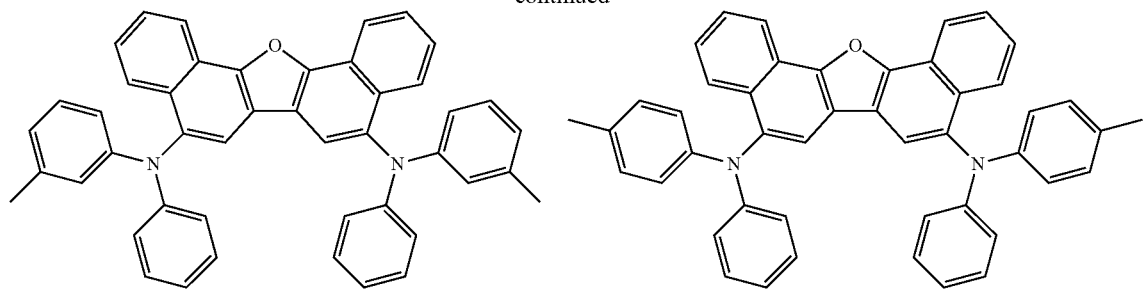
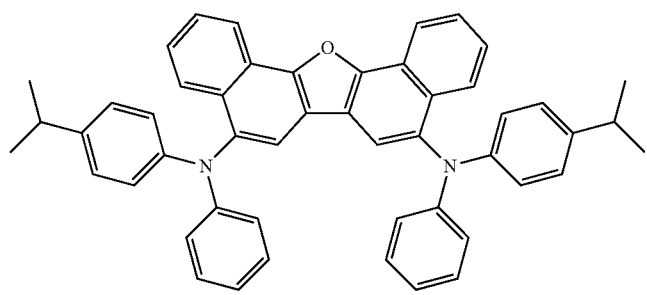
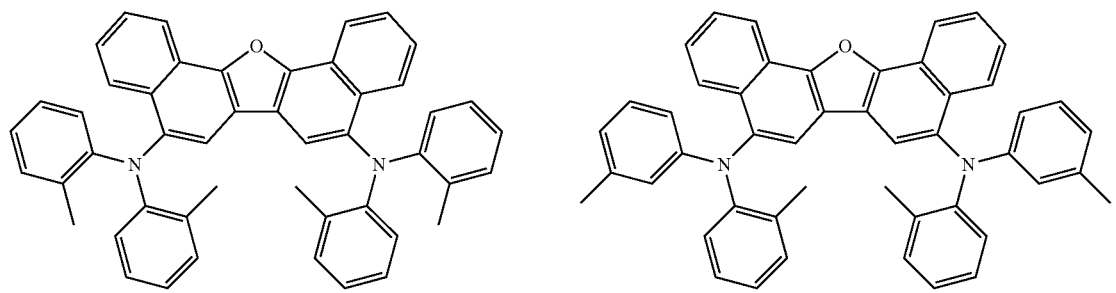
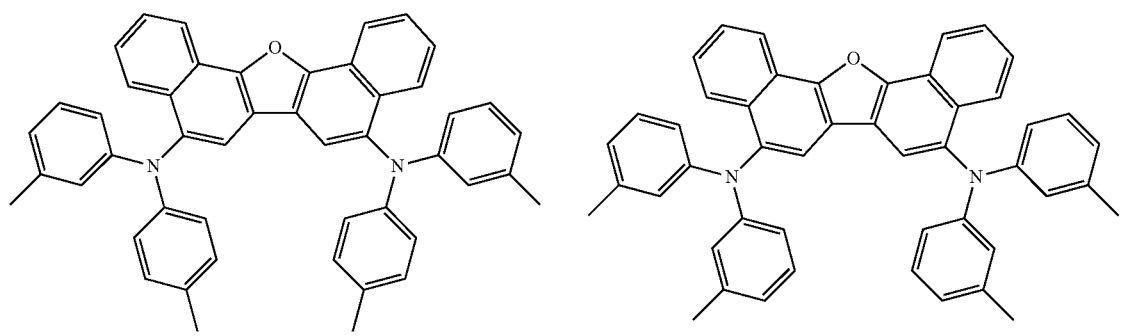
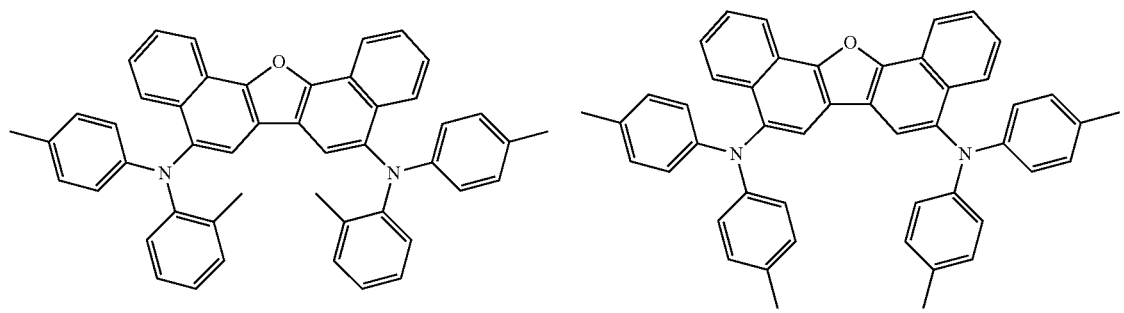

-continued
231
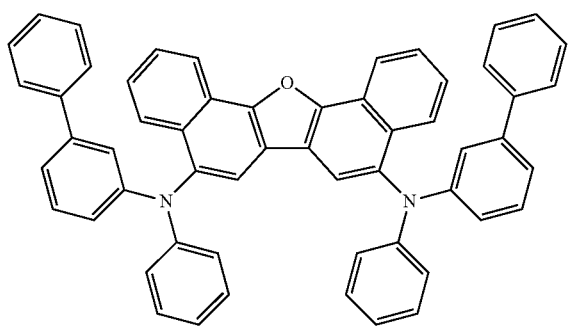
232
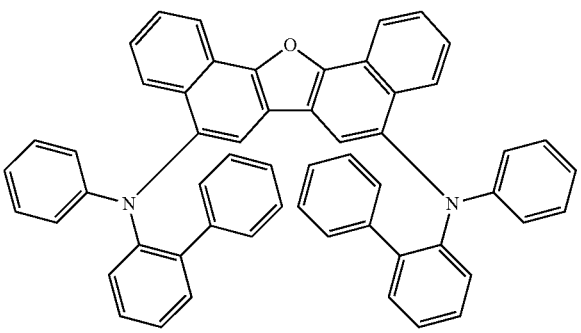
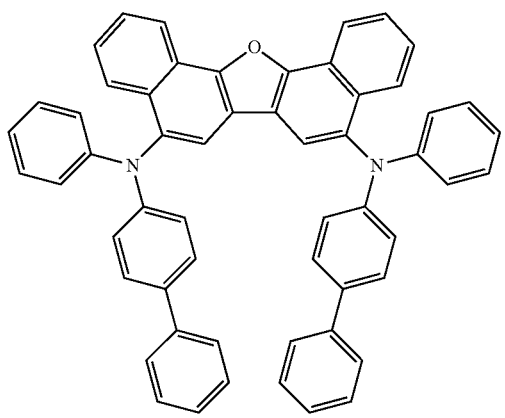
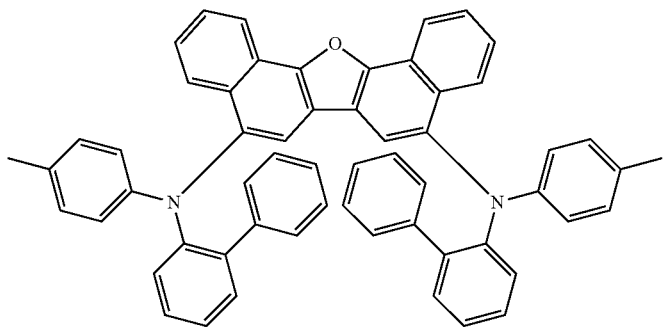
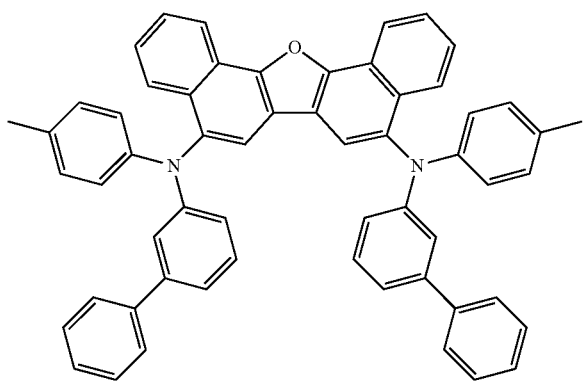

233
234
-continued
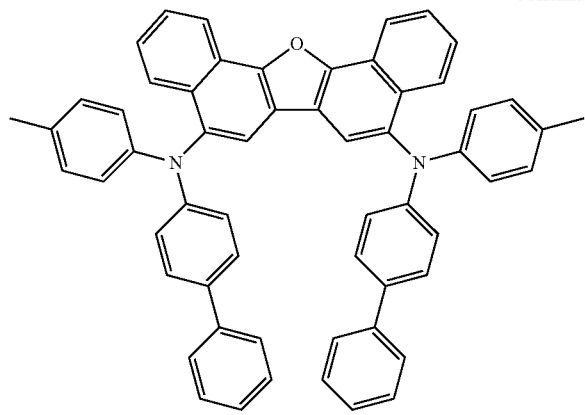
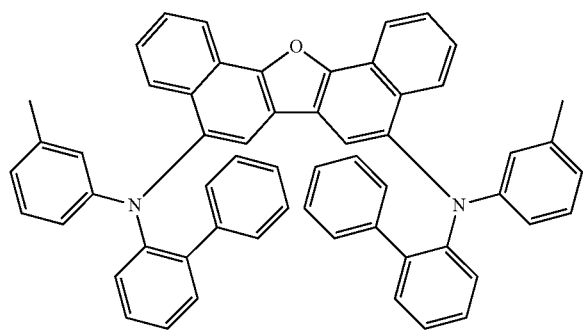
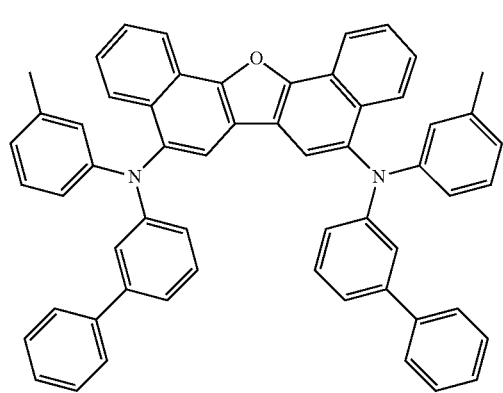
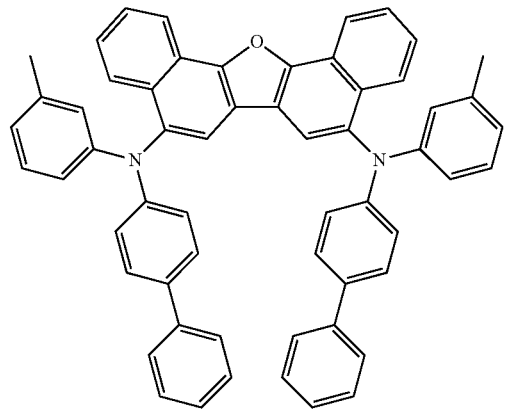
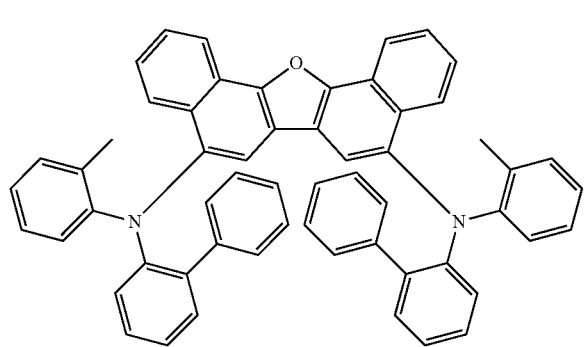
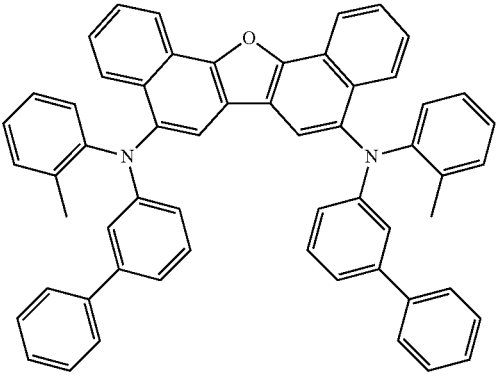

-continued
235
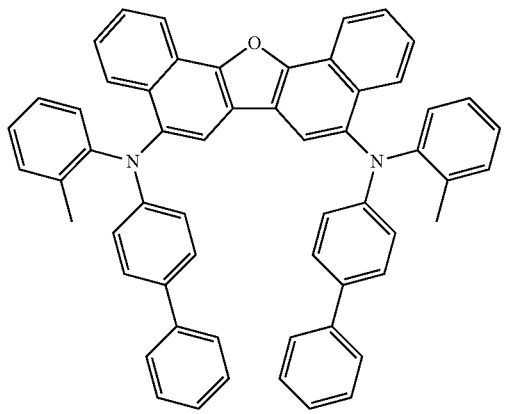
236
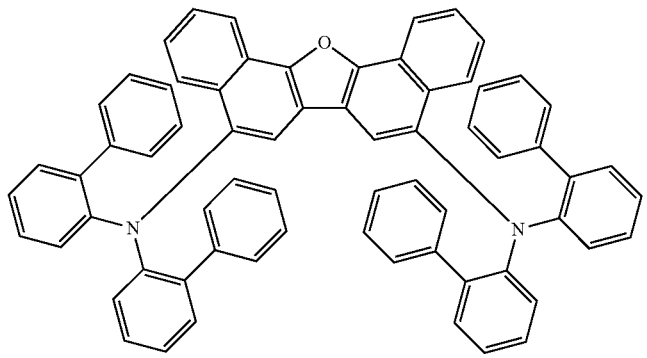
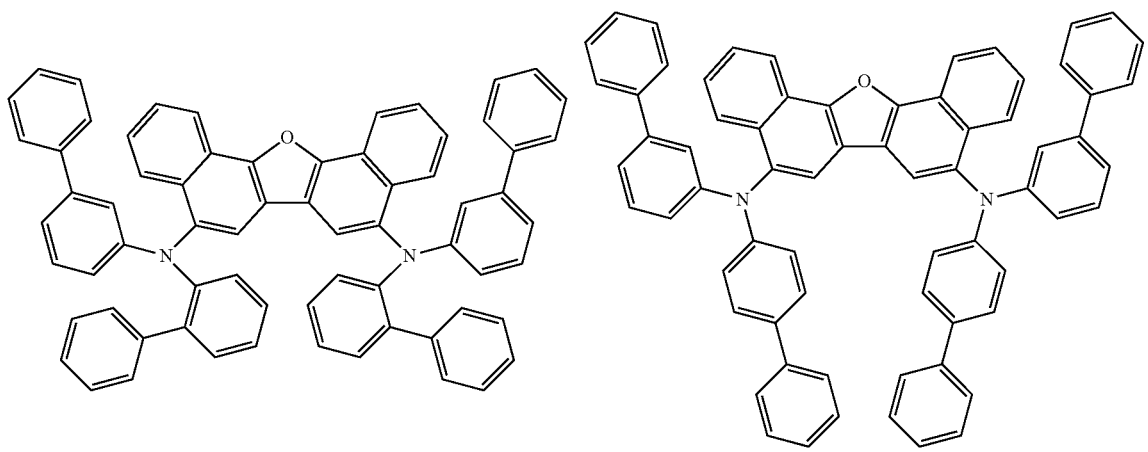
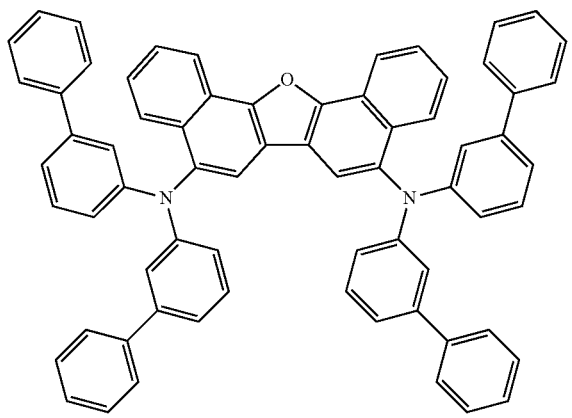
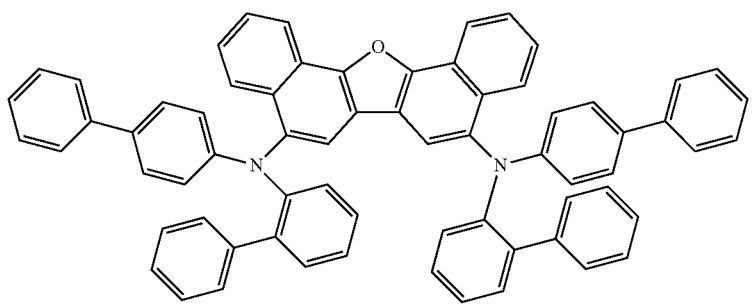

-continued
237
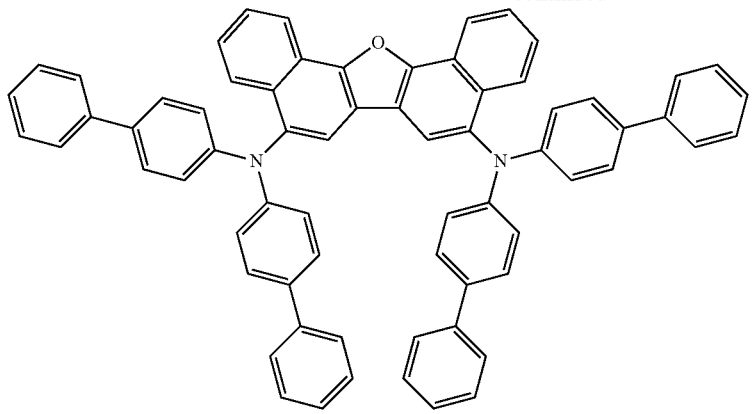
238
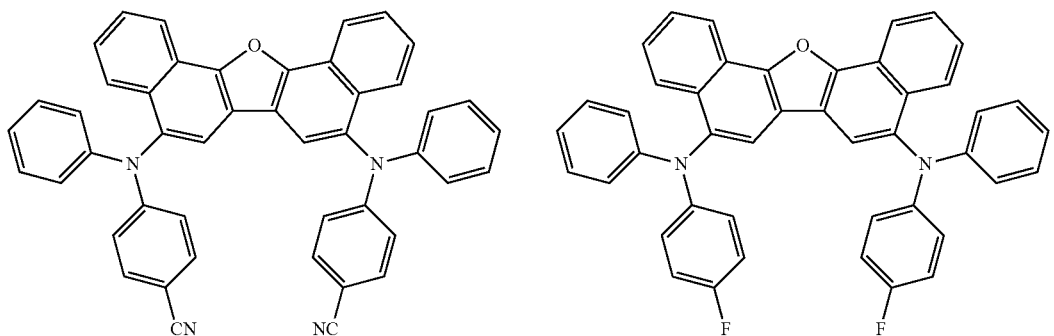
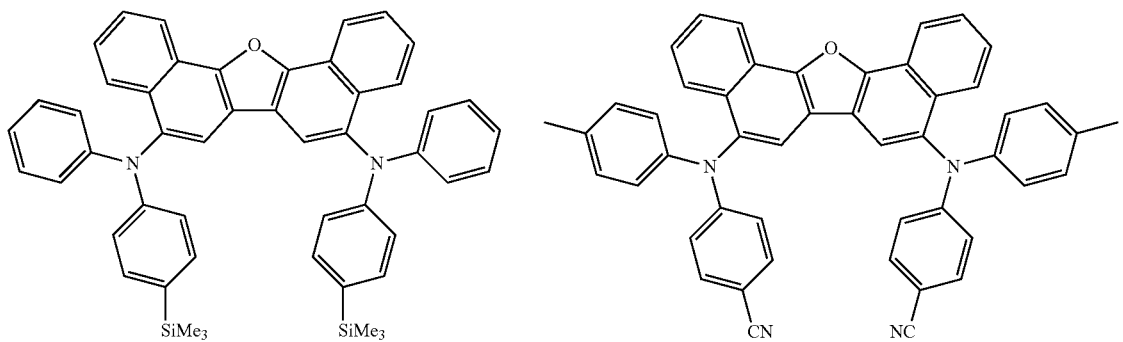
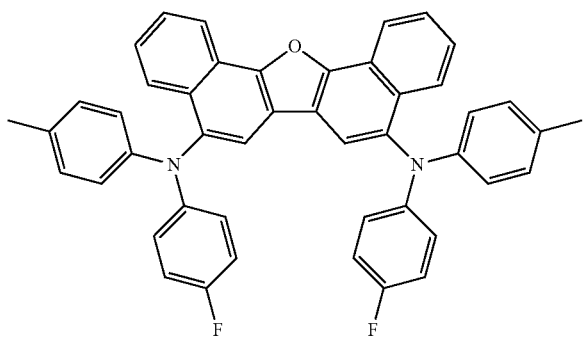

-continued
239 240
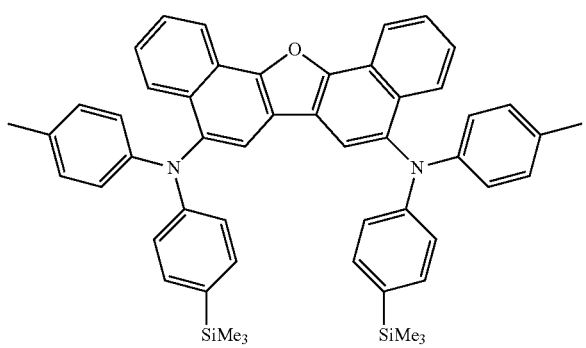 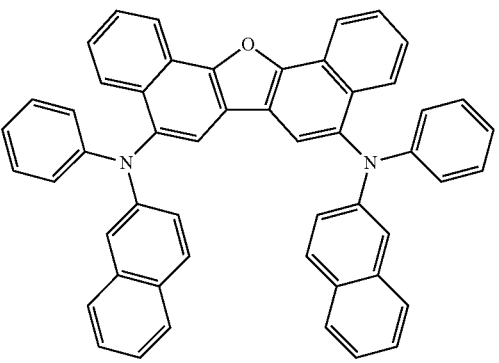
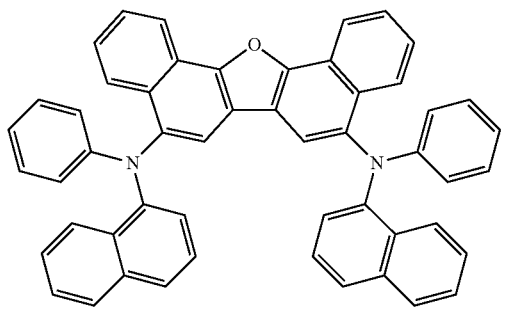 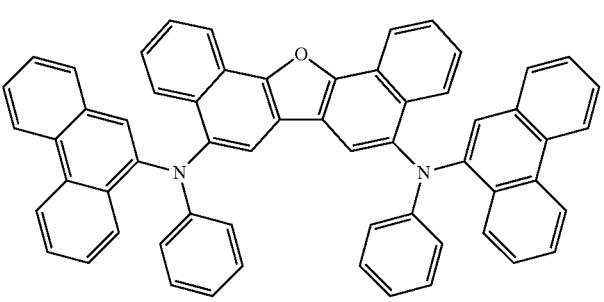
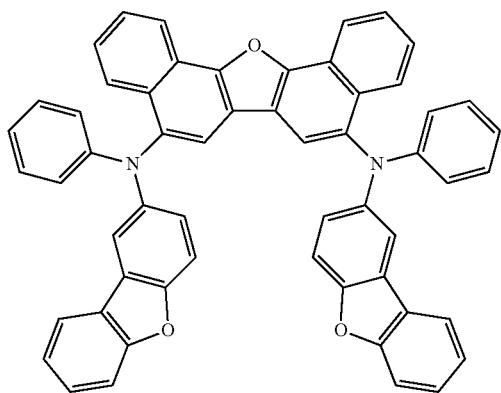 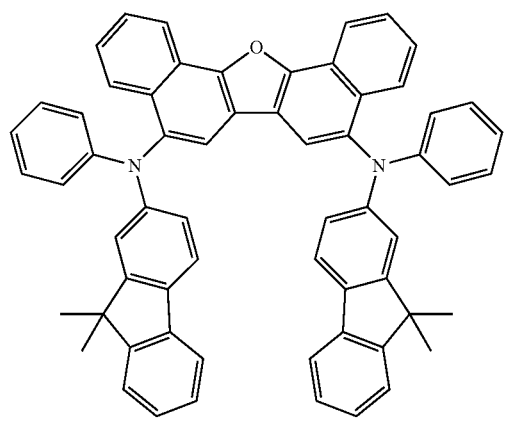
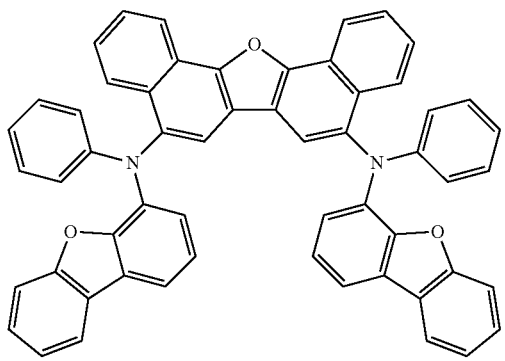 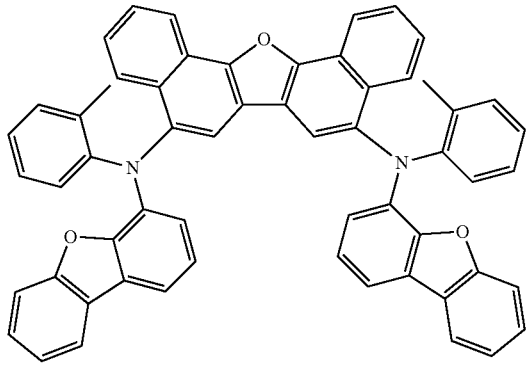

-continued
241 242
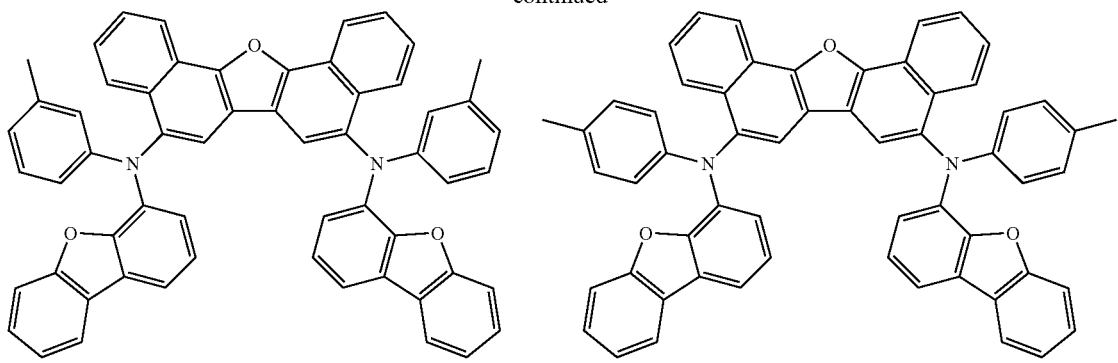
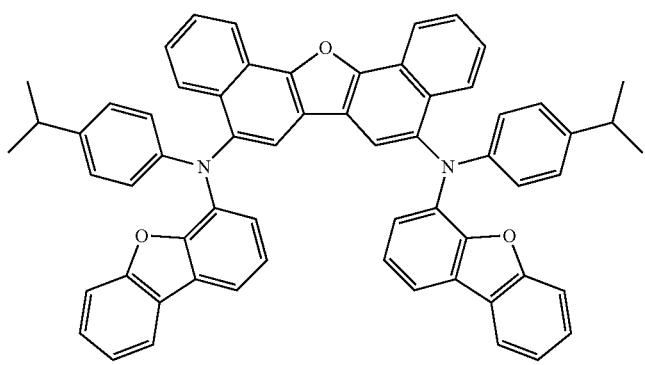
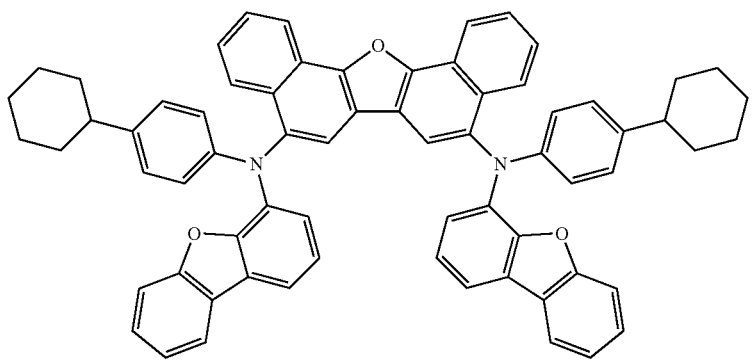
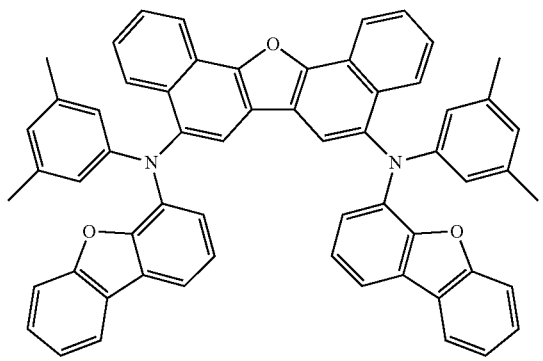

243  244
-continued
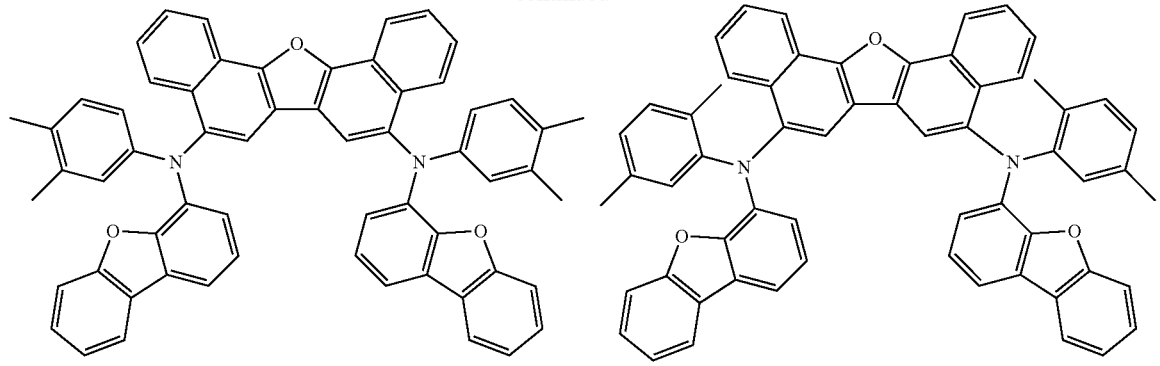
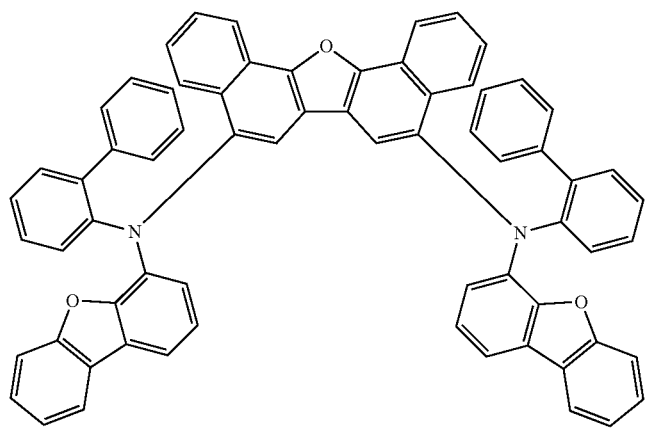
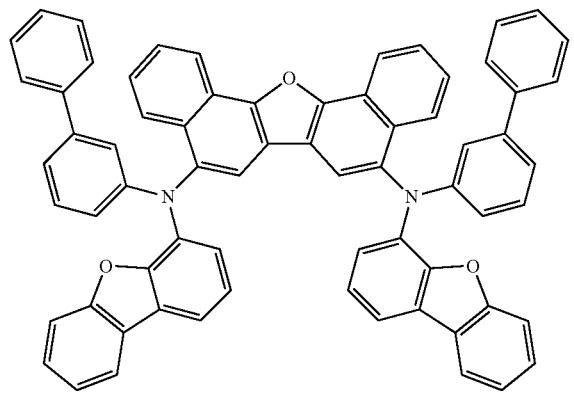
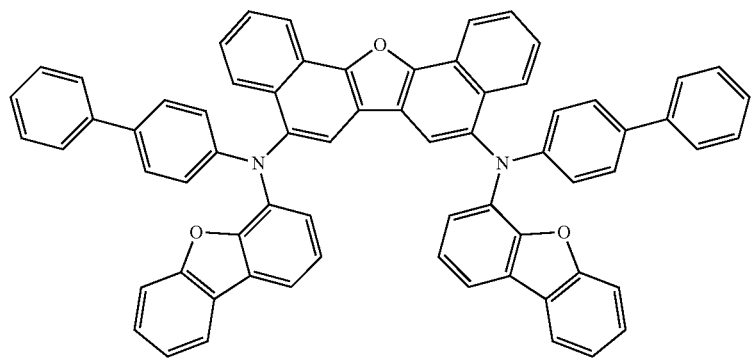

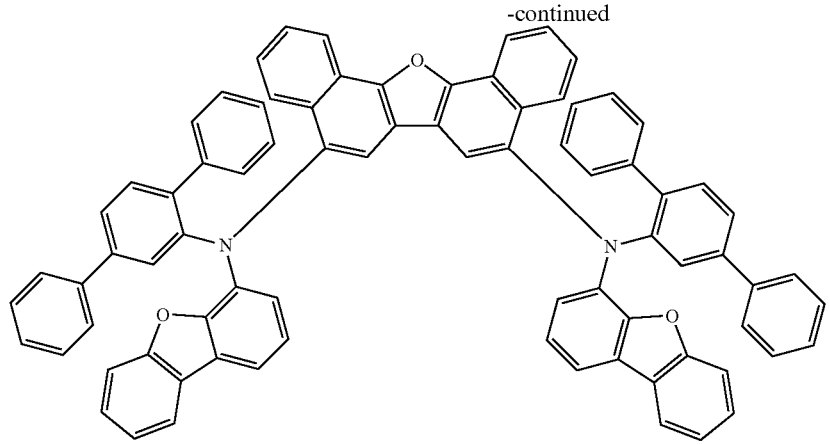
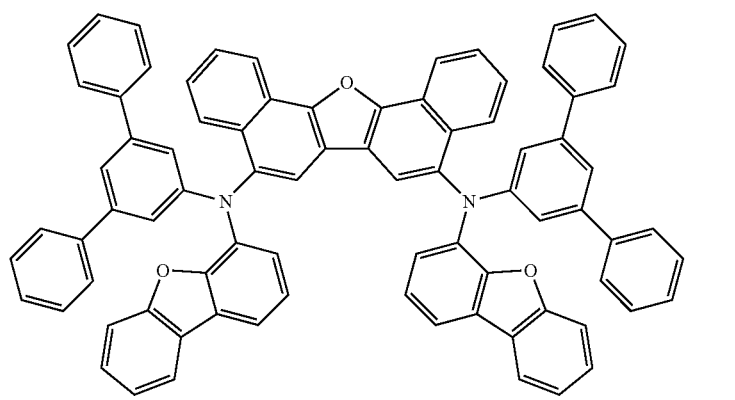
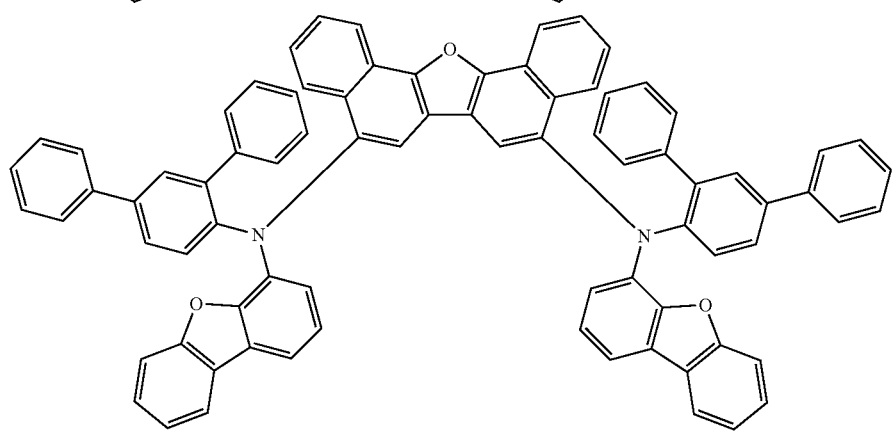
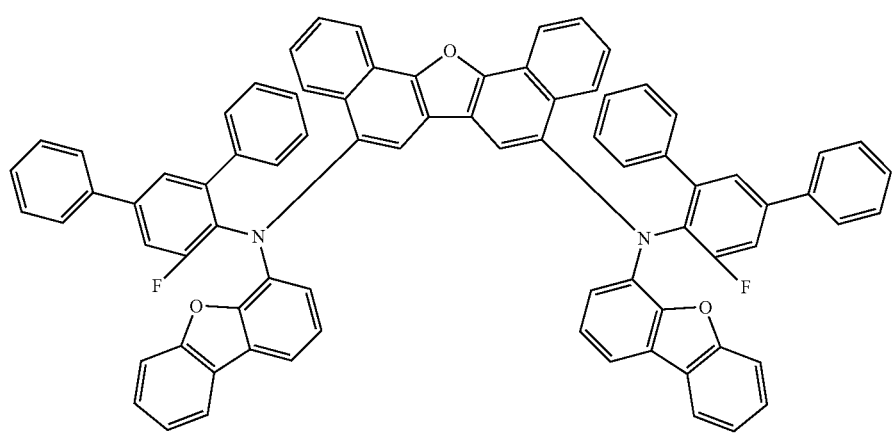

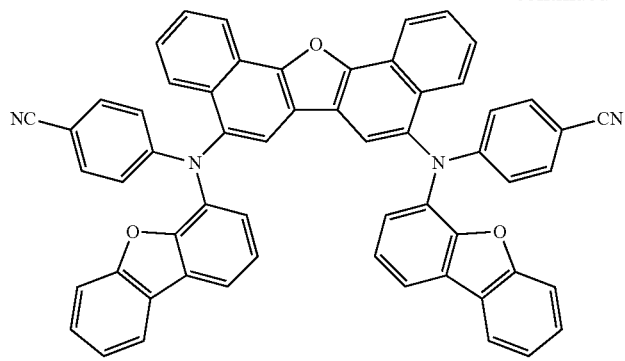
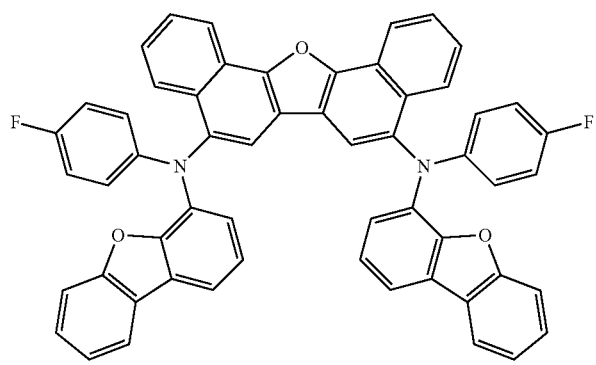
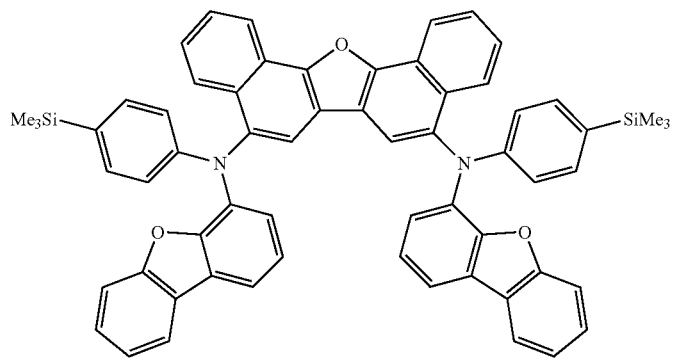
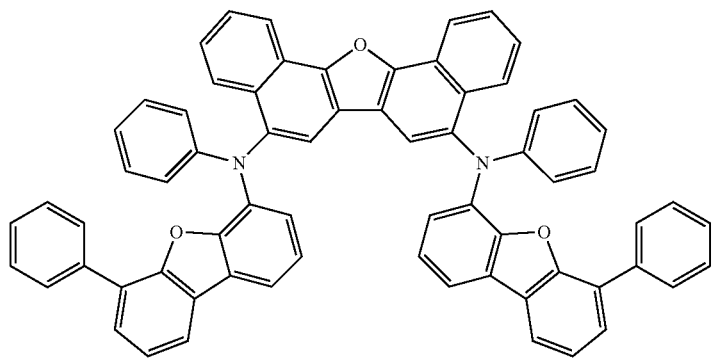

-continued
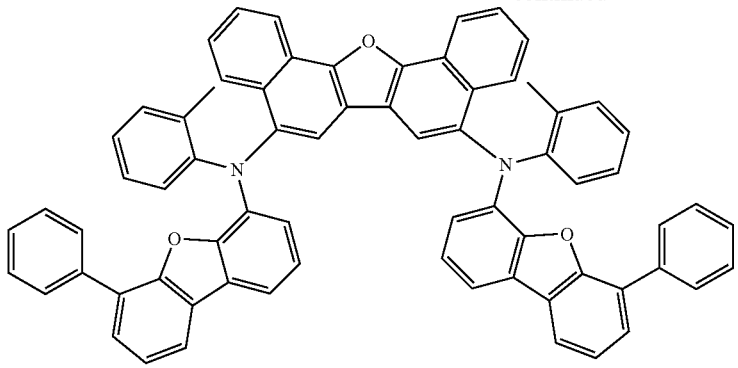
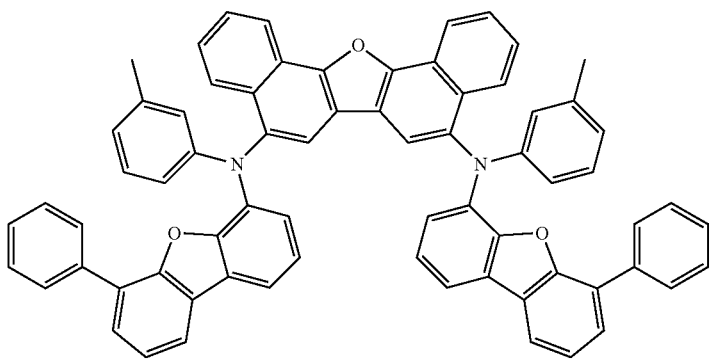
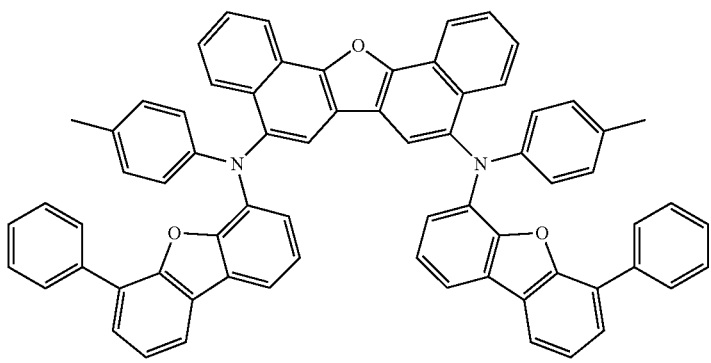
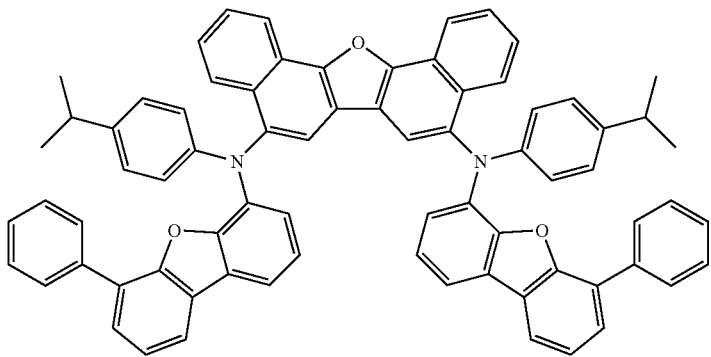

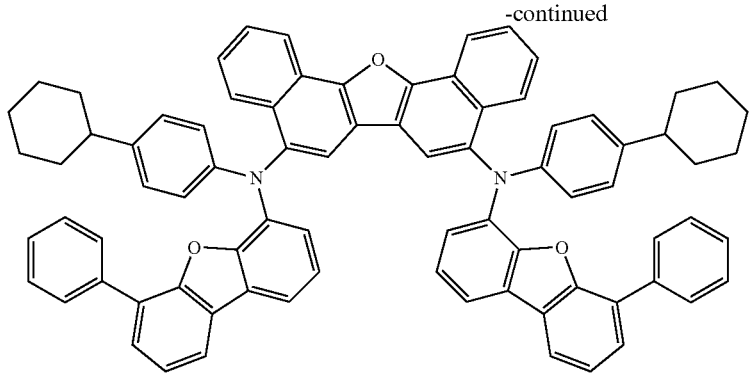
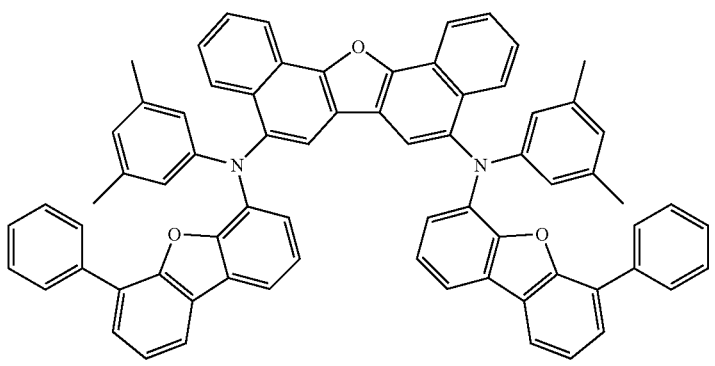
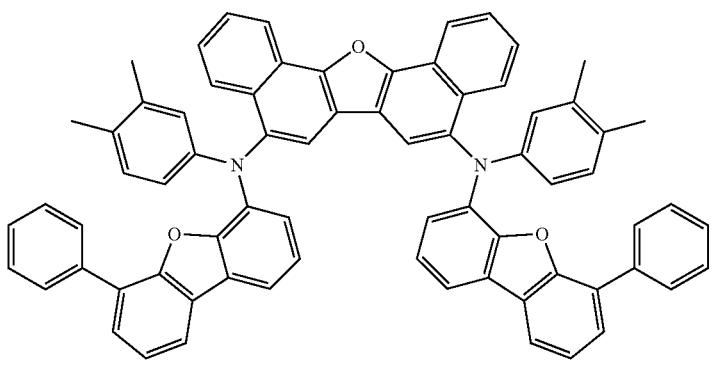
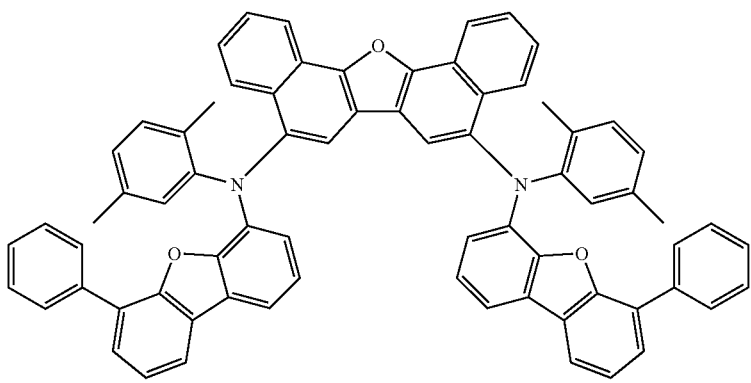

-continued
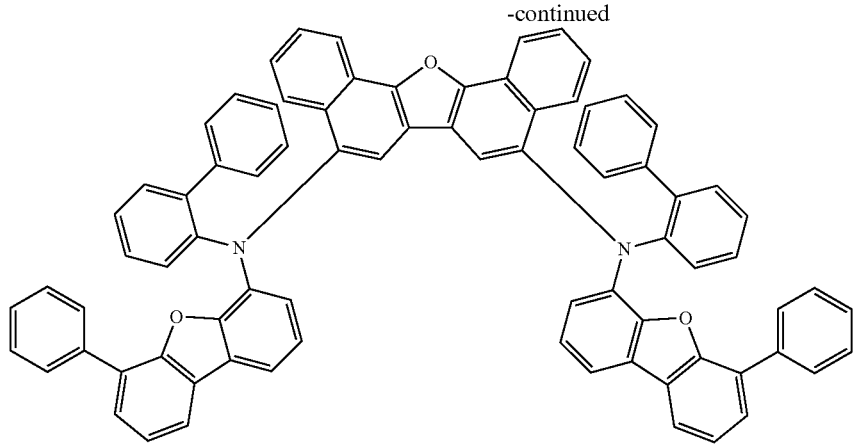
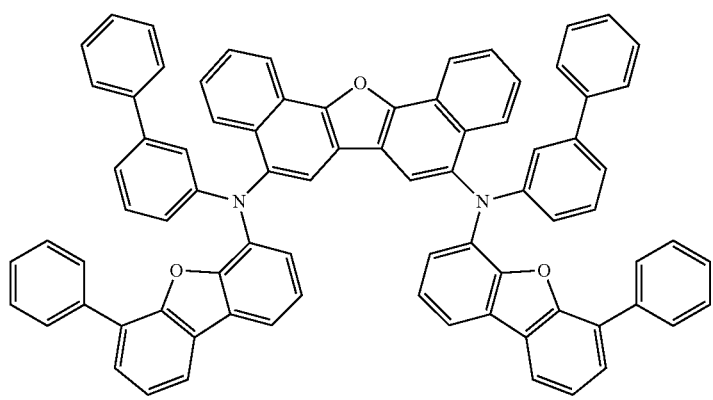
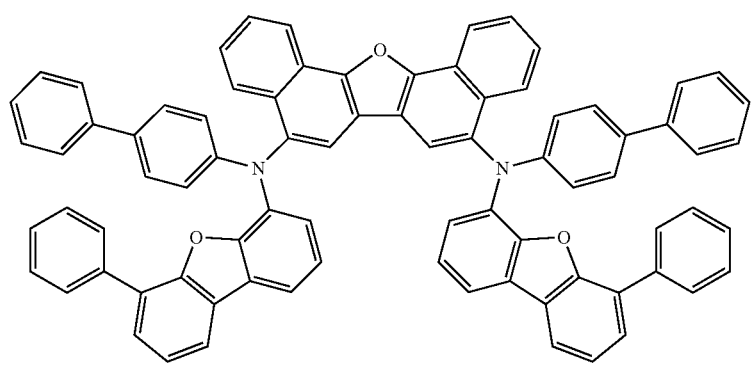
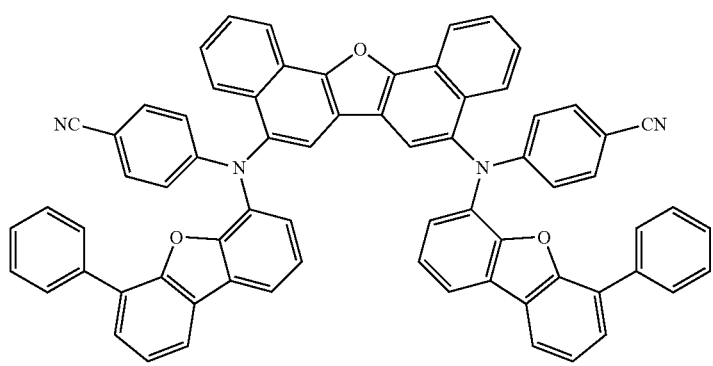

-continued
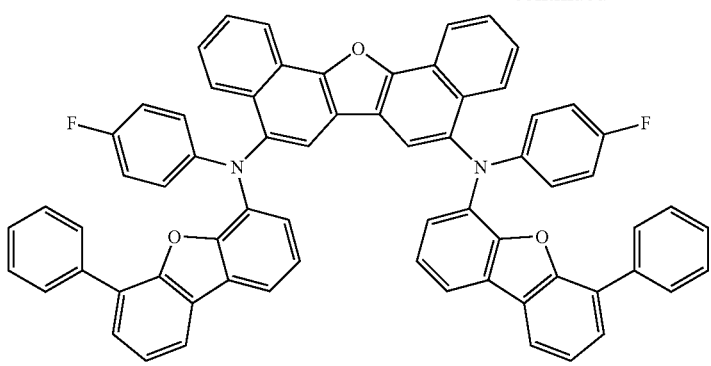
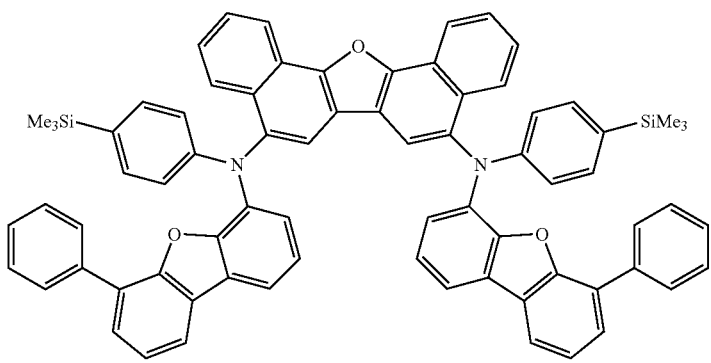
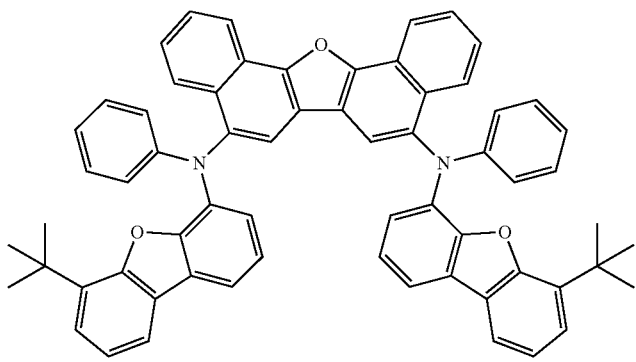
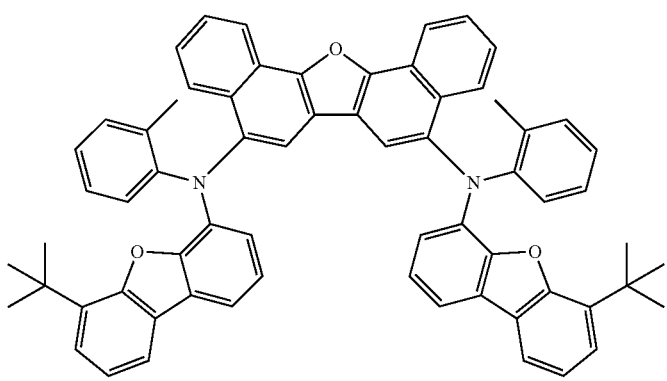

-continued
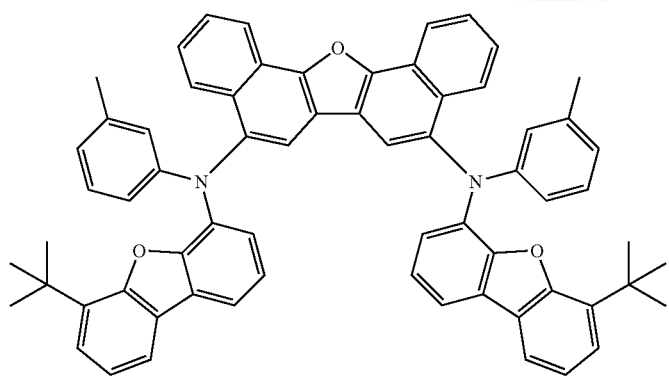
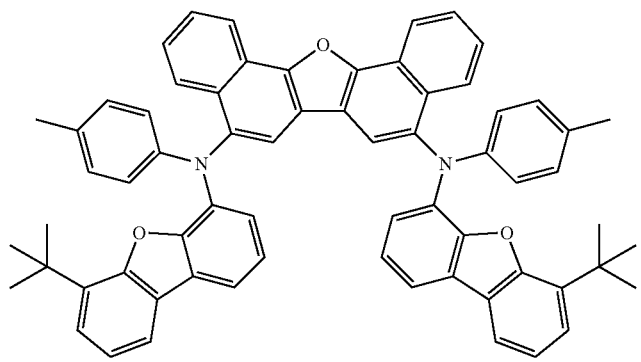
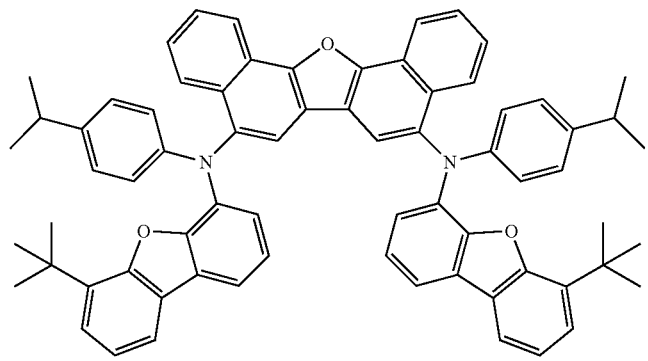
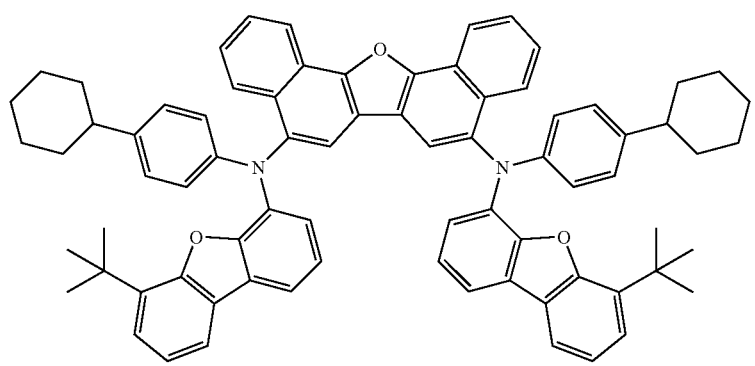

-continued
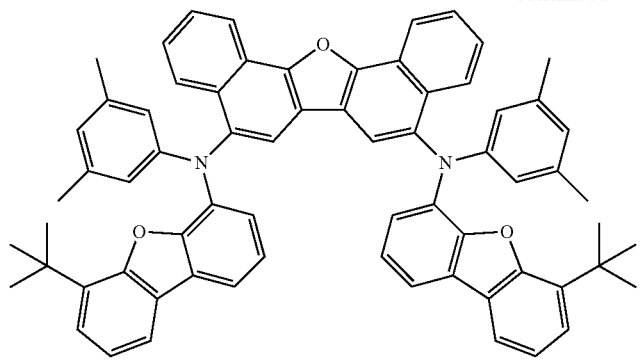
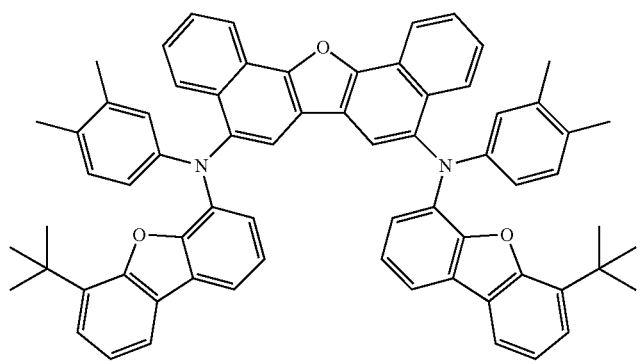
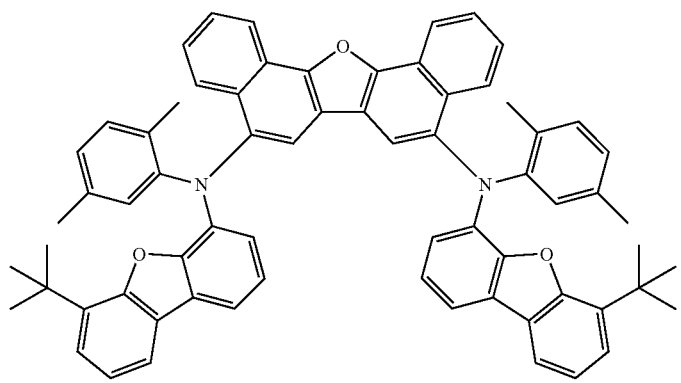
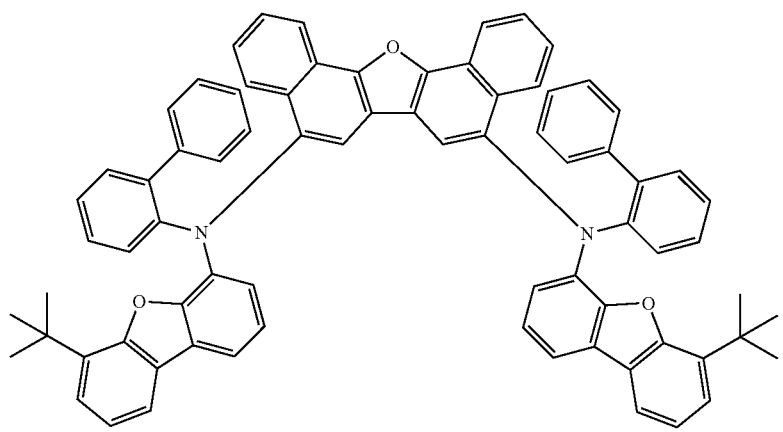

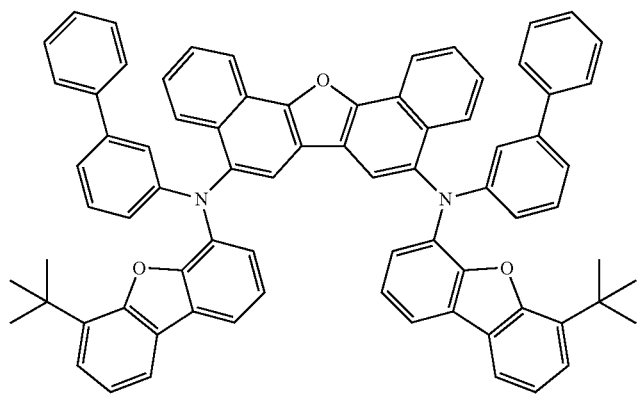
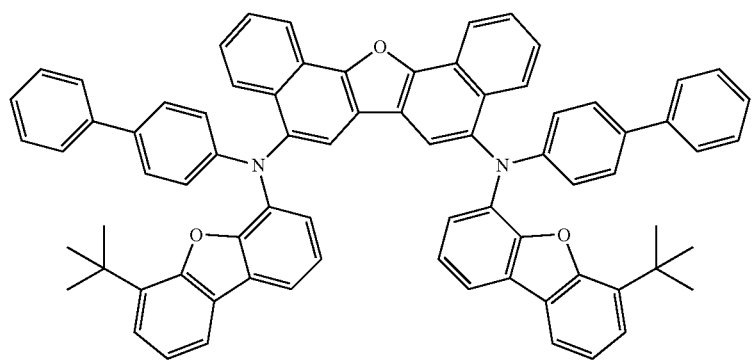
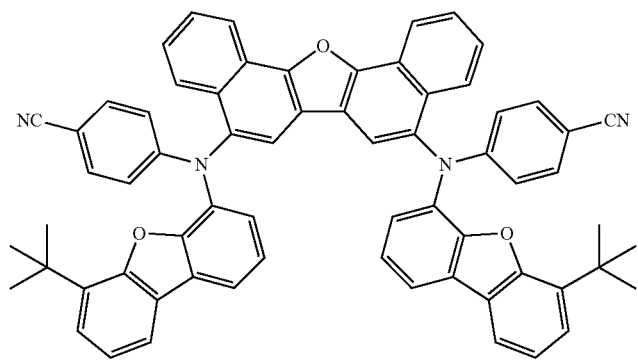
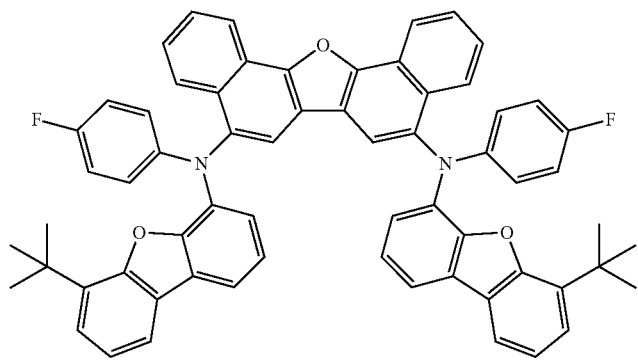

263
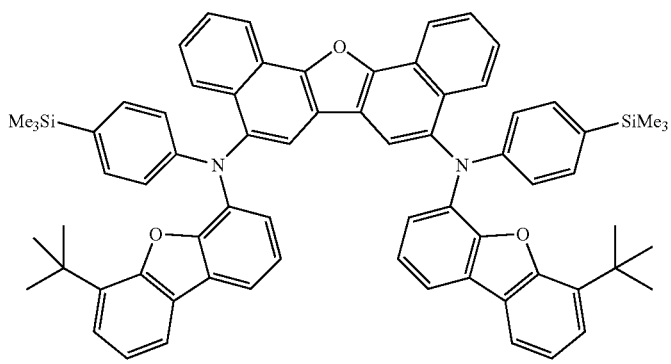
-continued
264
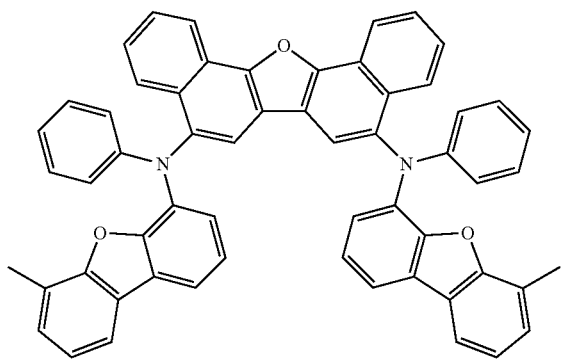
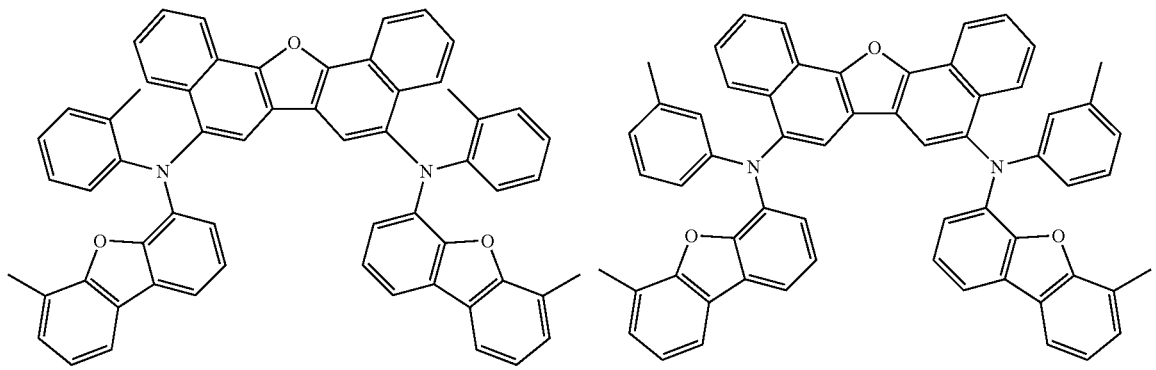
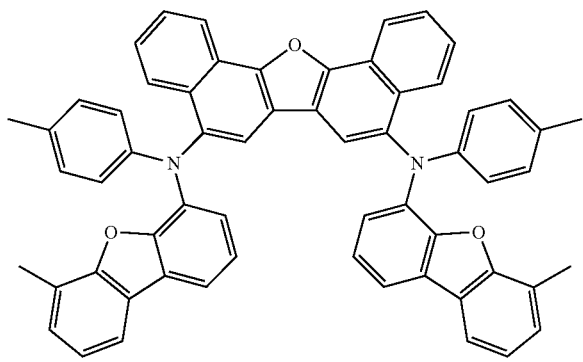

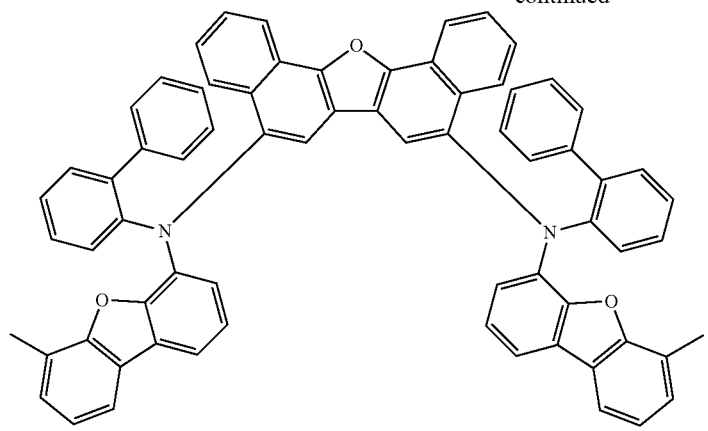
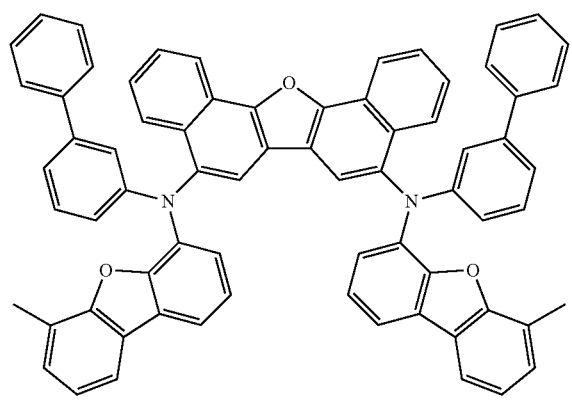
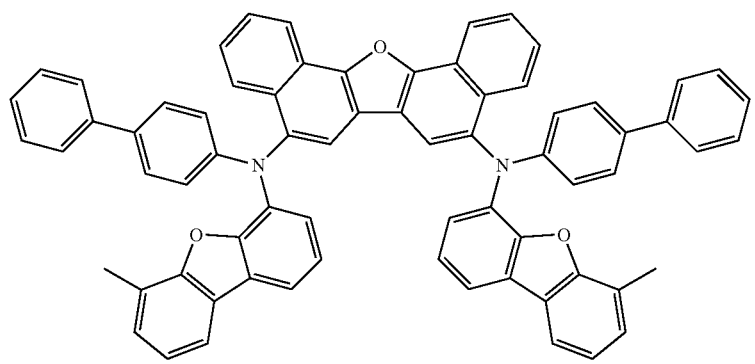
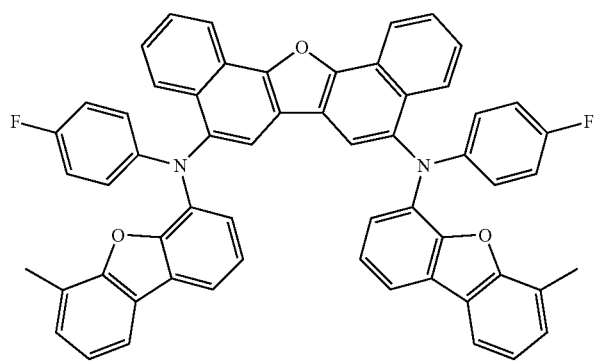

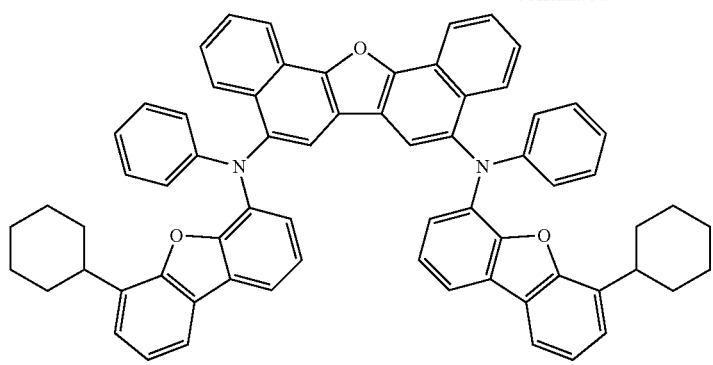
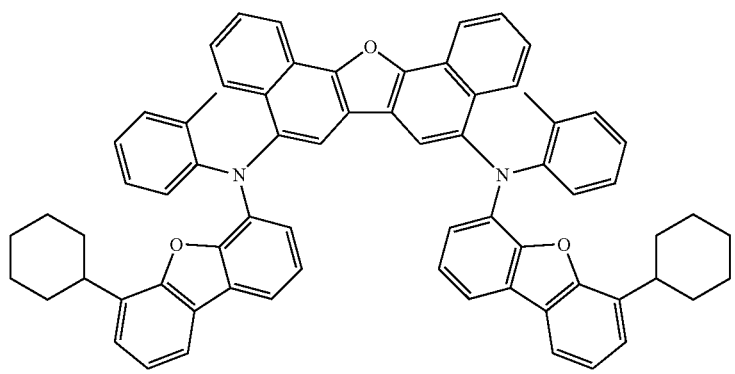
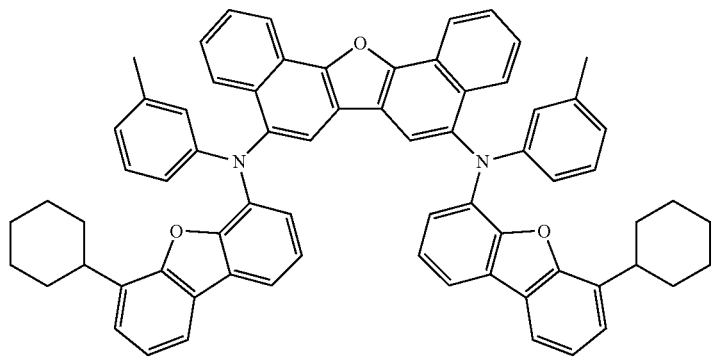
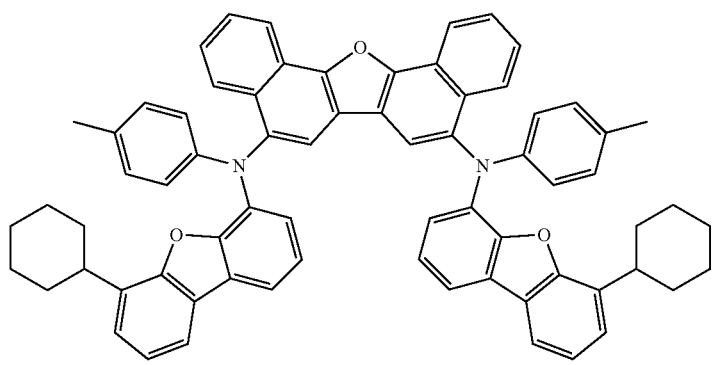

-continued
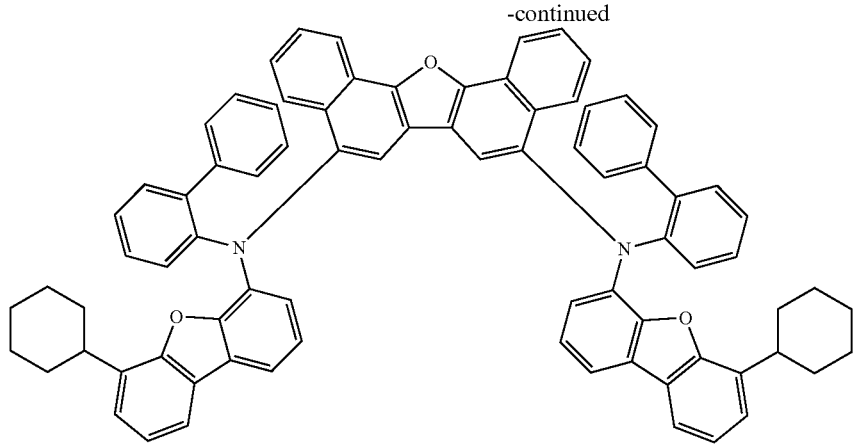
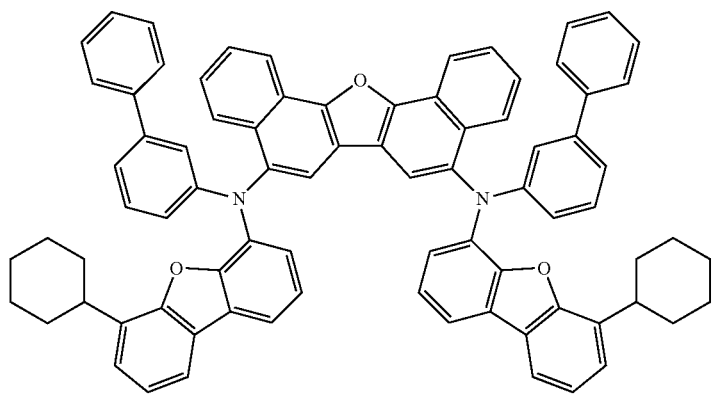
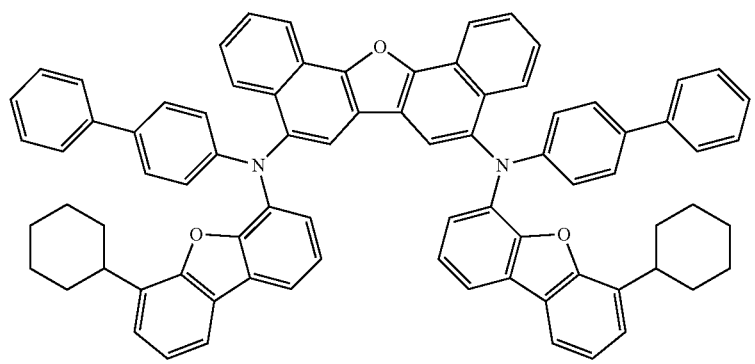
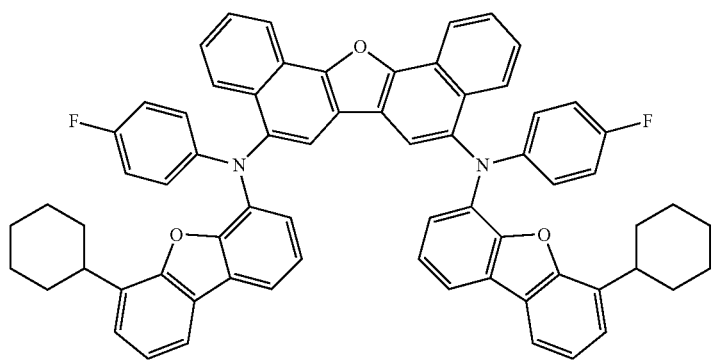

-continued
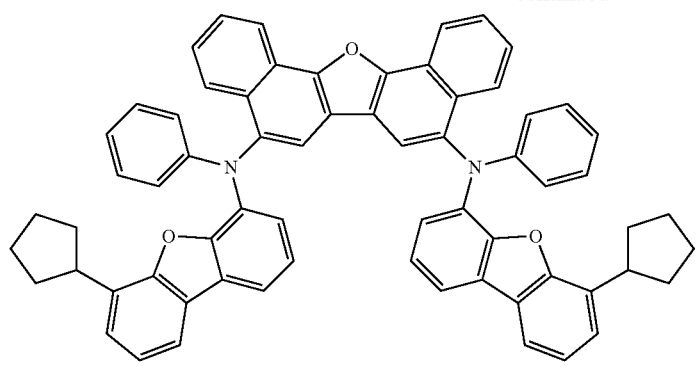
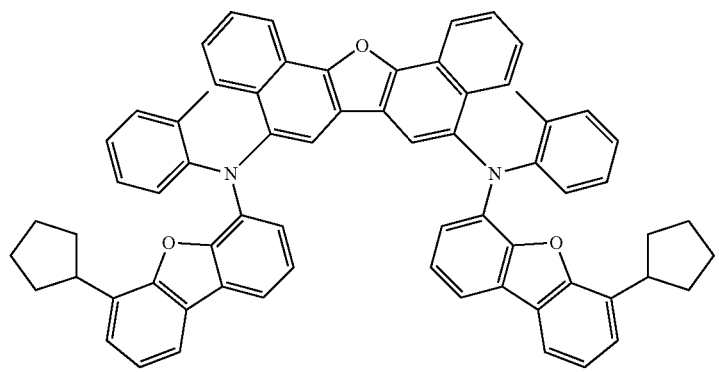
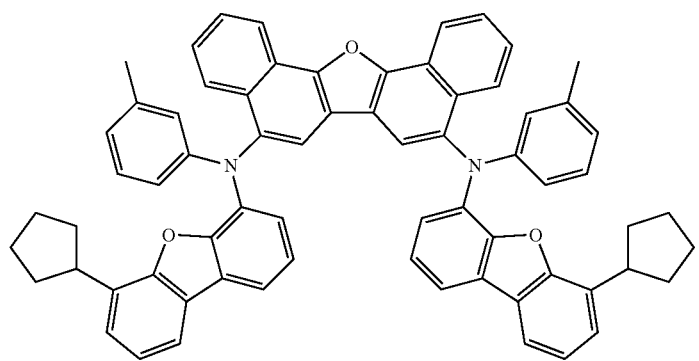
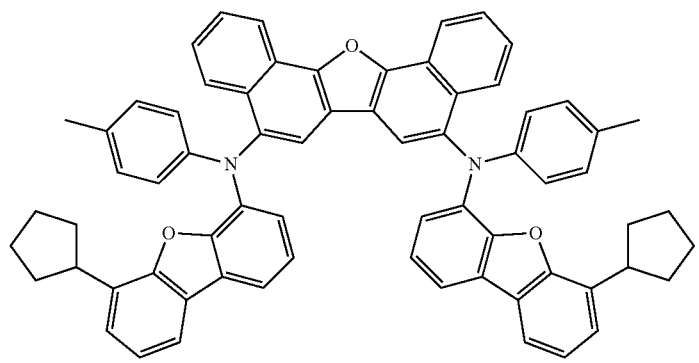

-continued
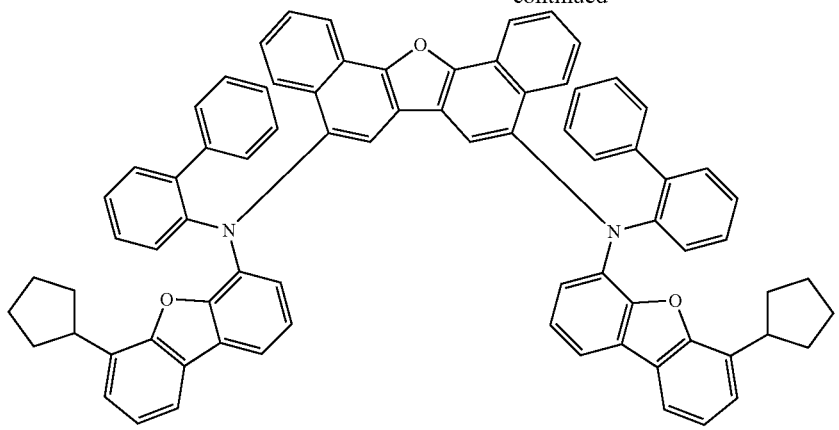
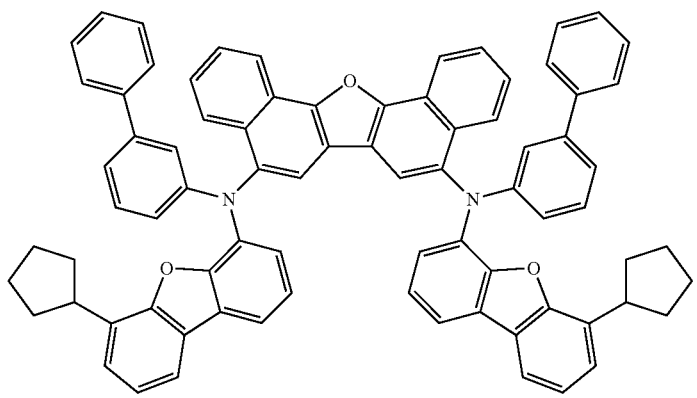
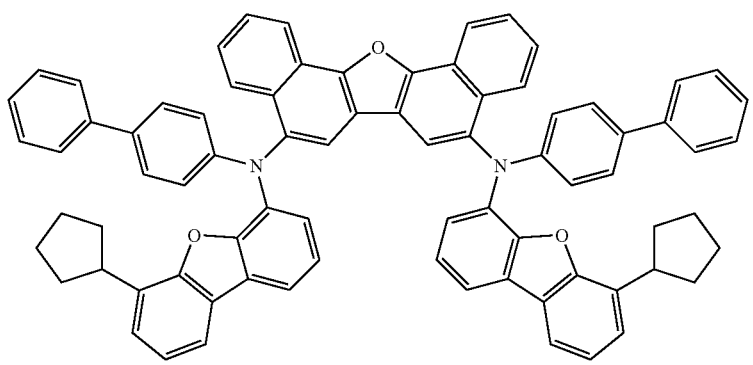
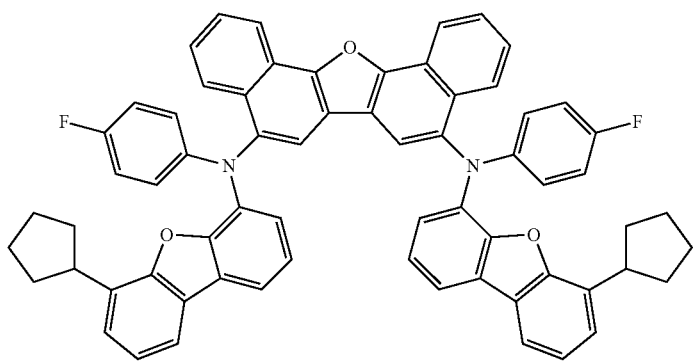

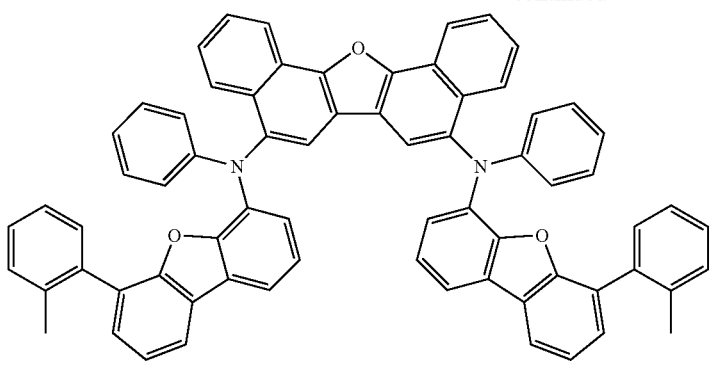
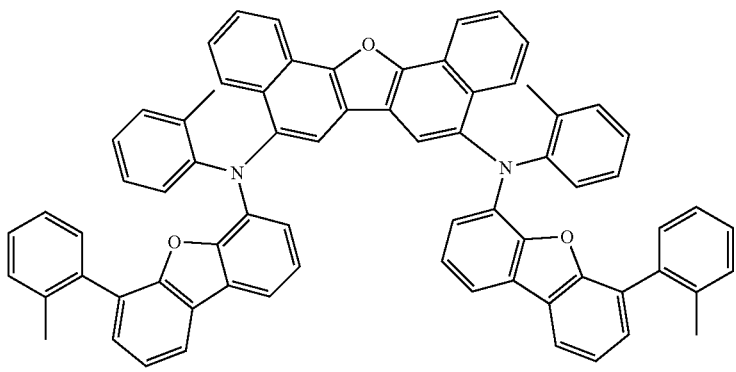
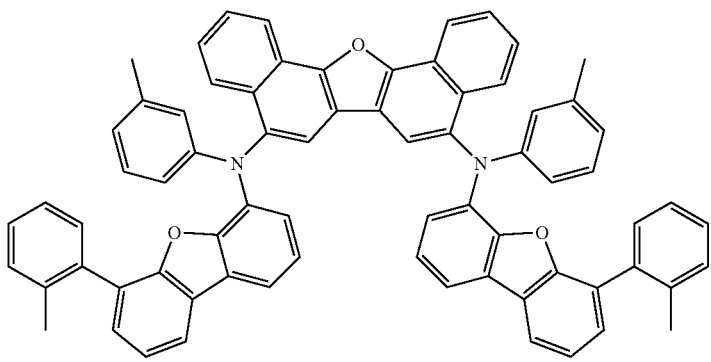
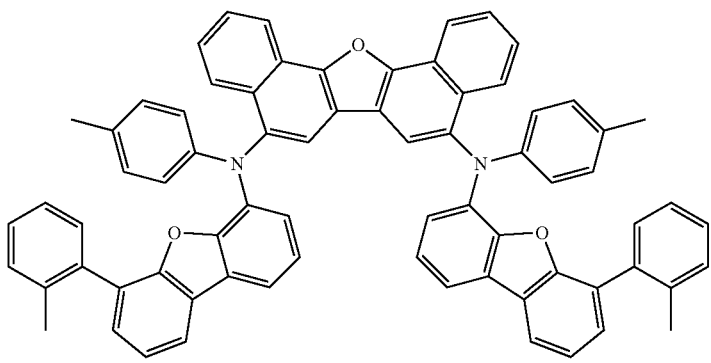

-continued
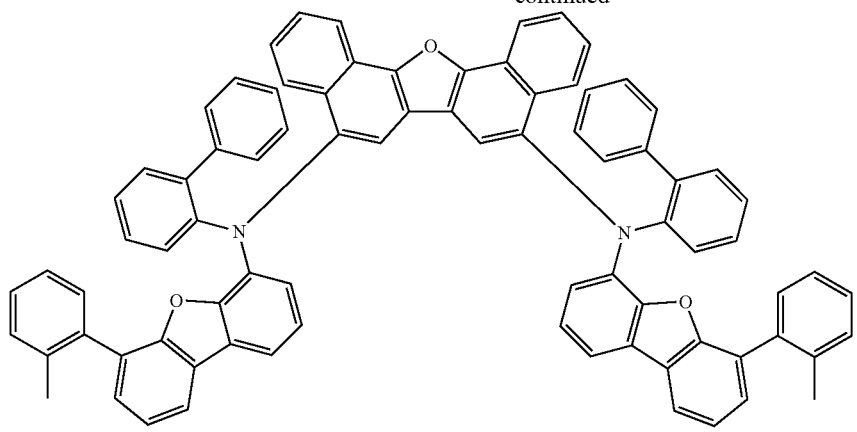
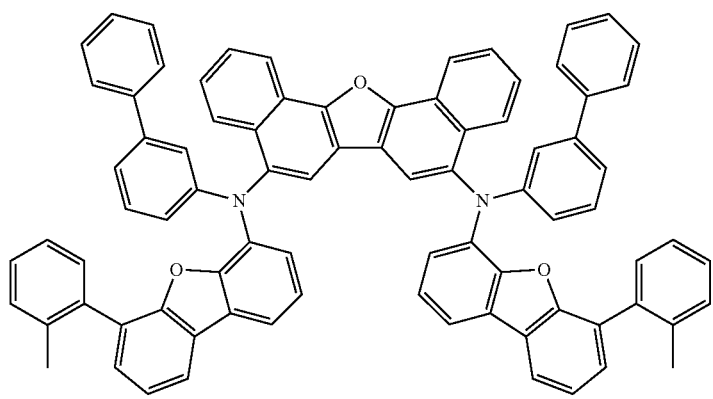
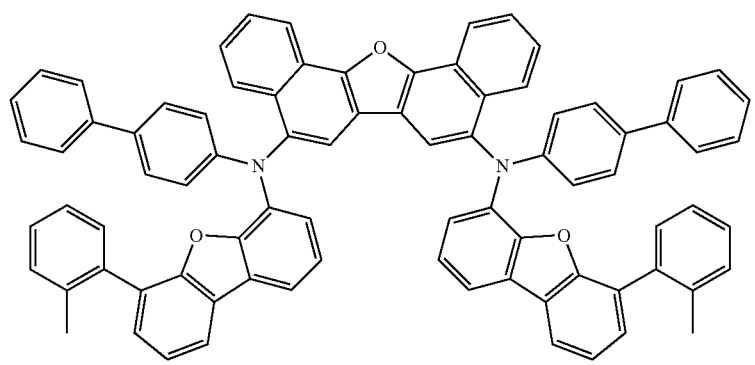
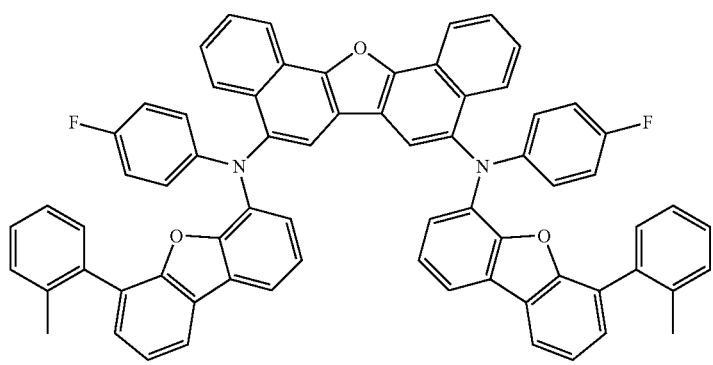

279
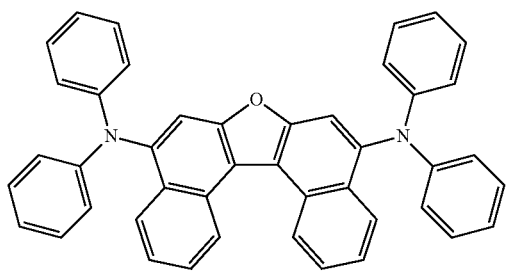
280
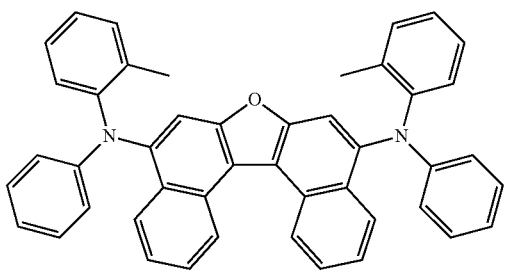
-continued
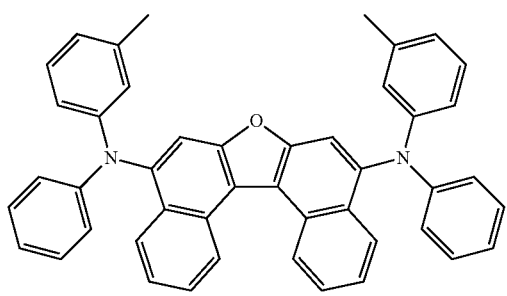
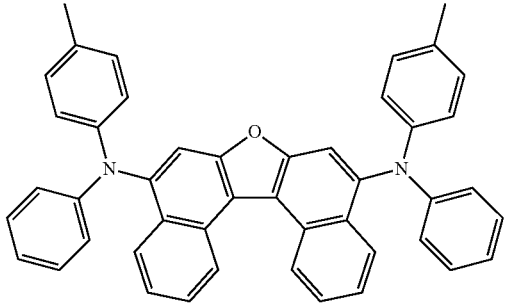
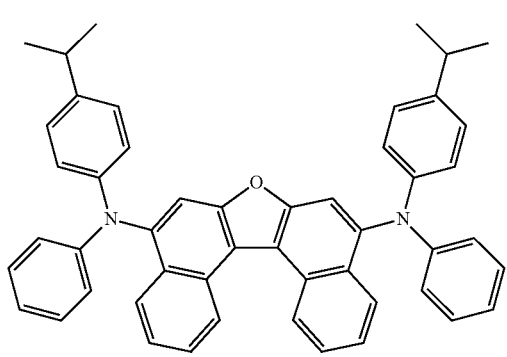
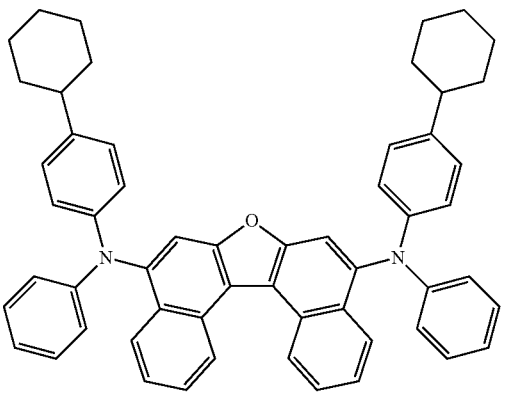
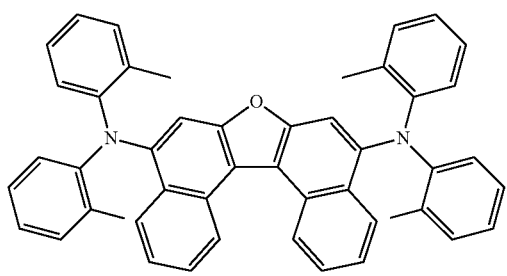
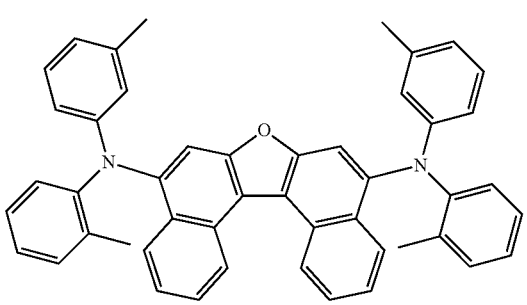
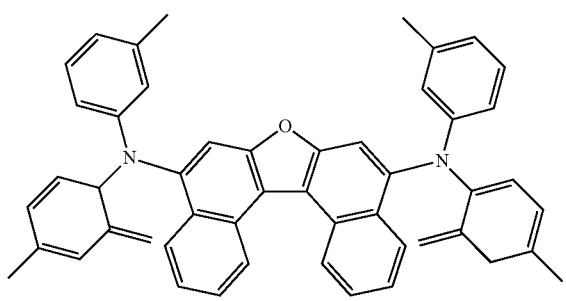
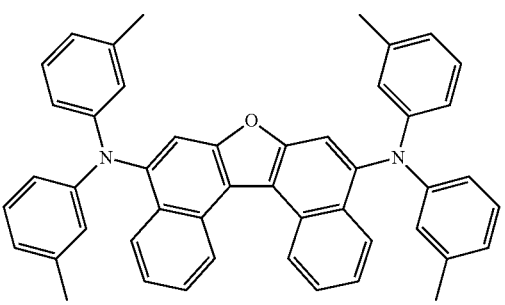

281
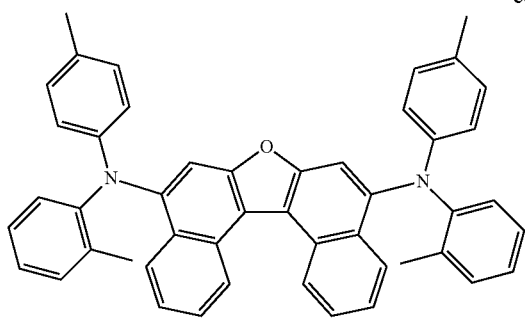
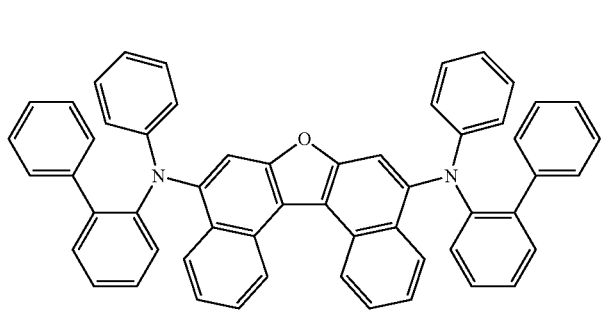
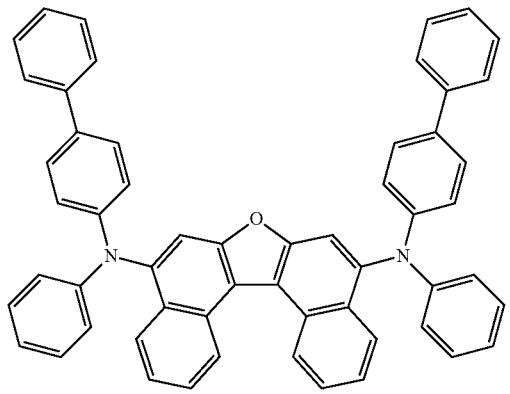
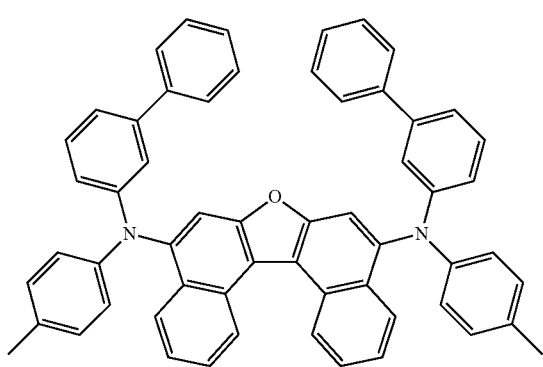
282
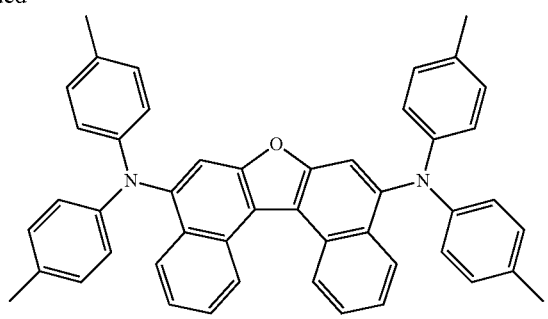
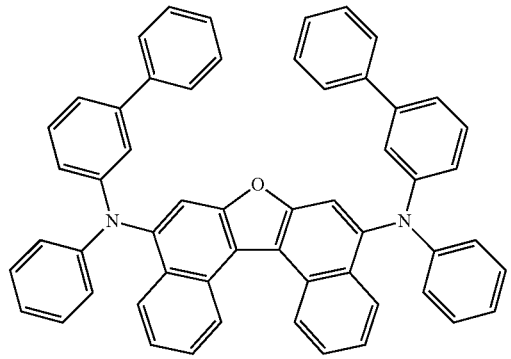
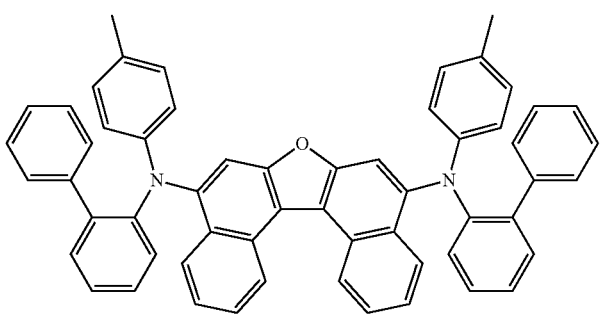
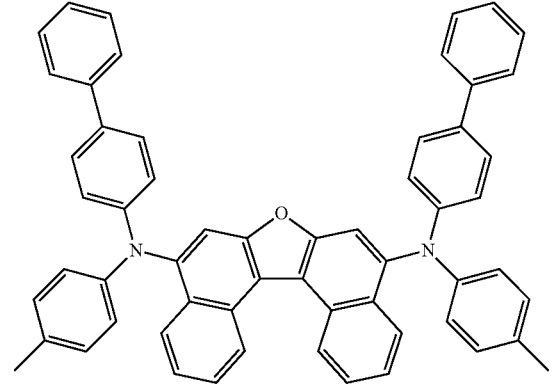

-continued
| 283 | 284 |
|---|---|
| 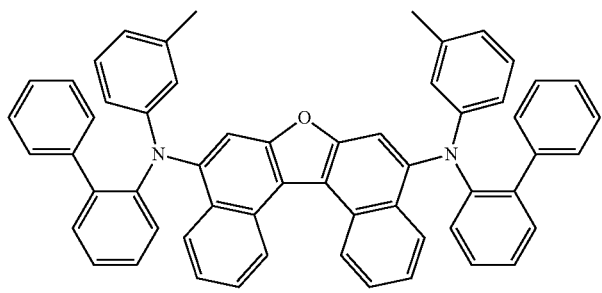 | 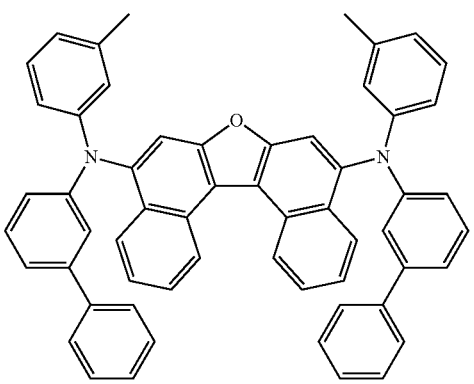 |
| 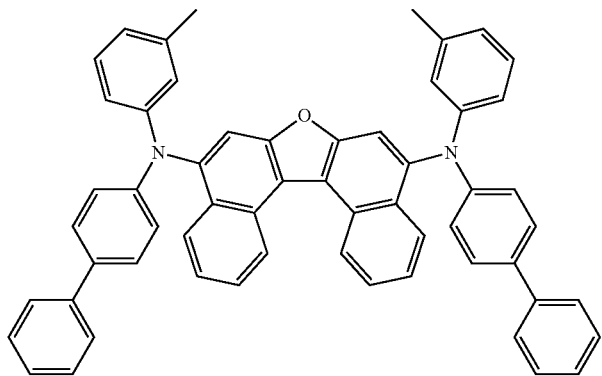 | 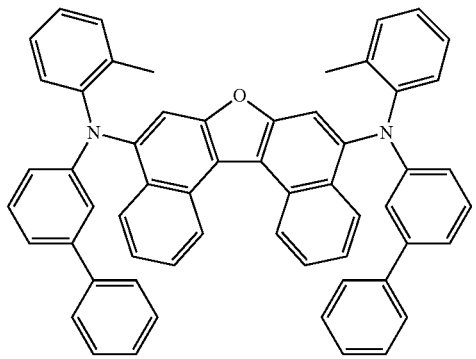 |
| 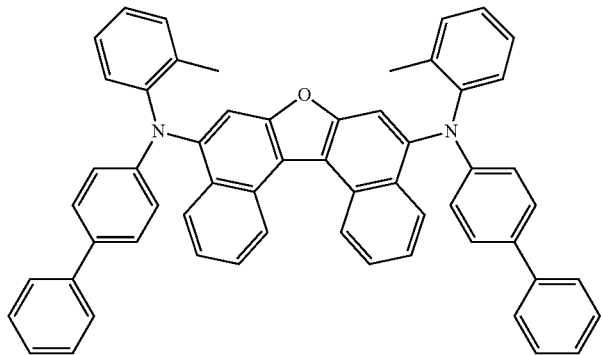 | |

-continued
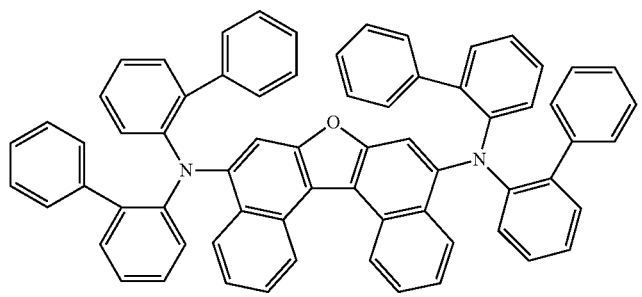
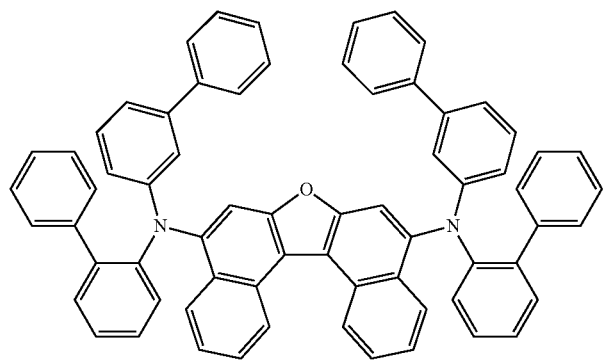
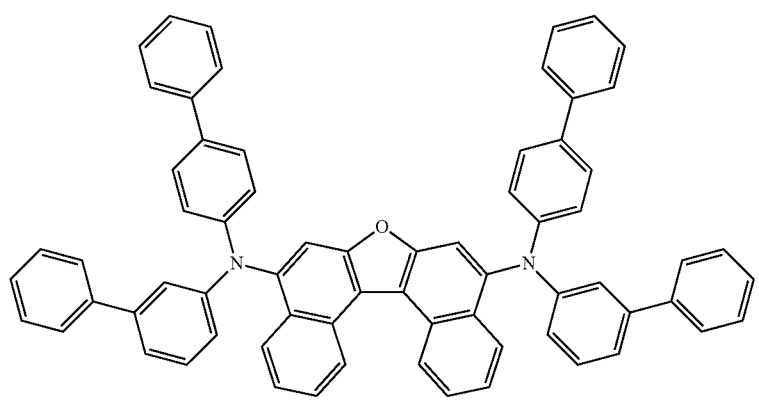
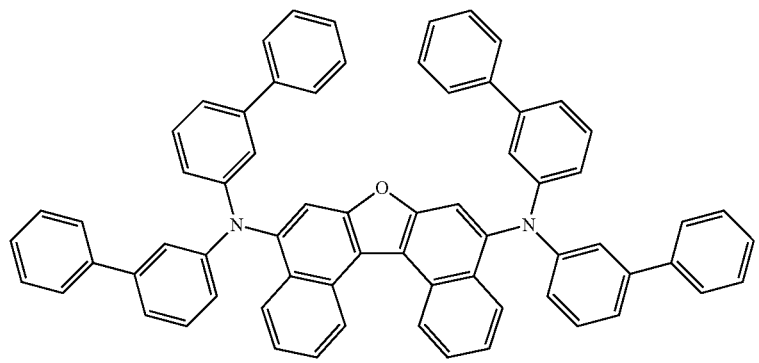

287 288
-continued
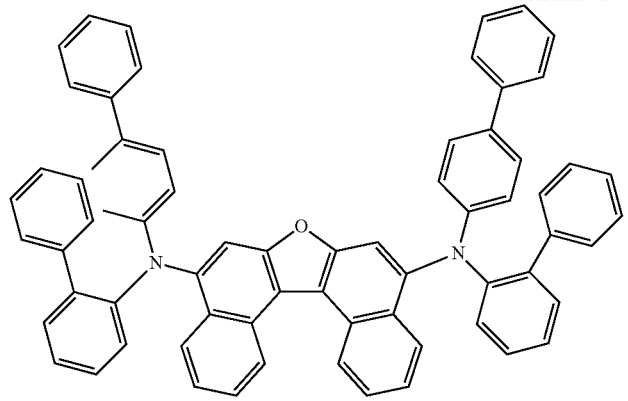
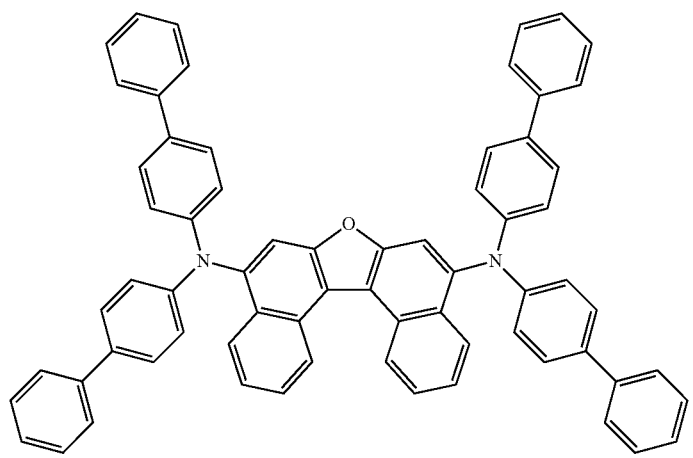
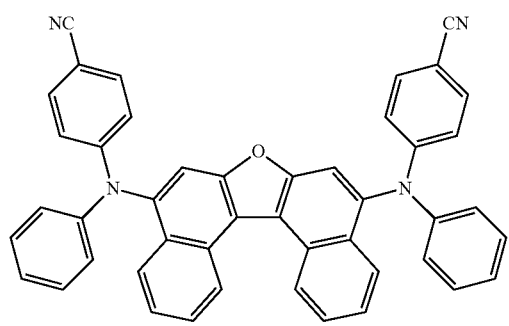 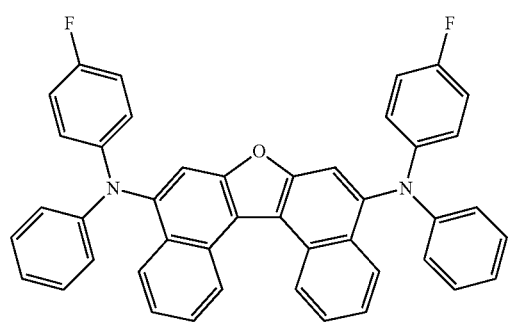
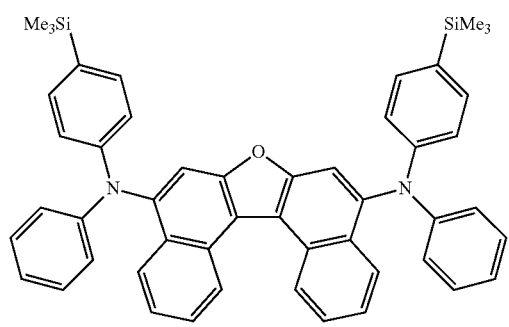 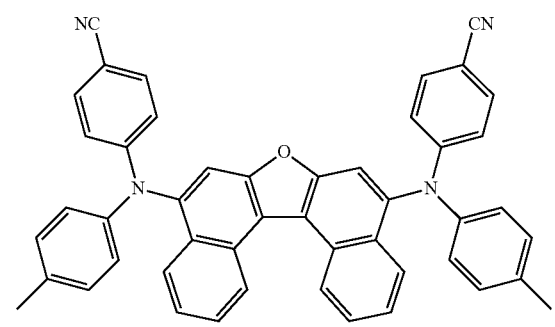

-continued
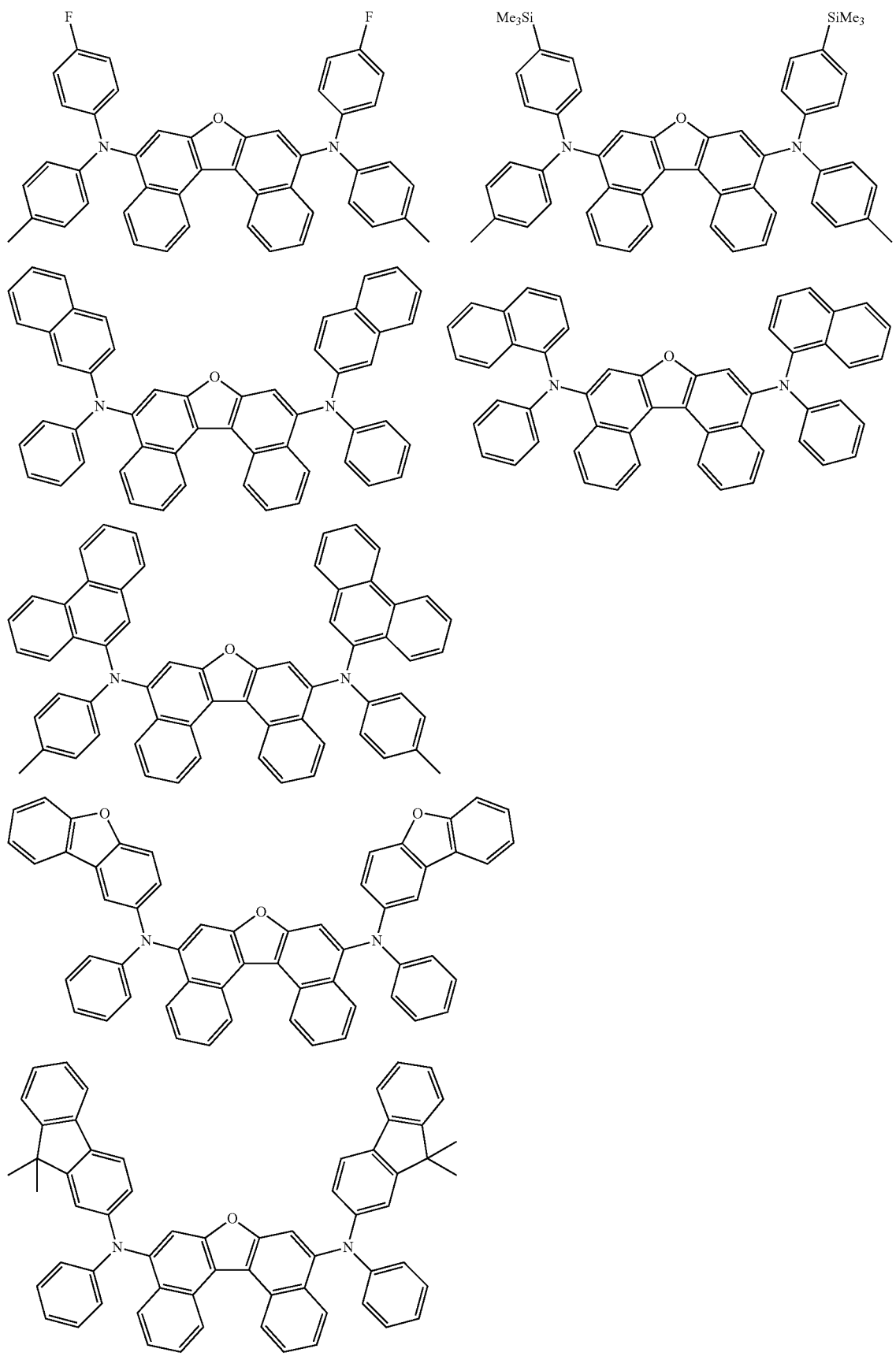

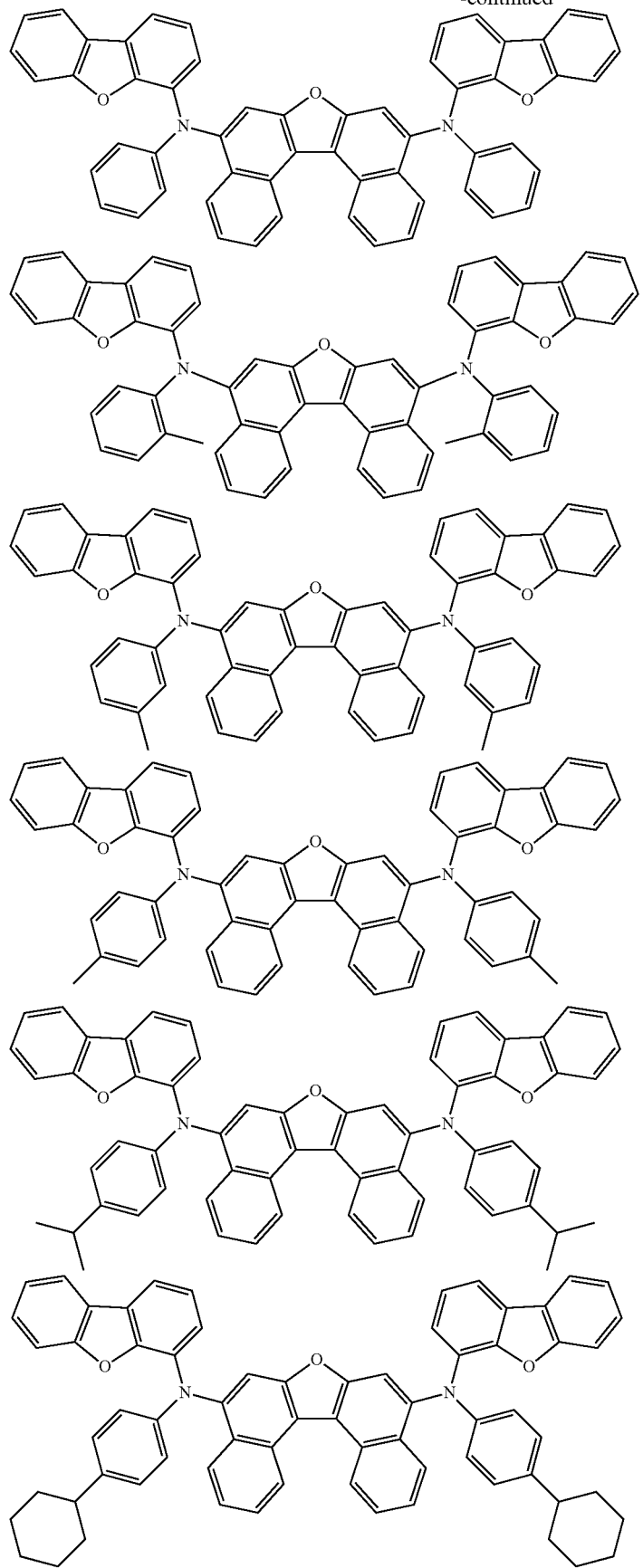

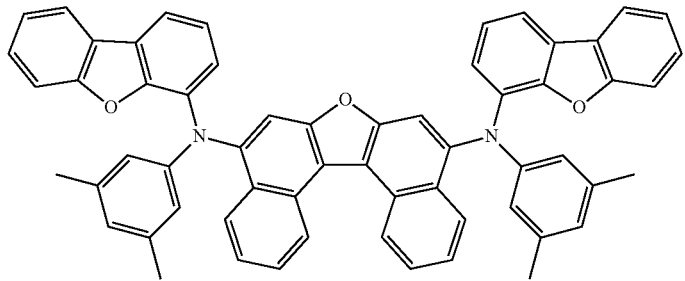
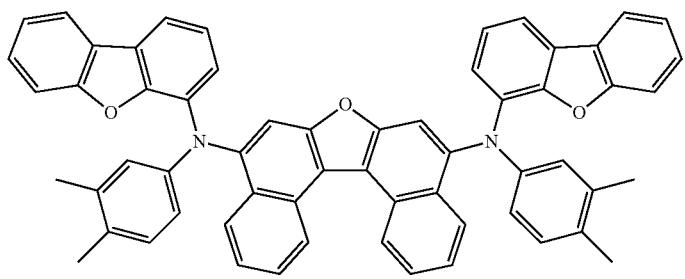
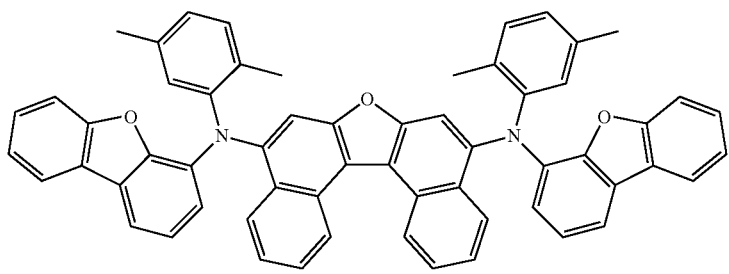
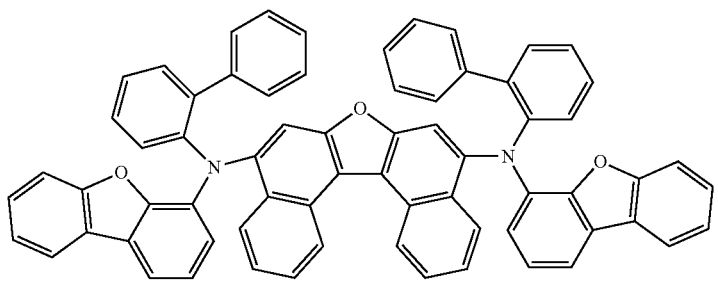
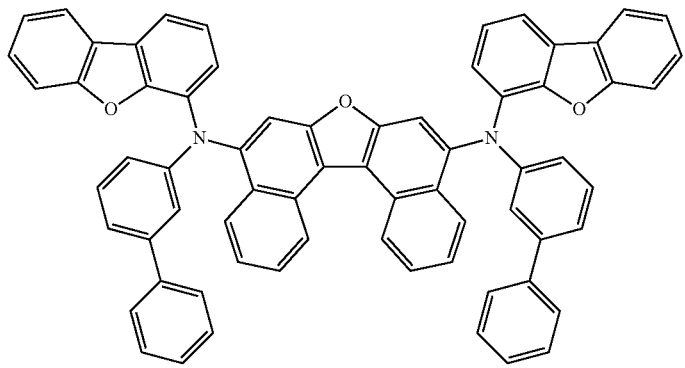

-continued
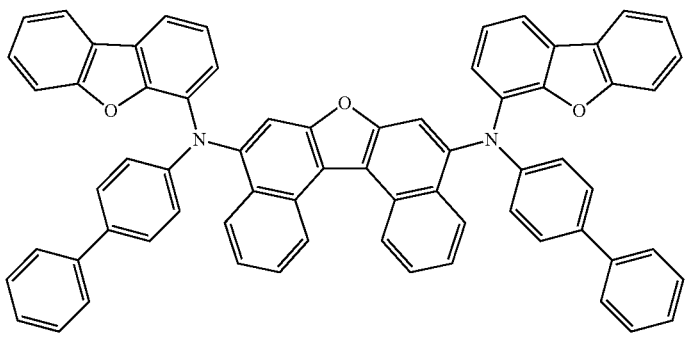
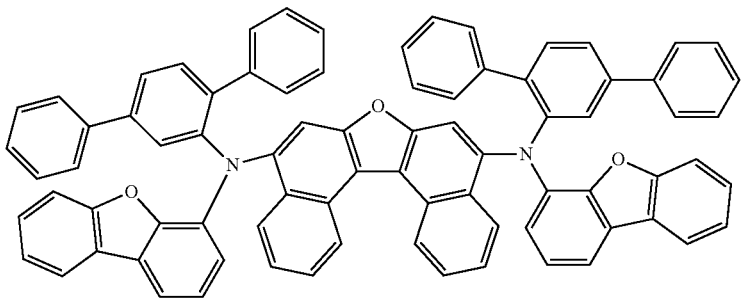
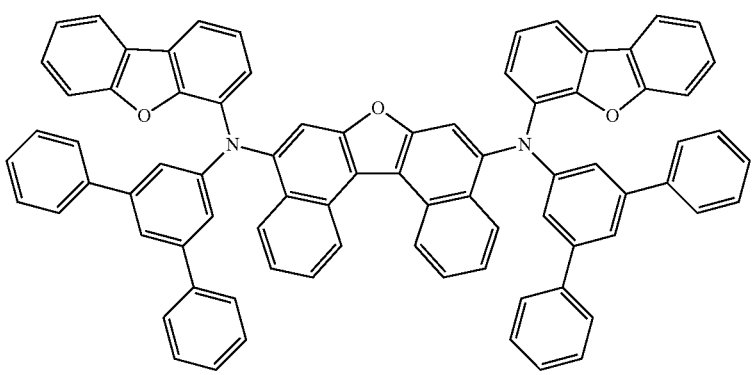
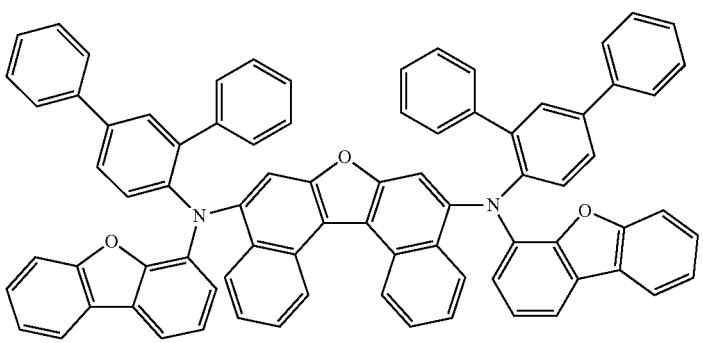
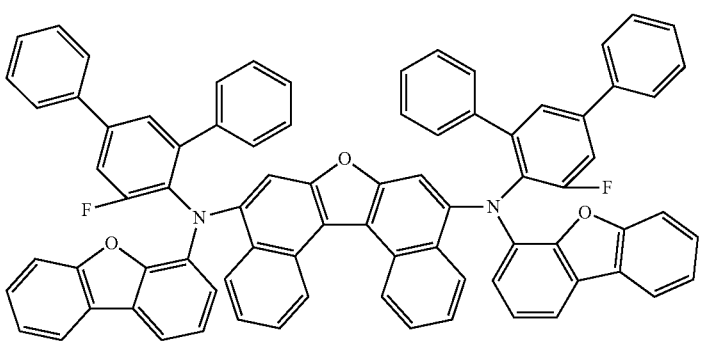

-continued
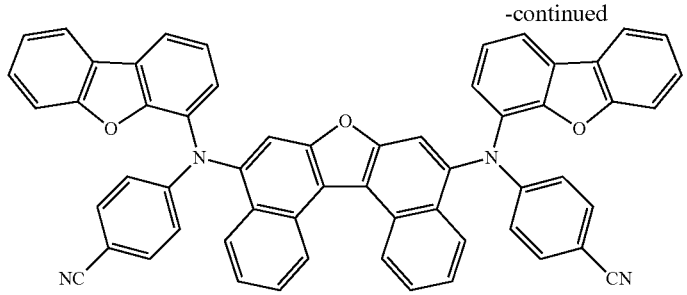
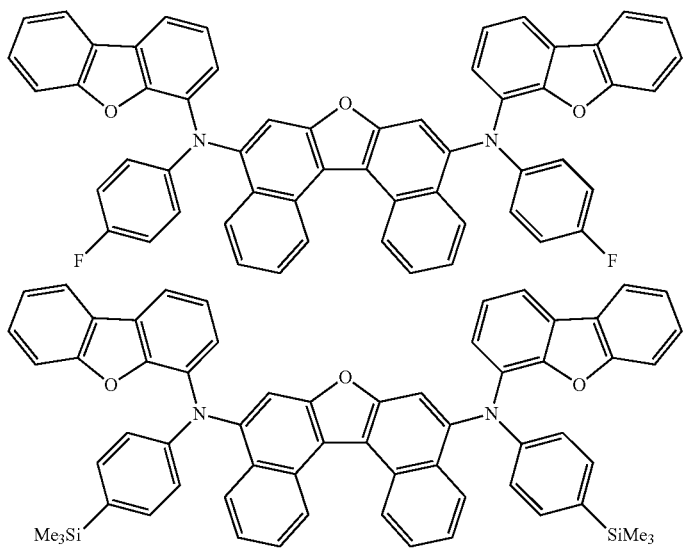
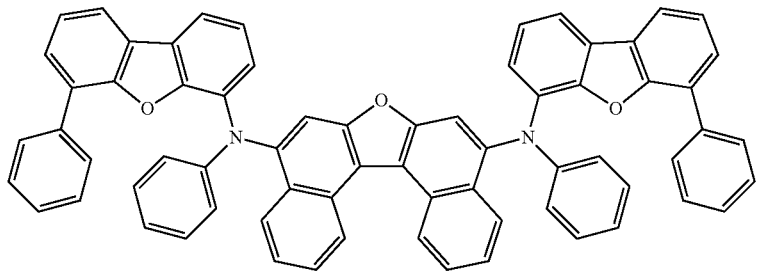
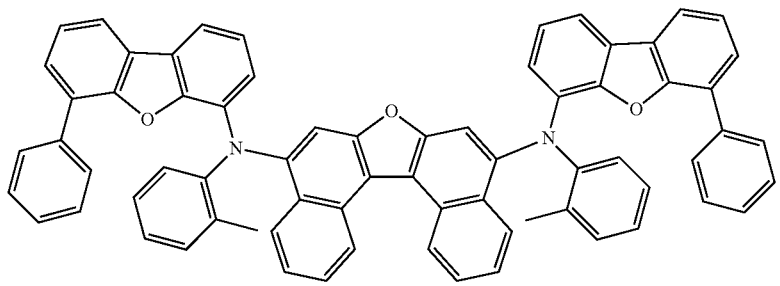
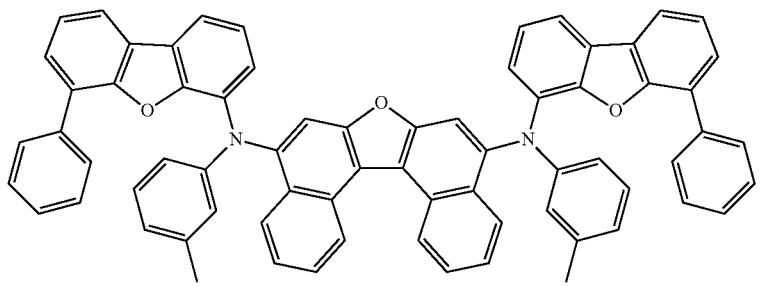

-continued
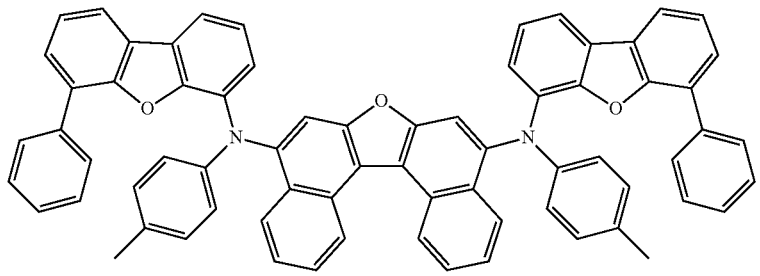
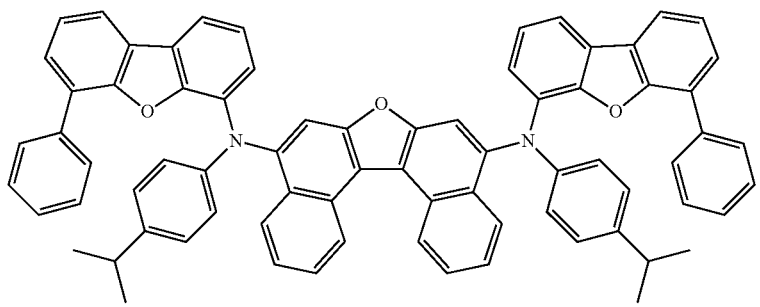
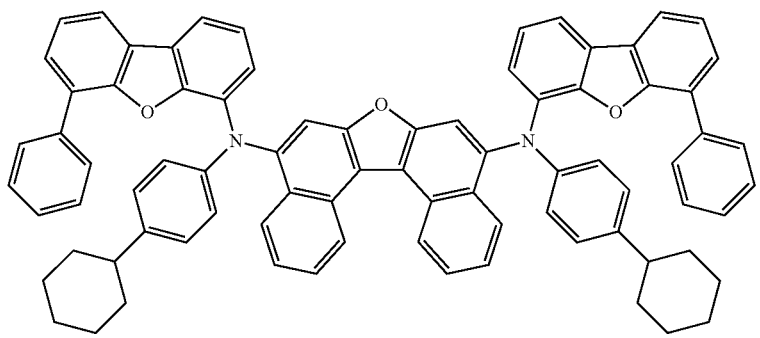
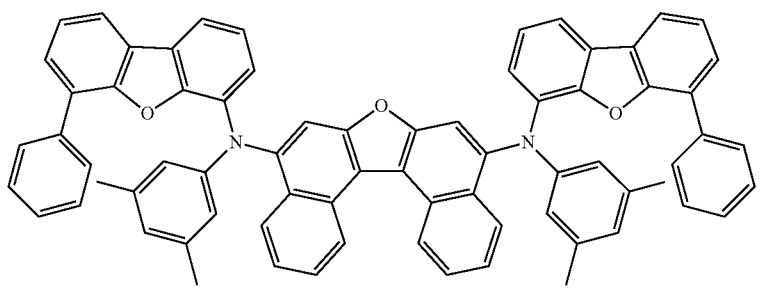
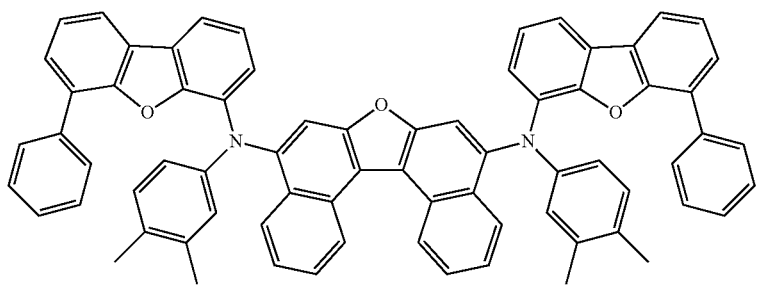

-continued
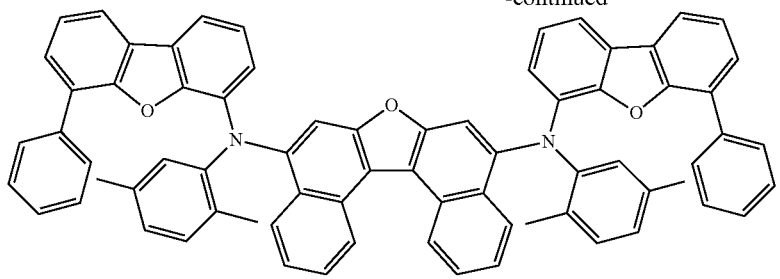
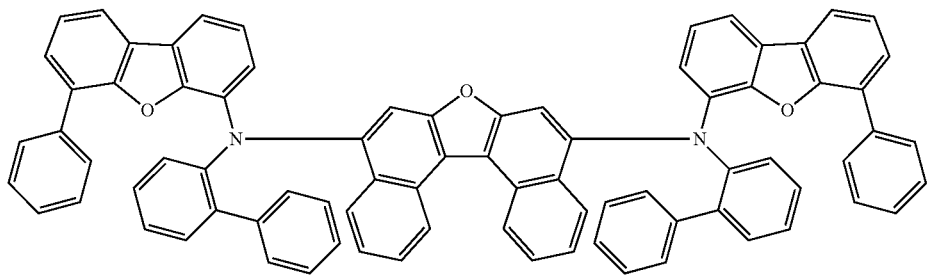
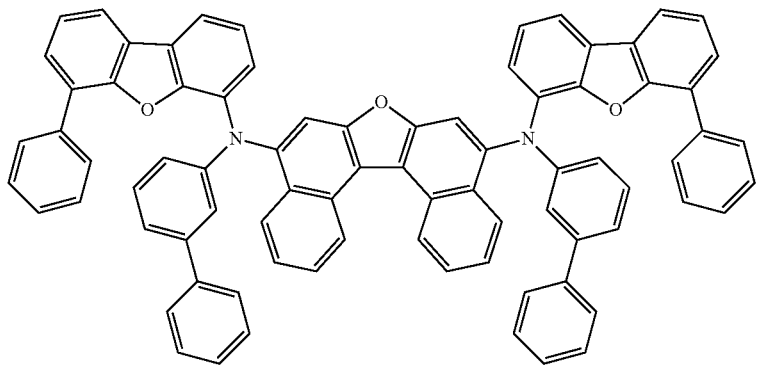
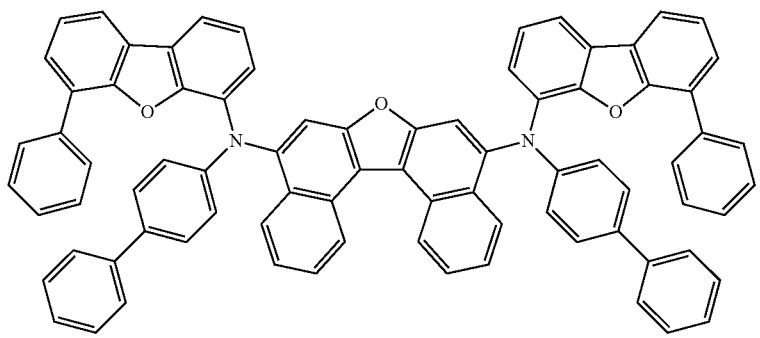
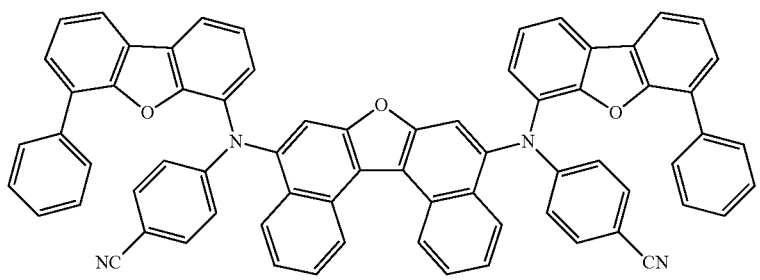

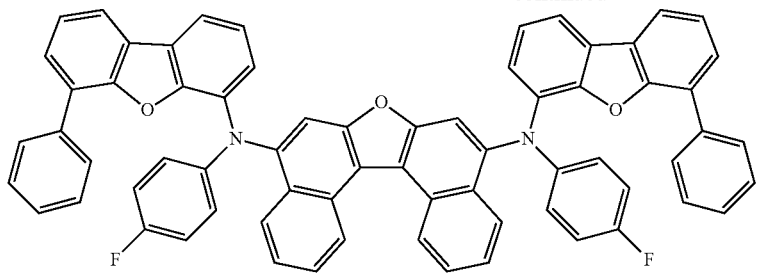
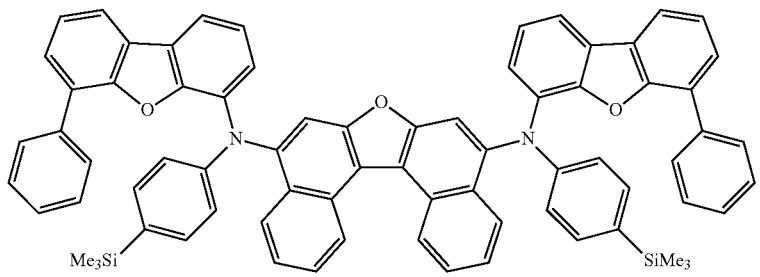
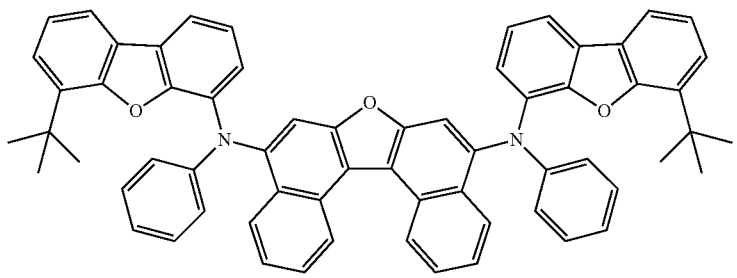
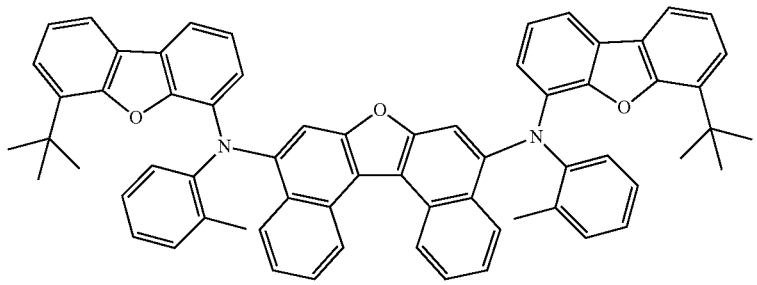
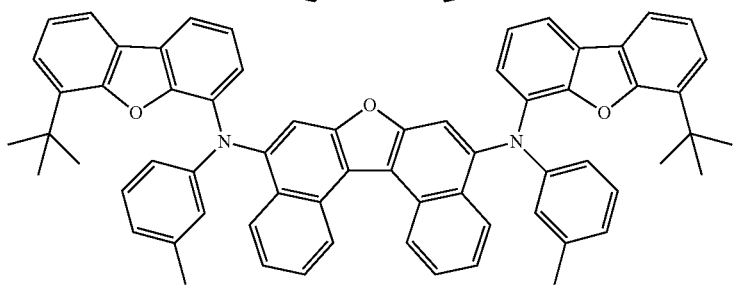
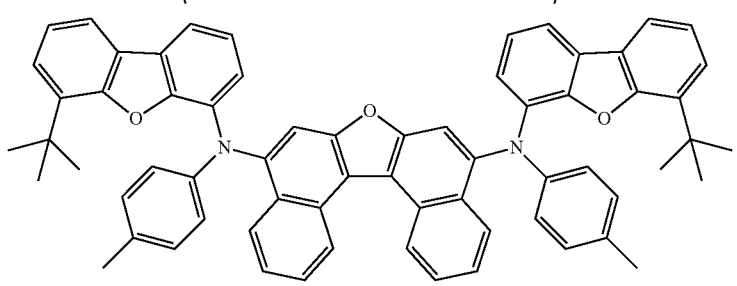

-continued
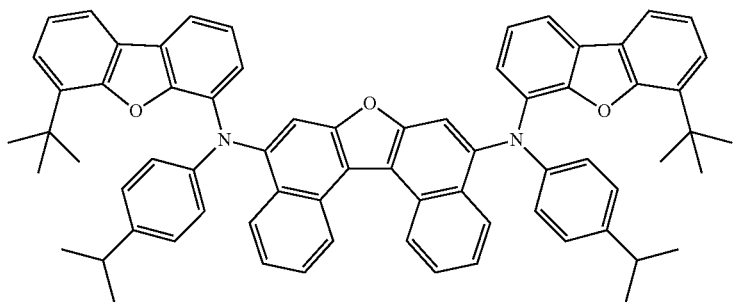
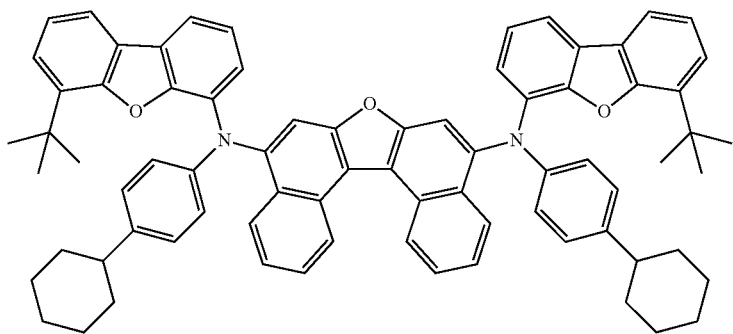
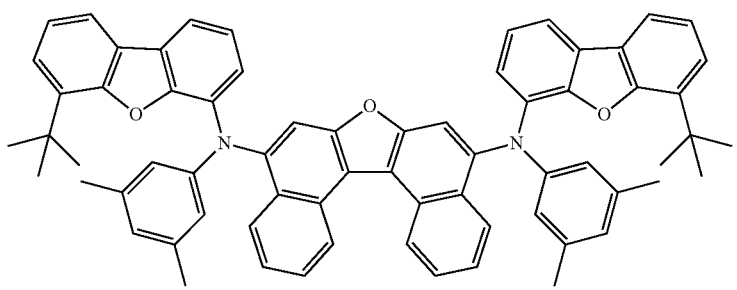
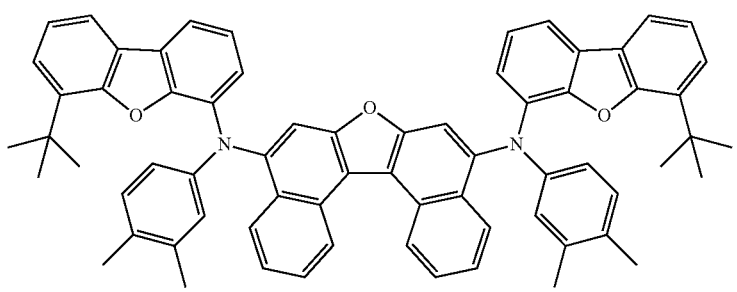
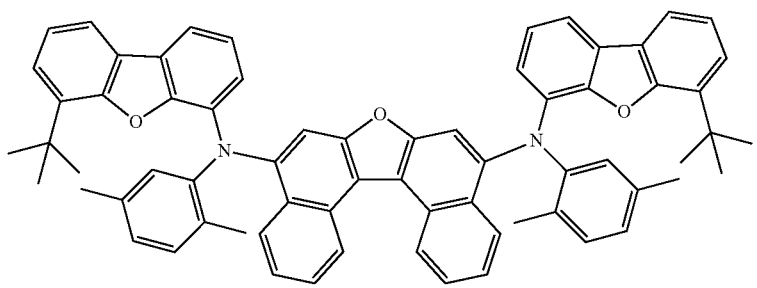

-continued
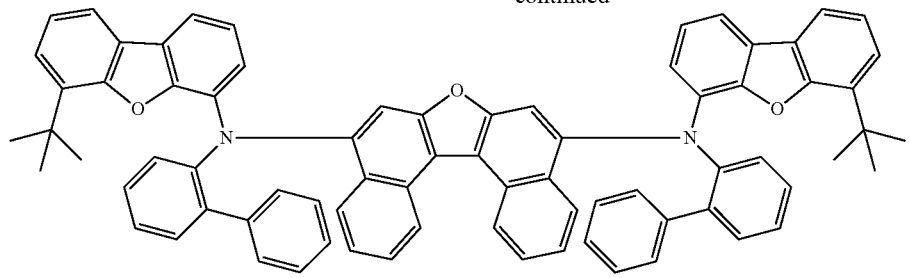
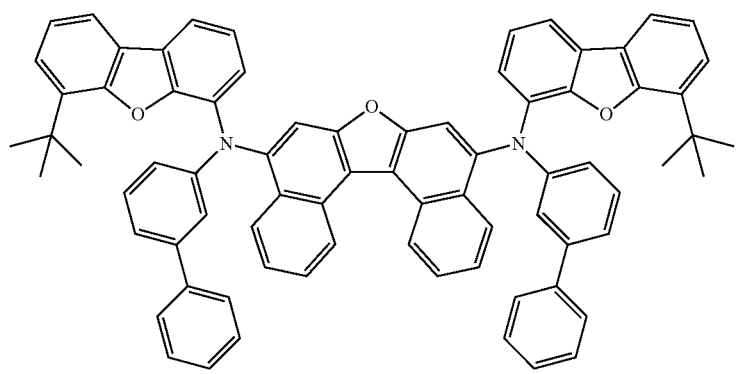
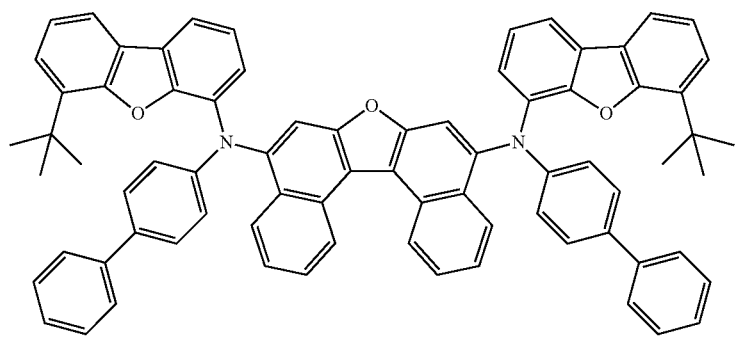
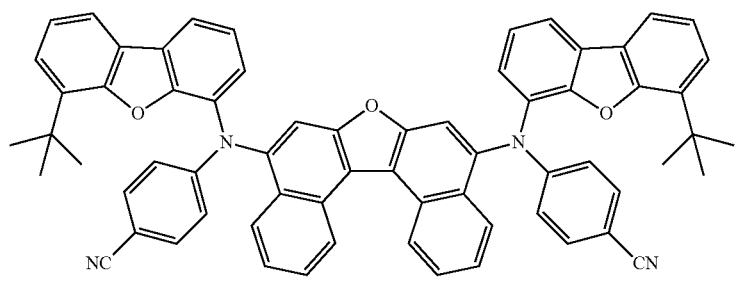
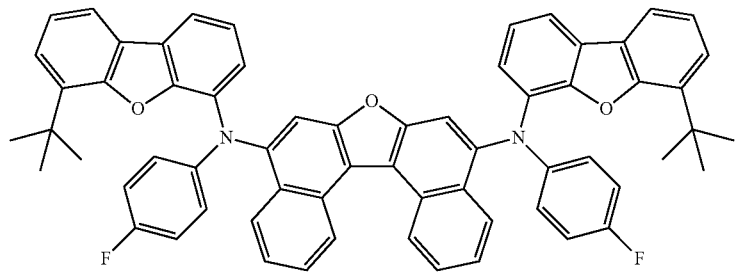

-continued
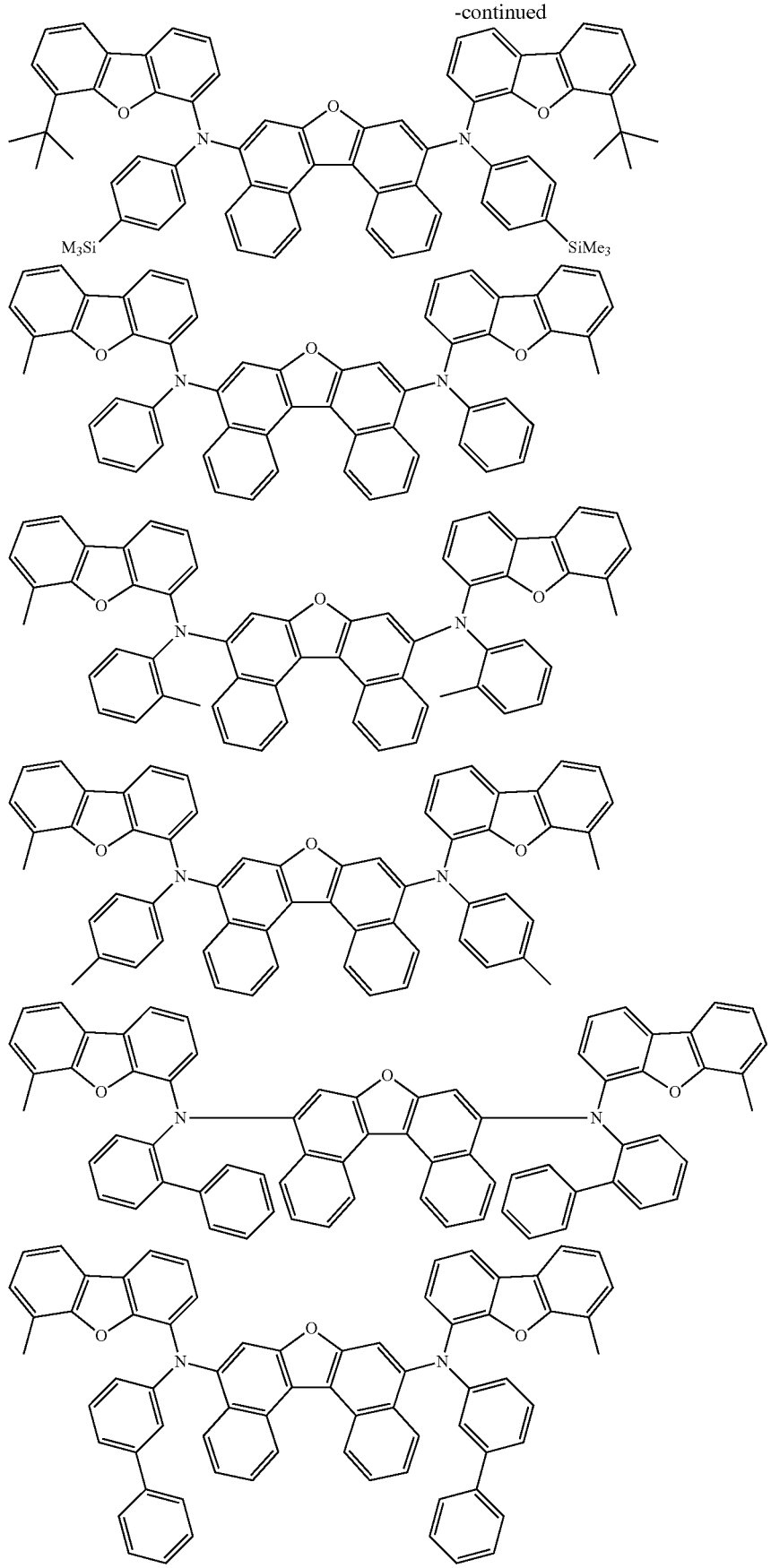

-continued
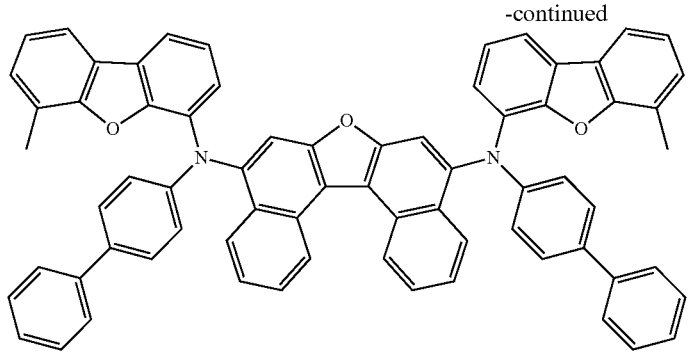
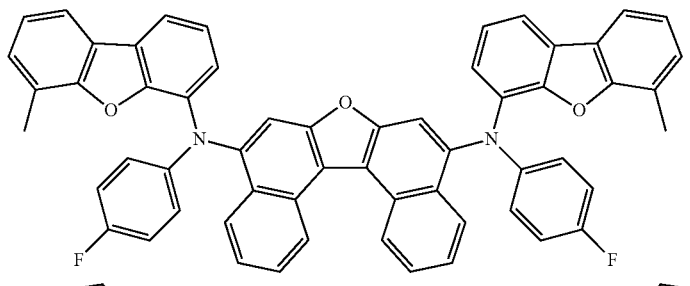
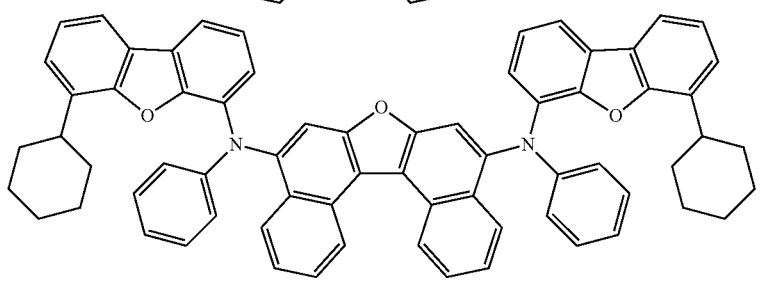
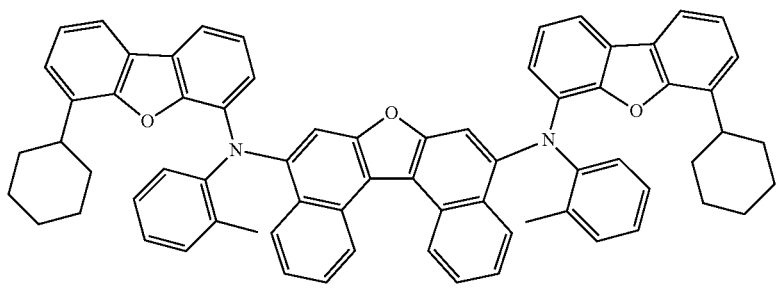
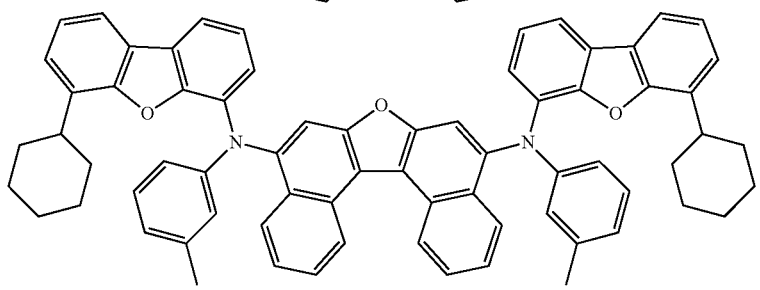
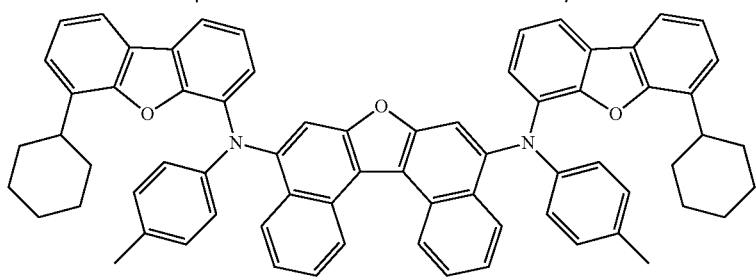

-continued
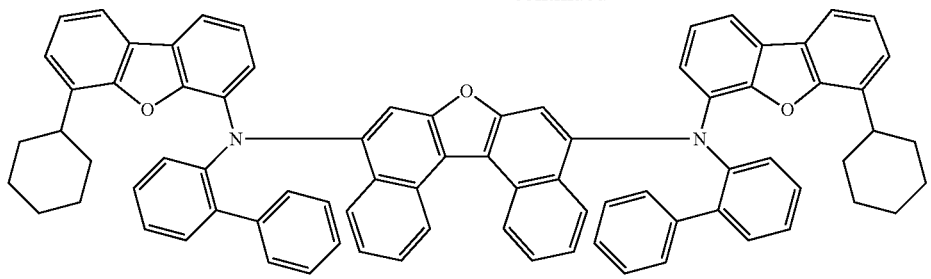
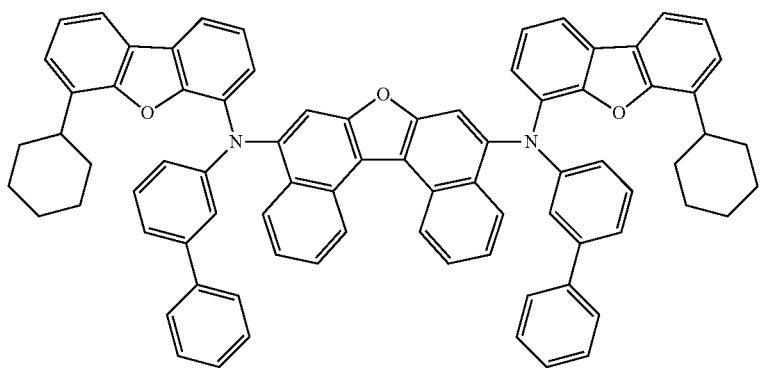
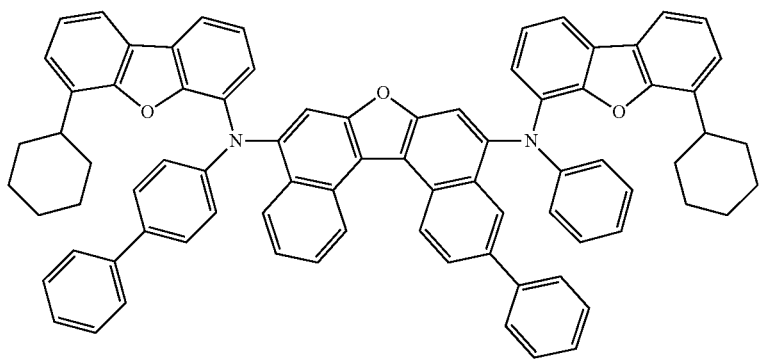
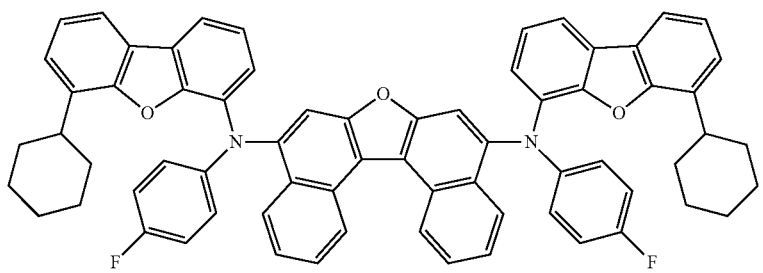
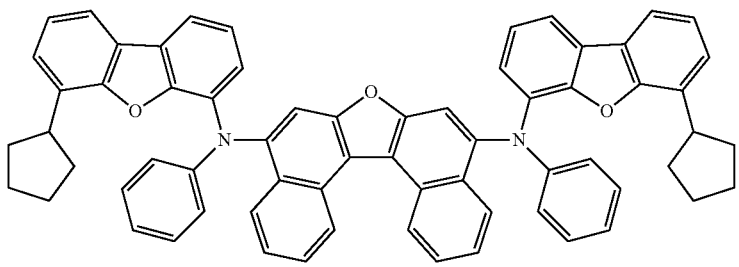

-continued
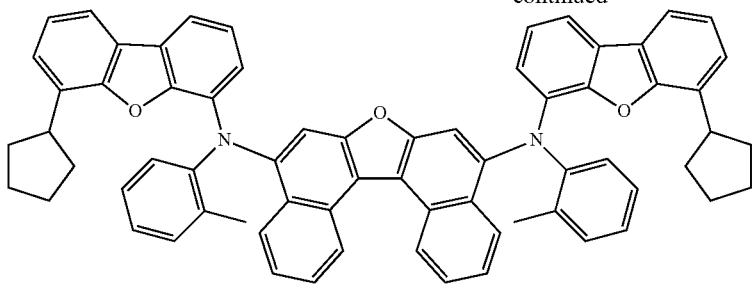
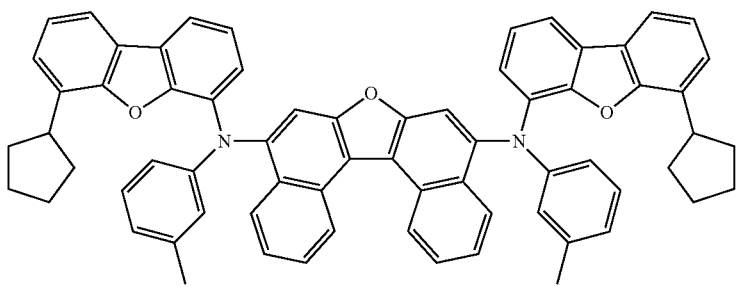
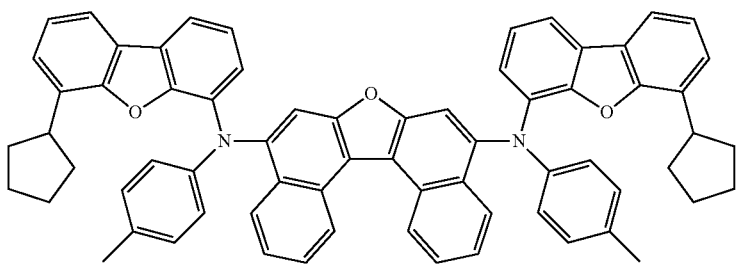
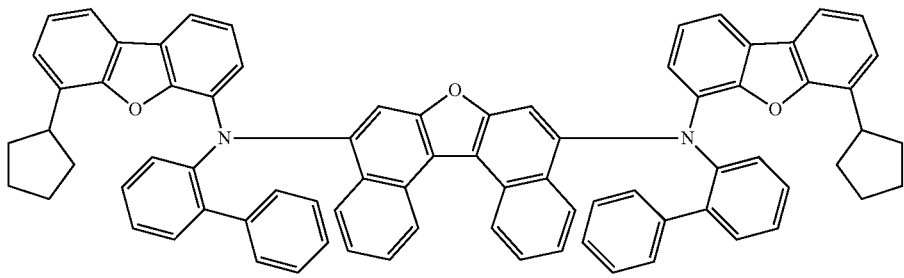
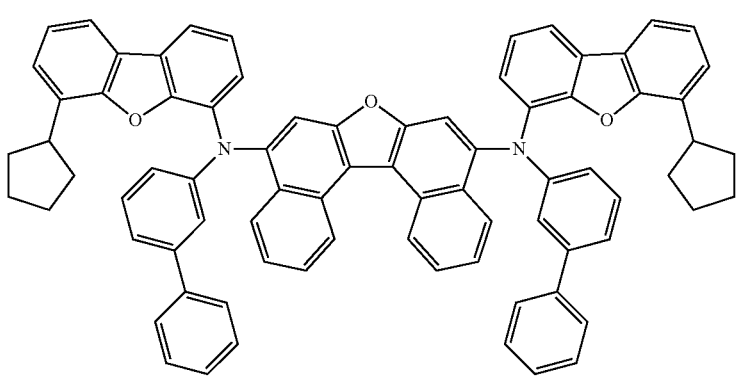

-continued
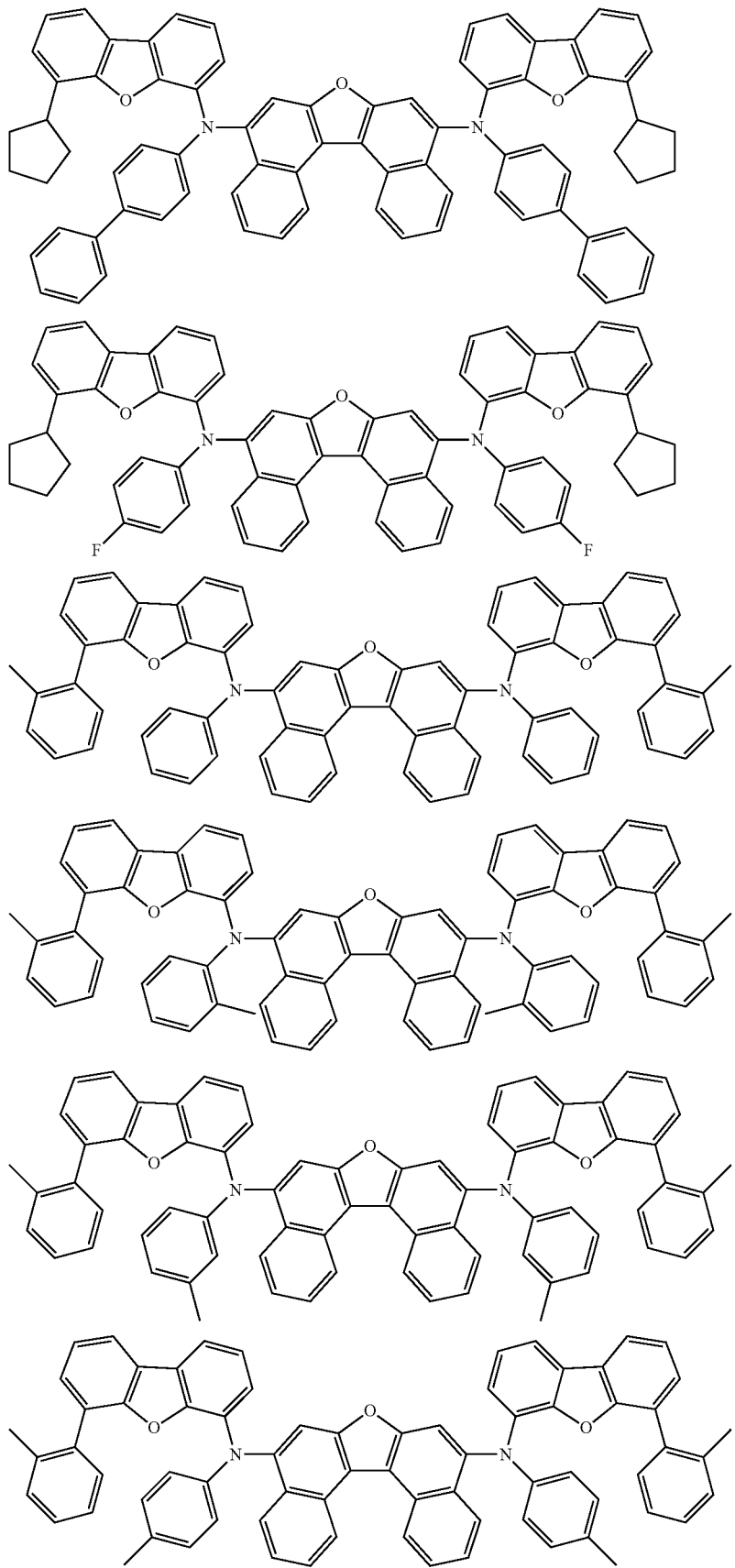

319 320
-continued
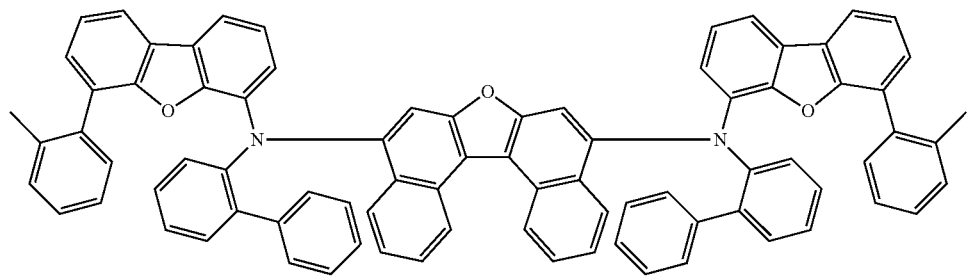
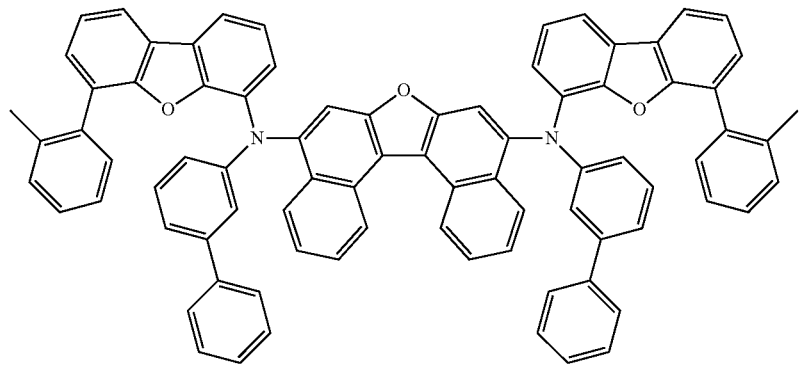
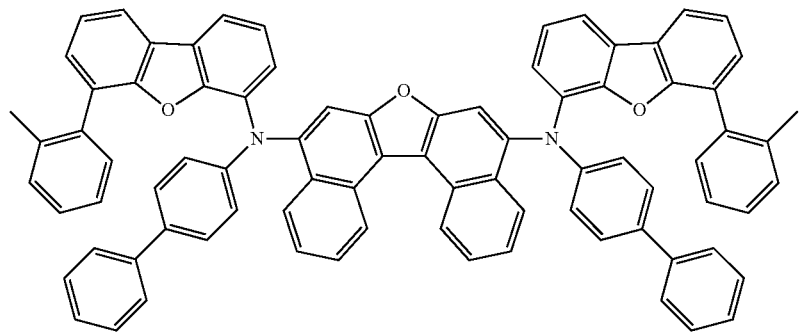
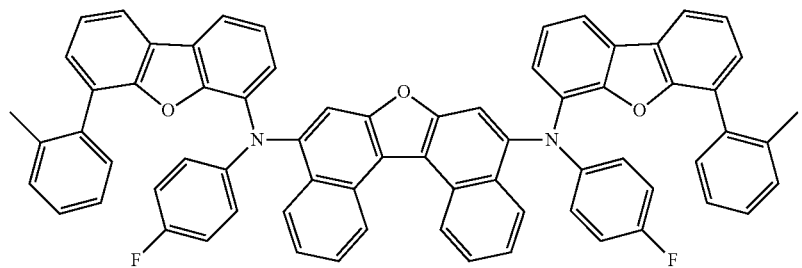
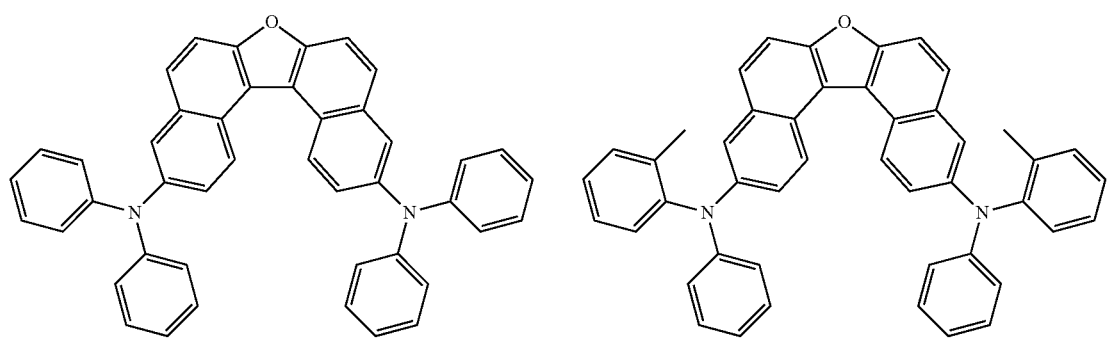

| 321 | 322 |
|---|---|
| 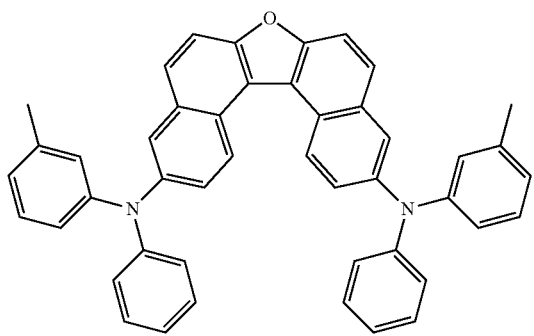 | 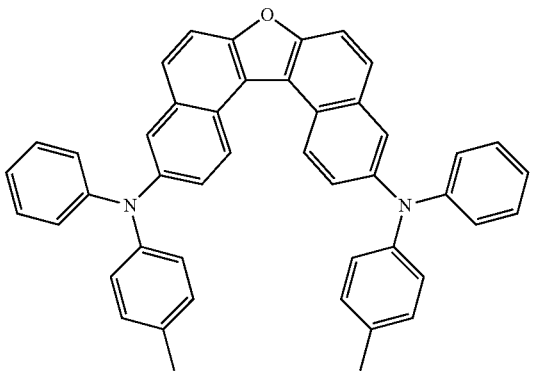 |
| 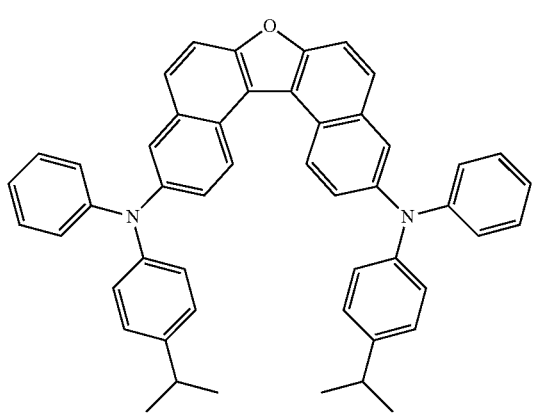 | 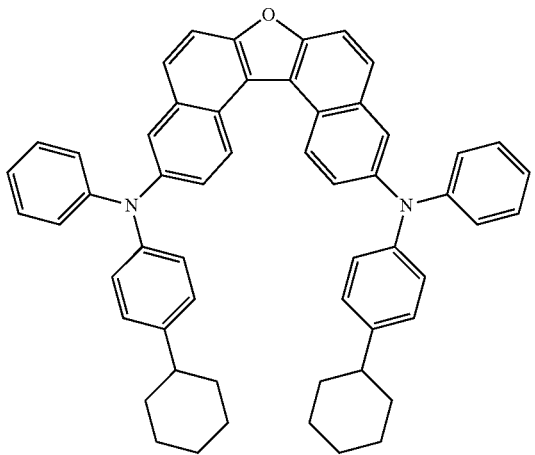 |
| 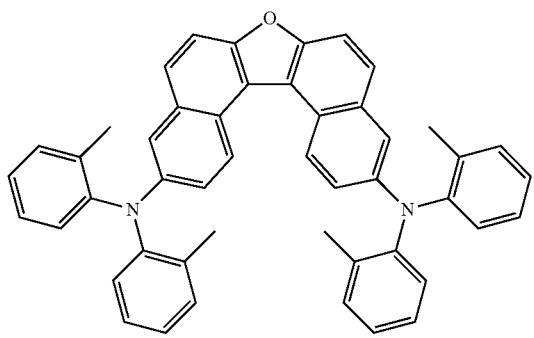 | 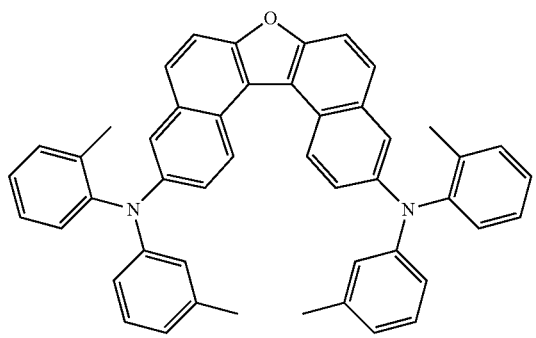 |
| 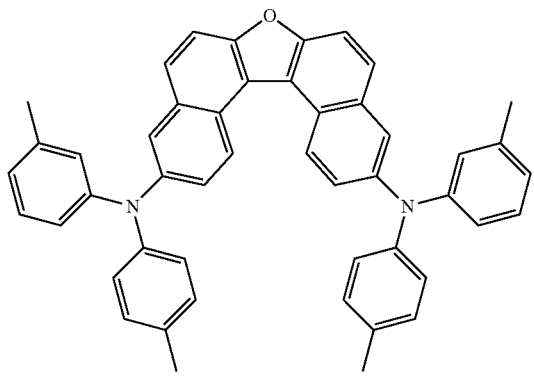 | 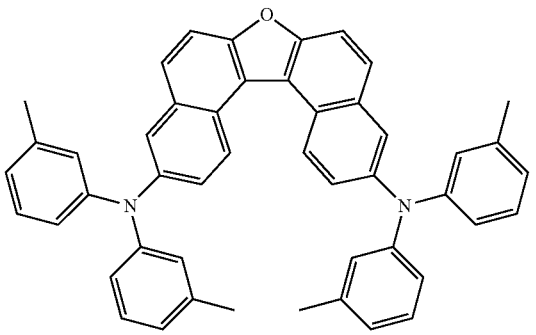 |

323  324
-continued
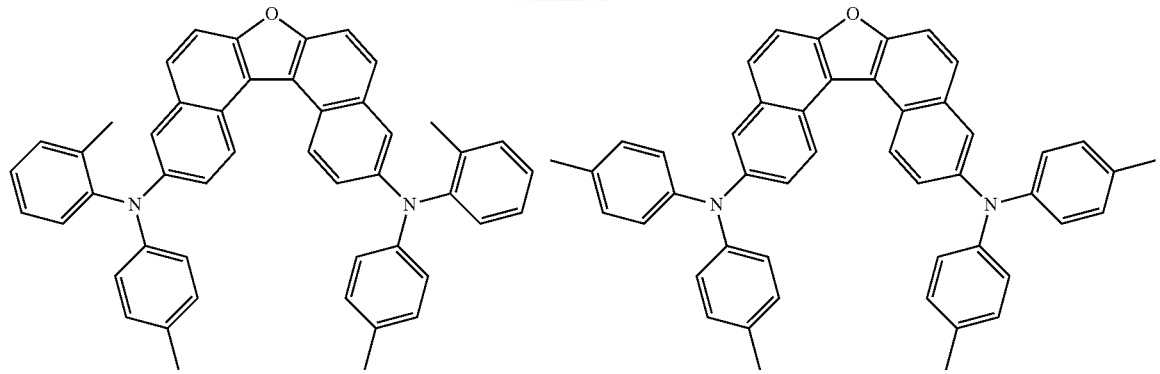
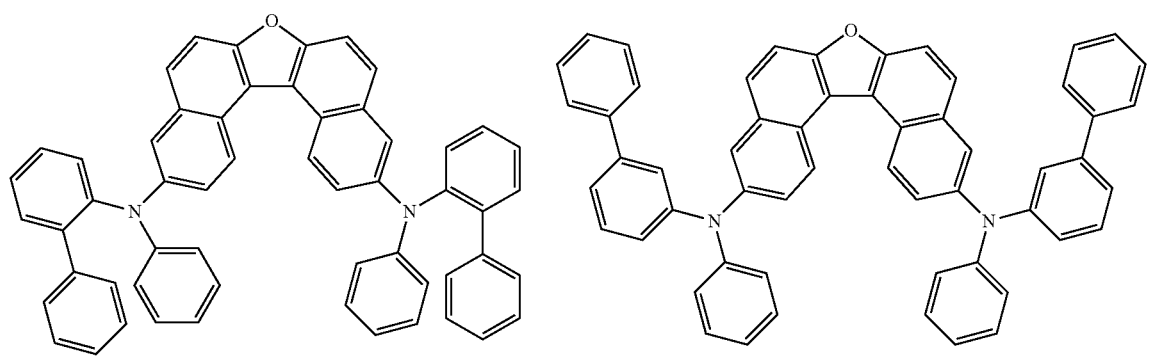
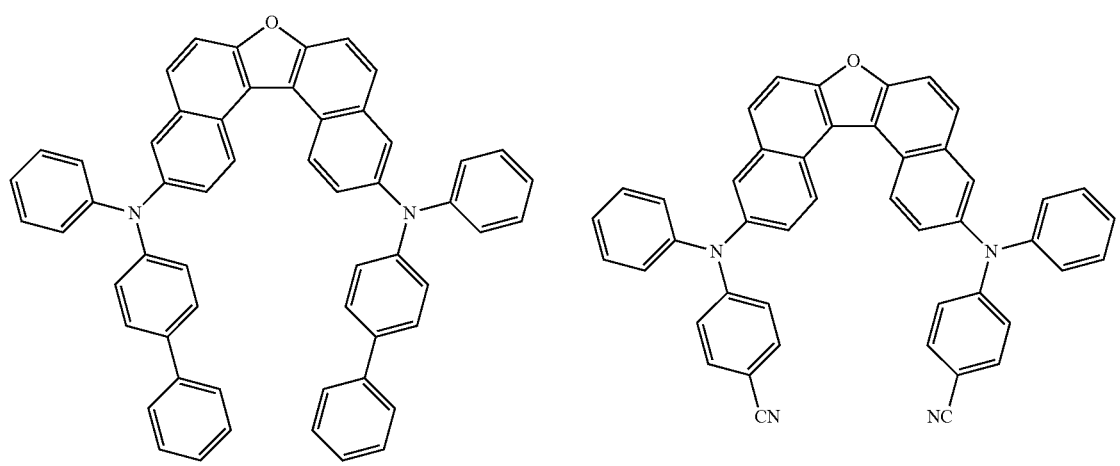
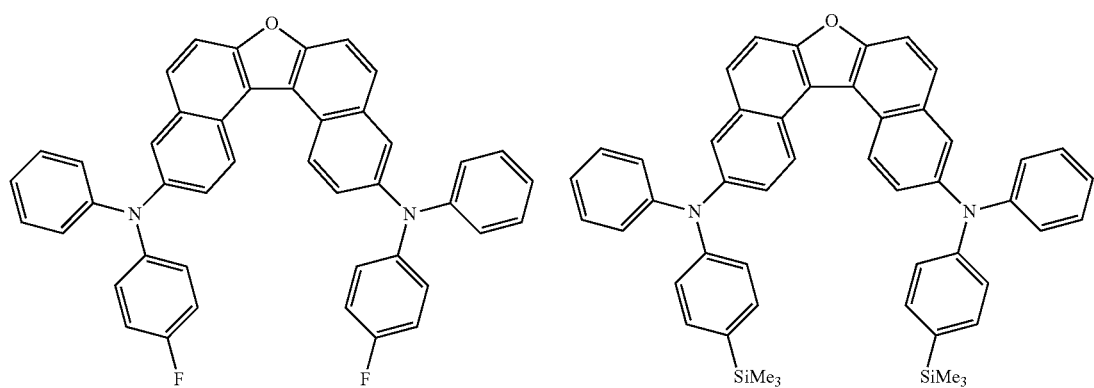

-continued
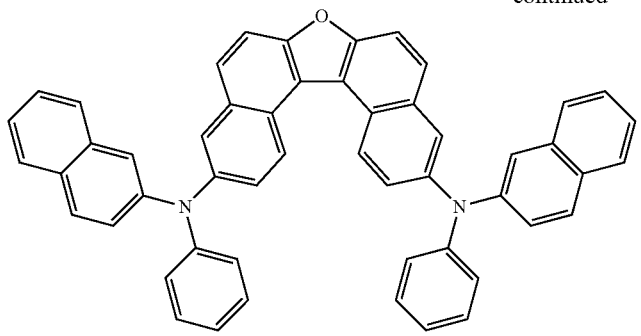
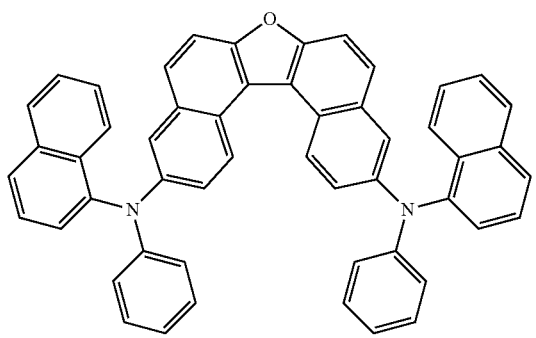
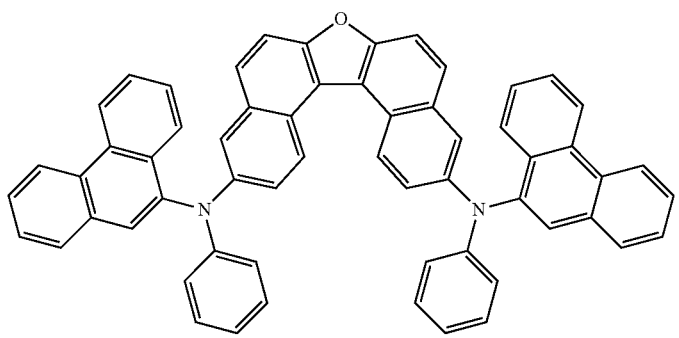
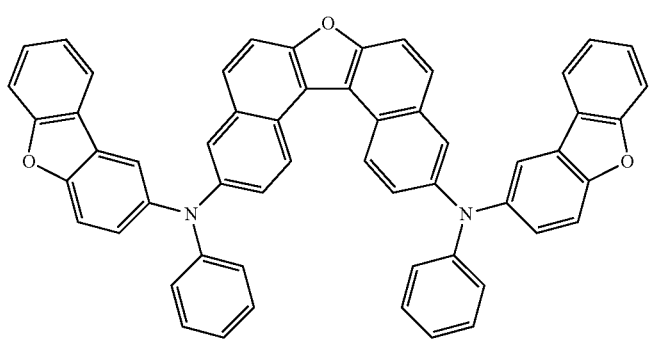
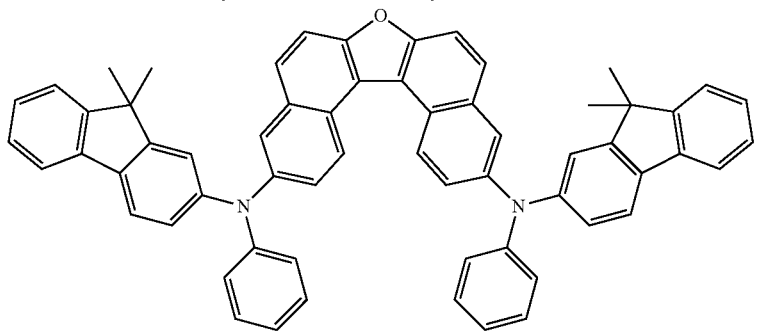

-continued
| 327 | 328 |
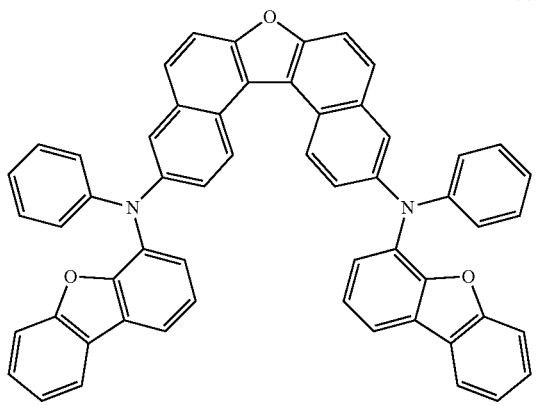 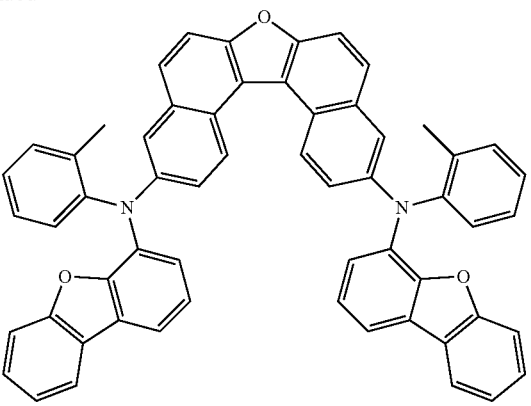
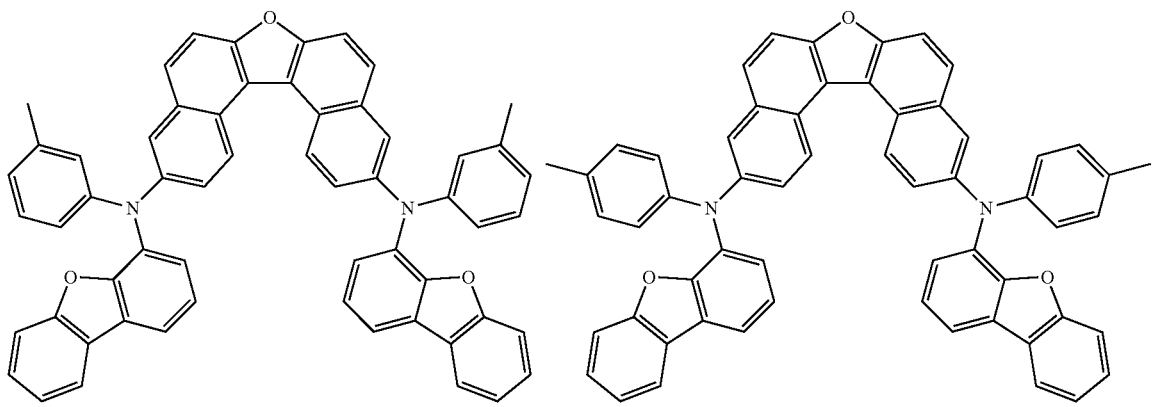
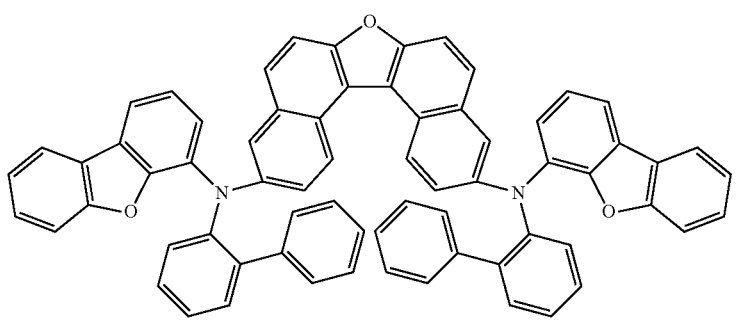
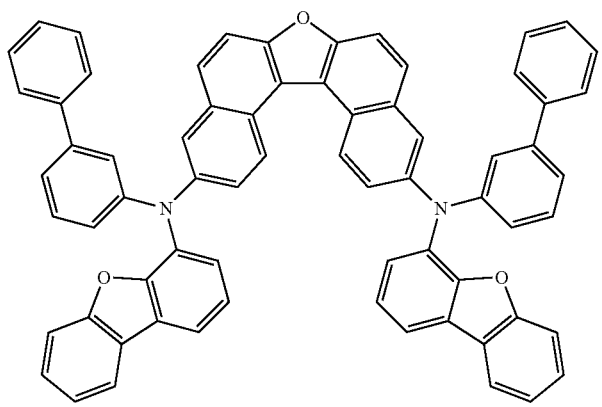

-continued
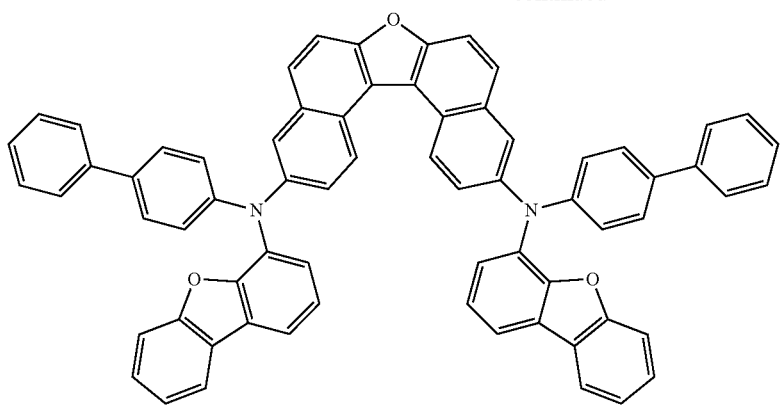
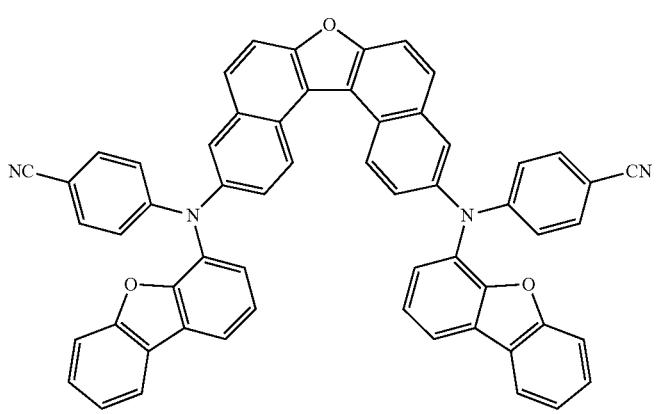
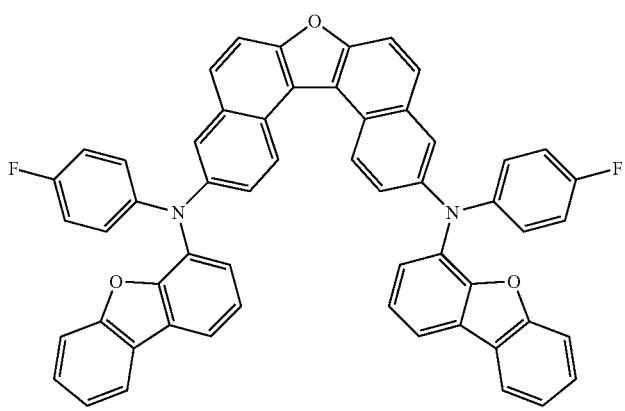
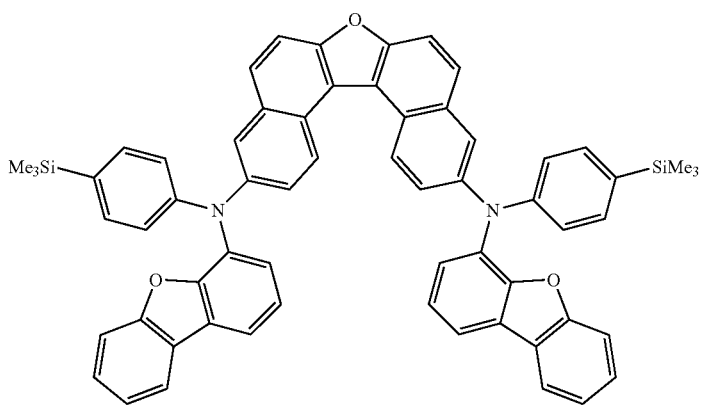

-continued
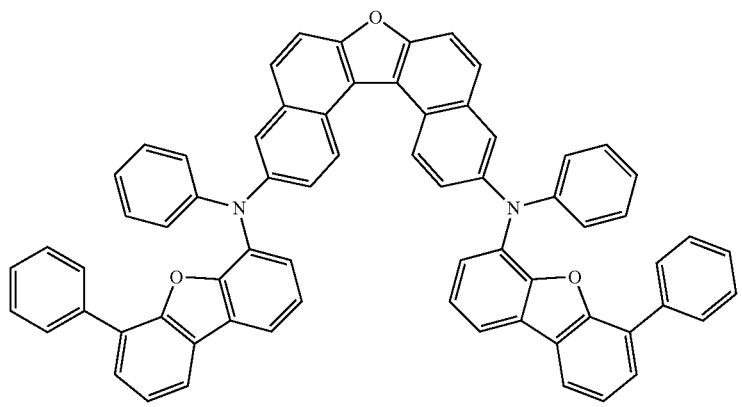
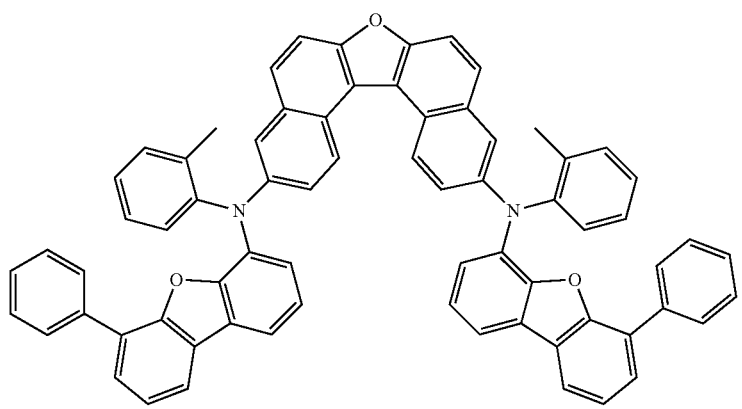
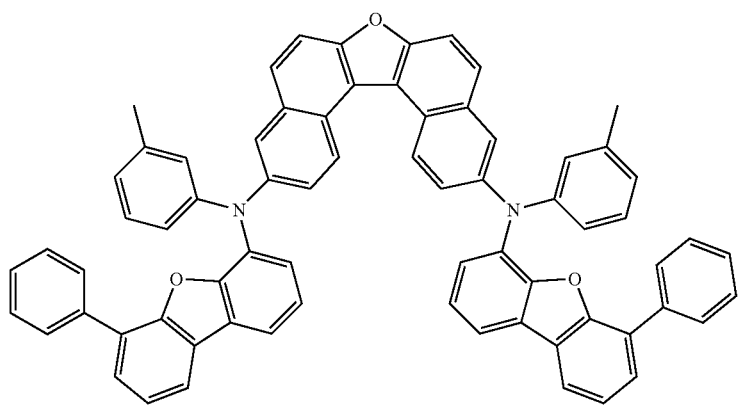
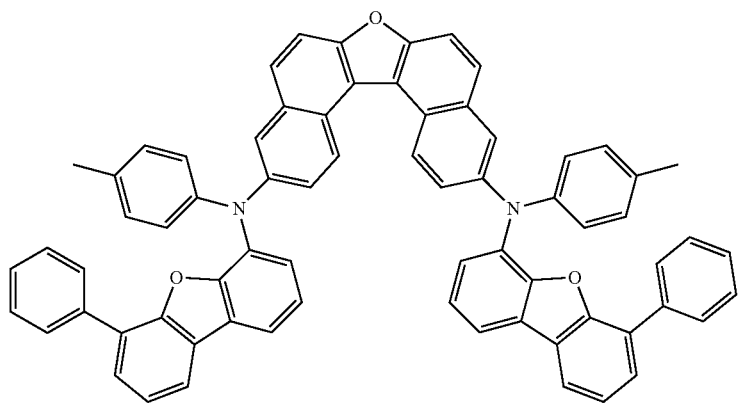

-continued
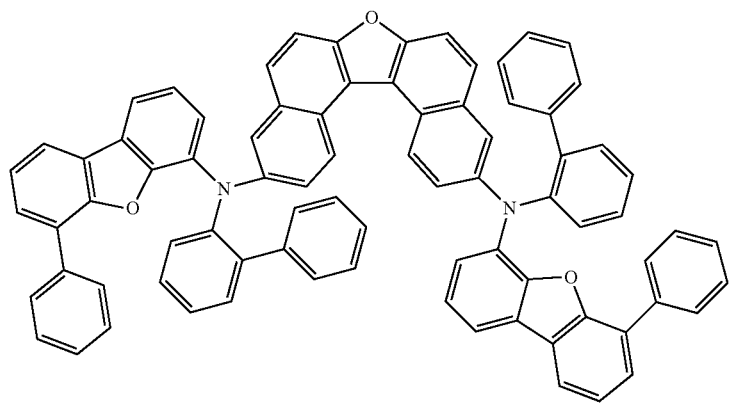
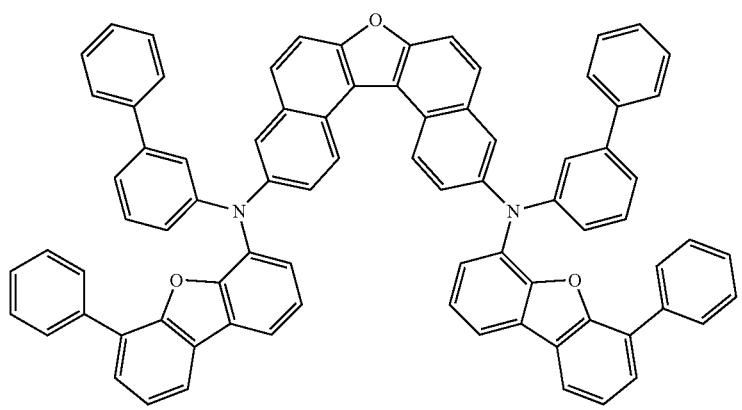
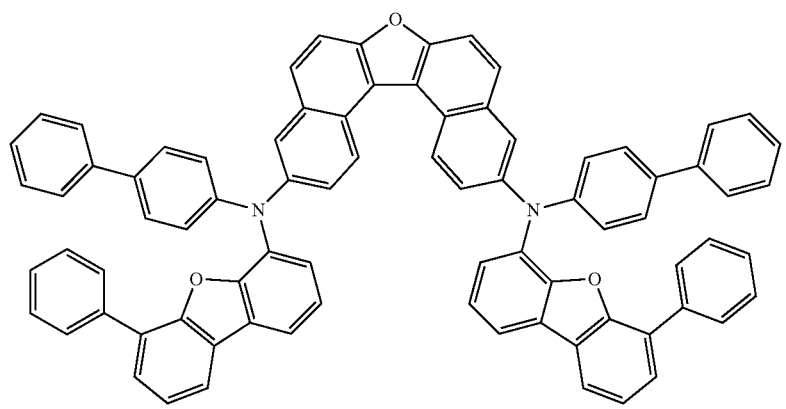
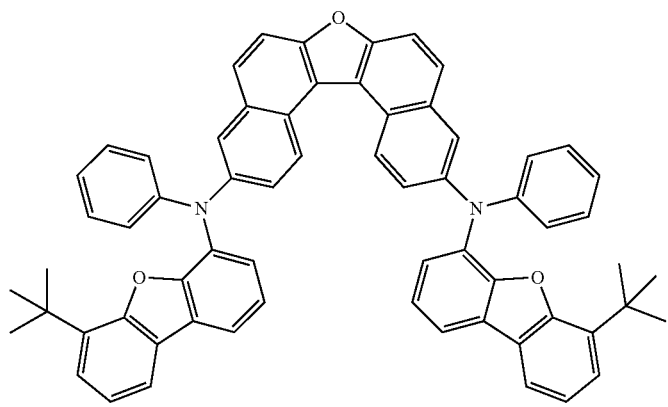

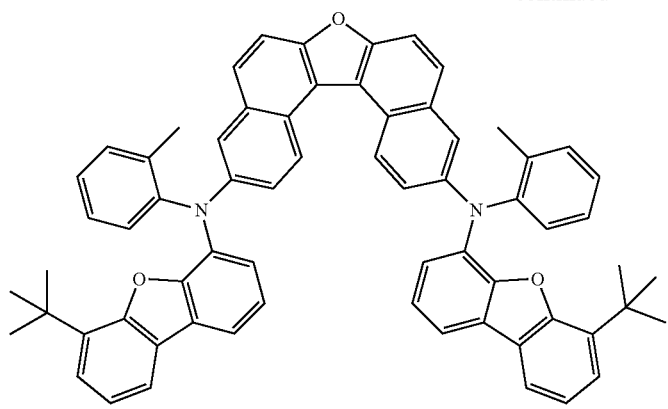
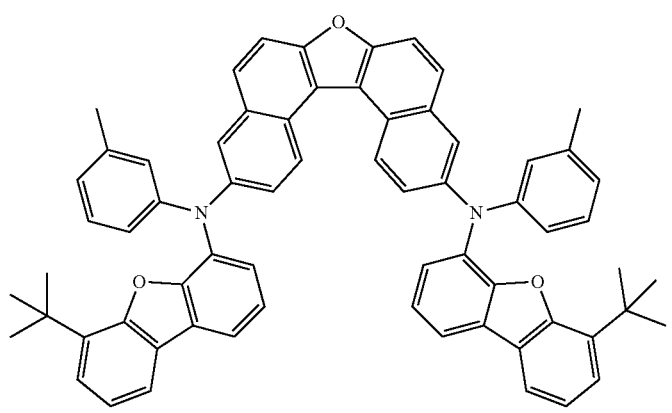
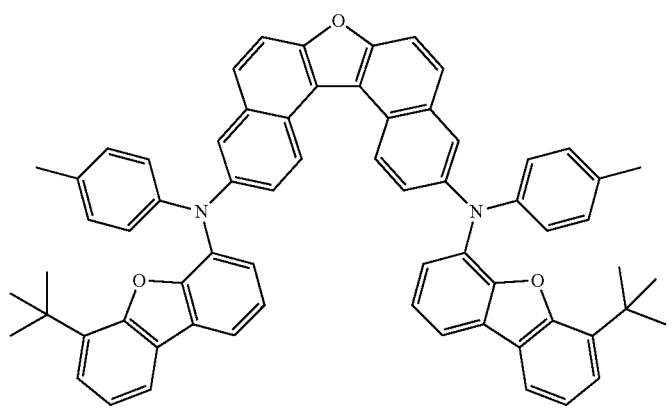
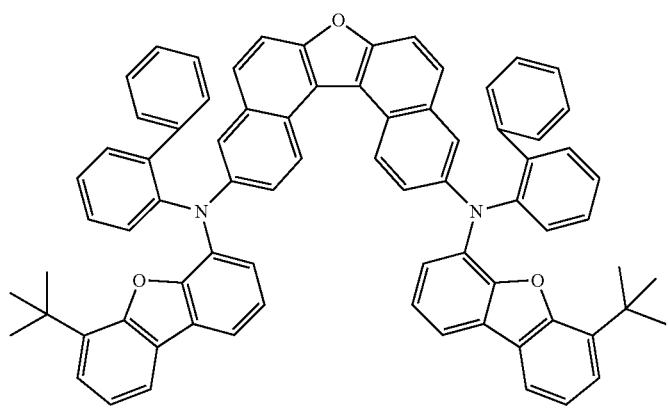

-continued
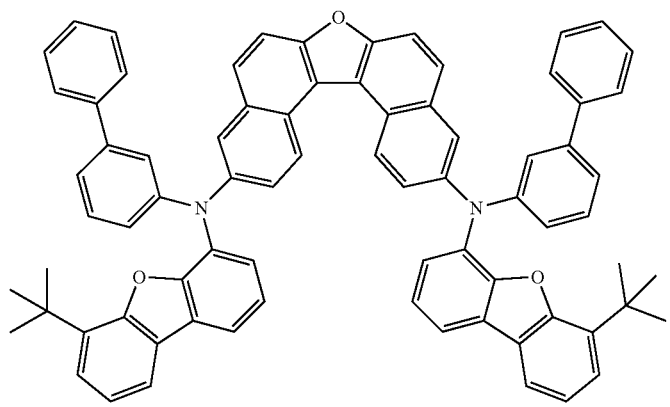
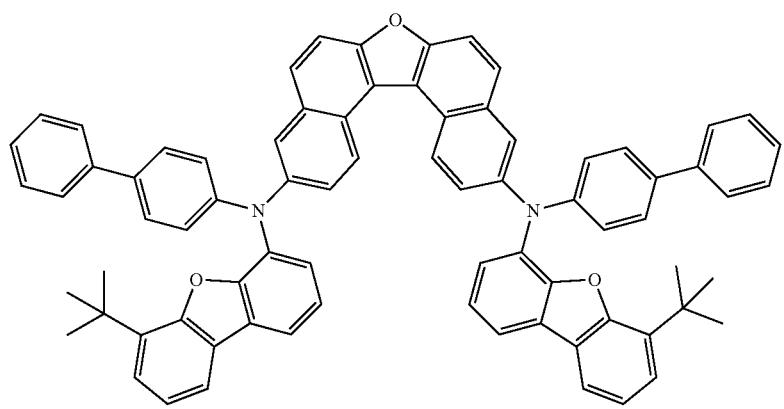
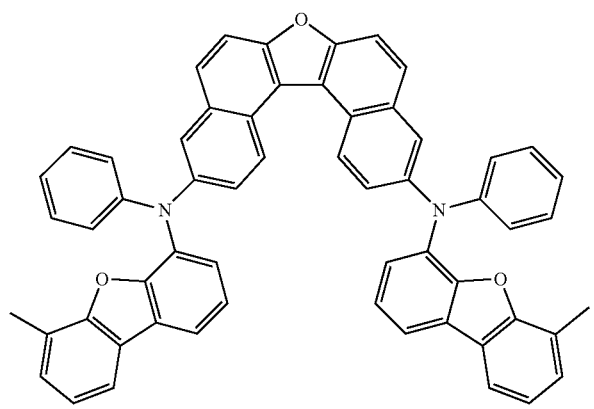
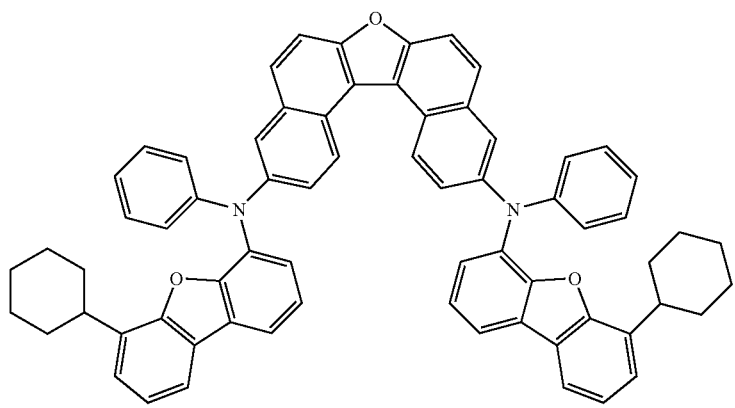

-continued
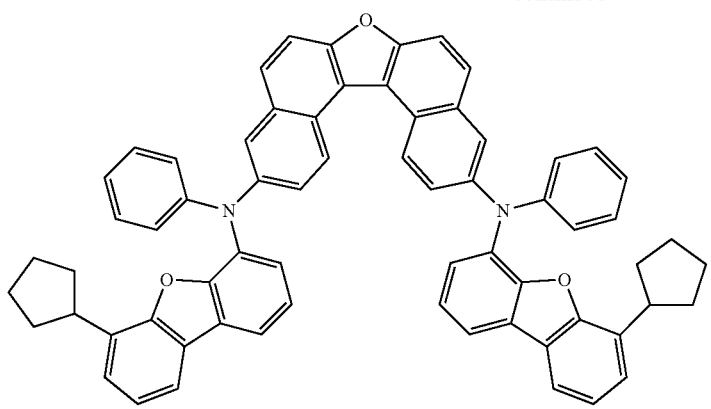
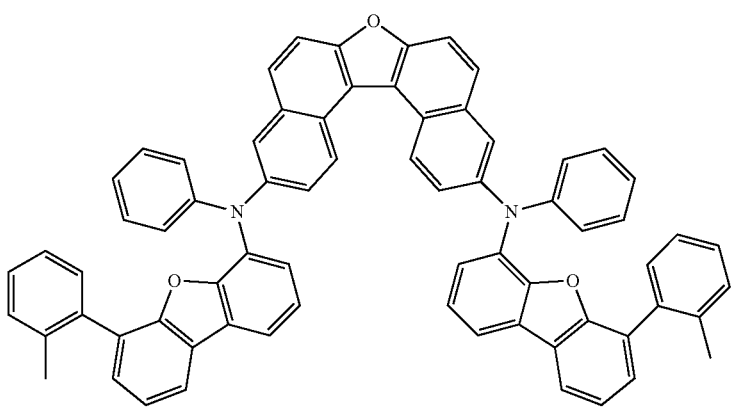
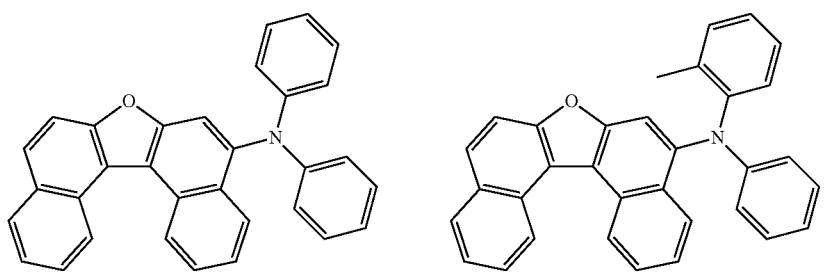
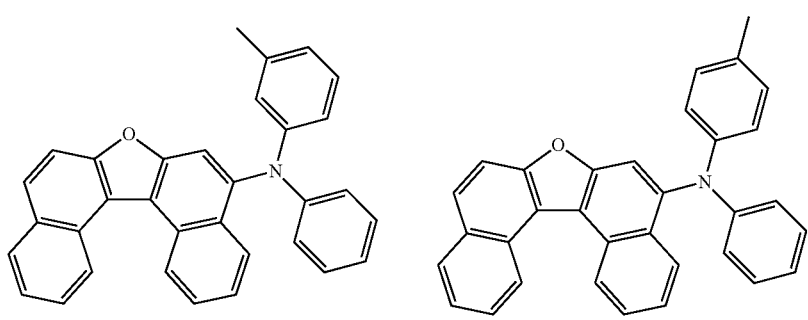

-continued
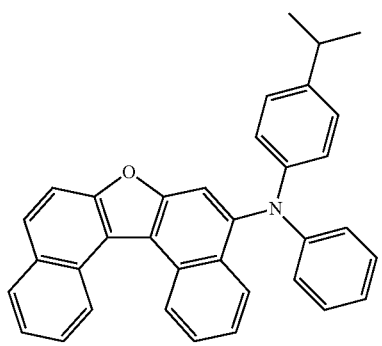
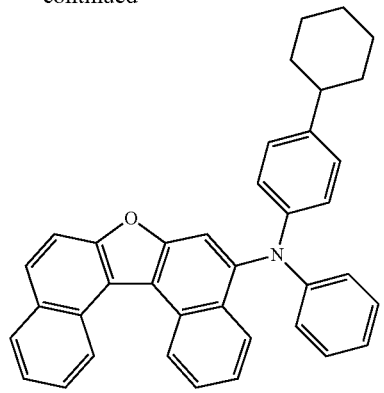
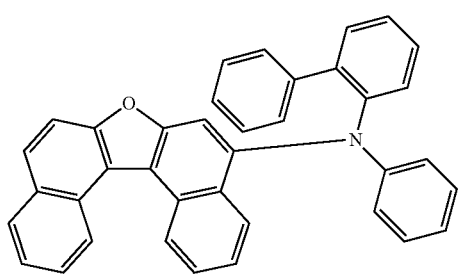
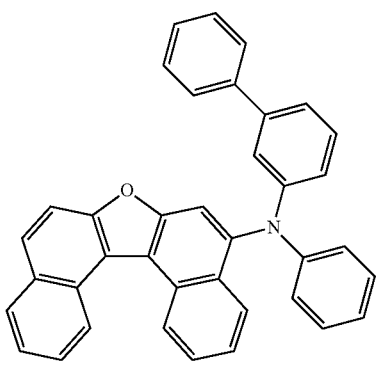
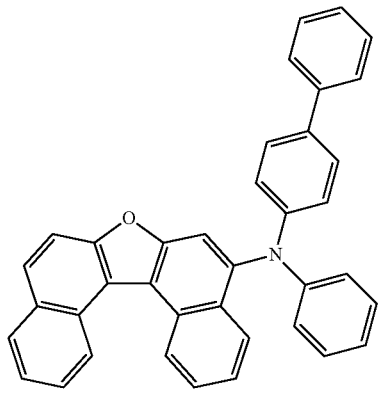
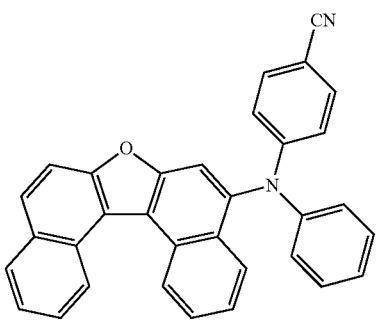
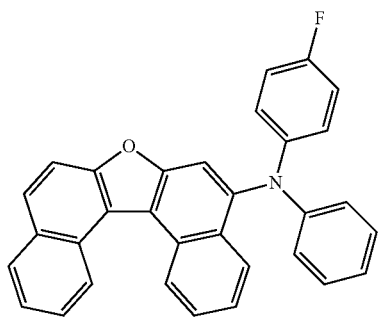
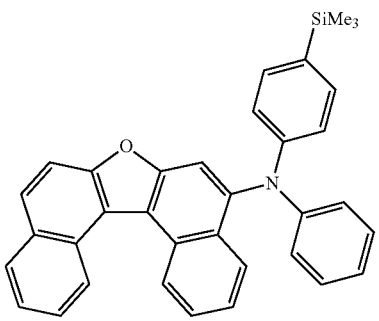

-continued
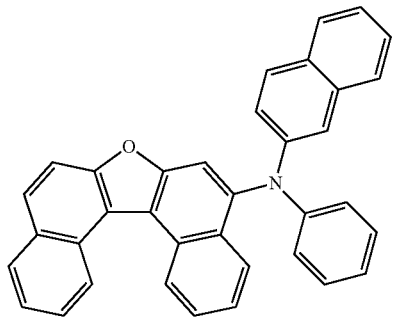
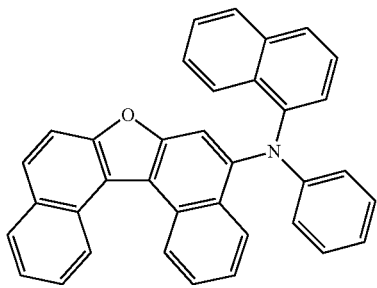
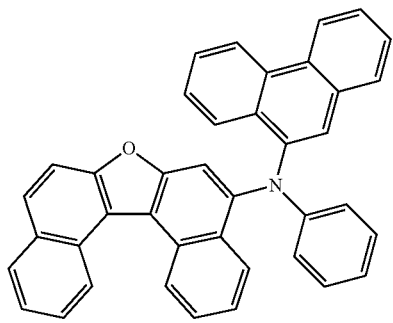
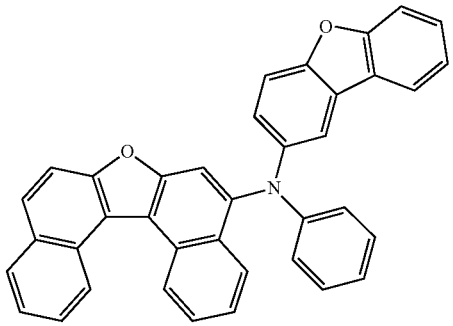
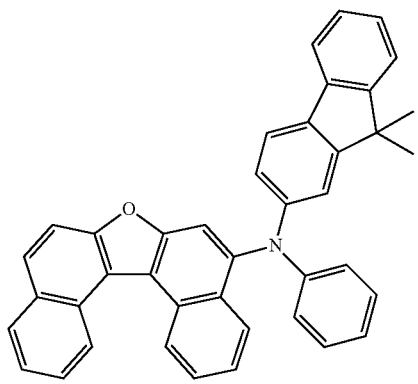
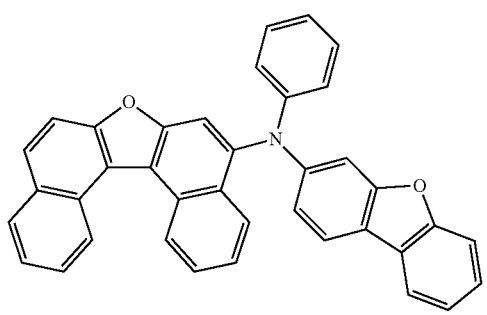
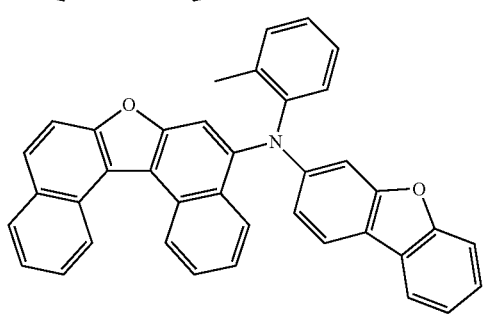
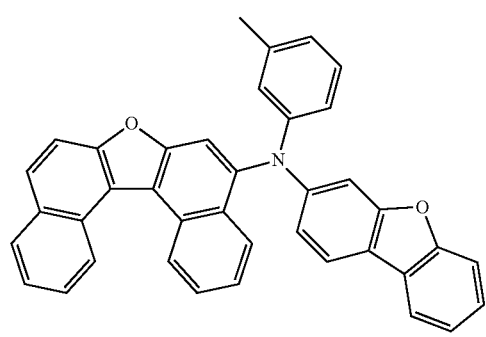
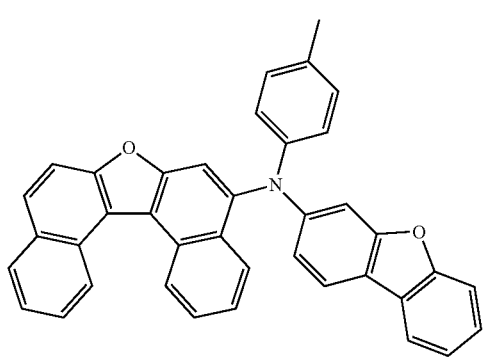
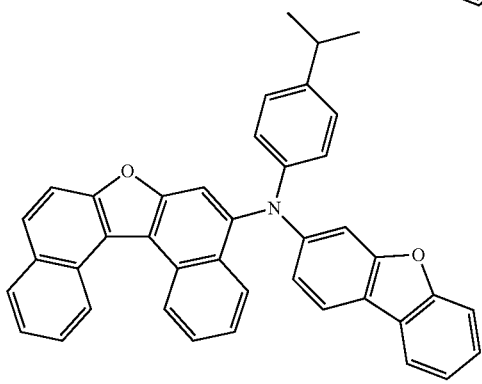

-continued
| 345 | 346 |
|---|---|
| 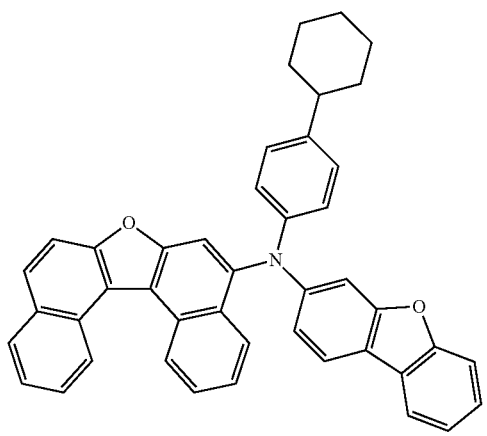 | 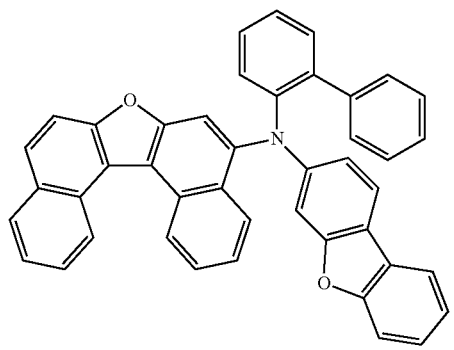 |
| 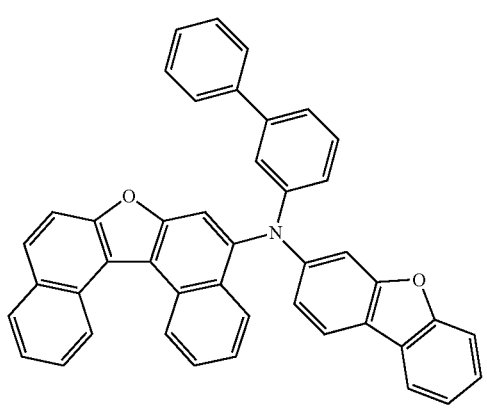 | 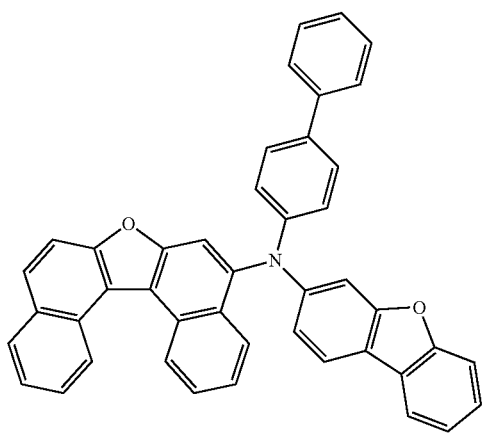 |
| 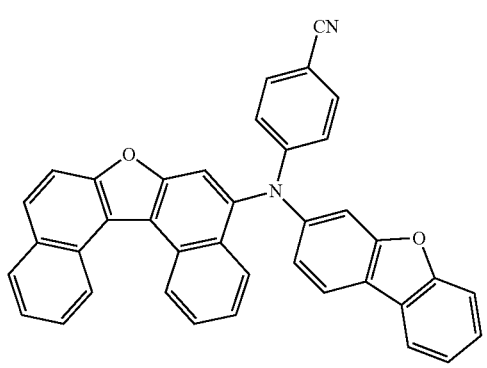 | 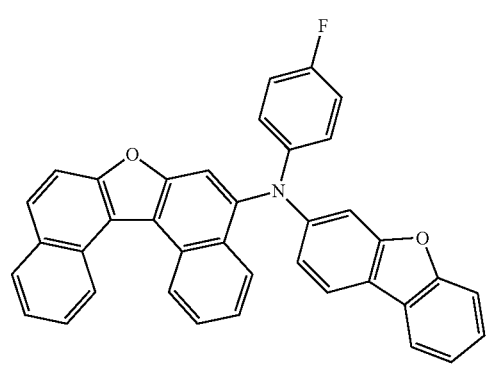 |
| 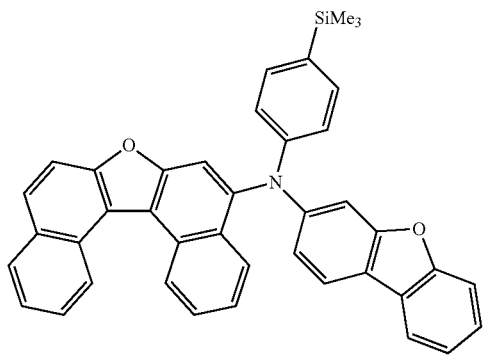 | 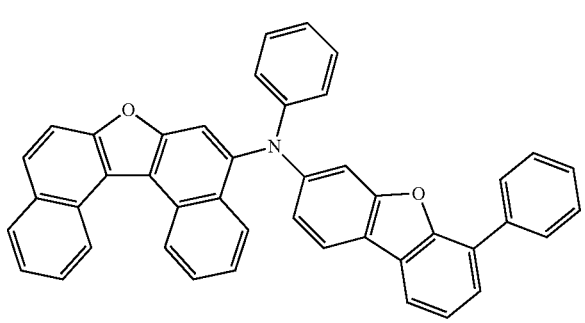 |

-continued
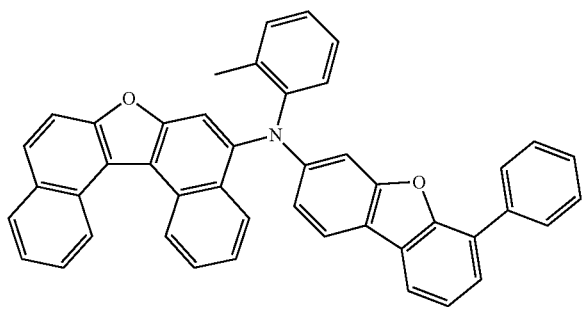
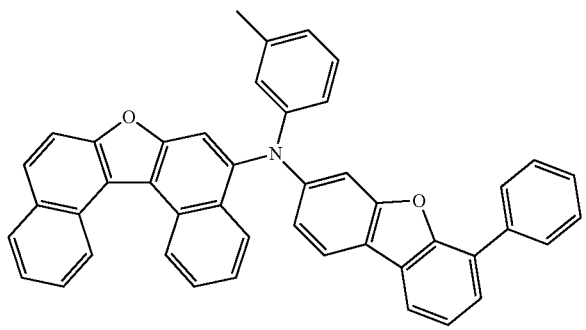
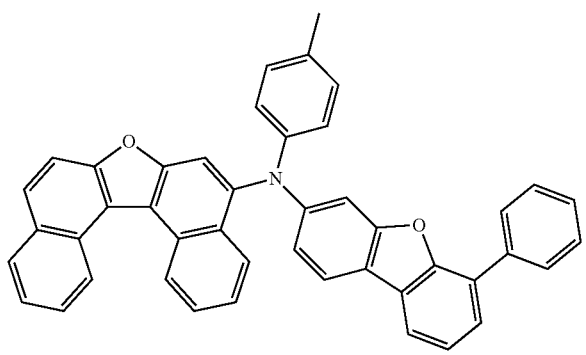
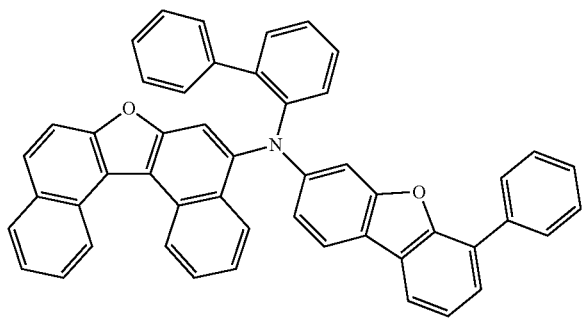
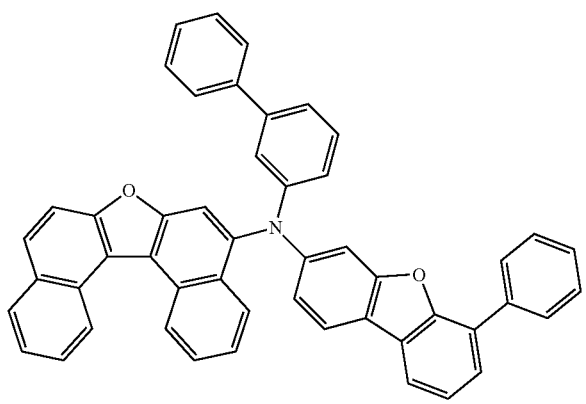

349 350
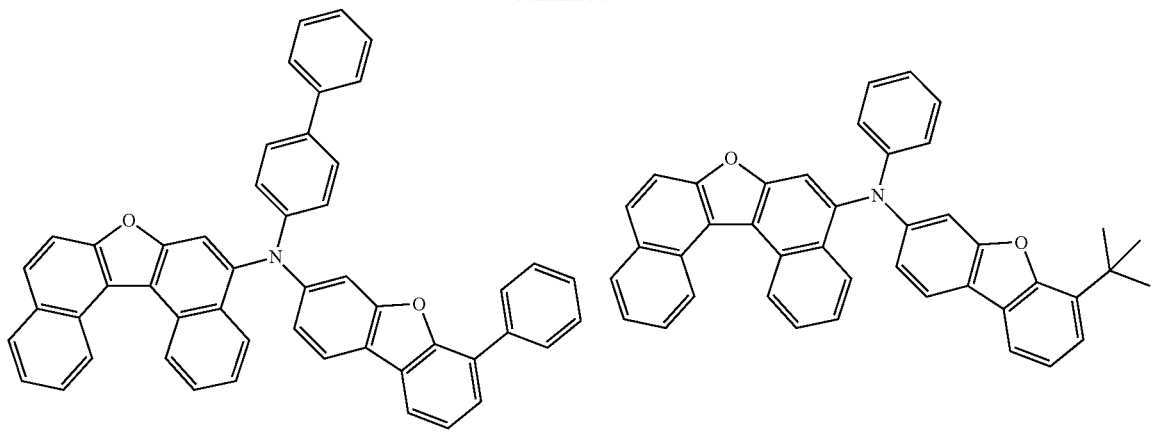
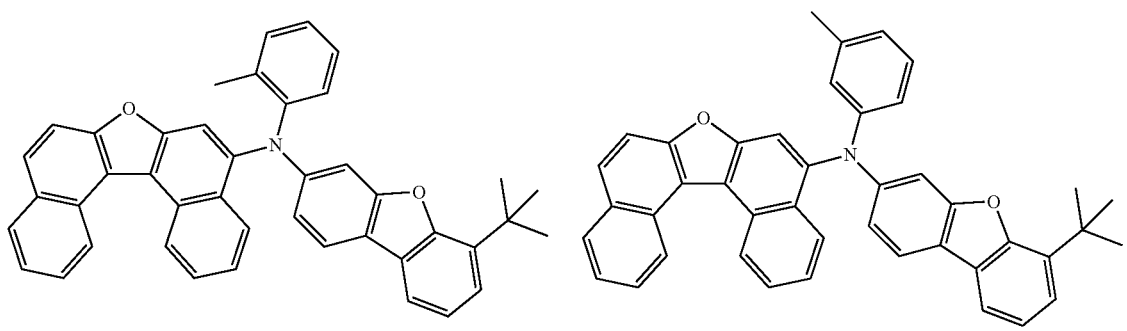
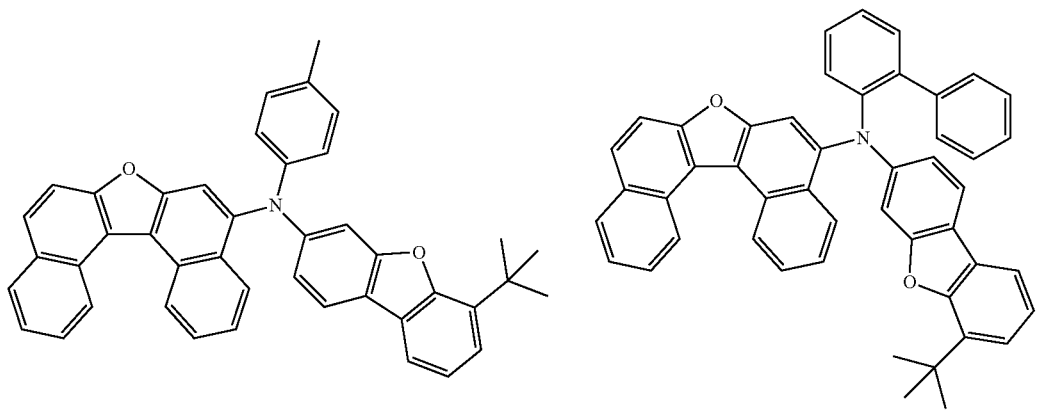
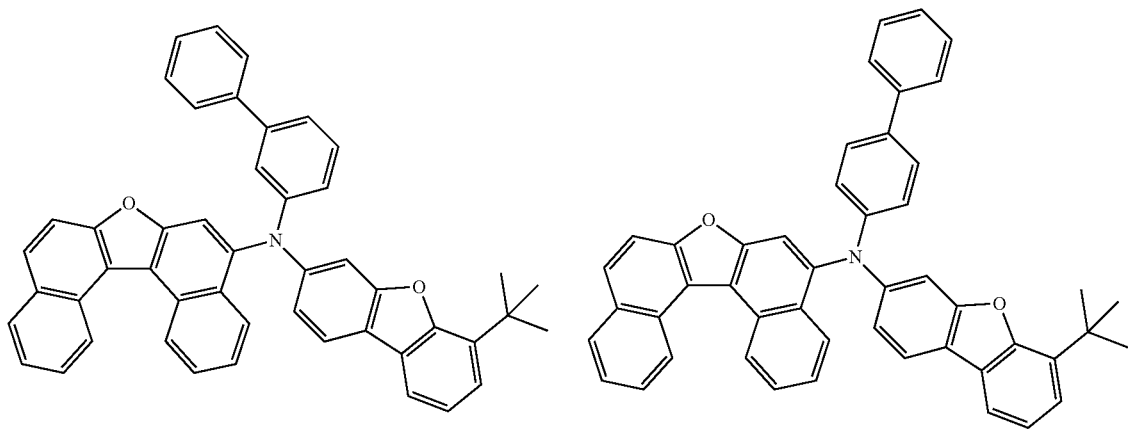

351    352
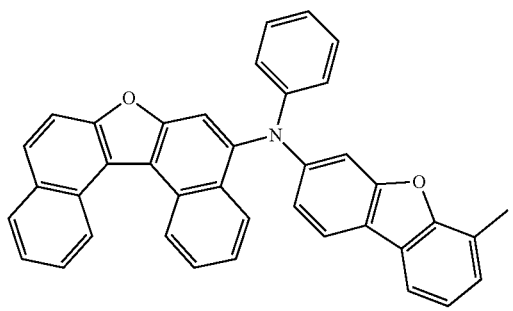 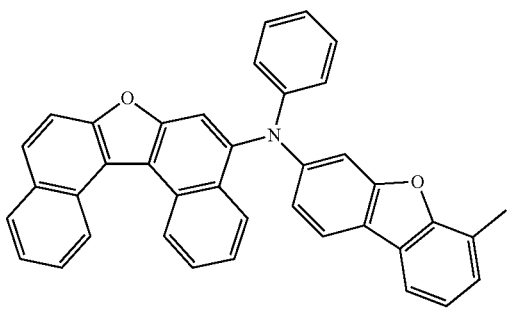
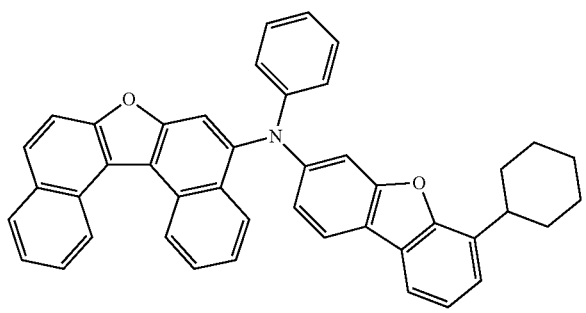
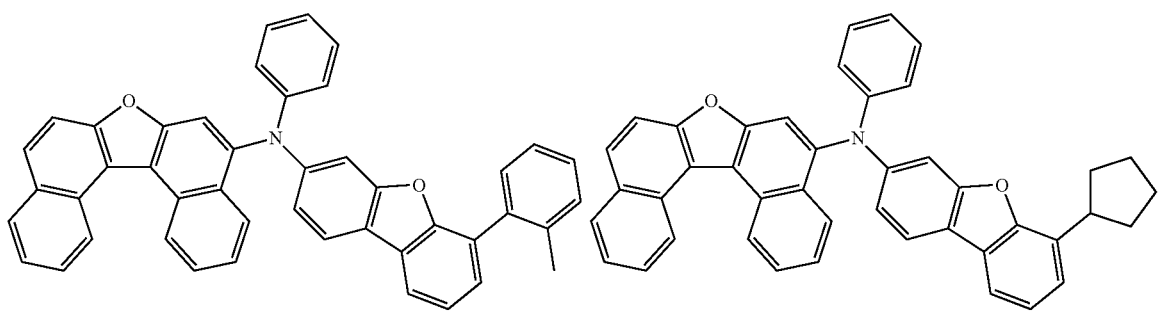
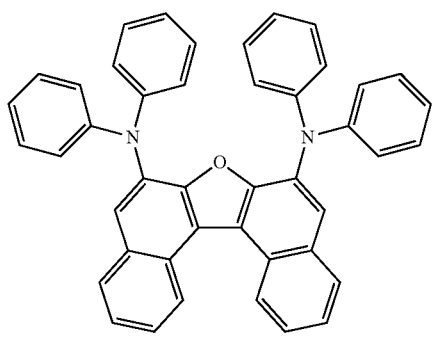 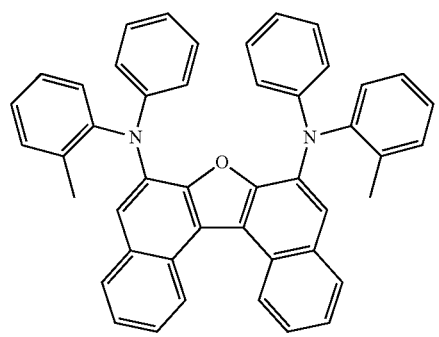
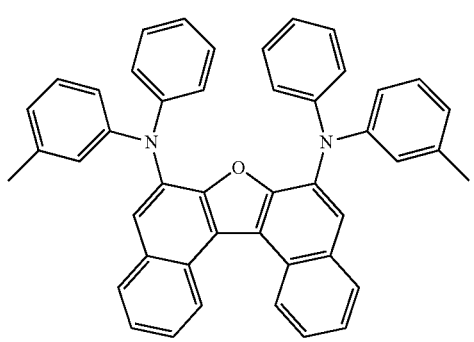 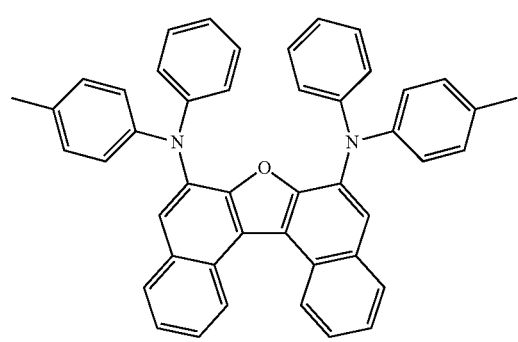

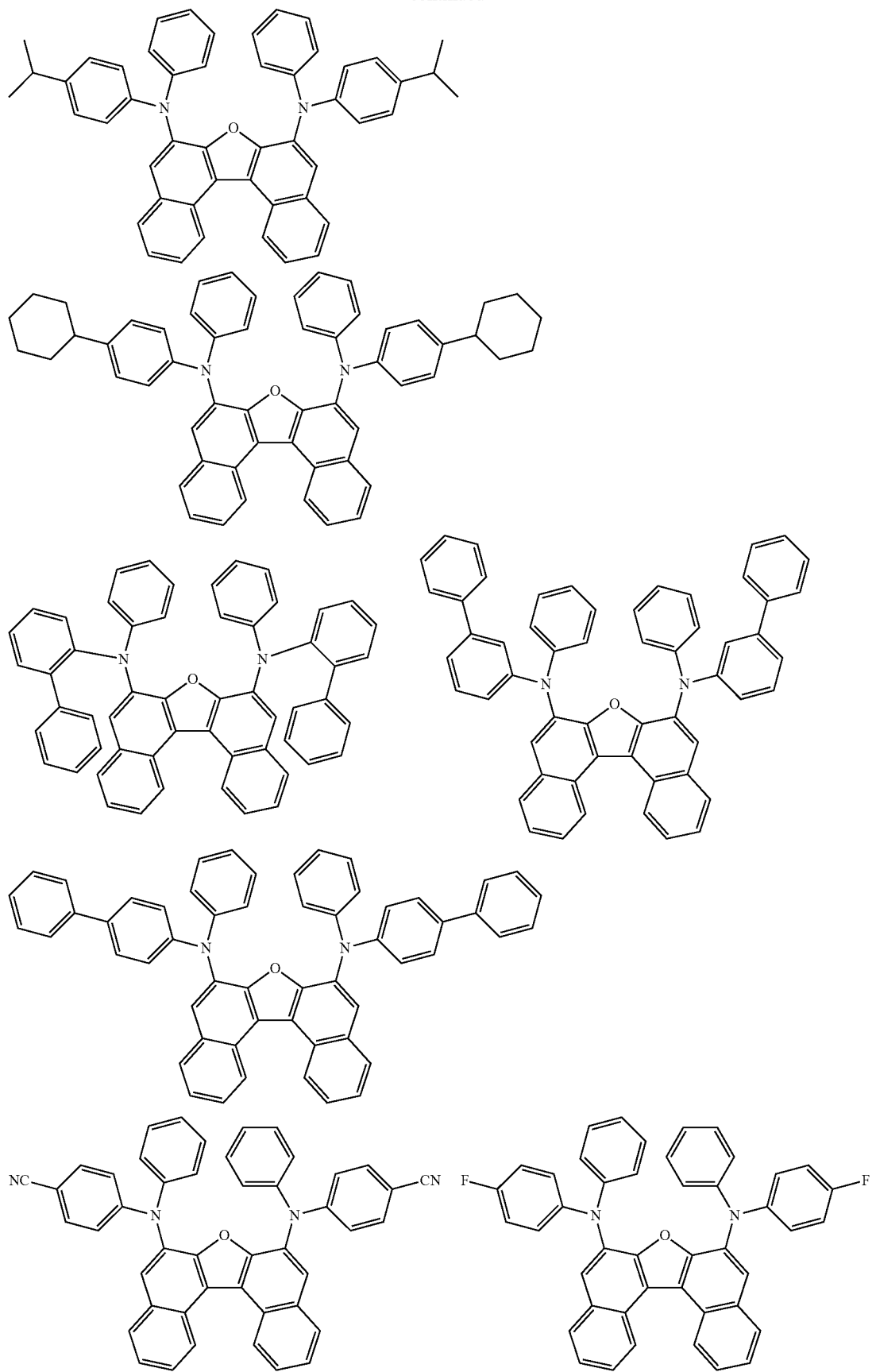

-continued
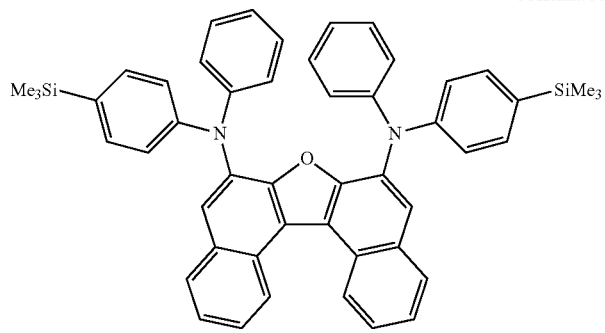
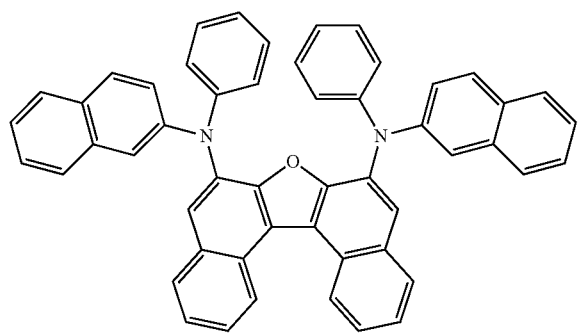
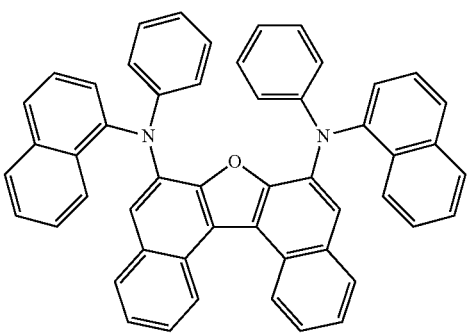
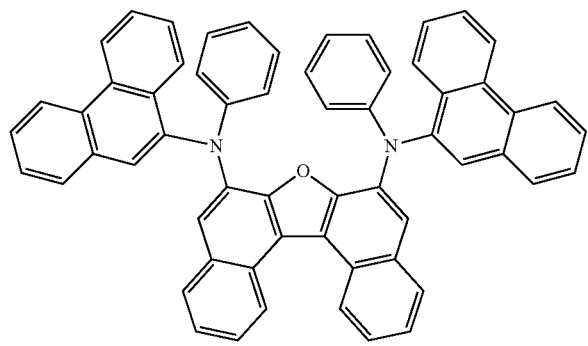
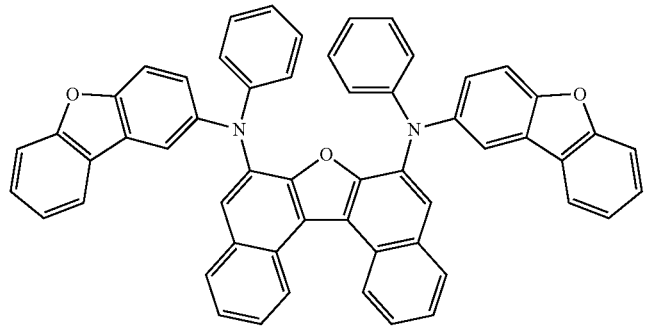
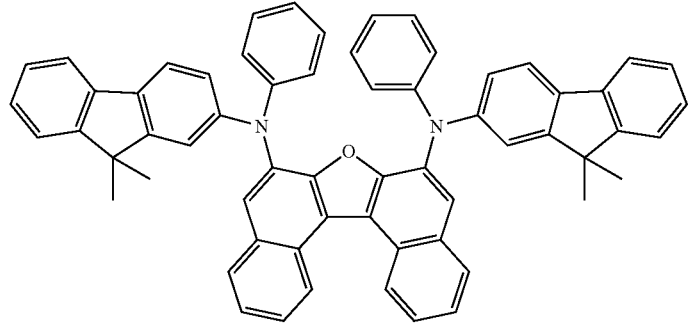

357
-continued
358
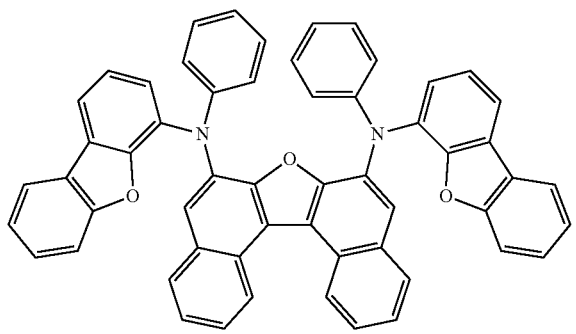
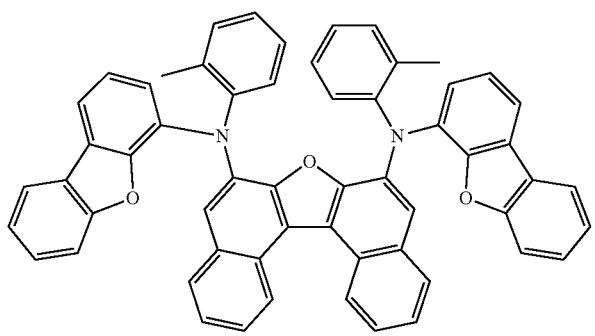
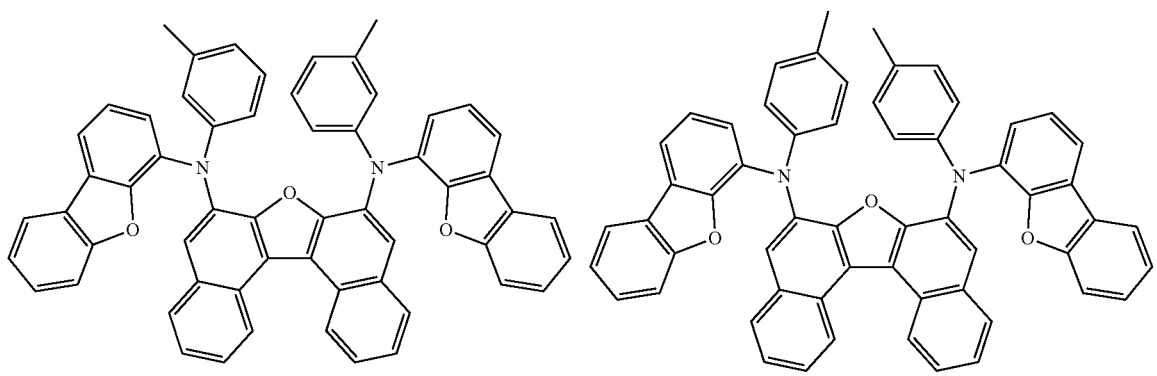
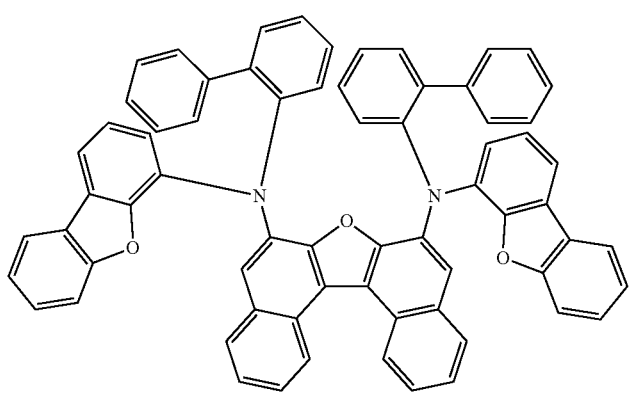

-continued
359
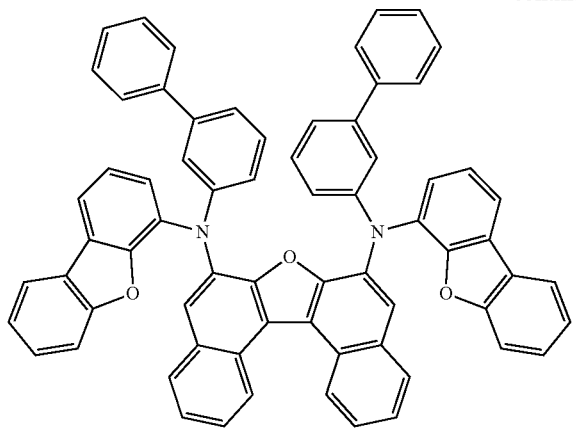
360
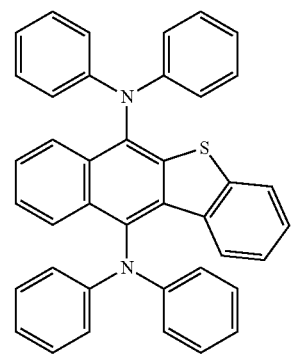
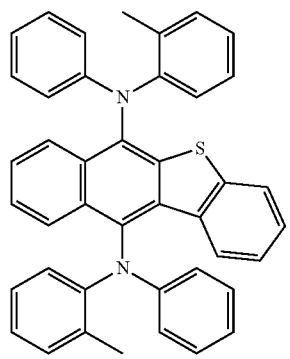
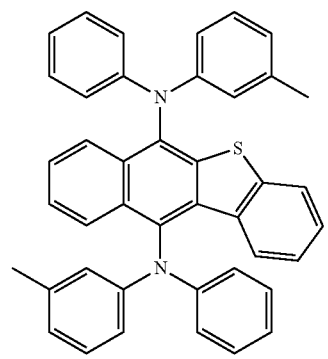
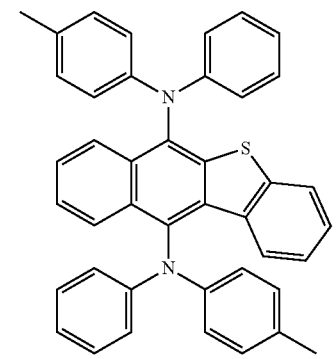
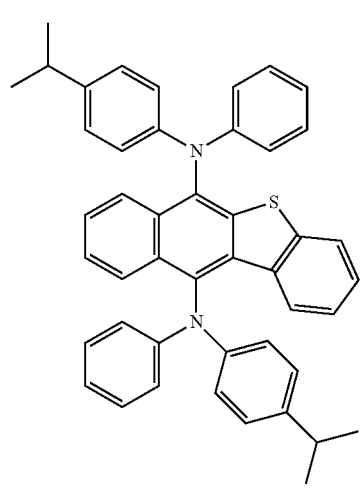
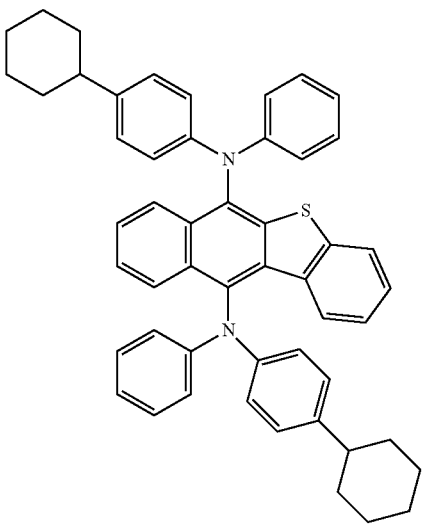
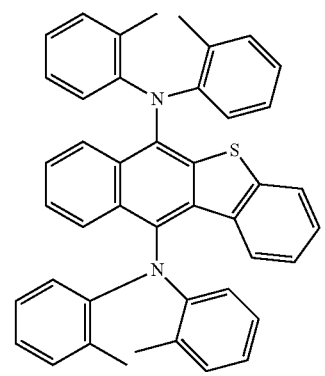

361 362
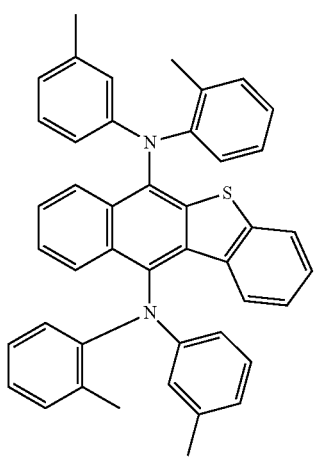
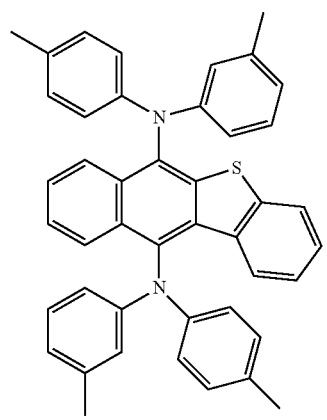
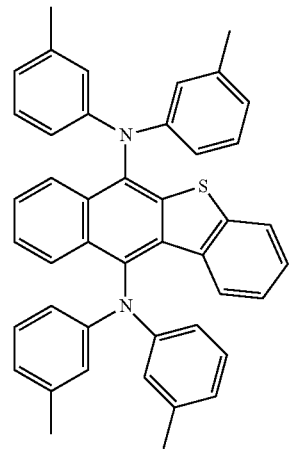
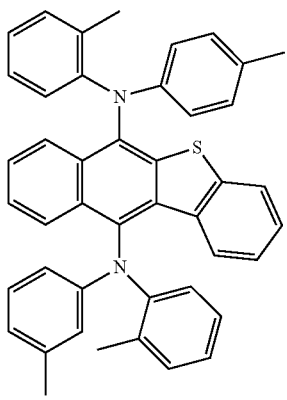
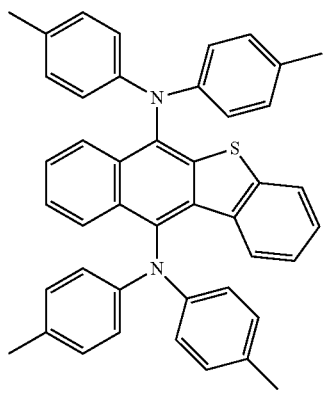
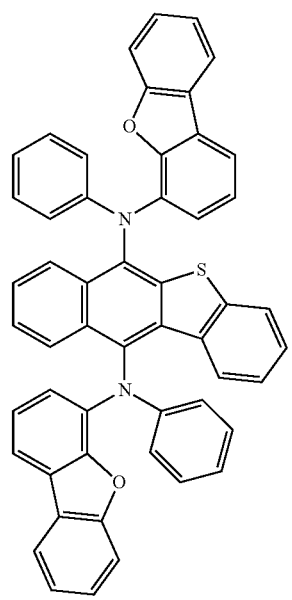
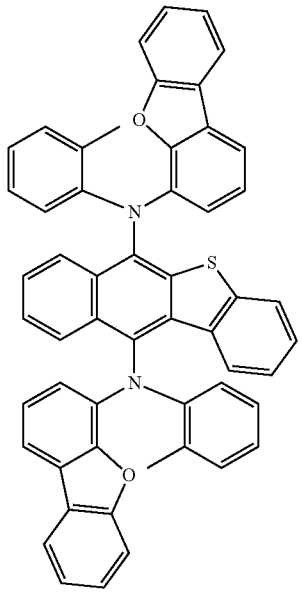
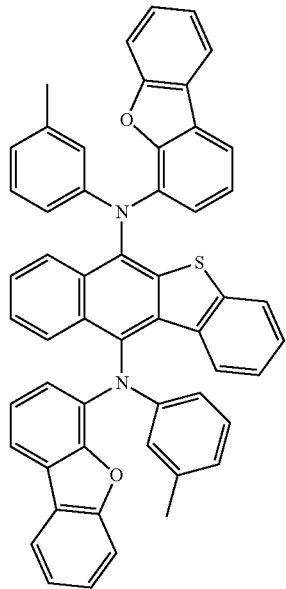
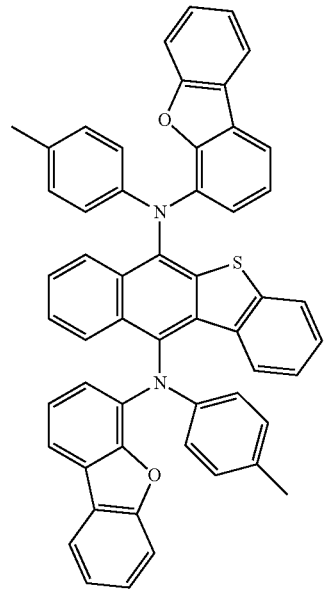

-continued
363
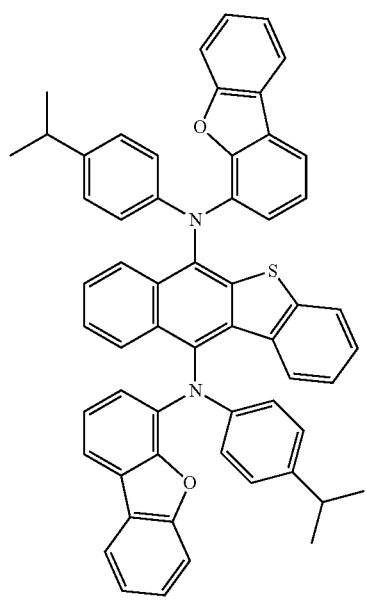
364
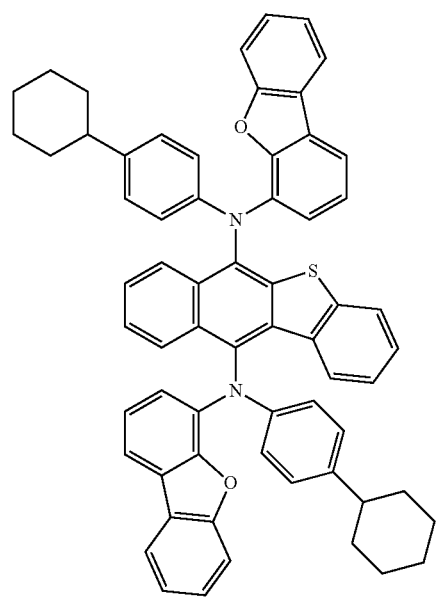
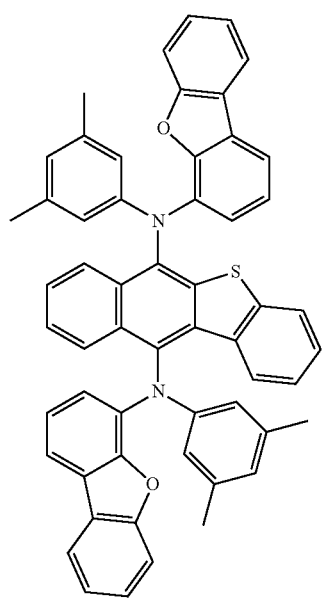
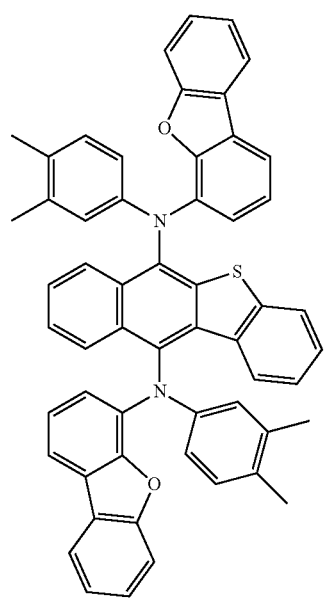
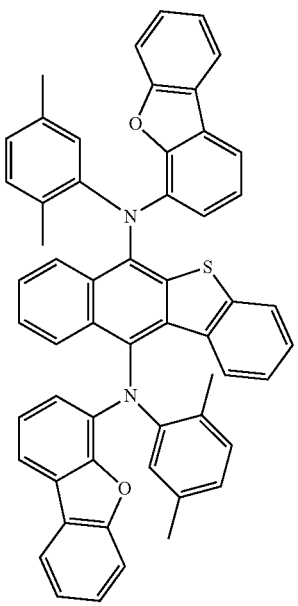

365
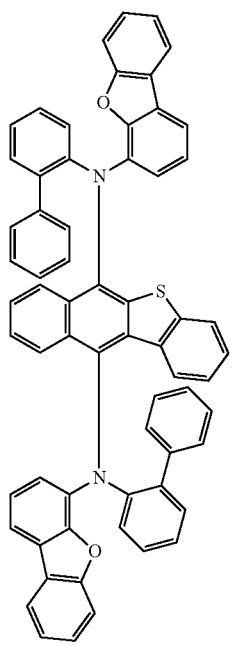 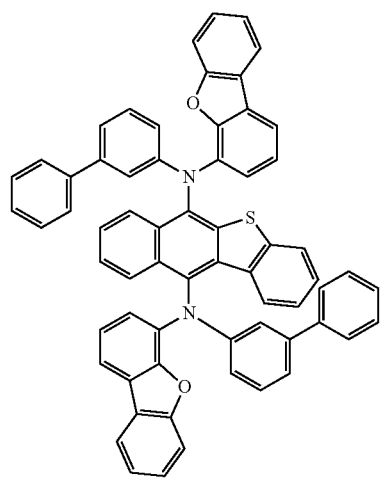
366
-continued
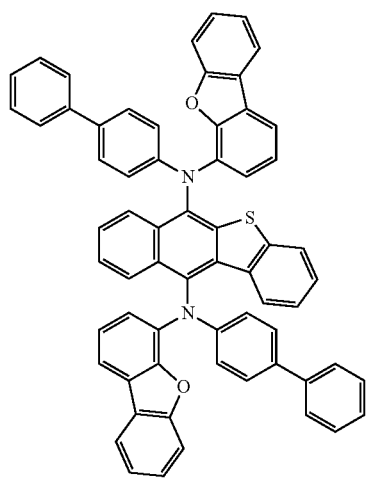
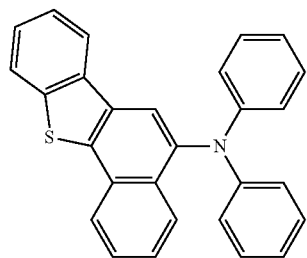 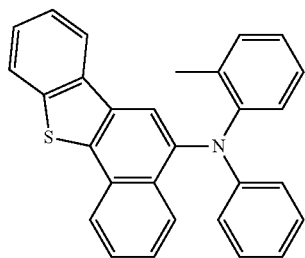 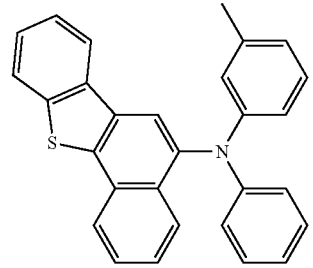
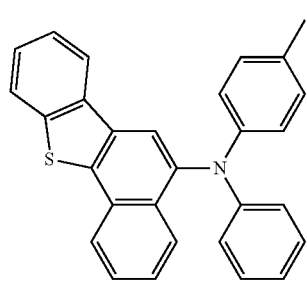 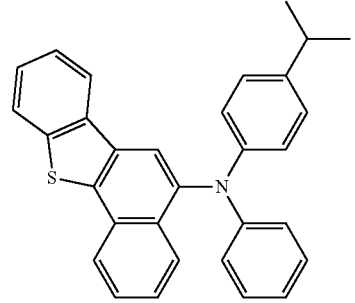 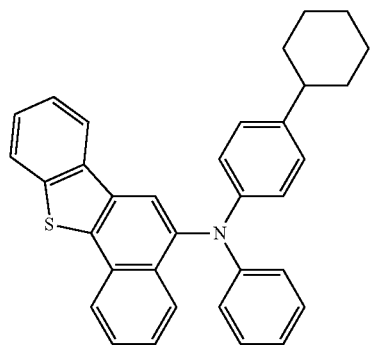
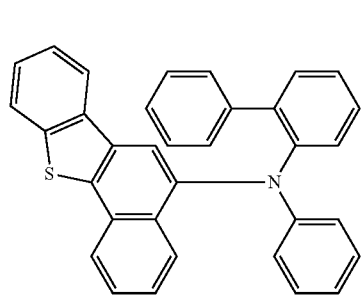 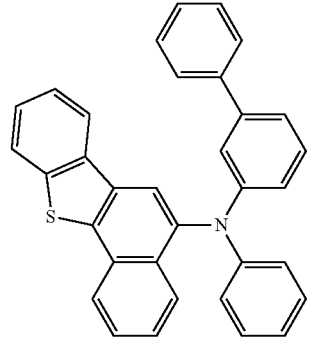 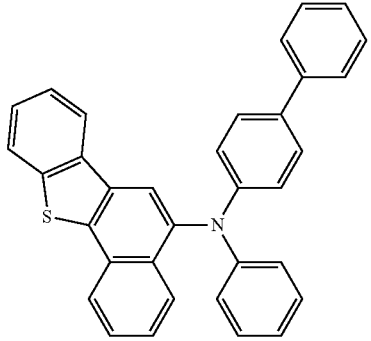

-continued
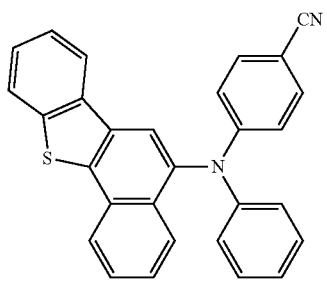 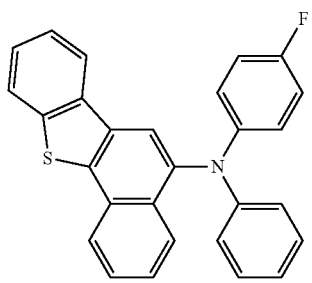 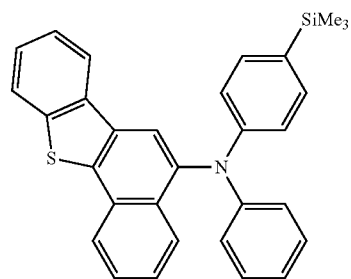
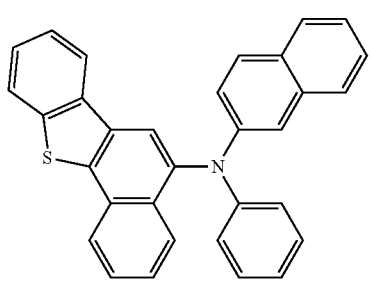 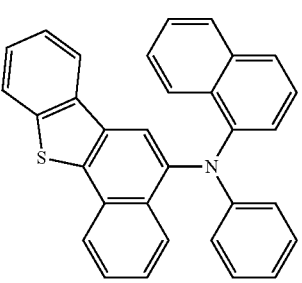 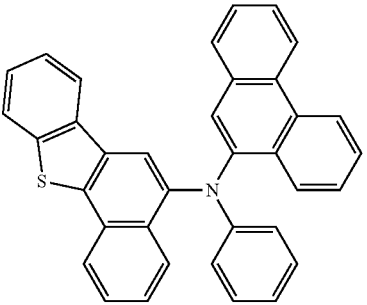
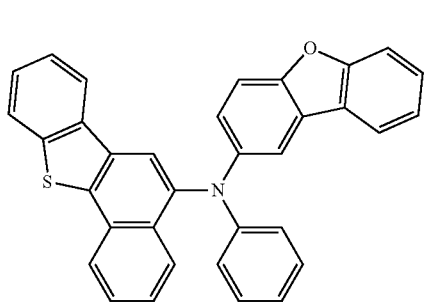 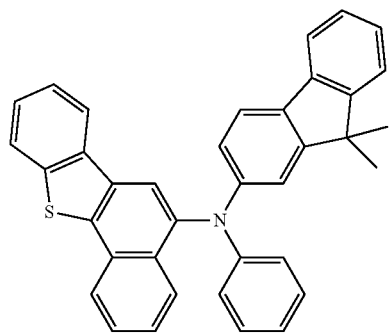
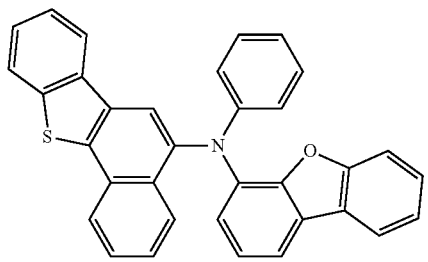 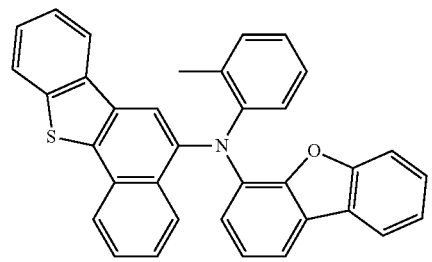
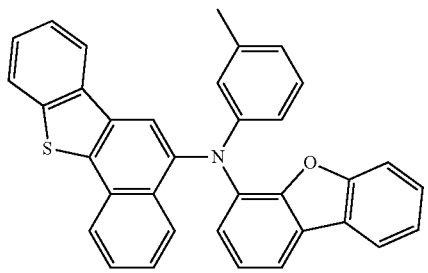 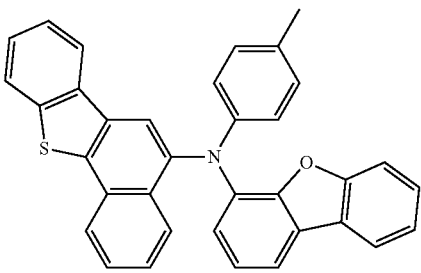

369
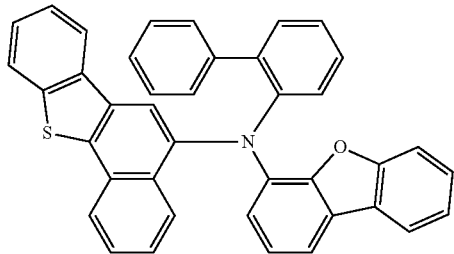
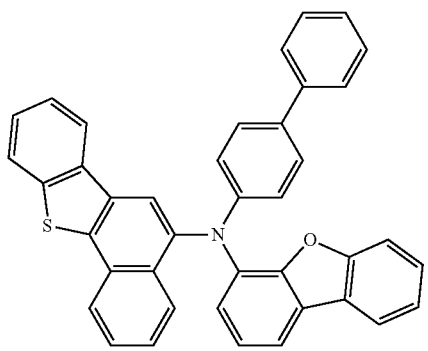
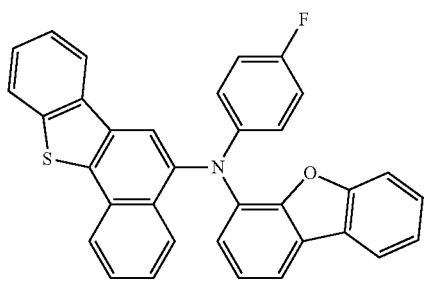
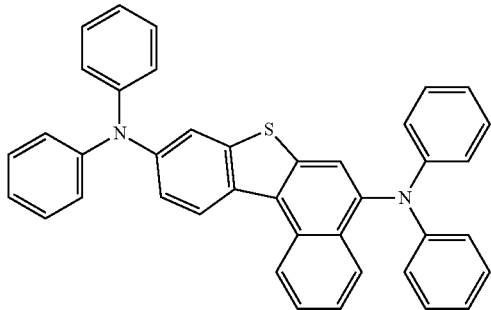
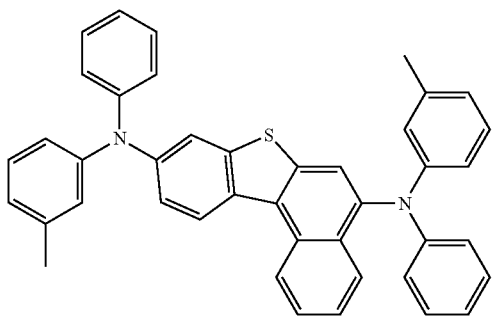
370
-continued
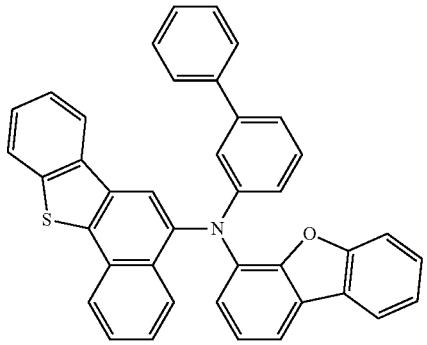
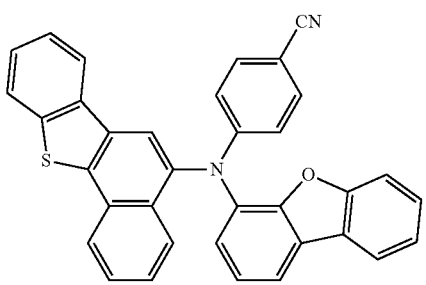
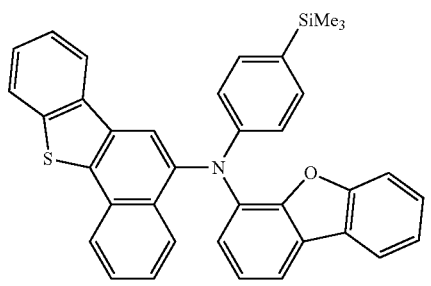
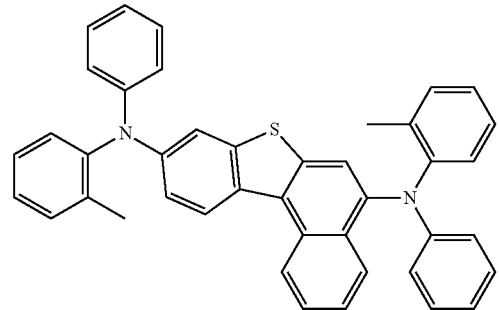
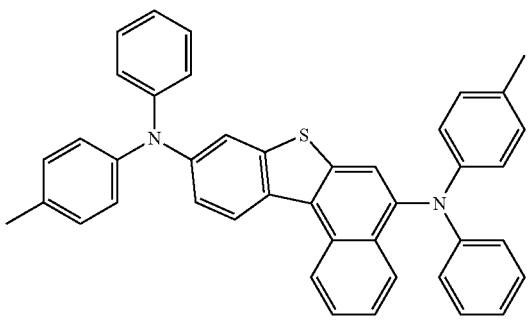

371            372
-continued
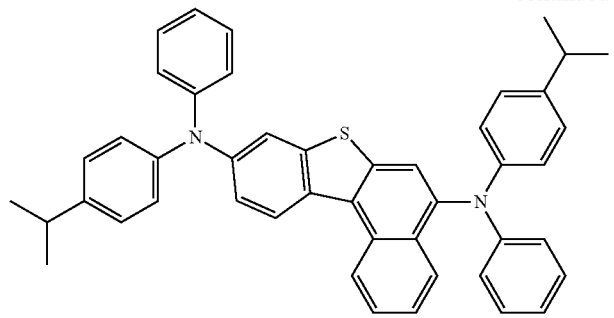
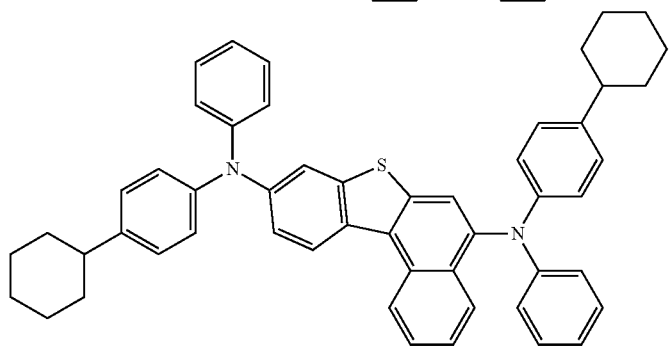
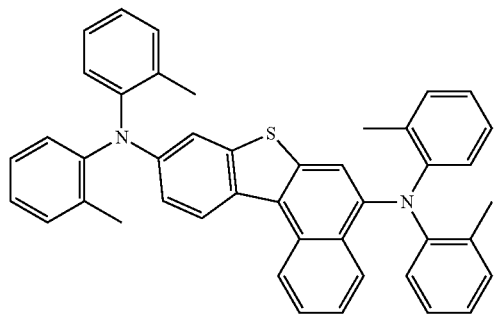
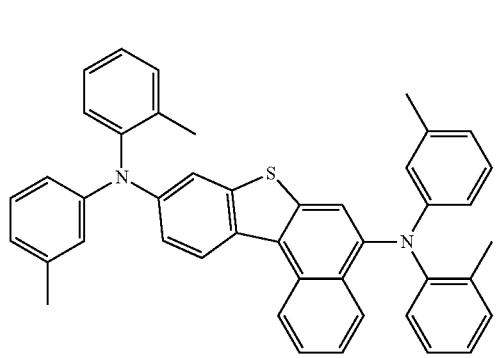
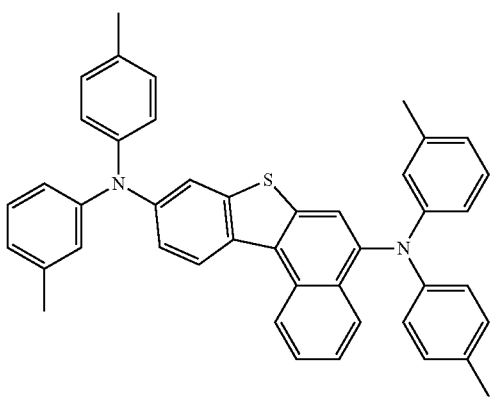
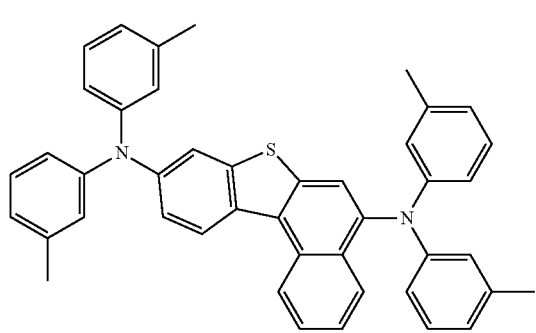
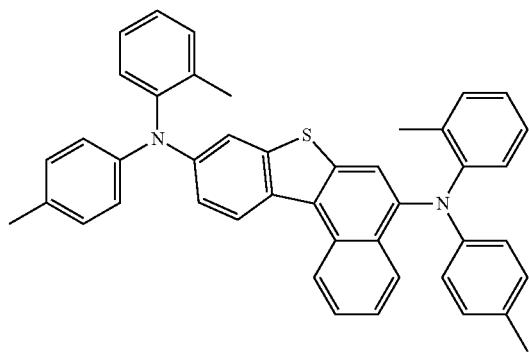

373 374
-continued
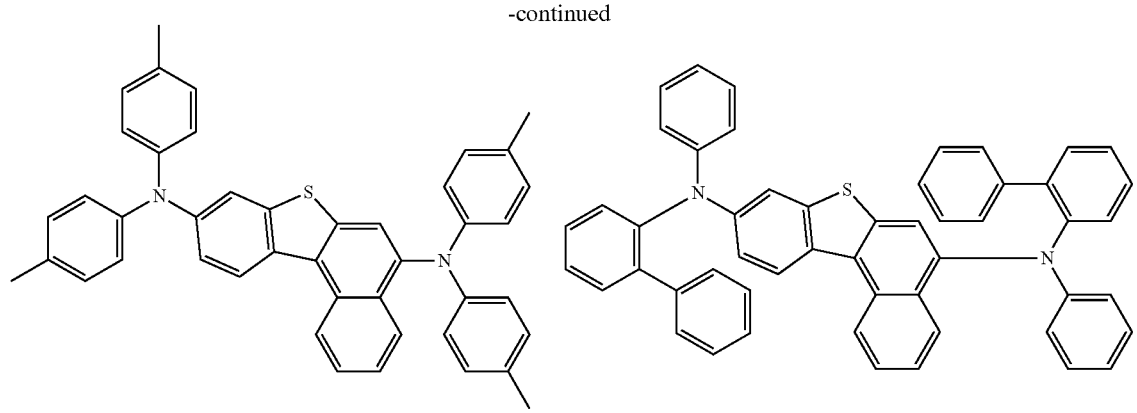
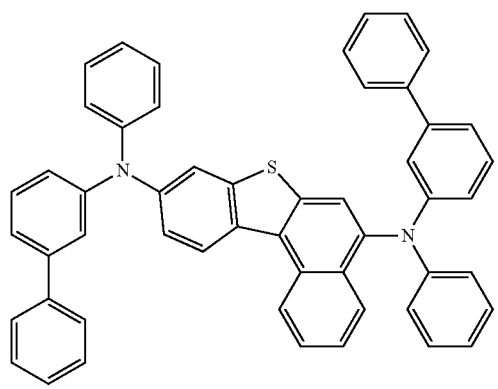
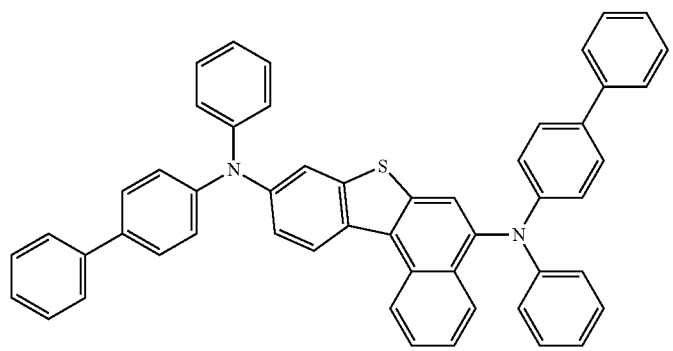
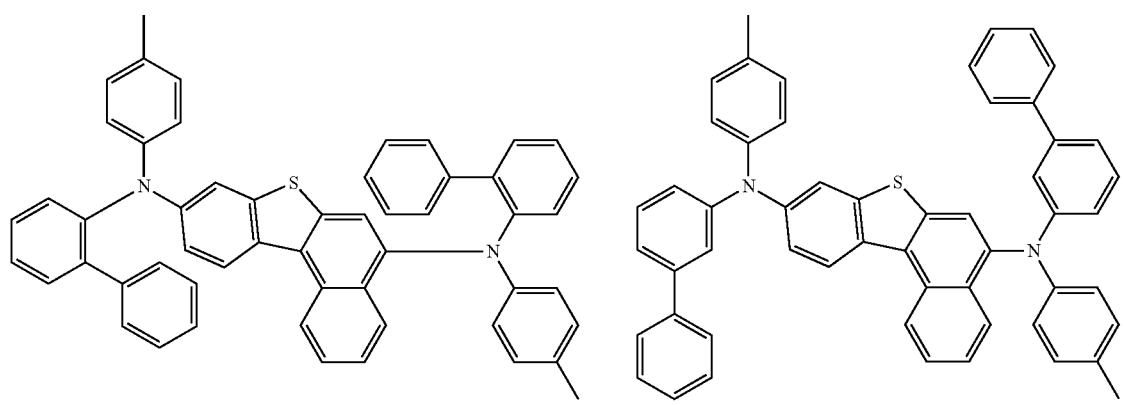

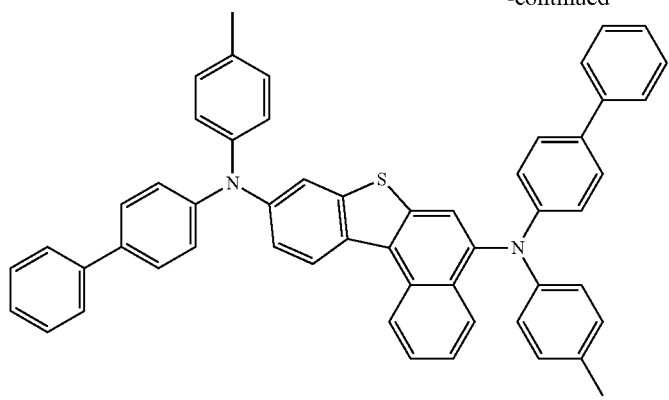
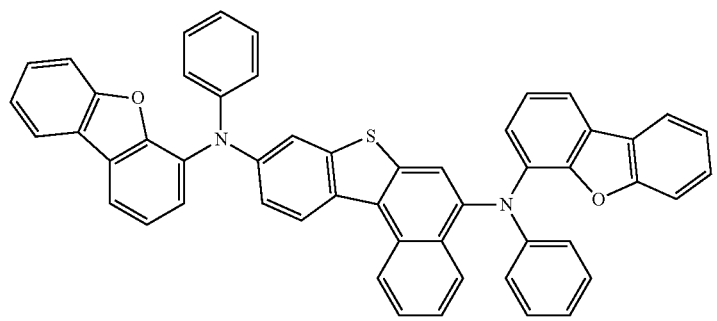
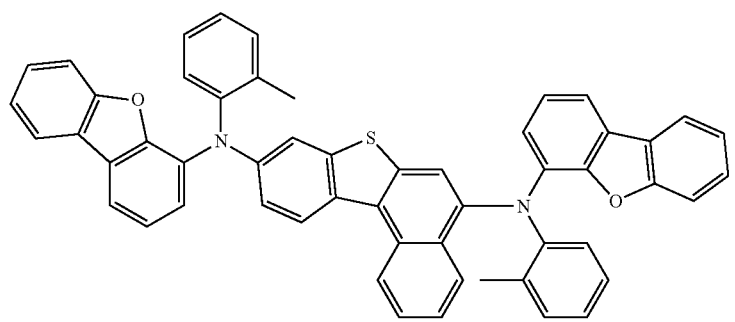
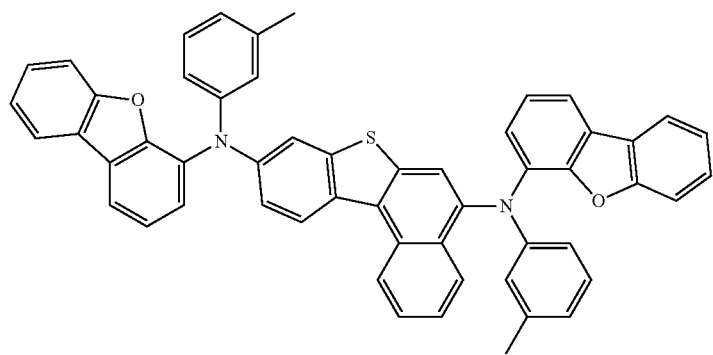

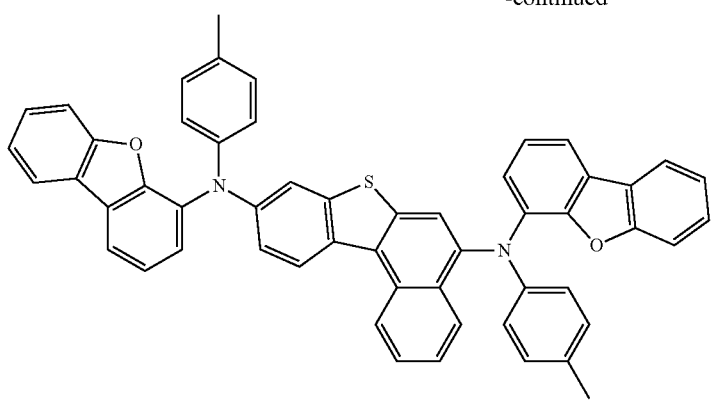
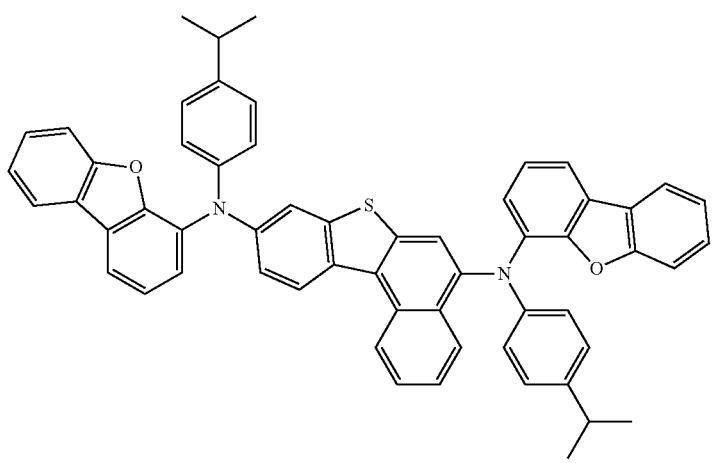
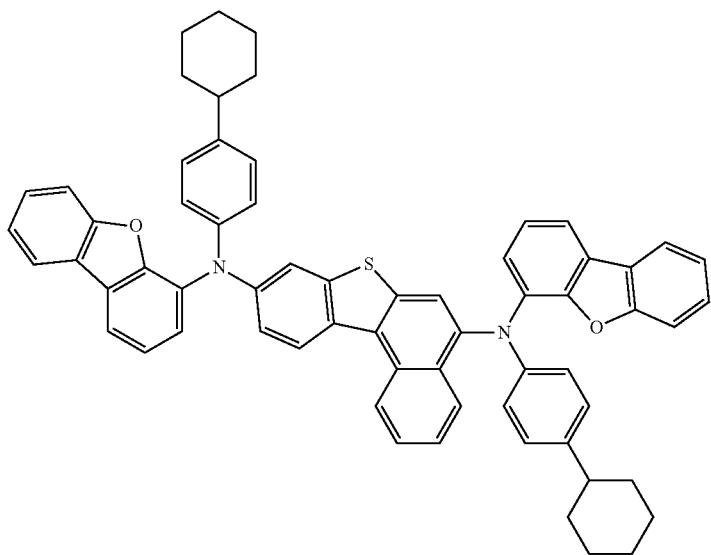

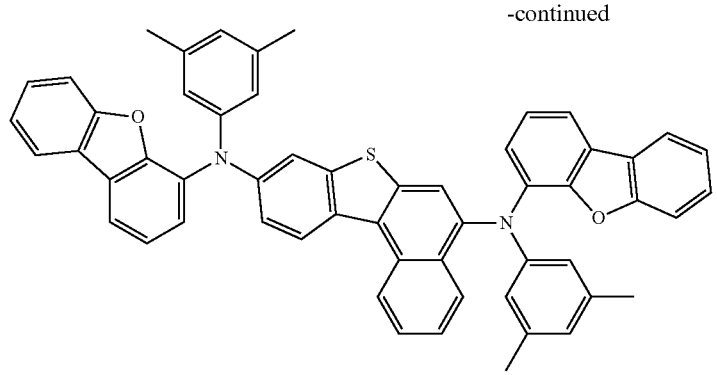
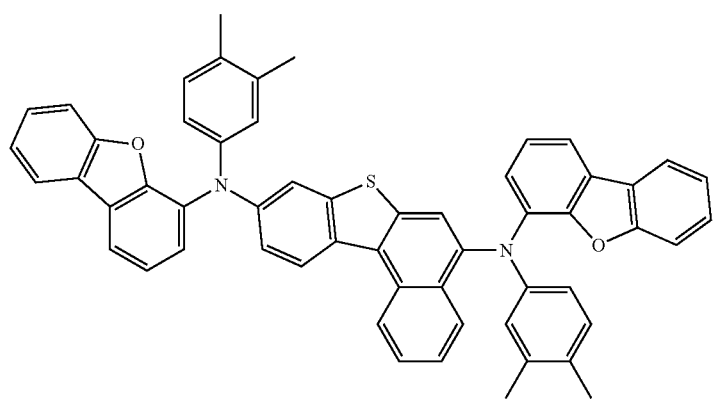
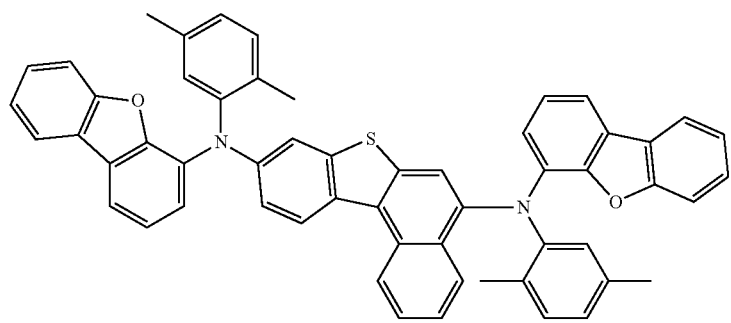
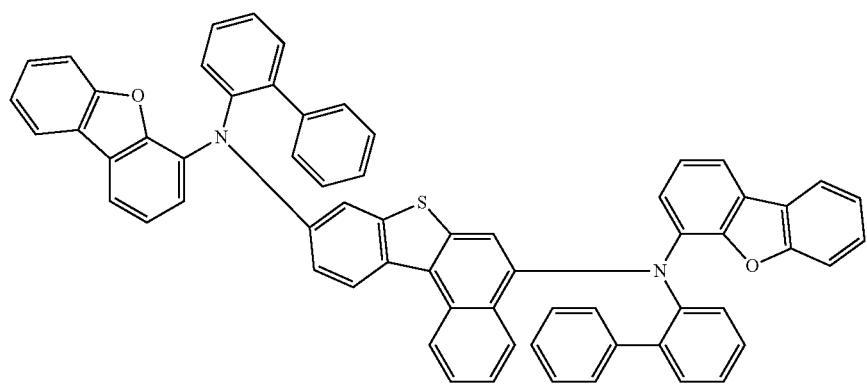

-continued
381
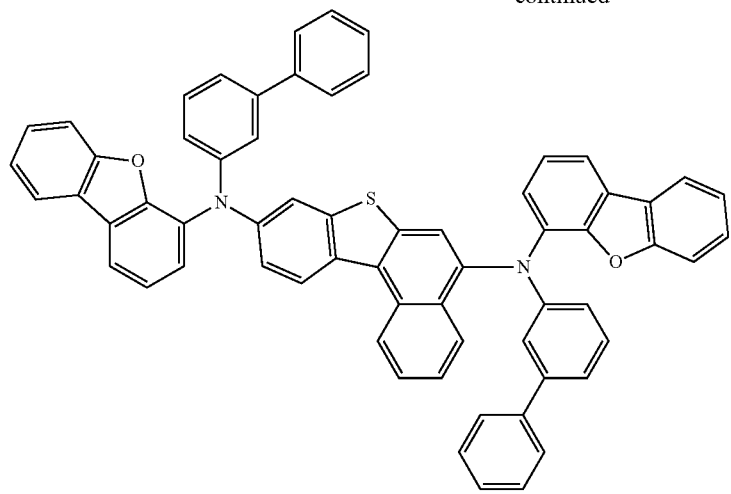
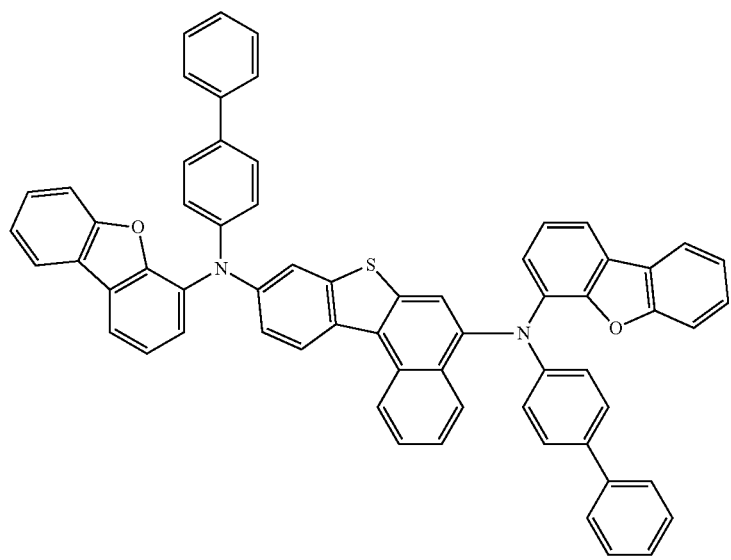
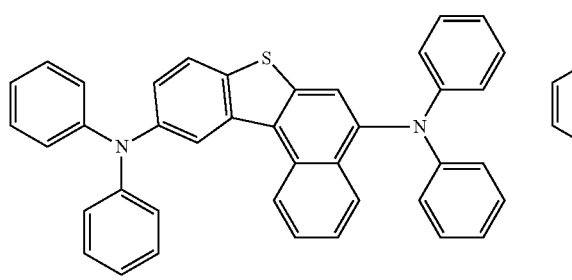
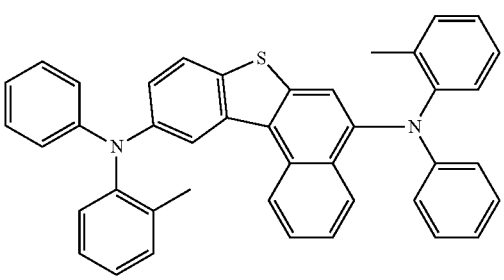
382
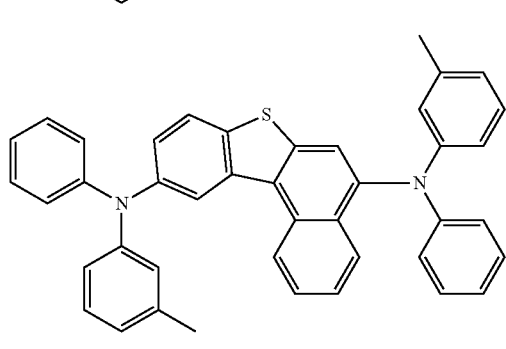
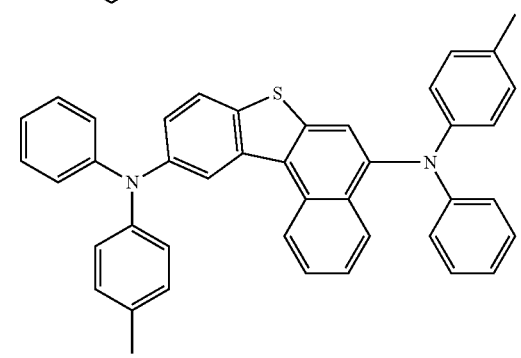

383
384
-continued
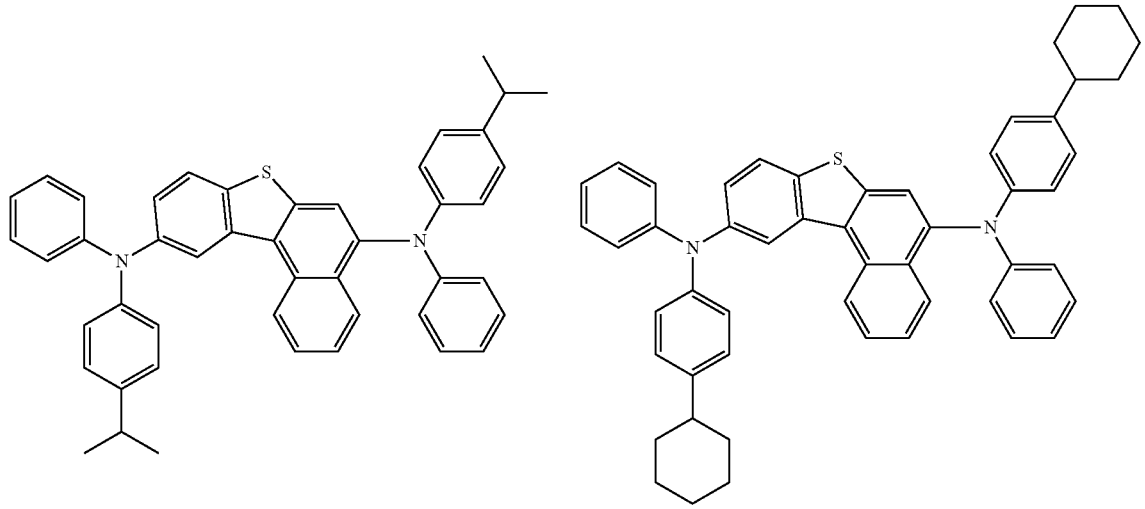
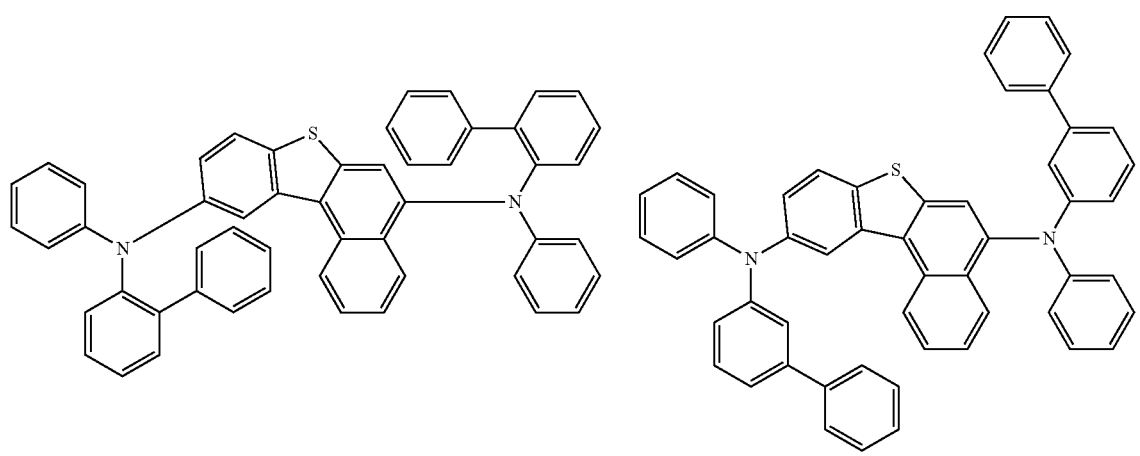
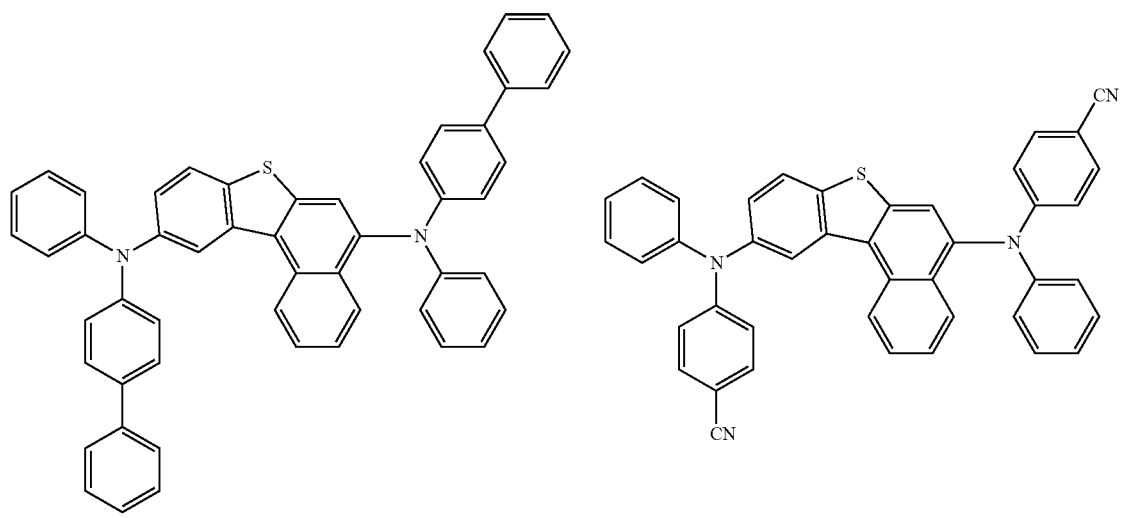

385 386
-continued
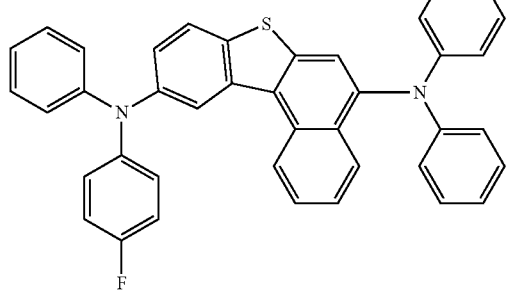
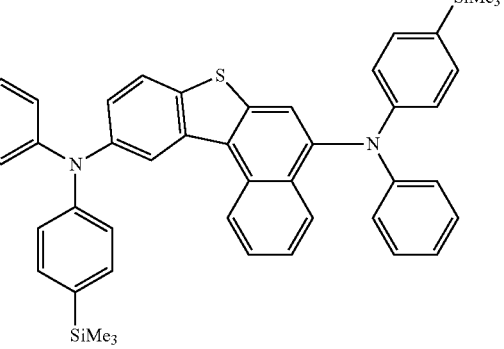
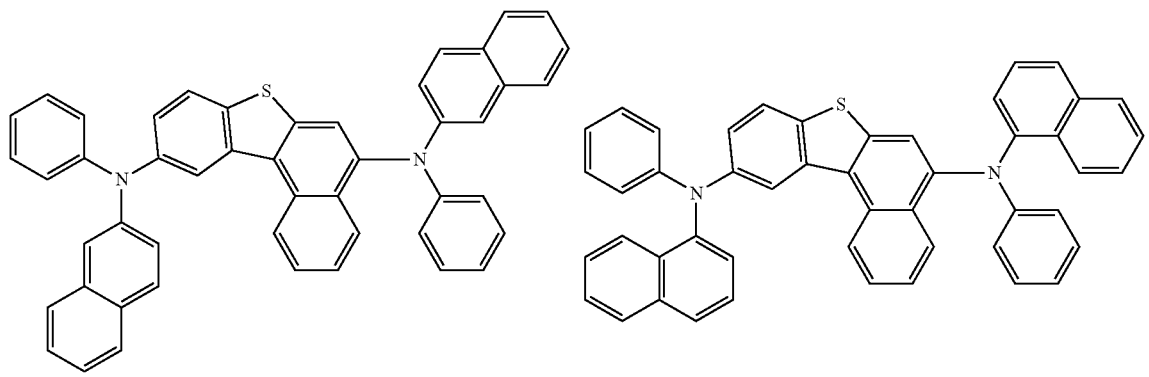
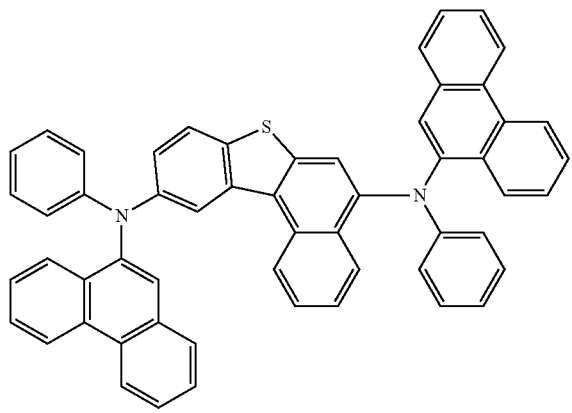
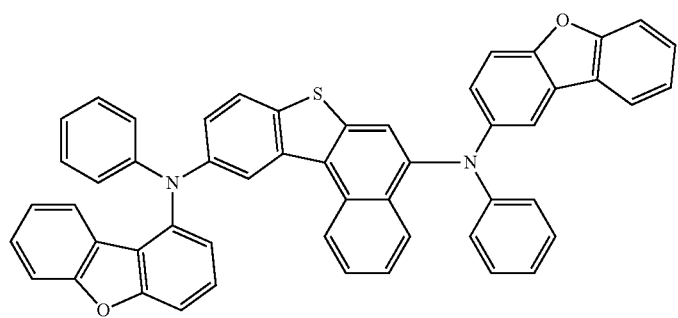

-continued
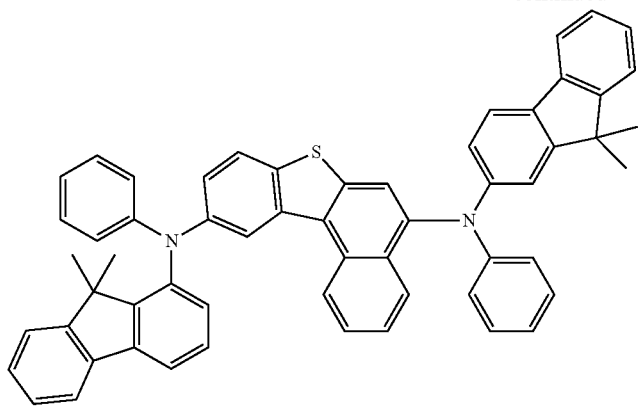
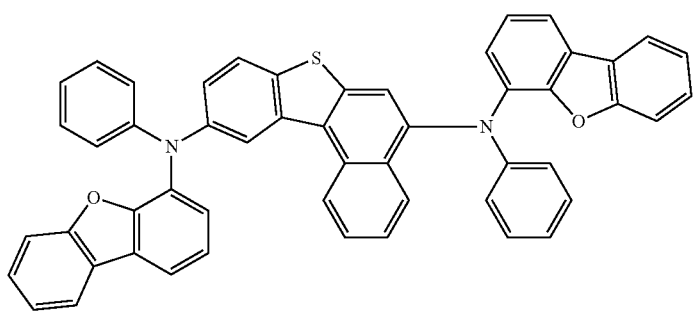
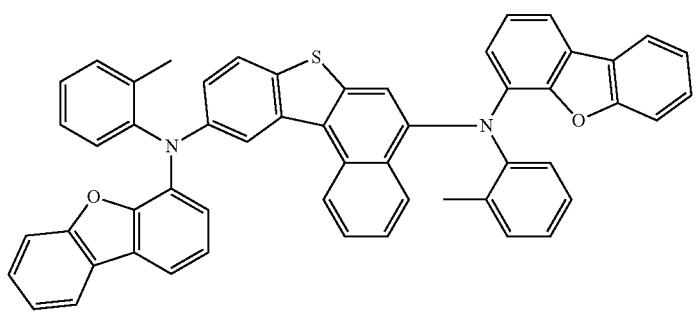
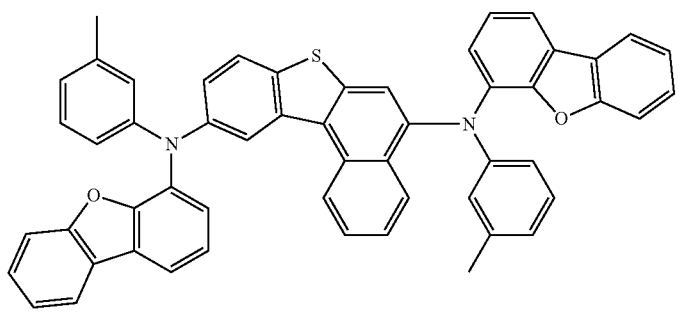
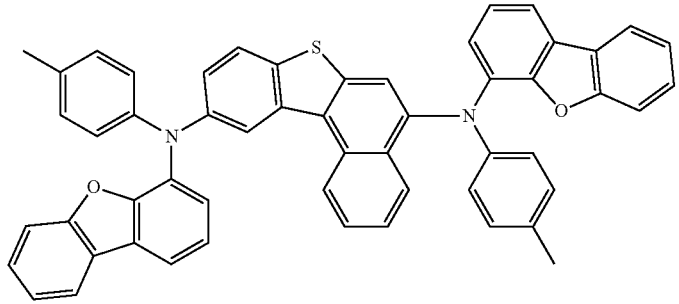

-continued
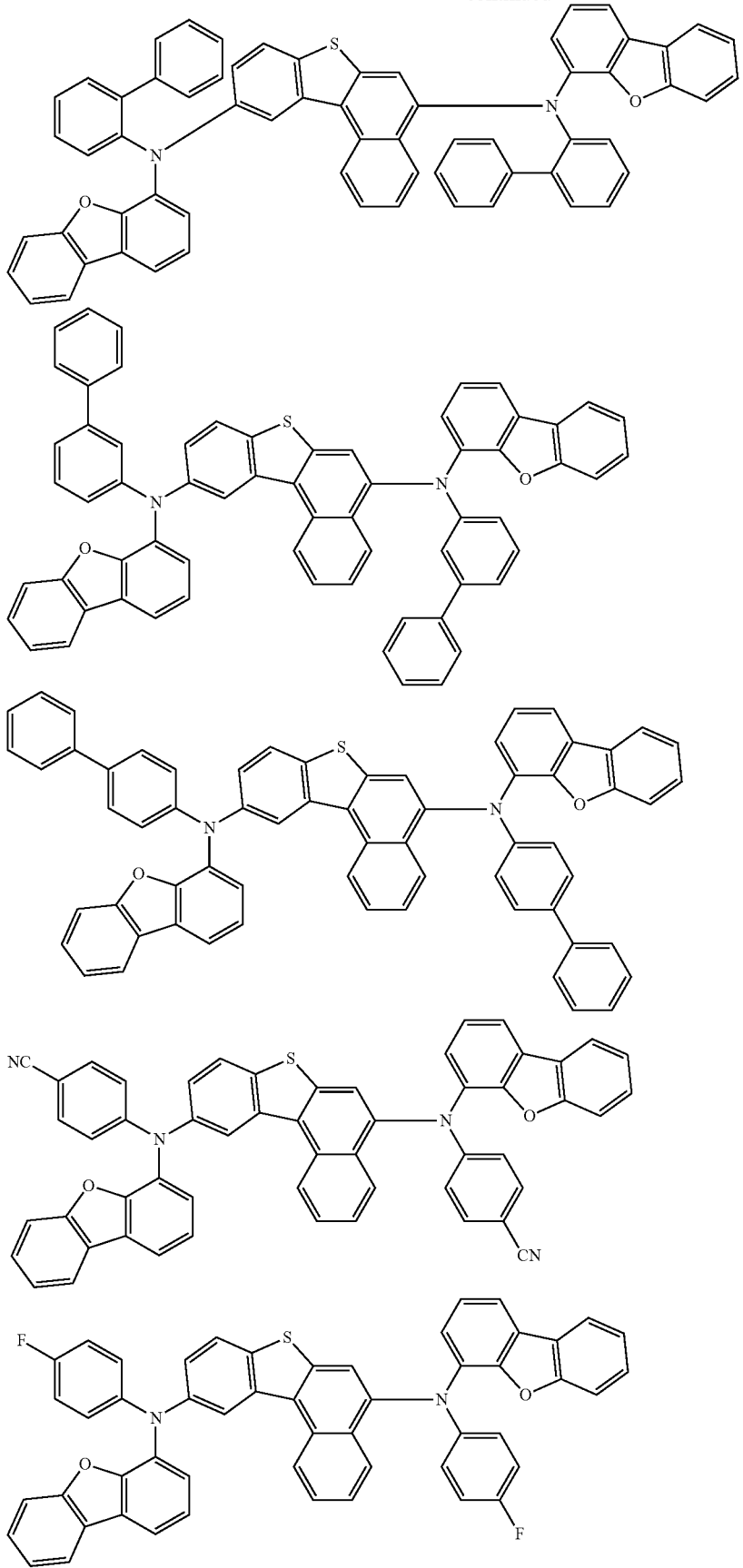

391 392
-continued
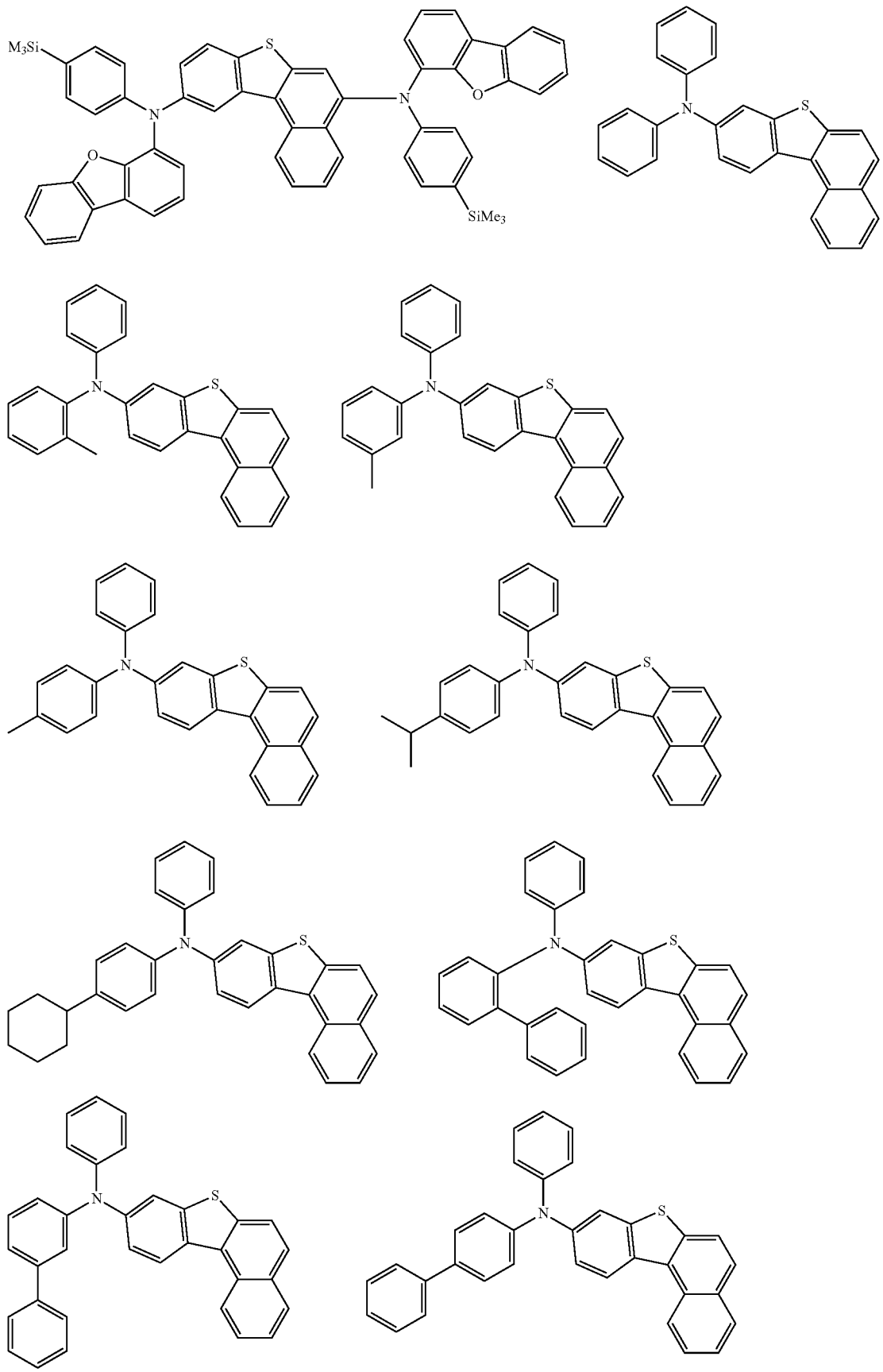

393
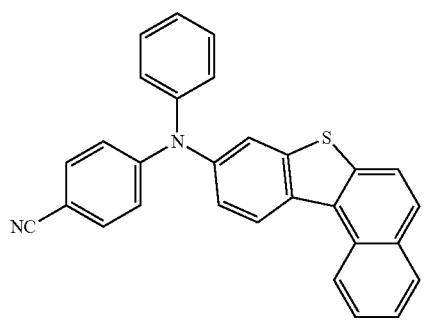
394
-continued
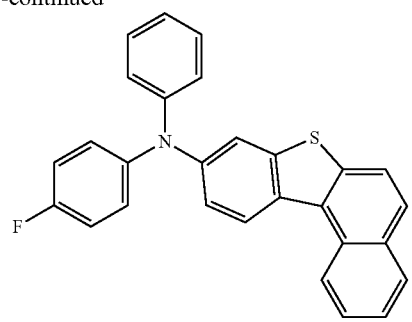
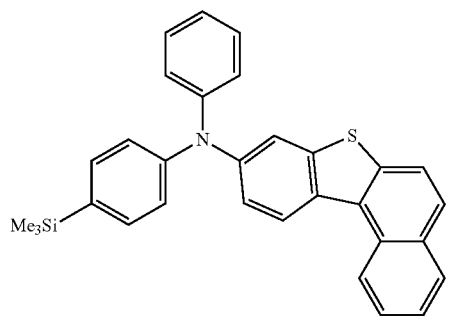
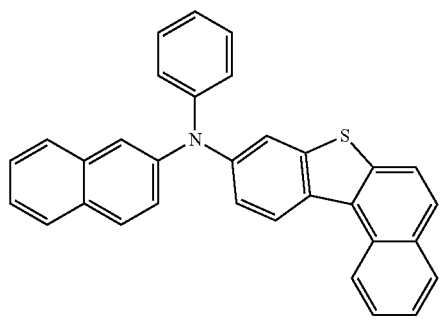
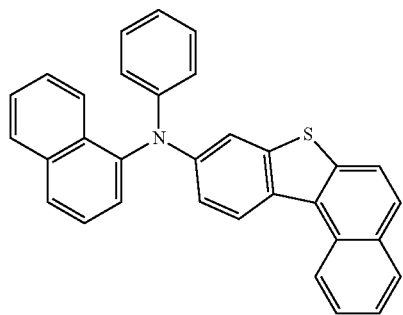
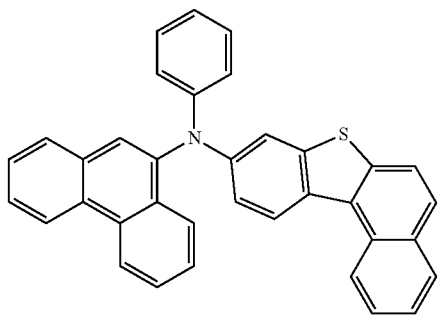
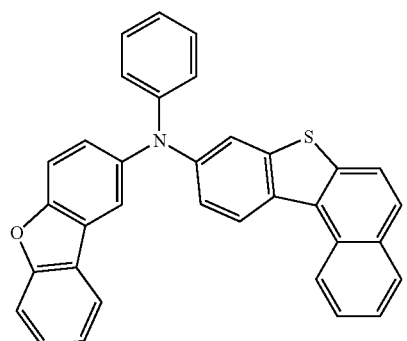
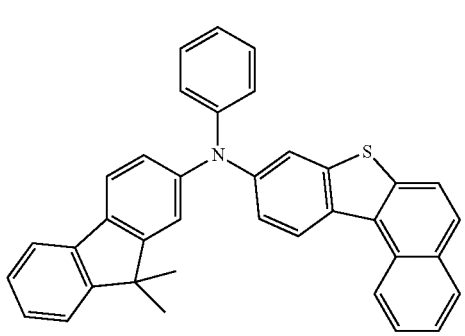
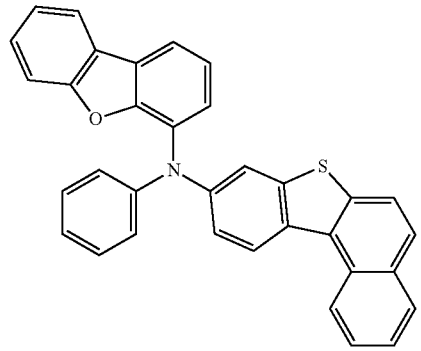
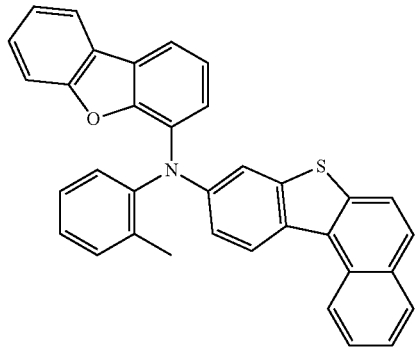

395
-continued
396
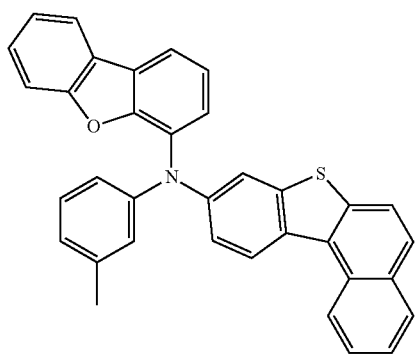
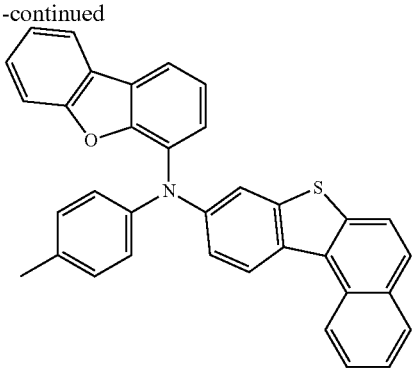
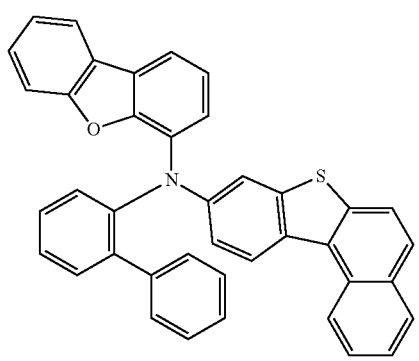
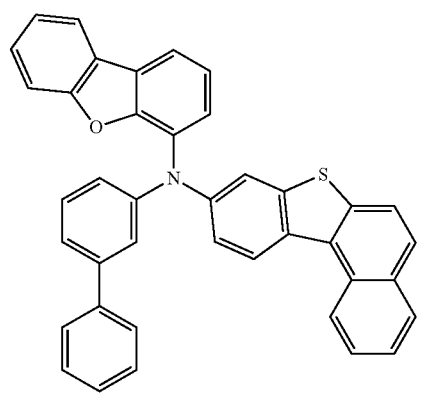
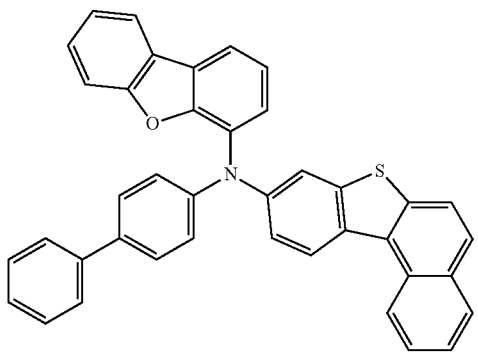
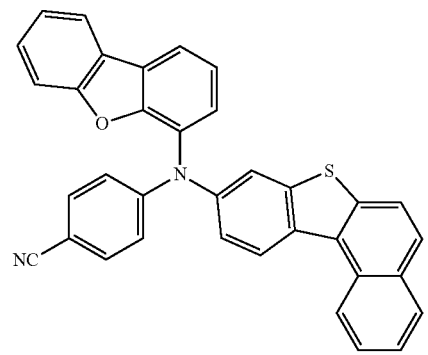
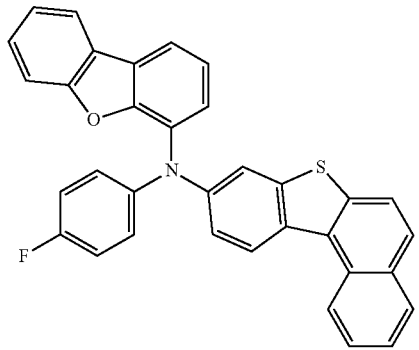
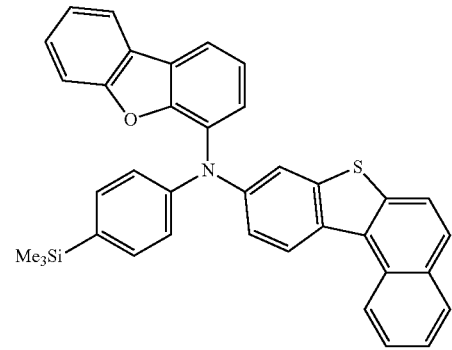

397 398
-continued
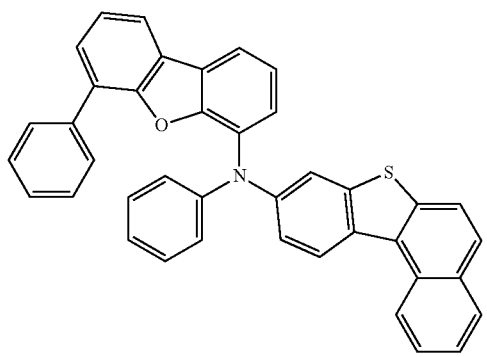
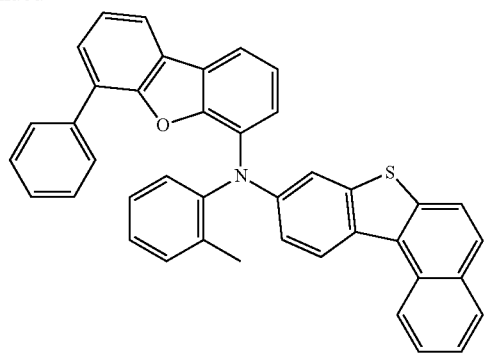
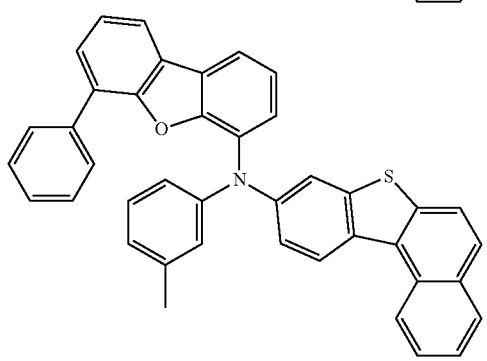
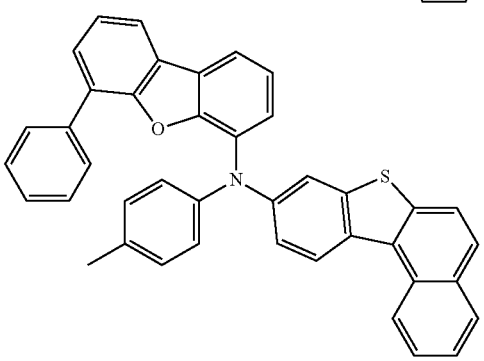
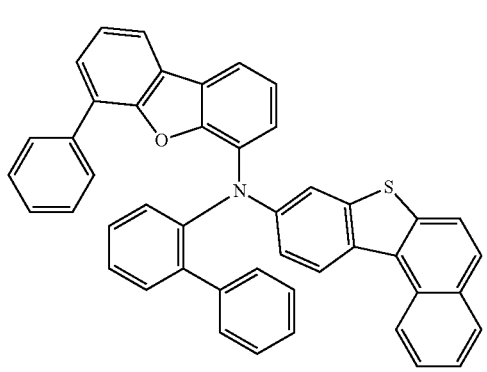
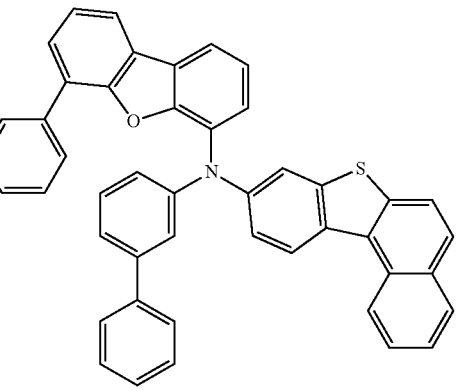
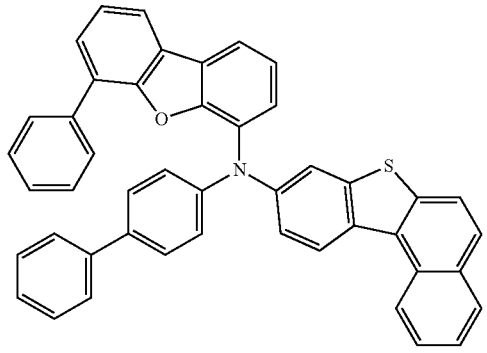
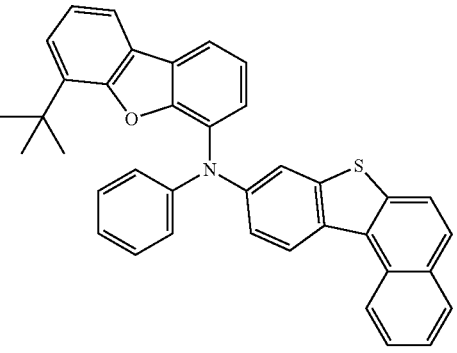
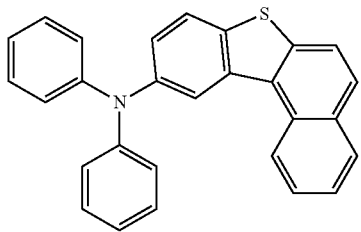
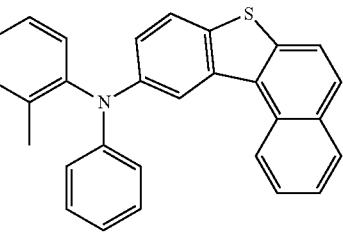

399
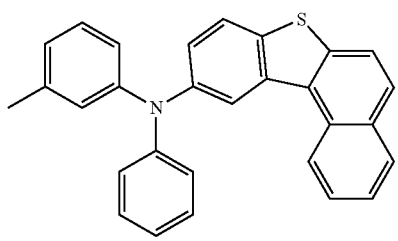
-continued
400
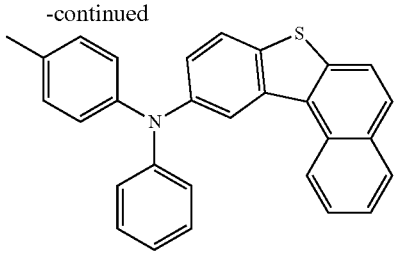
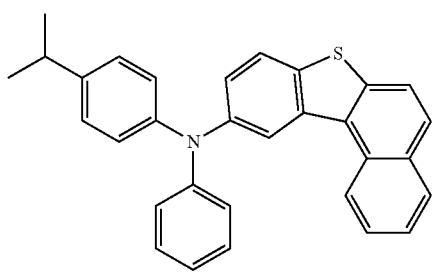
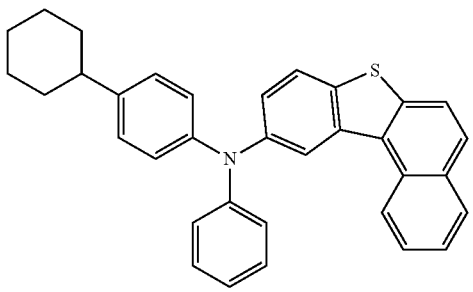
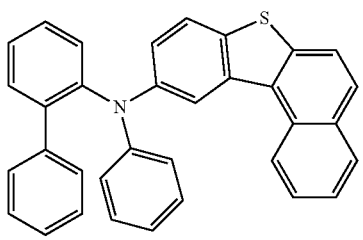
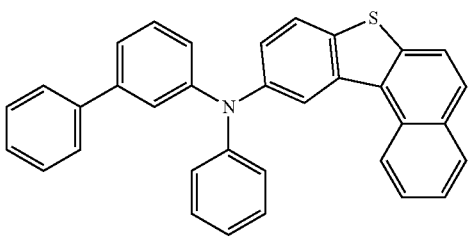
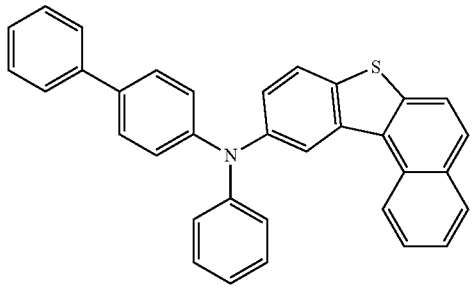
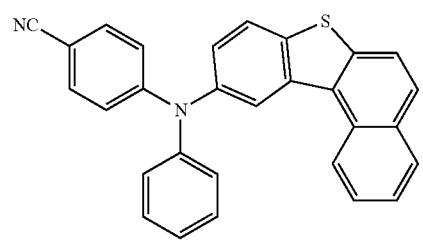
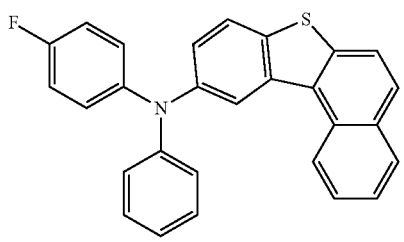
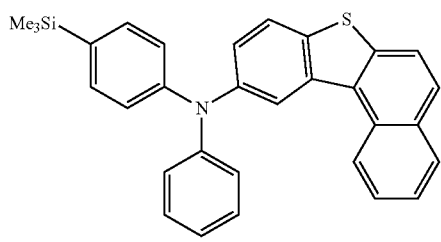
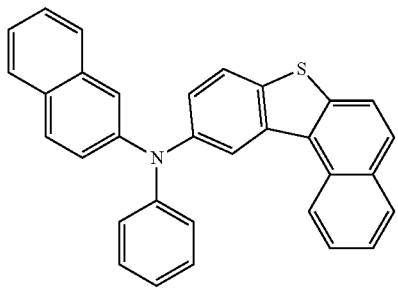
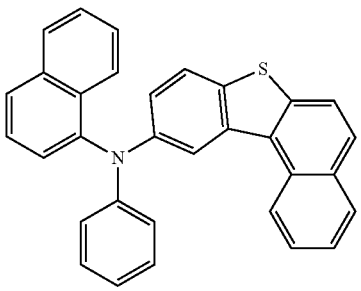

-continued
401
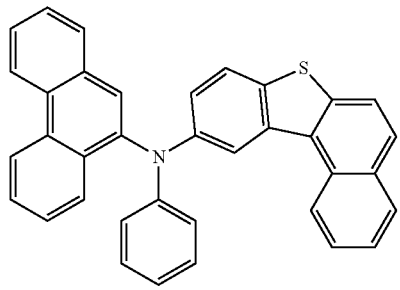
402
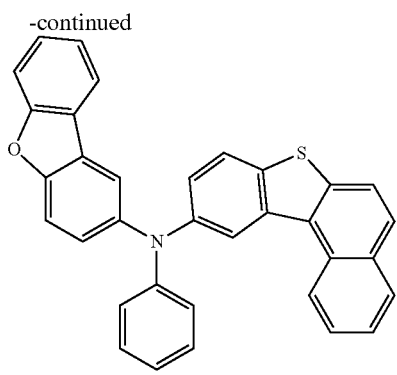
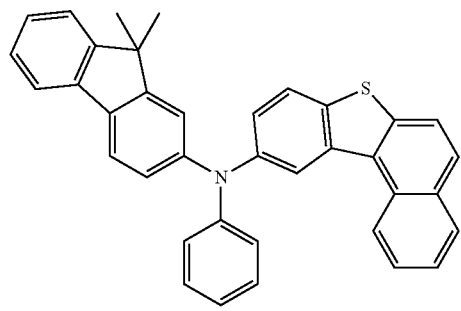
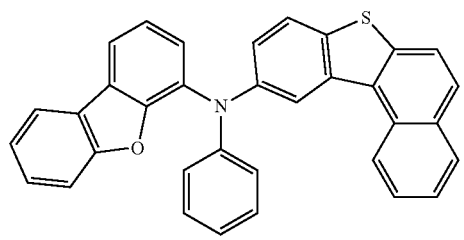
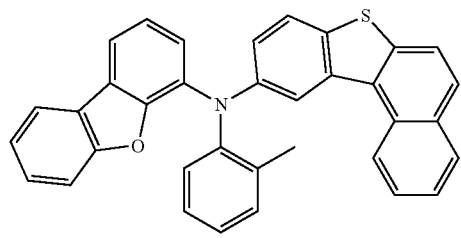
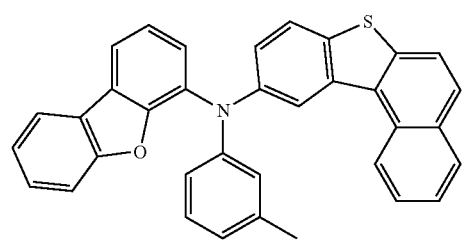
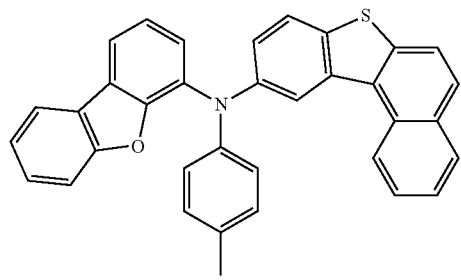
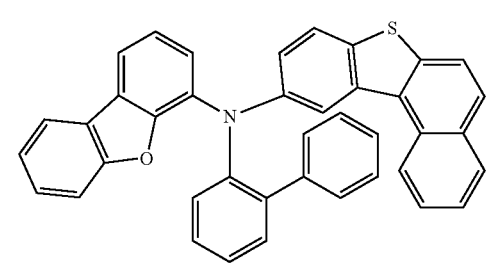
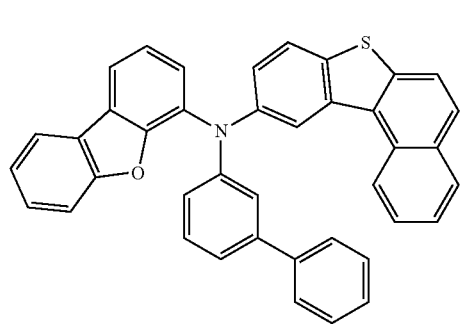
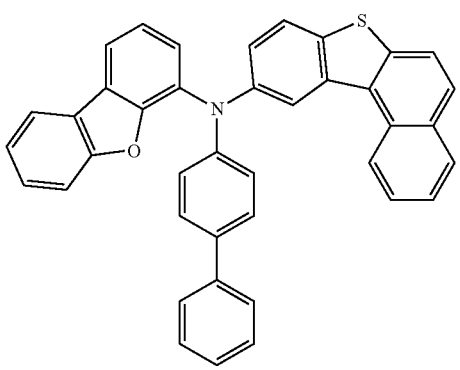

-continued
403
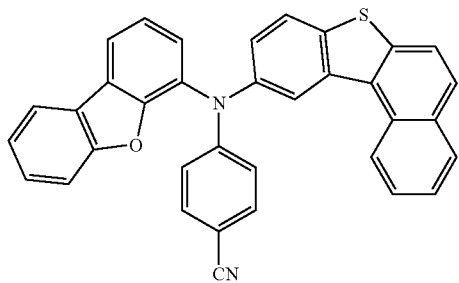
404
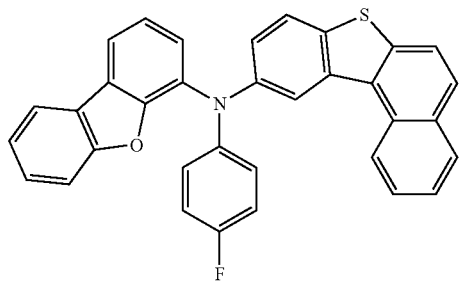
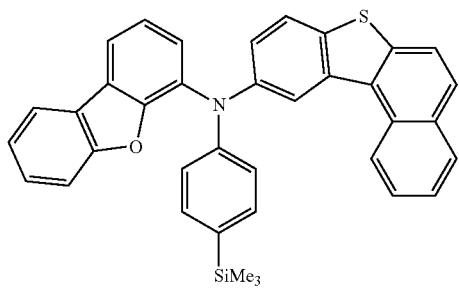
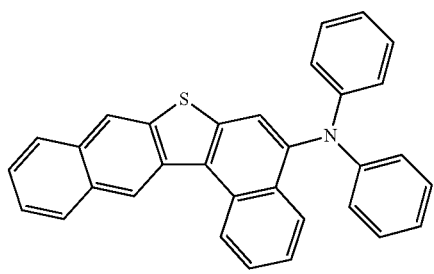
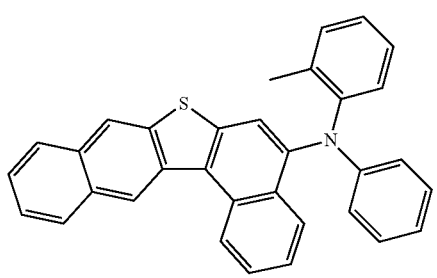
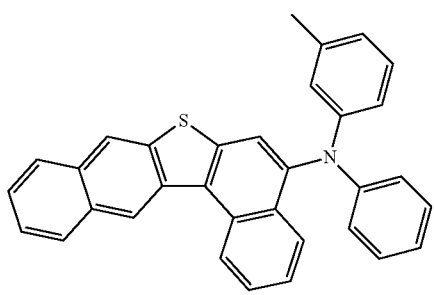
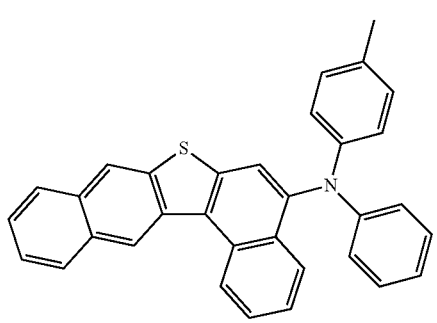
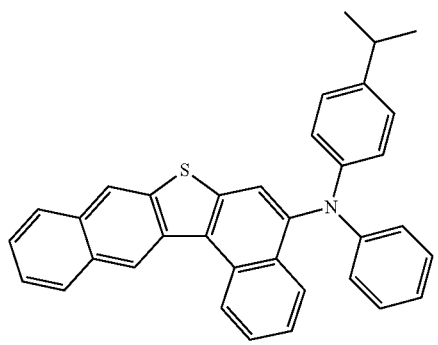
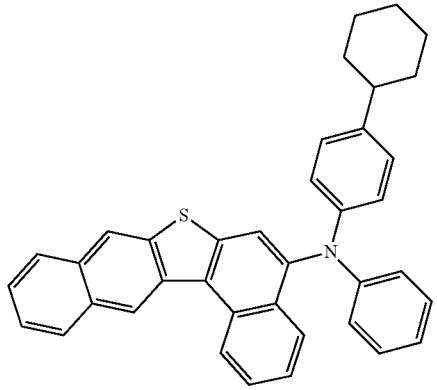
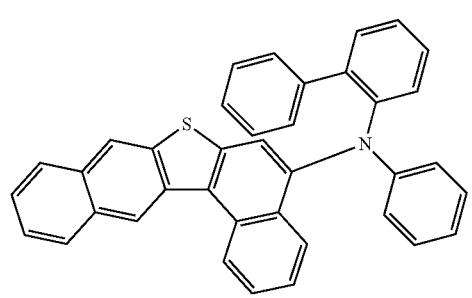

-continued
405        406
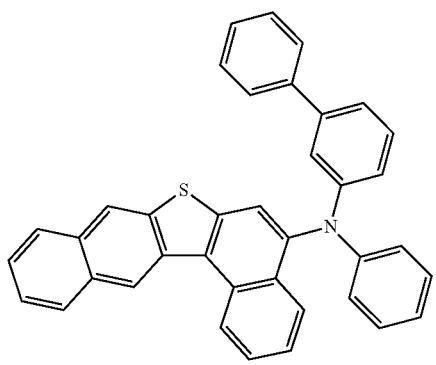 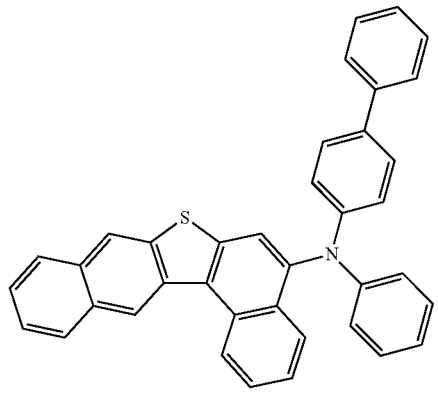
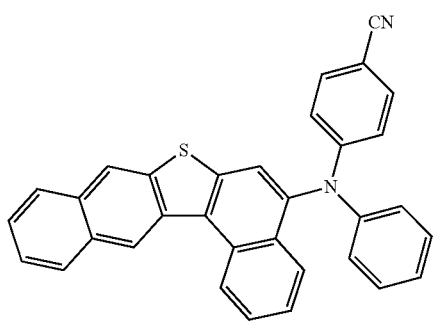 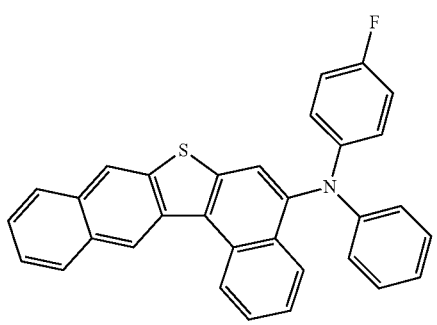
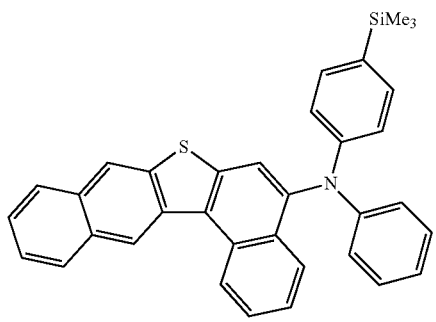 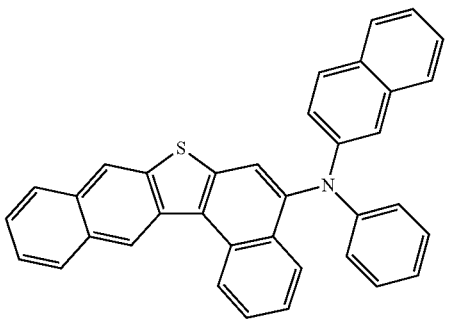
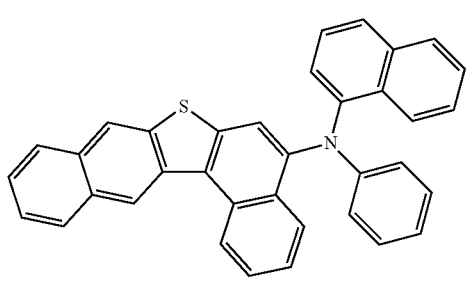 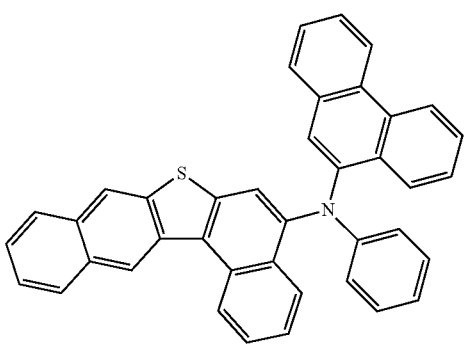

407 408
-continued
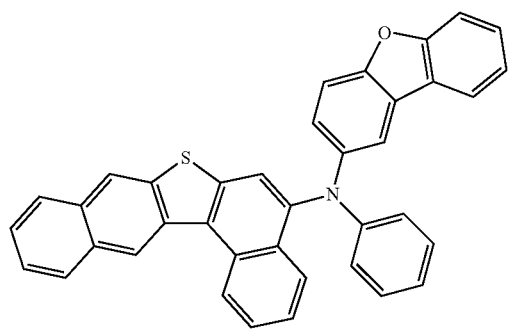
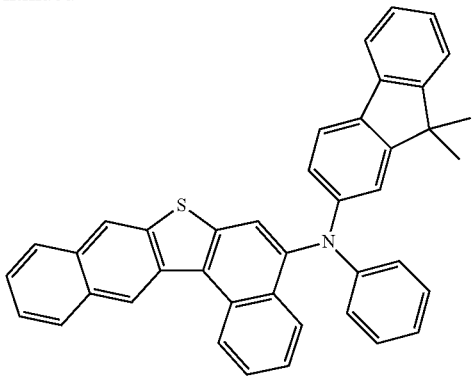
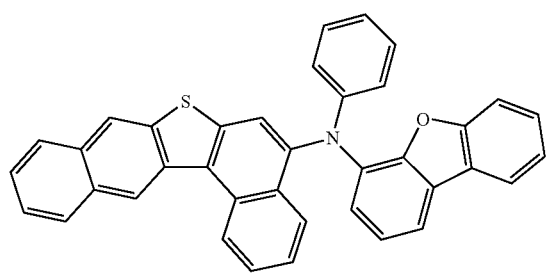
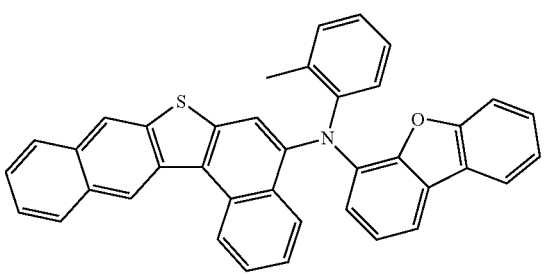
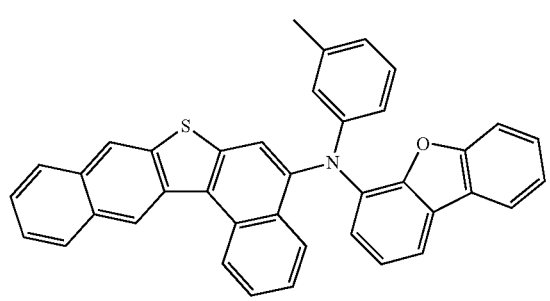
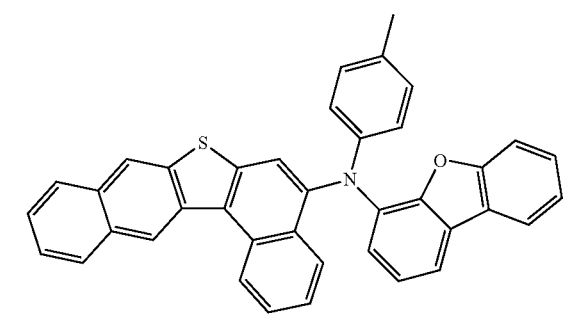
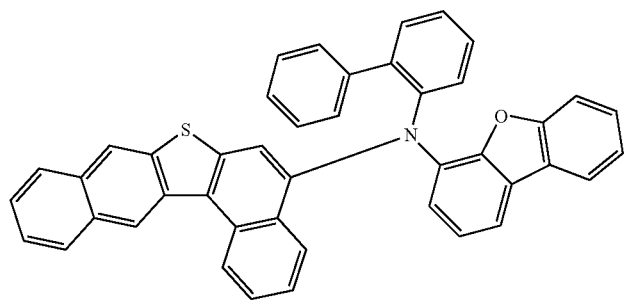
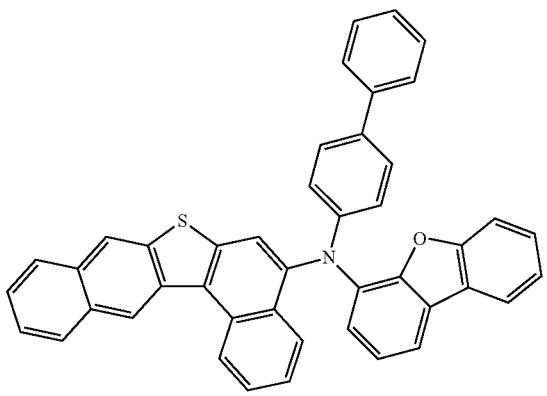

-continued
409 410
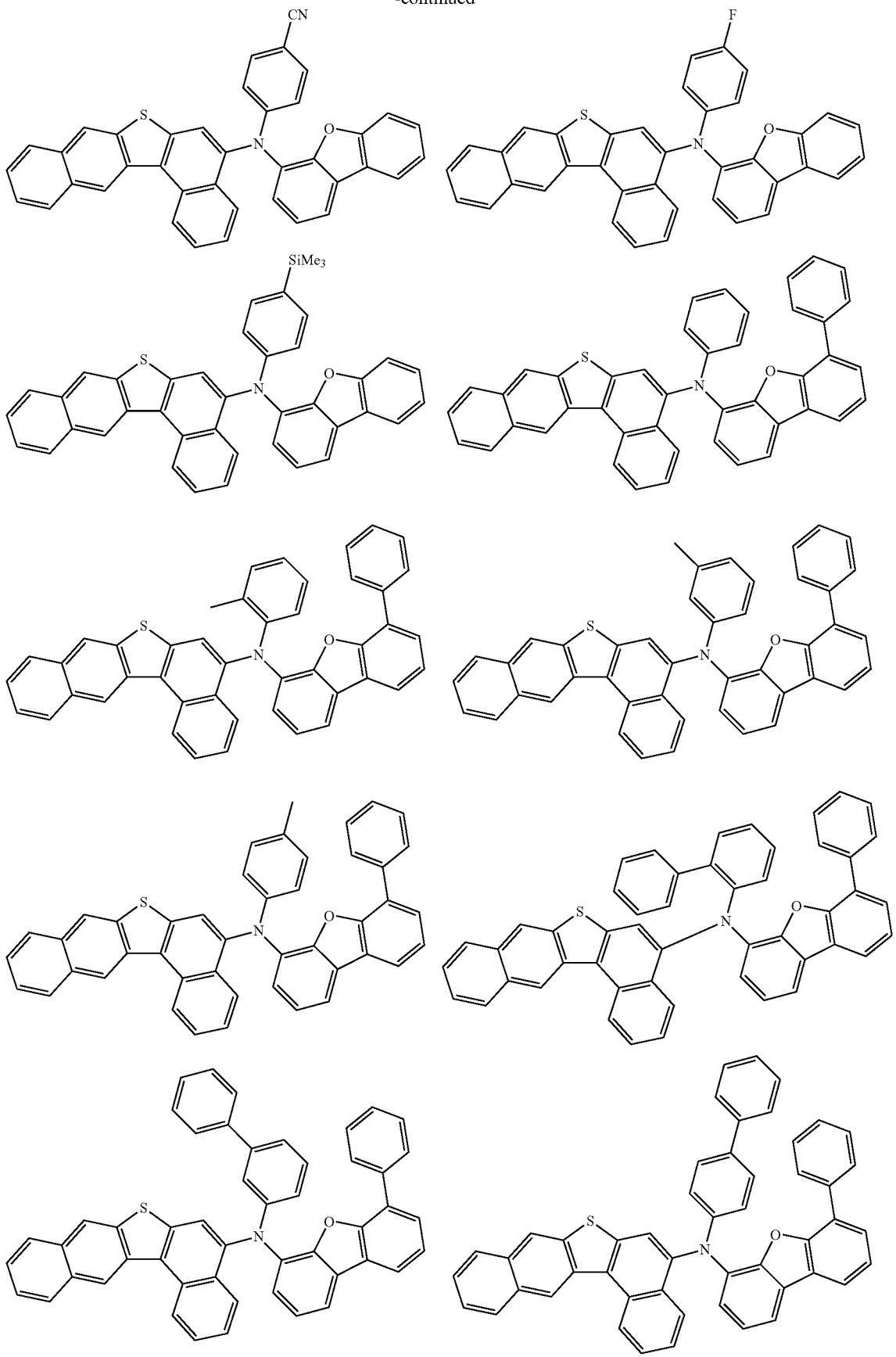

-continued
411
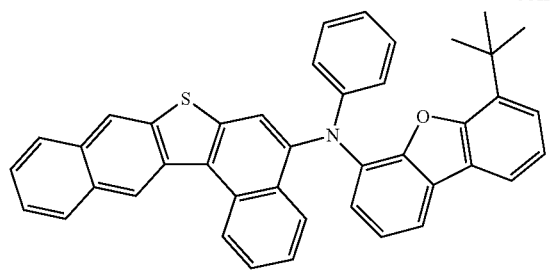
412
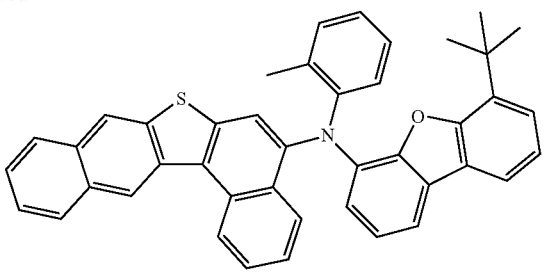
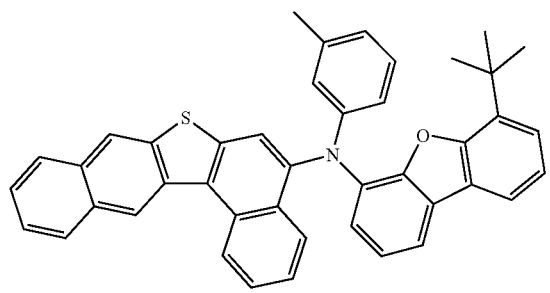
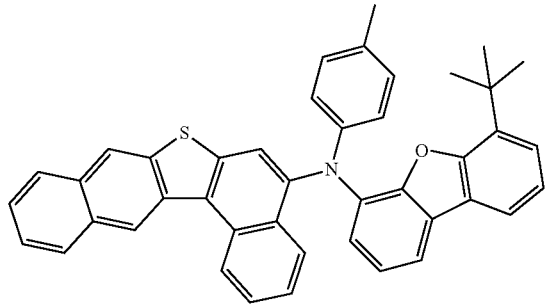
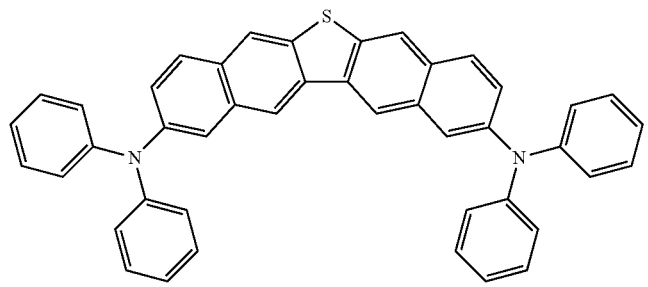
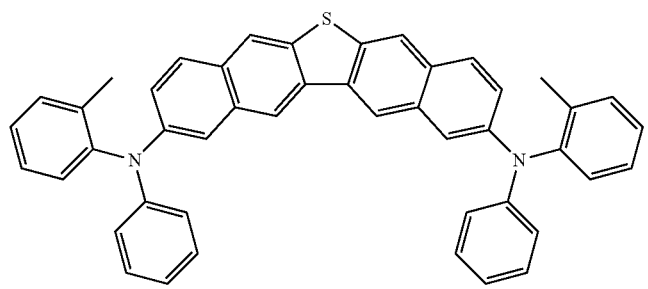
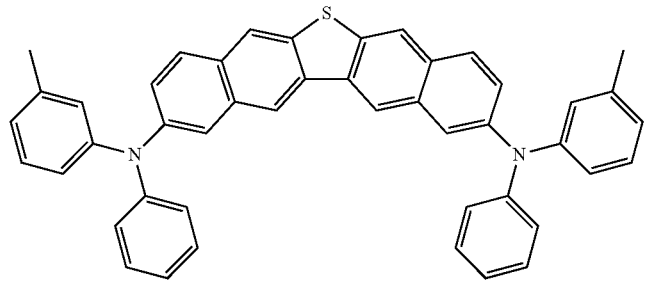
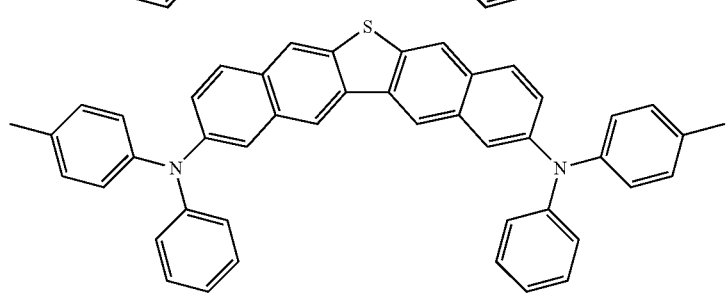

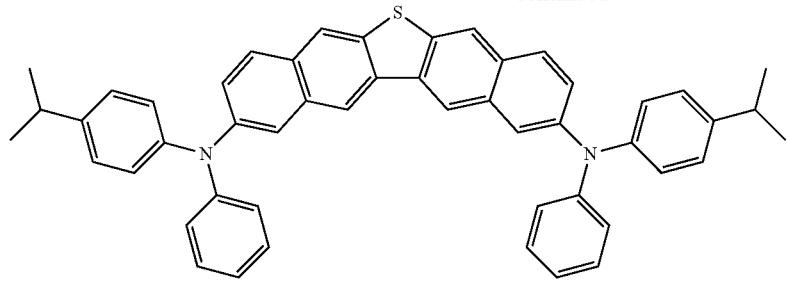
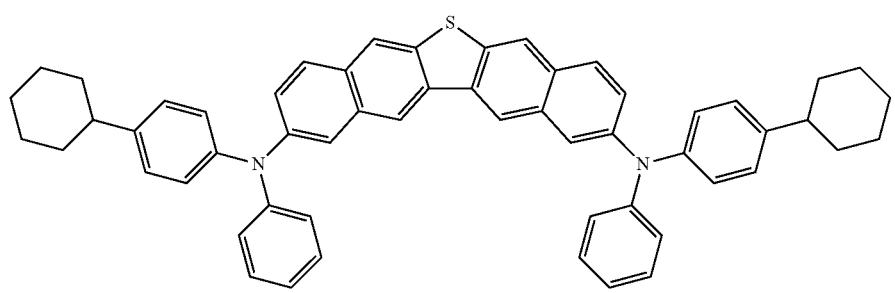
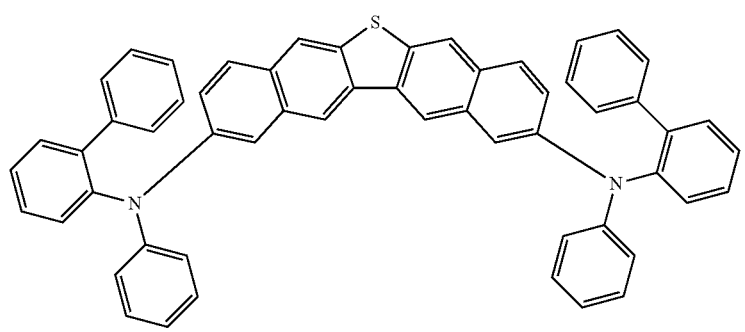
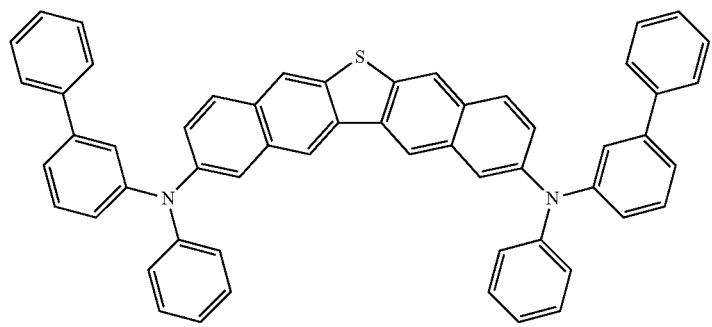
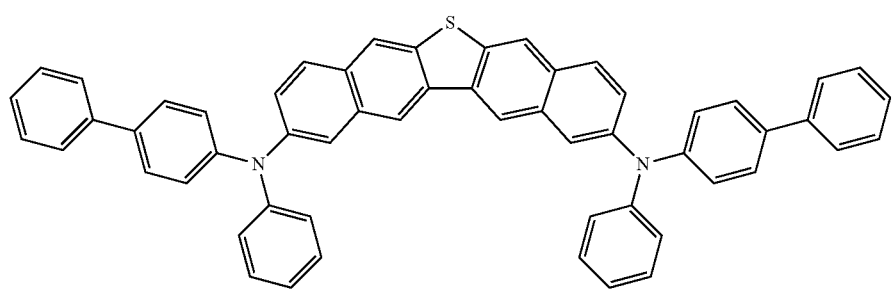

-continued
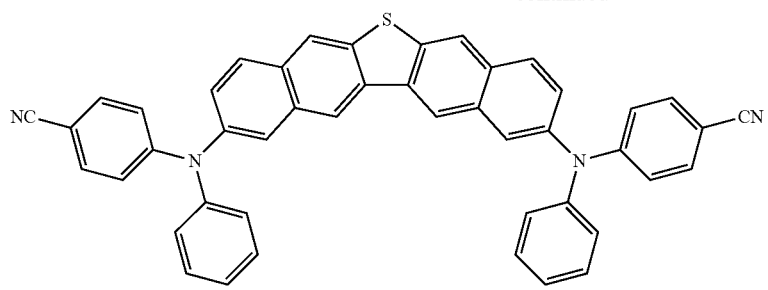
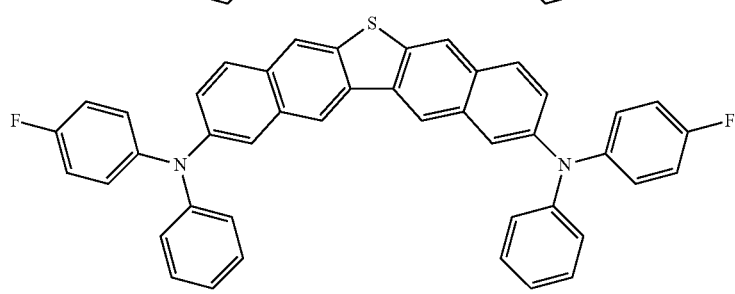
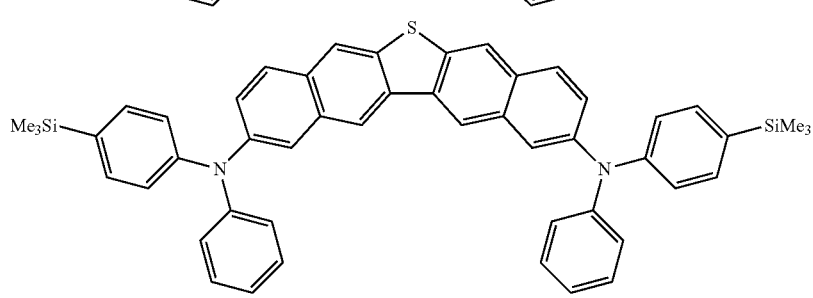
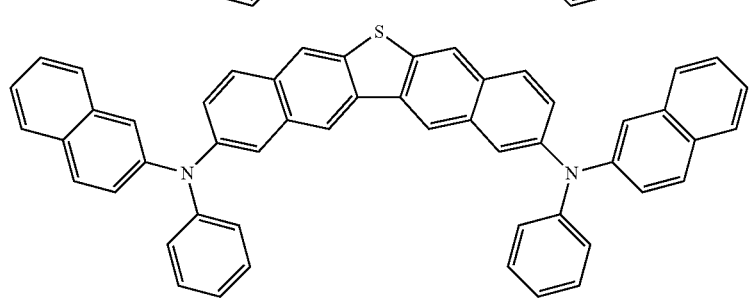
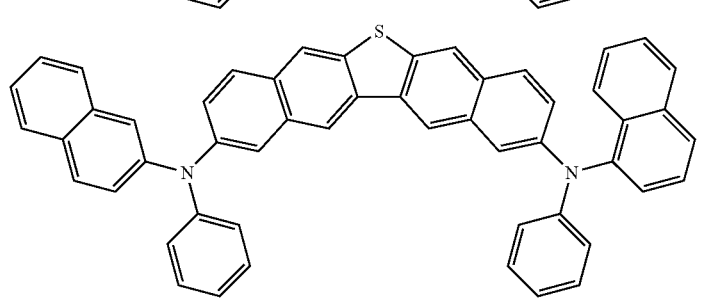
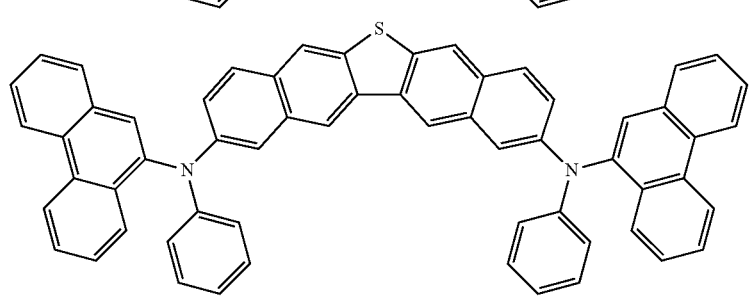

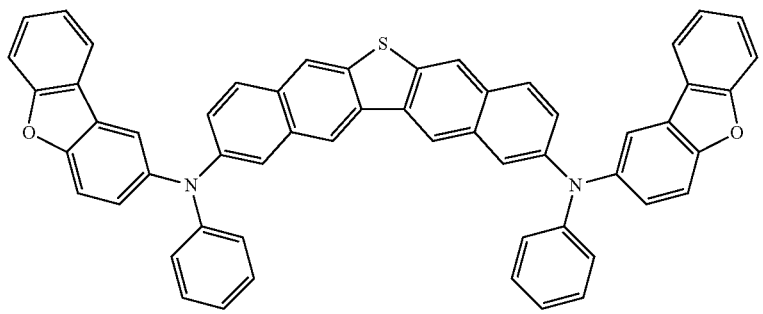
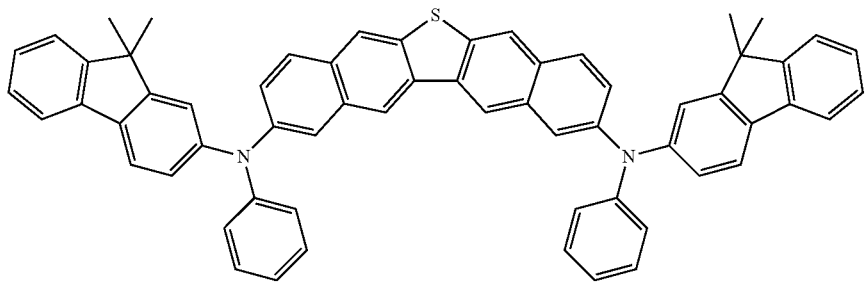
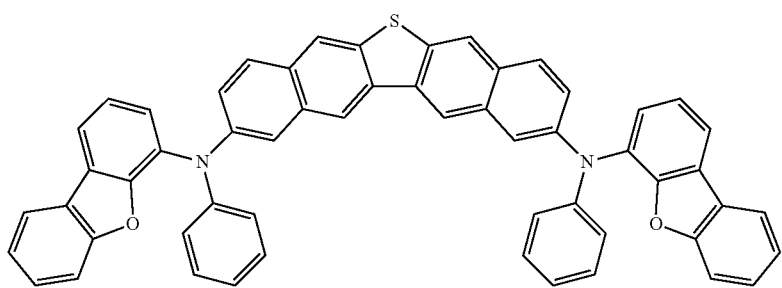
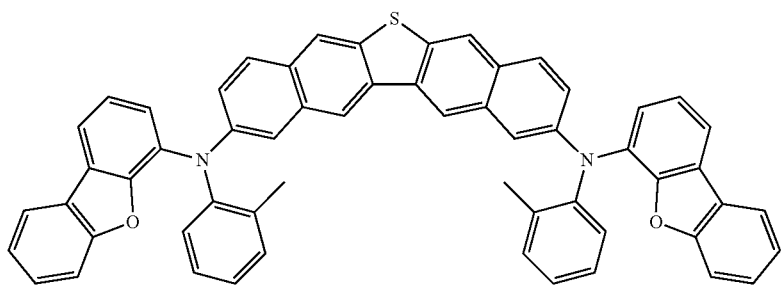
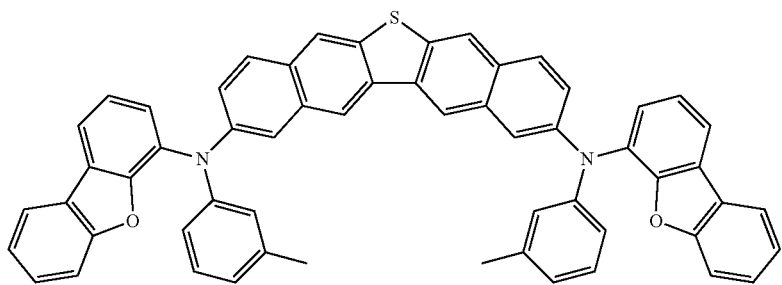

-continued
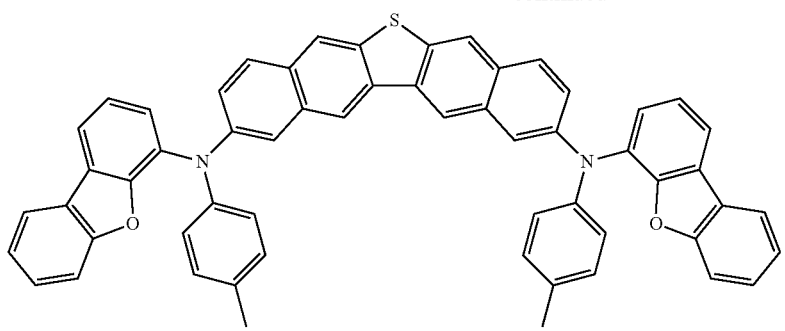
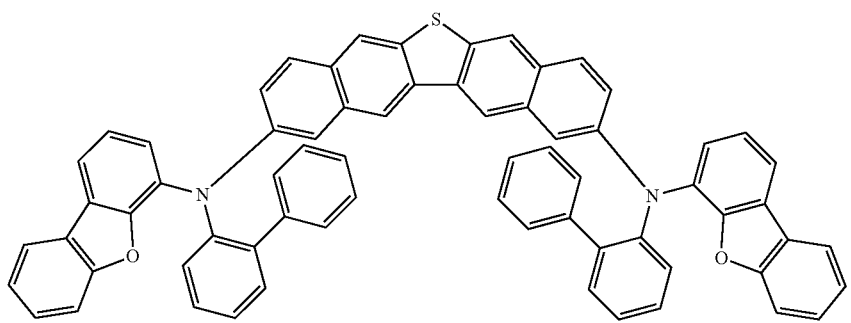
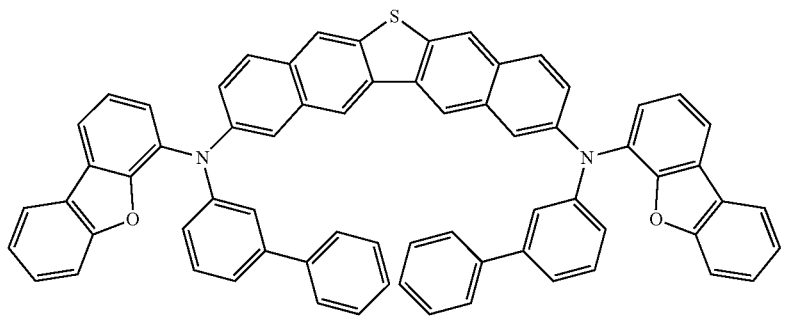
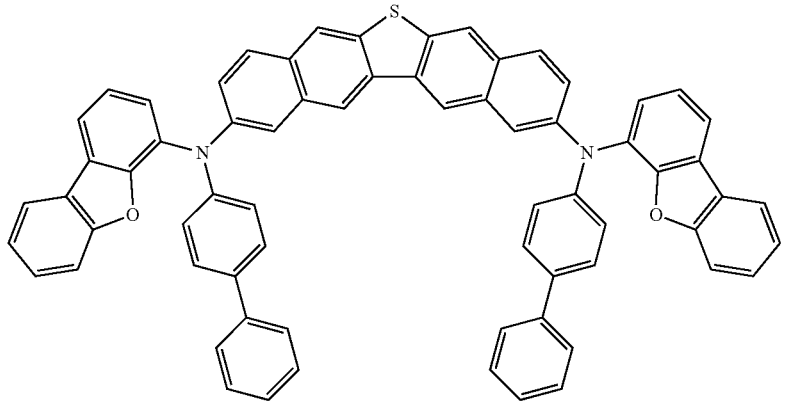
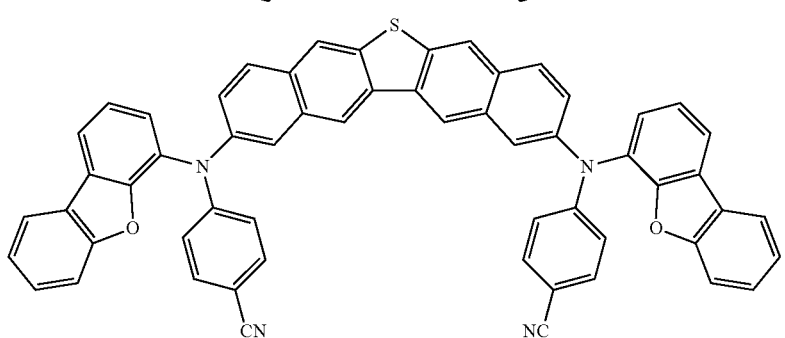

-continued
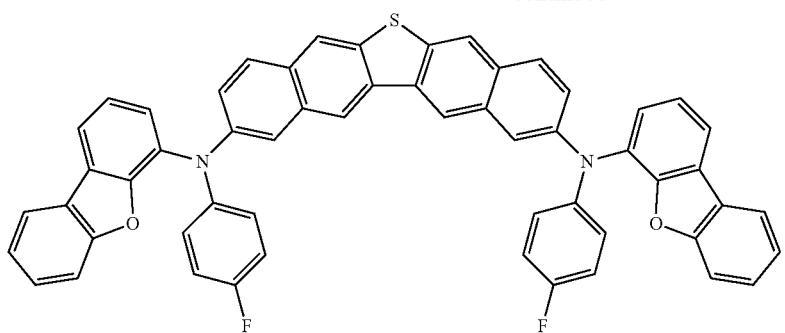
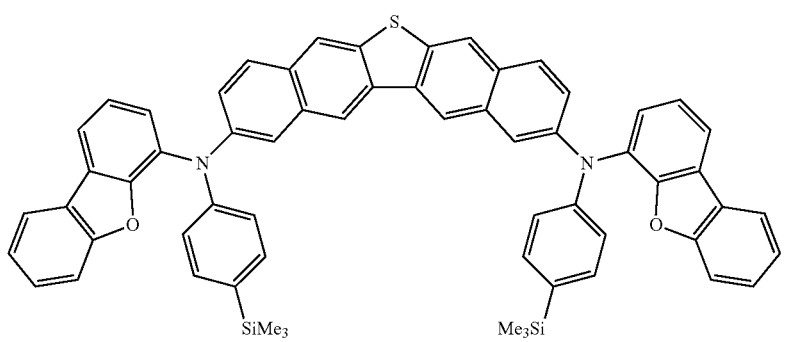
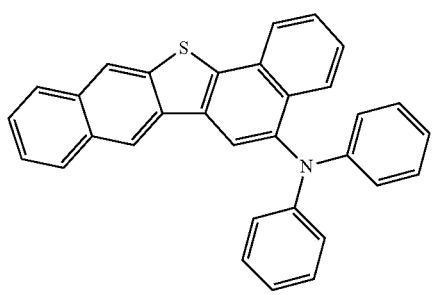
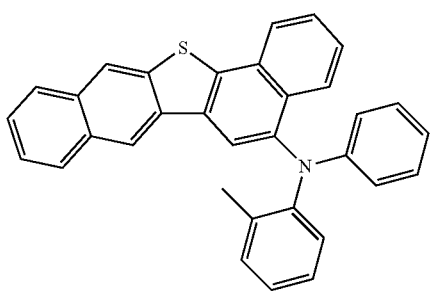
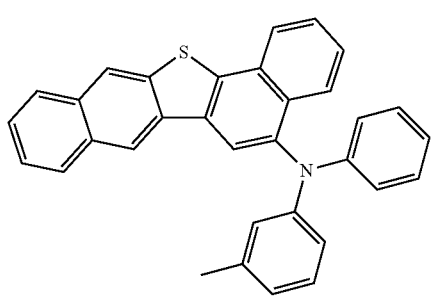
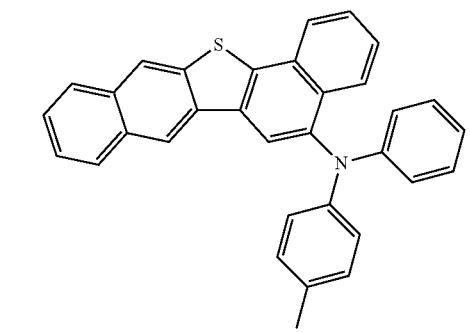
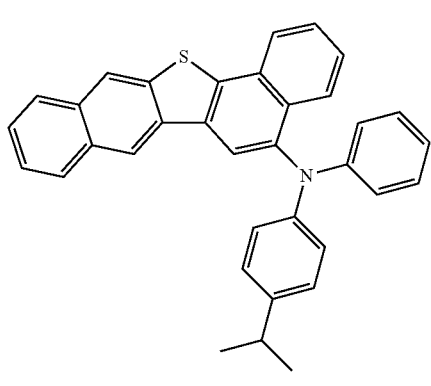
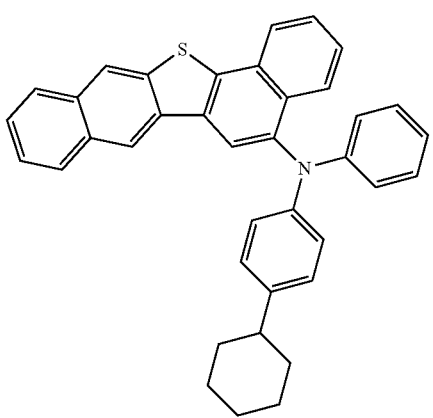

423
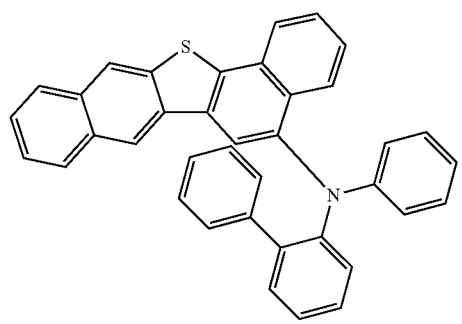
424
-continued
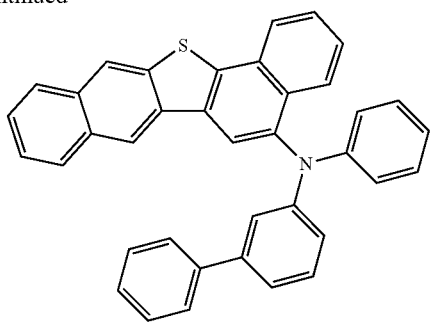
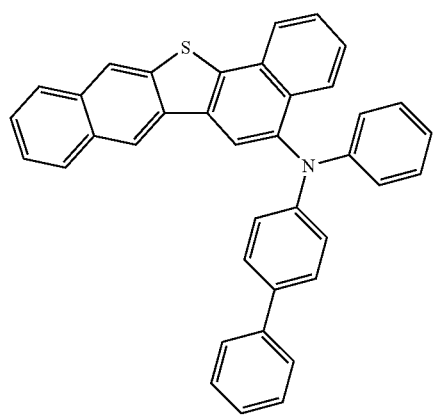
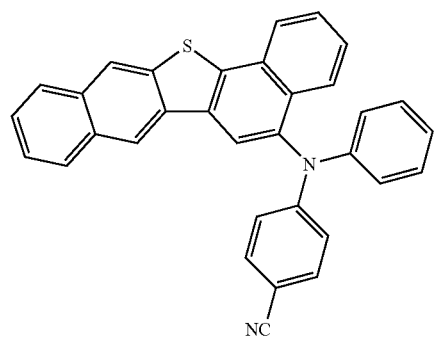
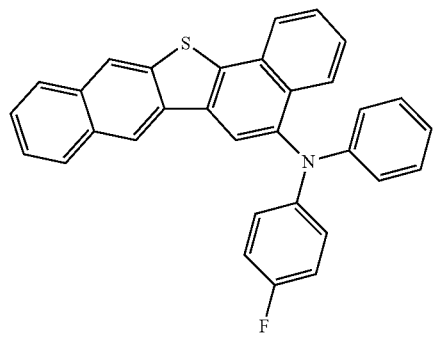
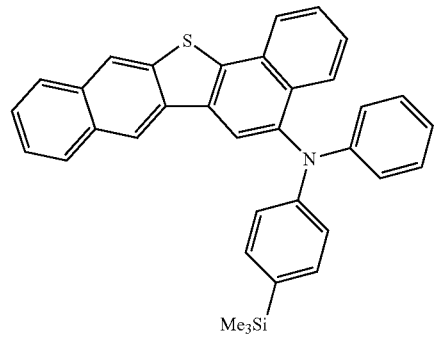
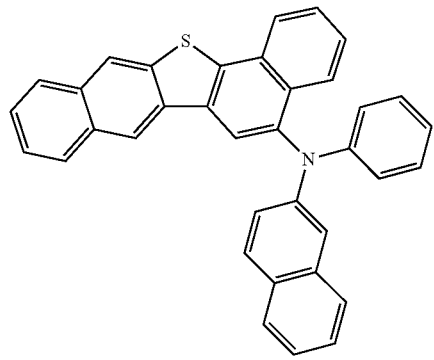
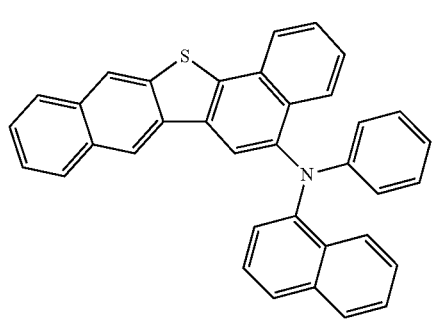

| 425 | 426 |
|---|---|
| 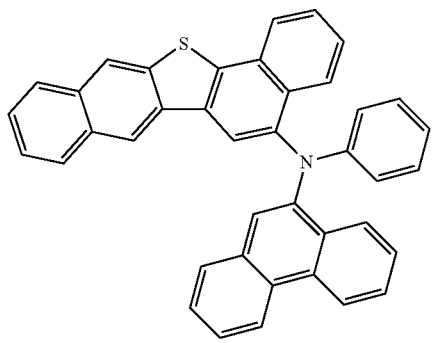 | 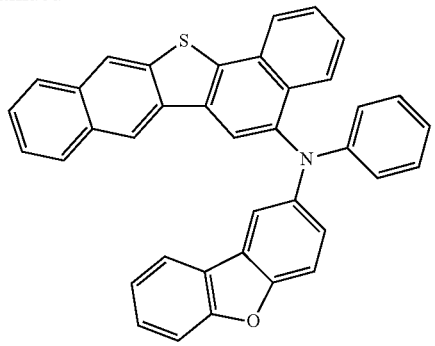 |
| 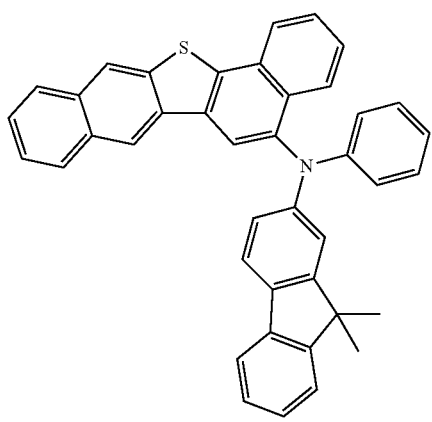 | 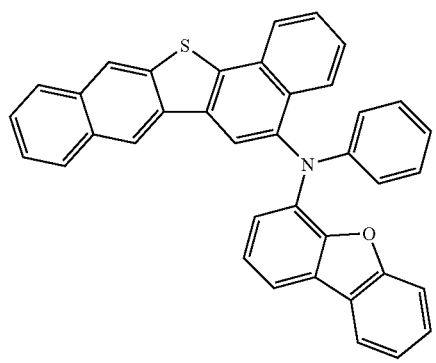 |
| 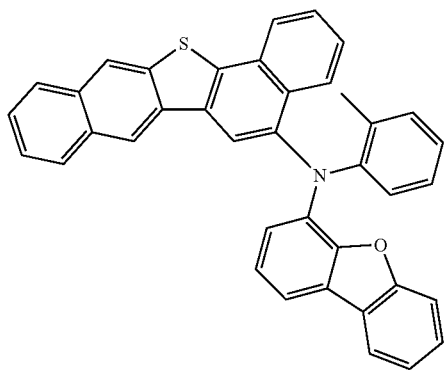 | 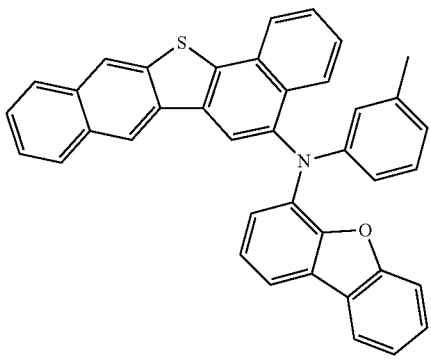 |
| 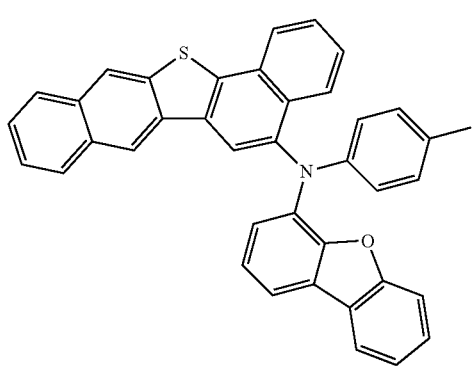 | 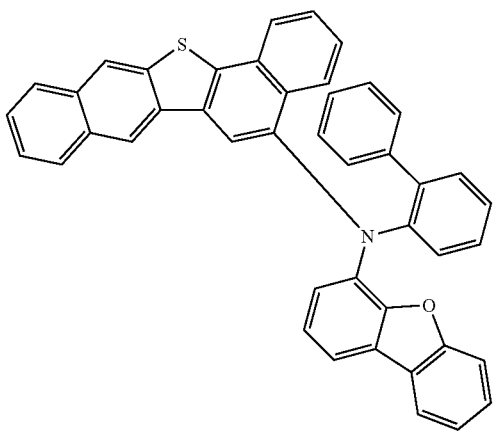 |
-continued -continued
427  428
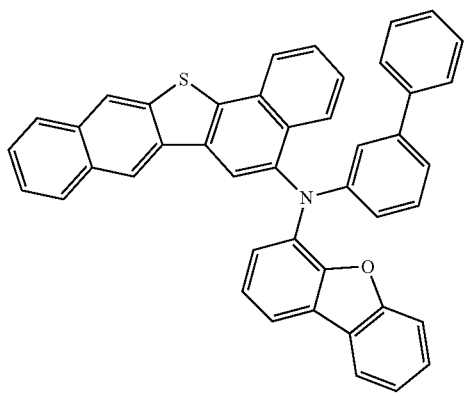
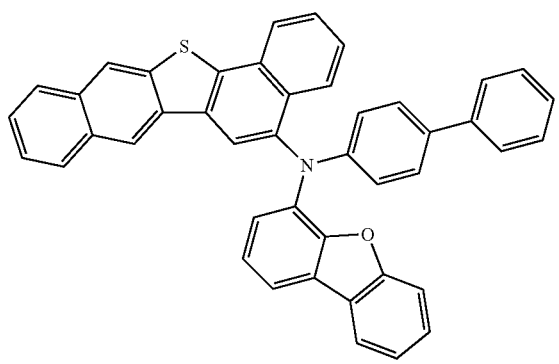
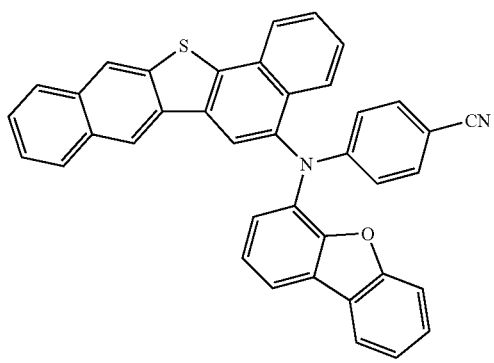
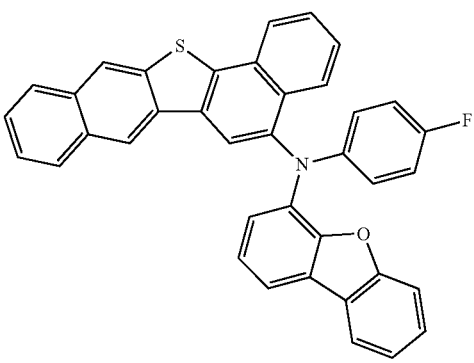
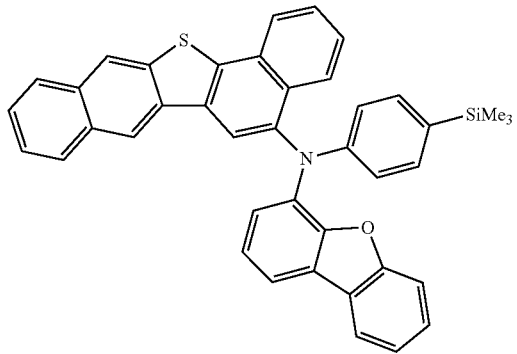
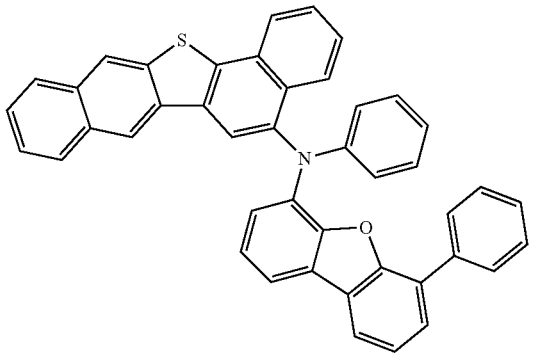
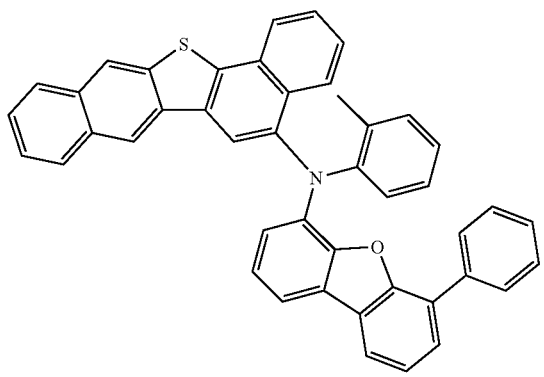
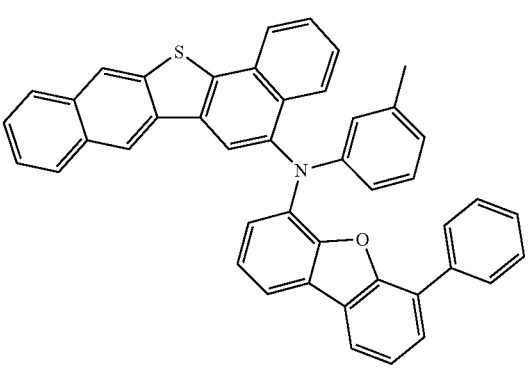

| 429 | 430 |
|---|---|
| 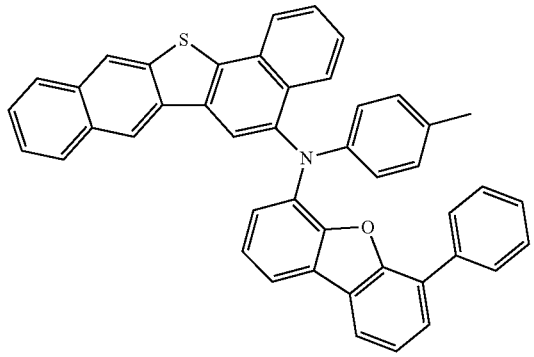 | 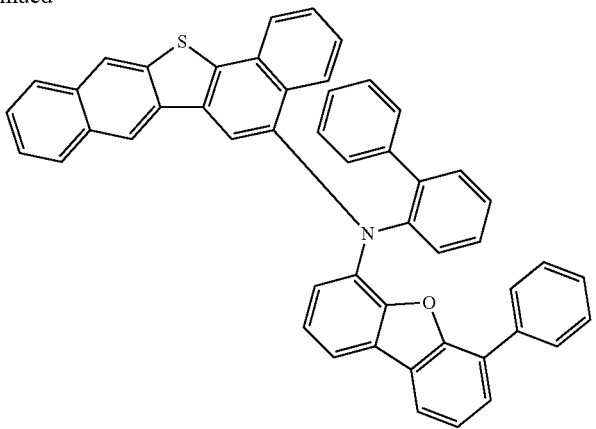 |
| 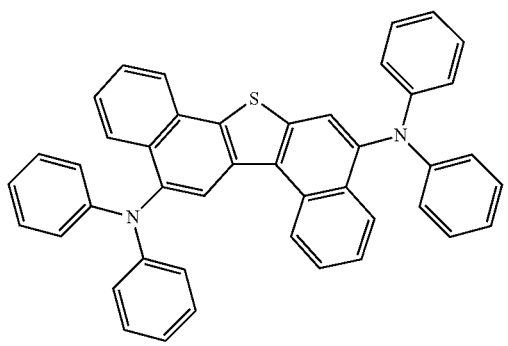 | 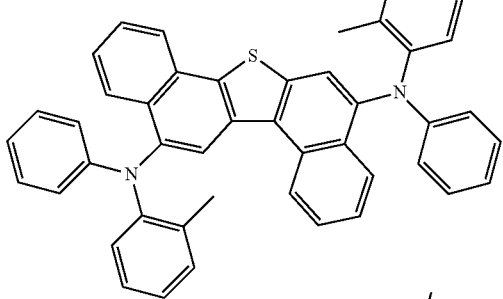 |
| 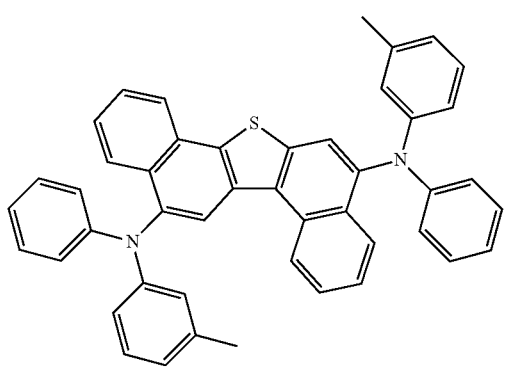 | 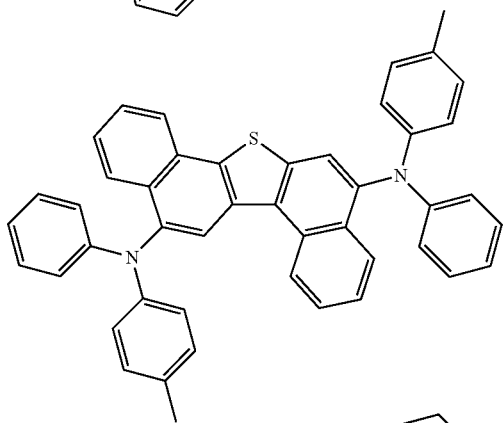 |
| 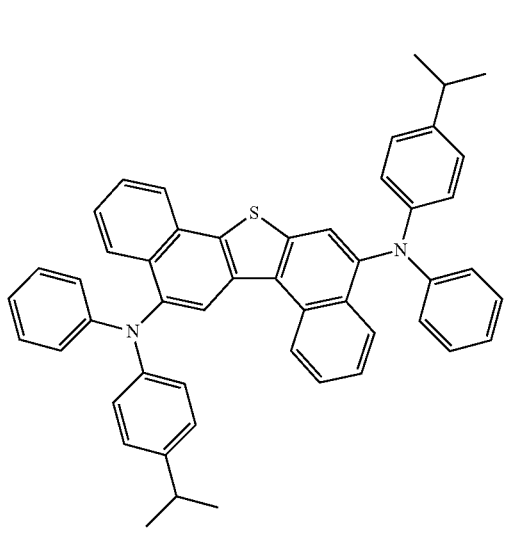 | 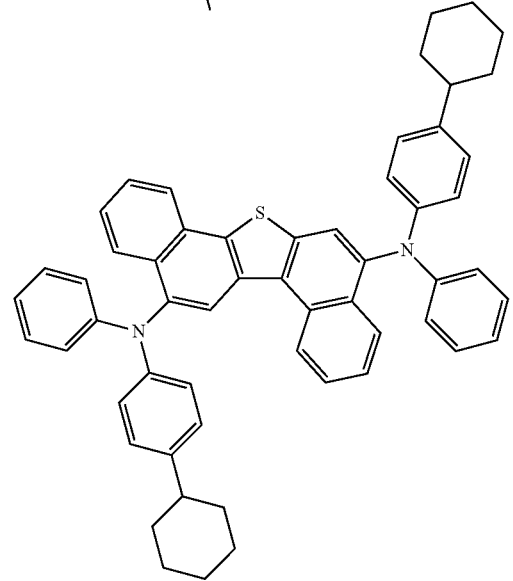 |

-continued
| 431 | 432 |
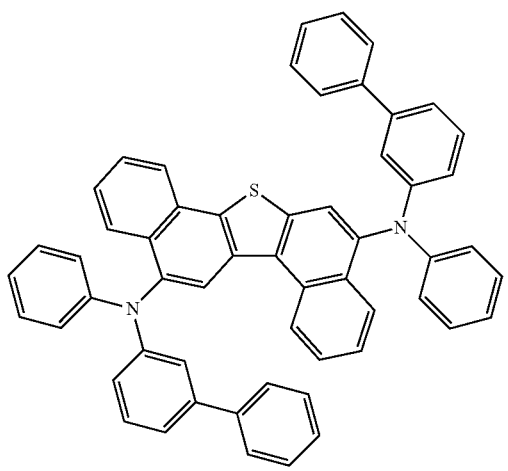 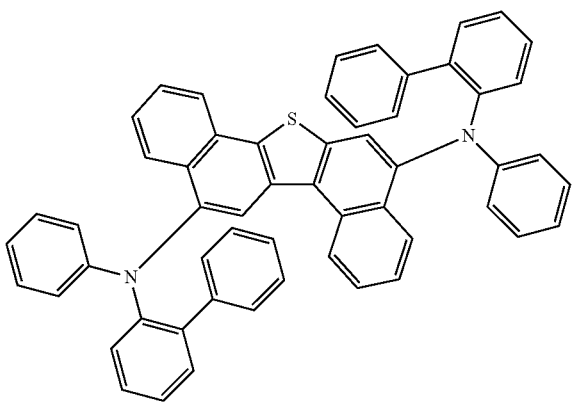
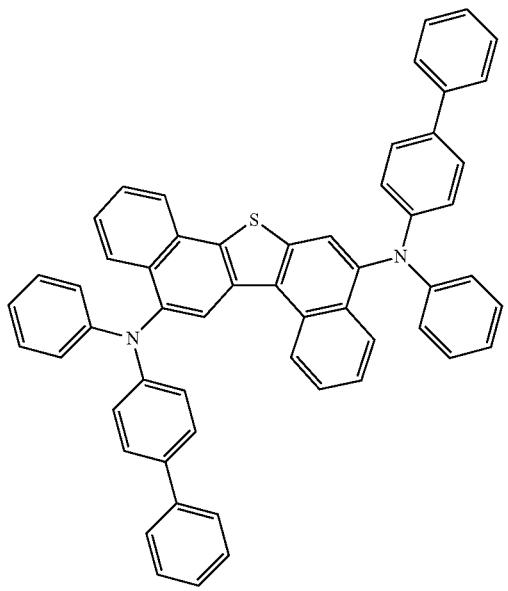 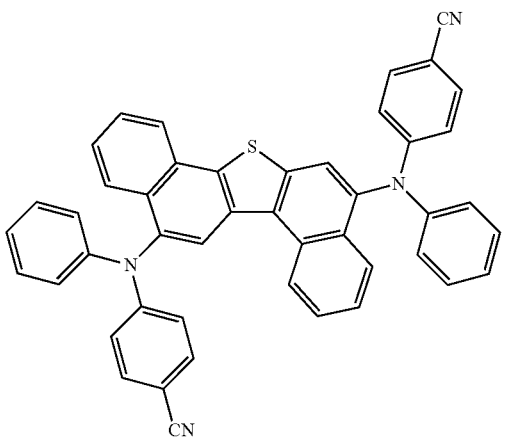
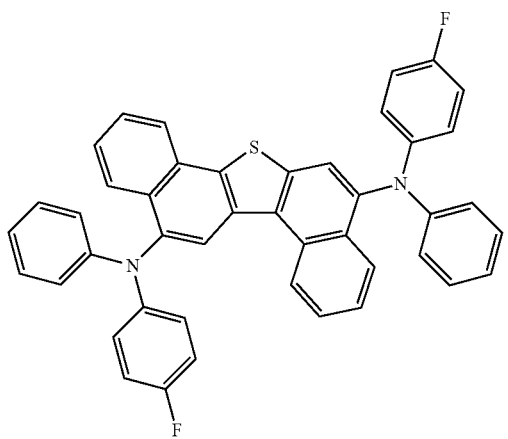 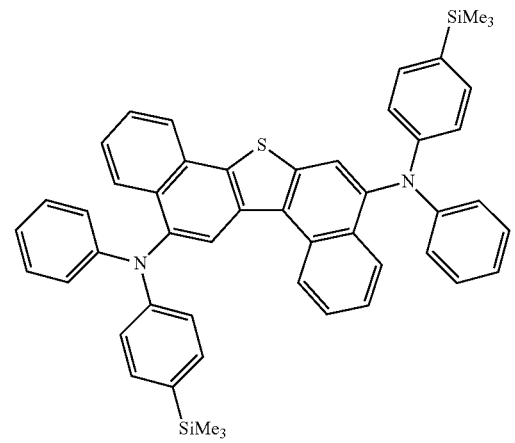

433 434
-continued
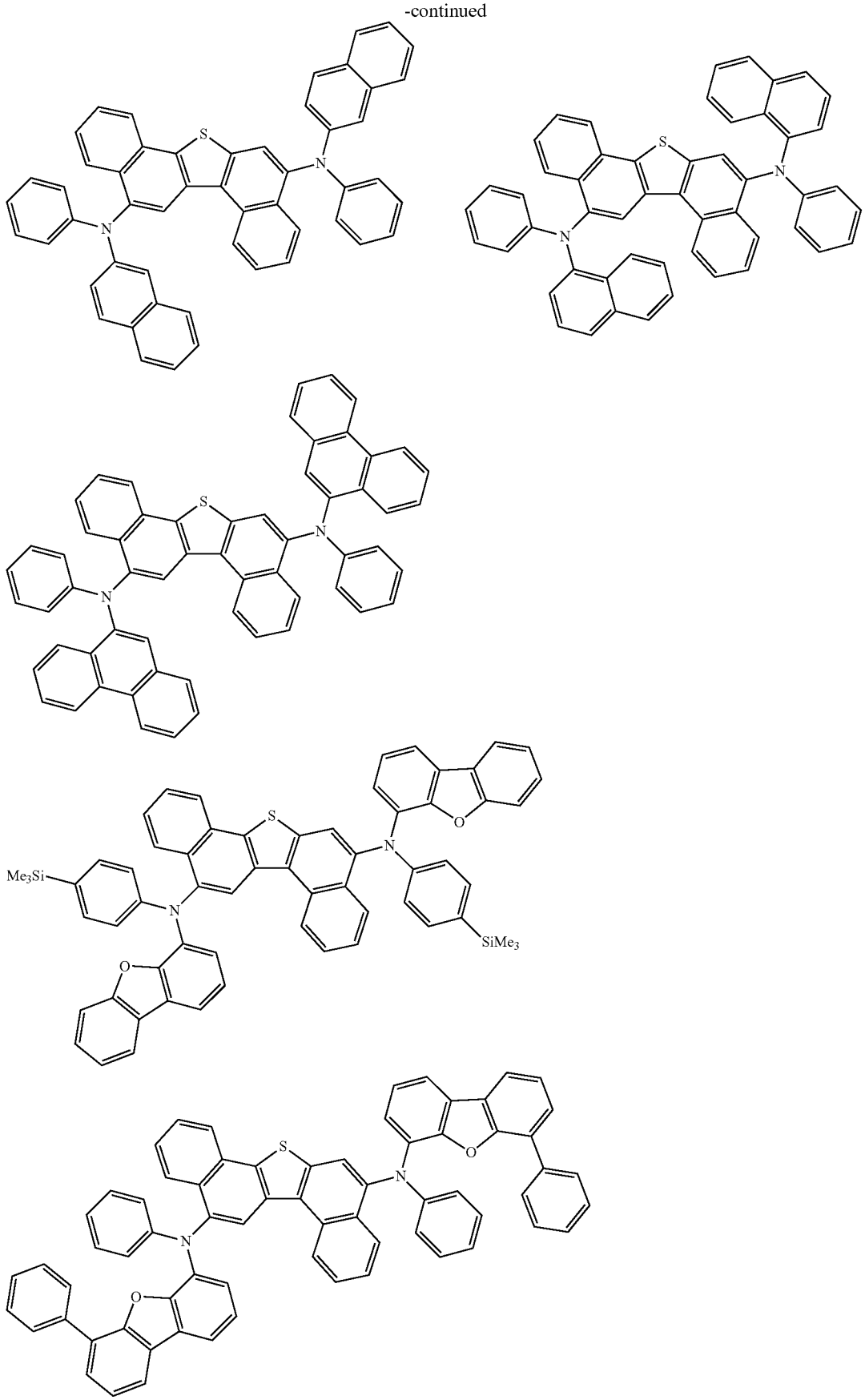

-continued
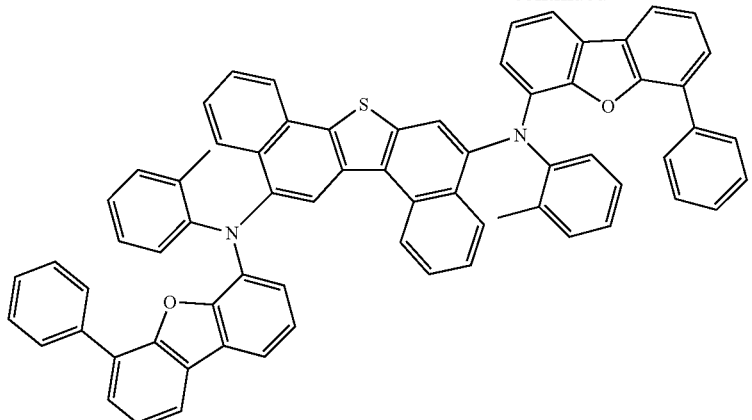
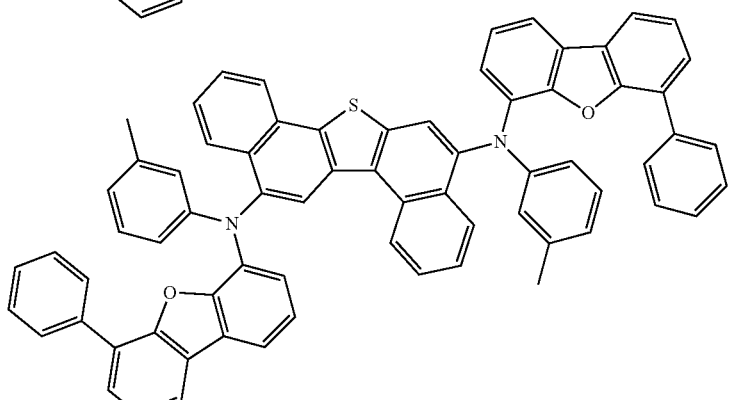
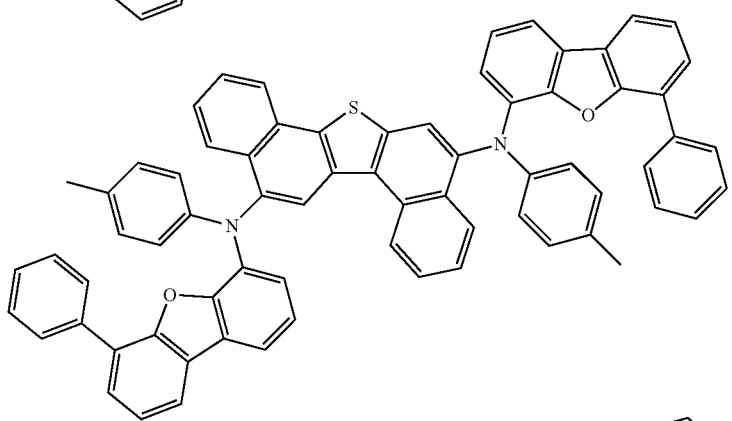
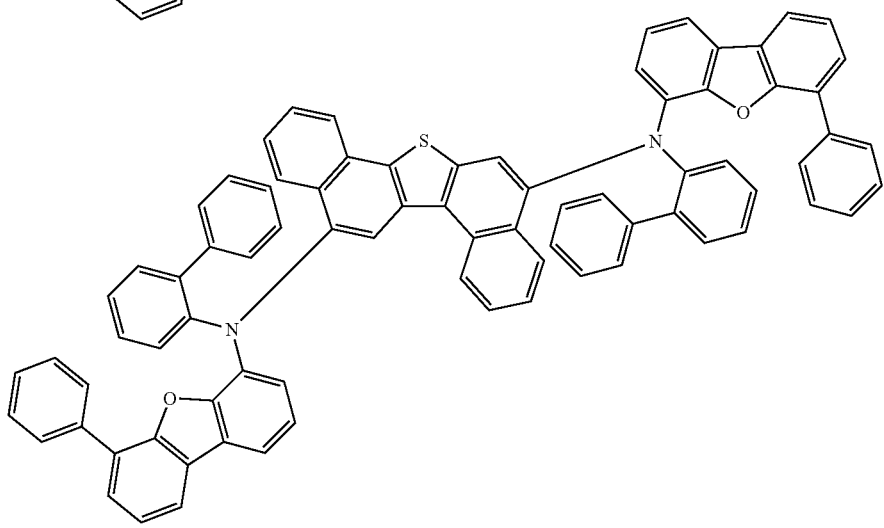

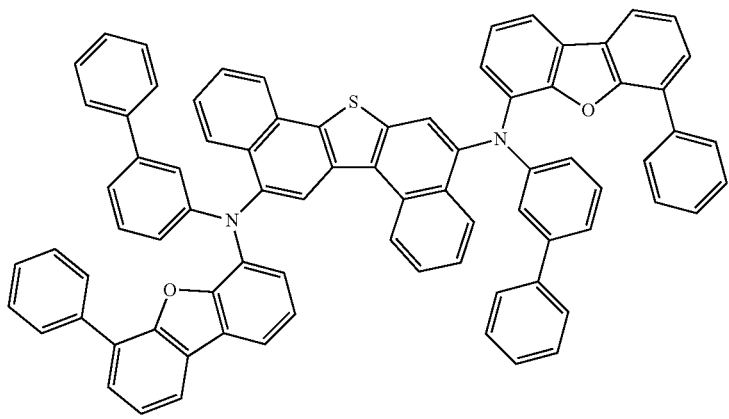
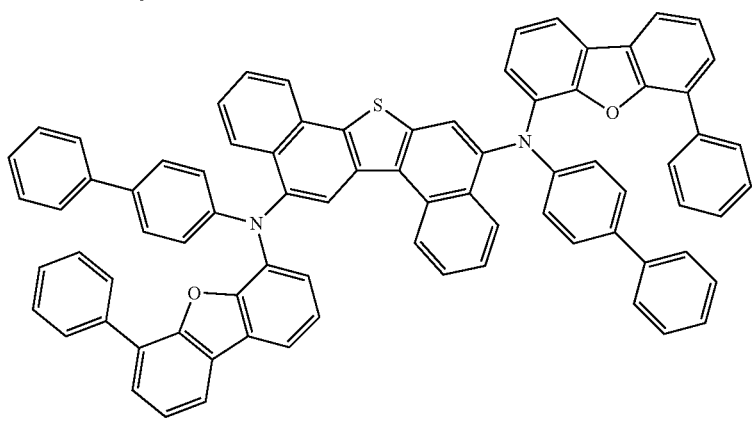
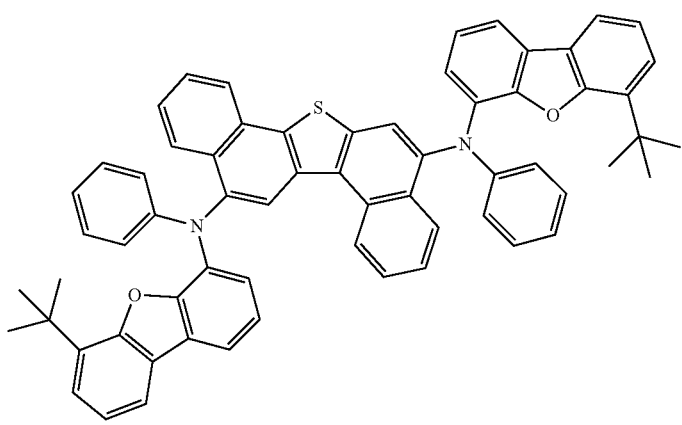
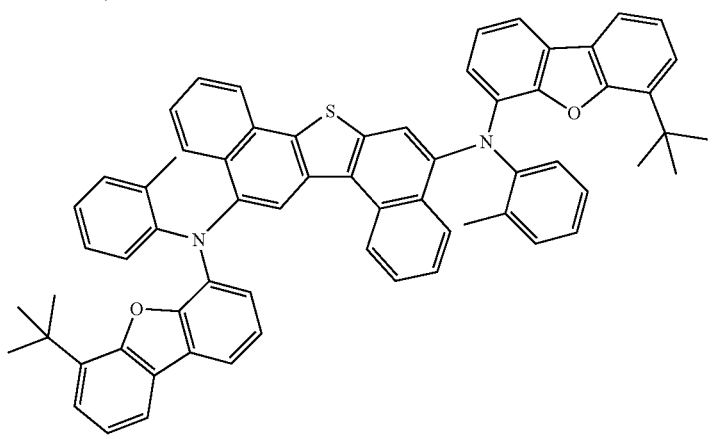

439
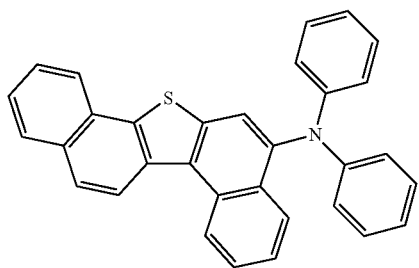
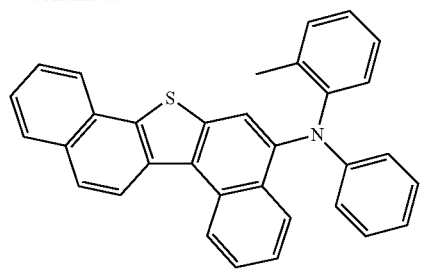
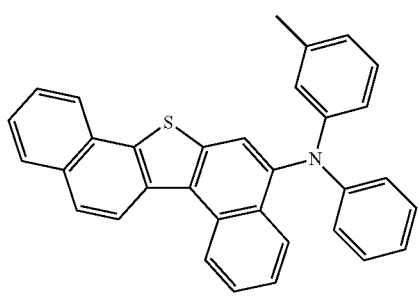
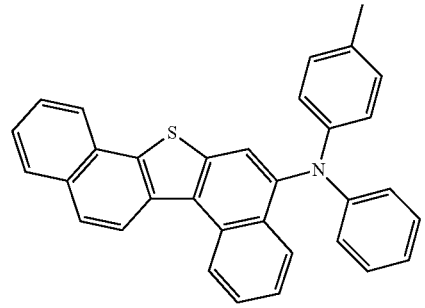
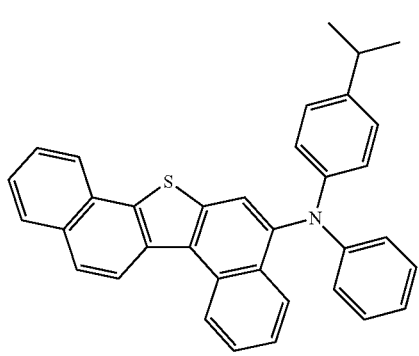
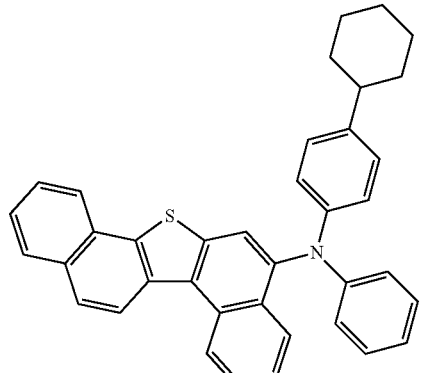
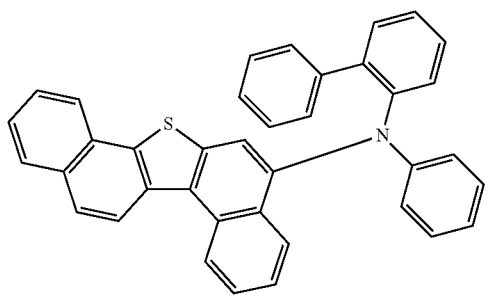
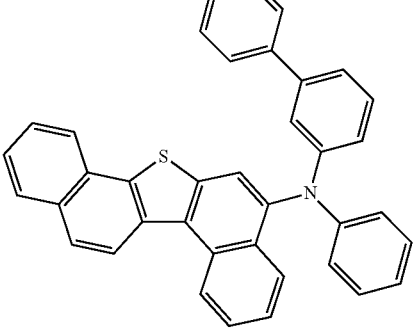
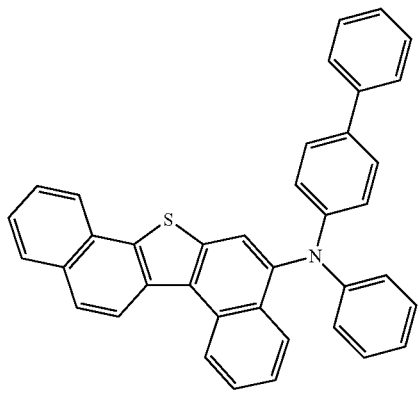
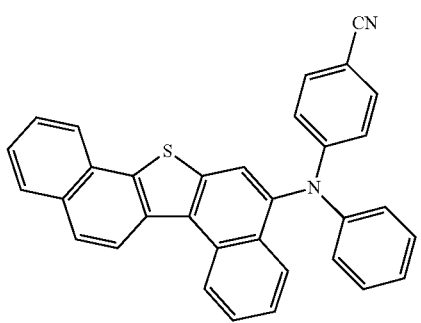

-continued
| 441 | 442 |
|---|---|
| 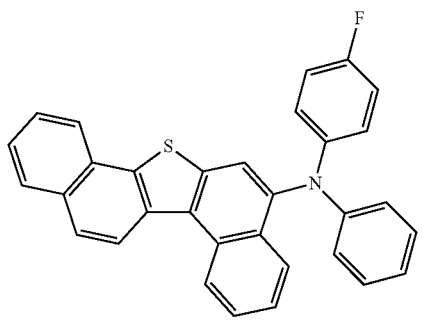 | 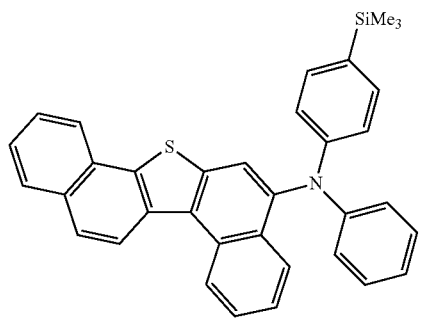 |
| 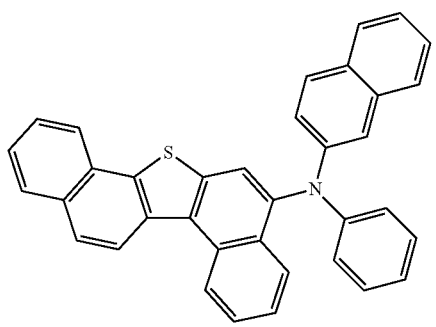 | 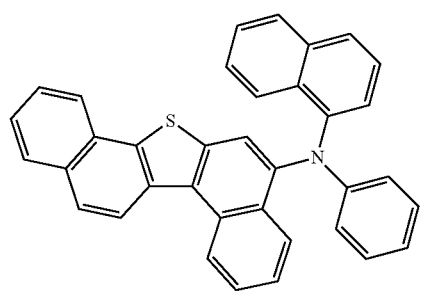 |
| 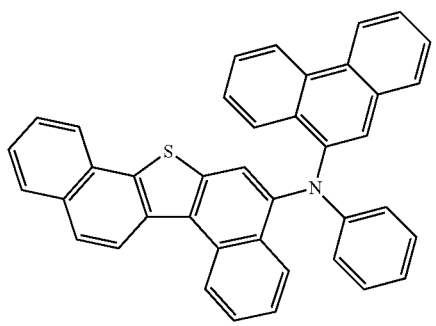 | 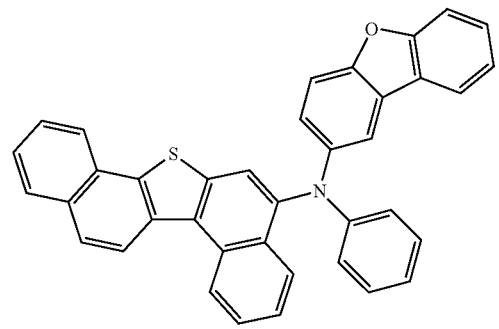 |
| 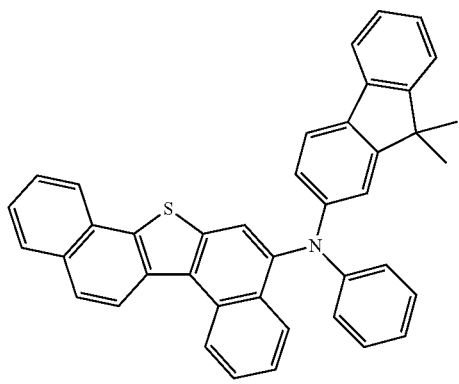 | 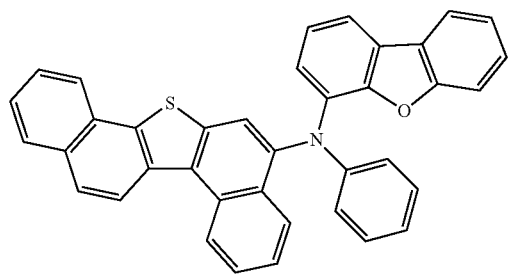 |
| 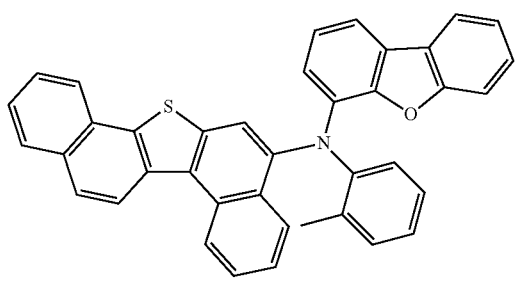 | 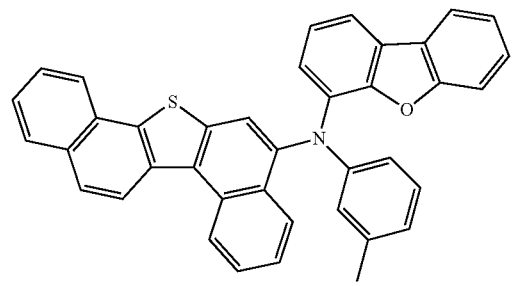 |

443
444
-continued
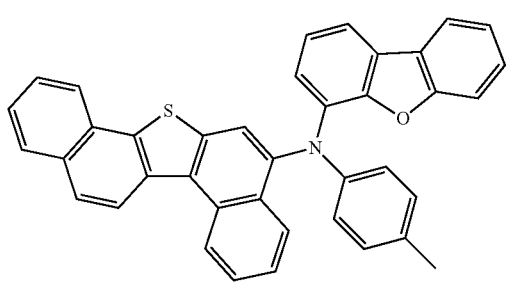
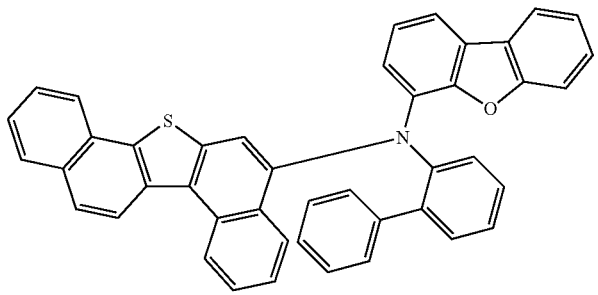
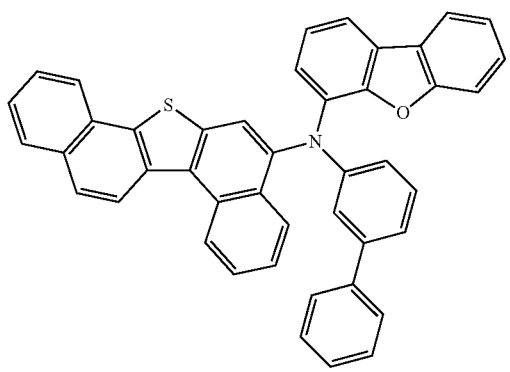
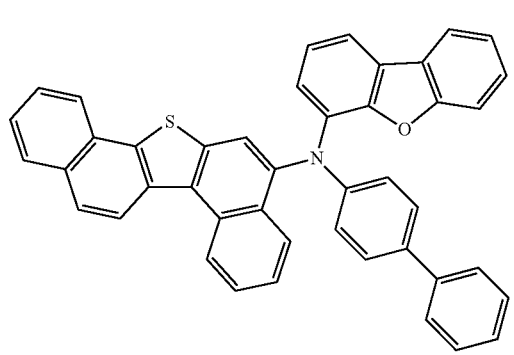
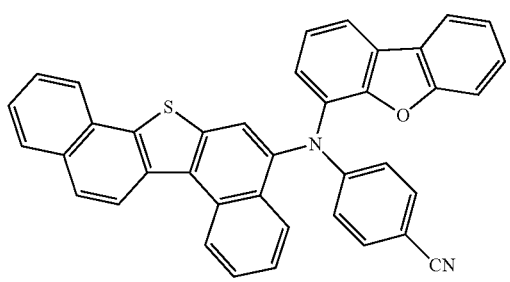
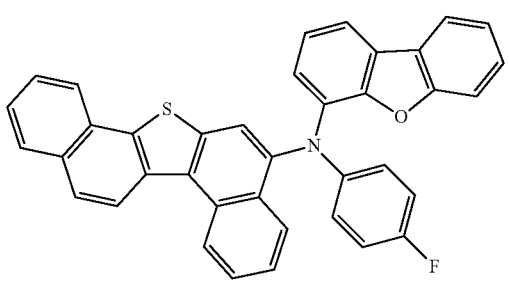
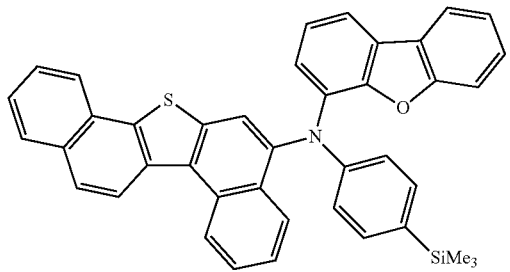
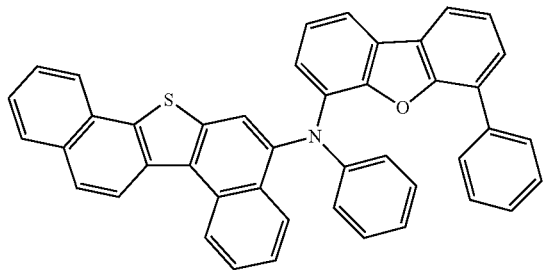
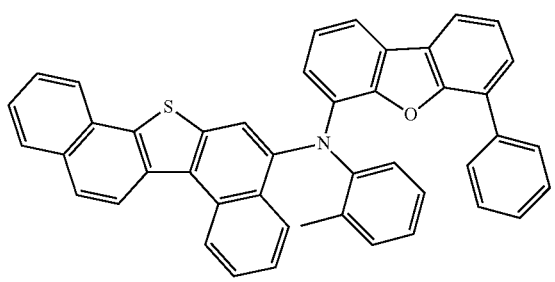
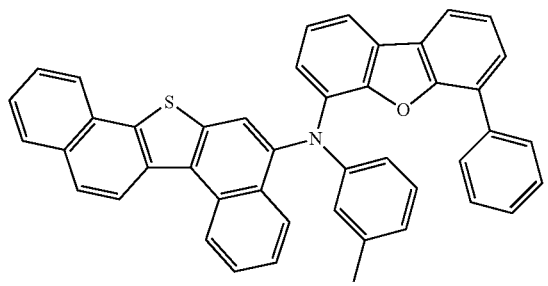

-continued
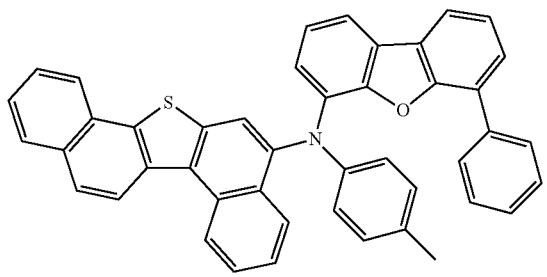
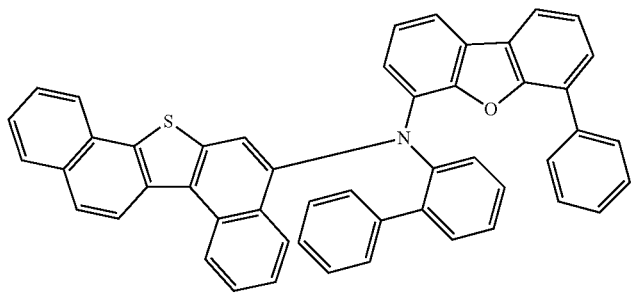
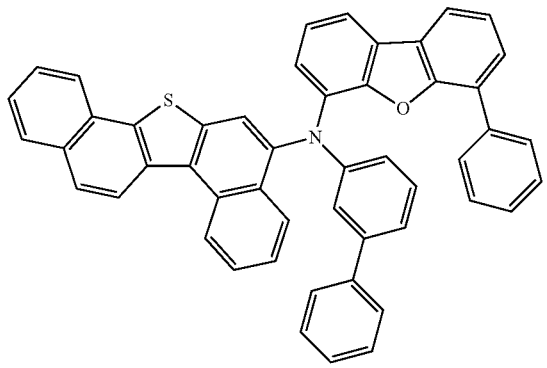
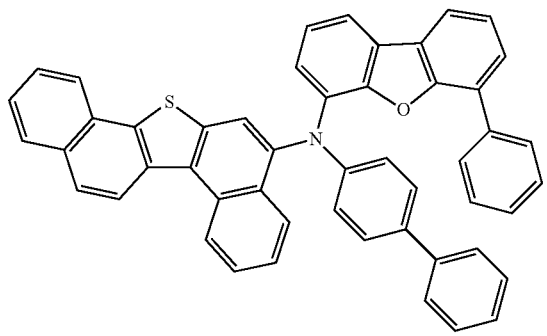
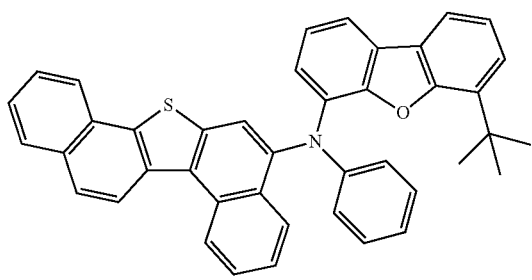
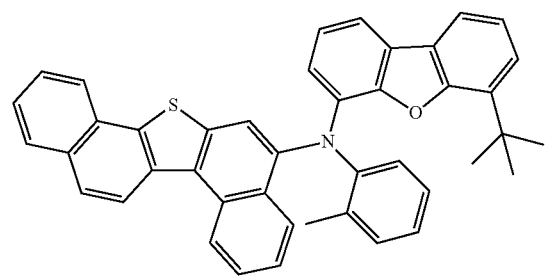
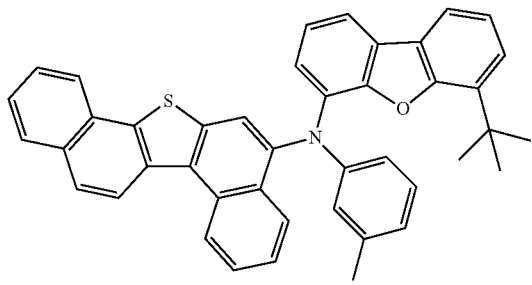
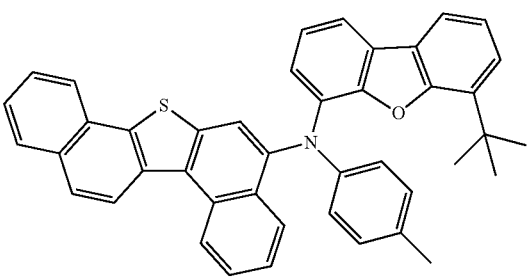

-continued
| 447 | 448 |
|---|---|
| 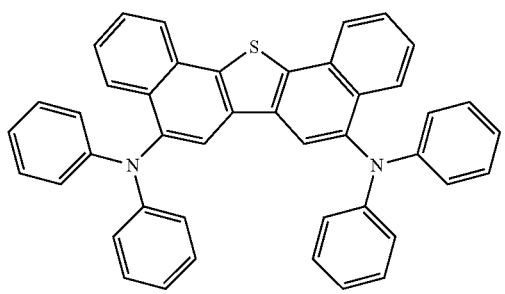 | 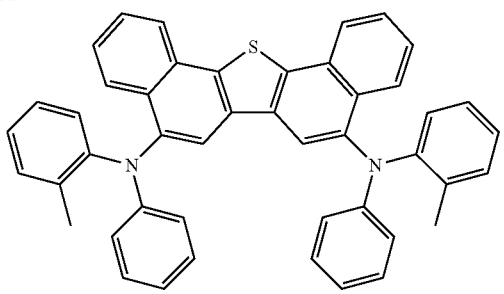 |
| 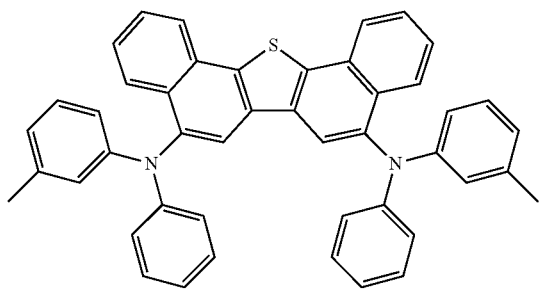 | 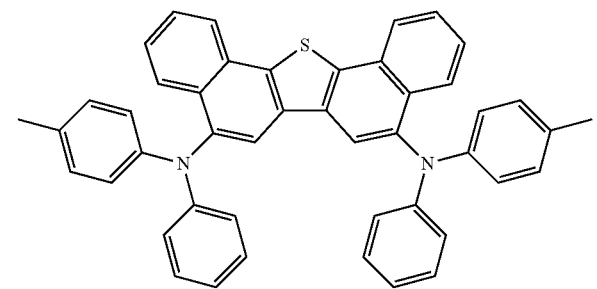 |
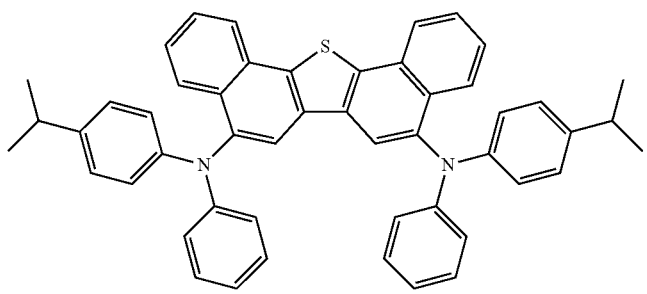
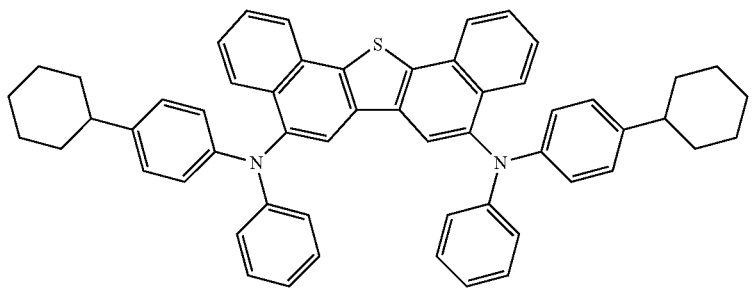
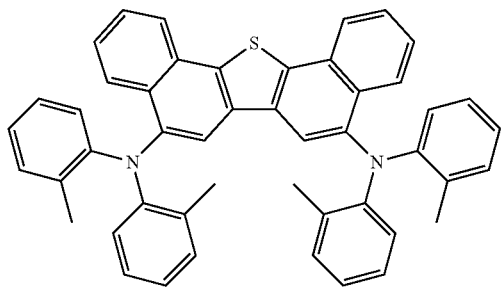
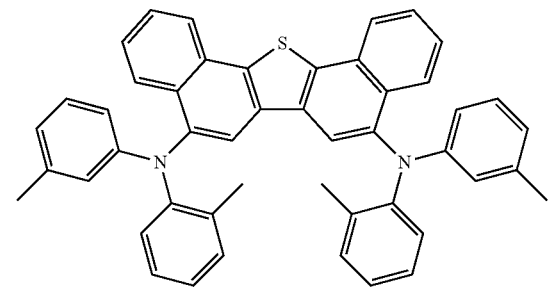

449 450
-continued
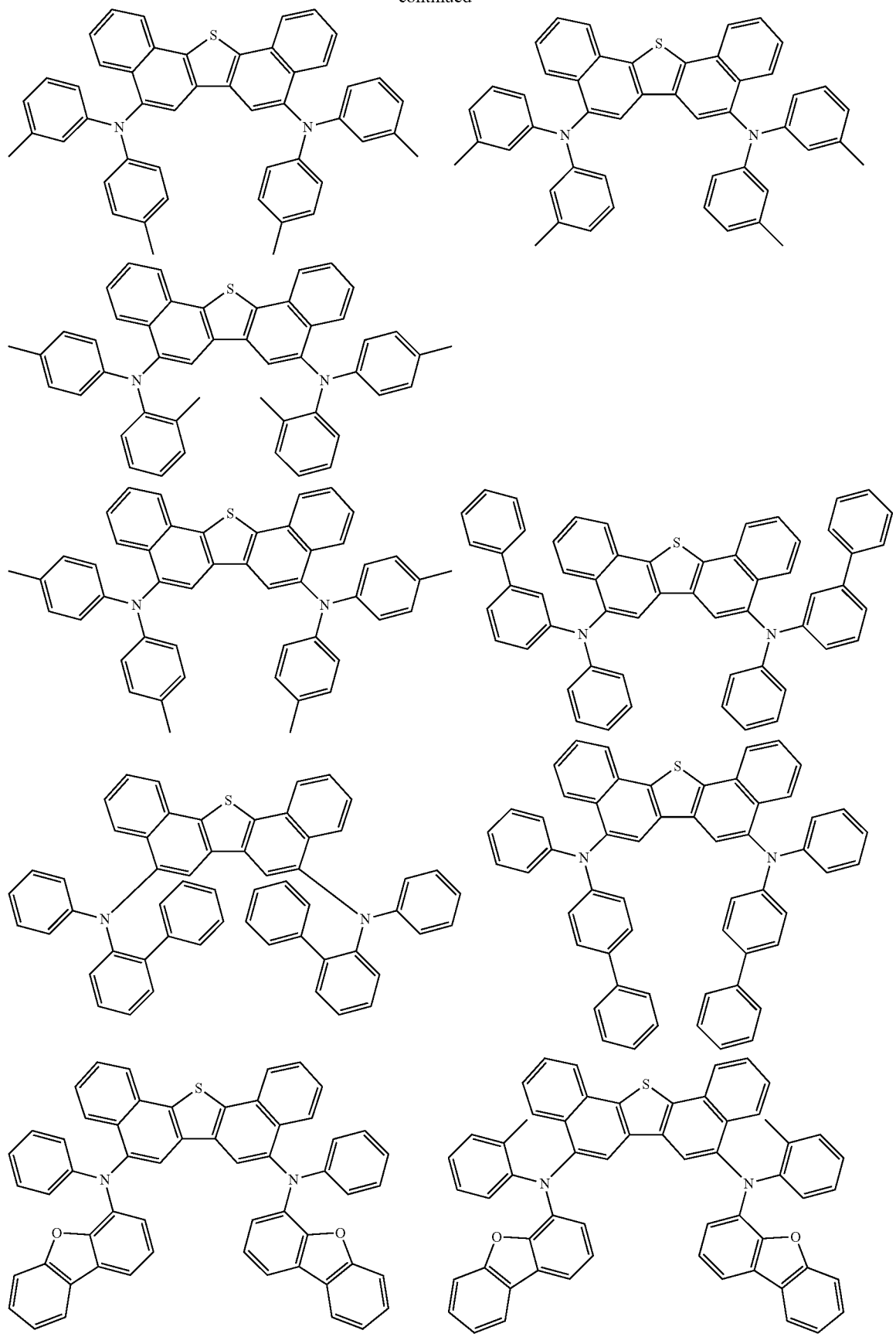

-continued
451 452
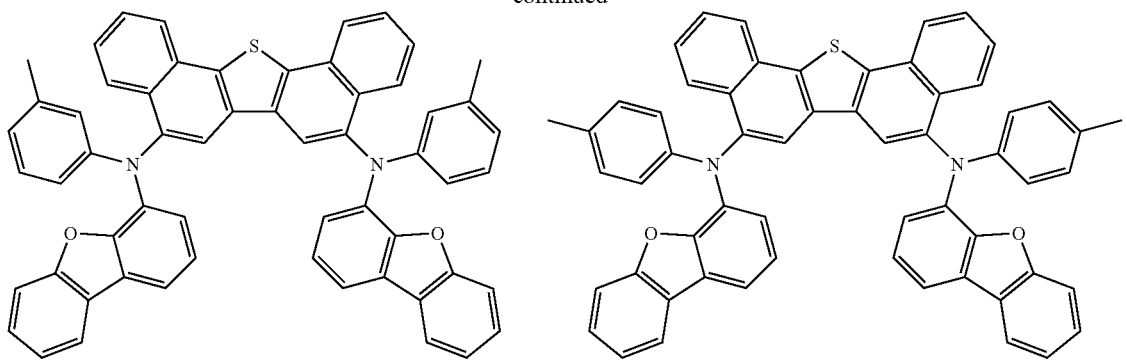
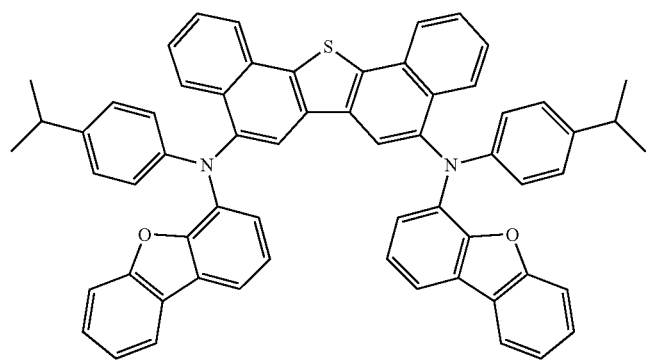
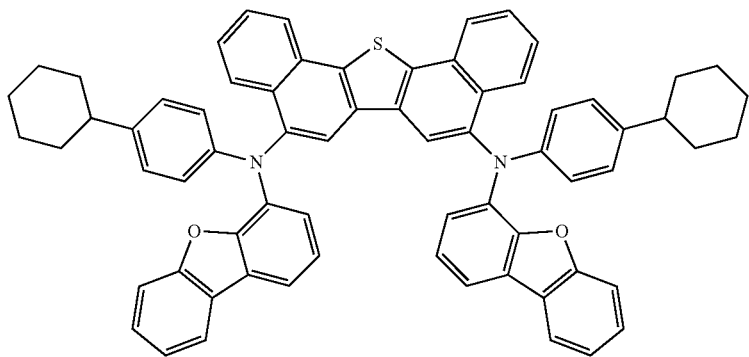
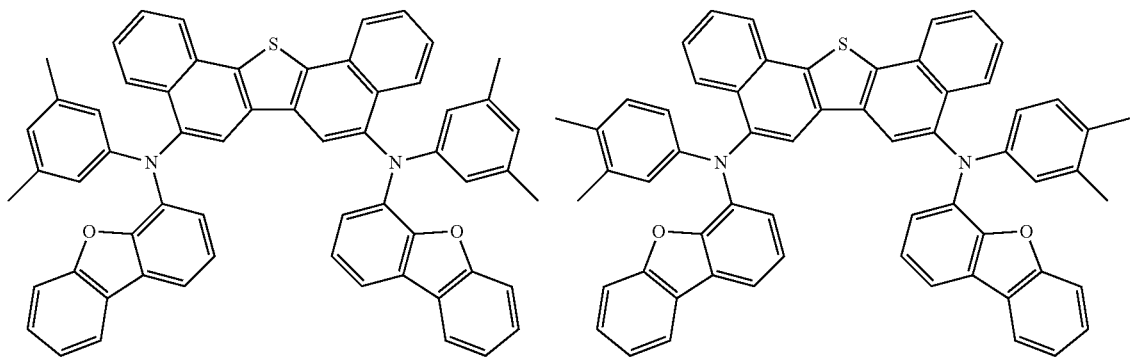

453 454
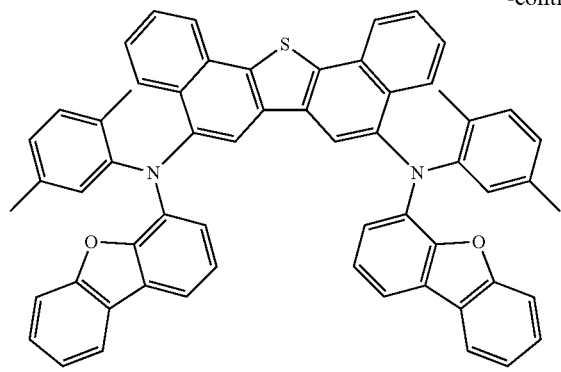
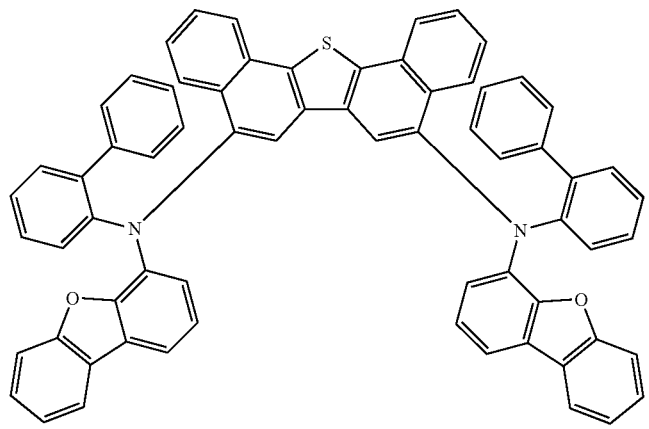
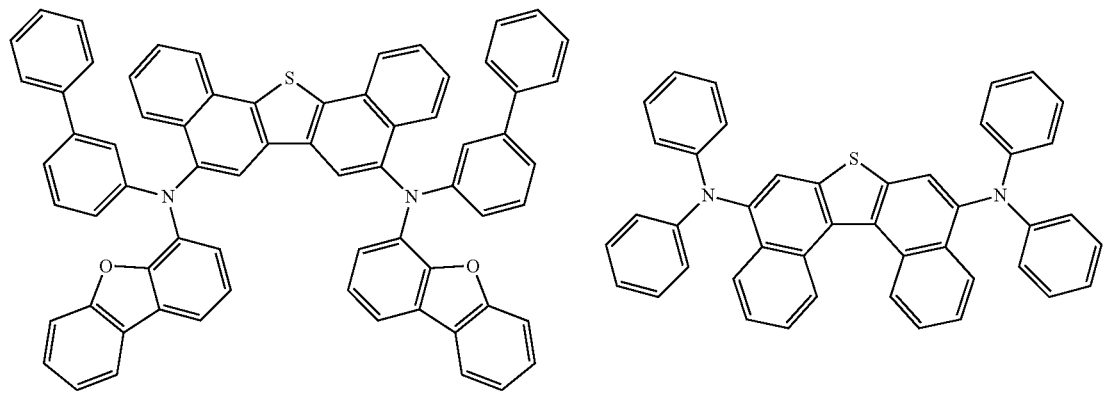
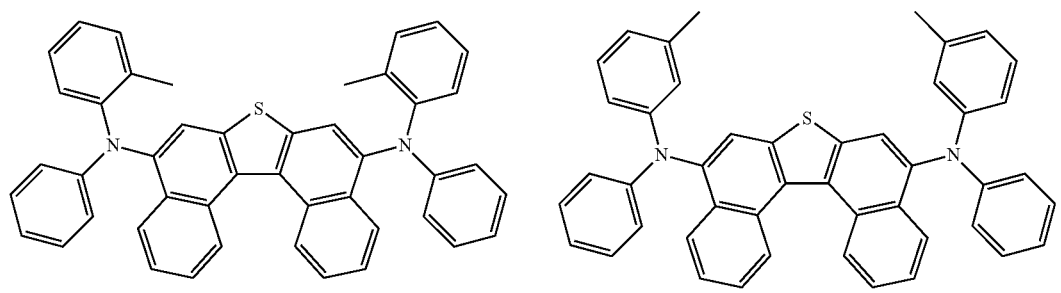

455
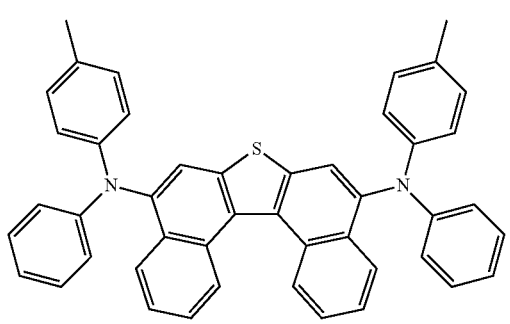
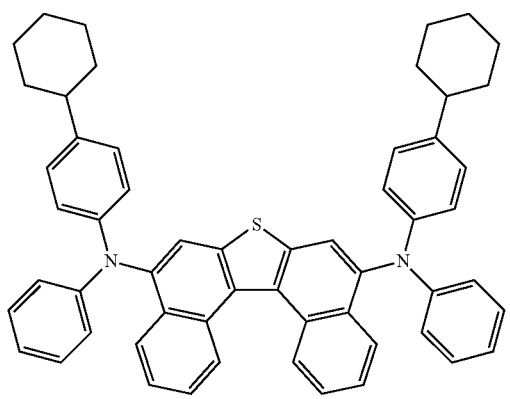
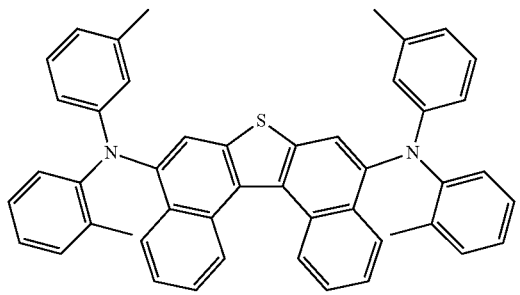
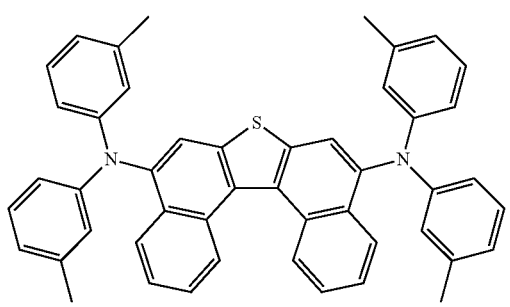
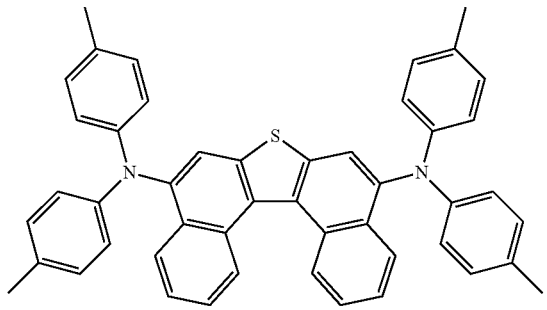
456
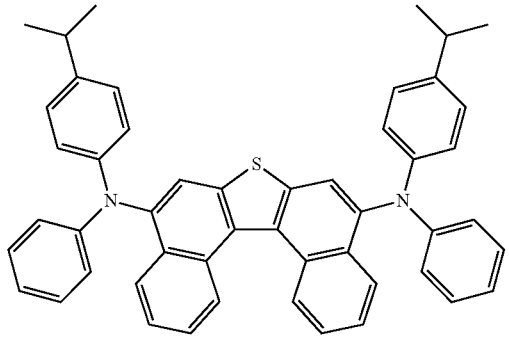
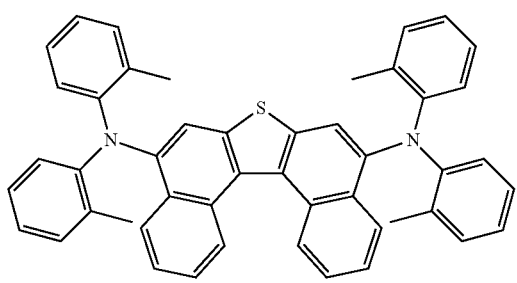
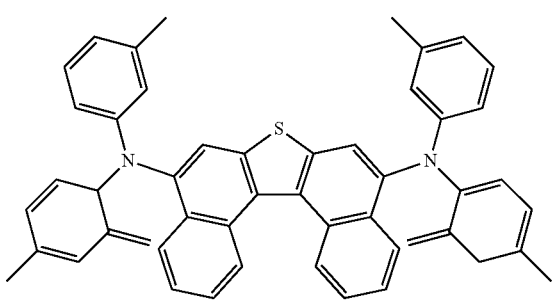
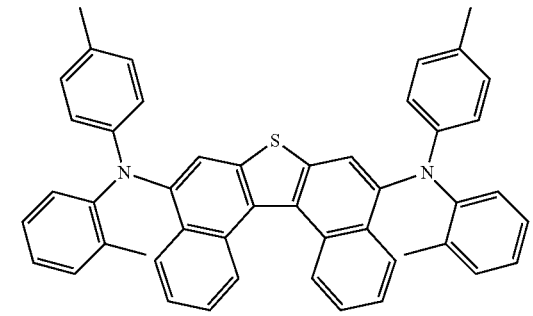
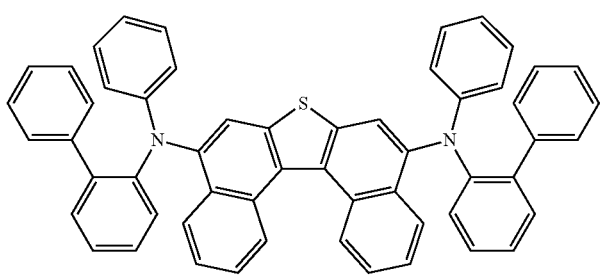

-continued
457 458
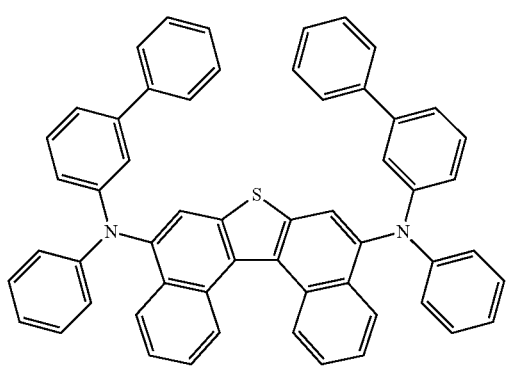 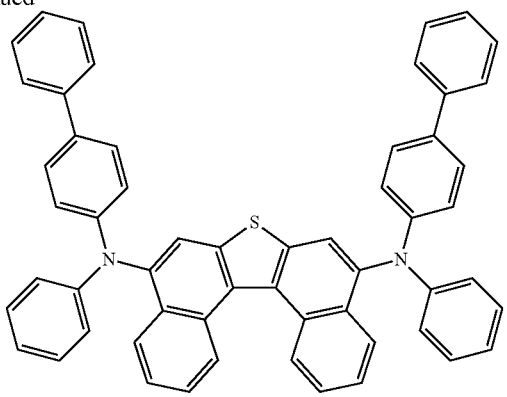
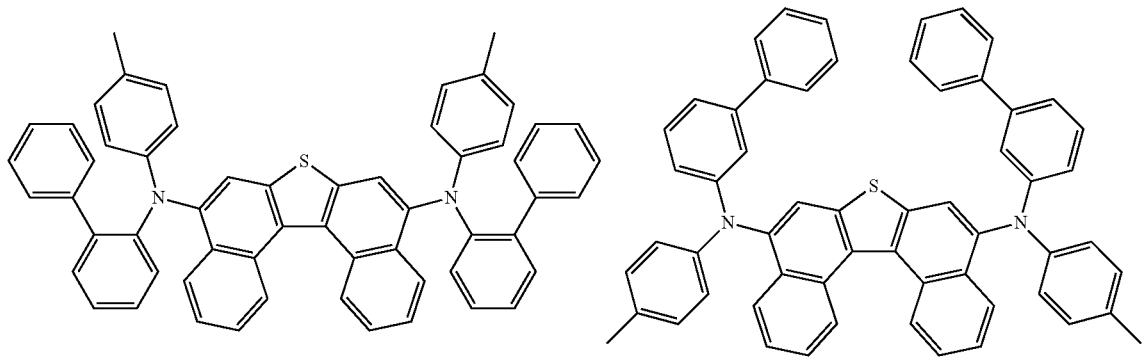
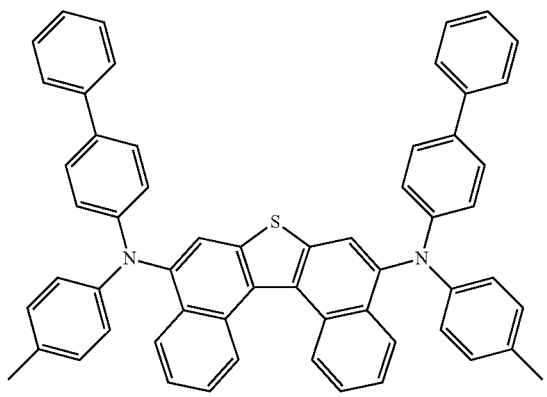
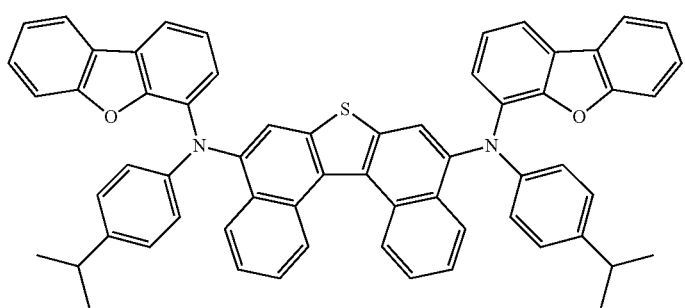

-continued
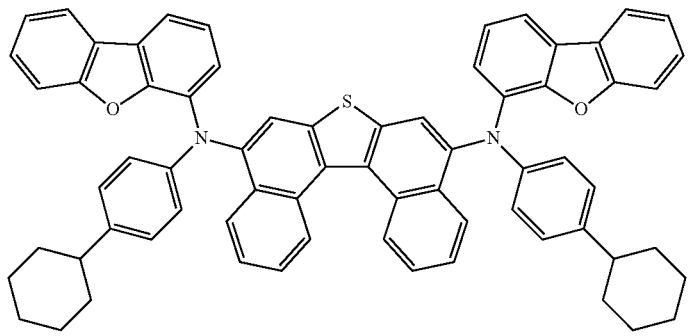
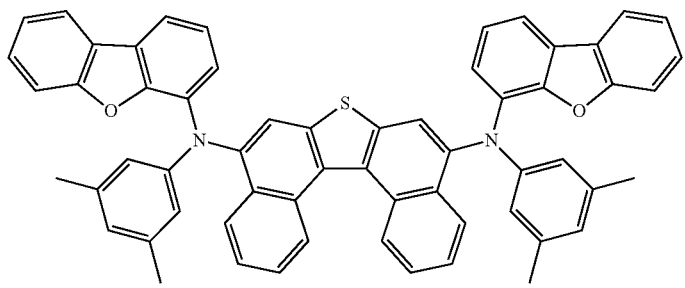
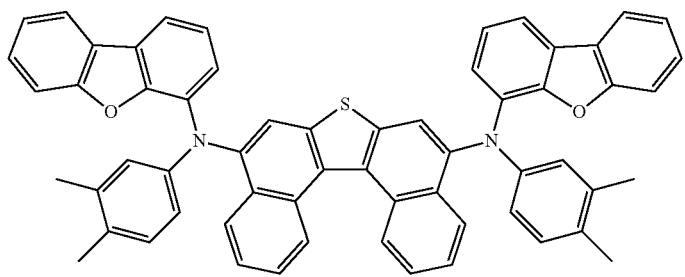
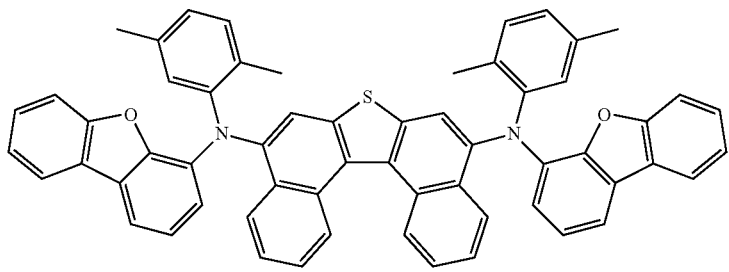
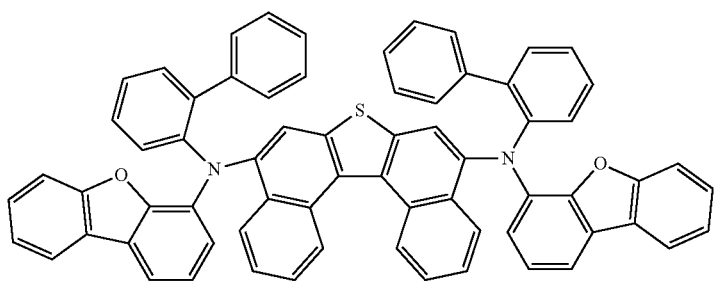

-continued
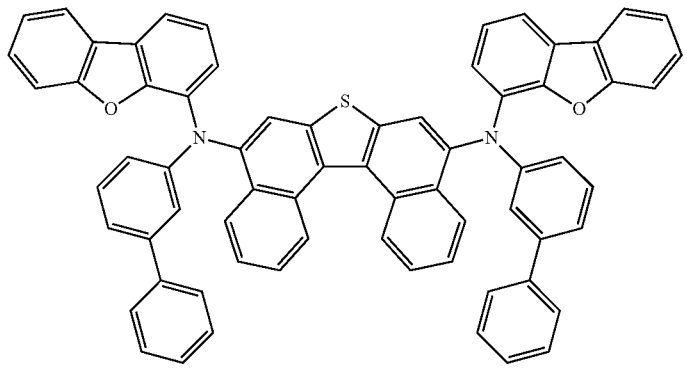
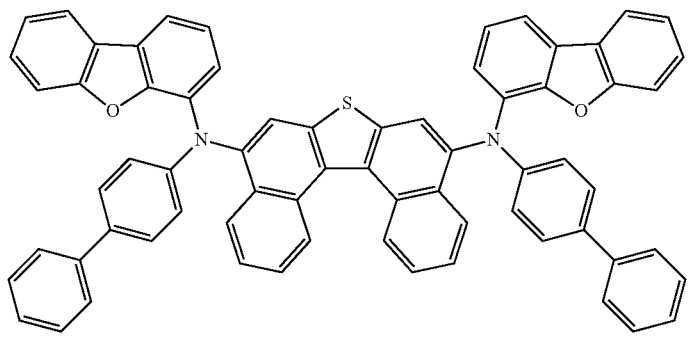
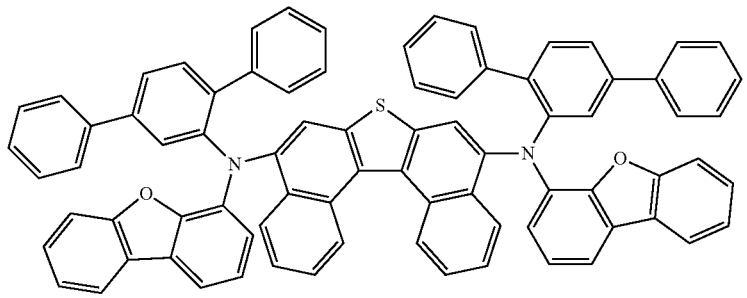
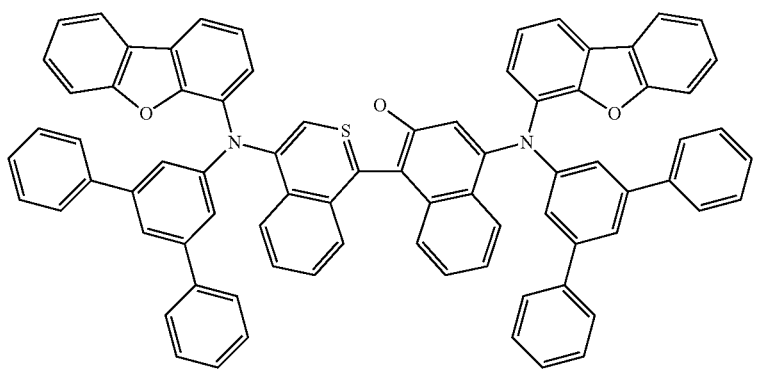
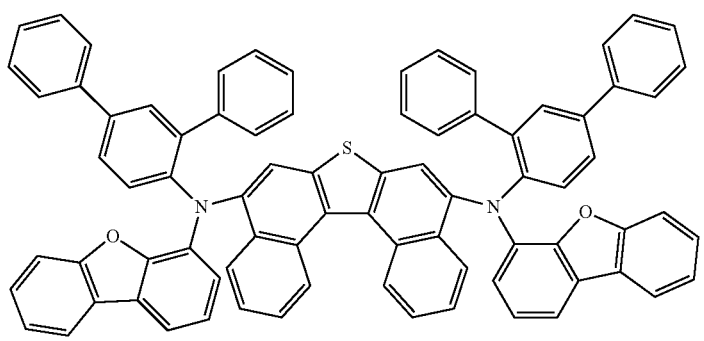

-continued
463 464
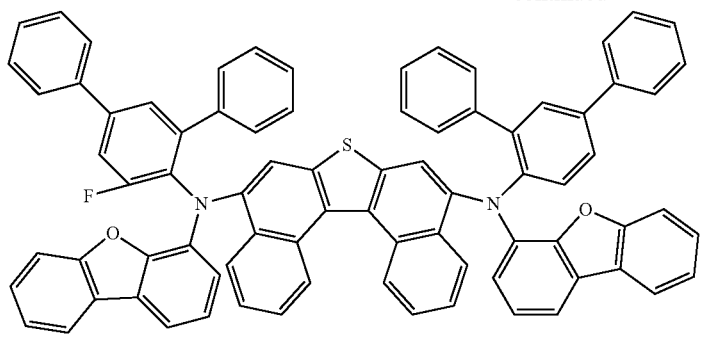
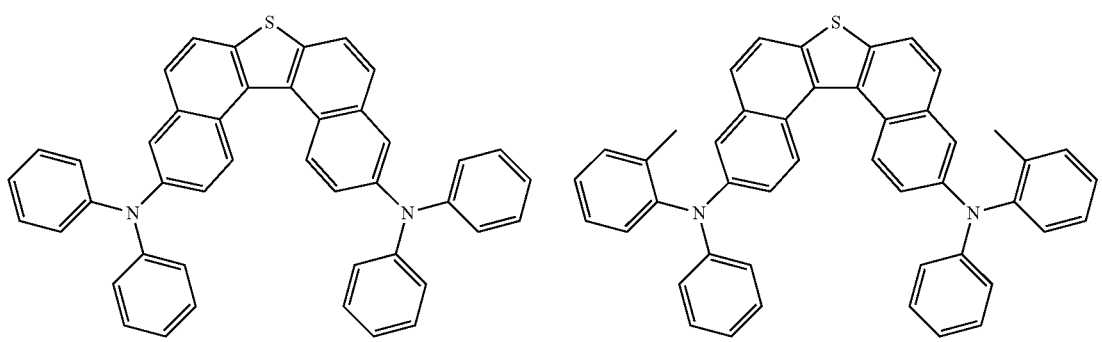
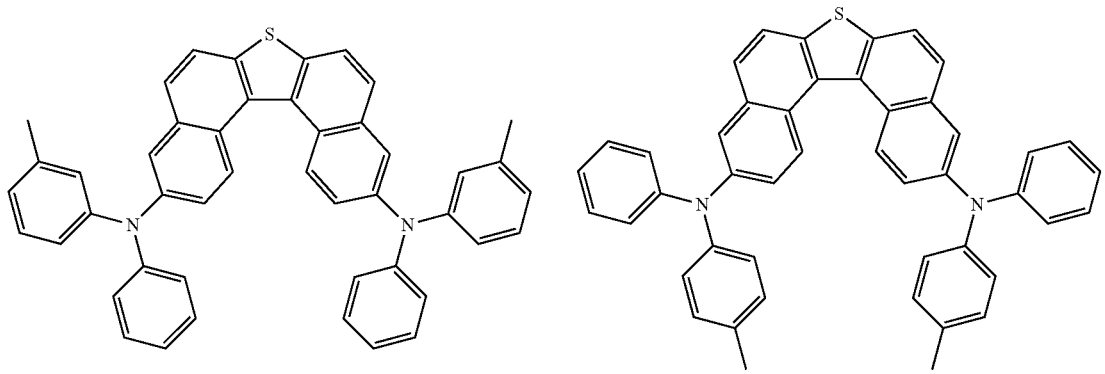
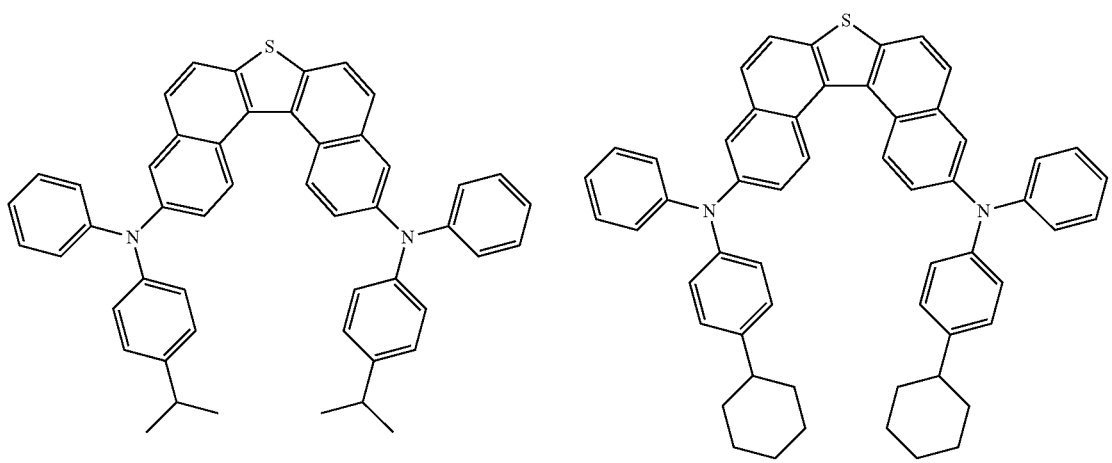

| 465 | 466 |
|---|---|
| 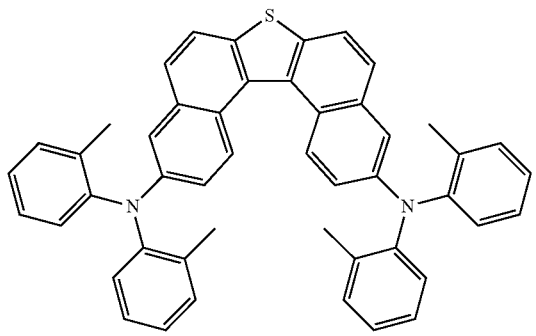 | 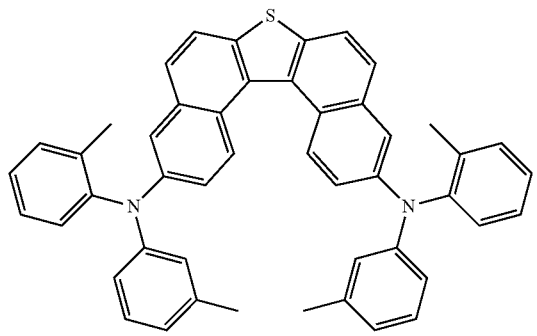 |
| 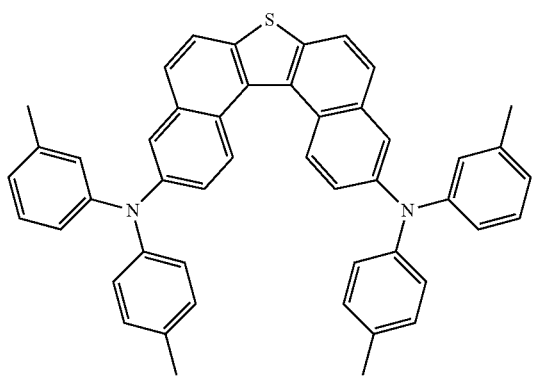 | 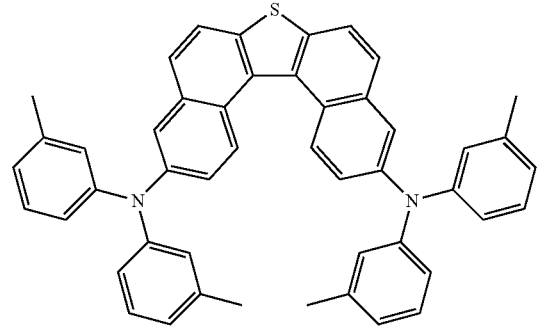 |
| 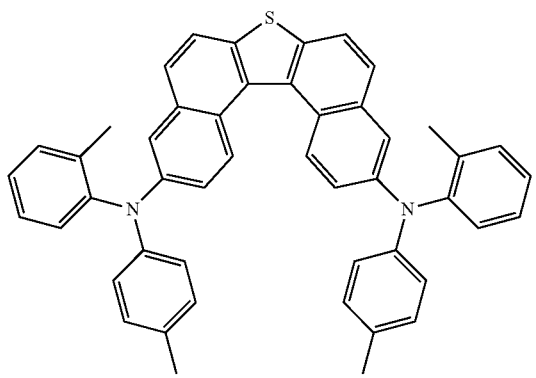 | 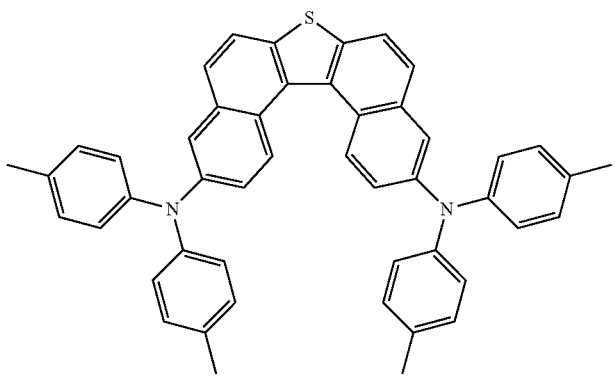 |
| 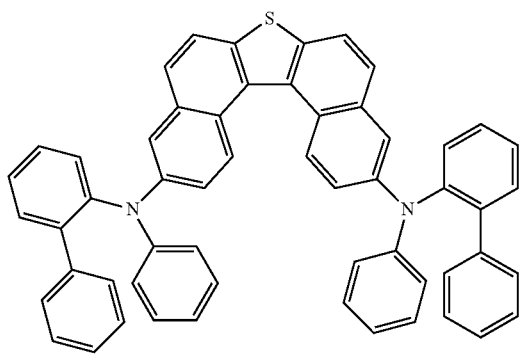 | 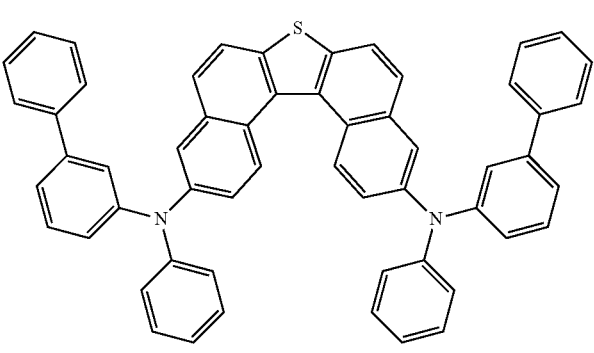 |

-continued
467 468
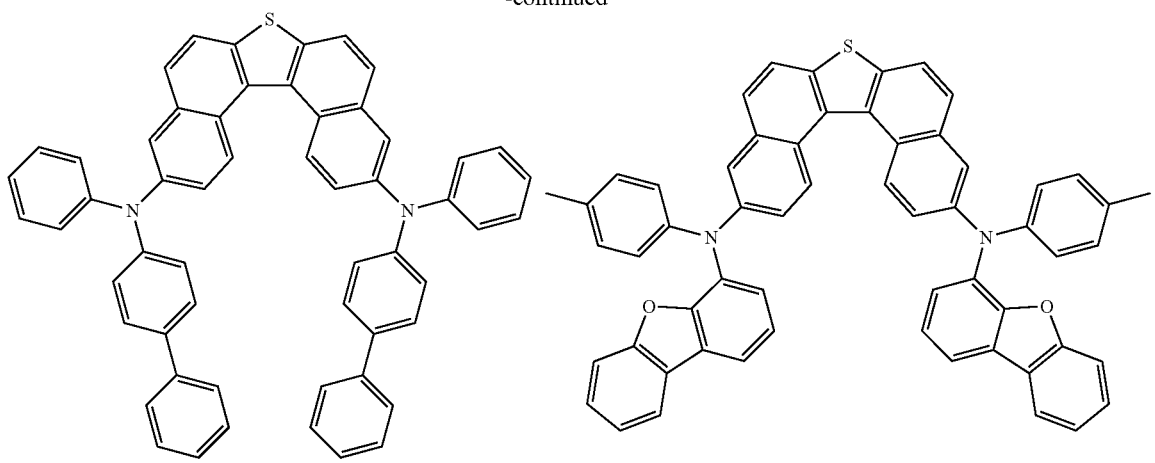
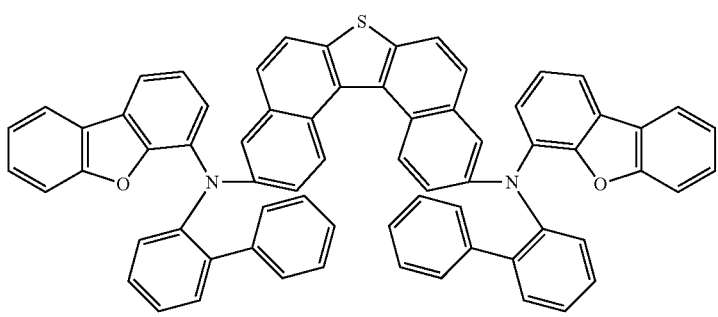
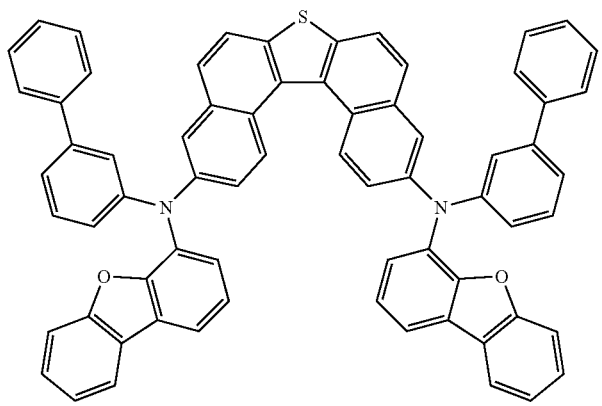
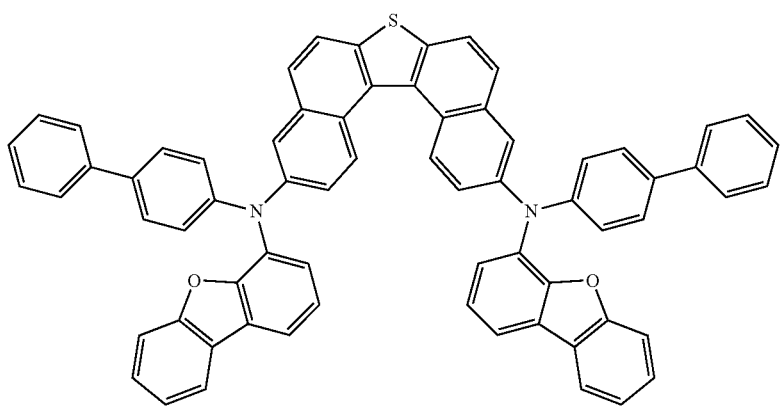

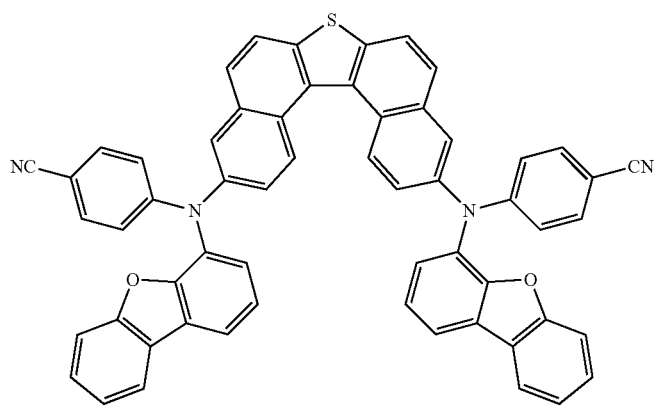
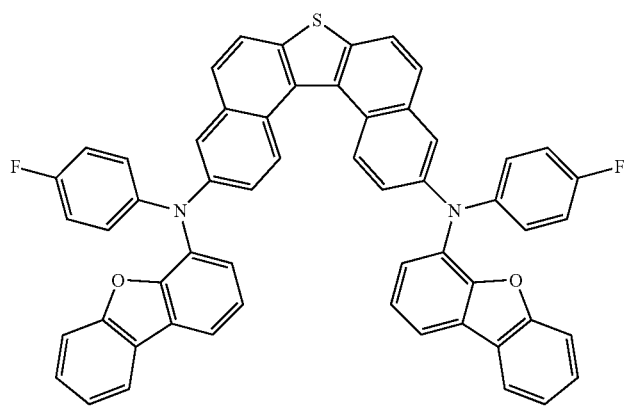
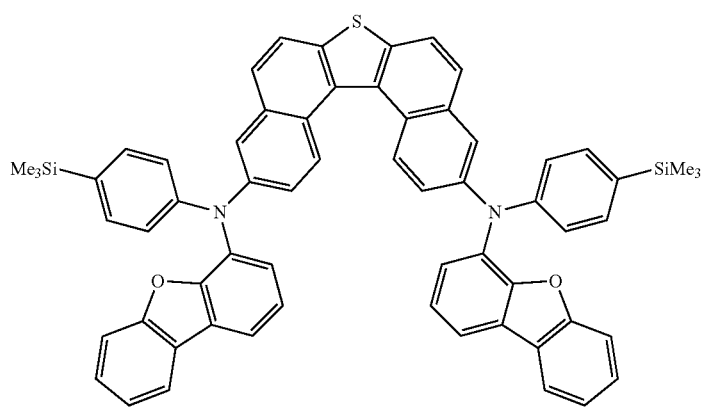
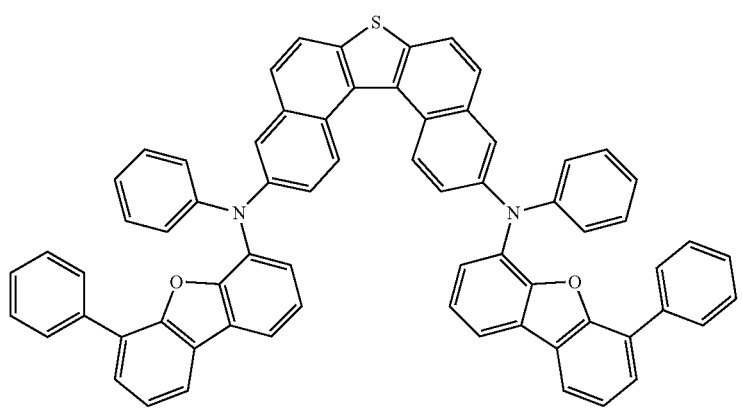

-continued
471
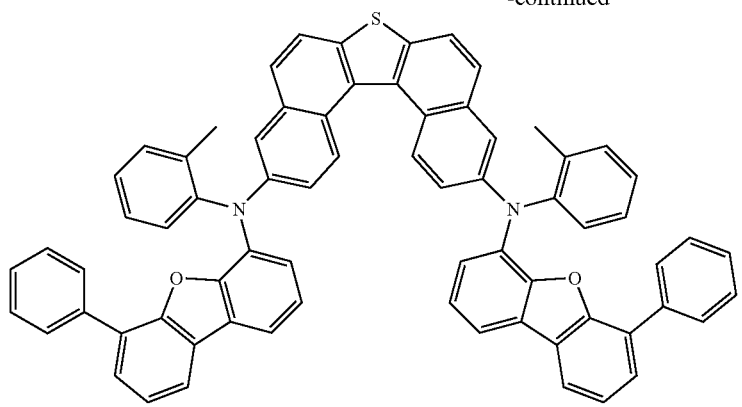
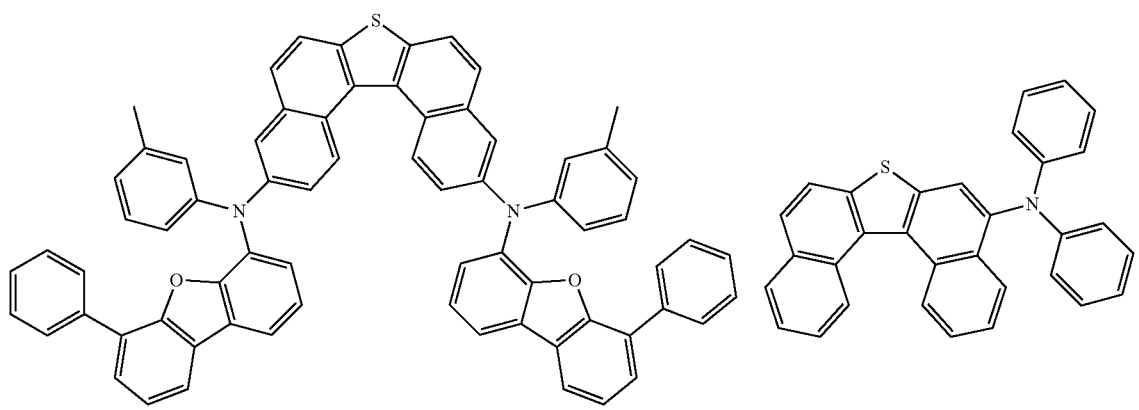
472
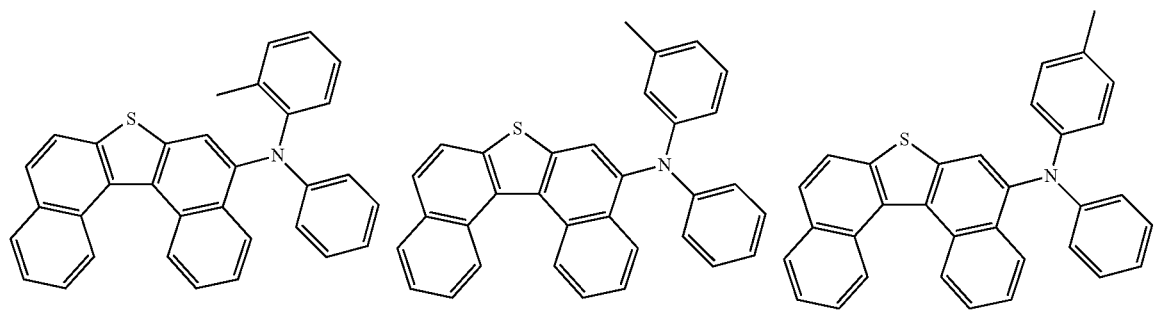
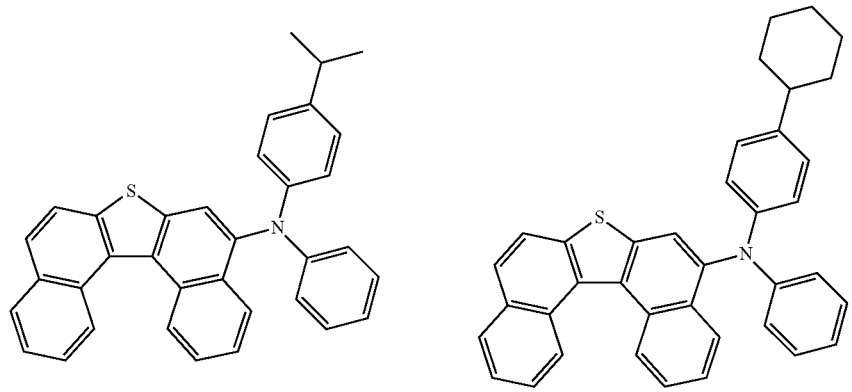

473 474
-continued
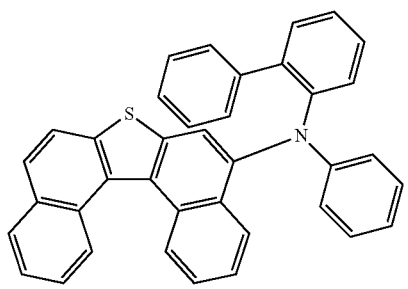
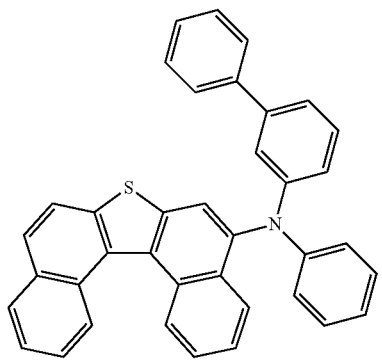
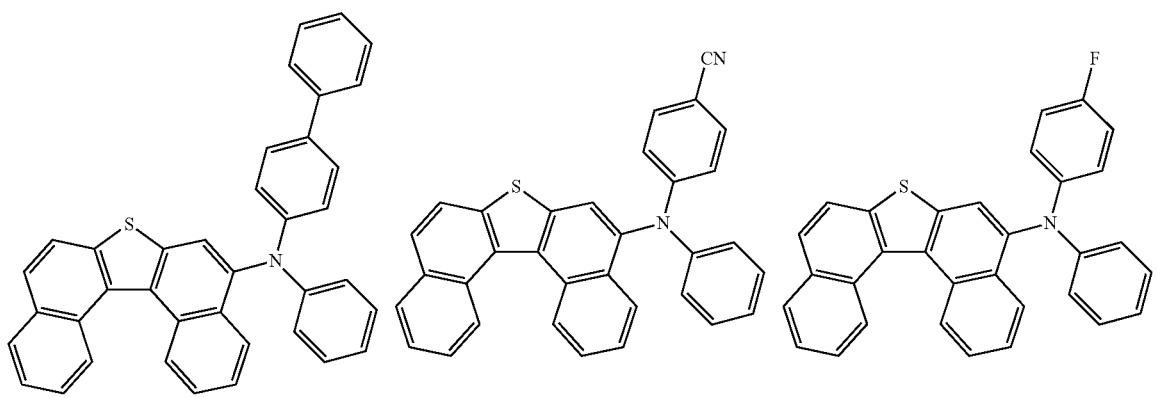
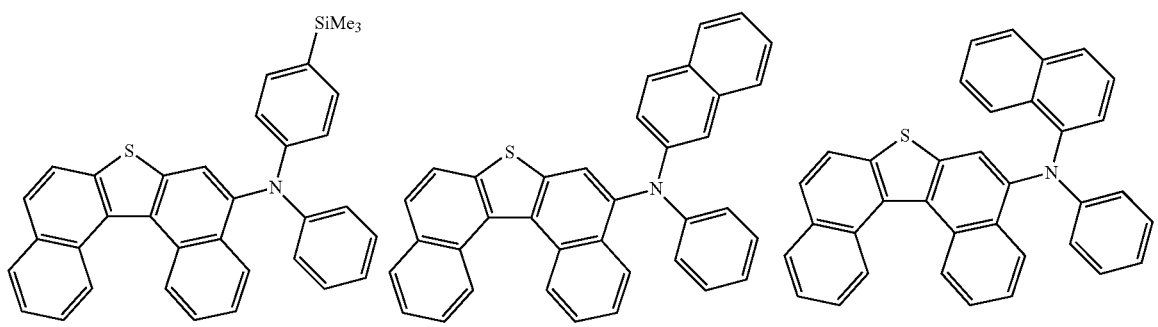
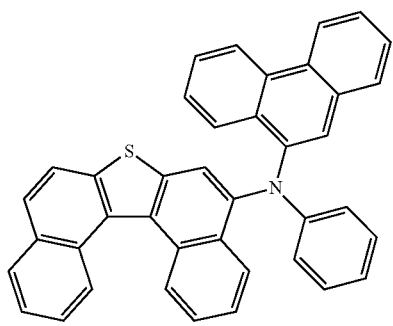
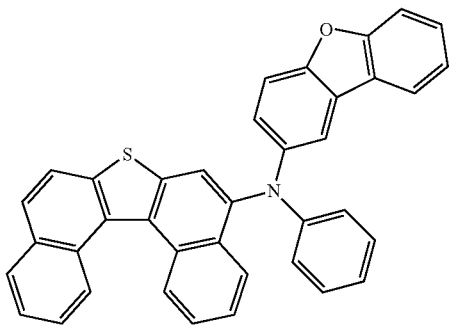

-continued
475
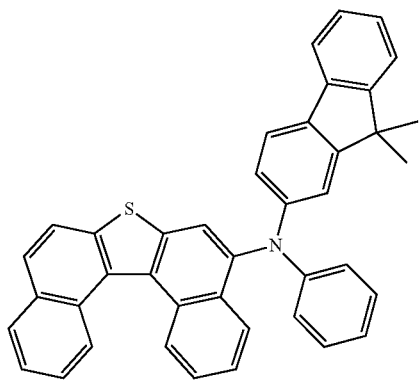
476
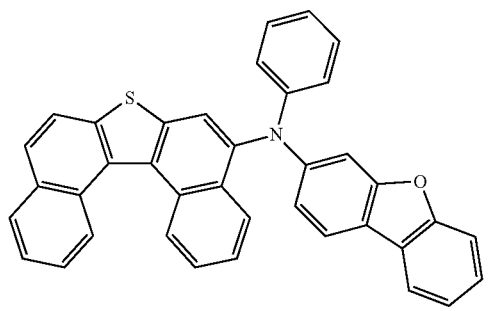
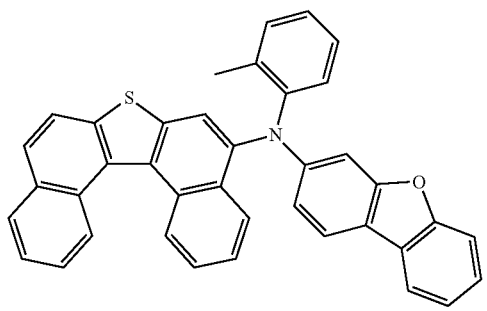
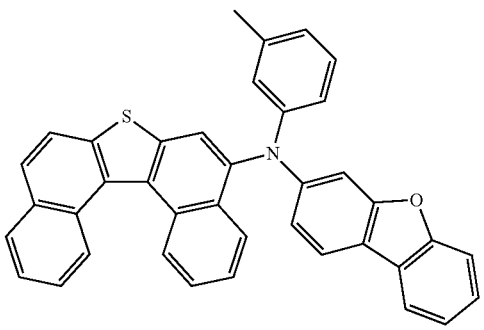
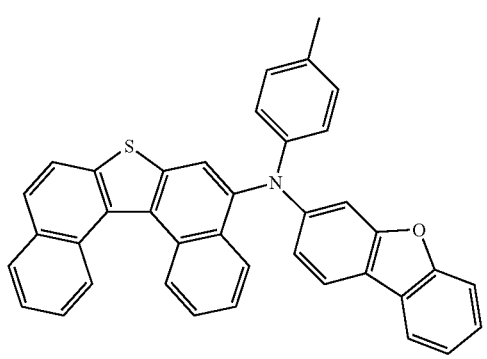
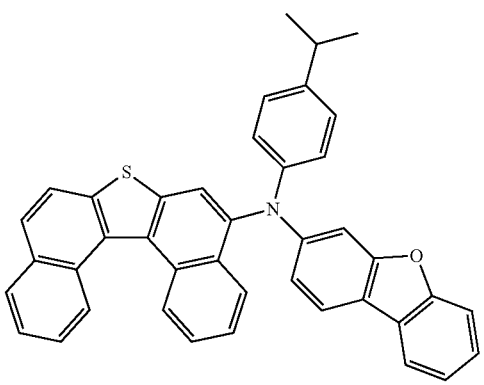
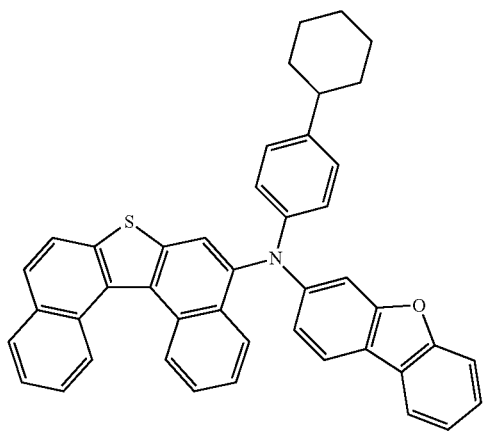
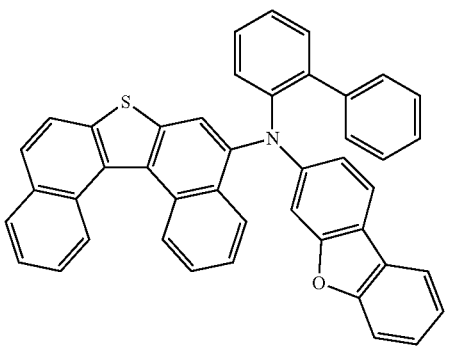

-continued
| 477 | 478 |
|---|---|
| 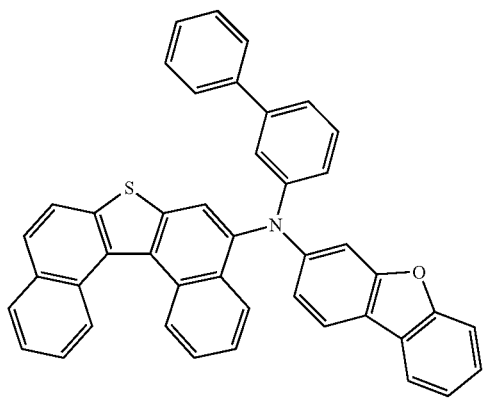 | 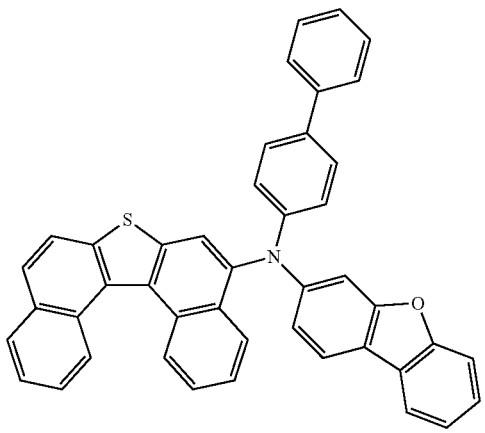 |
| 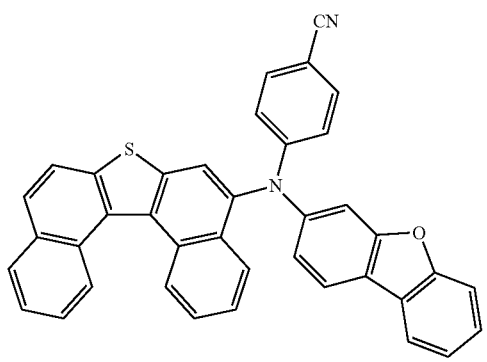 | 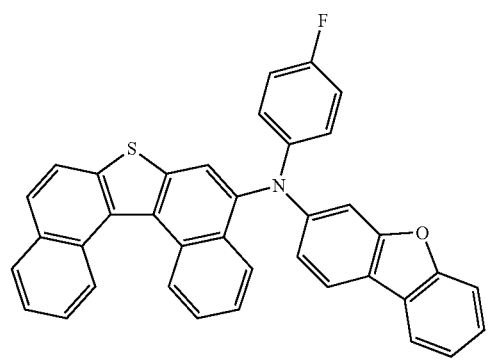 |
| 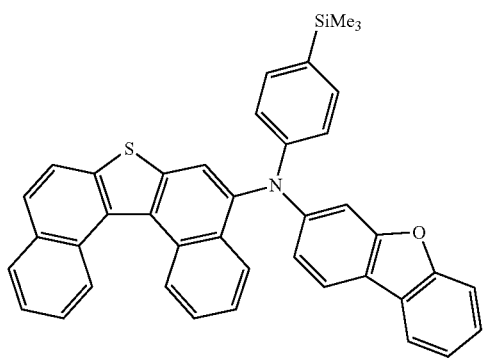 | 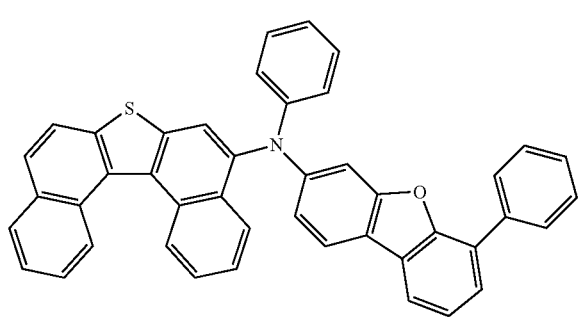 |
| 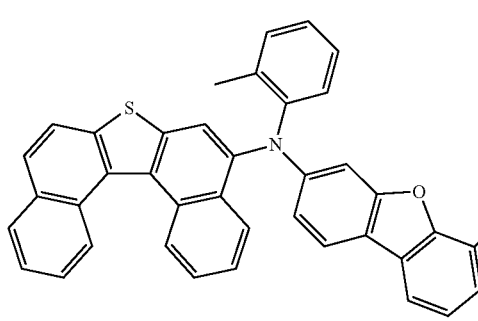 | 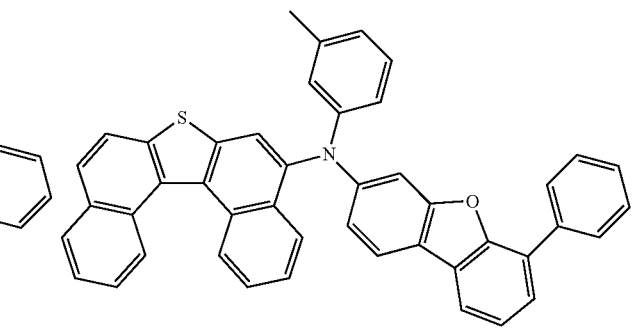 |

479 480
-continued
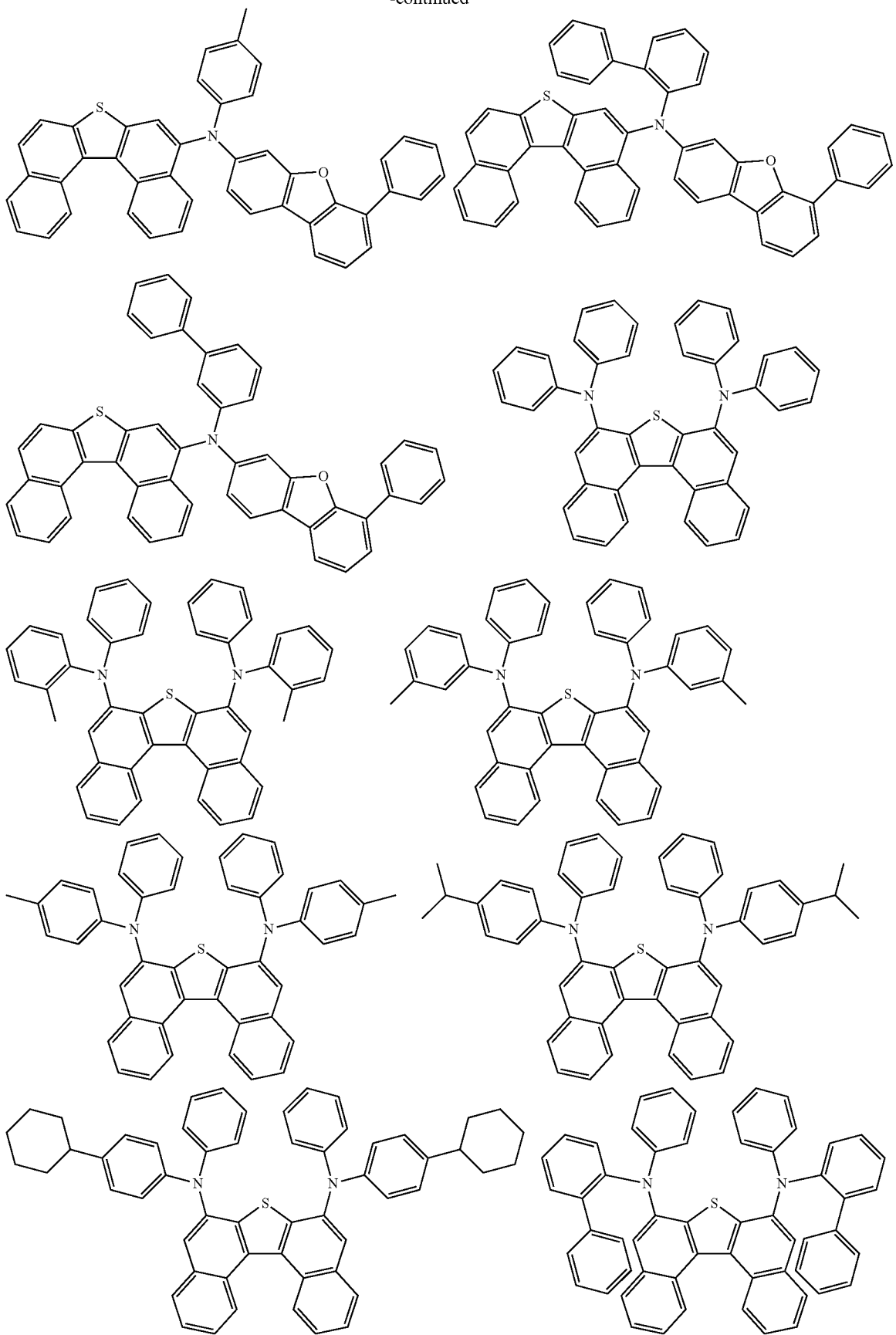

481 482
-continued
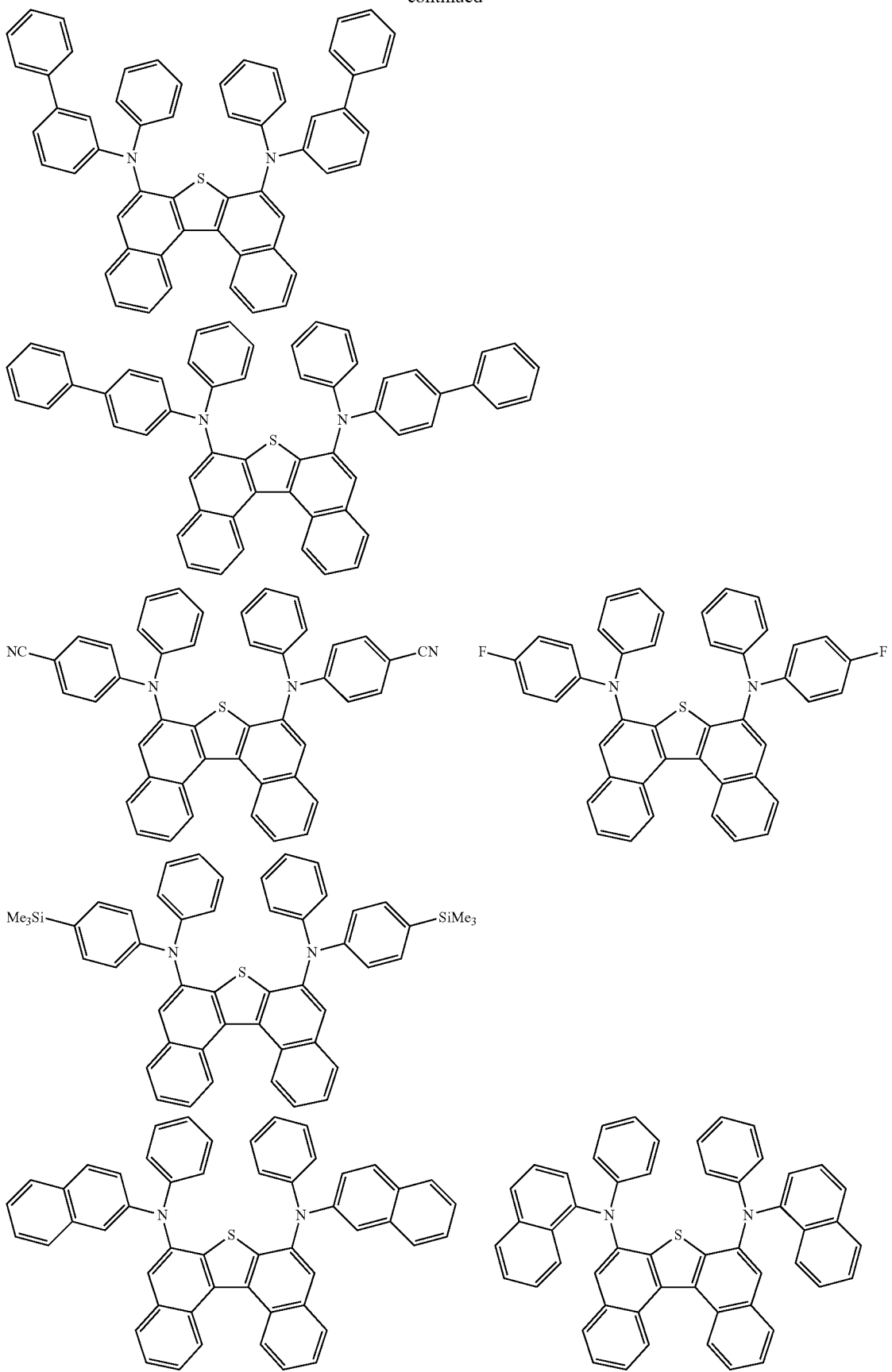

483
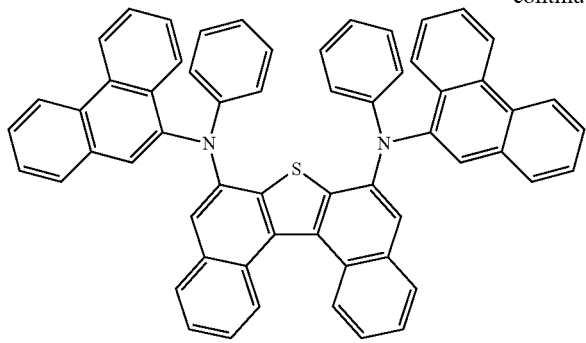
-continued
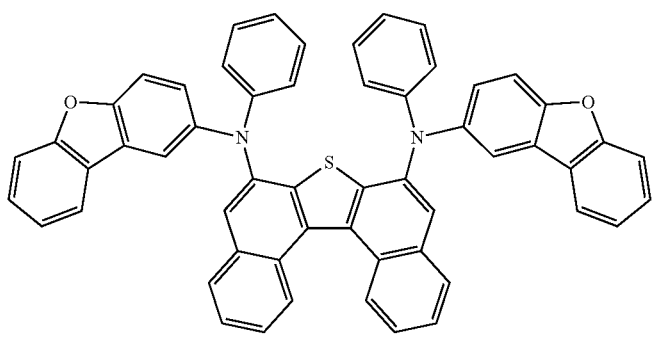
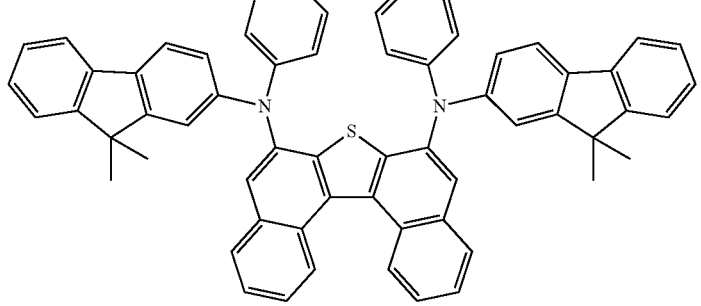
484
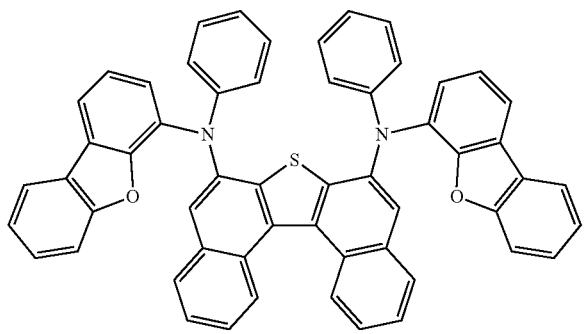
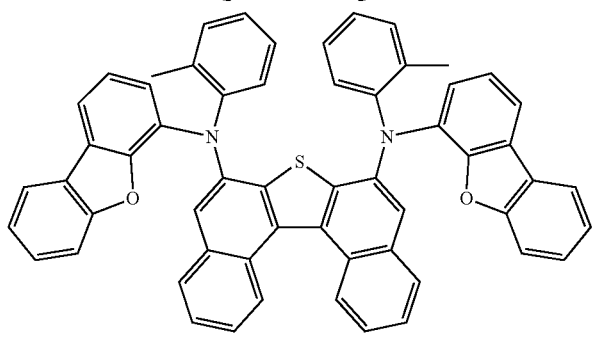

-continued

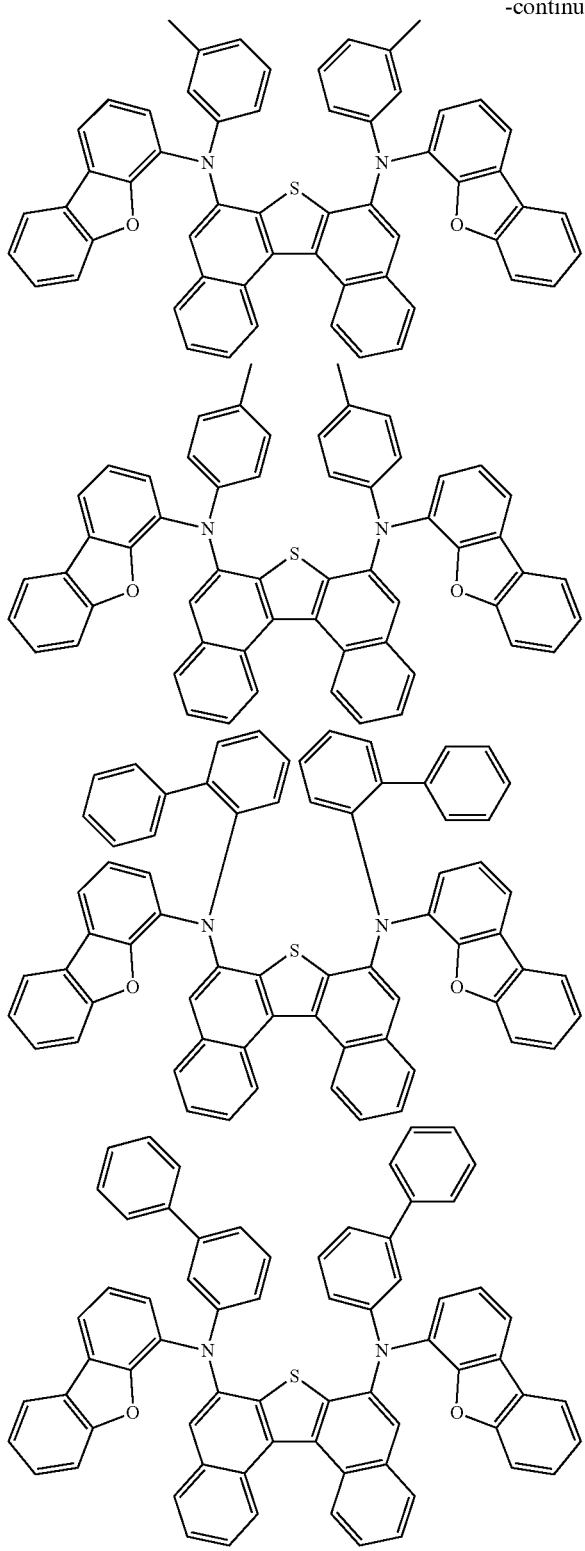

The amine compound is useful as a material for organic EL device, particularly as a dopant material for use in a fluorescent emitting layer.

Organic EL Device

The organic EL device of another embodiment of the invention will be described below.

The organic EL device comprises organic thin film layers between the cathode the anode. The organic thin film layers comprise a light emitting layer and at least one layer of the organic thin film layers comprises the amine compound mentioned above.

The organic thin film layer comprising the amine compound may include a hole transporting layer, a light emitting layer, a space layer, and a blocking layer, although not limited thereto. The amine compound is preferably used in a light emitting layer, particularly preferably in a fluorescent emitting layer as a dopant because it can be expected to make the organic EL device highly efficient.

The organic EL device may be any of a single color emitting device of fluorescent or phosphorescent type, a white-emitting device of fluorescent-phosphorescent hybrid type, an emitting device of a simple type having a single emission unit, and an emitting device of a tandem type having two or more emission units. The "emission unit" referred to herein is the smallest unit for emitting light by the recombination of injected holes and injected electrons, which comprises one or more organic layers wherein at least one layer is a light emitting layer.

Representative device structures of the simple-type organic EL device are shown below.

(1) Anode/Emission Unit/Cathode

The emission unit may be a laminate comprising two or more layers selected from a phosphorescent light emitting layer and a fluorescent light emitting layer. A space layer may be disposed between the light emitting layers to prevent the diffusion of excitons generated in the phosphorescent light emitting layer into the fluorescent light emitting layer. Representative layered structures of the emission unit are shown below.

(a) hole transporting layer/light emitting layer (/electron transporting layer);
(b) hole transporting layer/first fluorescent emitting layer/second fluorescent emitting layer (/electron transporting layer);
(c) hole transporting layer/phosphorescent emitting layer/space layer/fluorescent emitting layer (/electron transporting layer);
(d) hole transporting layer/first phosphorescent emitting layer/second phosphorescent emitting layer/space layer/fluorescent emitting layer (/electron transporting layer);
(e) hole transporting layer/first phosphorescent emitting layer/space layer/second phosphorescent emitting layer/space layer/fluorescent emitting layer (/electron transporting layer); and
(f) hole transporting layer/phosphorescent emitting layer/space layer/first fluorescent emitting layer/second fluorescent emitting layer (/electron transporting layer).

The emission color of the phosphorescent light emitting layer and that of the fluorescent light emitting layer may be different. For example, the layered structure of the laminated light emitting layer (d) may be hole transporting layer/first phosphorescent light emitting layer (red emission)/second phosphorescent light emitting layer (green emission)/space layer/fluorescent light emitting layer (blue emission)/electron transporting layer. An electron blocking layer may be disposed between the light emitting layer and the hole transporting layer or between the light emitting layer and the space layer, if necessary. Also, a hole blocking layer may be disposed between the light emitting layer and the electron transporting layer, if necessary. With such a electron blocking layer or a hole blocking layer, electrons and holes are confined in the light emitting layer to increase the degree of charge recombination in the light emitting layer, thereby improving the emission efficiency.

Representative device structure of the tandem-type organic EL device is shown below.

(2) Anode/First Emission Unit/Intermediate Layer/Second Emission Unit/Cathode

The layered structure of the first emission unit and the second emission unit may be selected from those described above with respect to the emission unit.

Generally, the intermediate layer is also called an intermediate electrode, an intermediate conductive layer, a charge generation layer, an electron withdrawing layer, a connecting layer, or an intermediate insulating layer. The intermediate layer may be formed by known materials so as to supply electrons to the first emission unit and holes to the second emission unit.

A schematic structure of an example of the organic EL device is shown in FIG. 1 wherein the organic EL device 1 is constructed by a substrate 2, an anode 3, a cathode 4, and an emission unit 10 (organic thin film layers) disposed between the anode 3 and the cathode 4. The emission unit 10 includes a light emitting layer 5 which comprises at least one fluorescent emitting layer containing a fluorescent host material and a fluorescent dopant. A hole injecting layer, a hole transporting layer, etc. 6 may be disposed between the light emitting layer 5 and the anode 3. An electron injecting layer, an electron transporting layer, etc. 7 may be disposed between the light emitting layer 5 and the cathode 4. An electron blocking layer may be disposed on the anode 3 side of the light emitting layer 5, and a hole blocking layer may be disposed on the cathode 4 side of the light emitting layer 5. With these blocking layers, electrons and holes are confined in the light emitting layer 5 to increase the degree of exciton generation in the light emitting layer 5.

In the present specification, the host is referred to as a fluorescent host when combinedly used with a fluorescent dopant and as a phosphorescent host when combinedly used with a phosphorescent dopant. Therefore, the fluorescent host and the phosphorescent host are not distinguished from each other merely by the difference in their molecular structures. Namely, the fluorescent host means a material for constituting a fluorescent emitting layer containing a fluorescent dopant and does not mean that the material is not usable as a material for constituting a phosphorescent emitting layer. The same also applies to the phosphorescent host.

Substrate

The organic EL device is formed on a light-transmissive substrate. The light-transmissive substrate serves as a support for the organic EL device and preferably a flat substrate having a transmittance of 50% or more to 400 to 700 nm visible light. Examples of the substrate include a glass plate and a polymer plate. The glass plate may include a plate made of soda-lime glass, barium-strontium-containing glass, lead glass, aluminosilicate glass, borosilicate glass, barium borosilicate glass, or quartz. The polymer plate may include a plate made of polycarbonate, acryl, polyethylene terephthalate, polyether sulfide, or polysulfone.

Anode

The anode of the organic EL device injects holes to the hole transporting layer or the light emitting layer, and an anode having a work function of 4.5 eV or more is effective. Examples of material for anode include indium tin oxide alloy (ITO), tin oxide (NESA), indium zinc oxide alloy, gold, silver, platinum, and copper. The anode is formed by making the electrode material into a thin film by a method, such as a vapor deposition method or a sputtering method. When getting the light emitted from the light emitting layer through the anode, the transmittance of anode to visible light is preferably 10% or more. The sheet resistance of anode is preferably several hundreds Ω/□ or less. The film thickness of anode depends upon the kind of material and generally 10 nm to 1 m, preferably 10 to 200 nm.

Cathode

The cathode injects electrons to the electron injecting layer, the electron transporting layer or the light emitting layer, and preferably formed from a material having a small work function. Examples of the material for cathode include, but not limited to, indium, aluminum, magnesium, magnesium-indium alloy, magnesium-aluminum alloy, aluminum-lithium alloy, aluminum-scandium-lithium alloy, and magnesium-silver alloy. Like the anode, the cathode is formed by making the material into a thin film by a method, such as the vapor deposition method and the sputtering method. The emitted light may be taken from the cathode, if appropriate.

Light Emitting Layer

The light emitting layer is an organic layer having a light emitting function and comprises a host material and a dopant material when a doping system is employed. The major function of the host material is to promote the recombination of electrons and holes and confine excitons in the light emitting layer. The dopant material causes the excitons generated by recombination to emit light efficiently.

In case of a phosphorescent device, the major function of the host material is to confine the excitons generated on the dopant in the light emitting layer.

To control the carrier balance in the light emitting layer, a double host (host and co-host) system may be used for the light emitting layer, for example, by combinedly using an electron transporting host and a hole transporting host.

The light emitting layer may be made into a double dopant layer, in which two or more kinds of dopant materials having high quantum yield are combinedly used and each dopant material emits light with its own color. For example, to obtain a yellow emission, a light emitting layer formed by co-depositing a host, a red-emitting dopant and a green-emitting dopant is used.

Electrons and holes can be accumulated in the interface between the light emitting layers by laminating two or more light emitting layers, thereby localizing the recombination region in the interface between the light emitting layer to improve the quantum efficiency.

The light emitting layer may be different in the hole injection ability and the electron injection ability, and also in the hole transporting ability and the electron transporting ability each being expressed by mobility.

The light emitting layer is formed, for example, by a known method, such as a vapor deposition method, a spin coating method, and LB method. Alternatively, the light emitting layer may be formed by making a solution of a binder, such as resin, and the material for the light emitting layer in a solvent into a thin film by a method such as spin coating.

The light emitting layer is preferably a molecular deposit film. The molecular deposit film is a thin film formed by depositing a vaporized material or a film formed by solidifying a material in the state of solution or liquid. The molecular deposit film can be distinguished from a thin film formed by LB method (molecular build-up film) by the differences in the assembly structures and higher order structures and the functional difference due to the structural differences.

The thickness of the light emitting layer is preferably 5 to 50 nm, more preferably 7 to 50 nm, and still more preferably 10 to 50 nm. If being 5 nm or more, the light emitting layer is easily formed. If being 50 nm or less, the increase in driving voltage is avoided.

Dopant

The fluorescent dopant (fluorescent emitting material) is a compound which emits light by releasing the energy of excited singlet state and not particularly limited as long as emitting light by releasing the energy of excited singlet state. Examples thereof include a fluoranthene derivative, a styrylarylene derivative, a pyrene derivative, an arylacetylene derivative, a fluorene derivative, a boron complex, a perylene derivative, an oxadiazole derivative, an anthracene derivative, a styrylamine derivative, and an arylamine derivative, with an anthracene derivative, a fluoranthene derivative, a styrylamine derivative, an arylamine derivative, a styrylarylene derivative, a pyrene derivative, and a boron complex being preferred, and an anthracene derivative, a fluoranthene derivative, a styrylamine derivative, an arylamine derivative, and a boron complex compound being more preferred.

The content of the phosphorescent dopant in the light emitting layer is not particularly limited and selected according to the use of the device. The content is preferably 0.1 to 70% by mass, more preferably 1 to 30% by mass, still more preferably 1 to 20% by mass, and particularly preferably 1 to 10% by mass. If being 0.1% by mass or more, the amount of light emission is sufficient. If being 70% by mass or less, the concentration quenching can be avoided.

Host

An anthracene derivative or a compound having a polycyclic aromatic skeleton, preferably an anthracene derivative is preferably used as the host for the light emitting layer.

For example, the following anthracene derivative represented by formula (5a) is used as the host for a blue-light emitting layer:

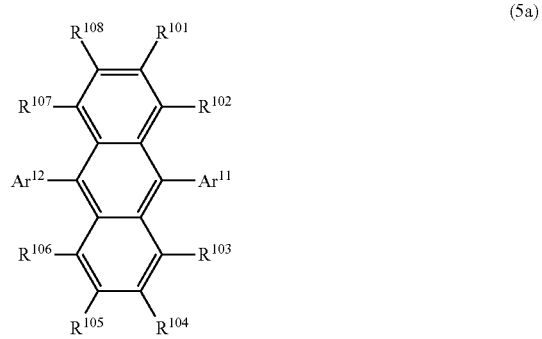

(5a)

wherein each of $Ar^{11}$ and $Ar^{12}$ independently represents a substituted or unsubstituted monocyclic group having 5 to 50 ring atoms or a substituted or unsubstituted fused ring group having 8 to 50 ring atoms. Each of $R^{101}$ to $R^{108}$ independently represents a group selected from a hydrogen atom, a substituted or unsubstituted monocyclic group having 5 to 50 ring atoms, a substituted or unsubstituted fused ring group having 8 to 50 ring atoms, a group constituted of a combination of the monocyclic group and the fused ring group, a substituted or unsubstituted alkyl group having 1 to 50 carbon atoms, a substituted or unsubstituted cycloalkyl group having 3 to 50 ring carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring carbon atoms, a substituted or unsubstituted silyl group, a halogen atom, and a cyano group. Preferred is the anthracene derivative wherein $R^{101}$ to $R^{108}$ are all hydrogen atoms, or one of $R^{101}$ and $R^{108}$, one of $R^{104}$ and $R^{105}$, both of $R^{101}$ and $R^{105}$, or both of $R^{108}$ and $R^{104}$ are selected from a monocyclic group having 5 to 50 ring atoms, preferably a phenyl group, a biphenylyl group, or a terphenylyl group; a substituted or unsubstituted alkyl group having 1 to 50 carbon atoms, preferably a methyl group, an ethyl group, a n-propyl group, an isopropyl group, a n-butyl group, an isobutyl group, a s-butyl group, and a t-butyl group; or a substituted silyl group, preferably a trimethylsilyl group. More preferred is the anthracene derivative wherein $R^{101}$ to $R^{108}$ are all hydrogen atoms.

In formula (5a), the monocyclic group is a group composed of only a ring structure having no fuse ring structure.

Examples of the monocyclic group having 5 to 50, preferably 5 to 30, and more preferably 5 to 20 ring atoms include an aromatic group, such as a phenyl group, a biphenylyl group, a terphenylyl group, and a quaterphenylyl group; and a heterocyclic group, such as a pyridyl group, a pyrazyl group, a pyrimidyl group, a triazinyl group, a furyl group, and a thienyl group, with a phenyl group, a biphenylyl group, and a terphenylyl group being preferable.

In formula (5a), the fused ring group is a group composed of two or more ring structures which are fused to each other.

Examples of the fused ring group having 8 to 50, preferably 8 to 30, and more preferably 8 to 20 ring atoms include a fused aromatic ring group, such as a naphthyl group, a phenanthryl group, an anthryl group, a chrysenyl group, a benzoanthryl group, a benzophenanthryl group, a triphenylenyl group, a benzochrysenyl group, an indenyl group, a fluorenyl group, a 9, 9-dimethylfluorenyl group, a benzofluorenyl group, a dibenzofluorenyl group, a fluoranthenyl group, and a benzofluoranthenyl group; and a fused heterocyclic group, such as a benzofuranyl group, a benzothiophenyl group, an indolyl group, a dibenzofuranyl group, a dibenzothiophenyl group, a carbazolyl group, a quinolyl group, and a phenanthrolinyl group, with a naphthyl group, a phenanthryl group, an anthryl group, a 9, 9-dimethylfluorenyl group, a fluoranthenyl group, a benzoanthryl group, a dibenzothiophenyl group, a dibenzofuranyl group, and a carbazolyl group being preferable.

The substituent of $Ar^{11}$ and $Ar^{12}$ is preferably selected from the monocyclic groups and the fused ring groups mentioned above.

In formula (5a), examples of the alkyl group, the cycloalkyl group, the alkoxy group, the alkyl portion and the aryl portion of the aralkyl group, the aryloxy group, the substituted silyl group (alkylsilyl group and arylsilyl group), and the halogen atom are as defined above with respect to $R^1$ to $R^8$ and $R^a$ to $R^d$ of formula (2).

In formula (5a), $R^{101}$ to $R^{108}$ are preferably all hydrogen atoms, or one of $R^{101}$ and $R^{108}$, one of $R^{104}$ and $R^{105}$, both of $R^{101}$ and $R^{105}$, or both of $R^{108}$ and $R^{104}$ are preferably selected from a monocyclic group having 5 to 50 ring atoms, for example, a phenyl group, a biphenylyl group, or a terphenylyl group; a substituted or unsubstituted alkyl group having 1 to 50 carbon atoms, for example, a methyl group, an ethyl group, a n-propyl group, an isopropyl group, a n-butyl group, an isobutyl group, a s-butyl group, and a t-butyl group; or a substituted silyl group, for example, a trimethylsilyl group, with $R^{101}$ to $R^{108}$ wherein all are hydrogen atoms being more preferred.

The anthracene derivative represented by formula (5a) is preferably any of the following anthracene derivatives (A), (B) and (C), and it is selected depending upon the constitution of the organic EL device to be applied or the required properties.

Anthracene Derivative (A)

The anthracene derivative (A) is represented by formula (5a) wherein each of $Ar^{11}$ and $Ar^{12}$ independently represents a substituted or unsubstituted fused ring group having 8 to 50 ring atoms. $Ar^{11}$ and $Ar^{12}$ may be the same or different.

The anthracene derivative represented by formula (5a) wherein $Ar^{11}$ and $Ar^{12}$ are different substituted or unsubstituted fused ring groups (inclusive of the difference in the positions connecting to the anthracene ring) is particularly preferable. Examples of the fused ring are as described above, with a naphthyl group, a phenanthryl group, a benzanthryl group, a 9, 9-dimethylfluorenyl group, and a dibenzofuranyl group being preferable.

Anthracene Derivative (B)

The anthracene derivative (B) is represented by the formula (5a) wherein one of $Ar^{11}$ and $Ar^{12}$ is a substituted or unsubstituted monocyclic group having 5 to 50 ring atoms and the other is a substituted or unsubstituted fused ring group having 8 to 50 ring atoms.

In a preferred anthracene derivative (B), $Ar^{12}$ is a naphthyl group, a phenanthryl group, a benzoanthryl group, a 9, 9-dimethylfluorenyl group, or a dibenzofuranyl group; and $Ar^{11}$ is an unsubstituted phenyl group or a phenyl group substituted with a monocyclic group or a fused ring group, for example, a phenyl group, a biphenyl group, a naphthyl group, a phenanthryl group, a 9, 9-dimethylfluorenyl group, or a dibenzofuranyl group.

Examples of the monocyclic groups and the fused ring groups are as described above.

In another preferred anthracene derivative (B), $Ar^{12}$ is a substituted or unsubstituted fused ring group having 8 to 50 ring atoms and $Ar^{11}$ is an unsubstituted phenyl group. The fused ring group is particularly preferably a phenanthryl group, a 9, 9-dimethylfluorenyl group, a dibenzofuranyl group, or a benzoanthryl group.

Anthracene Derivative (C)

The anthracene derivative (C) is represented by the formula (5a) wherein each of $Ar^{11}$ and $Ar^{12}$ independently represents a substituted or unsubstituted monocyclic group having 5 to 50 ring atoms.

In a preferred anthracene derivative (C), both of $Ar^{11}$ and $Ar^{12}$ are substituted or unsubstituted phenyl groups.

In a more preferred anthracene derivative (C), $Ar^{11}$ is an unsubstituted phenyl group and $Ar^{12}$ is a phenyl group substituted by a monocyclic group or a fused ring group; or each of $Ar^{11}$ and $Ar^{12}$ independently represents a phenyl group substituted by a monocyclic group or a fused ring group.

Examples of the monocyclic group and the fused ring group which are preferable as the substituent are as described above. The monocyclic ring as the substituent is more preferably a phenyl group and a biphenyl group, and the fused ring group as the substituent is more preferably a naphthyl group, a phenanthryl group, a 9, 9-dimethylfluorenyl group, a dibenzofuranyl group, and a benzoanthryl group.

Examples of the anthracene derivative represented by formula (5a) are described below EM1
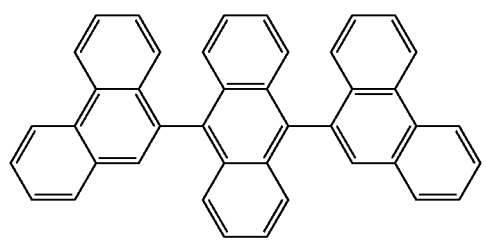
EM2
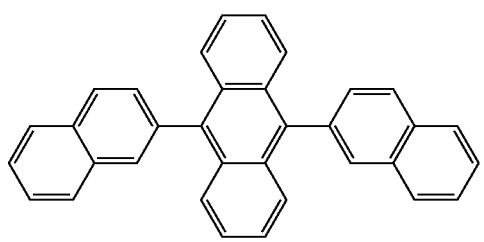
EM3
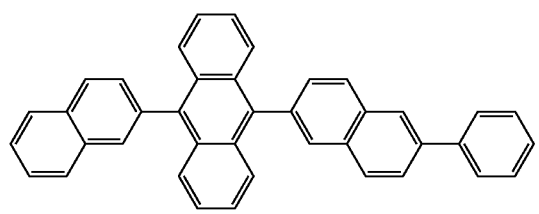
EM4
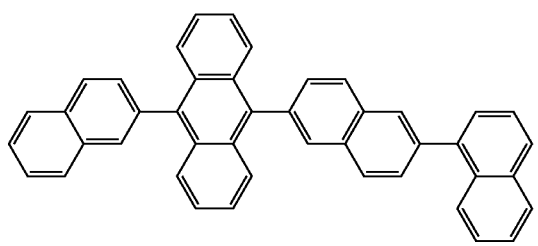
EM5
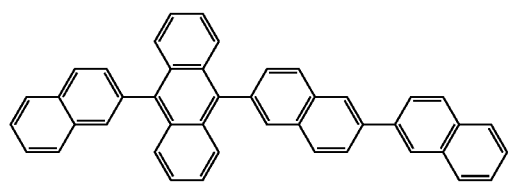
EM6
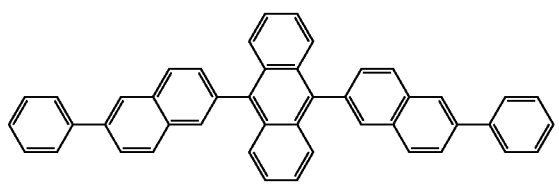
EM7
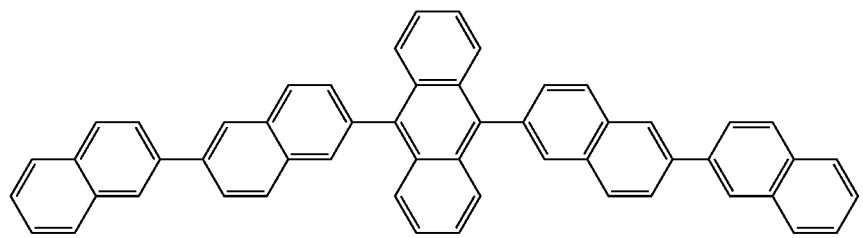
EM8
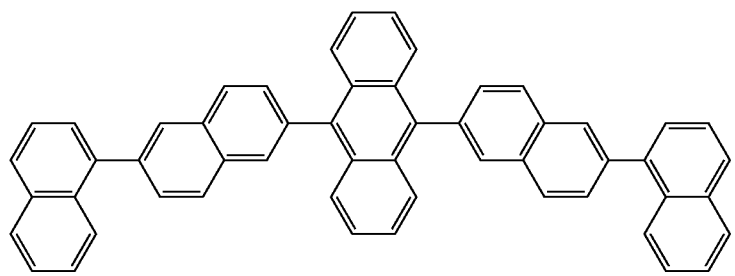
EM9
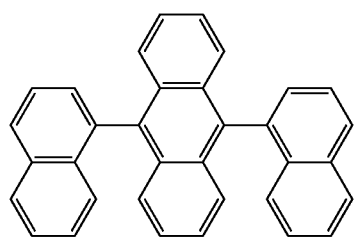
EM10
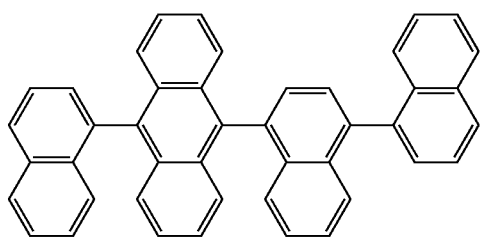

-continued
EM11
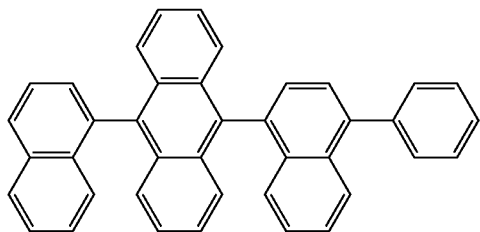
EM12
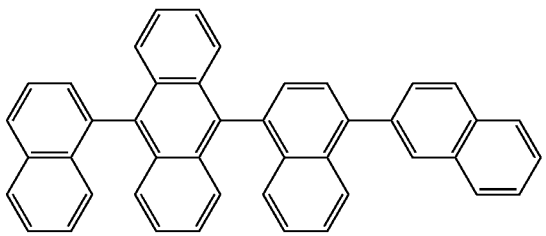
EM13
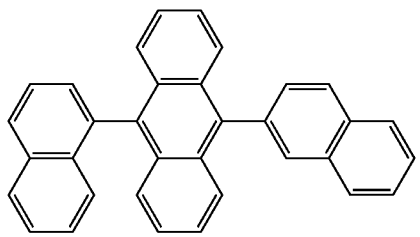
EM14
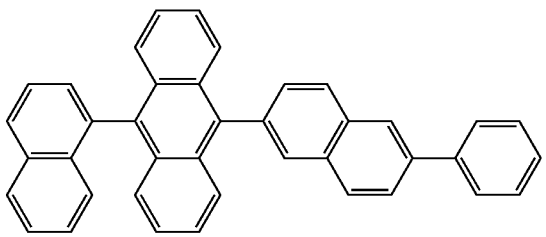
EM15
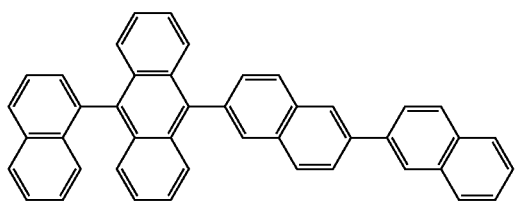
EM16
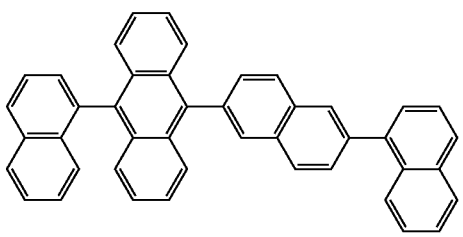
EM17
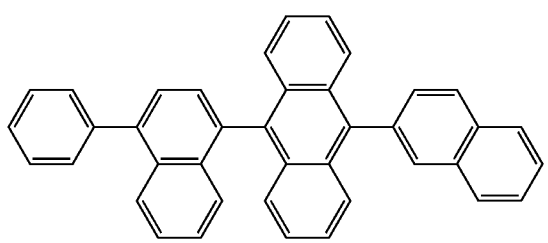
EM18
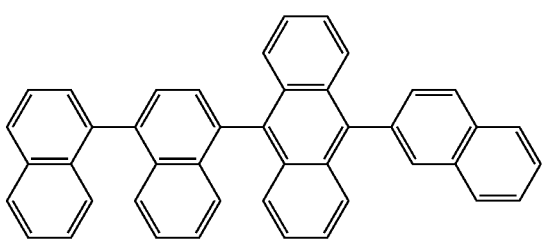
EM19
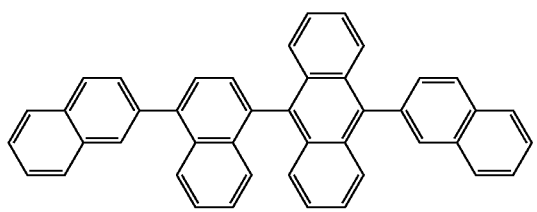
EM20
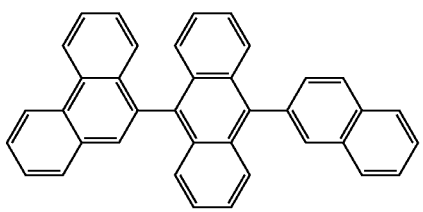
EM21
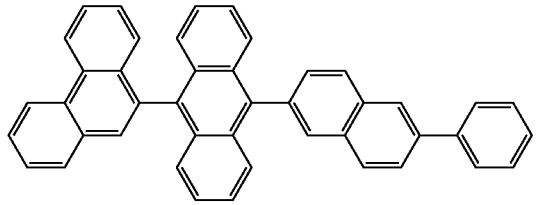
EM22
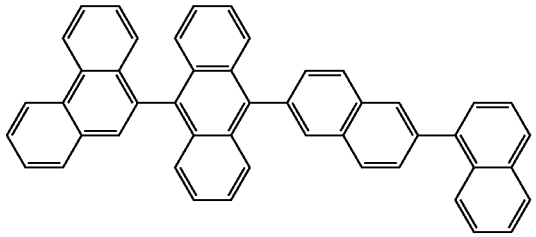

-continued

EM23  EM24  
EM25  EM26  
EM27  EM28  
EM29  EM30  
EM31  EM32

-continued
EM33
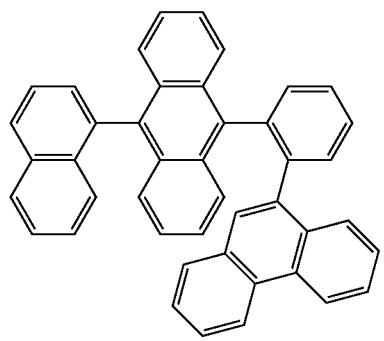
EM34
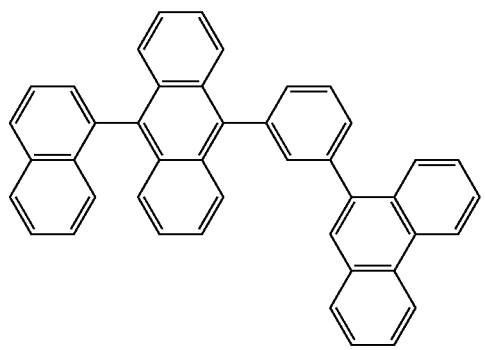
EM35
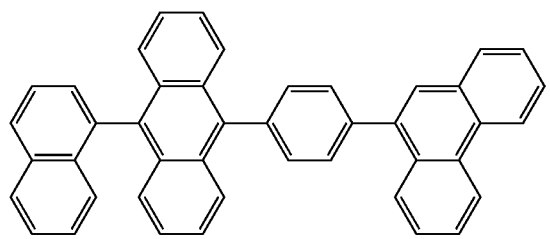
EM36
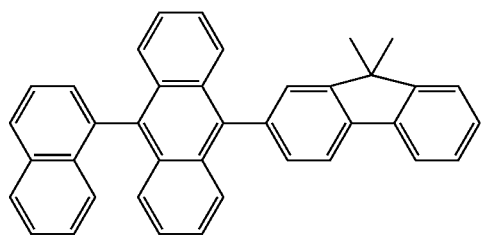
EM37
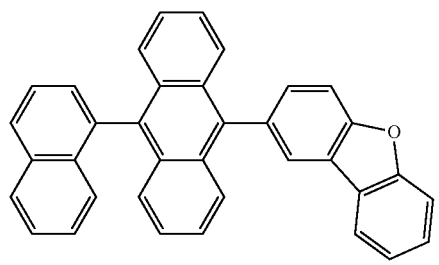
ME38
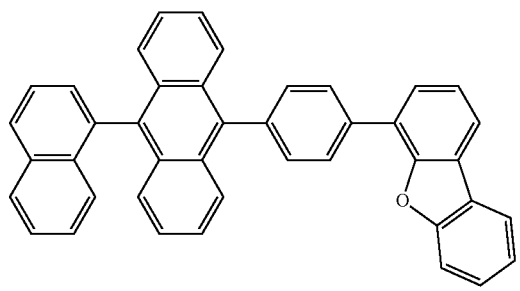
EM39
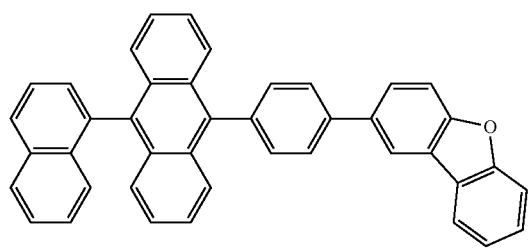
EM40
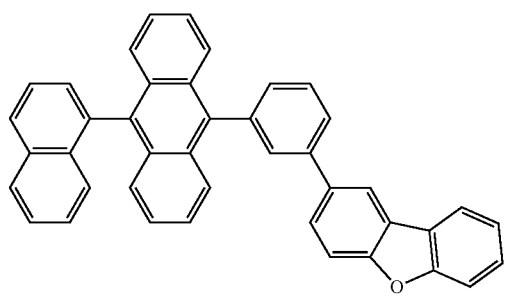
EM41
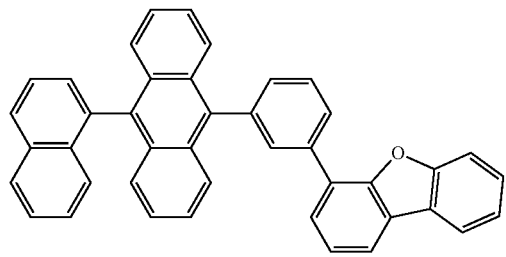
EM42
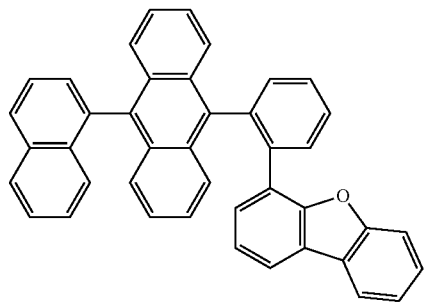

-continued
EM43
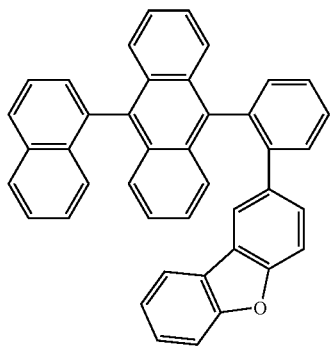
EM44
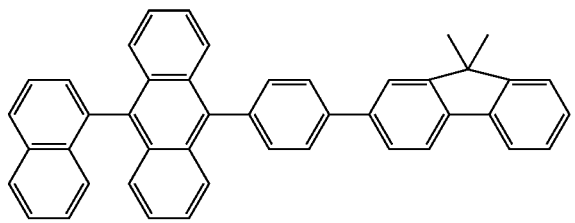
EM45
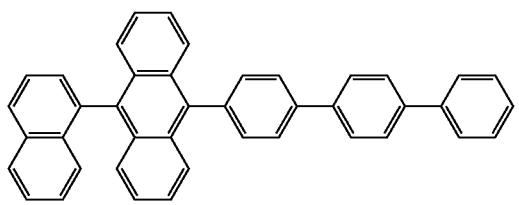
EM46
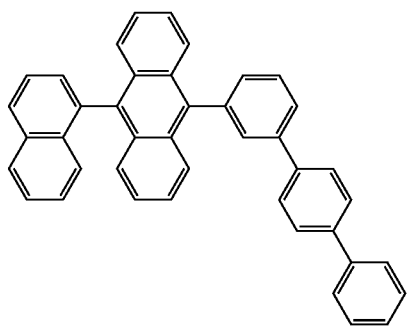
EM47
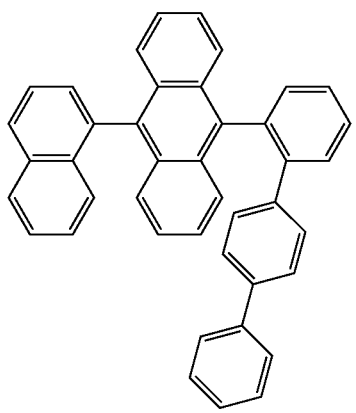
EM48
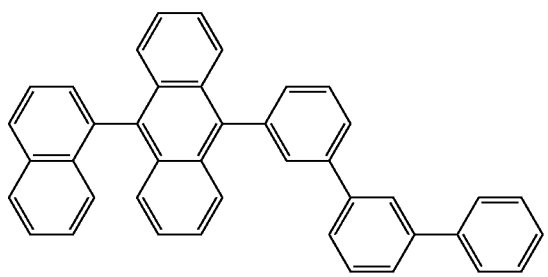
EM49
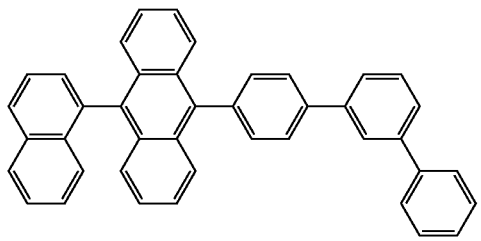
EM50
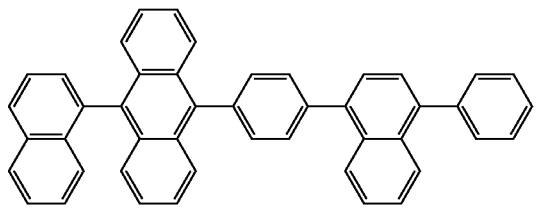
EM51
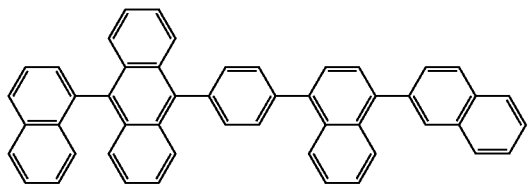
EM52
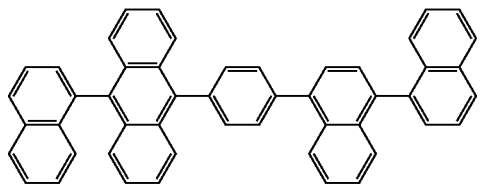

-continued

EM53 EM54

EM55 EM56

EM57 EM58

EM59 EM60

EM61 EM62

-continued
EM63
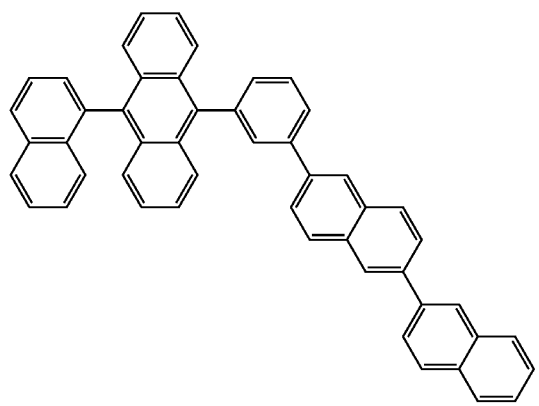
EM64
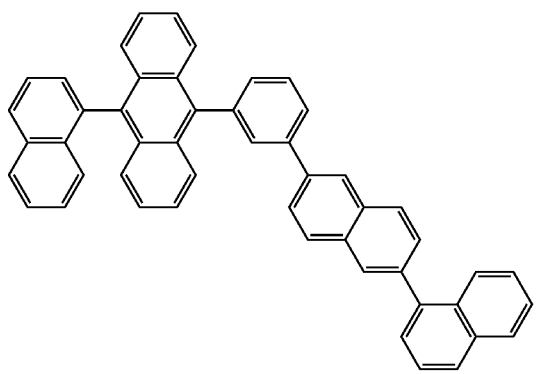
EM65
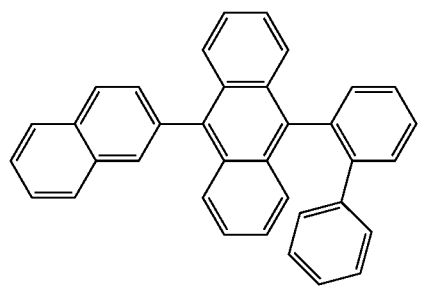
EM66
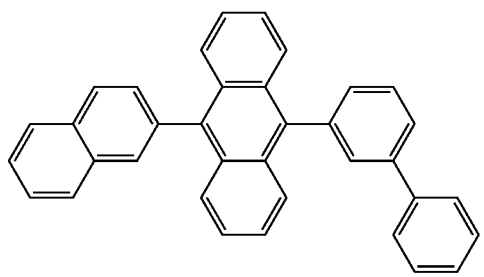
EM67
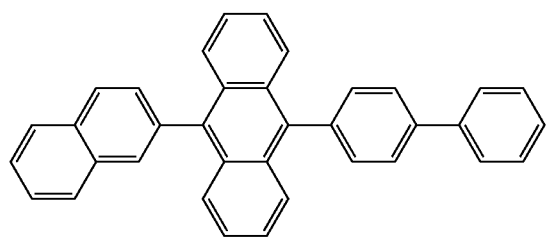
EM68
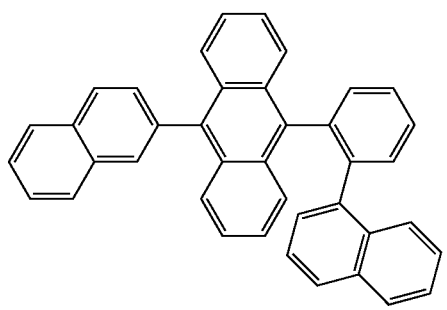
EM69
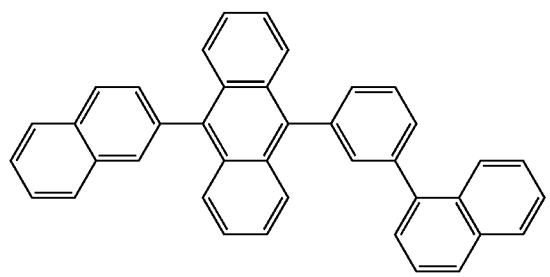
EM70
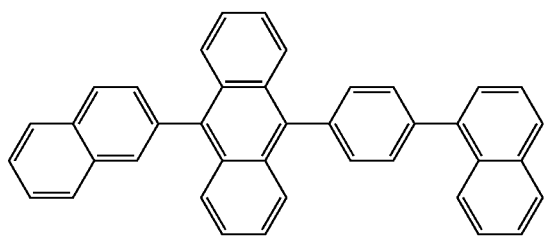

-continued
EM71
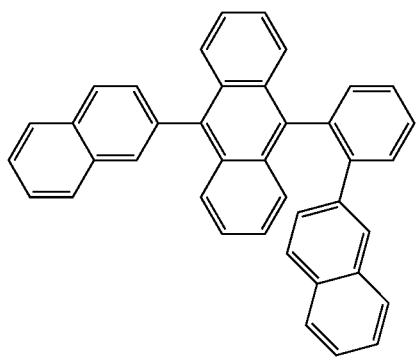
EM72
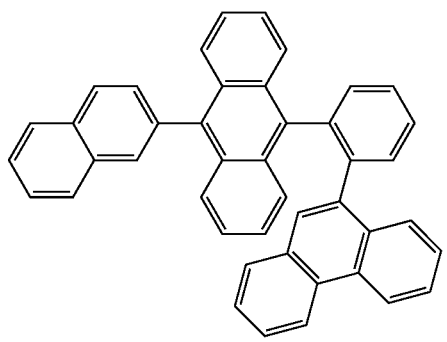
EM73
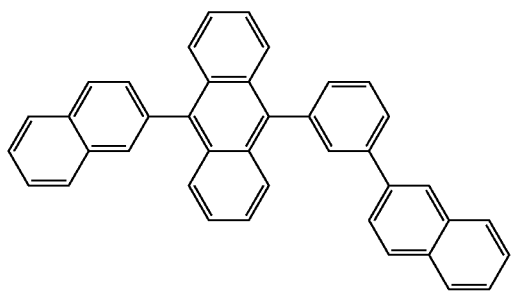
EM74
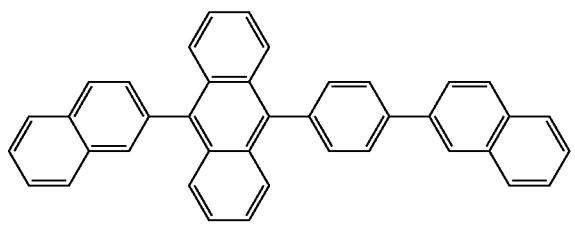
EM75
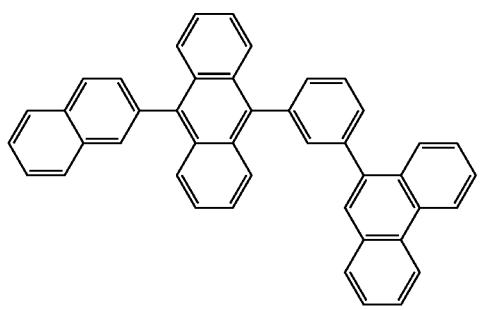
EM76
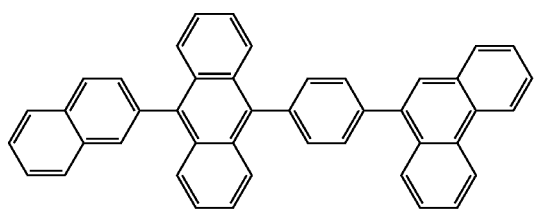
EM77
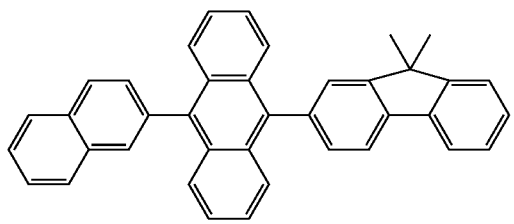
EM78
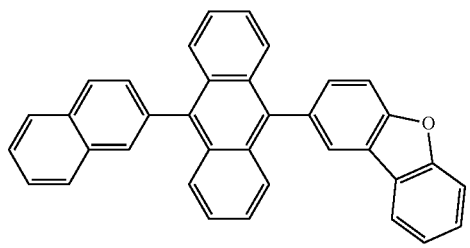
EM79
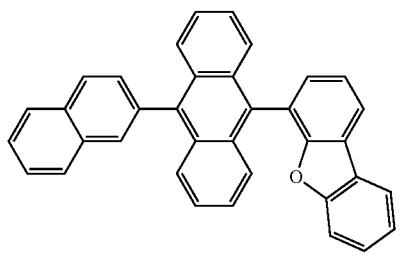
EM80
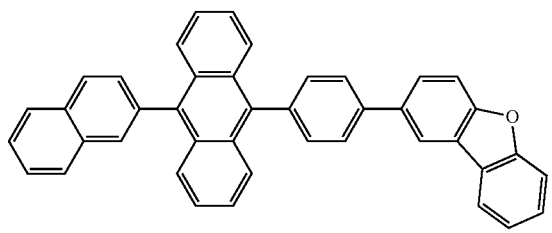

-continued
EM81
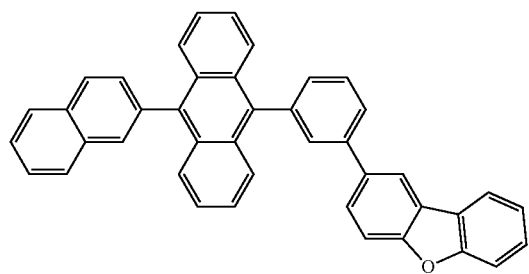
EM82
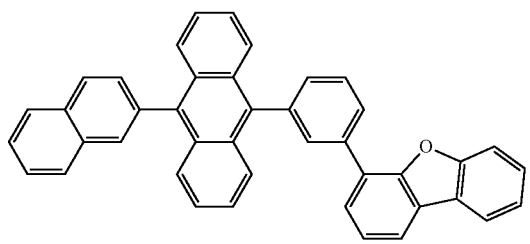
EM83
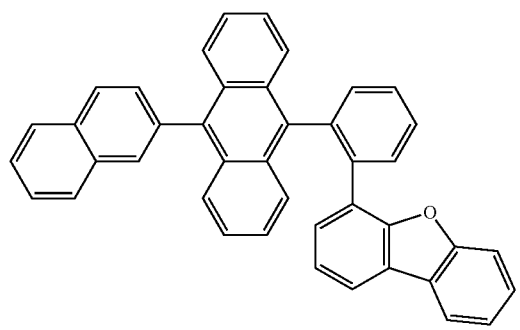
EM84
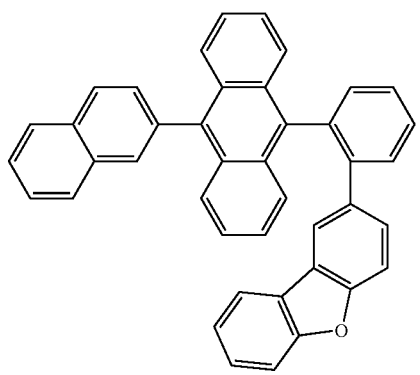
EM85
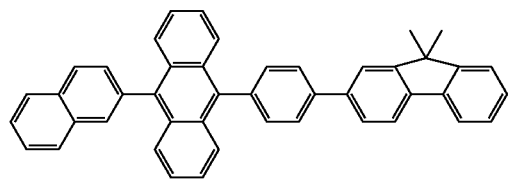
EM86
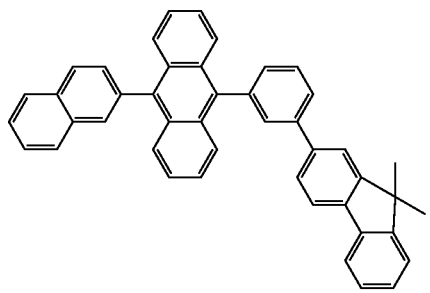
EM87
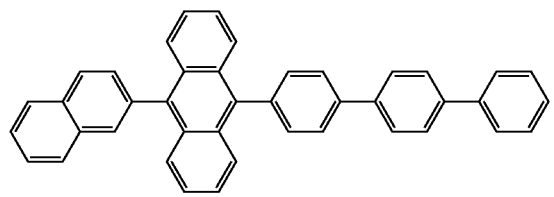
EM88
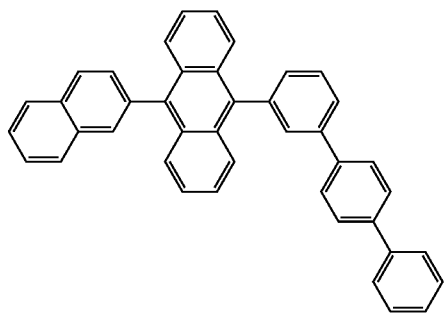

-continued
EM89
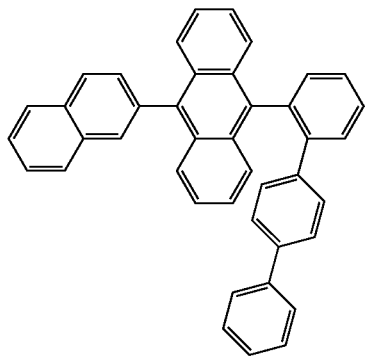
EM90
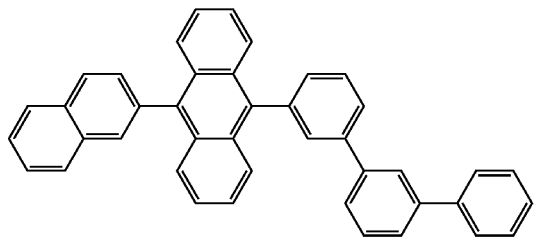
EM91
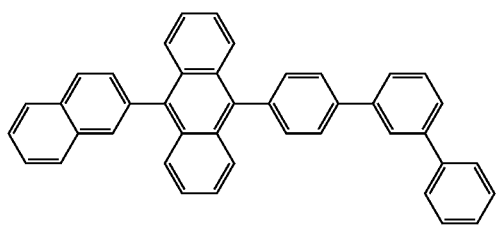
EM92
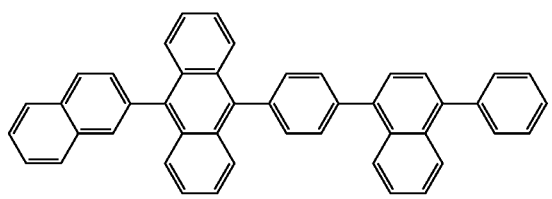
EM93
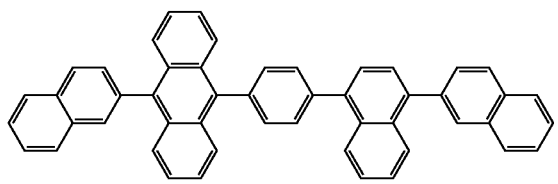
EM94
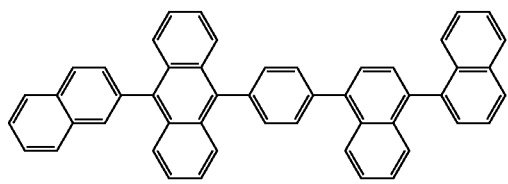
EM95
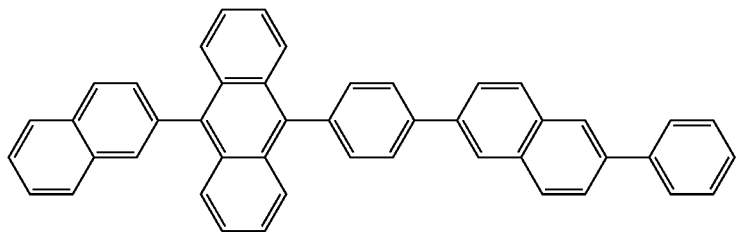
EM96
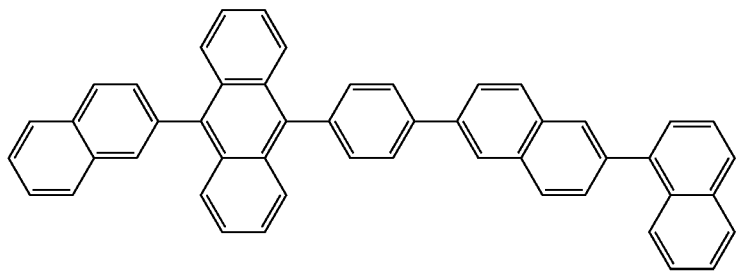
EM97
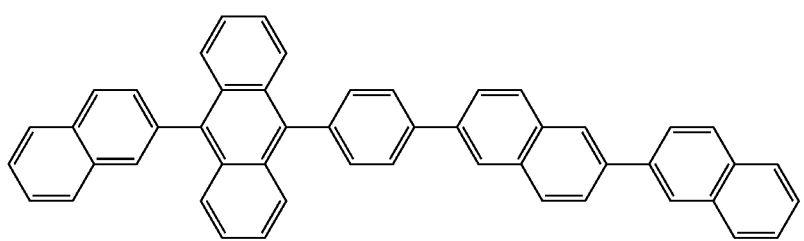

-continued
EM98
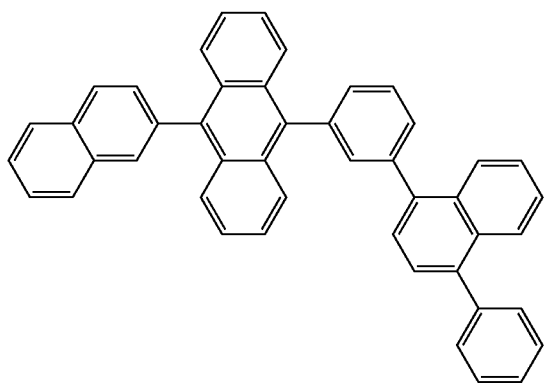
EM99
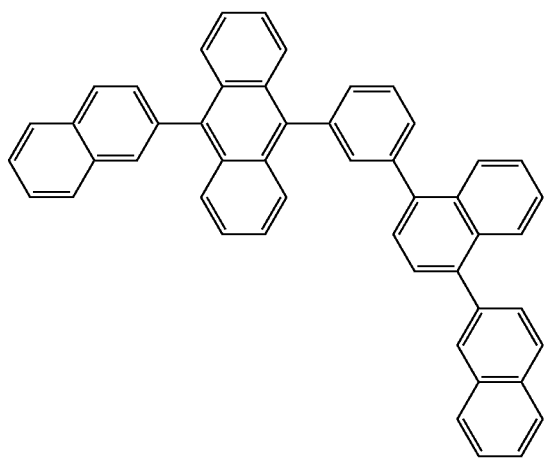
EM100
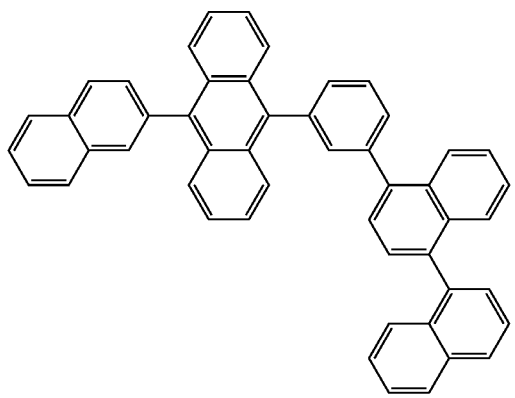
EM101
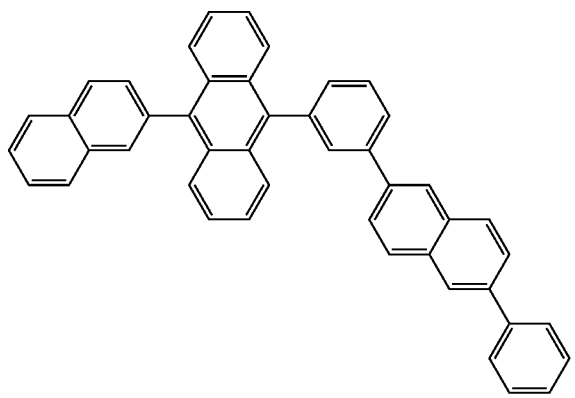
EM102
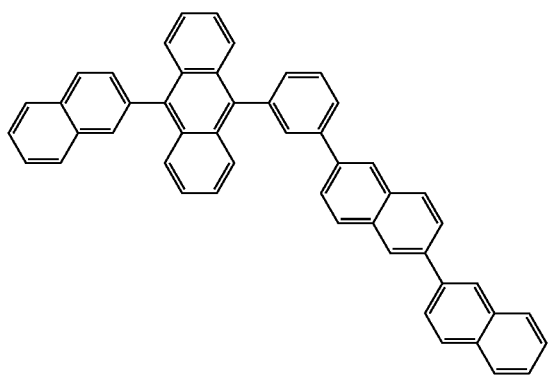
EM103
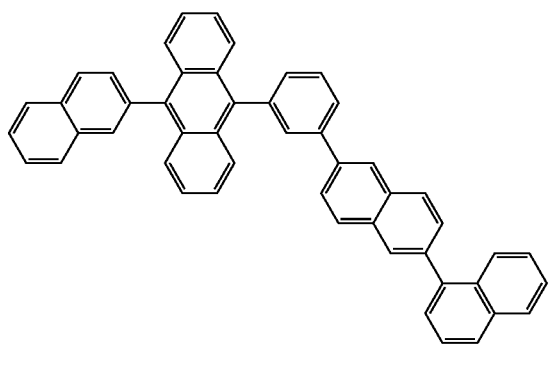
EM104
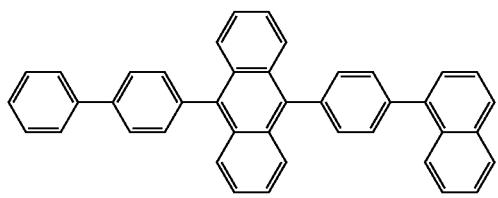
EM105
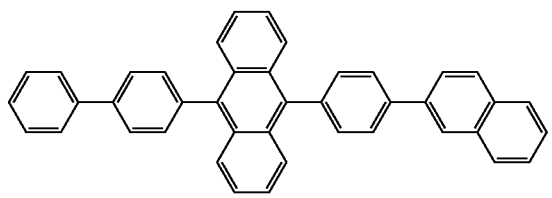

-continued
EM106
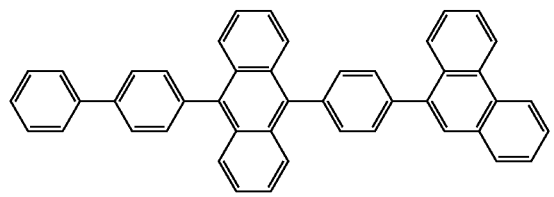
EM107
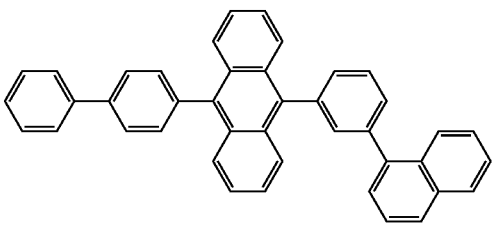
EM108
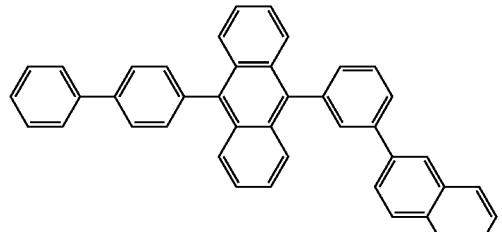
EM109
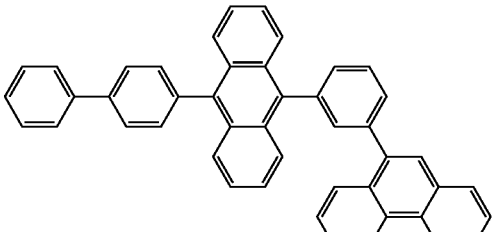
EM110
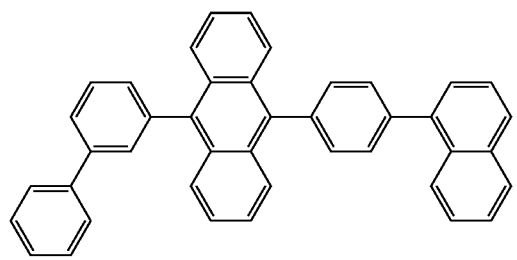
EM111
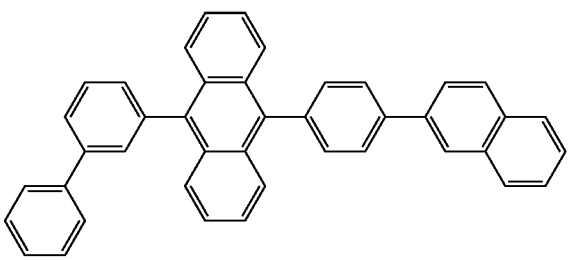
EM112
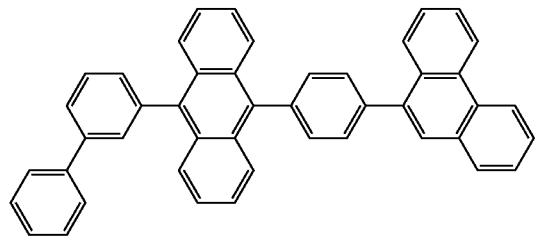
EM113
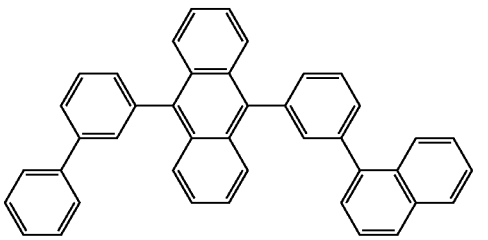
EM114
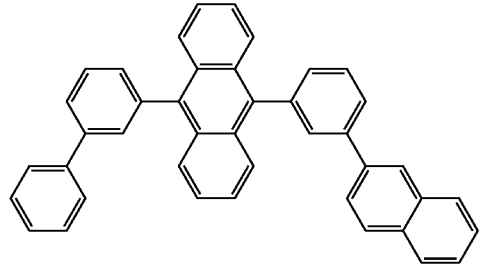
EM115
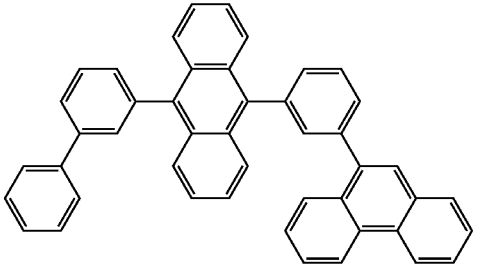
EM116
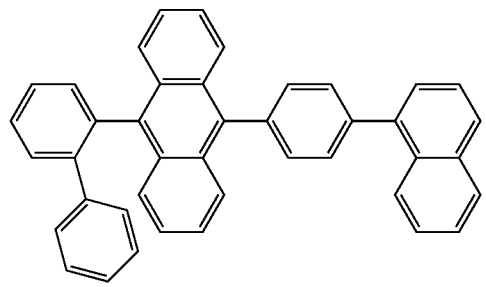
EM117
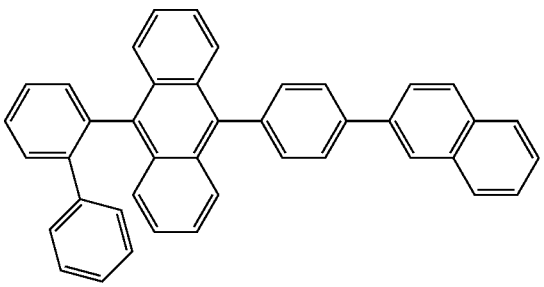

-continued
EM118
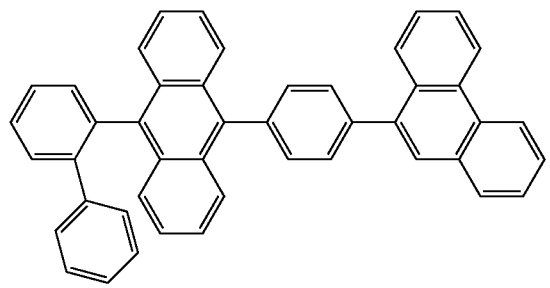
EM119
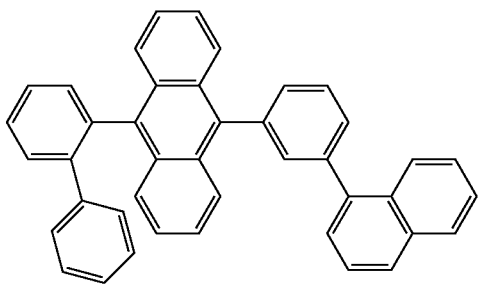
EM120
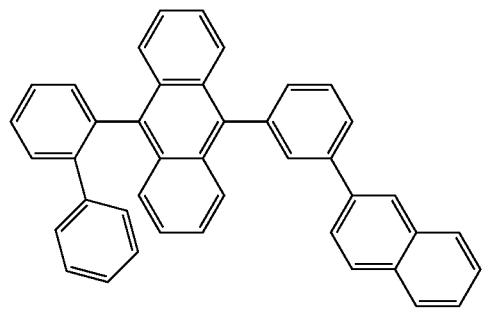
EM121
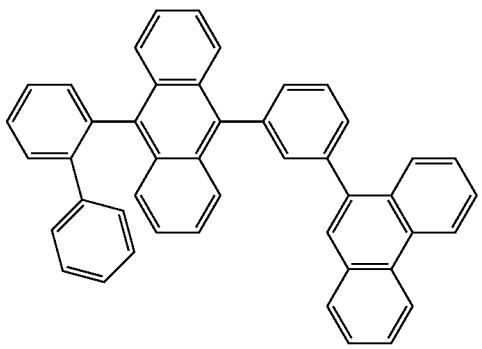
EM122
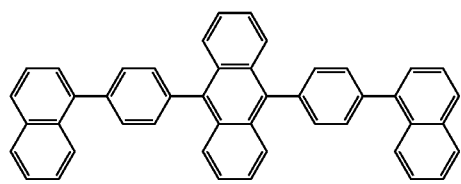
EM123
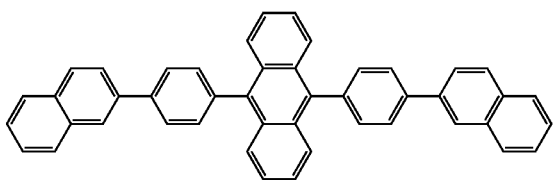
EM124
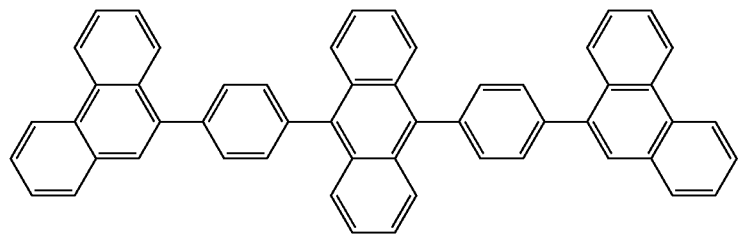
EM125
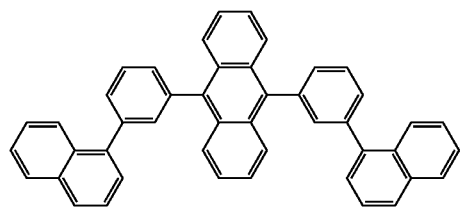
EM126
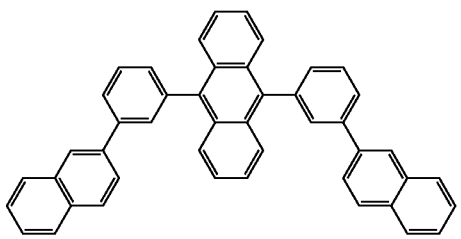
EM127
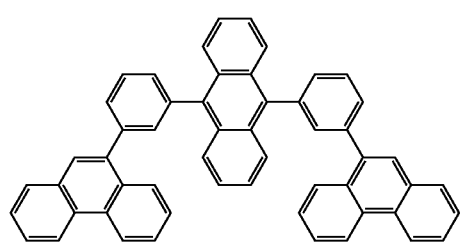
EM128
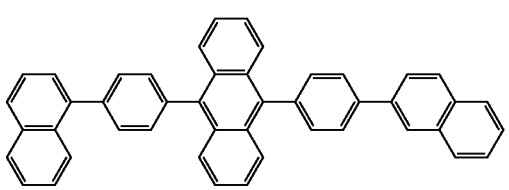

-continued
EM129
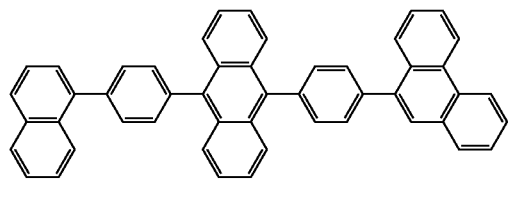
EM130
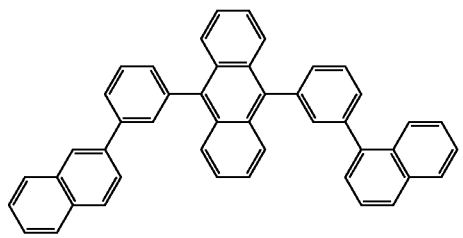
EM131
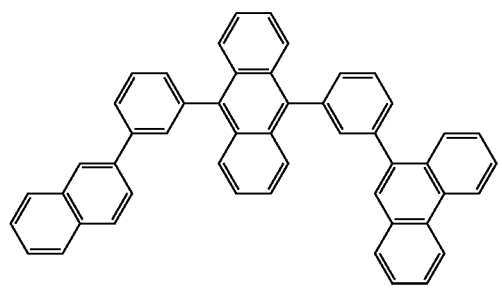
EM132
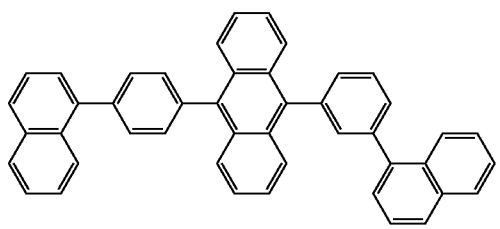
EM133
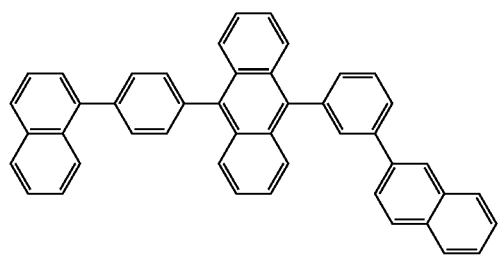
EM134
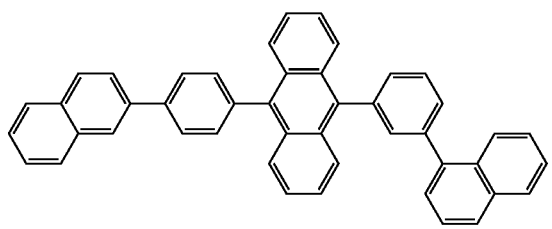
EM135
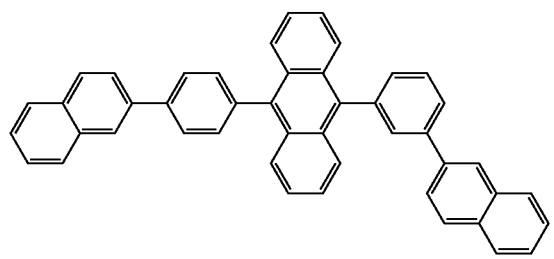
EM136
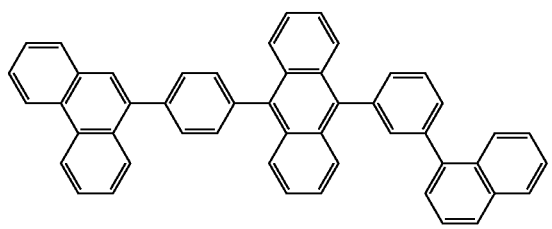
EM137
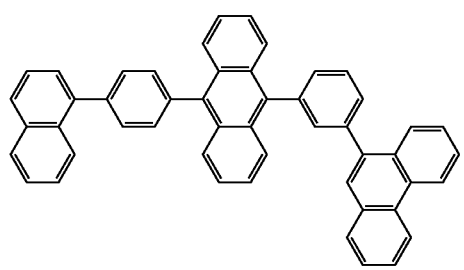
EM138
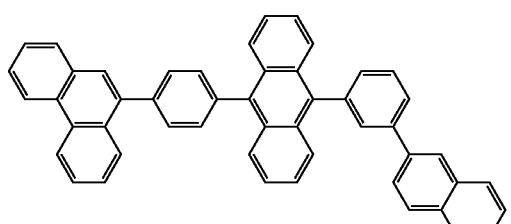

-continued
EM139
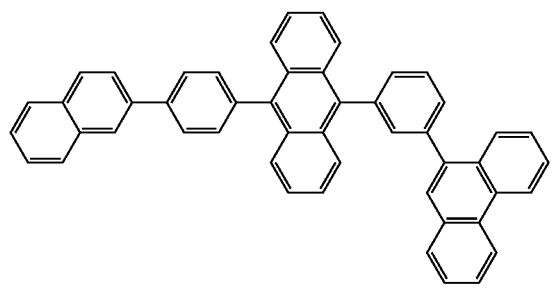
EM140
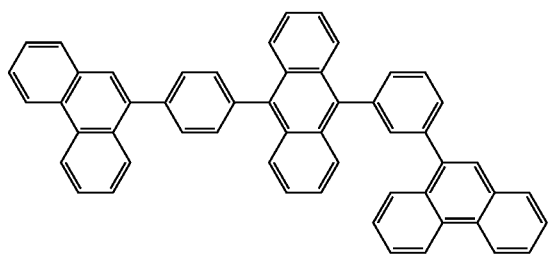
EM141
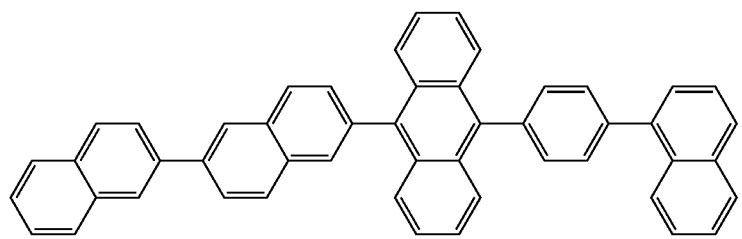
EM142
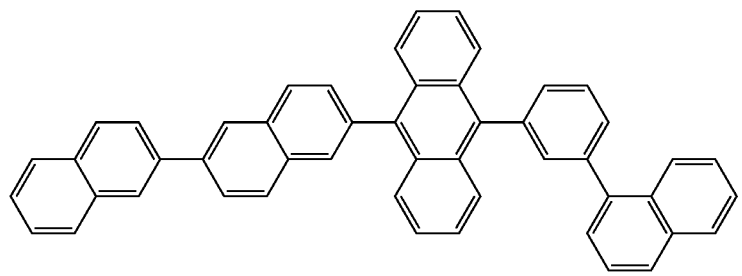
EM143
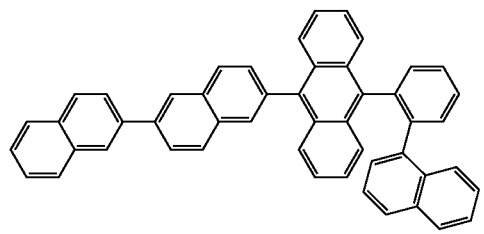
EM144
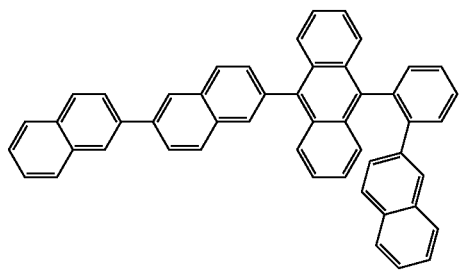
EM145
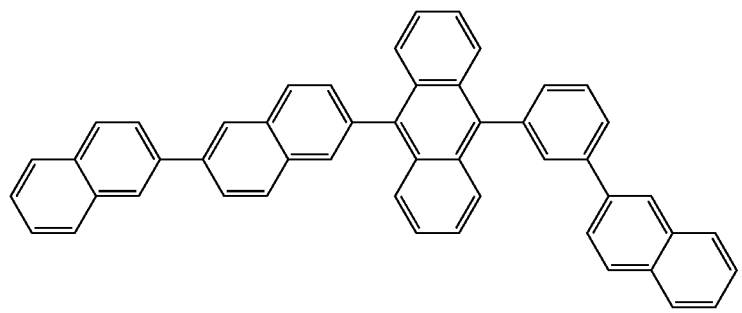

EM146
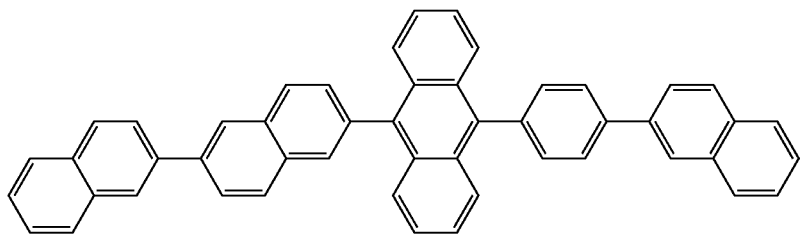
EM147
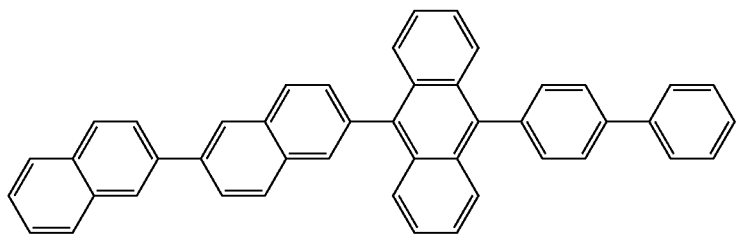
EM148 EM149
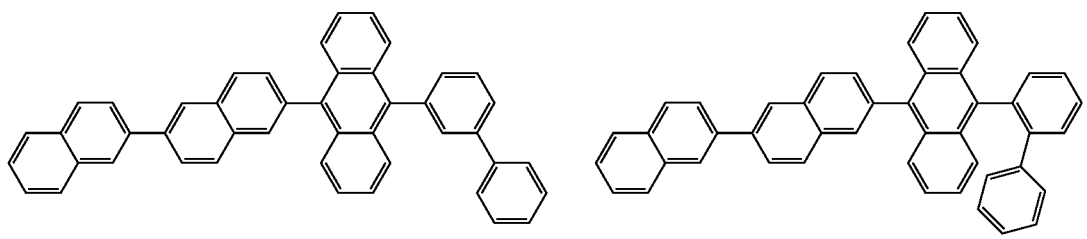
EM150
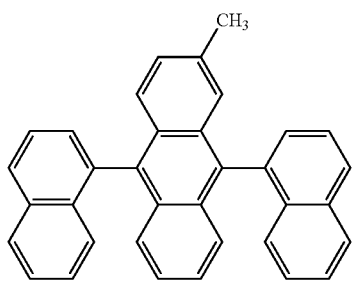
EM151
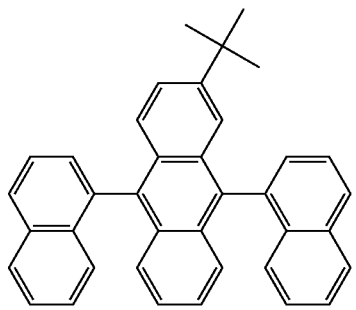
EM152
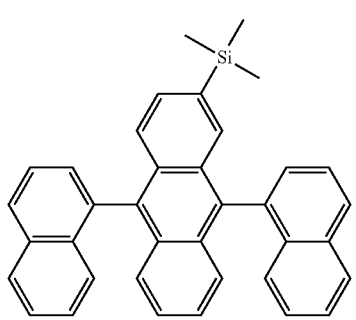
EM153
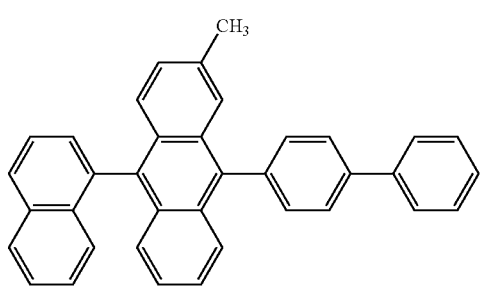

-continued
EM154
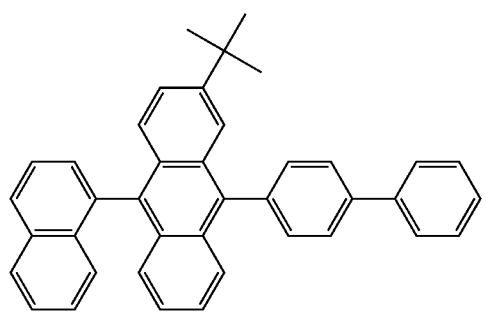
EM155
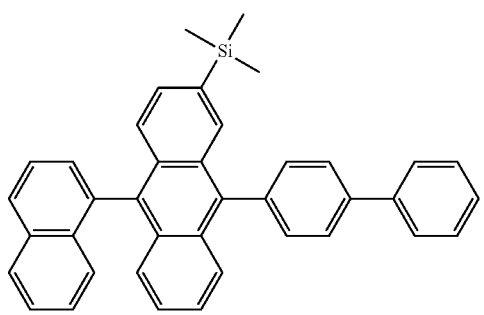
EM156
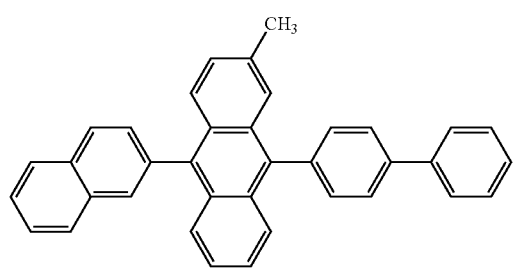
EM157
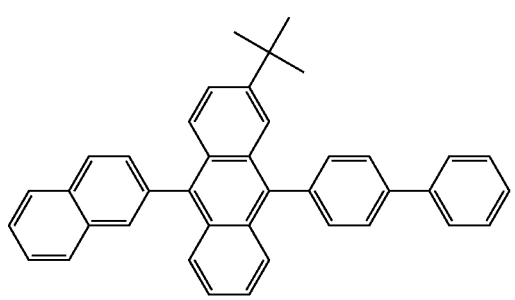
EM158
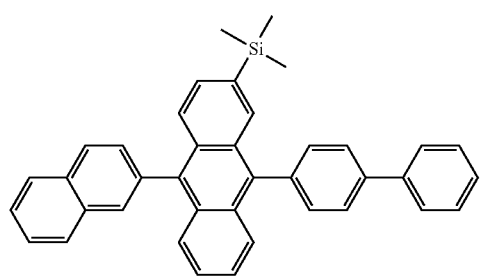
EM159
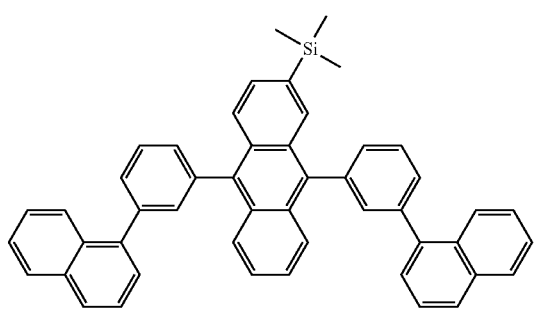
EM160
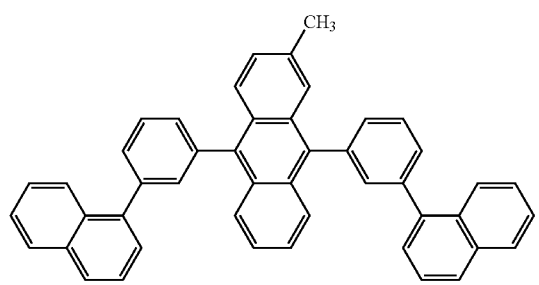
EM161
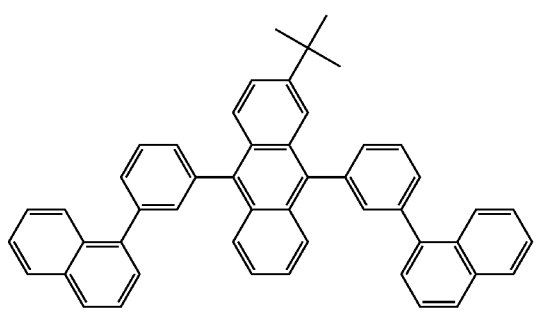

-continued
EM162
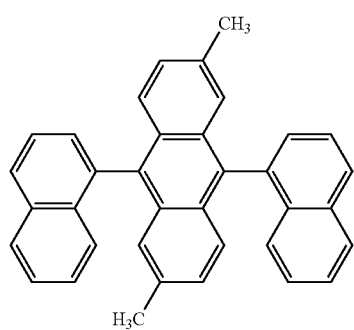
EM163
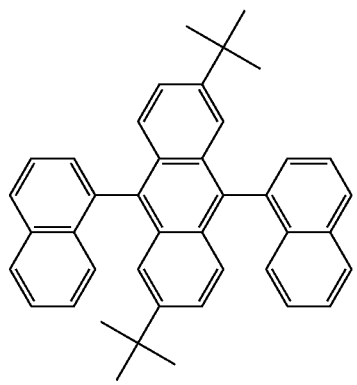
EM164
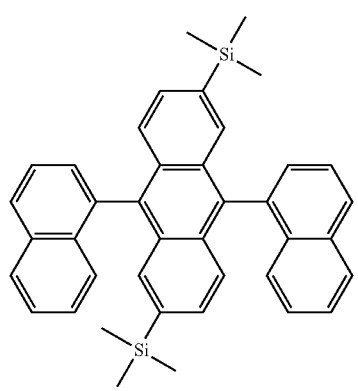
EM165
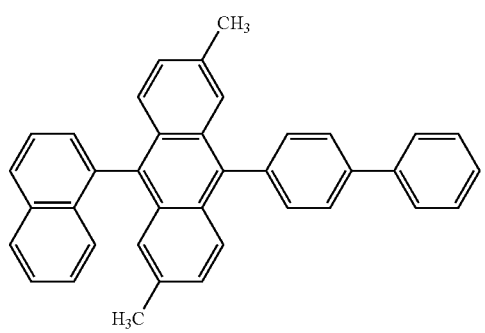
EM166
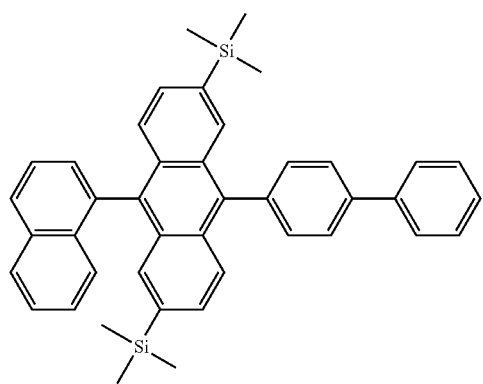
EM167
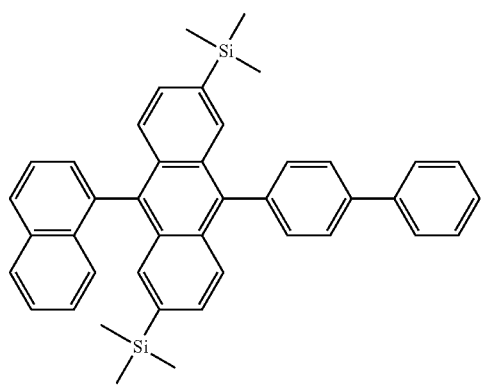
EM168
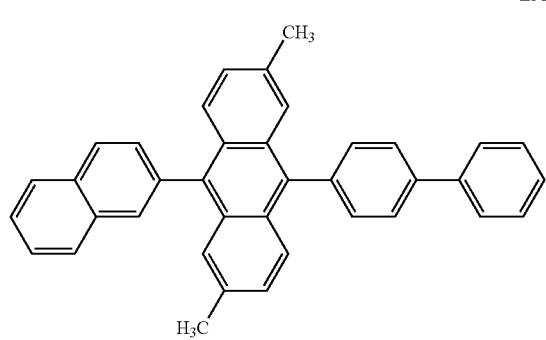
EM169
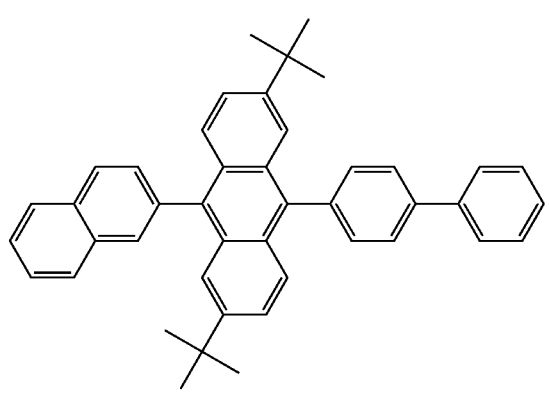

-continued
EM170
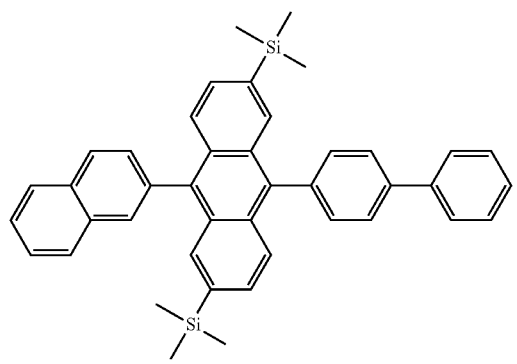
EM171
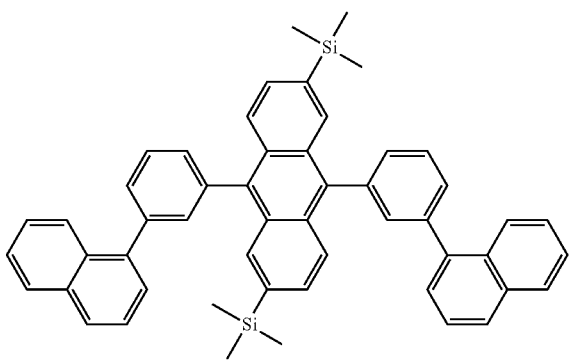
EM172
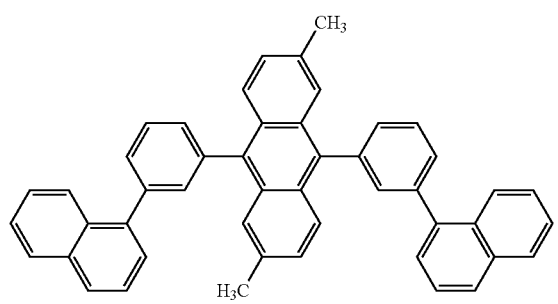
EM173
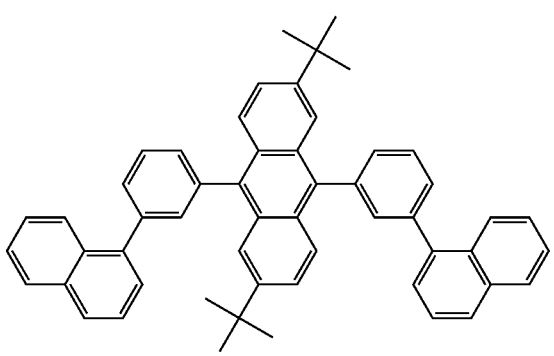
EM174
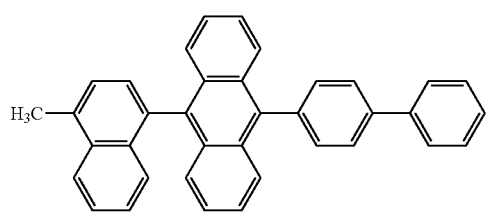
EM175
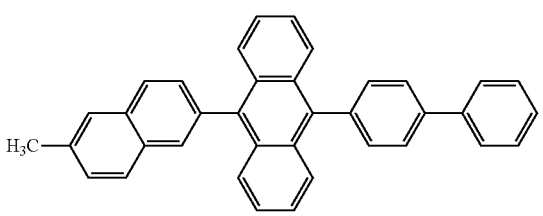
EM176
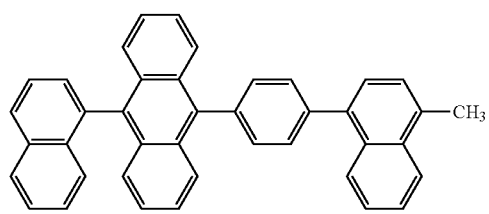
EM177
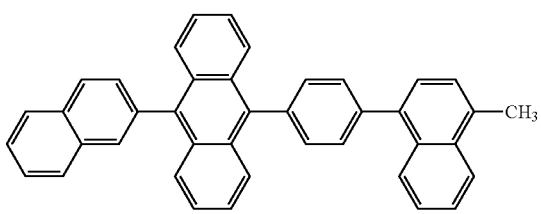
EM178
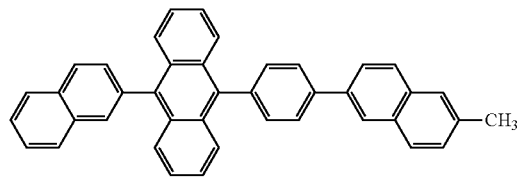
EM179
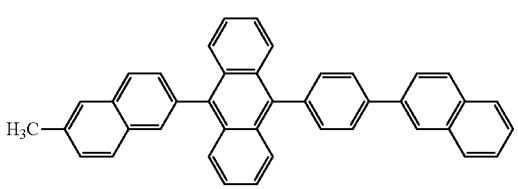

-continued
EM180
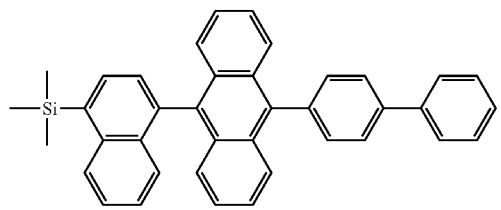
EM181
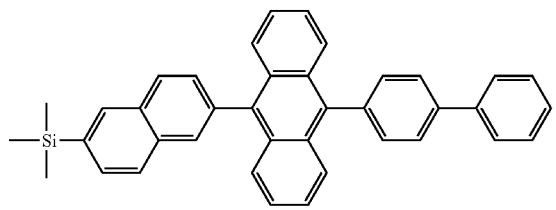
EM182
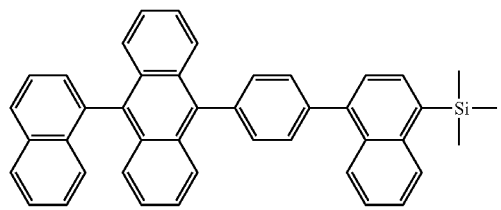
EM183
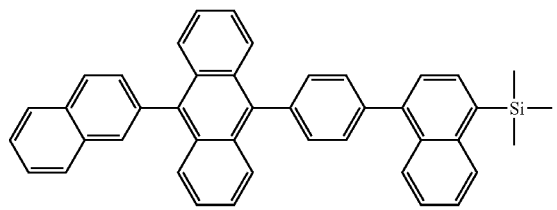
EM184
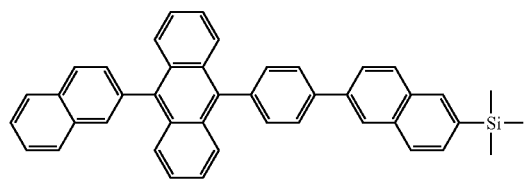
EM185
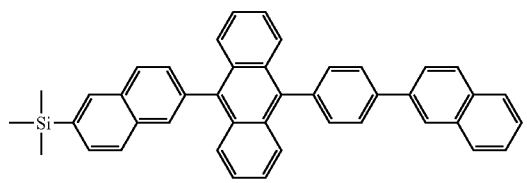
EM186
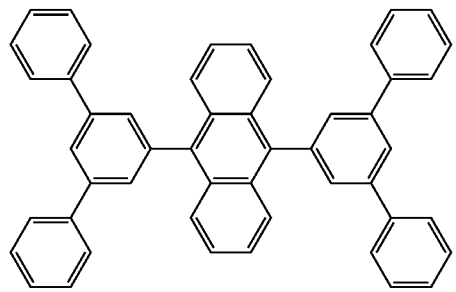
EM187
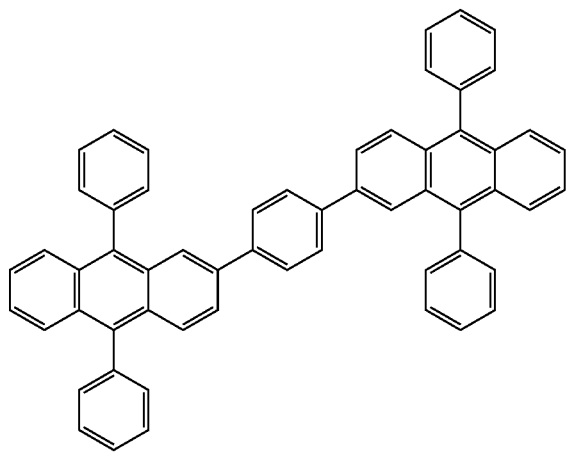
EM188
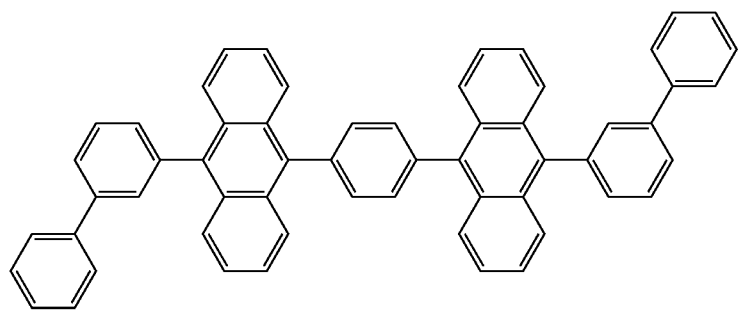

-continued
EM189
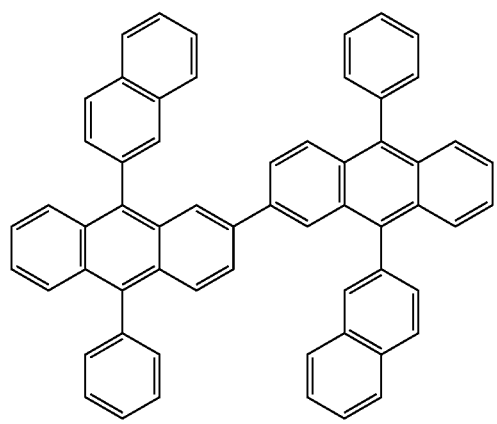
EM190
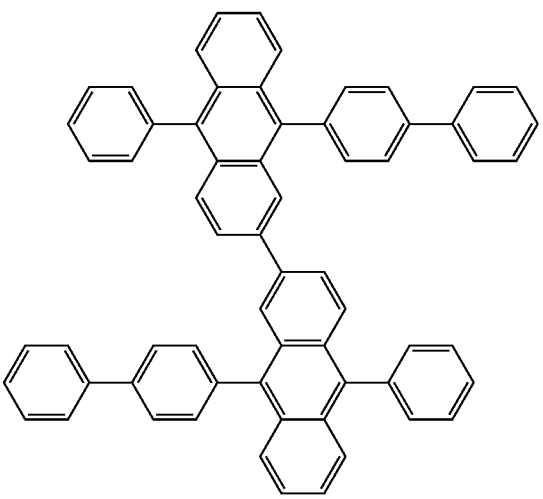
EM191
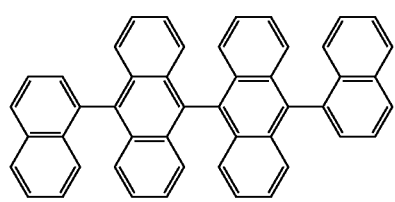
EM192
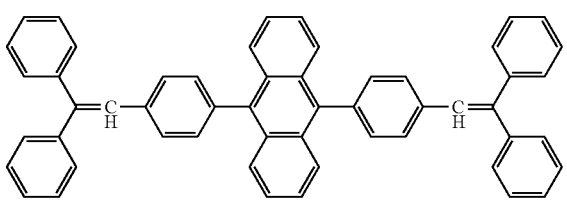
EM193
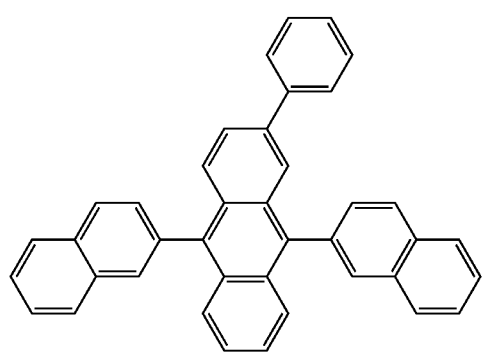
EM194
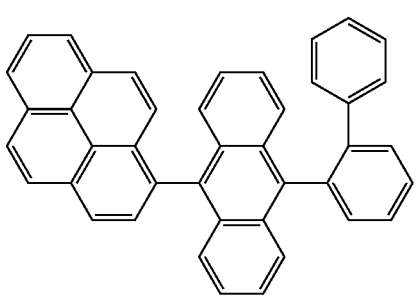
EM195
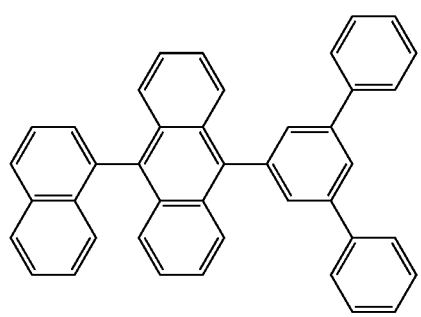
EM196
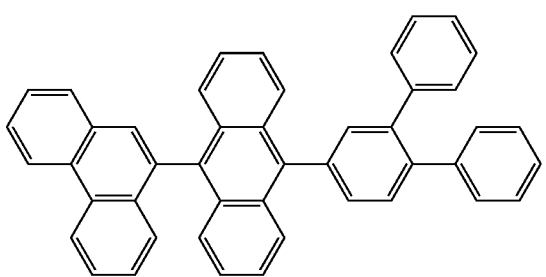

-continued
EM197
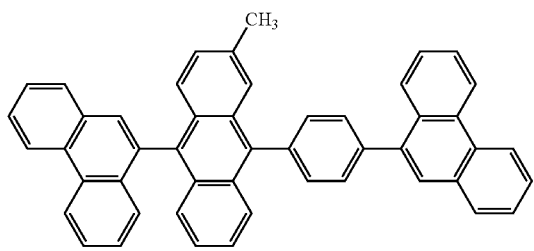
EM198
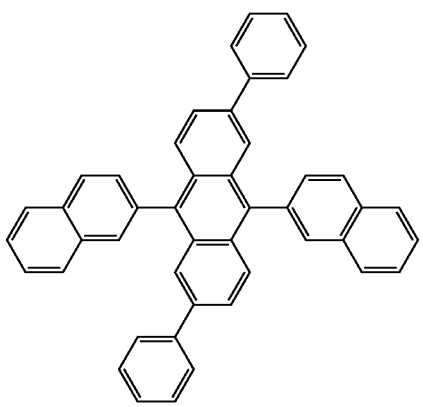
EM199
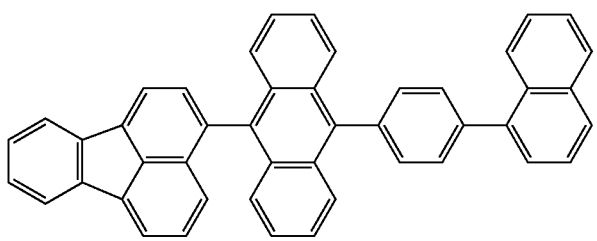
EM200
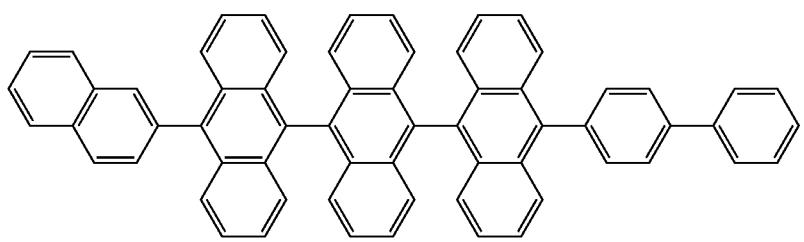
EM201
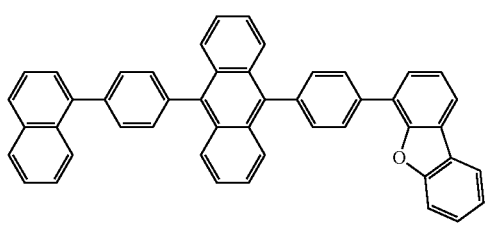
EM202
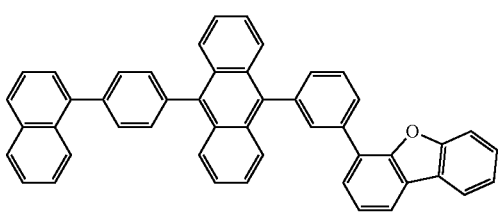
EM203
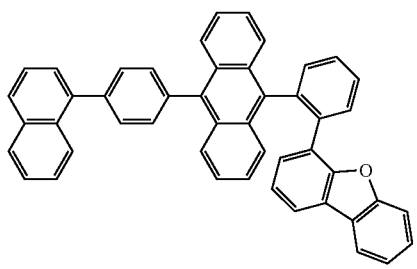
EM204
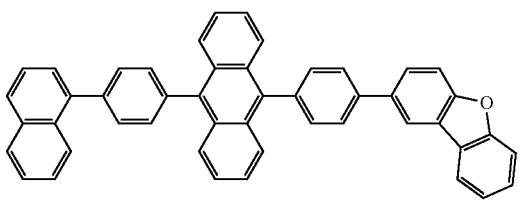

-continued
EM205
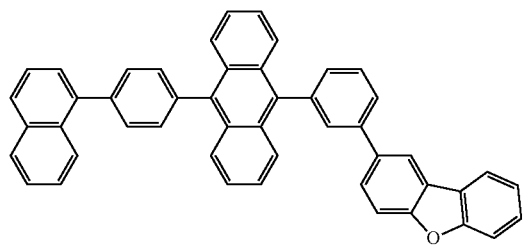
EM206
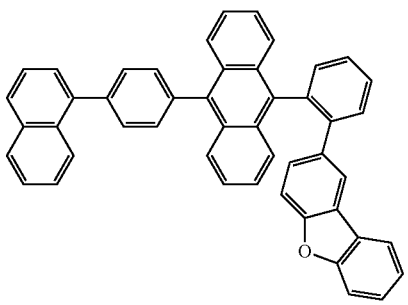
EM207
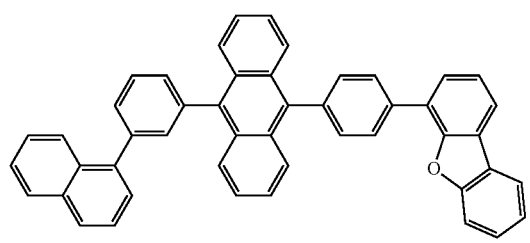
EM208
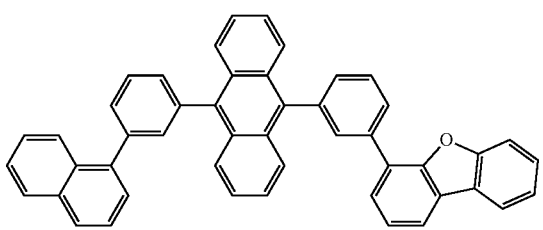
EM209
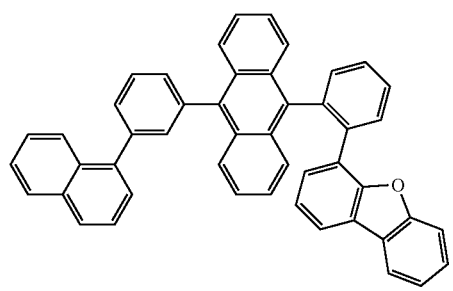
EM210
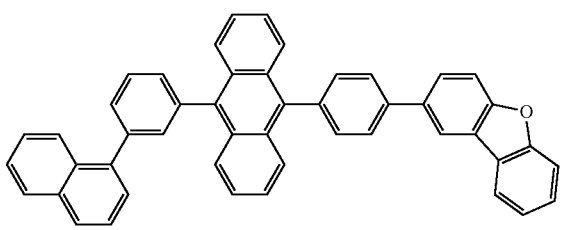
EM211
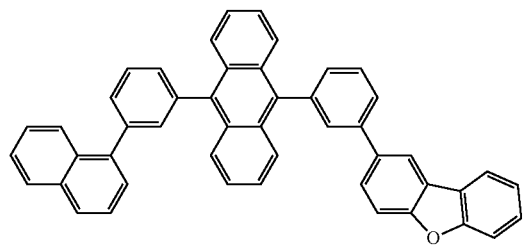
EM212
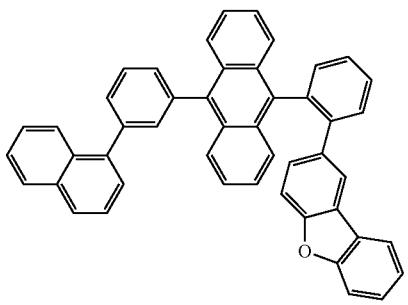
EM213
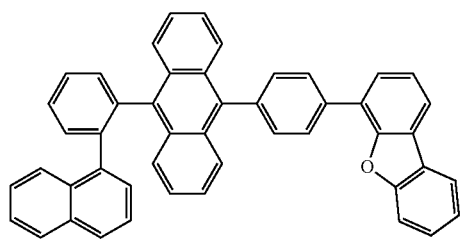
EM214
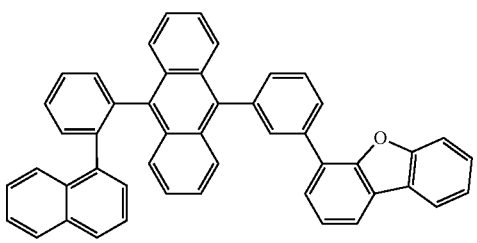

EM215
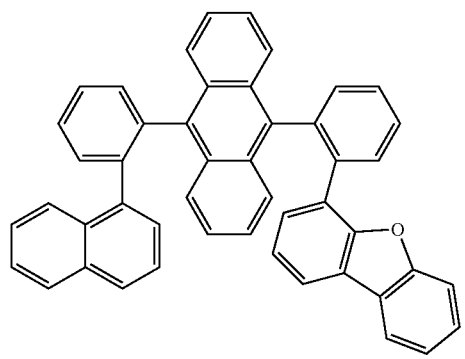
EM216
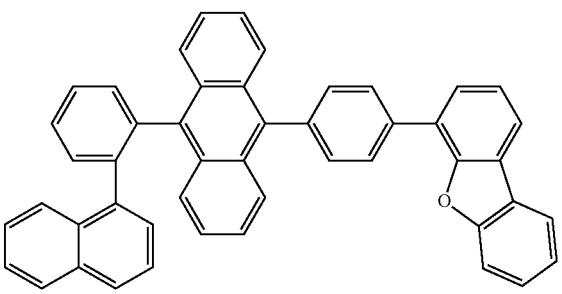
EM217
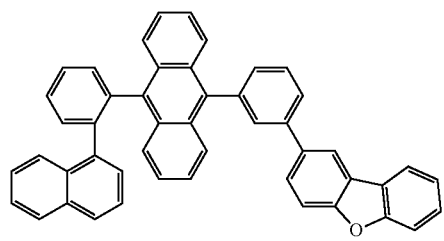
EM218
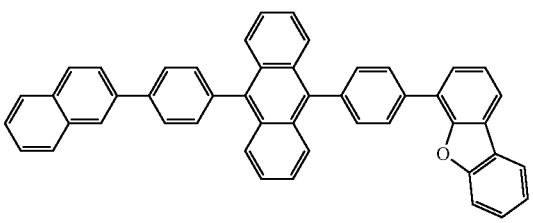
EM219
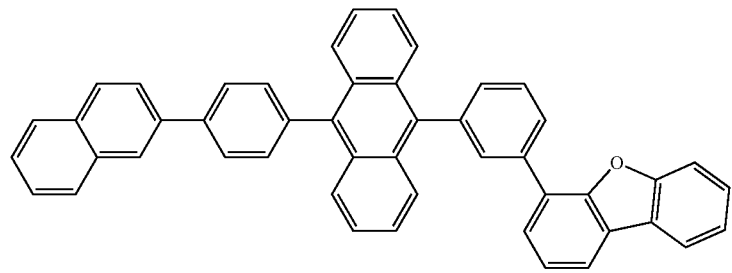
EM220
EM221
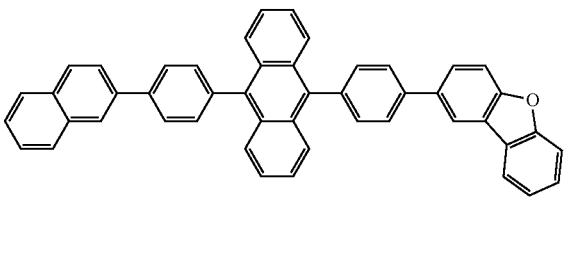
EM222
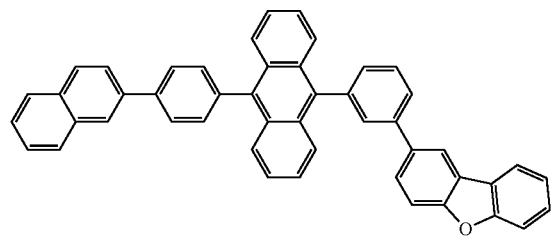
EM223
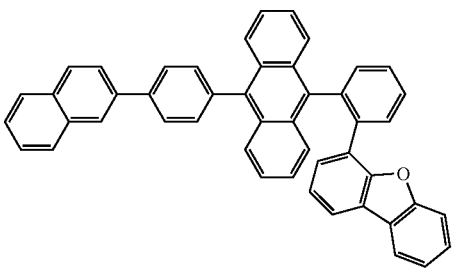

-continued
EM224
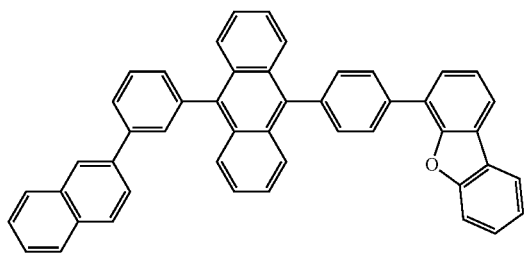
EM225
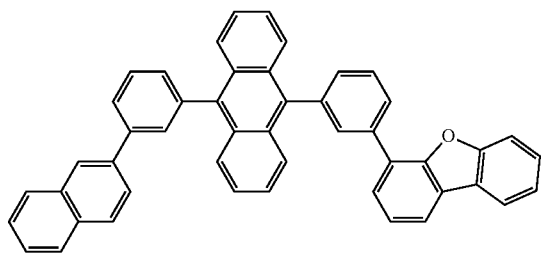
EM226
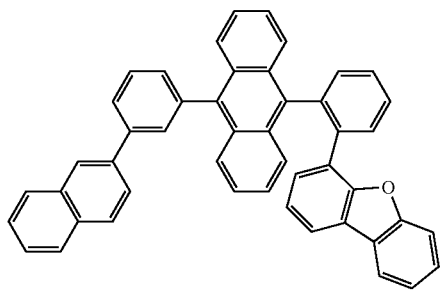
EM227
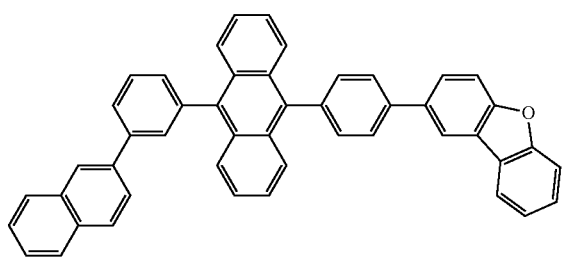
EM228
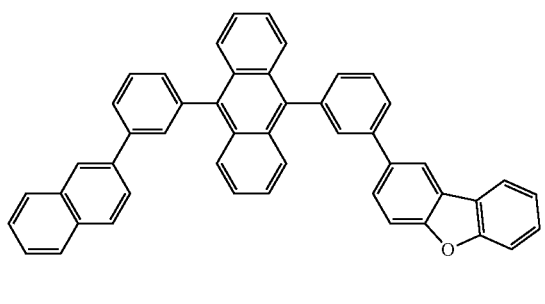
EM229
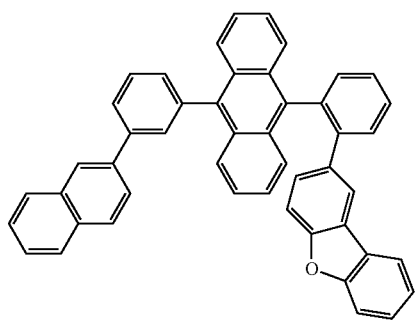
EM230
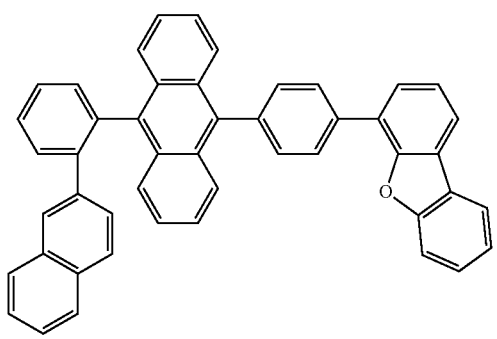
EM231
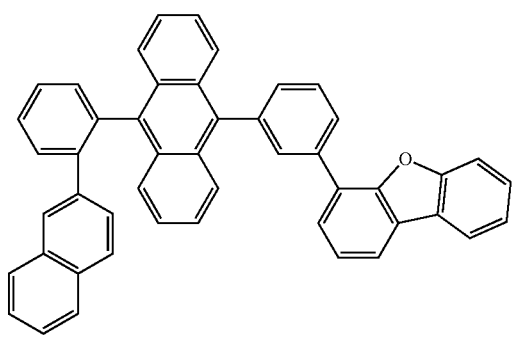
EM232
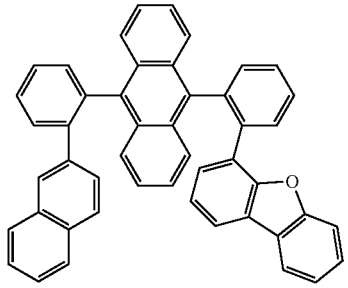
EM233
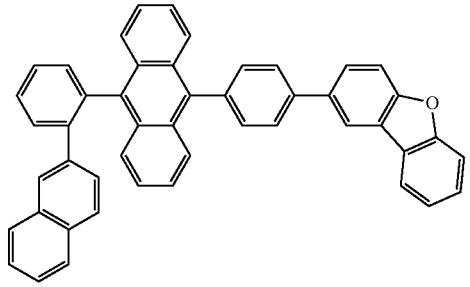

-continued
EM234
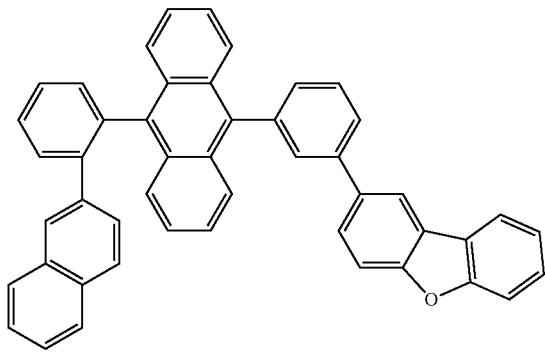
EM235
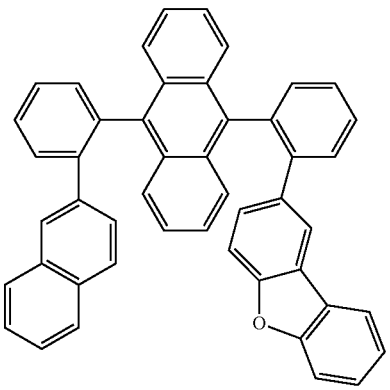
EM236
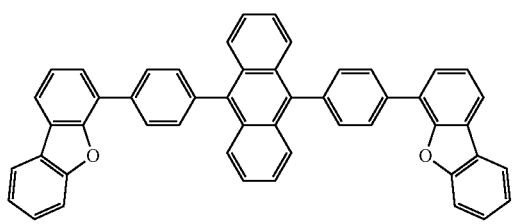
EM237
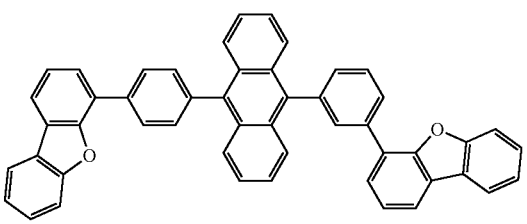
EM238
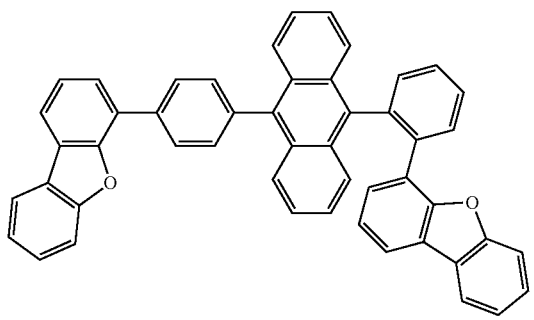
EM239
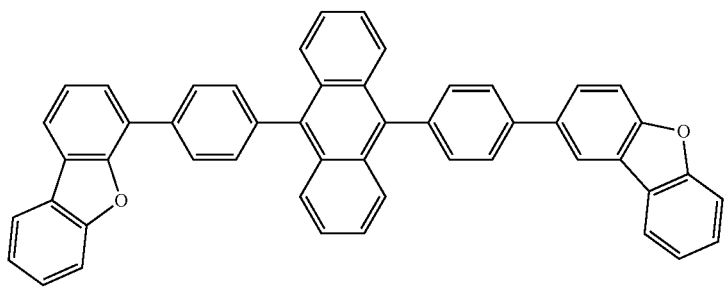
EM240
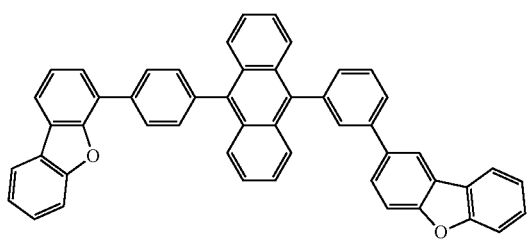
EM241
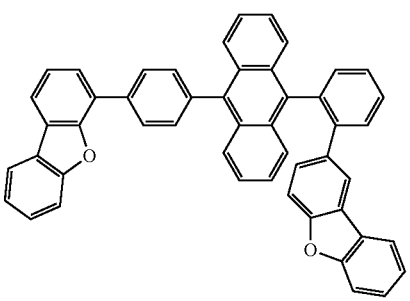

EM242
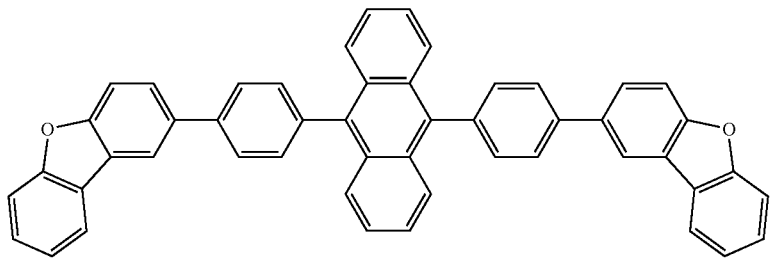
EM243
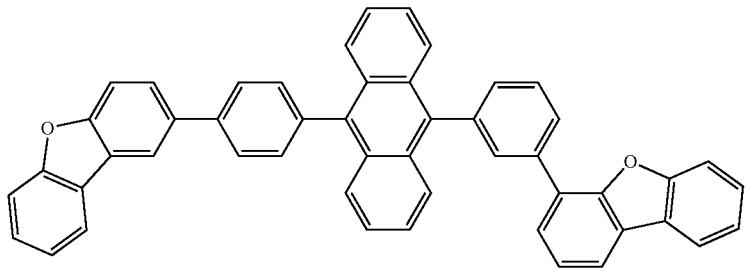
EM244
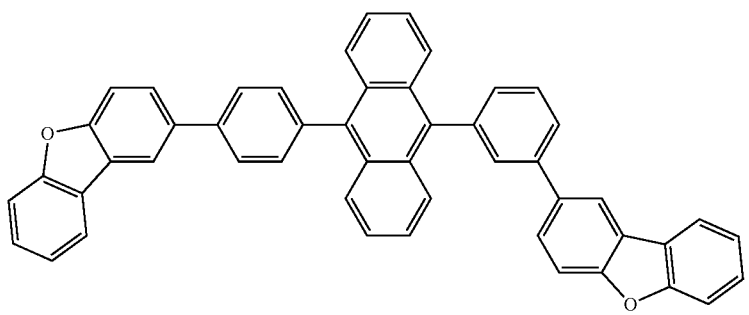
EM245
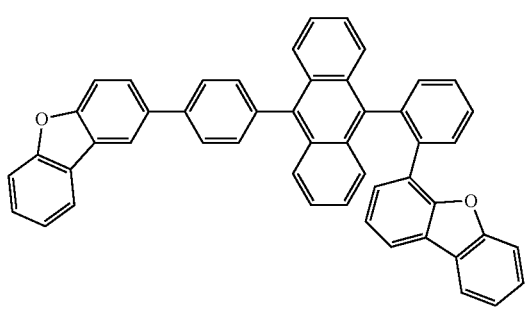
EM246
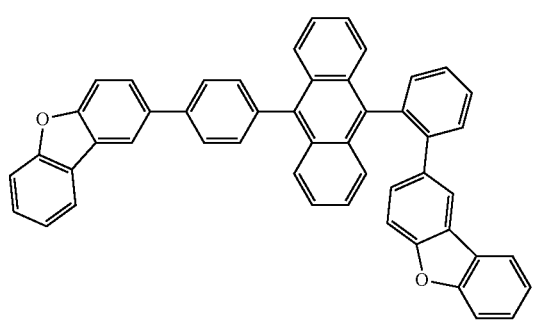
EM247
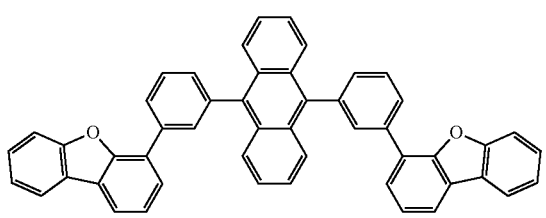
EM248
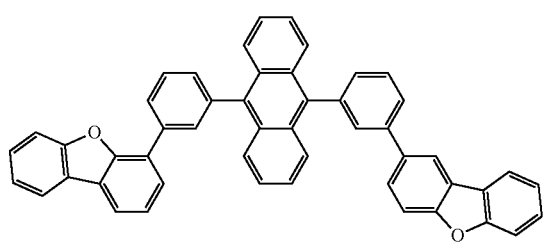

-continued
EM249
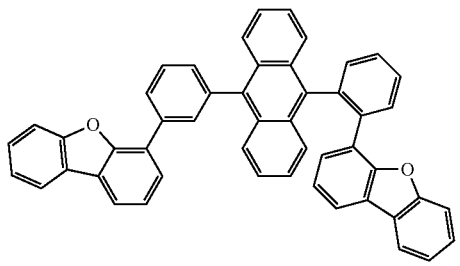
EM250
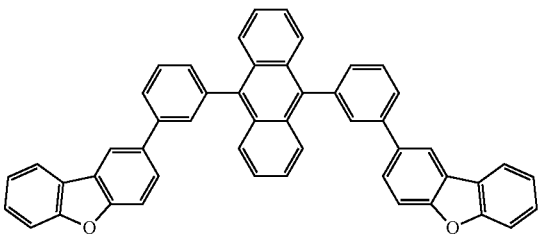
EM251
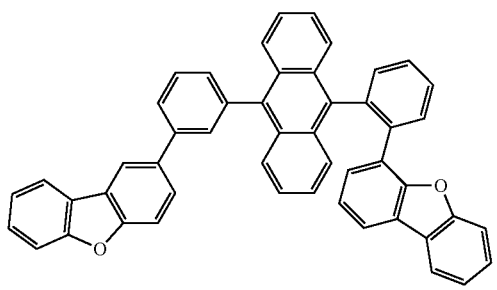
EM252
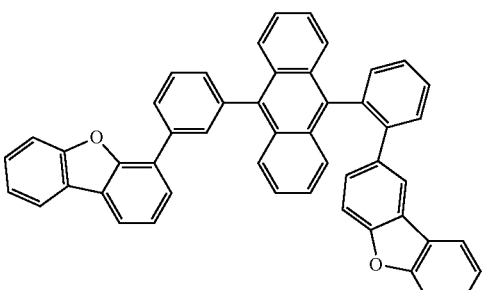
EM253
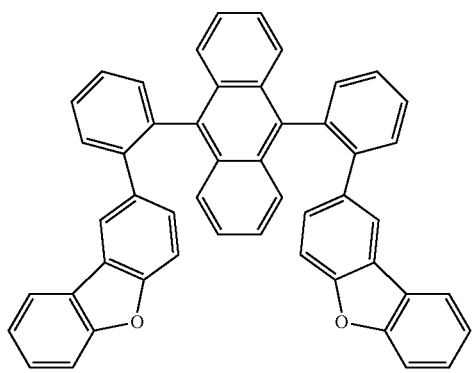
EM254
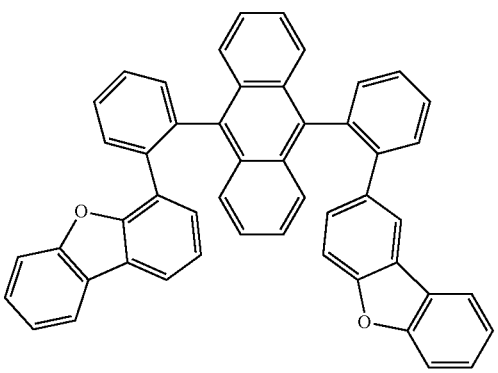
EM255
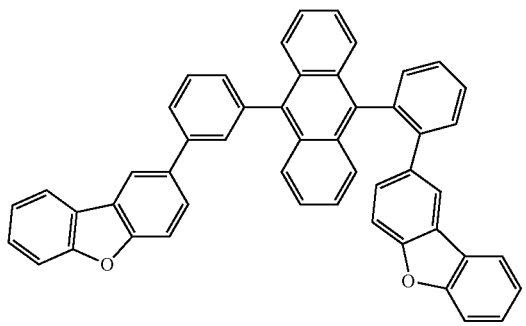
EM256
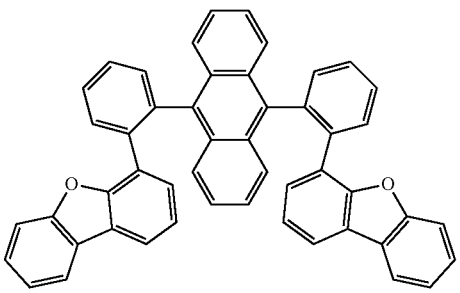
EM257
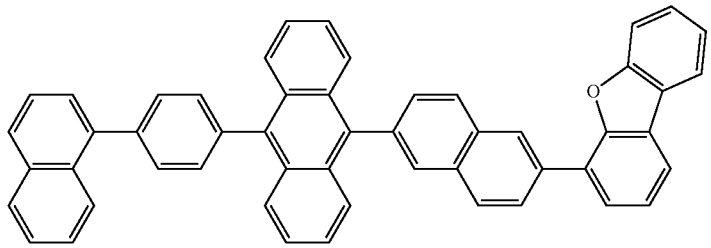

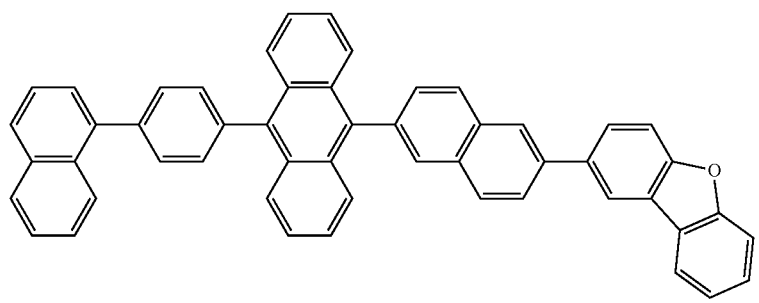
EM258
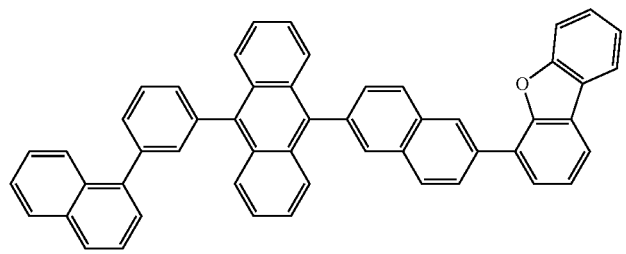
EM259
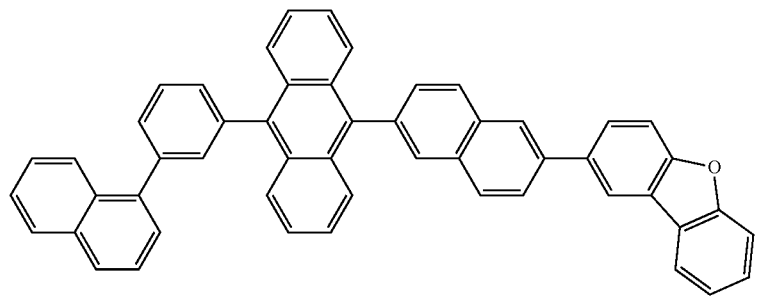
EM260
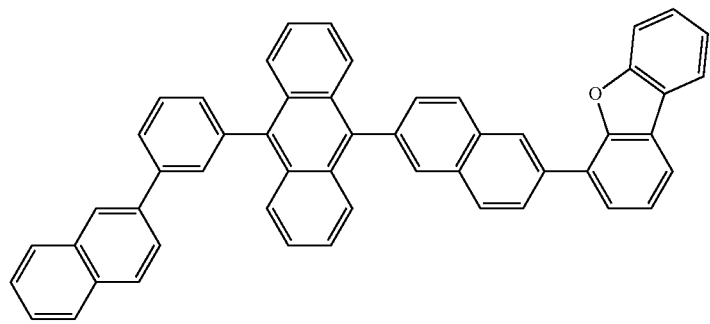
EM261
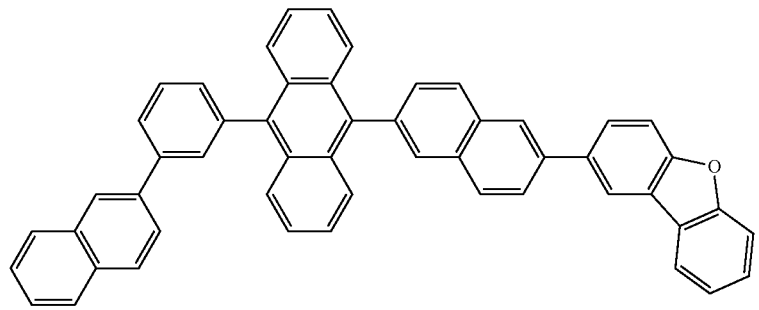
EM262

-continued
EM263
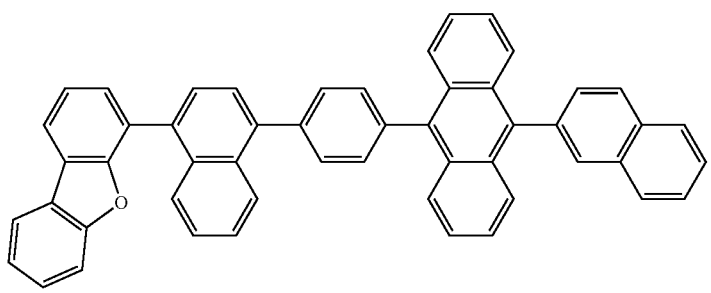
EM264
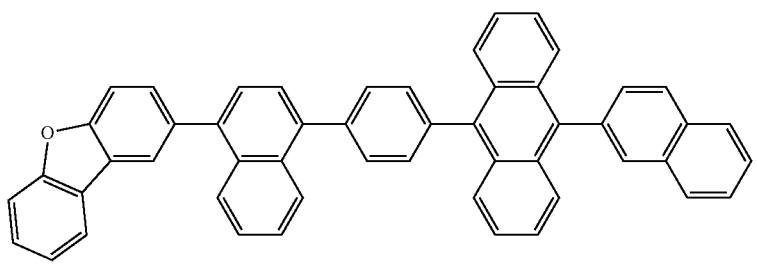
EM265
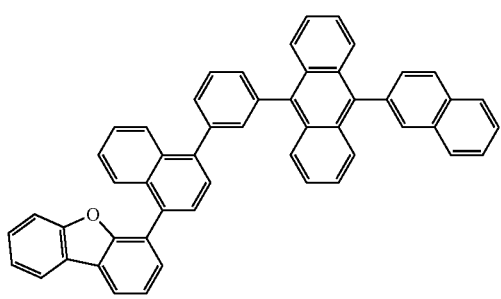
EM266
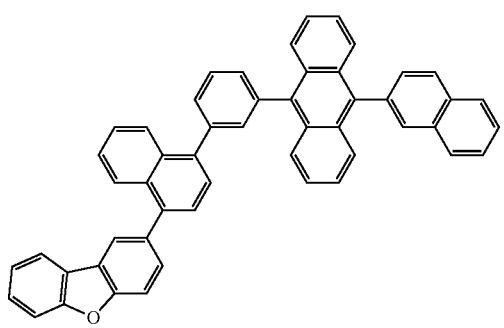
EM267
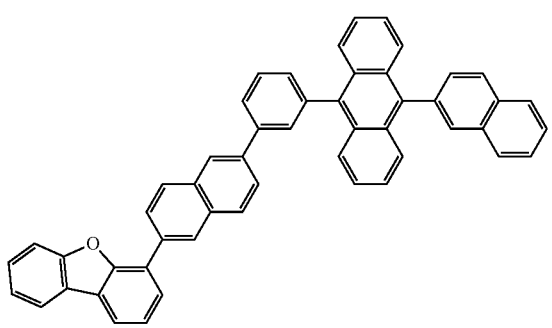
EM268
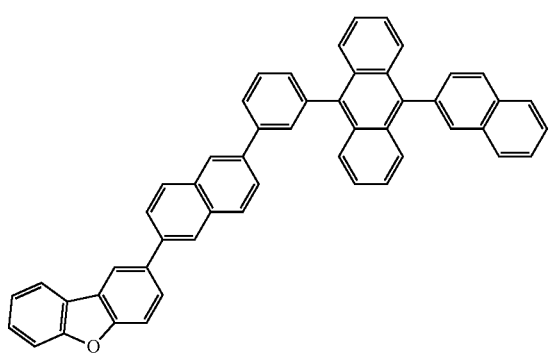
EM269
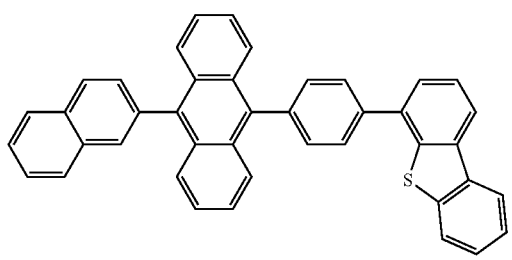
EM270
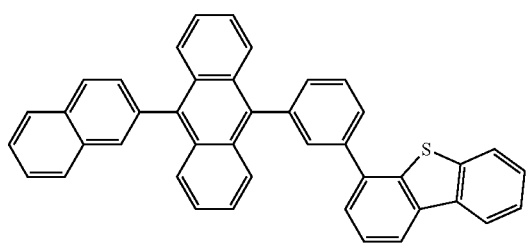

-continued
EM271
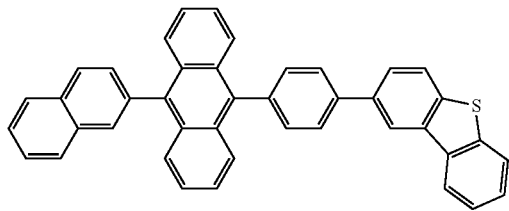
EM272
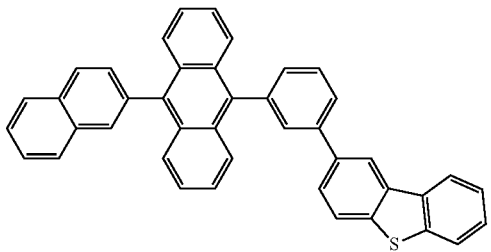
EM273
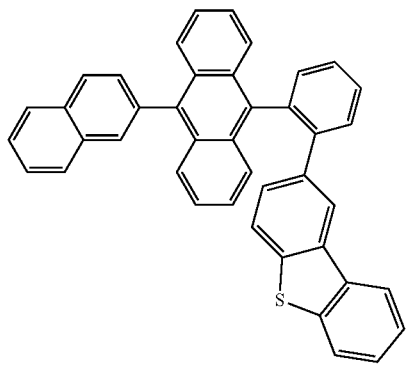
EM274
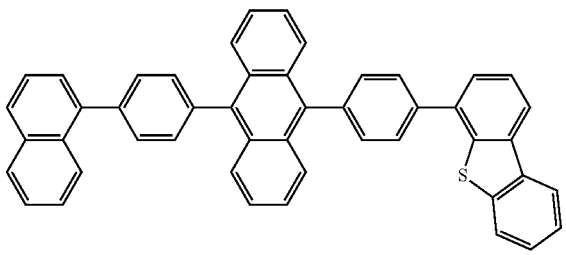
EM275
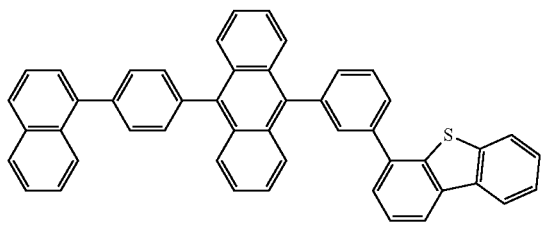
EM276
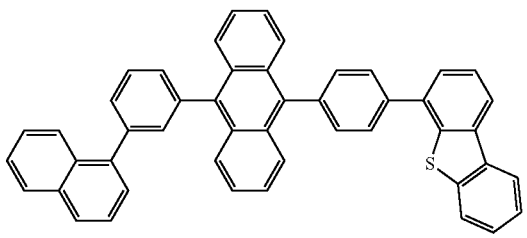
EM277
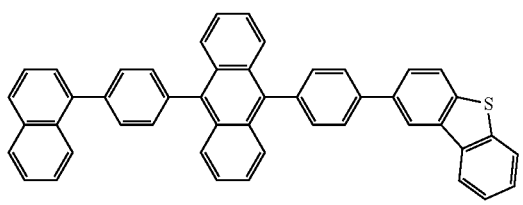
EM278
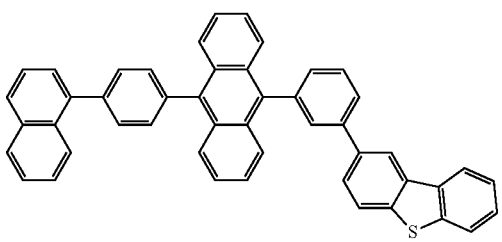
EM279
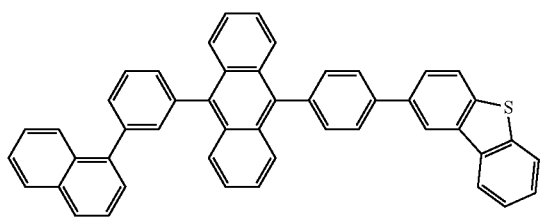
EM280
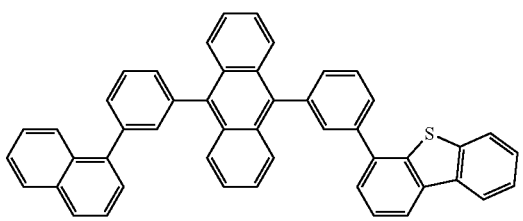

-continued
EM281
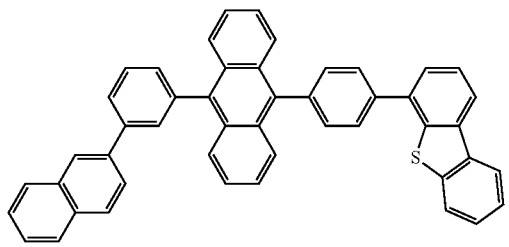
EM282
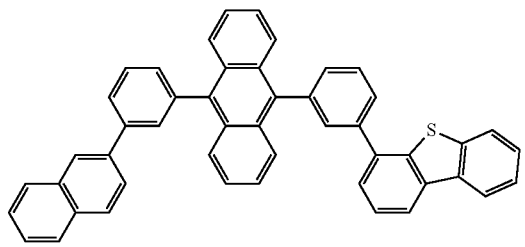
EM283
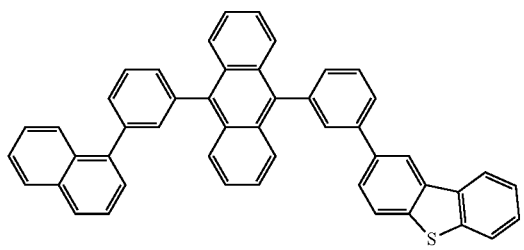
EM284
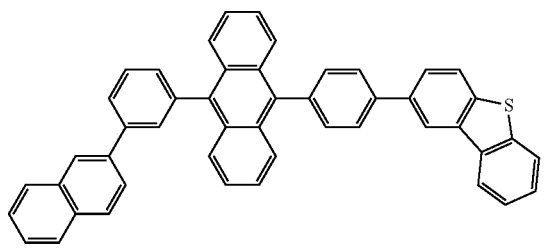
EM285
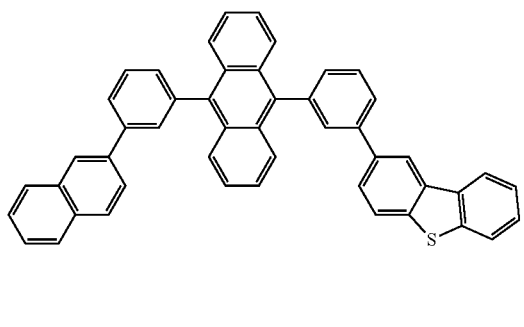
EM286
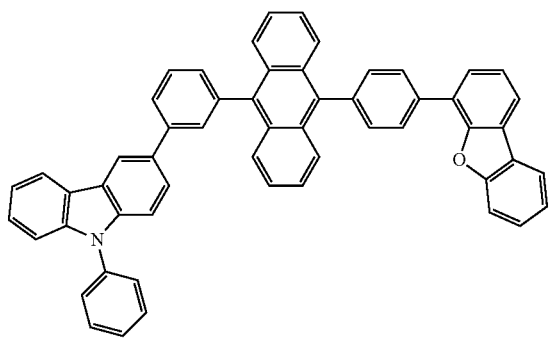
EM287
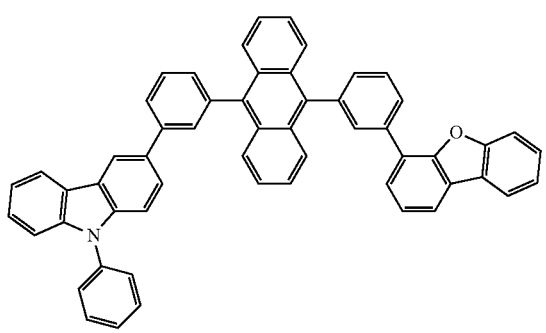
EM288
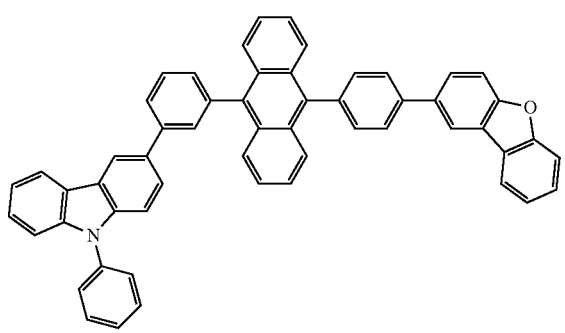
EM289
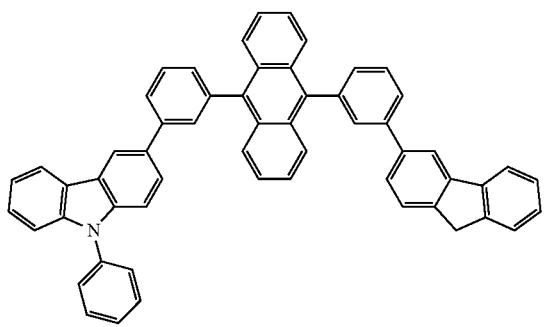
EM290
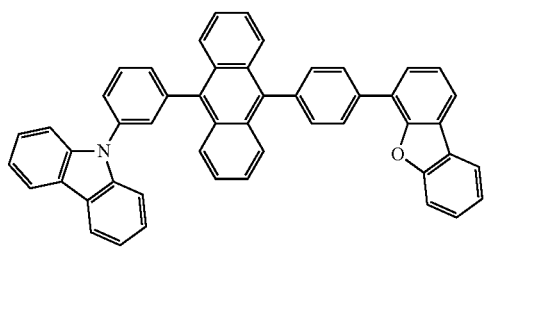

-continued
EM291
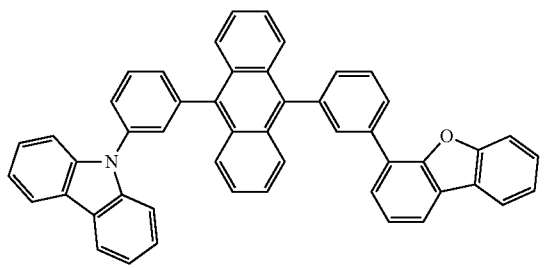
EM292
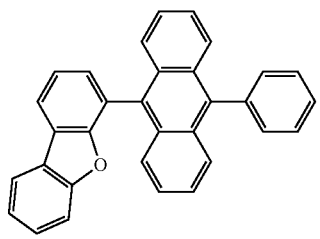
EM293
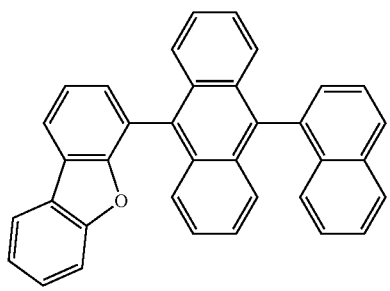
EM294
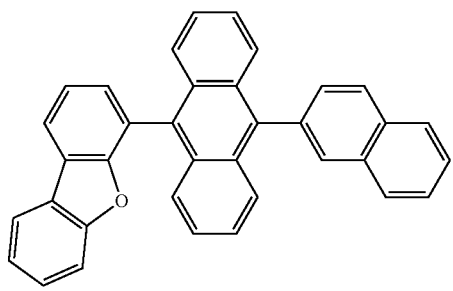
EM295
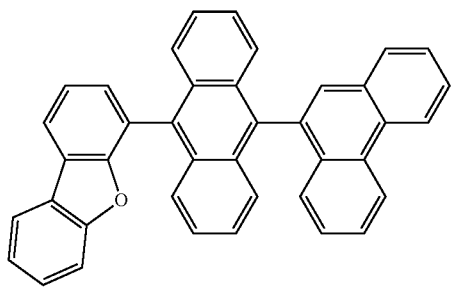
EM296
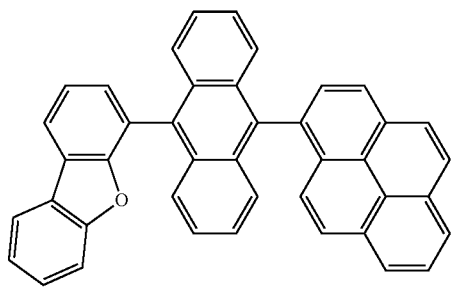
EM297
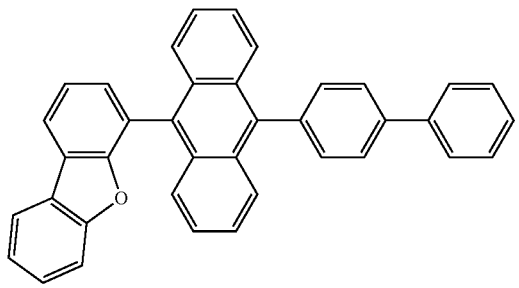
EM298
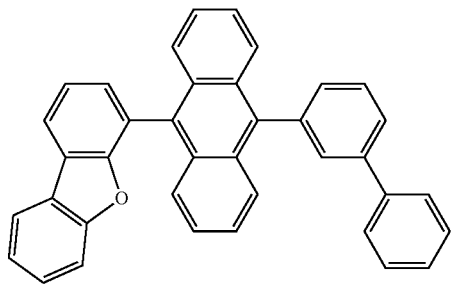
EM299
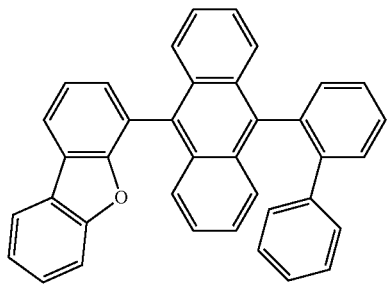
EM300
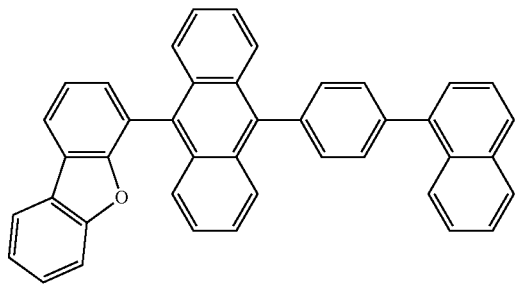

-continued
EM301
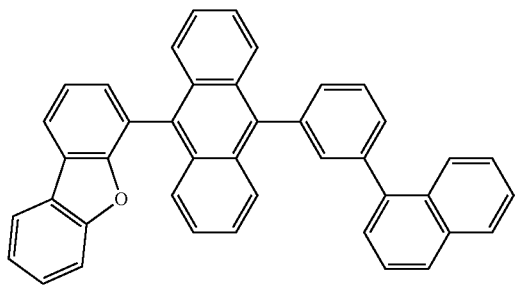
EM302
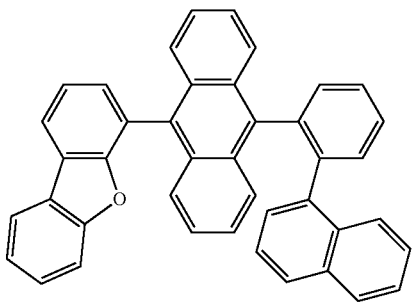
EM303
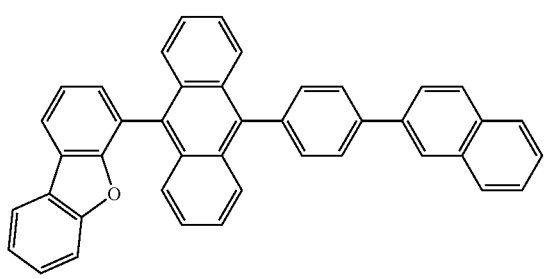
EM304
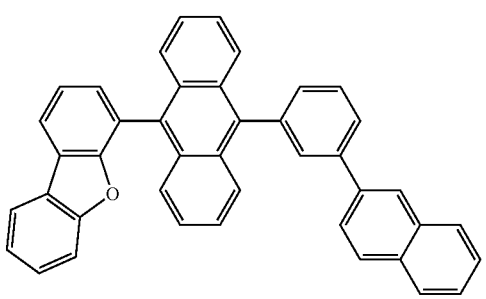
EM305
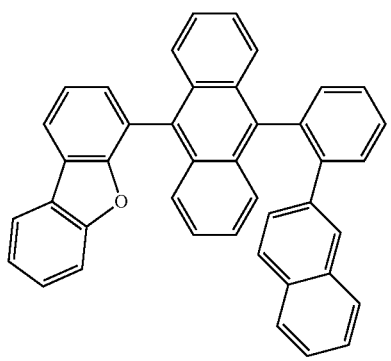
EM306
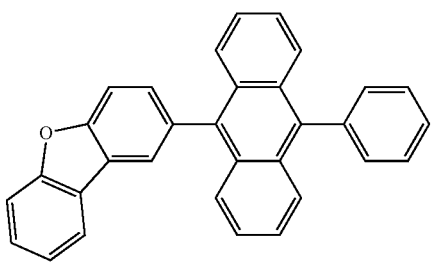
EM307
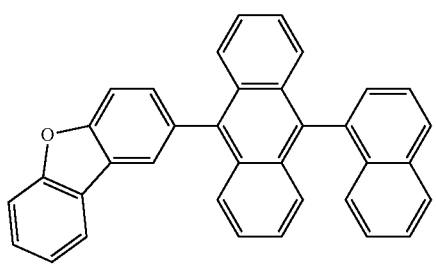
EM308
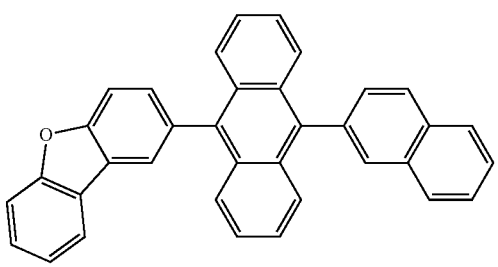
EM309
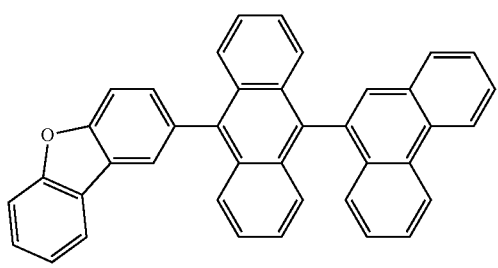
EM310
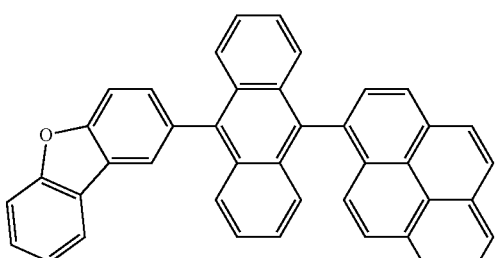

-continued
EM311
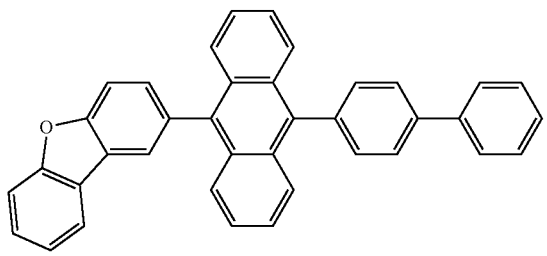
EM312
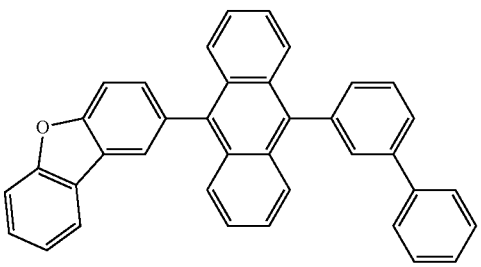
EM313
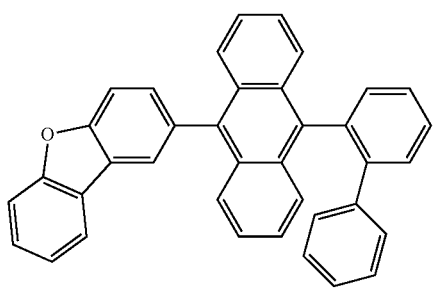
EM314
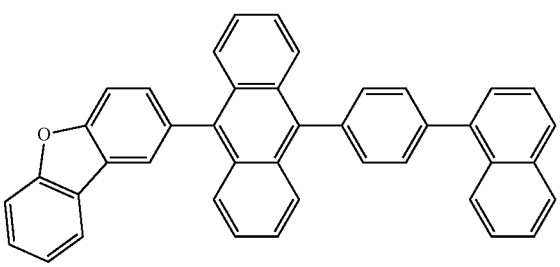
EM315
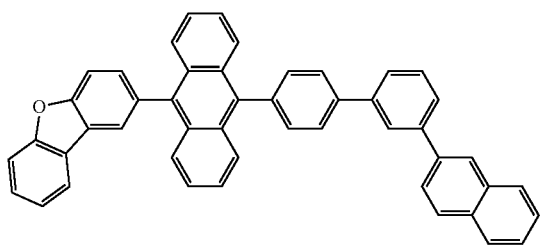
EM316
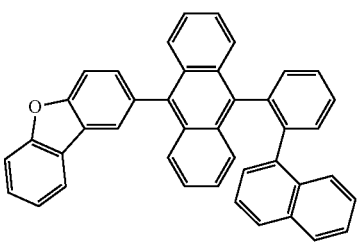
EM317
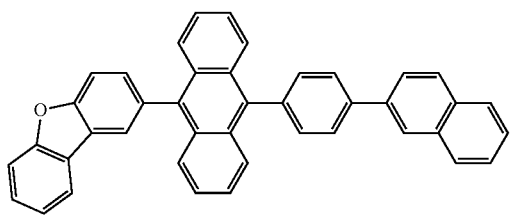
EM318
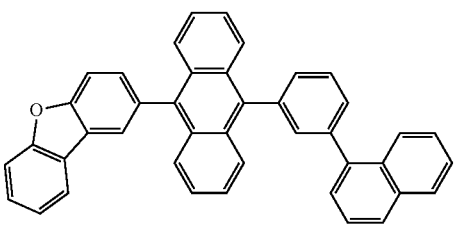
EM319
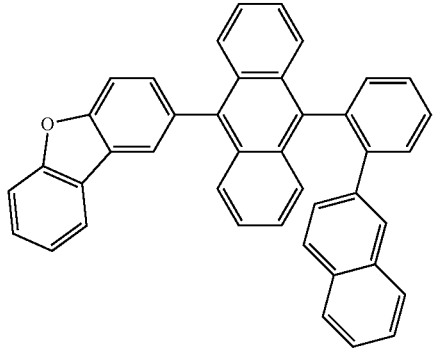
EM320
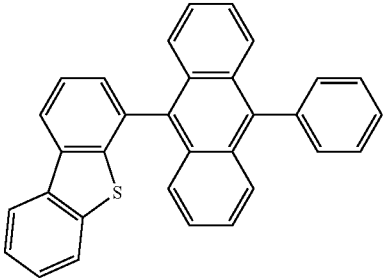

-continued
EM321
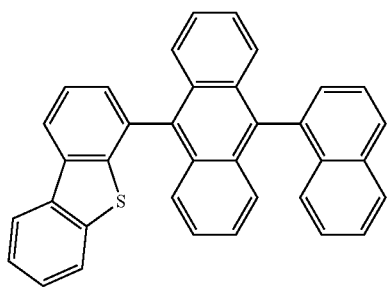
EM322
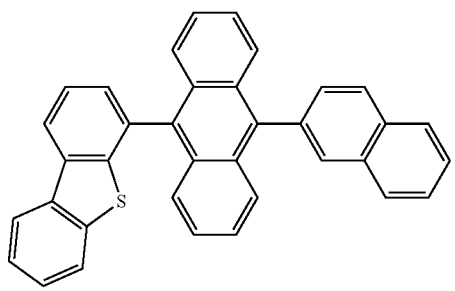
EM323
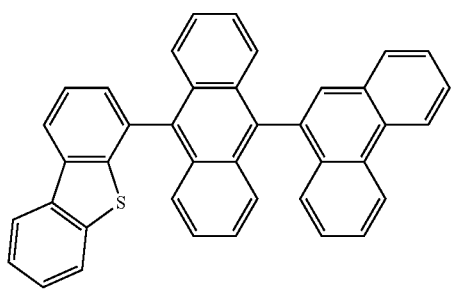
EM324
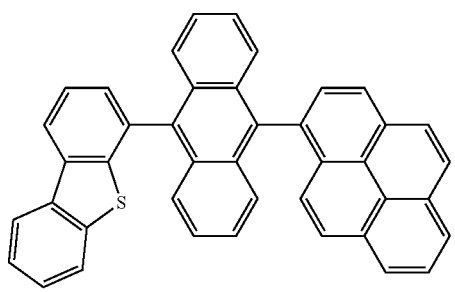
EM325
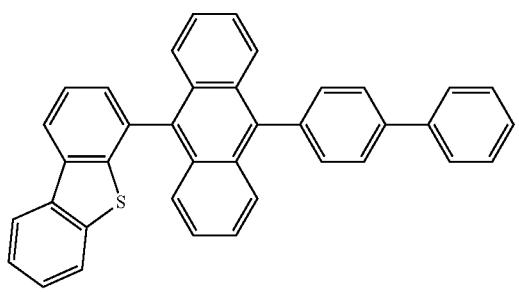
EM326
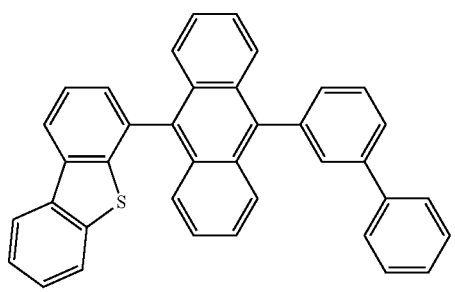
EM327
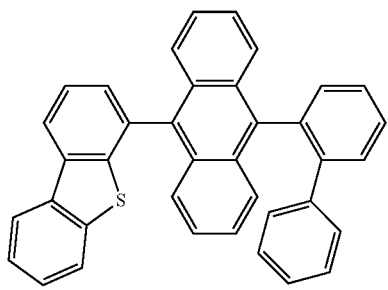
EM328
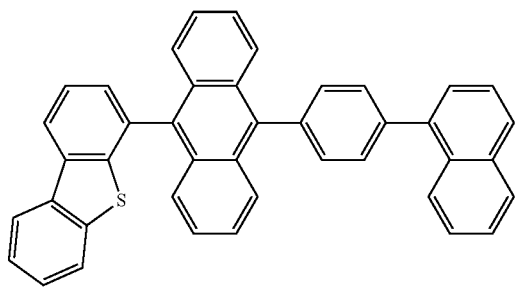
EM329
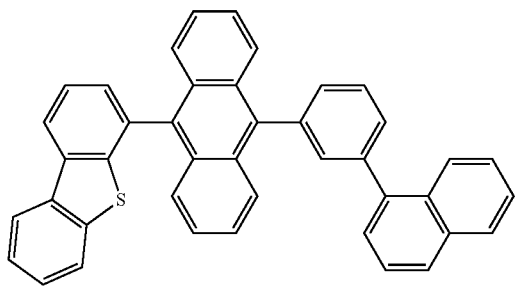
EM330
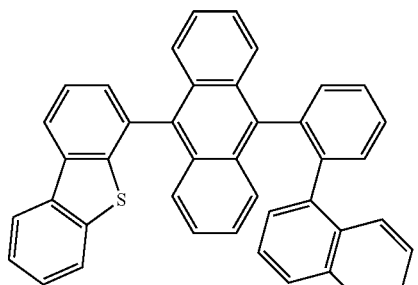

-continued
EM331
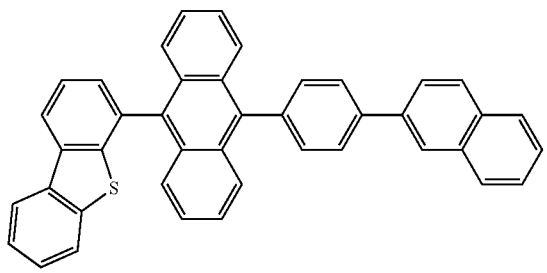
EM332
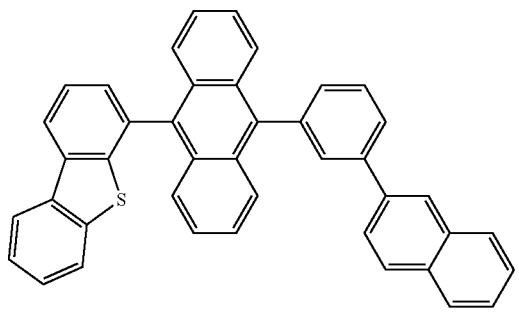
EM333
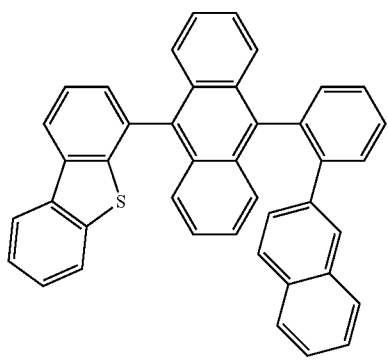
EM334
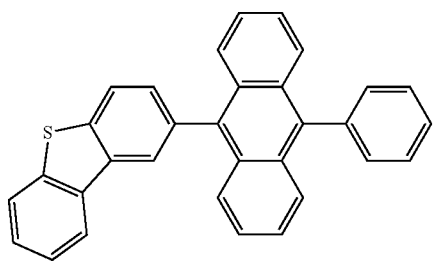
EM335
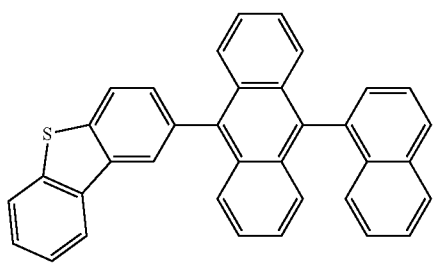
EM336
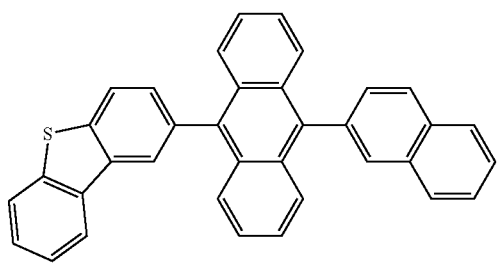
EM337
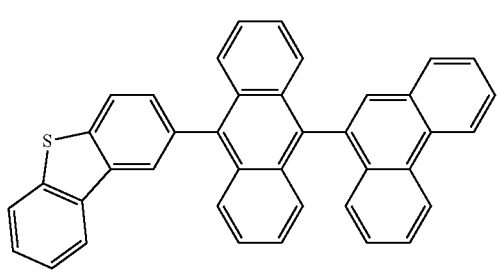
EM338
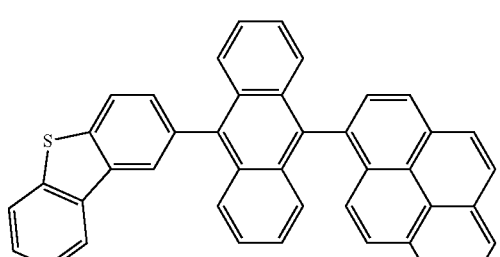
EM339
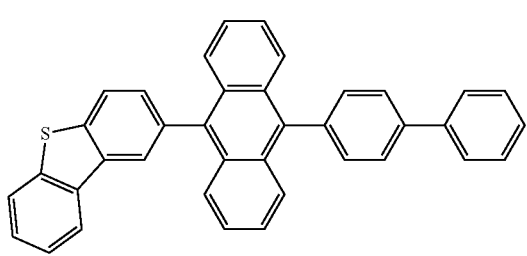
EM340
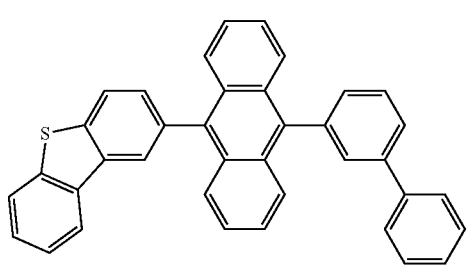

-continued
EM341
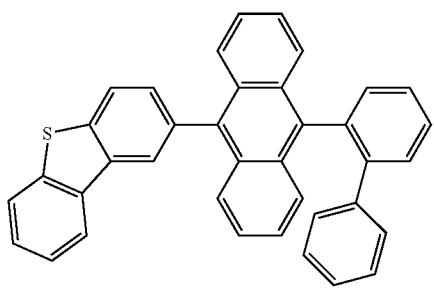
EM342
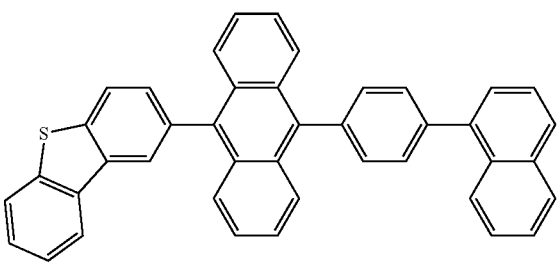
EM343
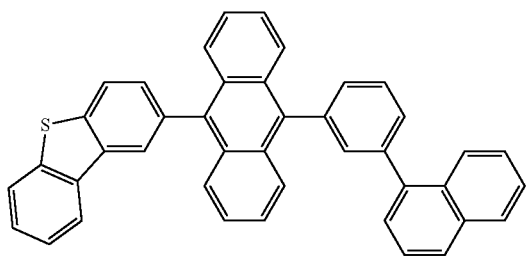
EM344
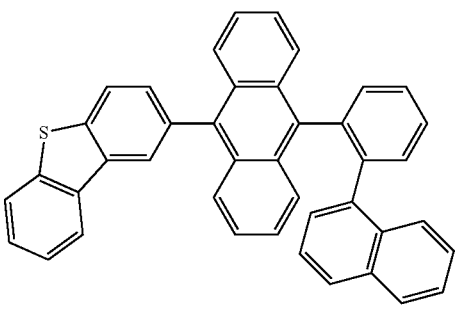
EM345
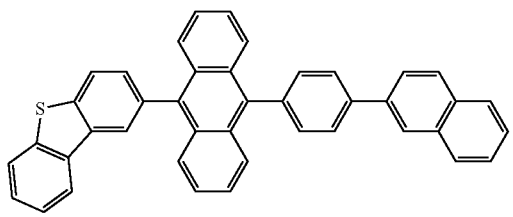
EM346
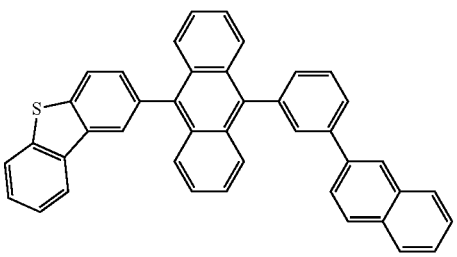
EM347
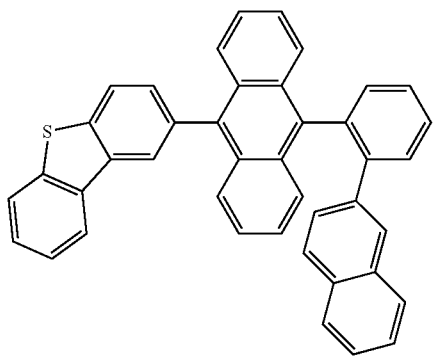
EM348
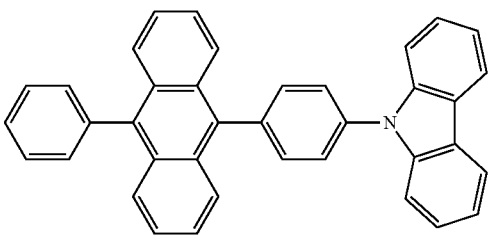
EM349
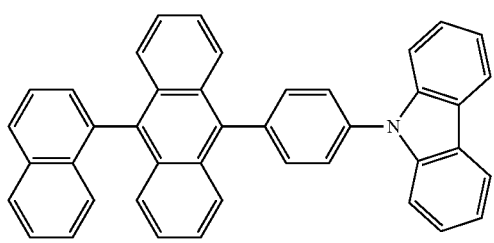
EM350
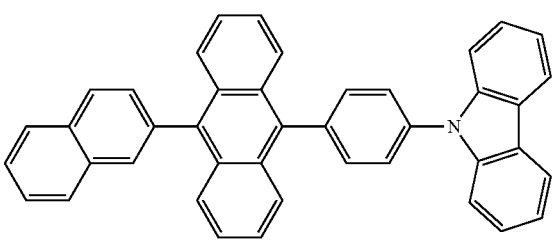

-continued
EM351
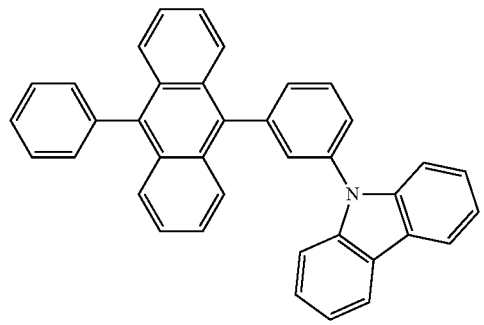
EM352
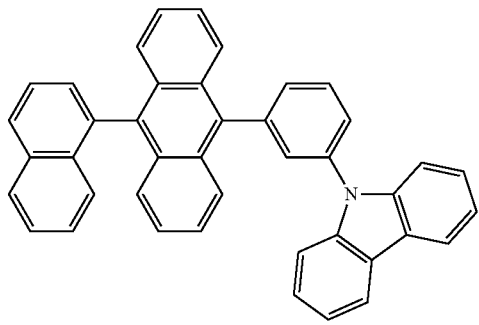
EM353
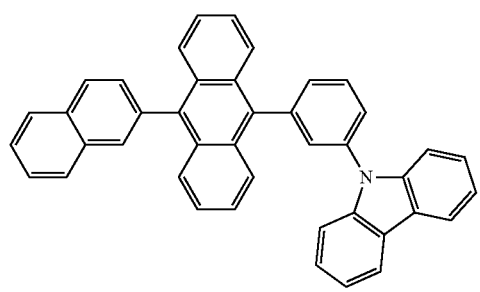
EM354
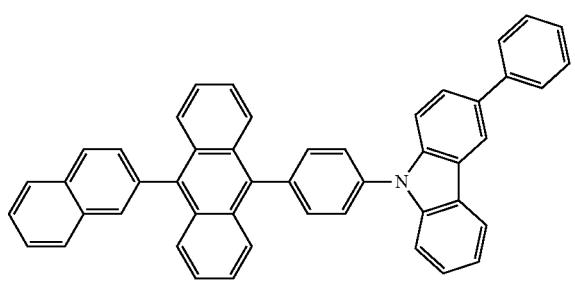
EM355
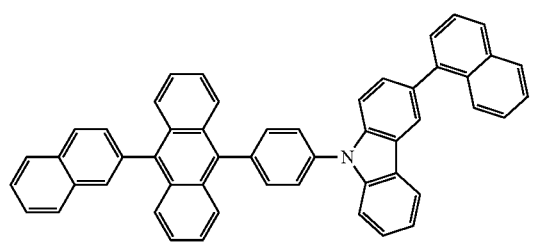
EM356
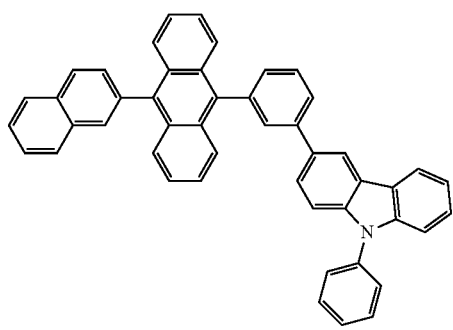
EM357
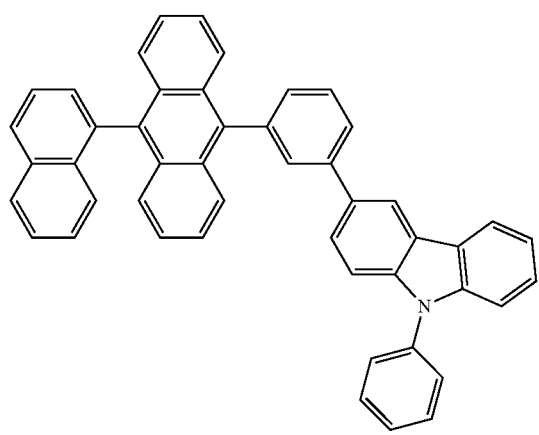
EM358
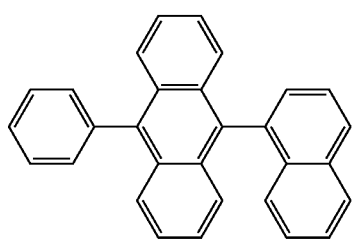

-continued
EM359
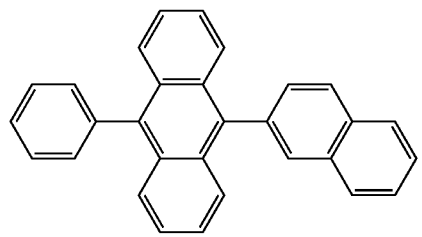
EM360
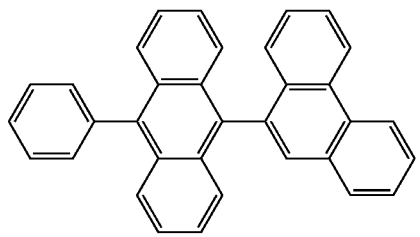
EM361
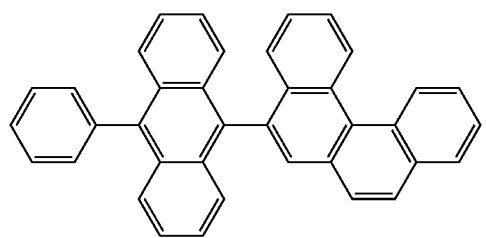
EM362
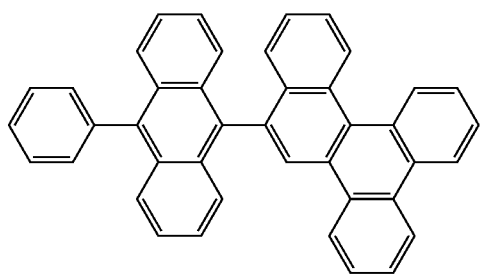
EM363
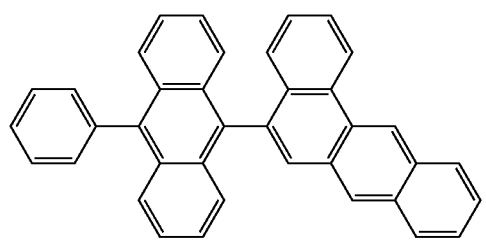
EM364
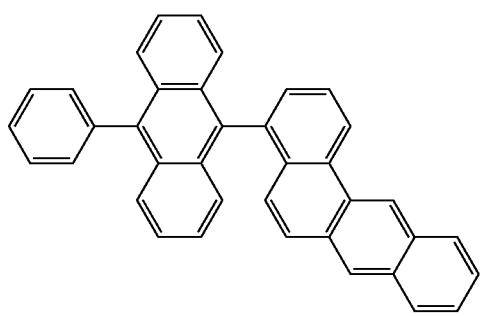
EM365
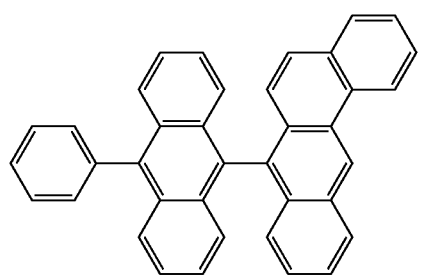
EM366
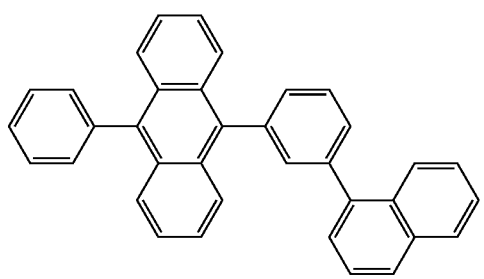
EM367
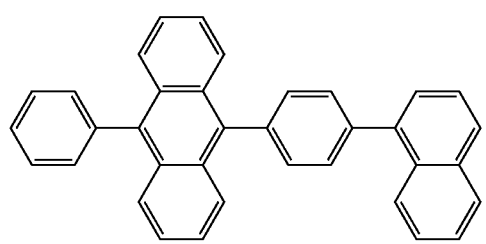
EM368
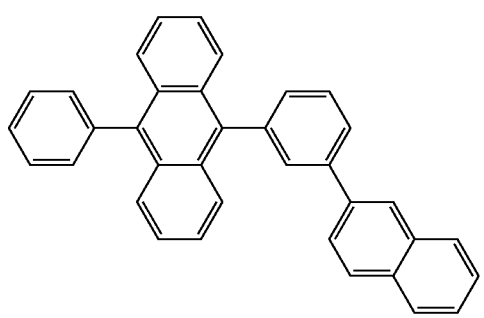

-continued
EM369
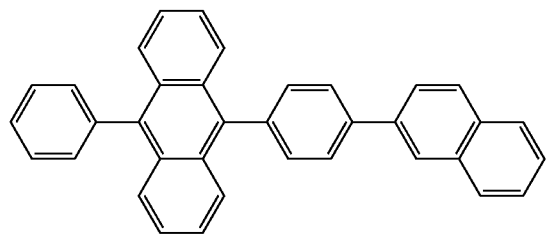
EM370
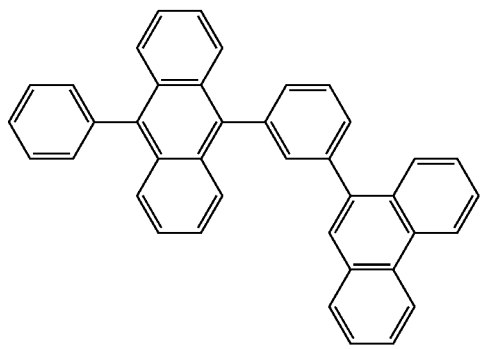
EM371
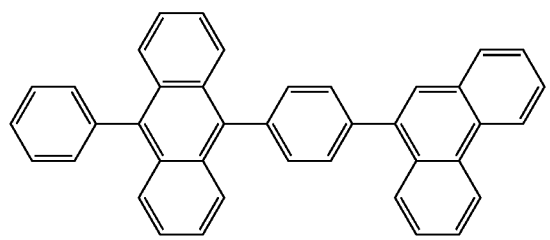
EM372
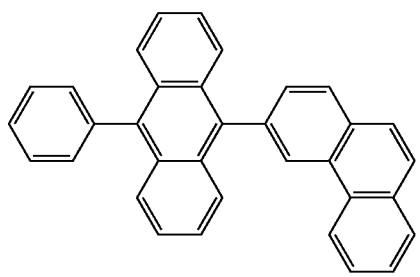
EM373
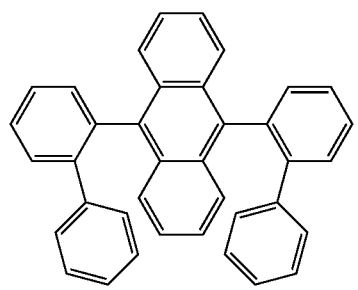
EM374
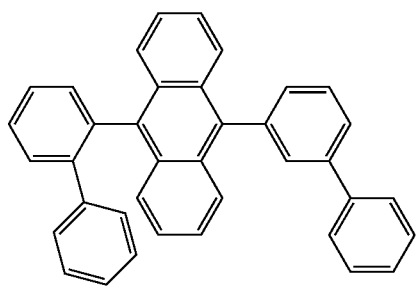
EM375
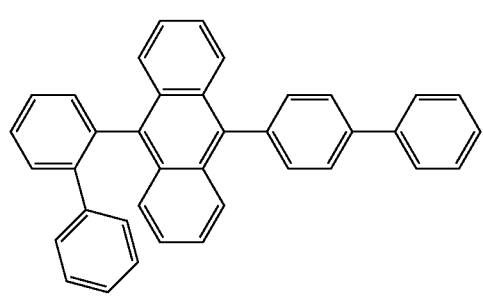
EM376
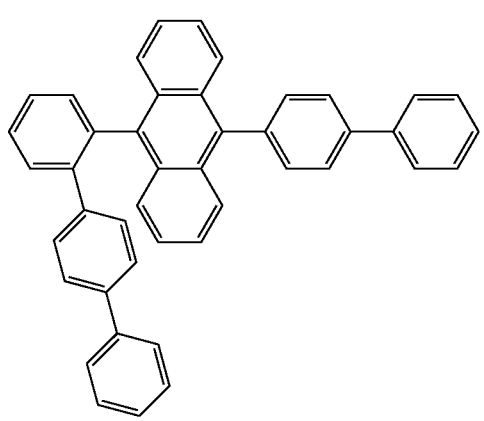

-continued
EM377
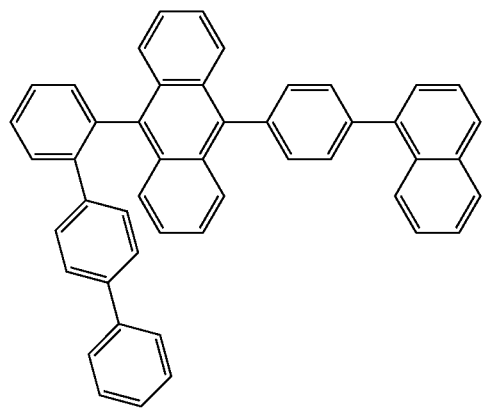
EM378
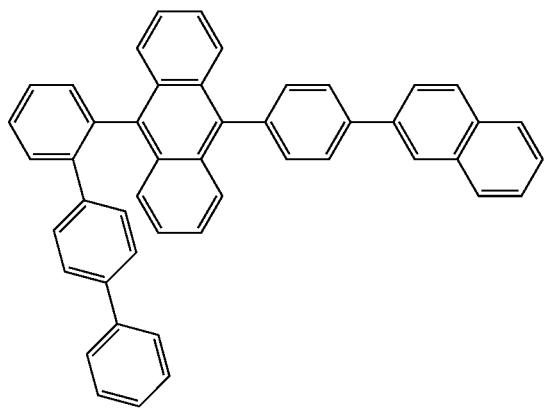
EM379
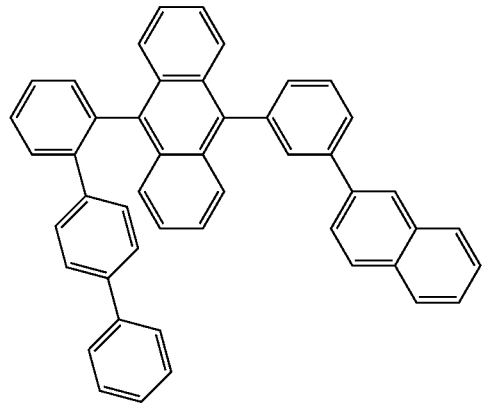
EM380
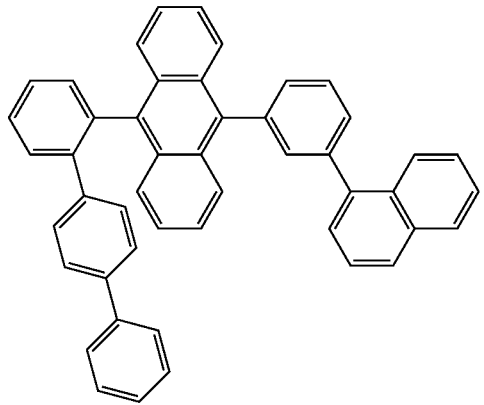
EM381
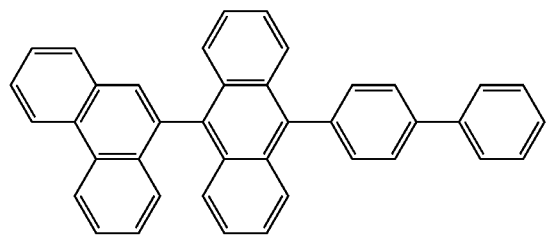
EM382
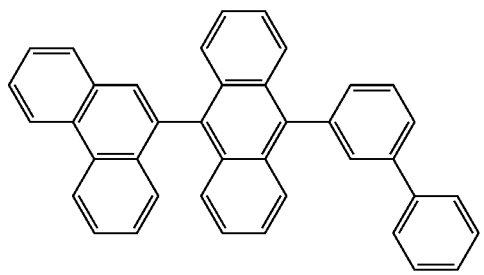
EM383
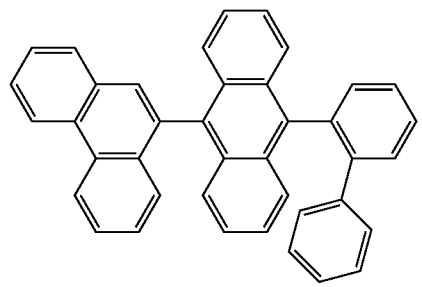
EM384
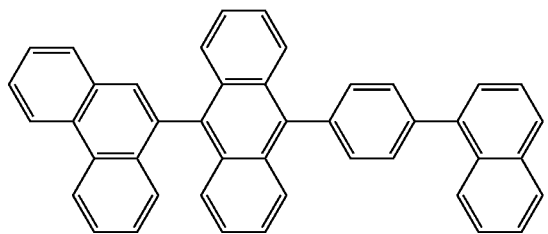

-continued
EM385
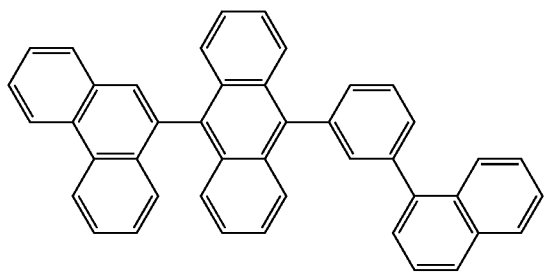
EM386
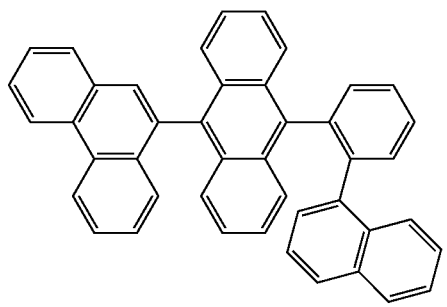
EM387
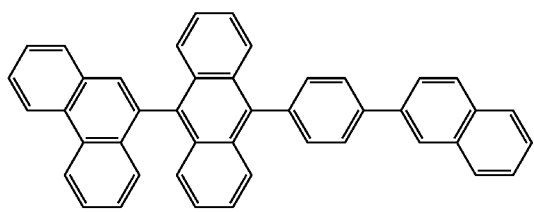
EM388
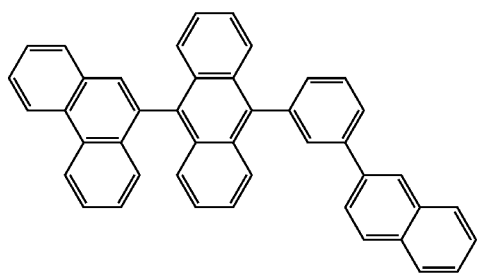
EM389
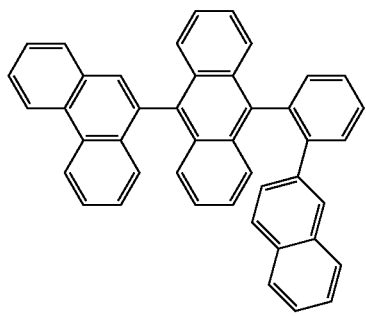
EM390
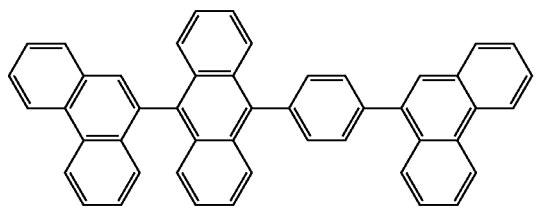
EM391
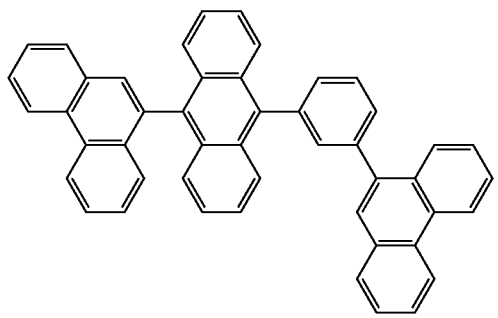
EM392
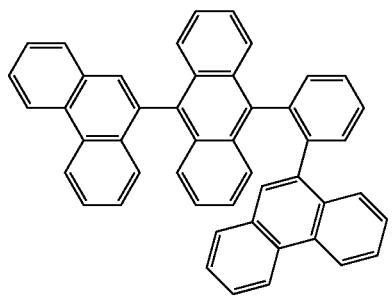
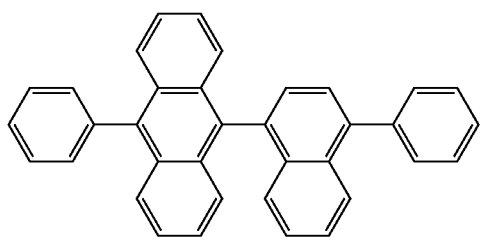
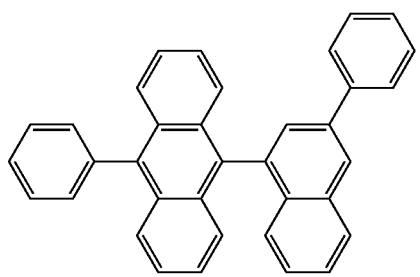

-continued
| 579 | 580 |
|---|---|
| 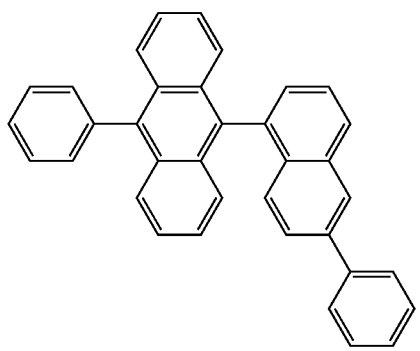 | 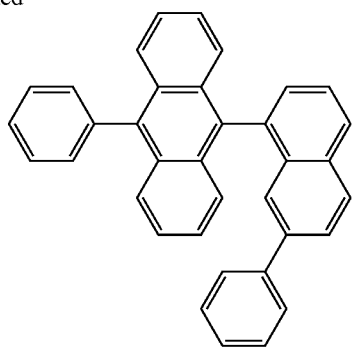 |
| 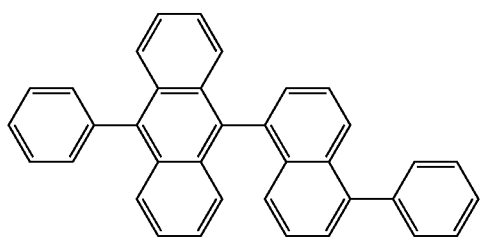 | 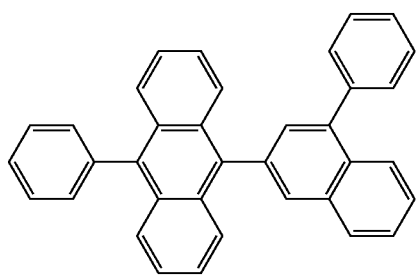 |
| 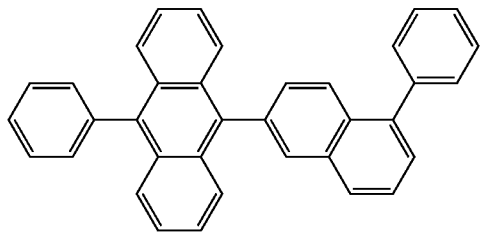 | 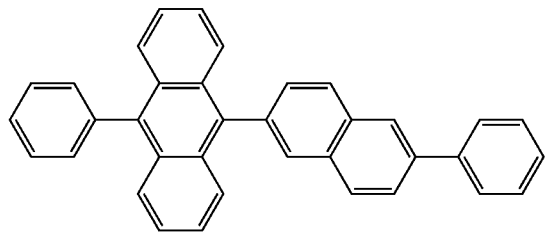 |
| 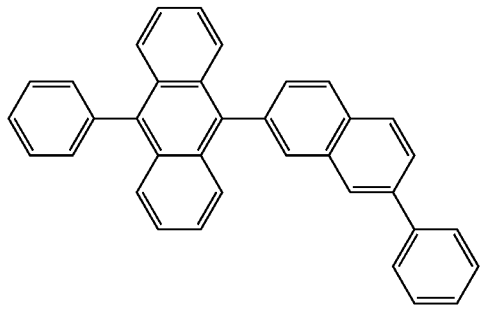 | 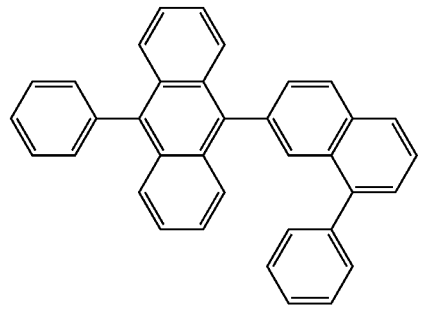 |
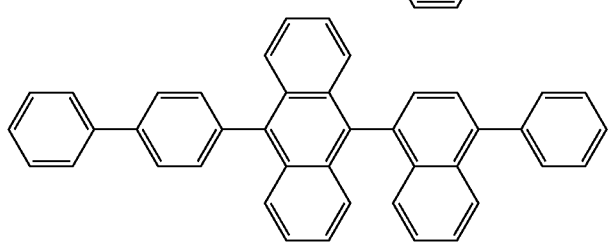
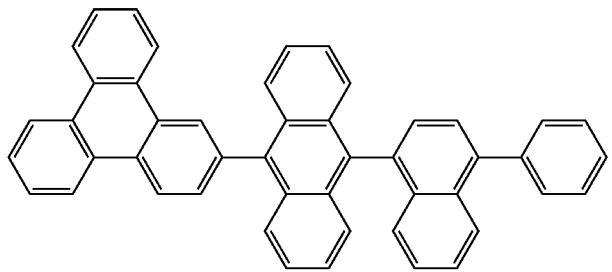

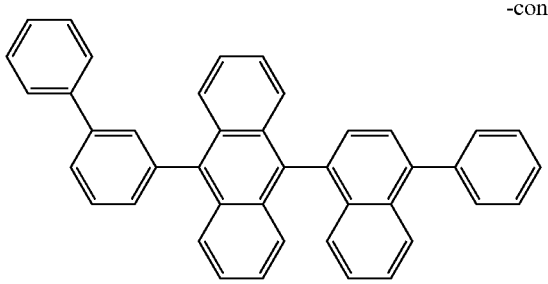
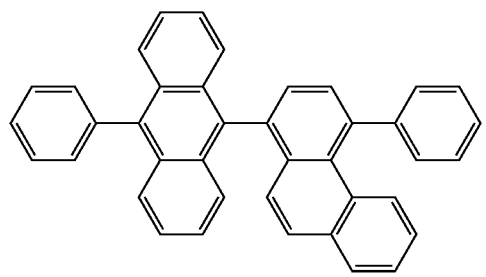

Electron-Donating Dopant

The organic EL device preferably comprises an electron-donating dopant in the interfacial region between the cathode and the light emitting unit. With such a construction, the organic EL device has an improved luminance and an elongated lifetime. The electron-donating dopant is a metal having a work function of 3.8 eV or less or a compound containing such metal. Examples thereof include at least one compound selected from alkali metal, alkali metal complex, alkali metal compound, alkaline earth metal, alkaline earth metal complex, alkaline earth metal compound, rare earth metal, rare earth metal complex, and rare earth metal compound.

Examples of the alkali metal include Na (work function: 2.36 eV), K (work function: 2.28 eV), Rb (work function: 2.16 eV), and Cs (work function: 1.95 eV), with those having a work function of 2.9 eV or less being particularly preferred. Examples of the alkaline earth metal include Ca (work function: 2.9 eV), Sr (work function: 2.0 to 2.5 eV), and Ba (work function: 2.52 eV), with those having a work function of 2.9 eV or less being particularly preferred. Examples of the rare earth metal include Sc, Y, Ce, Tb, and Yb, with those having a work function of 2.9 eV or less being particularly preferred.

Examples of the alkali metal compound include alkali oxide, such as $Li_2O$, $Cs_2O$, $K_2O$, and alkali halide, such as LiF, NaF, CsF, and KF, with LiF, $Li_2O$, and NaF being preferred. Examples of the alkaline earth metal compound include BaO, SrO, CaO, and mixture thereof, such as $Ba_xSr_{1-x}O$ (0<x<1) and $Ba_xCa_{1-x}O$ (0<x<1), with BaO, SrO, and CaO being preferred. Examples of the rare earth metal compound include $YbF_3$, $ScF_3$, $ScO_3$, $Y_2O_3$, $Ce_2O_3$, $GdF_3$, and $TbF_3$, with $YbF_3$, $ScF_3$, and $TbF_3$ being preferred.

Examples of the alkali metal complex, alkaline earth metal complex, and rare earth metal complex are not particularly limited as long as containing at least one metal ion selected from alkali metal ions, alkaline earth metal ions, rare earth metal ions, respectively. Examples of the ligand include quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfulborane, bipyridyl, phenanthroline, phthalocyanine, porphyrin, cyclopentadiene, β-diketones, azomethines, and derivative thereof.

The electron-donating dopant is added to the interfacial region preferably into a form of layer or island. The electron-donating dopant is added preferably by co-depositing the electron-donating dopant with the organic compound (light emitting material, electron injecting material, etc.) for forming the interfacial region by a resistance heating deposition method, thereby dispersing the electron-donating dopant into the organic material. The disperse concentration expressed by the molar ratio of the organic material and the electron-donating dopant is 100:1 to 1:100.

When the electron-donating dopant is formed into a form of layer, a light emitting material or an electron injecting material is made into a layer which serves as an organic layer in the interface, and then, the electron-donating dopant alone is deposited by a resistance heating deposition method into a layer having a thickness preferably 0.1 to 15 nm. When the electron-donating dopant is formed into a form of island, a light emitting material or an electron injecting material is made into a form of island which serves as an organic layer in the interface, and then, the electron-donating dopant alone is deposited by a resistance heating deposition method into a form of island having a thickness preferably 0.05 to 1 nm.

The molar ratio of the main component and the electron-donating dopant in the organic electroluminescence device is preferably 5:1 to 1:5.

Electron Transporting Layer

The electron transporting layer is an organic layer disposed between the light emitting layer and the cathode and transports electrons from the cathode to the light emitting layer. If two or more electron transporting layers are provided, the organic layer closer to the cathode may be called an electron injecting layer in some cases. The electron injecting layer injects electrons from the cathode to the organic layer unit efficiently.

An aromatic heterocyclic compound having one or more heteroatoms in its molecule is preferably used as the electron transporting material for the electron transporting layer, with a nitrogen-containing ring derivative being particularly preferred. The nitrogen-containing ring derivative is preferably an aromatic ring compound having a nitrogen-containing 6- or 5-membered ring or a condensed aromatic ring compound having a nitrogen-containing 6- or 5-membered ring.

The nitrogen-containing ring derivative is preferably, for example, a chelate metal complex having a nitrogen-containing ring represented by formula (A).

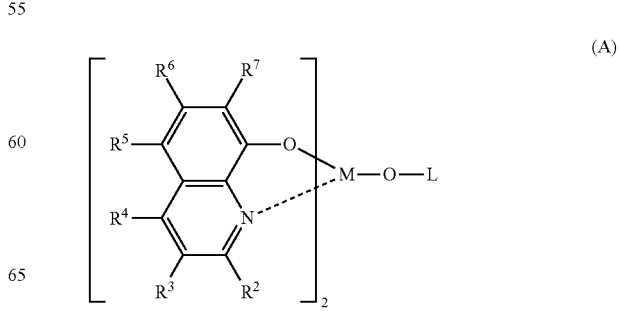

(A)

$R^2$ to $R^7$ of formula (A) each independently represent a hydrogen atom, a deuterium atom, a halogen atom, a hydroxyl group, an amino group, a hydrocarbon group having 1 to 40 carbon atoms, an alkoxy group having 1 to 40 carbon atoms, an aryloxy group having 6 to 50 carbon atoms, an alkoxycarbonyl group, or a heterocyclic group having 5 to 50 carbon atoms, each being optionally substituted.

M is aluminum (Al), gallium (Ga), or indium (In), with In being preferred.

L is a group represented by formula (A') or (A"):

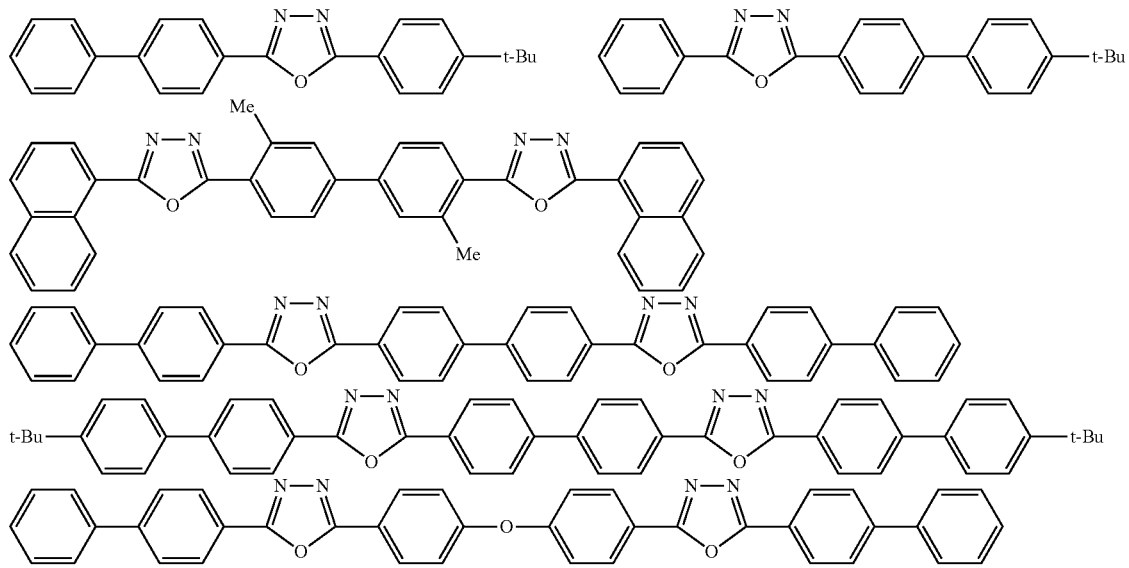

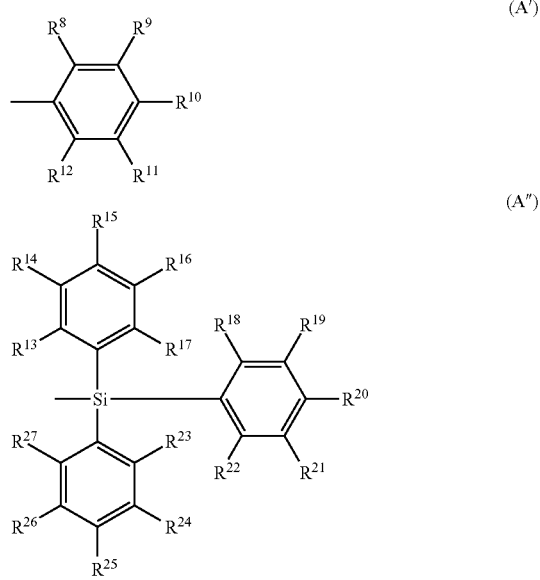

$R^8$ to $R^{12}$ in formula (A') each independently represent a hydrogen atom, a deuterium atom, or a substituted or unsubstituted hydrocarbon group having 1 to 40 carbon atoms. The adjacent two groups may form a ring structure. $R^{13}$ to $R^{27}$ in formula (A") each independently represent a hydrogen atom, a deuterium atom, or a substituted or unsubstituted hydrocarbon group having 1 to 40 carbon atoms. The adjacent two groups may form a ring structure.

The electron transporting compound for the electron transporting layer is preferably a metal complex including 8-hydroxyquinoline or its derivative, an oxadiazole derivative, and a nitrogen-containing heterocyclic derivative.

Electron transporting compounds which have a good thin film-forming property are preferably used. Examples of the electron transporting compound are shown below.

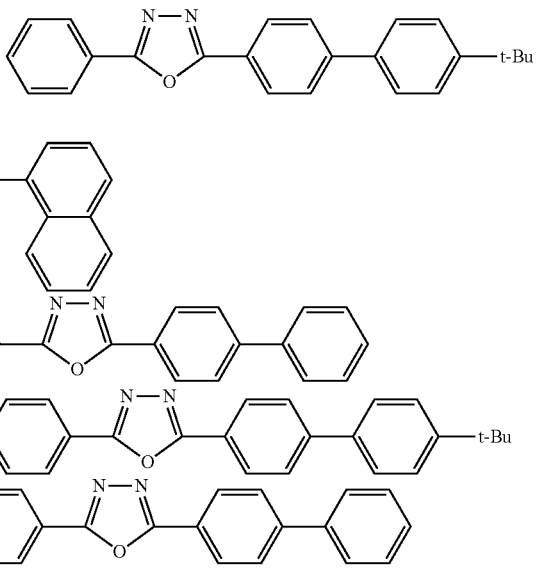

Examples of the nitrogen-containing heterocyclic derivative for use as the electron transporting compound include a nitrogen-containing heterocyclic derivative having the following formulae but exclusive of metal complex.

(D)

The electron transporting layer of the organic EL particularly preferably comprises at least one of the nitrogen-containing heterocyclic derivatives represented by formulae (60) to (62).

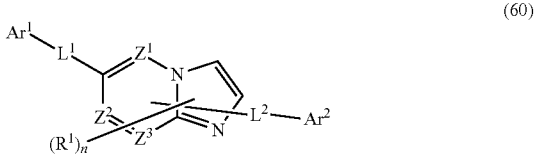

(60)

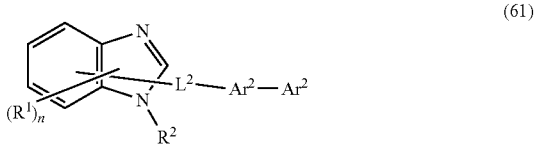

(61)

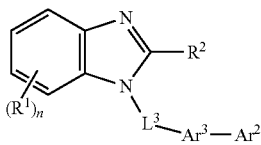

(62)

In formulae (60) to (62), $Z^1$, $Z^2$, and $Z^3$ each independently represent a nitrogen atom or a carbon atom.

$R^1$ and $R^2$ each independently represent a substituted or unsubstituted aryl group having 6 to 50 ring carbon atoms, a substituted or unsubstituted heterocyclic group having 5 to 50 ring atoms, a substituted or unsubstituted alkyl group having 1 to 20 carbon atoms, a substituted or unsubstituted haloalkyl group having 1 to 20 carbon atoms, or a substituted or unsubstituted alkoxyl group having 1 to 20 carbon atoms.

Subscript n is an integer of 0 to 5. If n is an integer of 2 or more, $R^1$ groups may be the same or different from each other. The adjacent two $R^1$ groups may bond to each other to form a substituted or unsubstituted hydrocarbon ring.

$Ar^1$ represents a substituted or unsubstituted aryl group having 6 to 50 ring carbon atoms or a substituted or unsubstituted heteroaryl group having 5 to 50 ring atoms.

$Ar^2$ represents a hydrogen atom, a substituted or unsubstituted alkyl group having 1 to 20 carbon atoms, a substituted or unsubstituted haloalkyl group having 1 to 20 carbon atoms, a substituted or unsubstituted alkoxyl group having 1 to 20 carbon atoms, a substituted or unsubstituted aryl group having 6 to 50 ring carbon atoms, or a substituted or unsubstituted heterocyclic group having 5 to 50 ring atoms.

However, one of $Ar^1$ and $Ar^2$ is a substituted or unsubstituted fused aromatic hydrocarbon group having 10 to 50 ring carbon atoms or a substituted or unsubstituted fused aromatic heterocyclic group having 9 to 50 ring atoms.

$Ar^3$ represents a substituted or unsubstituted arylene group having 6 to 50 ring carbon atoms or a substituted or unsubstituted heteroarylene group having 5 to 50 ring atoms.

$L^1$, $L^2$, and $L^3$ each independently represent a single bond, a substituted or unsubstituted arylene group having 6 to 50 ring carbon atoms or a substituted or unsubstituted divalent fused aromatic heterocyclic group having 9 to 50 ring atoms.

Examples of the nitrogen-containing heterocyclic derivatives represented by formulae (60) to (62) are shown below.

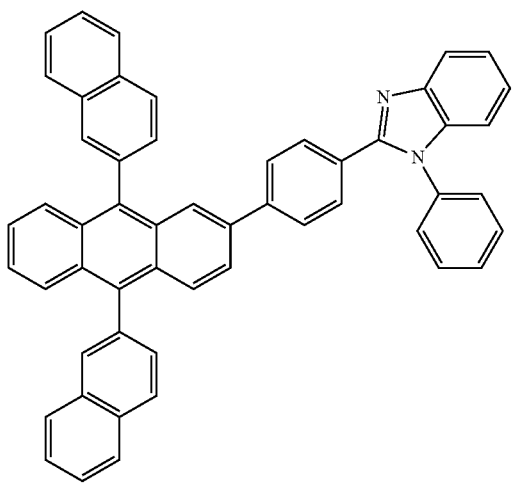

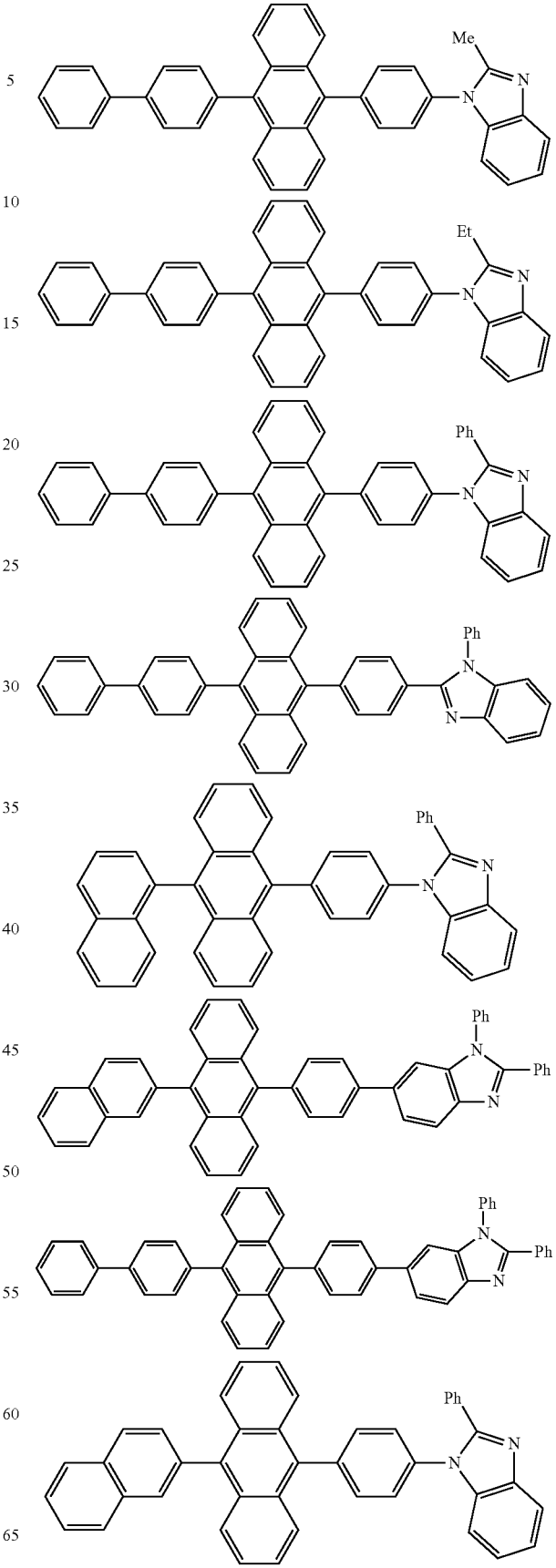

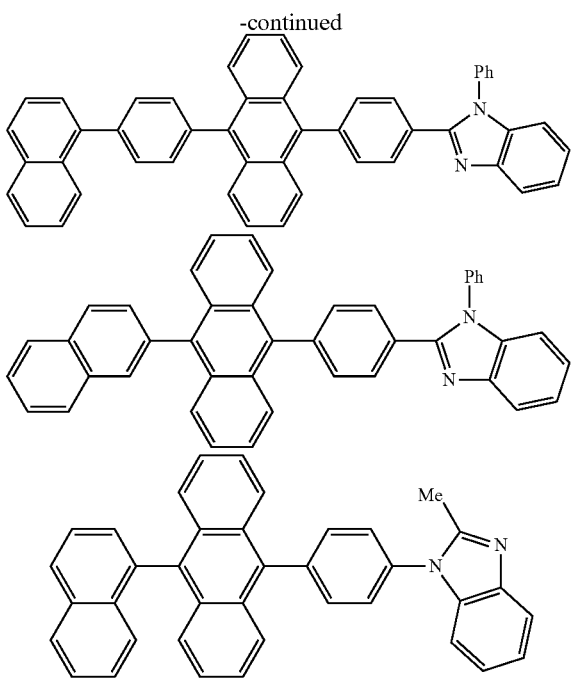

The thickness of the electron transporting layer is preferably 1 to 100 nm, although not particularly limited thereto.

The electron injecting layer which may be formed adjacent to the electron transporting layer preferably includes an inorganic compound, such as an insulating material and a semiconductor in addition to the nitrogen-containing ring derivative. The insulating material or semiconductor incorporated into the electron injecting layer effectively prevents the leak of electric current to enhance the electron injecting properties.

The insulating material is preferably at least one metal compound selected from the group consisting of alkali metal chalcogenides, alkaline earth metal chalcogenides, alkali metal halides and alkaline earth metal halides. The alkali metal chalcogenide, etc. incorporated into the electron injecting layer further enhances the electron injecting properties. Preferred examples of the alkali metal chalcogenides include $Li_2O$, $K_2O$, $Na_2S$, $Na_2Se$ and $Na_2O$, and preferred examples of the alkaline earth metal chalcogenides include CaO, BaO, SrO, BeO, BaS and CaSe. Preferred examples of the alkali metal halides include LiF, NaF, KF, LiCl, KCl and NaCl. Examples of the alkaline earth metal halides include fluorides such as $CaF_2$, $BaF_2$, $SrF_2$, $MgF_2$ and $BeF_2$ and halides other than fluorides.

Examples of the semiconductor may include oxide, nitride or oxynitride each containing at least one element selected from the group consisting of Ba, Ca, Sr, Yb, Al, Ga, In, Li, Na, Cd, Mg, Si, Ta, Sb and Zn. The semiconductor may be used singly or in combination of two or more. The inorganic compound forming the electron injecting layer preferably forms a microcrystalline or amorphous insulating thin film. When the electron injecting layer is formed from such an insulating thin film, the thin film is made more uniform to decrease the pixel defects such as dark spots. Examples of such inorganic compound include alkali metal chalcogenides, alkaline earth metal chalcogenides, alkali metal halides and alkaline earth metal halide, each being described above.

The thickness of the layer including the insulating material or the semiconductor is preferably about 0.1 to 15 nm. The electron injecting layer may include the electron-donating dopant described above.

Hole Transporting Layer

The hole transporting layer is an organic layer formed between the light emitting layer and the anode and has a function of transporting holes from the anode to the light emitting layer. When the hole transporting layer is formed by two or more layers, the layer closer to the anode may be defined as the hole injecting layer in some cases. The hole injecting layer has a function of efficiently injecting holes from the anode to the organic layer unit.

An aromatic amine compound, for example, the aromatic amine derivative represented by formula (I), is also preferably used as the material for forming the hole transporting layer.

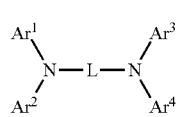

(I)

In the formula (I), each of $Ar^1$ to $Ar^4$ represents a substituted or unsubstituted aromatic hydrocarbon group or fused aromatic hydrocarbon group having 6 to 50 ring carbon atoms, a substituted or unsubstituted aromatic heterocyclic group or fused aromatic heterocyclic group having 5 to 50 ring atoms, or a group wherein the aromatic hydrocarbon group or fused aromatic hydrocarbon group is bonded to the aromatic heterocyclic group or fused aromatic heterocyclic group. $Ar^1$ and $Ar^2$, or $Ar^3$ and $Ar^4$ may form a ring.

L represents a substituted or unsubstituted aromatic hydrocarbon group or fused aromatic hydrocarbon group each having 6 to 50 ring carbon atoms or a substituted or unsubstituted aromatic heterocyclic group or fused aromatic heterocyclic group each having 5 to 50 ring atoms.

Examples of the compound represented by formula (I) are shown below.

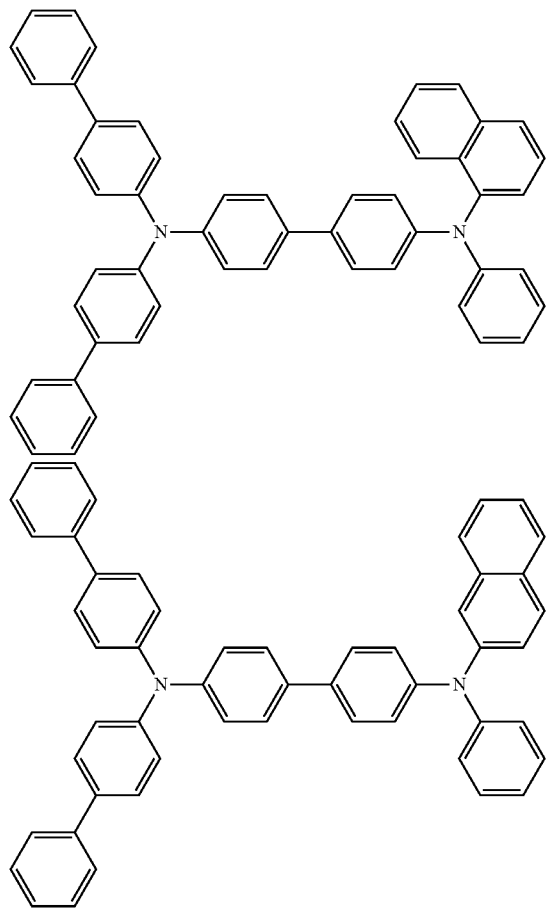

589
-continued
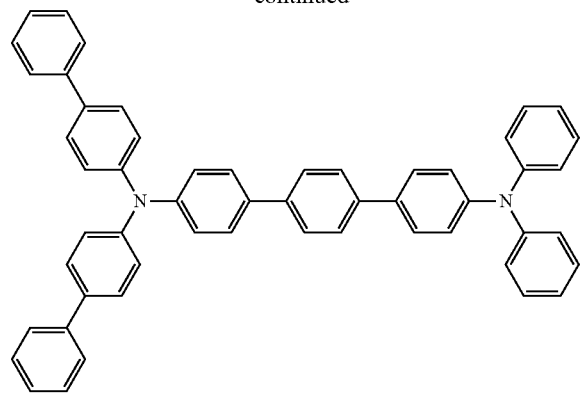
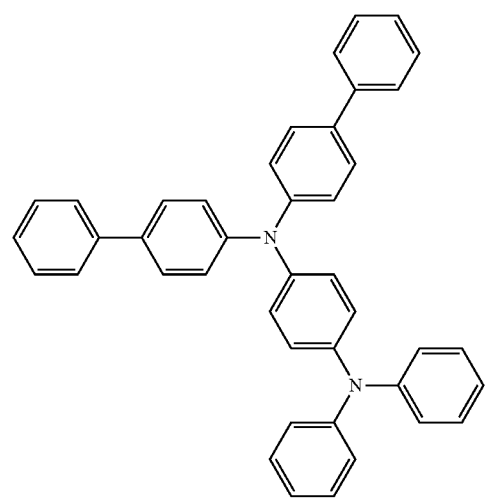
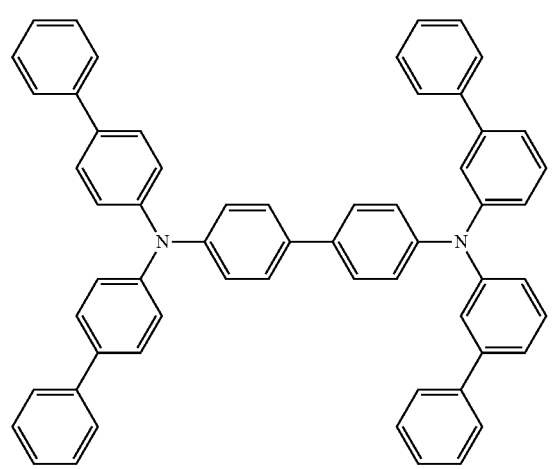
590
-continued
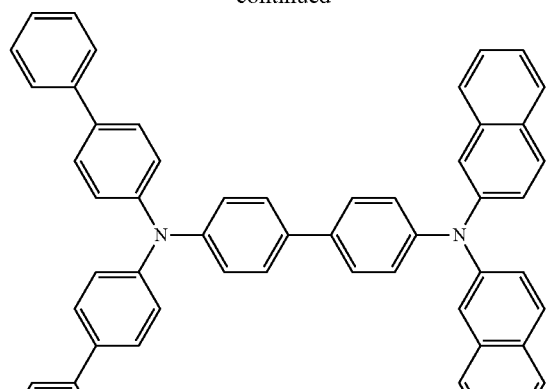
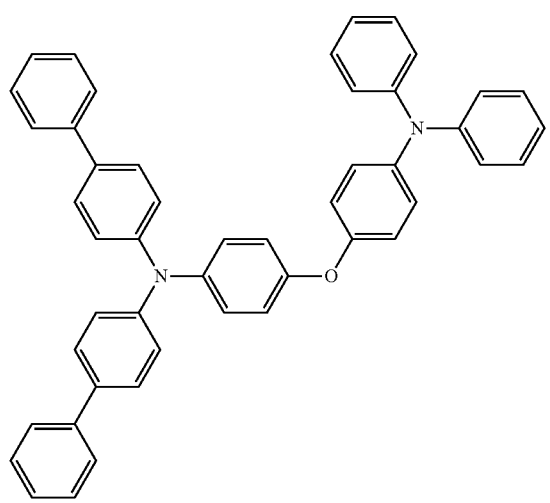

591
-continued
592
-continued
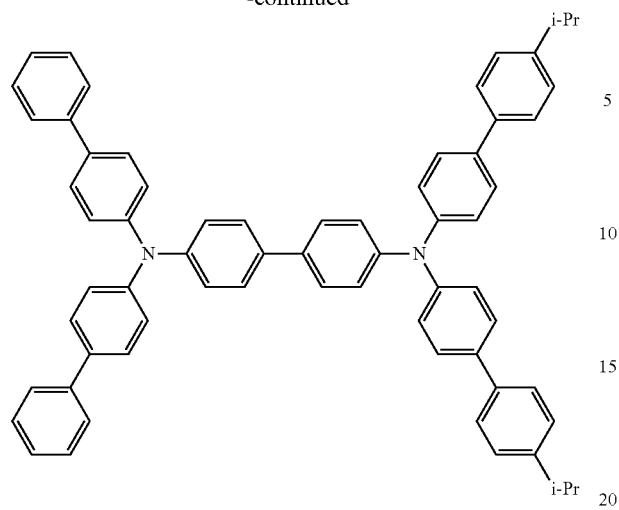
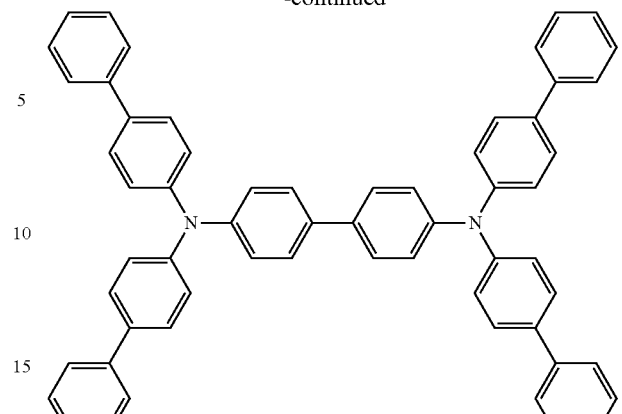
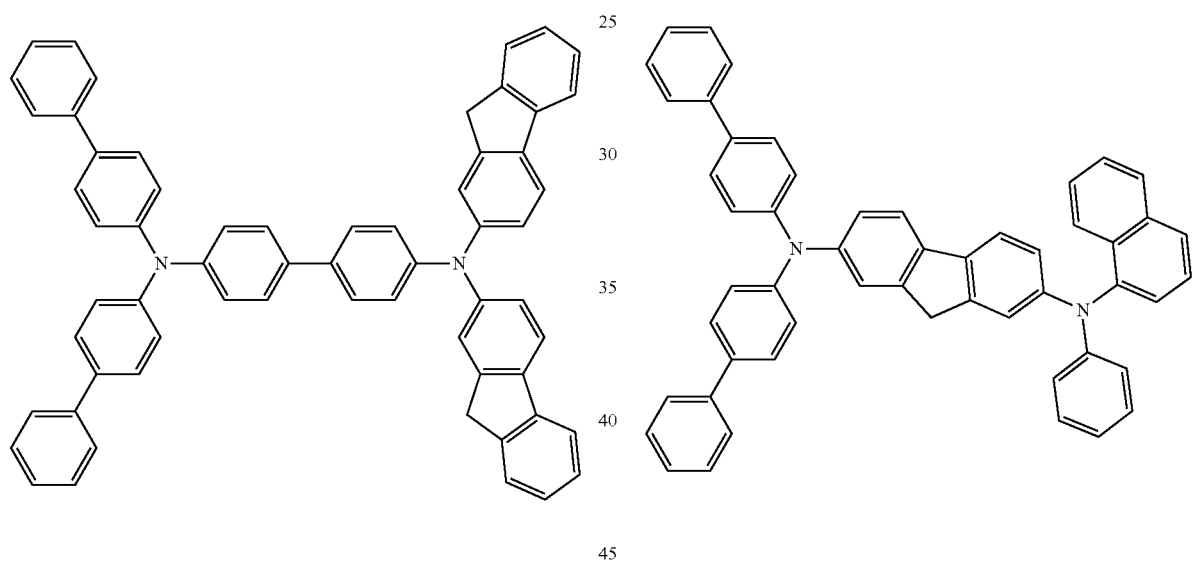
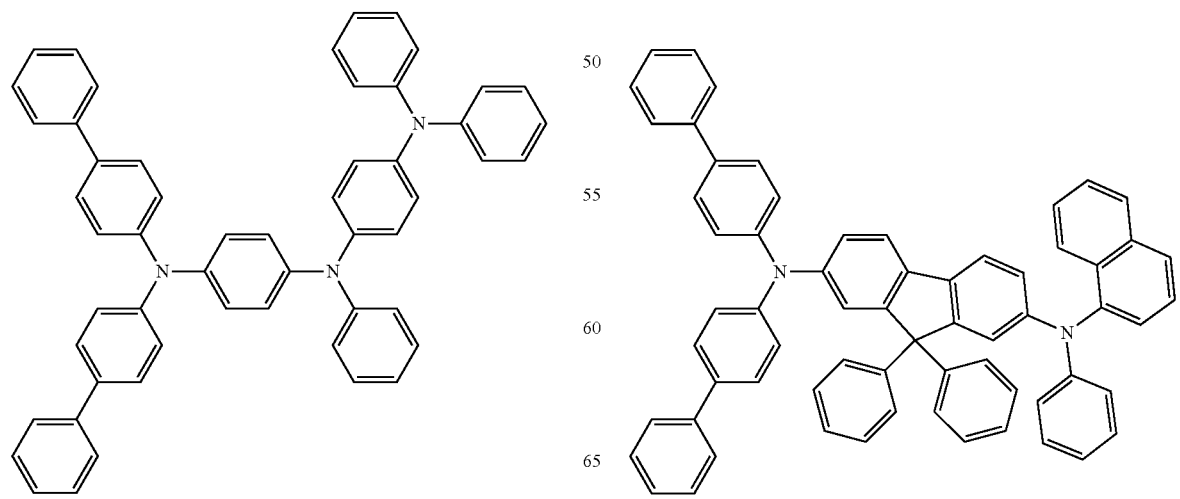

593
-continued
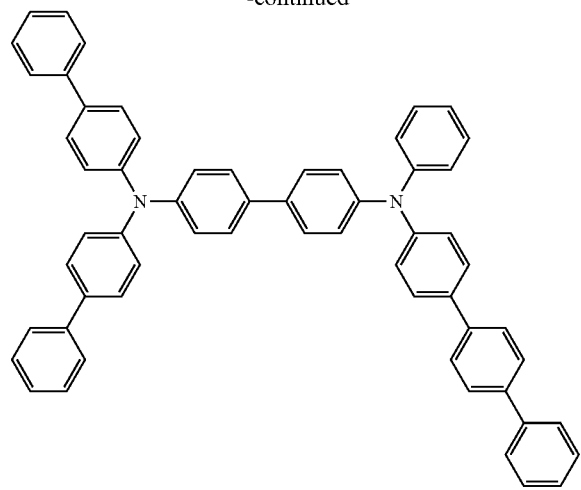
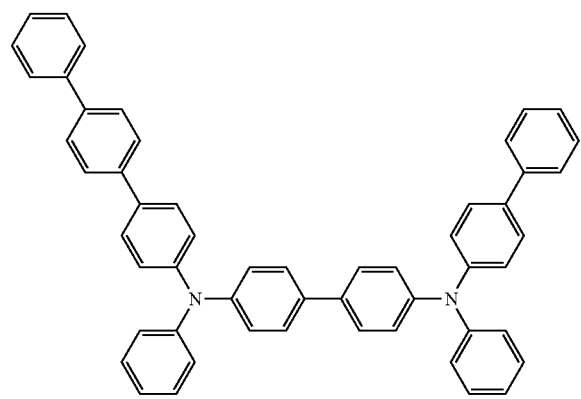
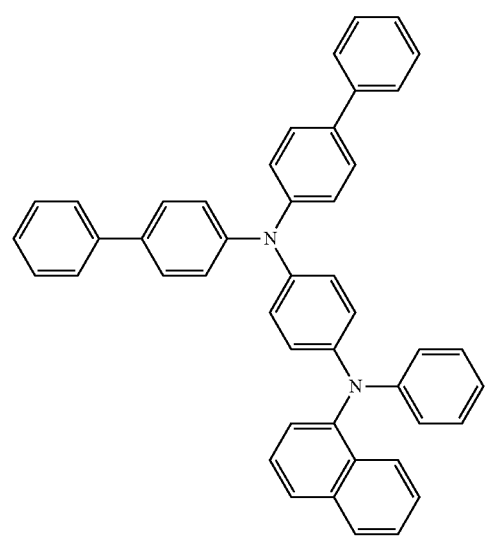
594
-continued
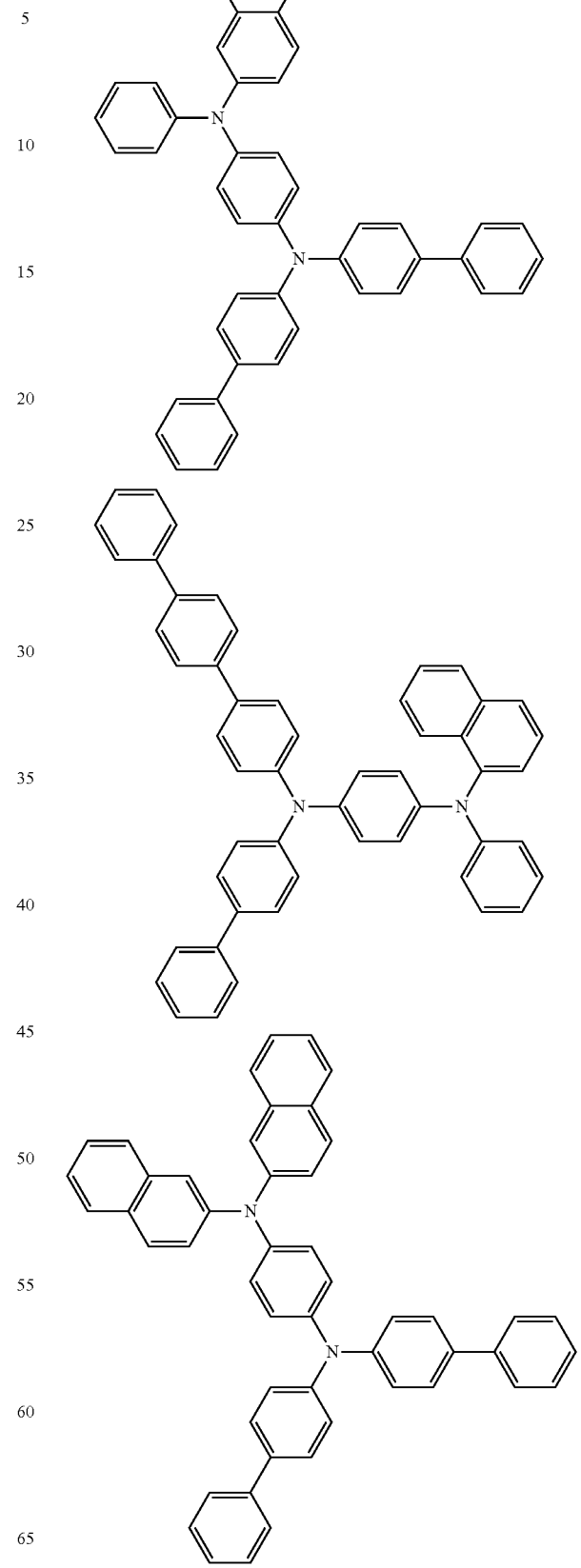

595
-continued
596
-continued
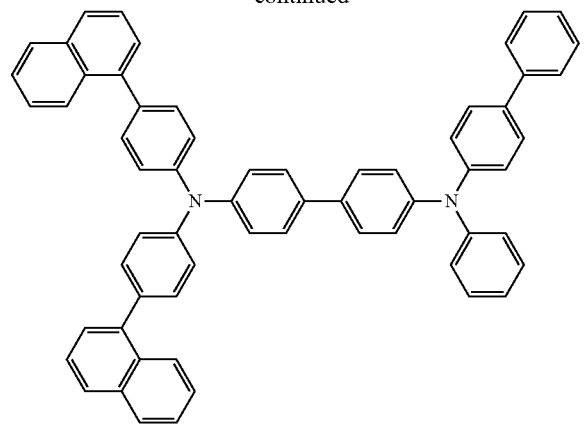
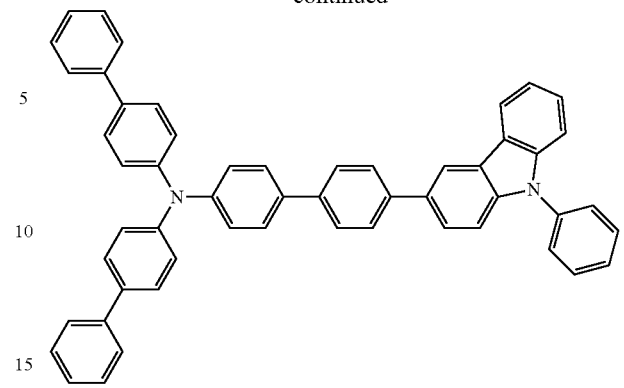
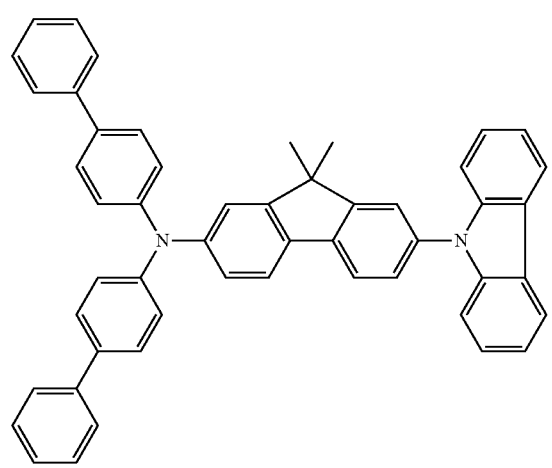
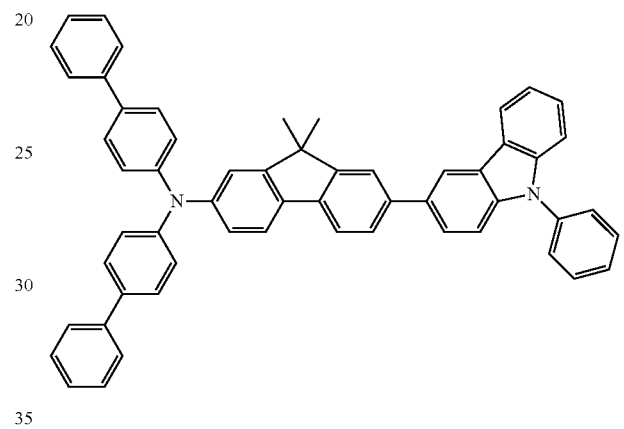
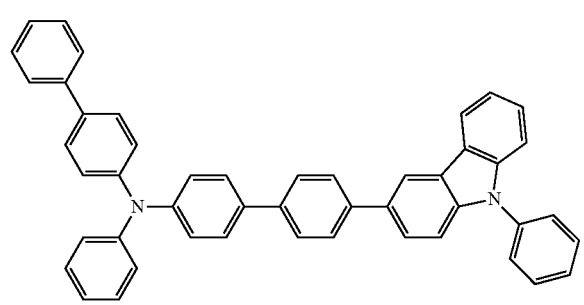
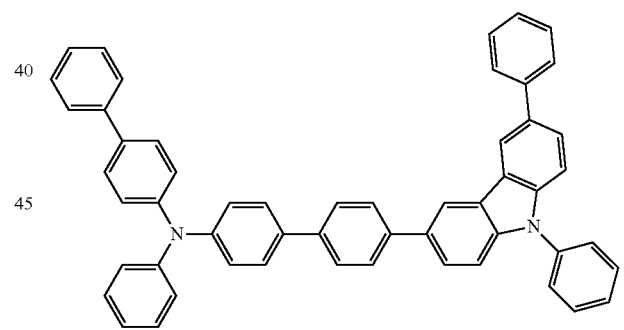
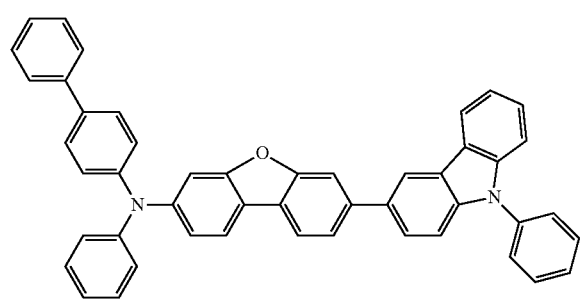
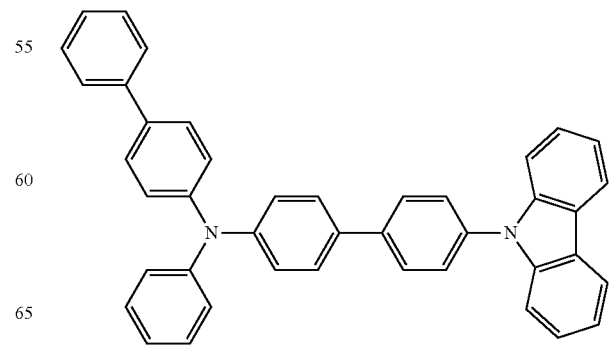

597
-continued
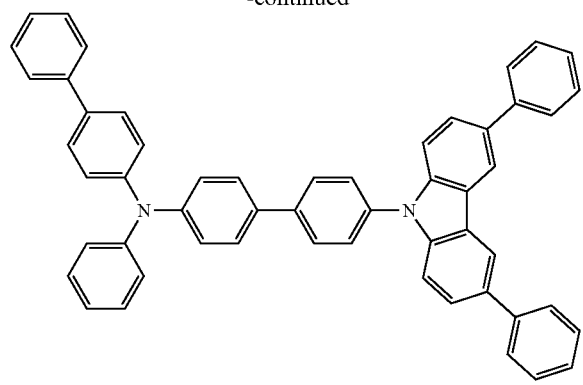
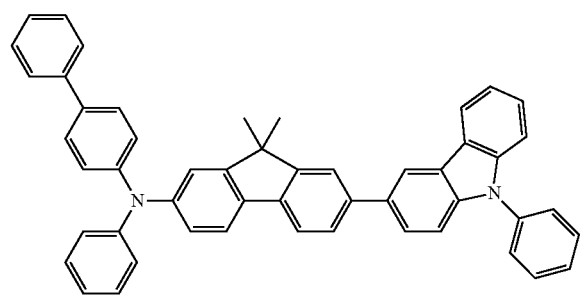 [SMILES: CC1(C)c2cc(-c3ccc4c(c3)c3ccccc3n4-c3ccccc3)ccc2-c2ccc(N(c3ccccc3)c3ccc(-c4ccccc4)cc3)cc21]
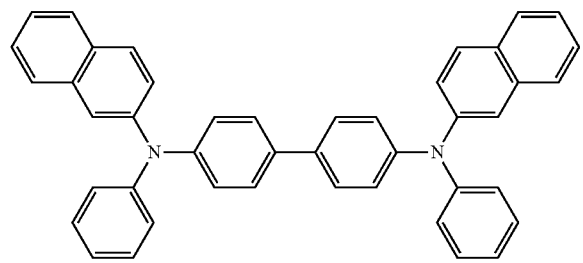
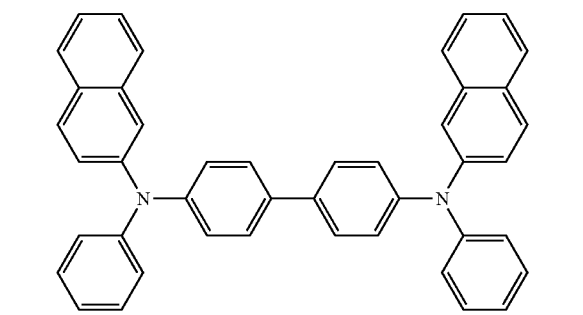
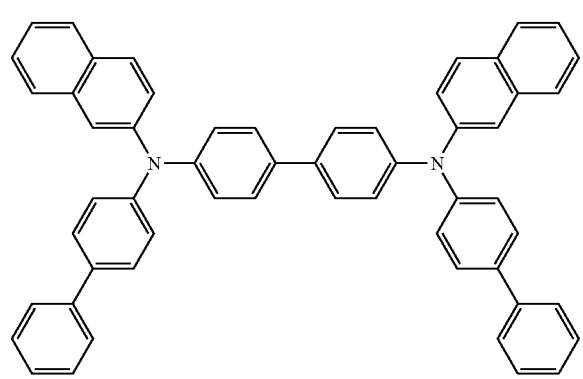
598
-continued
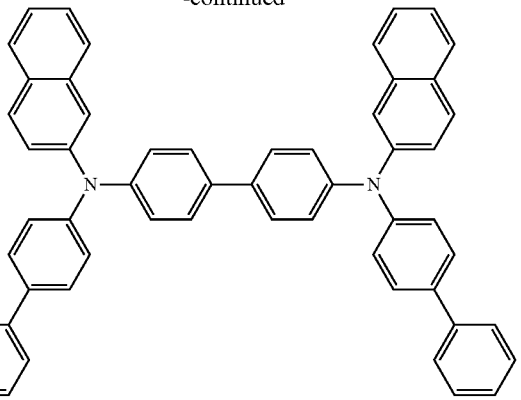
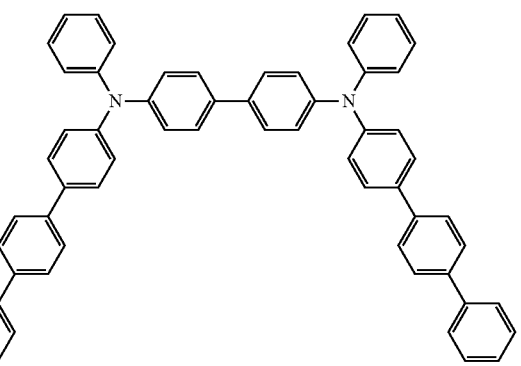
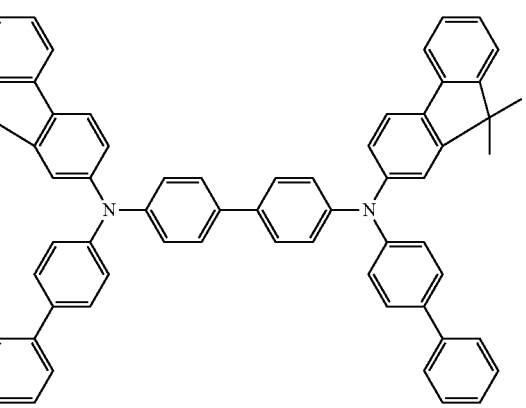
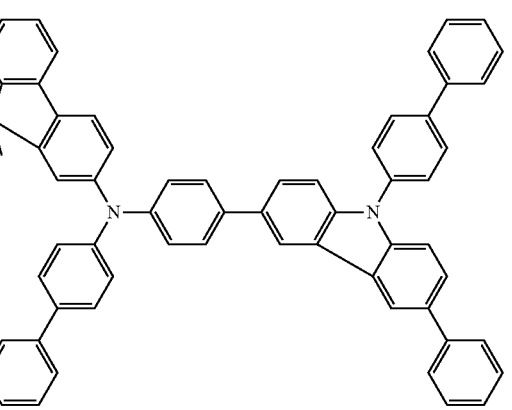

599
-continued
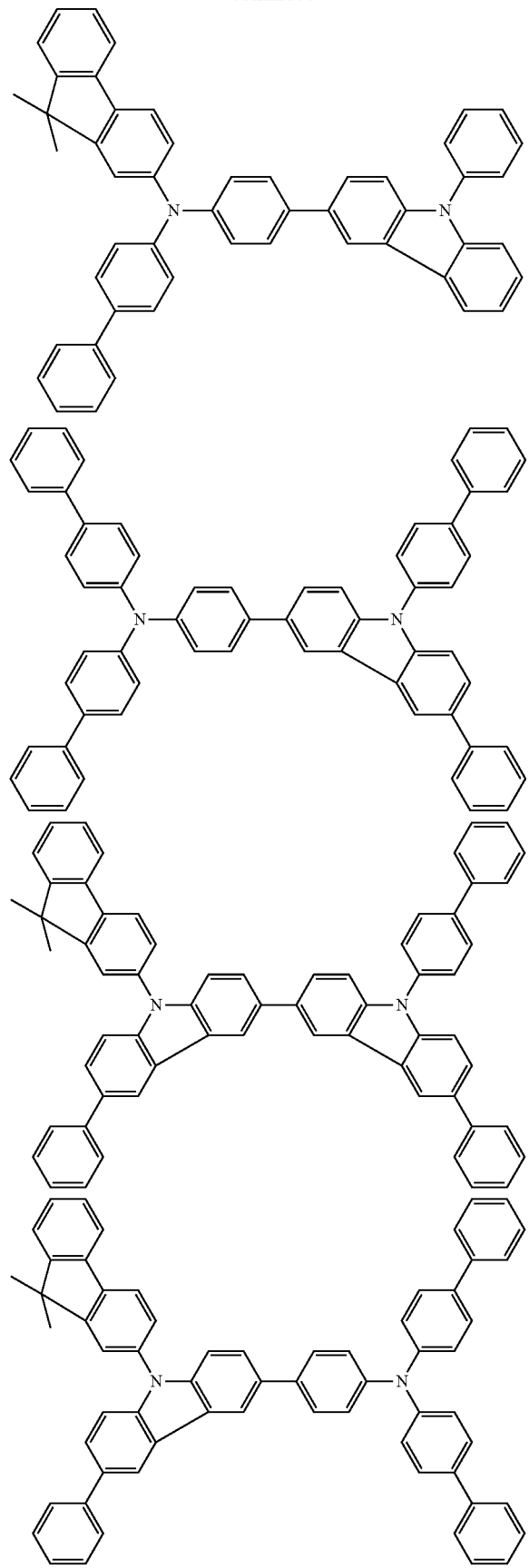
600
-continued
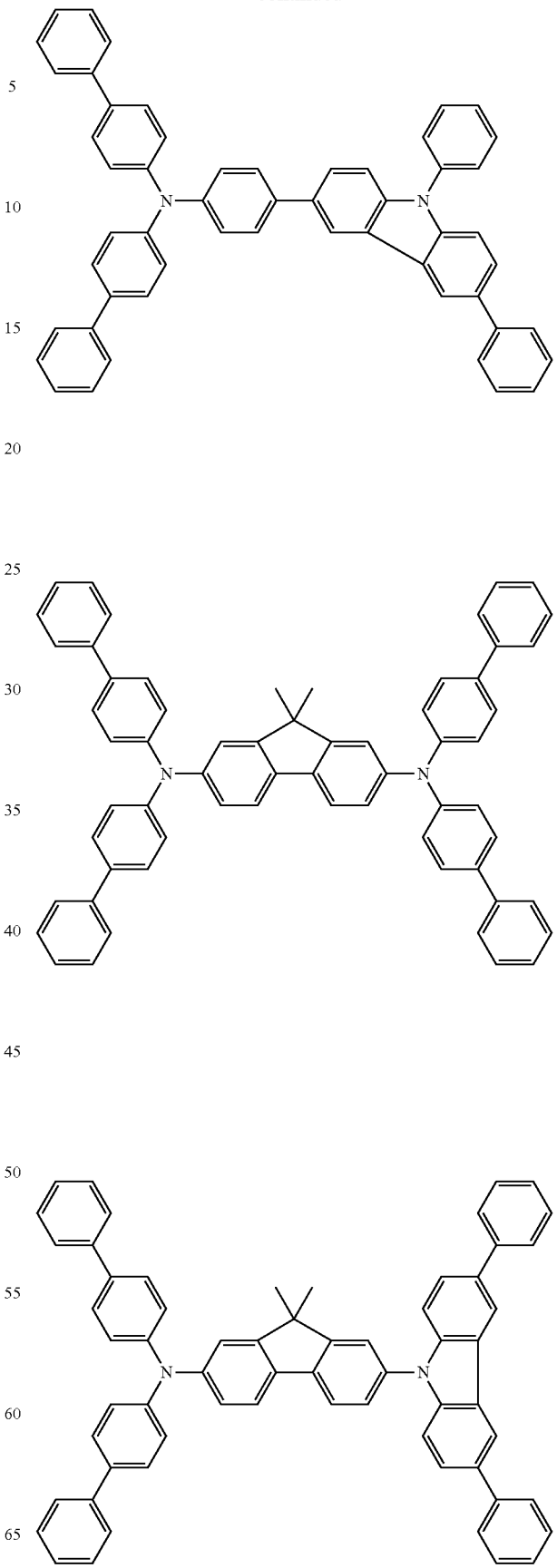

601
-continued
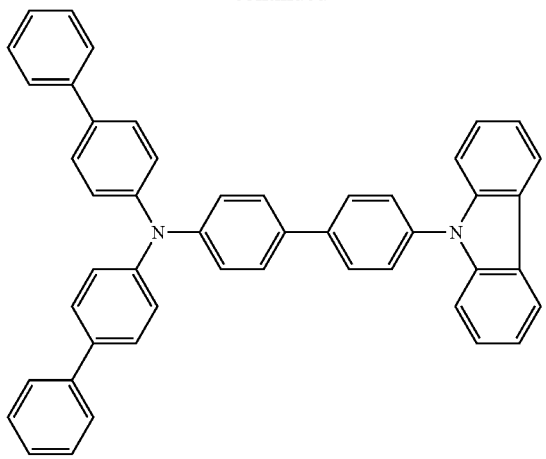
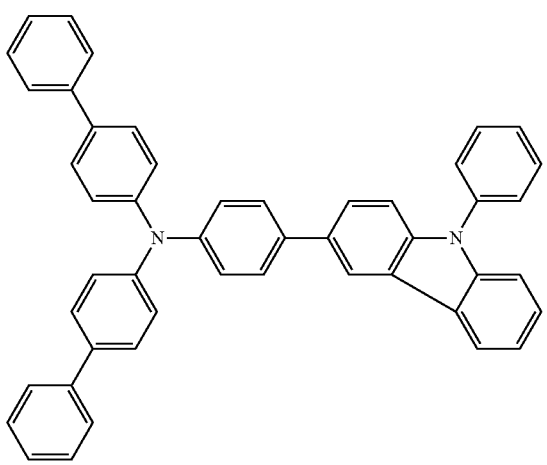
602
-continued
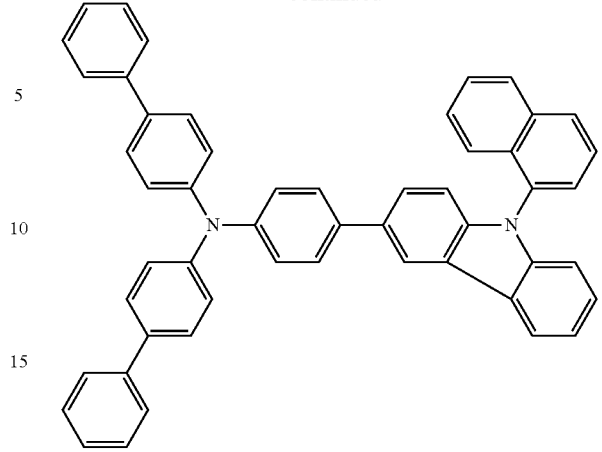
The aromatic amine represented by formula (II) is also preferably used as the material for forming the hole transporting layer.
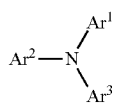
(II)
In formula (II), each of $Ar^1$ to $Ar^3$ is defined as in the definition of $Ar^1$ to $Ar^4$ of formula (I). Examples of the compounds represented by formula (II) are shown below, although not limited thereto.
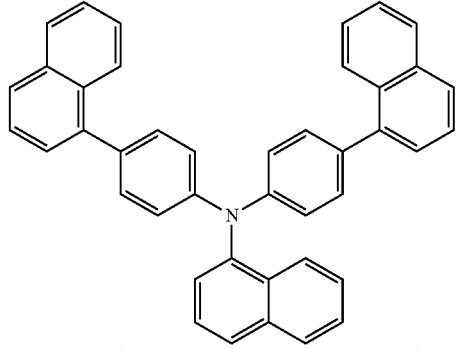
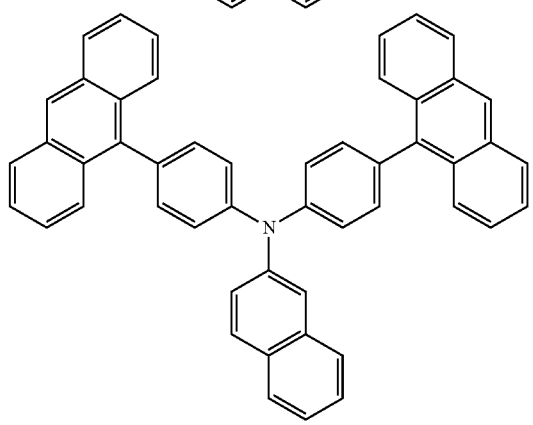

603
-continued
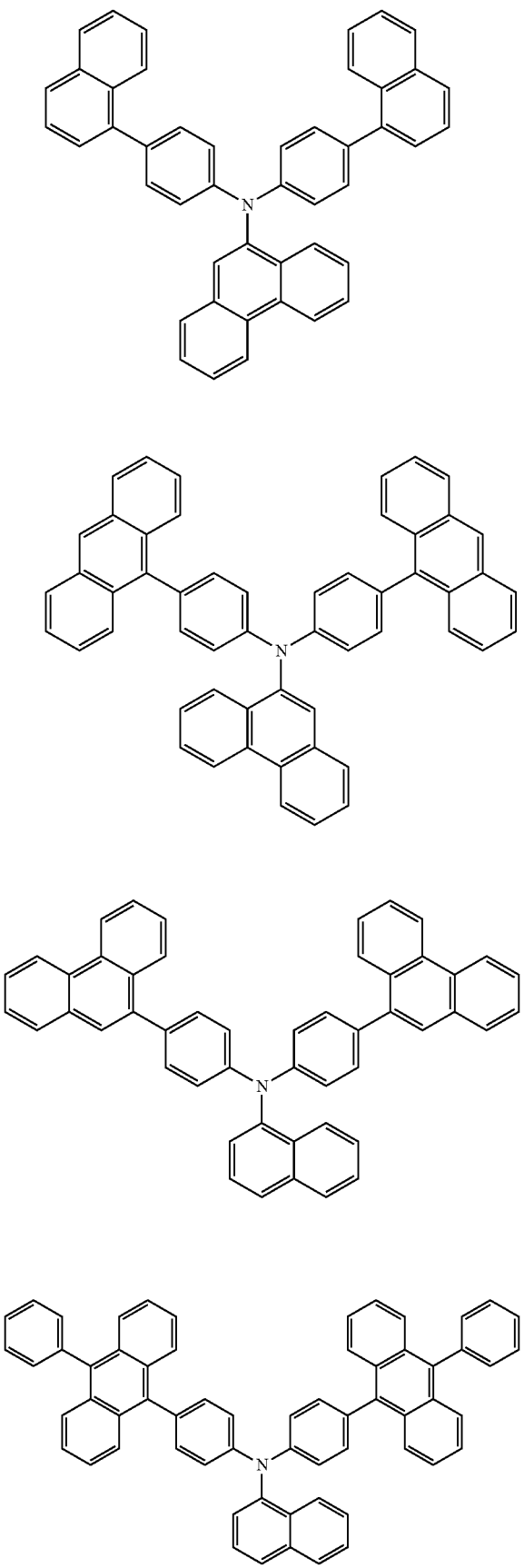
604
-continued
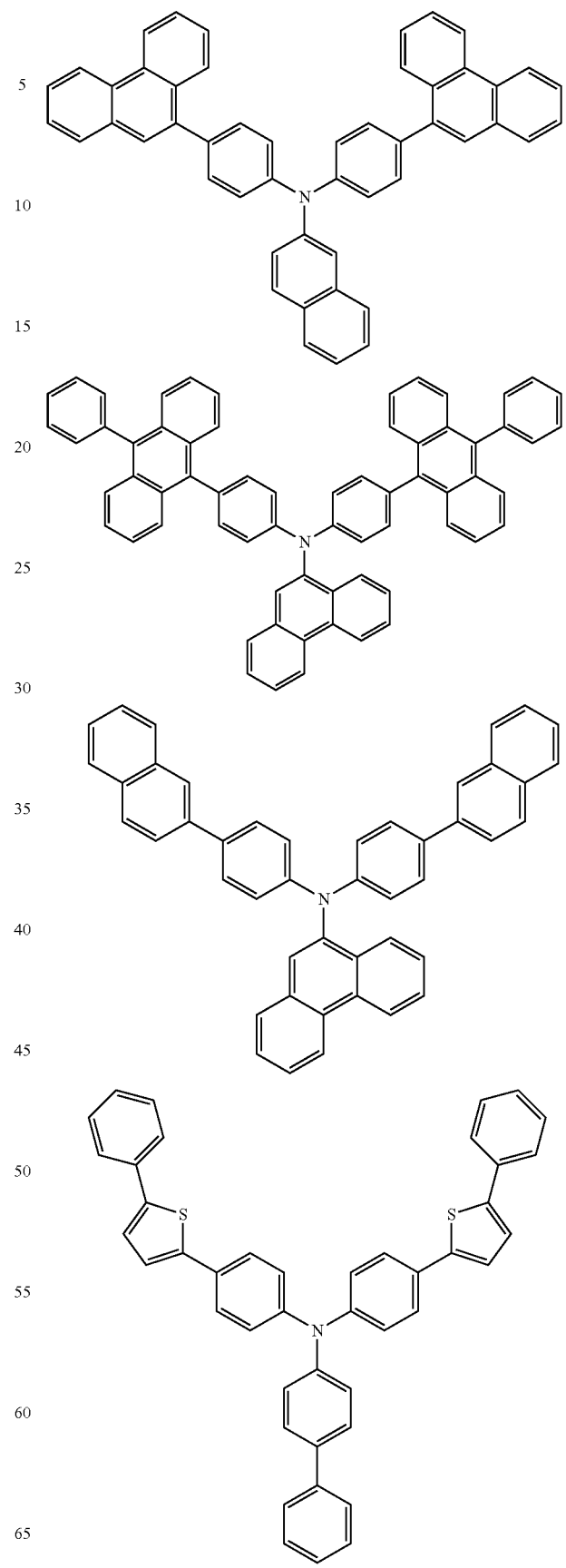

605
-continued
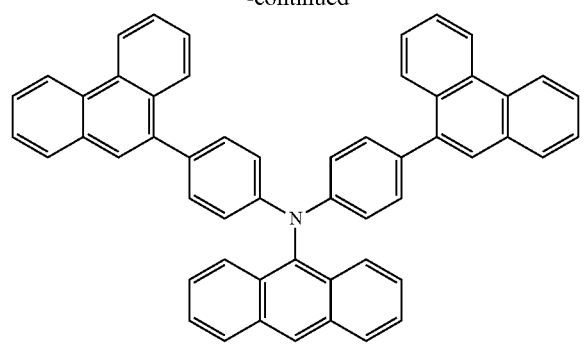
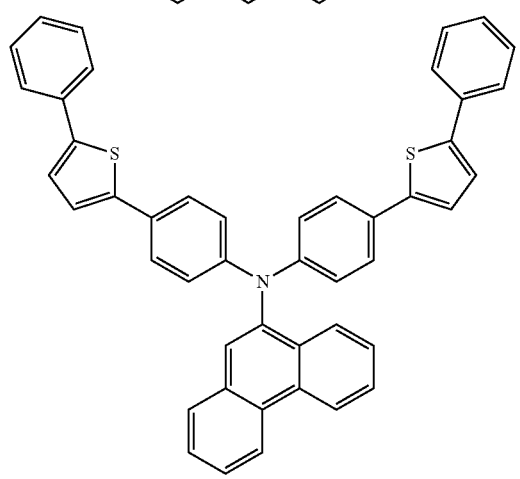
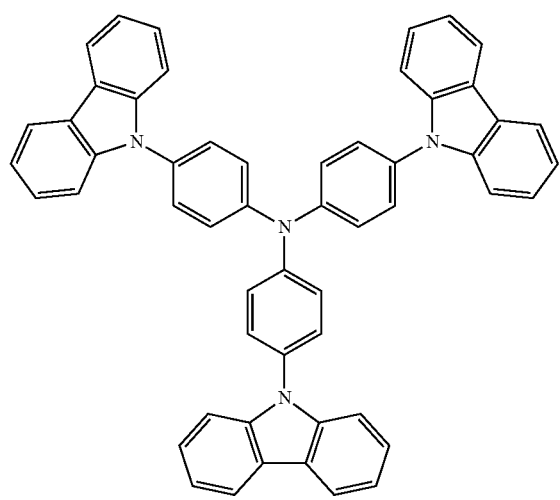
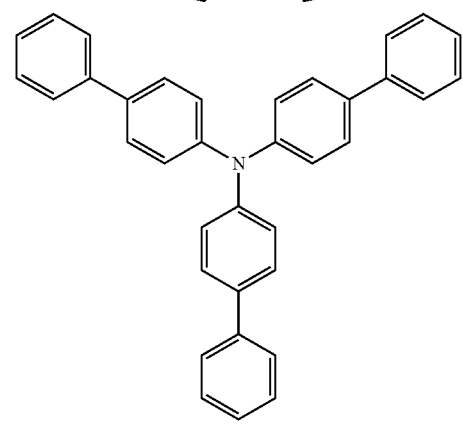
606
-continued
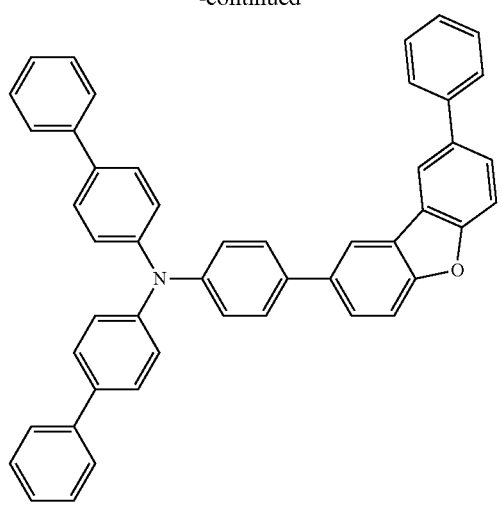
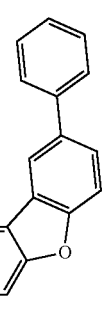
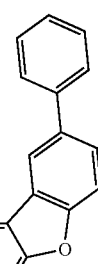

607
-continued
608
-continued
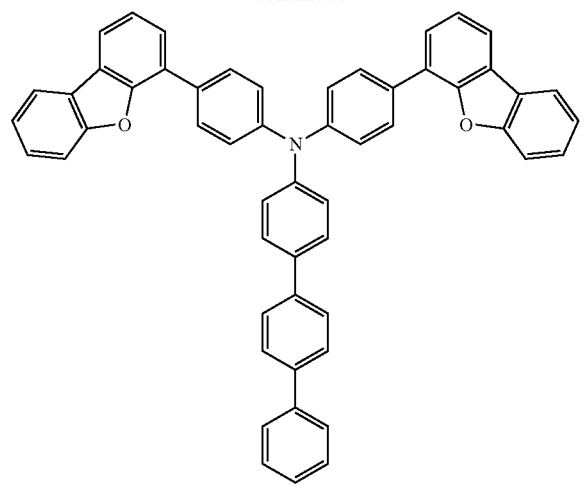
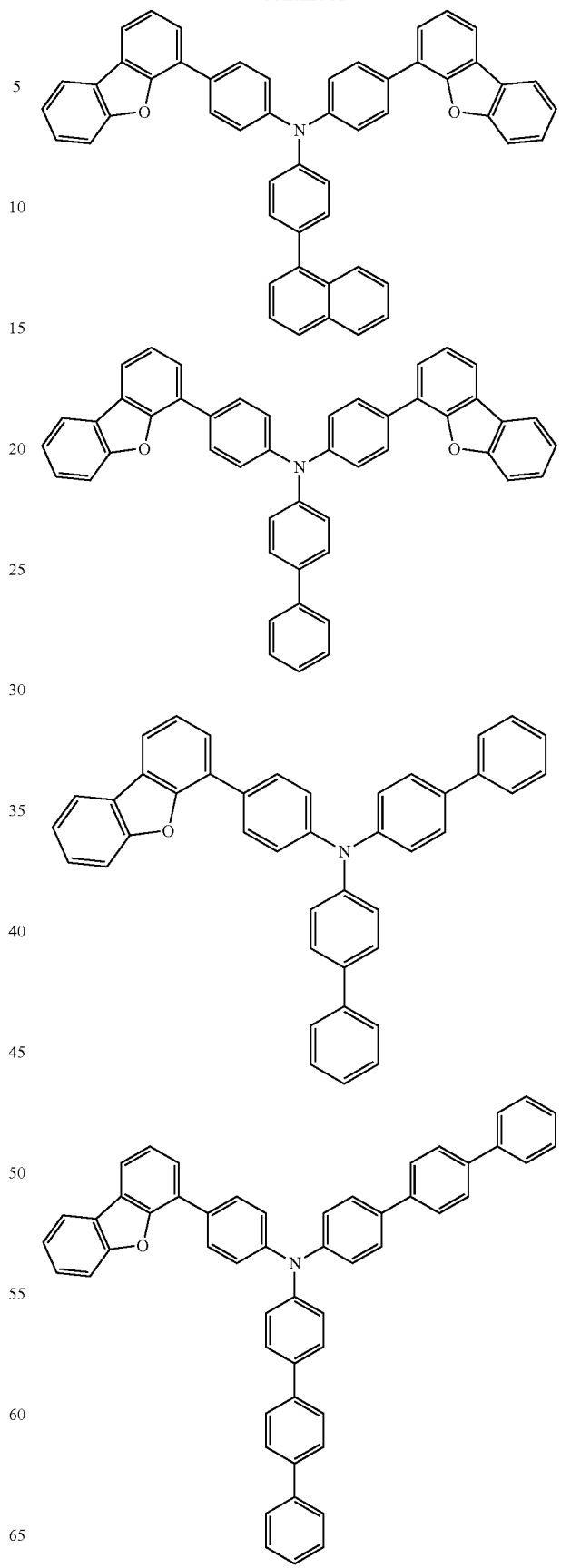

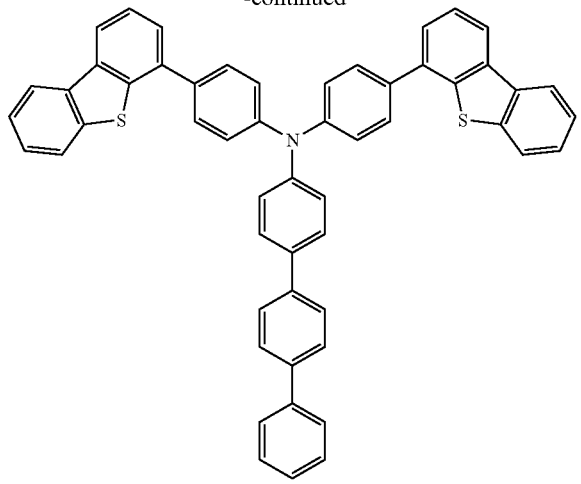

The hole transporting layer of the organic EL device may be made into two-layered structure of a first hole transporting layer (anode side) and a second hole transporting layer (cathode side).

The thickness of the hole transporting layer is preferably 10 to 200 nm, although not particularly limited thereto.

The organic EL device may have a layer comprising an acceptor material which is attached to the anode side of each of the hole transporting layer and the first hole transporting layer. With such a layer, it is expected that the driving voltage is lowered and the production cost is reduced.

The acceptor material is preferably a compound represented by the following formula:

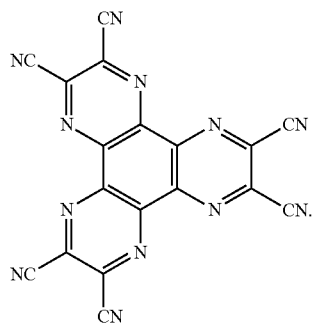 [SMILES: N#Cc1nc2c3nc(C#N)c(C#N)nc3c3nc(C#N)c(C#N)nc3c2nc1C#N]

The thickness of the layer comprising the acceptor material is preferably 5 to 20 nm, although not particularly limited thereto.

n/p Doping

The carrier injecting properties of the hole transporting layer and the electron transporting layer can be controlled by, as described in JP 3695714B, the doping (n) with a donor material or the doping (p) with an acceptor material.

A typical example of the n-doping is an electron transporting material doped with a metal, such as Li and Cs, and a typical example of the p-doping is a hole transporting material doped with an acceptor material such as, $F_4$TCNQ.

Space Layer

For example, in an organic EL device wherein a fluorescent light emitting layer and a phosphorescent light emitting layer are laminated, a space layer is disposed between the fluorescent light emitting layer and the phosphorescent light emitting layer to prevent the diffusion of excitons generated in the phosphorescent light emitting layer to the fluorescent light emitting layer or to control the carrier balance. The space layer may be disposed between two or more phosphorescent light emitting layers.

Since the space layer is disposed between the light emitting layers, a material combining the electron transporting ability and the hole transporting ability is preferably used for forming the space layer. To prevent the diffusion of triplet energy in the adjacent phosphorescent light emitting layer, the triplet energy of the material for the space layer is preferably 2.6 eV or more. The materials described with respect to the hole transporting layer are usable as the material for the space layer.

Blocking Layer

The organic EL device preferably has a blocking layer, such as an electron blocking layer, a hole blocking layer, and a triplet blocking layer, which is disposed adjacent to the light emitting layer. The electron blocking layer is a layer which prevents the diffusion of electrons from the light emitting layer to the hole transporting layer. The hole blocking layer is a layer which prevents the diffusion of holes from the light emitting layer to the electron transporting layer.

The triplet blocking layer prevents the diffusion of triplet excitons generated in the light emitting layer to adjacent layers and has a function of confining the triplet excitons in the light emitting layer, thereby preventing the deactivation of energy on molecules other than the emitting dopant of triplet excitons, for example, on molecules in the electron transporting layer.

The electron mobility of the electron injecting layer is preferably $10^{-6}$ cm$^2$/Vs or more at an electric field strength in a range of 0.04 to 0.5 MV/cm. Within the above range, the injection of electrons from the cathode to the electron transporting layer is promoted and the injection of electrons to the adjacent blocking layer and light emitting layer is also promoted, thereby enabling to drive a device at lower voltage.

EXAMPLES

The present invention will be described in more detail with reference to the examples. However, it should be noted that the scope of the invention is not limited to the following examples.

Synthesis Example 1 (Synthesis of Compound 1)

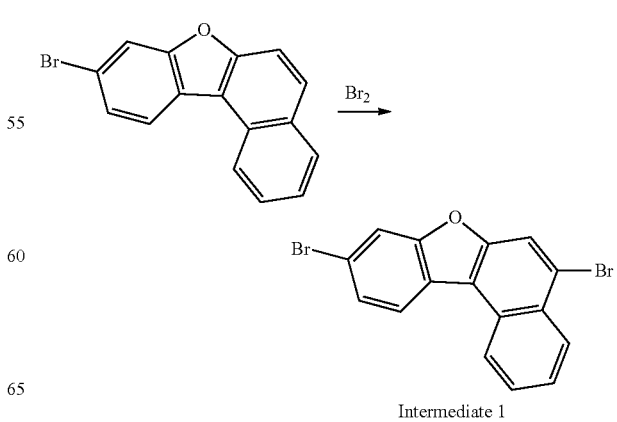

Intermediate 1

In a 500-mL four-necked flask, 9-bromonaphtho[2, 1-b]benzofuran (2.0 g, 6.7 mmol) was dissolved in chloroform (140 mL). After gradually adding a solution of bromine (0.4 mL, 7.8 mmol, 1.2 eq.) in chloroform (5.0 mL), the resultant mixture was stirred at room temperature for 5 h and at 50° C. for 2.5 h. The reaction solution was added with methanol, and the precipitated solid was collected by filtration to obtain the intermediate 1 (1.8 g, yield: 72%). The identification of the intermediate 1 was made by FDMS (field desorption mass spectrometry) analysis.

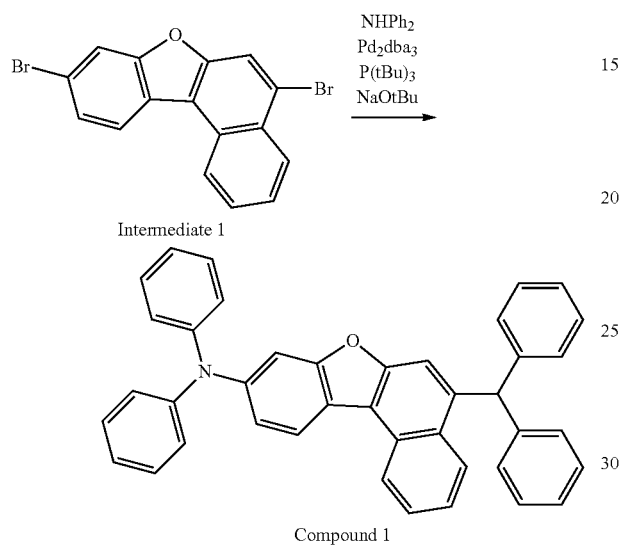

Compound 1

In a 500-mL four-necked flask, the intermediate 1 (1.8 g, 4.8 mmol), diphenylamine (2.0 g, 12 mmol, 2.5 eq.), tris(dibenzylideneacetone)palladium (0.26 g, 0.28 mmol, 6.0 mol %), and sodium t-butoxide (1.4 g, 15 mmol, 3.0 eq.) were charged. After replacing the inner atmosphere with nitrogen, dry toluene (50 mL) and a 3 M toluene solution of tri-t-butylphosphine (78 µL, 0.23 mmol, 4.8 mol %) were added, and the resultant mixture was refluxed for 11 h under heating.

After cooling to room temperature, the reaction solution was added with water and extracted with toluene. The extract was dried over sodium sulfate and concentrated under reduced pressure. The obtained crude product was purified by column chromatography to obtain the target compound 1 (1.5 g, 2.7 mmol, yield: 56%). The identification of the compound 1 was made by FDMS (field desorption mass spectrometry) analysis.

Synthesis Example 2 (Synthesis of Compound 2)

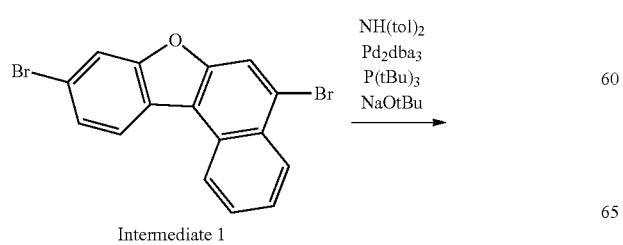

Intermediate 1

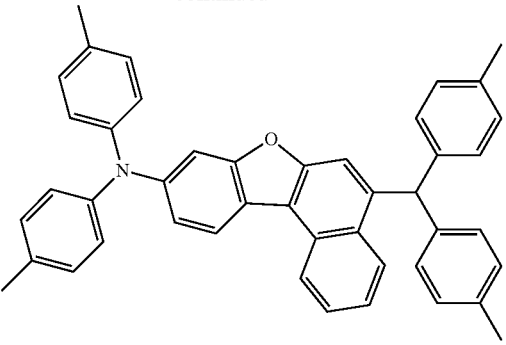

Compound 2

In a 500-mL four-necked flask, the intermediate 1 (2.4 g, 6.4 mmol), ditolylamine (2.5 g, 13 mmol, 2.0 eq.), tris(dibenzylideneacetone)palladium (0.35 g, 0.38 mmol, 6.0 mol %), and sodium t-butoxide (1.4 g, 15 mmol, 2.3 eq.) were charged. After replacing the inner atmosphere with nitrogen, dry toluene (60 mL) and a 3 M toluene solution of tri-t-butylphosphine (100 µL, 0.30 mmol, 4.7 mol %) were added, and the resultant mixture was refluxed for 16 h under heating.

After cooling to room temperature, the reaction solution was added with water and extracted with toluene. The extract was dried over sodium sulfate and concentrated under reduced pressure. The obtained crude product was purified by column chromatography to obtain the target compound 2 (1.6 g, 2.6 mmol, yield: 41%). The identification of the compound 2 was made by FDMS (field desorption mass spectrometry) analysis.

Synthesis Example 3 (Synthesis of Compound 3)

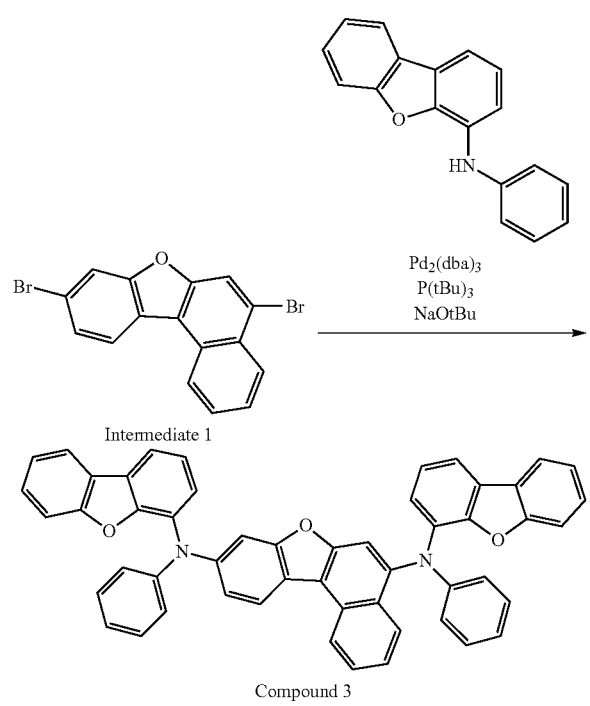

Compound 3

In a 300-mL three-necked flask, the intermediate 1 (3.0 g, 8.0 mmol), N-phenyl-2-dibenzofuranamine (4.2 g, 16 mmol, 2.0 eq.), tris(dibenzylideneacetone)palladium (0.44 g, 0.48 mmol, 6 mol %), a 8.23 M toluene solution of tri-t-butylphosphine (47 μL, 0.39 mmol, 4.8 mol %), and sodium t-butoxide (1.7 g, 18 mmol, 2.2 eq.) were charged. After adding dry toluene (32 mL), the resultant mixture was refluxed for 5 h under heating. The reaction solution was washed with a saturated saline solution and extracted with toluene. The organic layer was dried over sodium sulfate and then concentrated. The obtained crude product was purified by column chromatography to obtain the target compound 3 (4.4 g, 5.9 mmol, yield: 74%). The identification of the compound 3 was made by FDMS (field desorption mass spectrometry) analysis.

Synthesis Example 4 (Synthesis of Compound 4)

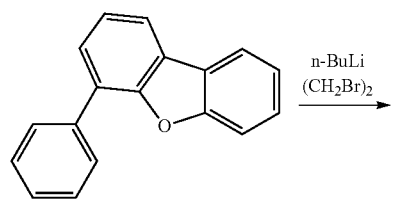

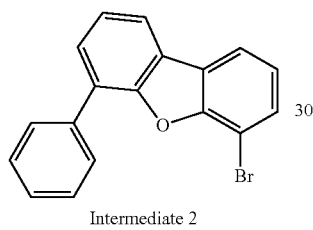

Intermediate 2

In a 500-mL three-necked flask, 4-phenyldibenzofuran (20 g, 82 mmol) was dissolved in dry THF (164 mL). The obtained solution was cooled to −68° C. in a dry ice-methanol bath and added with a 1.6 M hexane solution of n-butyllithium (56 mL, 90 mmol, 1.1 eq.). The temperature was gradually raised and the solution was stirred for 3 h at room temperature. The reaction solution was again cooled to −68° C. in a dry ice-methanol bath and added with 1, 2-dibromoethane (14 mL, 162 mmol, 2.0 eq.). The temperature was gradually raised and the solution was stirred for 3 h at room temperature. The obtained reaction solution was added with water and extracted with ethyl acetate. The organic layer was washed with a saturated saline solution, dried over sodium sulfate, and concentrated. The obtained crude product was purified by column chromatography to obtain the intermediate 2 (21 g, HPLC purity: 67% (inclusive of starting compound), yield: 67%). The identification of the intermediate 2 was made by FDMS (field desorption mass spectrometry) analysis.

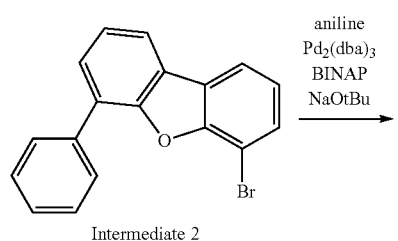

Intermediate 2

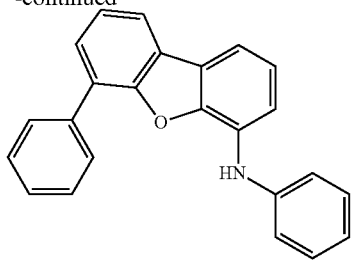

Intermediate 3

In a 1-L three-necked flask, the intermediate 2 (26 g, ca. 55 mmol), aniline (6.0 mL, 66 mmol, 1.2 eq.), tris(dibenzylideneacetone)palladium (0.75 g, 0.82 mmol, 1.5 mol %), 2, 2'-bis(diphenylphosphino)-1, 1'-binaphthyl (1.0 g, 1.6 mmol, 3 mol %), and sodium t-butoxide (5.8 g, 60 mmol, 1.1 eq.) were charged. After adding dry toluene (220 mL), the resultant mixture was refluxed for 6 h under heating. After washing with a saturated saline solution, the obtained solution was extracted with ethyl acetate. The extract was dried over sodium sulfate and concentrated. The obtained crude product was purified by column chromatography to obtain the intermediate 3 (16 g, 46 mmol, yield: 82%). The identification of the intermediate 3 was made by FDMS (field desorption mass spectrometry) analysis.

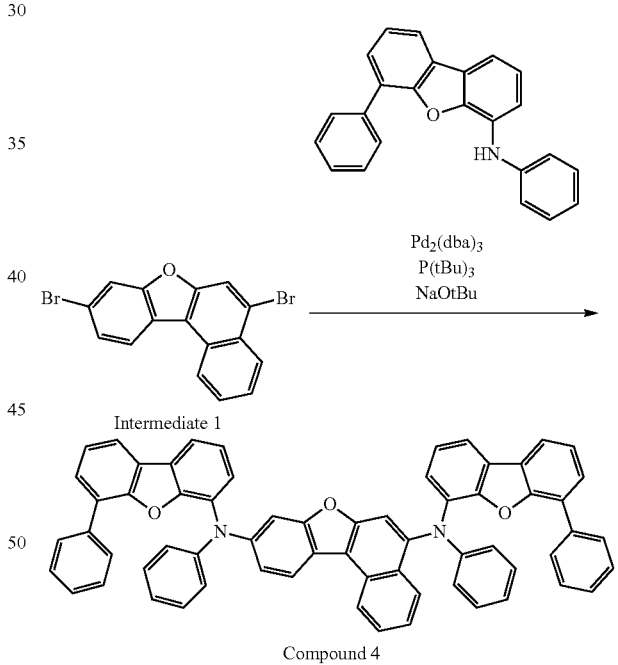

In a 300-mL three-necked flask, the intermediate 1 (3.0 g, 8.0 mmol), the intermediate 3 (5.4 g, 16 mmol, 2.0 eq.), tris(dibenzylideneacetone)palladium (0.44 g, 0.48 mmol, 6 mol %), a 8.23 M toluene solution of tri-t-butylphosphine (47 μL, 0.39 mmol, 4.8 mol %), and sodium t-butoxide (1.7 g, 18 mmol, 2.2 eq.) were charge. After adding dry toluene (48 mL), the resultant mixture was refluxed for 6 h under heating. The obtained reaction solution was washed with a saturated saline solution and extracted with toluene. The organic layer was dried over sodium sulfate and concentrated. The obtained crude product was purified by column chromatography to obtain the target compound 4 (5.1 g, 5.8 mmol, yield: 73%). The identification of the compound 4 was made by FDMS (field desorption mass spectrometry) analysis.

Synthesis Example 5 (Synthesis of Compound 5)

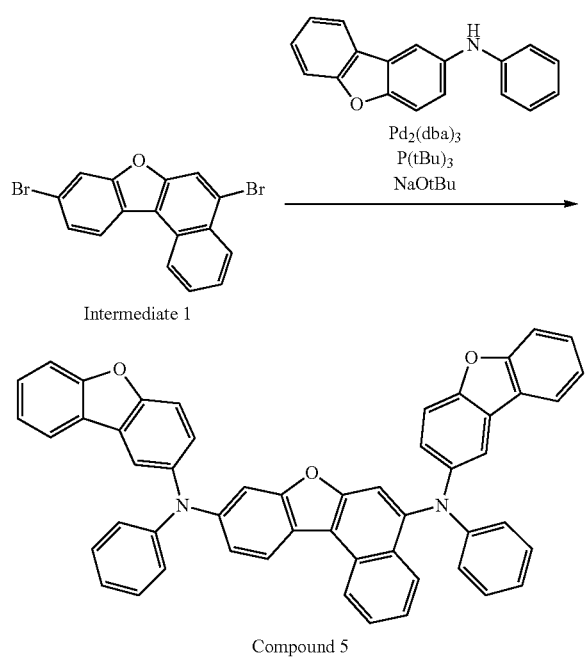

In a 300-mL three-necked flask, the intermediate 1 (3.0 g, 8.0 mmol), N-(dibenzofuran-2-yl)-N-phenylamine (4.2 g, 16 mmol, 2.0 eq.), tris(dibenzylideneacetone)palladium (0.44 g, 0.48 mmol, 6 mol %), a 8.23 M toluene solution of tri-t-butylphosphine (47 μL, 0.39 mmol, 4.8 mol %), and sodium t-butoxide (1.7 g, 18 mmol, 2.2 eq.) were charged. After adding dry toluene (48 mL), the resultant mixture was refluxed for 6 h under heating. The obtained reaction solution was washed with a saturated saline solution and extracted with toluene. The organic layer was dried over sodium sulfate and concentrated. The obtained crude product was purified by column chromatography to obtain the target compound 5 (0.98 g, 1.3 mmol, yield: 16%). The identification of the compound 5 was made by FDMS (field desorption mass spectrometry) analysis.

Synthesis Example 6 (Synthesis of Compound 6)

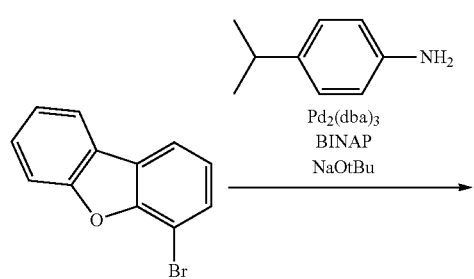

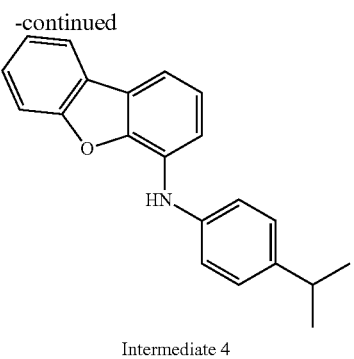

Intermediate 4

In a 1-L three-necked flask, 4-bromodibenzofuran (25.0 g, 101 mmol), 4-isopropylaniline (16.4 g, 121 mmol, 1.2 eq.), tris(dibenzylideneacetone)palladium (2.78 g, 3.04 mmol, 3 mol %), 2,2'-bis(diphenylphosphino)-1,1'-binaphthyl (1.51 g, 24.2 mmol, 2.4 mol %), and sodium t-butoxide (10.7 g, 111 mmol, 1.1 eq.) were charged. After adding dry toluene (405 mL), the resultant mixture was refluxed for 7 h under heating. The obtained reaction solution was added with a saturated saline solution and extracted with toluene. The organic layer was dried over sodium sulfate and concentrated. The obtained crude product was purified by column chromatography to obtain the intermediate 4 (8.2 g, 27.2 mmol, yield: 27%). The identification of the intermediate 4 was made by FDMS (field desorption mass spectrometry) analysis.

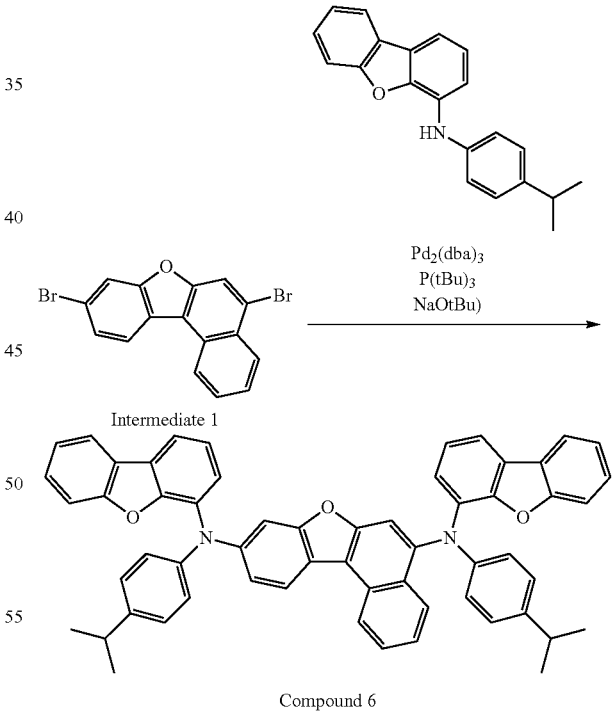

In a 300-mL three-necked flask, the intermediate 1 (3.0 g, 8.0 mmol), the intermediate 4 (4.8 g, 16 mmol, 2.0 eq.), tris(dibenzylideneacetone)palladium (0.44 g, 0.48 mmol, 6 mol %), a 8.23 M toluene solution of tri-t-butylphosphine (47 μL, 0.39 mmol, 4.8 mol %), and sodium t-butoxide (1.7 g, 18 mmol, 2.2 eq.) were charged. After adding dry toluene (48 mL), the resultant mixture was refluxed for 6 h under heating. The obtained reaction solution was washed with a saturated saline solution and extracted with toluene. The organic layer was dried over sodium sulfate and concentrated. The obtained crude product was purified by column chromatography to obtain the target compound 6 (5.0 g, 6.1 mmol, yield: 76%). The identification of the compound 6 was made by FDMS (field desorption mass spectrometry) analysis.

Synthesis Example 7 (Synthesis of Compound 7)

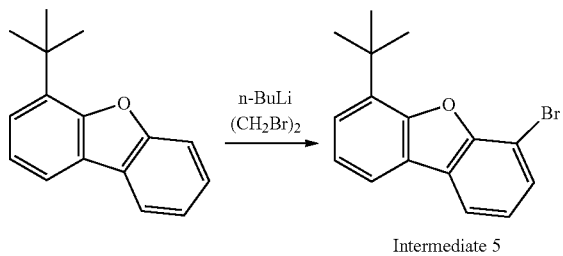 [SMILES: CC(C)(C)c1cccc2c1oc1ccccc12 ; CC(C)(C)c1cccc2c1oc1c(Br)cccc12]

Intermediate 5

In a 500-mL three-necked flask, 4-(t-butyl)dibenzofuran (17.4 g, 78 mmol) was dissolved in dry THF (155 mL). The obtained solution was cooled to −68° C. in a dry ice-methanol bath and added with a 1.6 M hexane solution of n-butyllithium (53 mL, 85 mmol, 1.1 eq.) The temperature was gradually raised and the solution was stirred for 3 h at room temperature. The reaction solution was again cooled to −68° C. in a dry ice-methanol bath and added with 1,2-dibromoethane (13 mL, 150 mmol, 2.0 eq.). The temperature was gradually raised and the solution was stirred for 3 h at room temperature. The obtained reaction solution was added with water and extracted with ethyl acetate. The organic layer was washed with a saturated saline solution, dried over sodium sulfate, and concentrated. The obtained crude product was purified by column chromatography to obtain the intermediate 5 (21 g, HPLC purity: 80% (inclusive of starting compound), 55 mmol, yield: 71%). The identification of the intermediate 5 was made by FDMS (field desorption mass spectrometry) analysis.

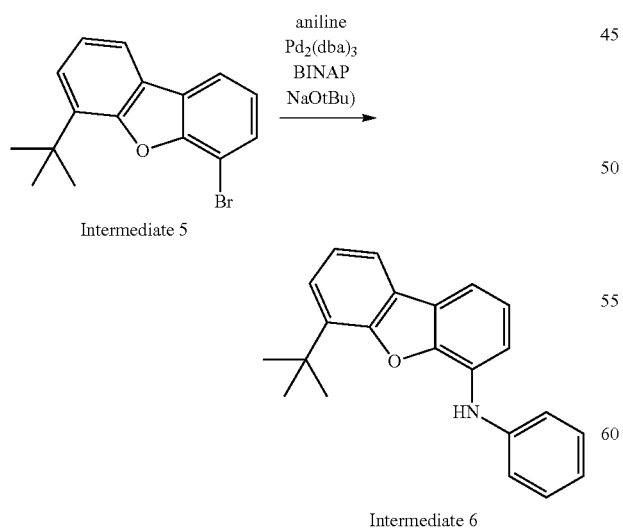

Intermediate 6

In a 1-L three-necked flask, the intermediate 5 (20 g, ca. 55 mmol), aniline (6.0 mL, 65 mmol, 1.2 eq.), tris(dibenzylideneacetone)palladium (0.75 g, 0.82 mmol, 1.5 mol %), 2,2′-bis(diphenylphosphino)-1,1′-binaphthyl (1.0 g, 1.6 mmol, 3.0 mol %), and sodium t-butoxide (5.8 g, 60 mmol, 1.1 eq.) were charged. After adding dry toluene (220 mL), the resultant mixture was refluxed for 6 h under heating. The obtained reaction solution was added with a saturated saline solution and extracted with toluene. The organic layer was dried over sodium sulfate and concentrated. The obtained crude product was purified by column chromatography to obtain the intermediate 6 (16 g, 49 mmol, yield: 89%). The identification of the intermediate 6 was made by FDMS (field desorption mass spectrometry) analysis.

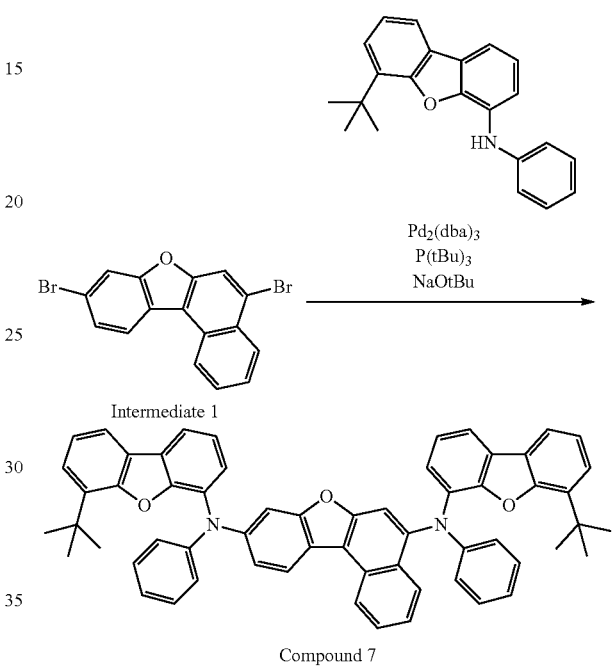

Compound 7

In a 300-mL three-necked flask, the intermediate 1 (3.0 g, 8.0 mmol), the intermediate 6 (5.0 g, 24 mmol, 2.0 eq.), tris(dibenzylideneacetone)palladium (0.44 g, 0.48 mmol, 6 mol %), a 8.23 M toluene solution of tri-t-butylphosphine (47 μL, 0.39 mmol, 4.8 mol %), and sodium t-butoxide (1.7 g, 18 mmol, 2.2 eq.) were charged. After adding dry toluene (48 mL), the resultant mixture was refluxed for 6 h under heating. The obtained reaction solution was washed with a saturated saline solution and extracted with toluene. The organic layer was dried over sodium sulfate and concentrated. The obtained crude product was purified by column chromatography to obtain the target compound 7 (5.17 g, 6.1 mmol, yield: 76%). The identification of the compound 7 was made by FDMS (field desorption mass spectrometry) analysis.

Synthesis Example 8 (Synthesis of Compound 8)

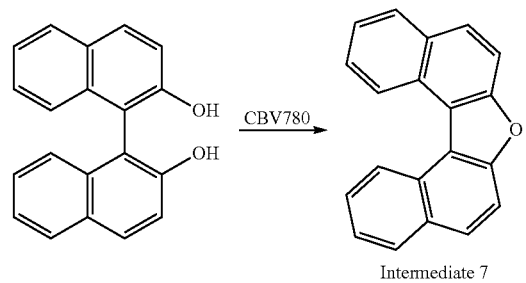

Intermediate 7

In a 300-mL round flask, 1,1'-bi-2-naphthol (5.4 g, 19 mmol) and Zeolith CBV780 (manufactured by Zeolyst Inc.) (2.5 g) were suspended in o-dichlorobenzene (30 mL). The suspension was refluxed for 18 h under heating, and then, filtered under heating and washed with hot toluene. The filtrate was concentrated to such degree that o-dichlorobenzene still remained and then added with methanol to precipitate solid. The solid was collected by filtration to obtain the intermediate 7 as white powder (4.6 g, 18 mmol, 90%). The identification of the intermediate 7 was made by FDMS (field desorption mass spectrometry) analysis.

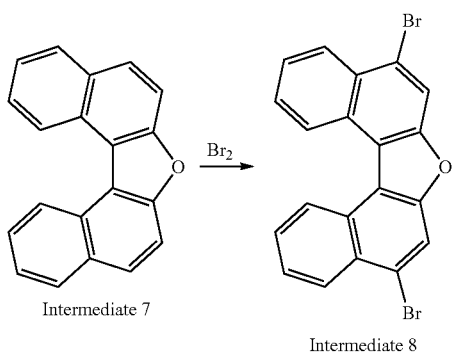

In a 300-mL three-necked flask, the intermediate 7 (1.0 g, 3.7 mmol) was dissolved in chloroform (40 mL). After adding a chloroform solution (2 mL) of bromine (0.4 mL, 7.8 mmol, 2.1 eq.) slowly, the solution was stirred at room temperature for 2 h. The resultant solution was added with methanol to precipitate solid. The solid was collected by filtration to obtain the intermediate 8 (1.5 g, 3.5 mmol, 94%). The identification of the intermediate 8 was made by FDMS (field desorption mass spectrometry) analysis.

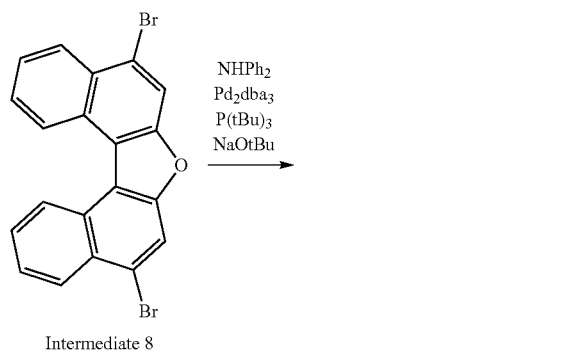

In a 500-mL four-necked flask, the intermediate 8 (1.5 g, 3.5 mmol), diphenylamine (1.5 g, 8.9 mmol, 2.5 eq.), tris(dibenzylideneacetone)palladium (0.20 g, 0.21 mmol, 6.0 mol %), and sodium t-butoxide (0.85 g, 8.8 mmol, 2.5 eq.) were charged. After replacing the inner atmosphere with nitrogen, dry toluene (40 mL) and a 3 M toluene solution of tri-t-butylphosphine (56 μL, 0.17 mmol, 4.9 mol %) were added, and the resultant mixture was refluxed for 12 h under heating. After cooling to room temperature, the reaction solution was added with water and extracted with toluene. The extract was dried over sodium sulfate and concentrated under reduced pressure. The obtained crude product was purified by column chromatography to obtain the target compound 8 (1.2 g, 2.0 mmol, yield: 57%). The identification of the compound 8 was made by FDMS (field desorption mass spectrometry) analysis.

Synthesis Example 9 (Synthesis of Compound 9)

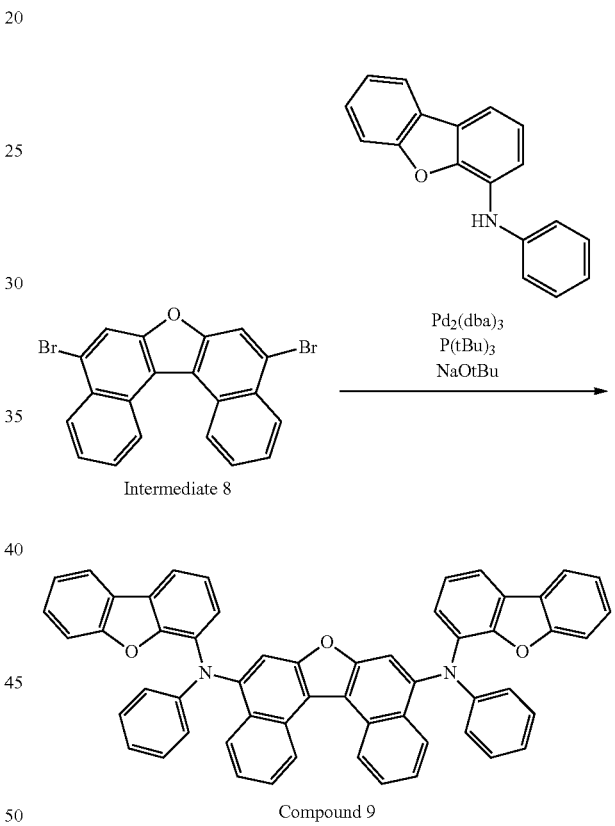

In a 300-mL three-necked flask, the intermediate 8 (5.0 g, 12 mmol), N-phenyl-2-dibenzofuranamine (6.1 g, 24 mmol, 2.0 eq.), tris(dibenzylideneacetone)palladium (0.65 g, 0.71 mmol, 6 mol %), a 8.23 M toluene solution of tri-t-butylphosphine (69 μL, 0.57 mmol, 4.8 mol %), and sodium t-butoxide (2.5 g, 26 mmol, 2.2 eq.) were charged. After adding dry toluene (48 mL), the resultant mixture was refluxed for 6 h under heating. The obtained reaction solution was washed with a saturated saline solution and extracted with toluene. The organic layer was dried over sodium sulfate and concentrated. The obtained crude product was purified by column chromatography to obtain the target compound 9 (6.4 g, 8.2 mmol, yield: 68%). The identification of the compound 9 was made by FDMS (field desorption mass spectrometry) analysis.

Synthesis Example 10 (Synthesis of Compound 10)

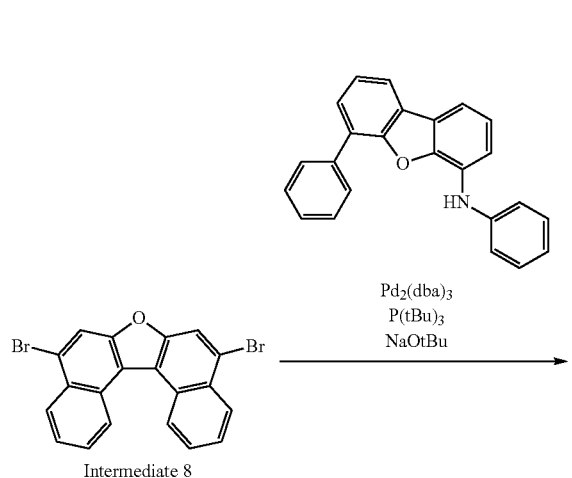

Intermediate 8

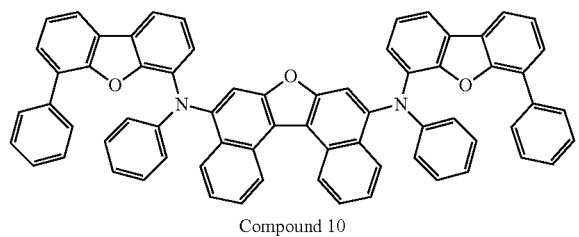

Compound 10

In a 300-mL three-necked flask, the intermediate 8 (5.0 g, 12 mmol), the intermediate 3 (7.9 g, 24 mmol, 2.0 eq.), tris(dibenzylideneacetone)palladium (0.64 g, 0.70 mmol, 6 mol %), a 8.23 M toluene solution of tri-t-butylphosphine (68 L, 0.56 mmol, 4.8 mol %), and sodium t-butoxide (2.5 g, 26 mmol, 2.2 eq.) ware charged. After adding dry toluene (47 mL), the resultant mixture was refluxed for 3 h under heating. The obtained reaction solution was added with a saturated saline solution and extracted with toluene. The extract was dried over sodium sulfate and concentrated. The obtained crude product was purified by column chromatography to obtain the target compound 10 (2.5 g, 2.7 mmol, yield: 23%). The identification of the compound 10 was made by FDMS (field desorption mass spectrometry) analysis.

Synthesis Example 11 (Synthesis of Compound 11)

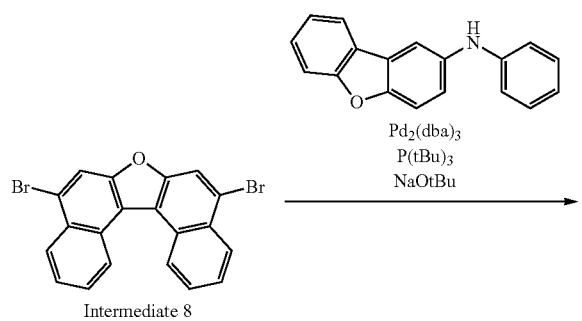

Intermediate 8

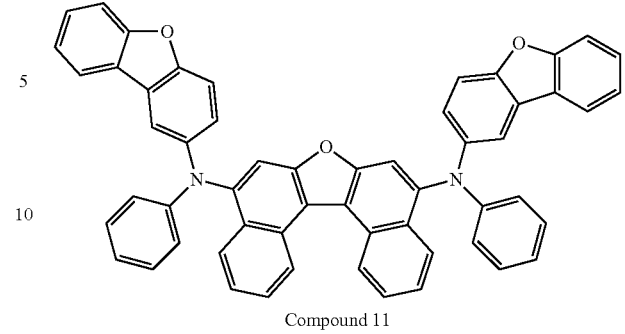

Compound 11

In a 300-mL three-necked flask, the intermediate 8 (5.0 g, 12 mmol), N-(dibenzofuran-2-yl)-N-phenylamine (6.3 g, 24 mmol, 2.0 eq.), tris(dibenzylideneacetone)palladium (0.64 g, 0.70 mmol, 6 mol %), a 8.23 M toluene solution of tri-t-butylphosphine (68 μL, 0.56 mmol, 4.8 mol %), and sodium t-butoxide (2.5 g, 26 mmol, 2.2 eq.) were charged. After adding dry toluene (50 mL), the resultant mixture was refluxed for 7 h under heating. The obtained reaction solution was washed with a saturated saline solution. The organic layer was dried over sodium sulfate and concentrated. The obtained crude product was purified by column chromatography to obtain the target compound 11 (3.14 g, 4.0 mmol, yield: 33%). The identification of the compound 11 was made by FDMS (field desorption mass spectrometry) analysis.

Synthesis Example 12 (Synthesis of Compound 12)

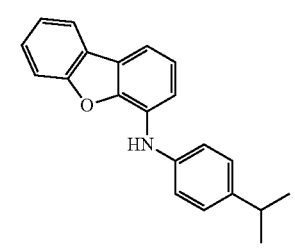

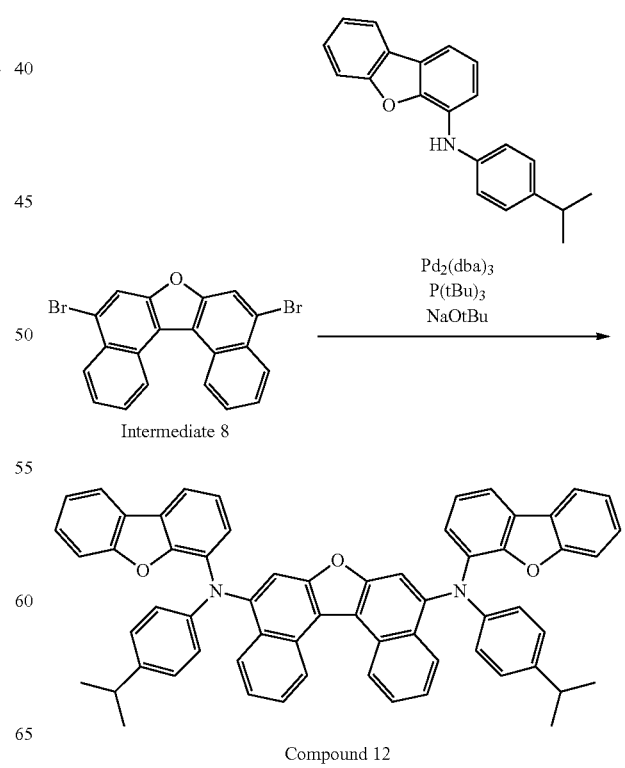

Intermediate 8

Compound 12

In a 300-mL three-necked flask, the intermediate 8 (5.0 g, 12 mmol), the intermediate 4 (7.1 g, 24 mmol, 2.0 eq.), tris(dibenzylideneacetone)palladium (0.64 g, 0.70 mmol, 6 mol %), a 8.23 M toluene solution of tri-t-butylphosphine (68 µL, 0.56 mmol, 4.8 mol %), and sodium t-butoxide (2.5 g, 26 mmol, 2.2 eq.) were charged. After adding dry toluene (46 mL), the resultant mixture was refluxed for 7 h under heating. The obtained reaction solution was washed with a saturated saline solution. The organic layer was dried over sodium sulfate and concentrated. The obtained crude product was purified by column chromatography to obtain the target compound 12 (2.3 g, 2.7 mmol, yield: 23%). The identification of the compound 12 was made by FDMS (field desorption mass spectrometry) analysis.

Synthesis Example 13 (Synthesis of Compound 13)

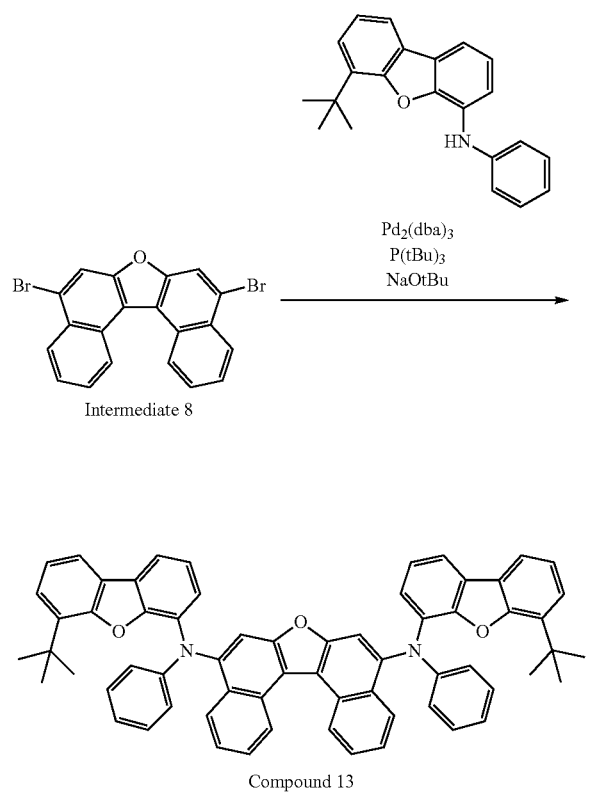

In a 300-mL three-necked flask, the intermediate 8 (5.0 g, 12 mmol), the intermediate 6 (7.4 g, 24 mmol, 2.0 eq.), tris(dibenzylideneacetone)palladium (0.64 g, 0.70 mmol, 6 mol %), a 8.23 M toluene solution of tri-t-butylphosphine (68 L, 0.56 mmol, 4.8 mol %), and sodium t-butoxide (2.5 g, 26 mmol, 2.2 eq.) were charged. After adding toluene (50 mL), the resultant mixture was refluxed for 7 h under heating. The obtained reaction solution was washed with a saturated saline solution. The organic layer was dried over sodium sulfate and concentrated. The obtained crude product was purified by column chromatography to obtain the target compound 13 (6.4 g, 7.2 mmol, yield: 60%). The identification of the compound 13 was made by FDMS (field desorption mass spectrometry) analysis.

Example 1

A glass substrate of 25 mm×75 mm×1.1 mm thickness having an ITO transparent electrode (product of Geomatec Co., Ltd.) was cleaned by ultrasonic cleaning in isopropyl alcohol for 5 min and then UV ozone cleaning for 30 min. The thickness of the ITO transparent electrode was 130 nm.

The cleaned glass substrate having the ITO transparent electrode line was mounted to a substrate holder of a vacuum vapor deposition apparatus. The following compound (HI-1) was vapor-deposited so as to cover the ITO transparent electrode line to form an HI-1 film with a thickness of 5 nm, thereby forming a hole injecting layer.

Then, on the HI-1 film, the following compound HT-1 was vapor-deposited into an HT-1 film with a thickness of 80 nm to form a first hole transporting layer.

Then, on the HT-1 film, the following compound HT-2 was vapor-deposited into an HT-2 film with a thickness of 15 nm to form a second hole transporting layer.

Further, on the HT-2 film, the compound BH-1 was vapor-deposited into a light emitting layer with a thickness of 25 nm. Simultaneously, the compound 2 as the fluorescent emitting material was vapor co-deposited. The concentration of the compound 2 was 5.0% by mass of the total of the compound BH-1 and the compound 2. The vapor co-deposited film functions as a light emitting layer.

On the light emitting layer, the following compound ET-1 was vapor-deposited into an ET-1 film with a thickness of 20 nm to form a first electron transporting layer.

Then, on the ET-1 film, the following compound ET-2 was vapor-deposited into an ET-2 film with a thickness of 5 nm to form a second electron transporting layer.

Then, on the ET-2 film, LiF was vapor-deposited into a LiF film with a thickness of 1 nm at a film-forming speed of 0.1 Å/min to form an electron injecting electrode (cathode).

Finally, on the LiF film, metallic Al was vapor-deposited into a metallic Al film with a thickness of 80 nm to form a metallic Al cathode, thereby obtaining an organic EL device.

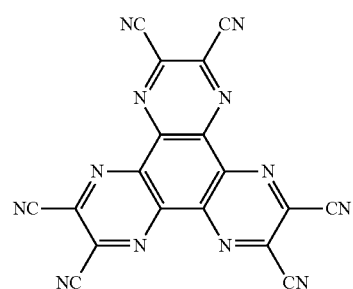

HT-1
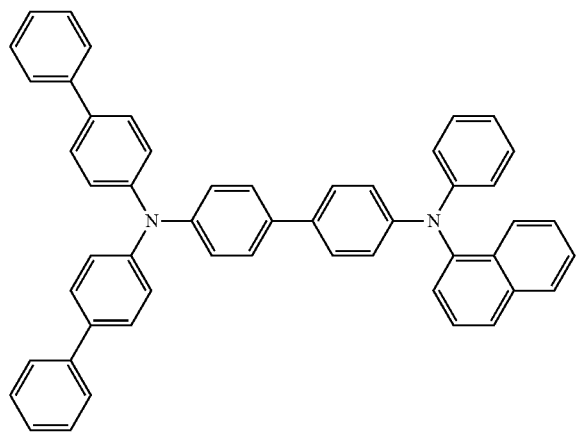
ET-1
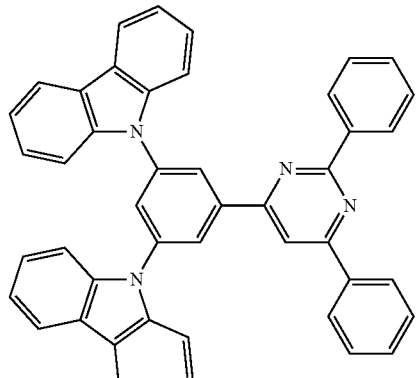
HT-2
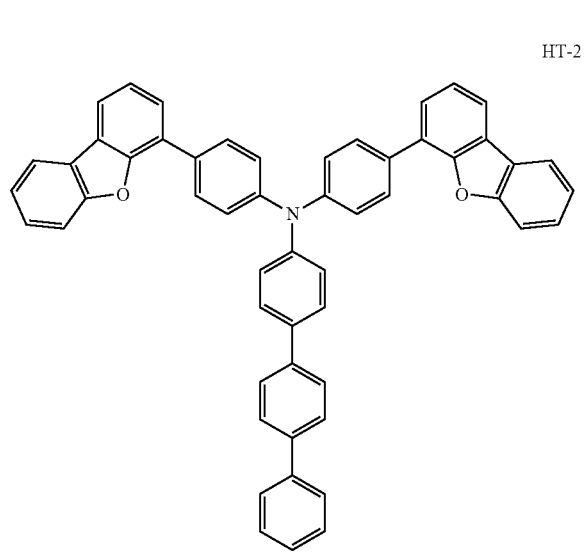
ET-2
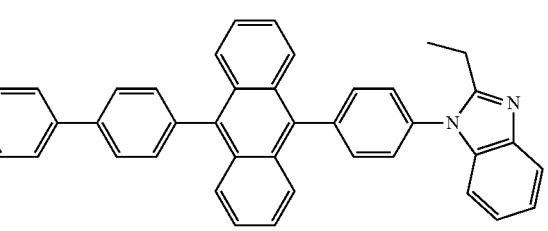
Compound 2
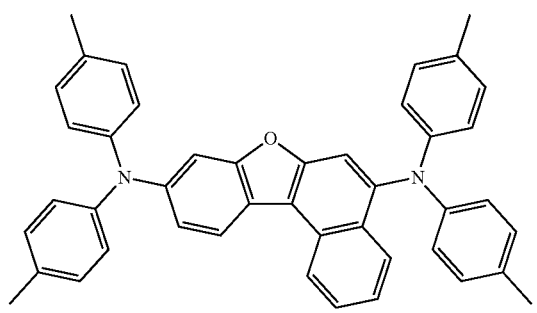
BH-1
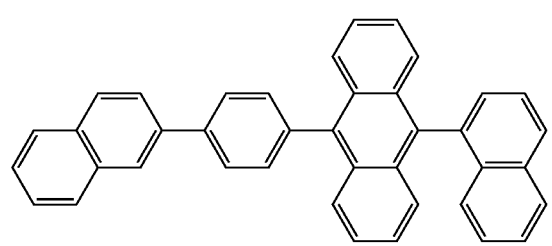
Examples 2 to 3
Each organic EL device was produced in the same manner as in Example 1 except for using the compound 9 (Example 2) and the compound 10 (Example 3) in place of the compound 2.
compound 9
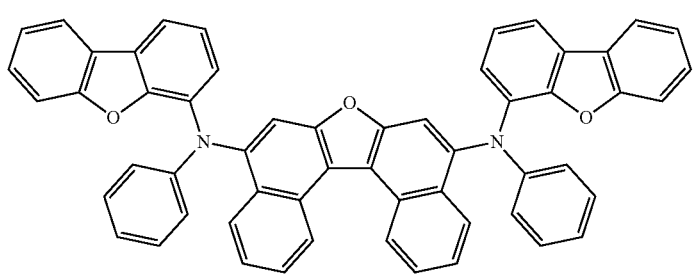

-continued

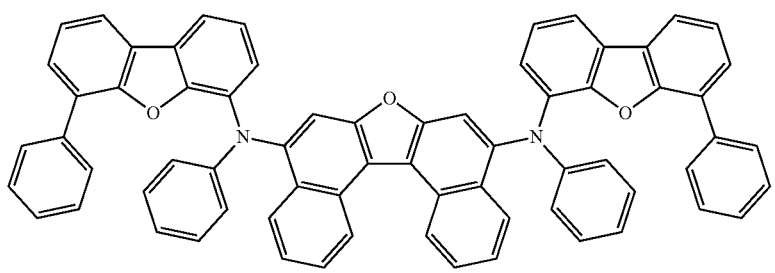

Compound 10

Evaluation of Organic EL Device

The obtained organic EL devices were measured for the driving voltage, the external quantum efficiency EQE, and the main peak wavelength $\lambda_p$ by applying voltage to give a current density of 10 mA/cm². The results are shown in Table 1.

TABLE 1

| | Compound | Driving voltage (V) | External quantum efficiency (%) | Emitting color |
|---|---|---|---|---|
| Example 1 | compound 2 | 3.6 | 9.6 | blue |
| Example 2 | compound 9 | 3.6 | 9.6 | blue |
| Example 3 | compound 10 | 3.6 | 9.5 | blue |

As seen from Table 1, the amine compound of the invention realizes an organic EL device having high emission efficiency even at a low driving voltage.

INDUSTRIAL APPLICABILITY

By using the combination of the materials of the invention, an organic EL device with a long lifetime and a high efficiency at a low driving voltage is obtained.

REFERENCE NUMERALS

1: Organic electroluminescence device
2: Substrate
3: Anode
4: Cathode
5: Light emitting layer
6: Hole injecting/transporting layer
7: Electron injecting/transporting layer
10: Emission unit

What is claimed is:

1. An amine compound represented by formula (I):

$$B\text{-}(A)_n \tag{1}$$

wherein:

n is 1;

B represents a structure represented by formula (2) shown below;

A represents a group represented by formula (6) shown below:

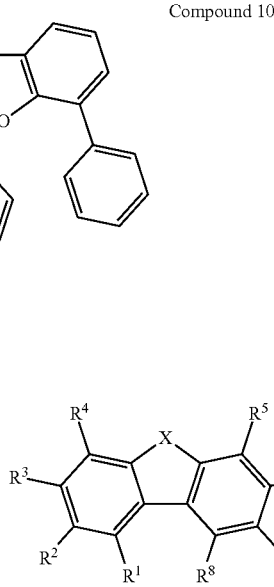

(2)

wherein two adjacent groups in at least one pair of $R^1$ and $R^2$, $R^2$ and $R^3$, $R^3$ and $R^4$, $R^5$ and $R^6$, $R^6$ and $R^7$, and $R^7$ and $R^8$ are bonded to each other to form a divalent group represented by formula (3):

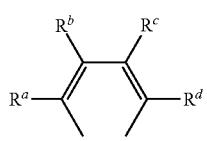

(3)

n group of $R^1$ to $R^8$ and $R^a$ to $R^d$ represents a single bond which is bonded to the group A represented by formula (6);

each of $R^1$ to $R^8$ which does not form the divalent group and does not represent the single bond bonded to the group A represented by formula (6), and each of $R^a$ to $R^d$ which does not represent the single bond bonded to the group A represented by formula (6) are independently selected from a hydrogen atom, a fluorine atom, a cyano group, a substituted or unsubstituted alkyl group having 1 to 20 carbon atoms, a substituted or unsubstituted cycloalkyl group having 3 to 20 ring carbon atoms, a substituted or unsubstituted aryl group having 6 to 30 ring carbon atoms, a substituted or unsubstituted alkoxy group having 1 to 20 carbon atoms, a substituted or unsubstituted aryloxy group having 6 to 30 ring carbon atoms, a substituted or unsubstituted alkylthio group having 1 to 20 carbon atoms, a substituted or unsubstituted arylthio group having 6 to 30 ring carbon atoms, a substituted or unsubstituted alkylsilyl group having 3 to 50 carbon atoms, a substituted or unsubstituted arylsilyl group having 6 to 50 ring carbon atoms, and a substituted or unsubstituted heterocyclic group having 5 to 30 ring atoms; and X represents an oxygen atom; and

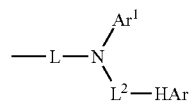
(6)

wherein:

Ar¹ represents a substituted or unsubstituted aryl group having 6 to 30 ring carbon atoms or a substituted or unsubstituted heterocyclic group having 5 to 30 ring atoms;

L represents an arylene group having 6 to 30 ring carbon atoms, a heteroarylene group having 5 to 30 ring atoms, or a divalent linking group formed by bonding 2 to 4 groups selected from the arylene groups and the heteroarylene groups;

L² represents a single bond, an arylene group having 6 to 30 ring carbon atoms, a heteroarylene group having 5 to 30 ring atoms, or a divalent linking group formed by bonding 2 to 4 groups selected from the arylene groups and the heteroarylene groups; and HAr represents a structure represented by formula (7):

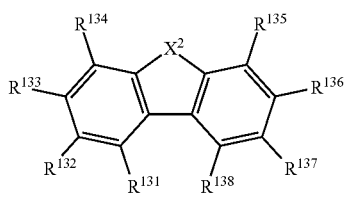
(7)

wherein:

X² represents an oxygen atom or a sulfur atom;

one of $R^{131}$ to $R^{138}$ represents a single bond bonded to L², and the others of $R^{131}$ to $R^{138}$ each independently represent a hydrogen atom, a fluorine atom, a cyano group, a substituted or unsubstituted alkyl group having 1 to 20 carbon atoms, a substituted or unsubstituted cycloalkyl group having 3 to 20 ring carbon atoms, a substituted or unsubstituted aryl group having, 6 to 30 ring carbon atoms, a substituted or unsubstituted alkoxy group having 1 to 20 carbon atoms, a substituted or unsubstituted aryloxy group having 6 to 30 ring carbon atoms, a substituted or unsubstituted alkylthio group having 1 to 20 carbon atoms, a substituted or unsubstituted arylthio group having 6 to 30 ring carbon atoms, a substituted or unsubstituted alkylsilyl group having 3 to 50 carbon atoms, a substituted or unsubstituted aryls group having 6 to 50 ring carbon atoms, or a substituted or unsubstituted heterocyclic group having 5 to 30 ring atoms.

2. The amine compound according to claim 1, wherein one pair selected from R¹ and R², R² and R³, R³ and R⁴, R⁵ and R⁶, R⁶ and R⁷, and R⁷ and R⁸ forms the divalent group represented by formula (3).

3. The amine compound according to claim 1, wherein the structure B is represented by any of formulae (11) to (13):

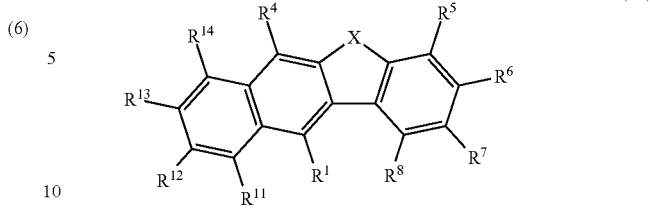
(11)

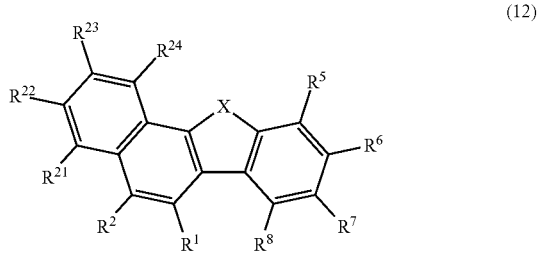
(12)

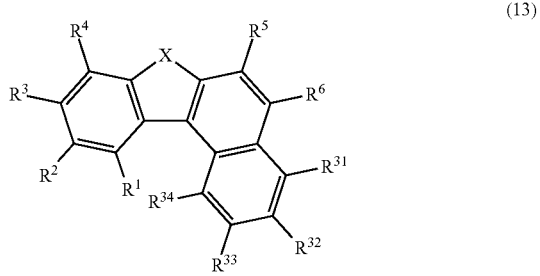
(13)

wherein X and R¹ to R⁸ are as defined above, and R¹¹ to R¹⁴, R²¹ to R²⁴, and R³¹ to R³⁴ are defined as in $R^a$ to $R^d$.

4. The amine compound according to claim 1, wherein two pairs selected from R¹ and R², R² and R³, R³ and R⁴, R⁵ and R⁶, R⁶ and R⁷, and R⁷ and R⁸ form the divalent groups represented by formula (3).

5. The amine compound according to claim 1, wherein the structure B is represented by any of formulae (14) to (19):

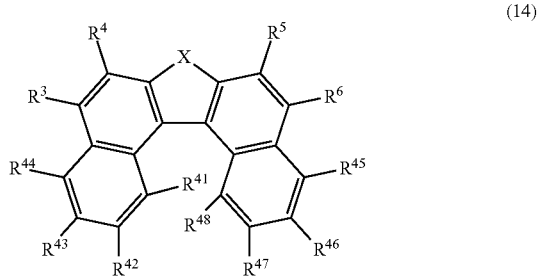
(14)

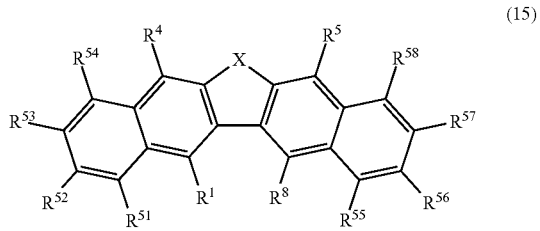
(15)

-continued

(16)
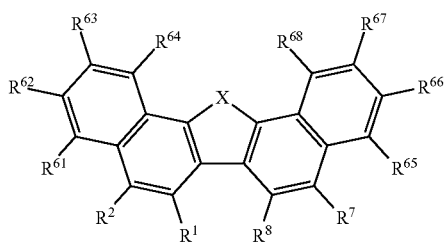

(17)
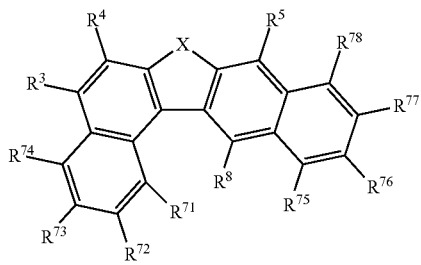

(18)
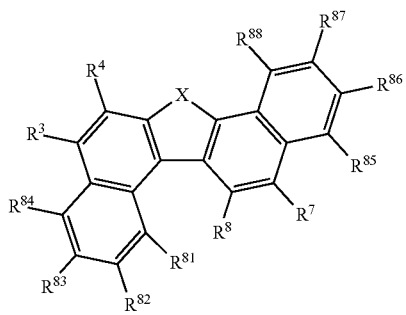

(19)
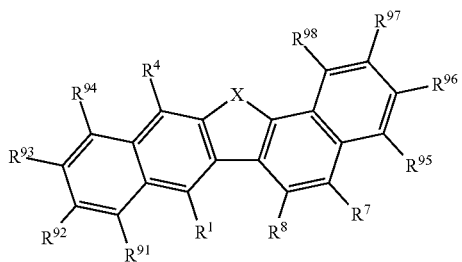

wherein X and R$^1$ to R$^8$ are as defined above, and R$^{41}$ to R$^{48}$, R$^{51}$ to R$^{58}$, R$^{61}$ to R$^{68}$, R$^{71}$ to R$^{78}$, R$^{81}$ to R$^{88}$, and R$^{91}$ to R$^{98}$ are defined as in R$^a$ to R$^d$.

6. The amine compound according to claim 1, wherein the structure B is represented by any of formulae (14) to (16):

(14)
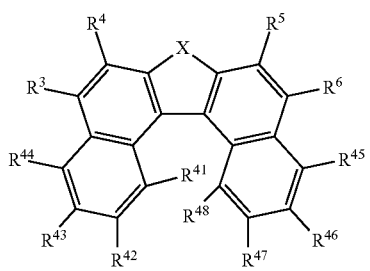

-continued

(15)
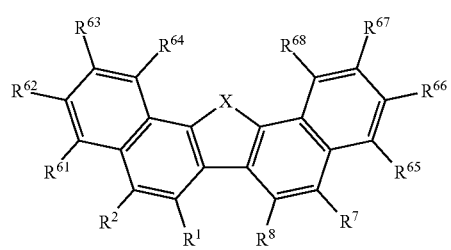

(16)
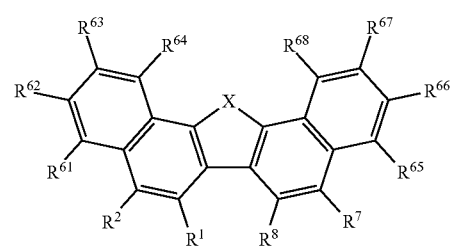

wherein X, R$^1$ to R$^8$, R$^{41}$ to R$^{48}$, R$^{51}$ to R$^{58}$, and R$^{61}$ to R$^{68}$ are as defined above.

7. The amine compound according to claim 1, wherein one of R$^{132}$, R$^{134}$, R$^{135}$, and R$^{137}$ represents a single bond bonded to L$^2$.

8. An organic electroluminescence device which comprises a cathode, an anode, and one or more organic thin film layers which are disposed between the cathode and the anode, wherein the organic thin film layers comprise a light emitting layer, and at least one layer of the organic thin film layers comprises at least one amine compound according to claim 1.

9. The organic electroluminescence device according to claim 8, wherein the light emitting layer comprises the amine compound.

10. The organic electroluminescence device according to claim 8, wherein the at least one layer comprises the amine compound and an anthracene derivative represented by formula (5a):

(5a)
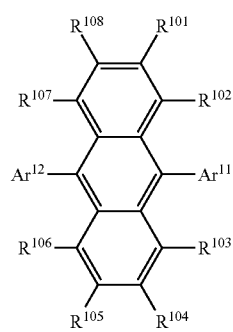

wherein each of Ar$^{11}$ and Ar$^{12}$ independently represents a substituted or unsubstituted monocyclic group having 5 to 50 ring atoms or a substituted or unsubstituted fused ring group having 8 to 50 ring atoms, and each of R$^{101}$ to R$^{108}$ independently represents a group selected from a hydrogen atom, a substituted or unsubstituted monocyclic group having 5 to 50 ring atoms, a substituted or unsubstituted fused ring group having 8 to 50 ring atoms, a group constituted of a combination of the monocyclic group and the fused ring group, a substituted or unsubstituted alkyl group having 1 to 50 carbon atoms, a substituted or unsubstituted cycloalkyl group having 3 to 50 ring carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring carbon atoms, a substituted or unsubstituted silyl group, a halogen atom, and a cyano group.

11. The organic electroluminescence device according to claim 10, wherein each of $Ar^{11}$ and $Ar^{12}$ of formula (5a) independently represents the substituted or unsubstituted fused ring group having 8 to 50 ring atoms.

12. The organic electroluminescence device according to claim 10, wherein one of $Ar^{11}$ and $Ar^{12}$ of formula (5a) represents the substituted or unsubstituted monocyclic group having 5 to 50 ring carbon atoms, and the other represents the substituted or unsubstituted fused ring group having 8 to 50 ring atoms.

13. The organic electroluminescence device according to claim 12, wherein in formula (5a), $Ar^{12}$ represents a naphthyl group, a phenanthryl group, a benzanthryl group, a 9,9-dimethylfluorenyl group, or a dibenzofuranyl group, and $Ar^{11}$ represents an unsubstituted phenyl group or a phenyl group substituted with the monocyclic group or the fused ring group.

14. The organic electroluminescence device according to claim 12, wherein in formula (5a), $Ar^{12}$ represents the substituted or unsubstituted fused ring group having 8 to 50 ring atoms, and $Ar^{11}$ represents an unsubstituted phenyl group.

15. The organic electroluminescence device according to claim 10, wherein each of $Ar^{11}$ and $Ar^{12}$ of formula (5a) independently represents the substituted or unsubstituted monocyclic group having 5 to 50 ring atoms.

16. The organic electroluminescence device according to claim 15, wherein each of $Ar^{11}$ and $Ar^{12}$ of formula (5a) independently represents a substituted or unsubstituted phenyl group.

17. The organic electroluminescence device according to claim 15, wherein in formula (5a), $Ar^{11}$ represents an unsubstituted phenyl group, and $Ar^{12}$ represents a phenyl group substituted with the monocyclic group or the fused ring group.

18. The organic electroluminescence device according to claim 15, wherein each of $Ar^{11}$ and $Ar^{12}$ of formula (5a) independently represents a phenyl group substituted with the monocyclic group or the fused ring group.

* * * * *

UNITED STATES PATENT AND TRADEMARK OFFICE
CERTIFICATE OF CORRECTION

PATENT NO. : 10,270,040 B2
APPLICATION NO. : 15/658596
DATED : April 23, 2019
INVENTOR(S) : Yoichi Ikeda et al.

Page 1 of 1

It is certified that error appears in the above-identified patent and that said Letters Patent is hereby corrected as shown below:

In the Claims

Column 629, Line 58, Claim 1, "aryls group having" should read --arlylsilyl group having--.

Signed and Sealed this
Twenty-eighth Day of April, 2020

Andrei Iancu
*Director of the United States Patent and Trademark Office*